(12) United States Patent
Miyake et al.

(10) Patent No.: US 7,747,390 B2
(45) Date of Patent: *Jun. 29, 2010

(54) DIGITAL CELL

(75) Inventors: Masato Miyake, Amagasaki (JP);
Tomohiro Yoshikawa, Amagasaki (JP);
Jun Miyake, Amagasaki (JP)

(73) Assignee: National Institute of Advanced Industrial Science and Technology, Chiyoda-Ku (JP)

( * ) Notice: Subject to any disclaimer, the term of this patent is extended or adjusted under 35 U.S.C. 154(b) by 681 days.

This patent is subject to a terminal disclaimer.

(21) Appl. No.: 10/562,469

(22) PCT Filed: Jun. 25, 2004

(86) PCT No.: PCT/JP2004/009404

§ 371 (c)(1),
(2), (4) Date: May 31, 2006

(87) PCT Pub. No.: WO2005/021744

PCT Pub. Date: Mar. 10, 2005

(65) Prior Publication Data

US 2006/0253258 A1    Nov. 9, 2006

(30) Foreign Application Priority Data

Jun. 25, 2003  (JP) ............................. 2003-181915
Aug. 7, 2003   (JP) ............................. 2003-289469

(51) Int. Cl.
G06F 19/00   (2006.01)
G06F 15/00   (2006.01)

(52) U.S. Cl. ........................................... 702/19
(58) Field of Classification Search .................. None
See application file for complete search history.

(56) References Cited

U.S. PATENT DOCUMENTS 5,777,888 A    7/1998  Rine et al. ................ 364/496

| | | | |
|---|---|---|---|
| 7,003,440 B2 | 2/2006 | Gojobori et al. ............. 703/11 |
| 2001/0034748 A1* | 10/2001 | Bimson et al. ............. 707/530 |
| 2002/0055935 A1* | 5/2002 | Rosenblum ............ 707/104.1 |
| 2002/0072116 A1 | 6/2002 | Bhatia et al. ............... 435/366 |
| 2002/0197718 A1 | 12/2002 | Myles et al. ............... 435/395 |

FOREIGN PATENT DOCUMENTS

| WO | WO 98/06874 | * | 2/1998 |
|---|---|---|---|
| WO | 98/38490 A1 | | 9/1998 |
| WO | WO 99/60094 | | 11/1999 |
| WO | WO 00/03246 | | 1/2000 |
| WO | WO 01/63245 A2 | | 8/2001 |
| WO | WO 02/07100 A1 | | 1/2002 |

OTHER PUBLICATIONS

Maxwell et al. Elecroporation of Mammalian Cells with a Firefly Luciferase Expression Plasmid: Kinetics of Transient Expressiojn Differ Markedly among Cell Types DNA vol. 7, pp. 557-562 (1988).*
Hashino et al. Effects of Fibronectin Fragments on DNA Transfection into Mammalian Cells by Electroporation Journal of Biochemistry vol. 122, pp. 490-493 (1997).*

* cited by examiner

Primary Examiner—John S Brusca
(74) Attorney, Agent, or Firm—SEED IP Law Group PLLC

(57) ABSTRACT

It is intended to provide a method and system for carrying out data production with respect to the actual status of cells as a profile. It is also intended to provide a system and method for presenting time-lapse and/or real-time information of cell interior directly, or as it is, from the viewpoint of a complex system. It is further intended to provide a method of presenting a digital cell. Thus, there is provided a method of producing profile data relating to cell information, comprising the step (a) of arranging cells in an immobilized form on a support and the step (b) of monitoring over time biological factors on or inside the cells or an aggregate thereof, thereby producing profile data for the cells. Furthermore, there is provided a method of producing a digital cell, comprising procuring experimental data by the use of the above method.

9 Claims, 53 Drawing Sheets

FIG.2
Fibronectin (43kDa fragment)
Fibronectin (72kDa fragment)

FIG.4

Fibronectin structure

N-term ┤ 29kD │ 43kD ├──────────── C-term
                └─ 72kD ─┘

| | Binding molecules | |
|---|---|---|
| Fragments | 29 kD | Actin, Heparin, Fibrin, etc. |
| | 43 kD | Collagen (Gelatin) |

| | 29 kD | 43 kD | 72 kD |
|---|---|---|---|
| TF efficiency | ◎ | ○ | ◎ |
| Cross-contamination | none | some | some |

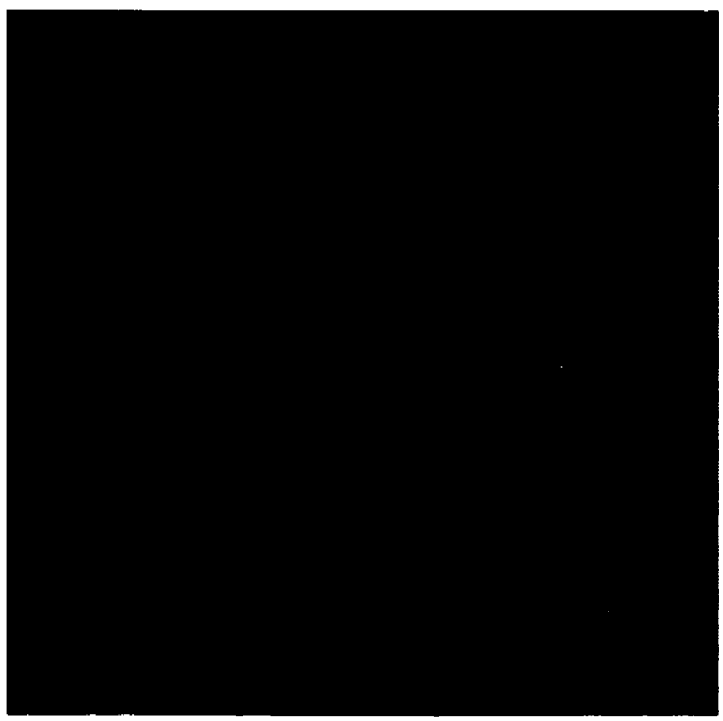
FIG.8
Fibronectin(−)
Fibronectin(+)

FIG. 13A Expression vectors

Inkjet printing

Pour cell suspension into dish

Cultivation in dish

Cultivation

Transfected cell clusters can be detected only in spotting area

FIG. 14D

For HEK293

| | | |
|---|---|---|
| DMEM (serum free) | 9.5 | uL |
| Plasmid DNA (1mg/mL) | 1.5 | uL |
| TransFast (1mg/mL) | 9.0 | uL |
| DMEM (serum free) | 5.0 | uL |
| Fibronectin (4mg/mL) | 5.0 | uL |
| Final volume | 30.0 | uL |

Scheme for HEK293

1.5mL micro-tube

↓ ←DMEM

↓ ←Plasmid DNA mix        Incubate for 2-3 days

↓ ←TransFast  at 37°C in 5% $CO_2$ mix completely and incubate for 15 min at RT

↓ ←DMEM

↓ ←Fibronectin mix completely

↓ ready to print

For HeLa, NIH3T3-3, HepG2

| | | |
|---|---|---|
| DMEM (serum free) | 14.5 | uL |
| Plasmid DNA (1mg/mL) | 1.5 | uL |
| Lipofectamine2000 | 4.5 | uL |
| DMEM (serum free) | 5.0 | uL |
| Fibronectin (4mg/mL) | 5.0 | uL |
| Final volume | 30.0 | uL |

Scheme for HeLa, NIH3T3-3, and HepG2

1.5mL micro-tube

↓ ←DMEM

↓ ←Plasmid DNA mix

↓ ←Lipofectamine2000 mix completely and incubate for 15 min at RT

↓ ←DMEM

↓ ←Fibronectin mix completely

↓ ready to print

For hMSCs

| | N/P=5 | N/P=10 | N/P=20 | |
|---|---|---|---|---|
| DMEM (serum free) | 12.75 | 12.0 | 10.5 | uL |
| Plasmid DNA (1mg/mL) | 1.5 | 1.5 | 1.5 | uL |
| JetPEI (x4) conc. | 0.75 | 1.5 | 3.0 | uL |
| Fibronectin (4mg/mL) | 5.0 | 5.0 | 5.0 | uL |
| Final volume | 20.0 | 20.0 | 20.0 | uL |

Scheme for hMSCs 1.5mL micro-tube

↓ ←DMEM

↓ ←Plasmid DNA mix

↓ ←jetPEI mix completely and incubate for 15 min at RT

↓ ←Fibronectin mix completely

↓ ready to print

FIG.16C

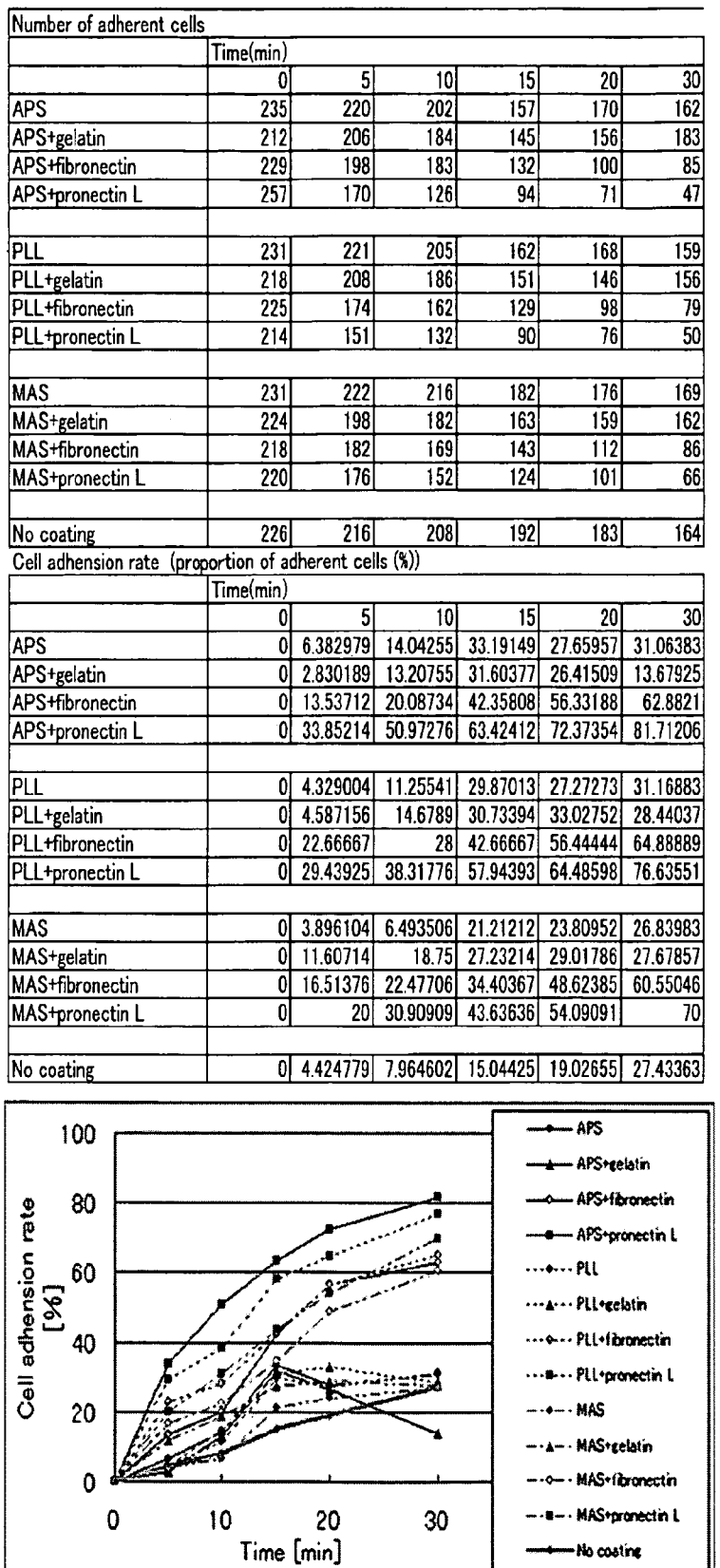

| Number of adherent cells | | | | | | |
|---|---|---|---|---|---|---|
| | Time(min) | | | | | |
| | 0 | 5 | 10 | 15 | 20 | 30 |
| APS | 235 | 220 | 202 | 157 | 170 | 162 |
| APS+gelatin | 212 | 206 | 184 | 145 | 156 | 183 |
| APS+fibronectin | 229 | 198 | 183 | 132 | 100 | 85 |
| APS+pronectin L | 257 | 170 | 126 | 94 | 71 | 47 |
| | | | | | | |
| PLL | 231 | 221 | 205 | 162 | 168 | 159 |
| PLL+gelatin | 218 | 208 | 186 | 151 | 146 | 156 |
| PLL+fibronectin | 225 | 174 | 162 | 129 | 98 | 79 |
| PLL+pronectin L | 214 | 151 | 132 | 90 | 76 | 50 |
| | | | | | | |
| MAS | 231 | 222 | 216 | 182 | 176 | 169 |
| MAS+gelatin | 224 | 198 | 182 | 163 | 159 | 162 |
| MAS+fibronectin | 218 | 182 | 169 | 143 | 112 | 86 |
| MAS+pronectin L | 220 | 176 | 152 | 124 | 101 | 66 |
| | | | | | | |
| No coating | 226 | 216 | 208 | 192 | 183 | 164 |

| Cell adhesion rate (proportion of adherent cells (%)) | | | | | | |
|---|---|---|---|---|---|---|
| | Time(min) | | | | | |
| | 0 | 5 | 10 | 15 | 20 | 30 |
| APS | 0 | 6.382979 | 14.04255 | 33.19149 | 27.65957 | 31.06383 |
| APS+gelatin | 0 | 2.830189 | 13.20755 | 31.60377 | 26.41509 | 13.67925 |
| APS+fibronectin | 0 | 13.53712 | 20.08734 | 42.35808 | 56.33188 | 62.8821 |
| APS+pronectin L | 0 | 33.85214 | 50.97276 | 63.42412 | 72.37354 | 81.71206 |
| | | | | | | |
| PLL | 0 | 4.329004 | 11.25541 | 29.87013 | 27.27273 | 31.16883 |
| PLL+gelatin | 0 | 4.587156 | 14.6789 | 30.73394 | 33.02752 | 28.44037 |
| PLL+fibronectin | 0 | 22.66667 | 28 | 42.66667 | 56.44444 | 64.88889 |
| PLL+pronectin L | 0 | 29.43925 | 38.31776 | 57.94393 | 64.48598 | 76.63551 |
| | | | | | | |
| MAS | 0 | 3.896104 | 6.493506 | 21.21212 | 23.80952 | 26.83983 |
| MAS+gelatin | 0 | 11.60714 | 18.75 | 27.23214 | 29.01786 | 27.67857 |
| MAS+fibronectin | 0 | 16.51376 | 22.47706 | 34.40367 | 48.62385 | 60.55046 |
| MAS+pronectin L | 0 | 20 | 30.90909 | 43.63636 | 54.09091 | 70 |
| | | | | | | |
| No coating | 0 | 4.424779 | 7.964602 | 15.04425 | 19.02655 | 27.43363 |

FIG.18A
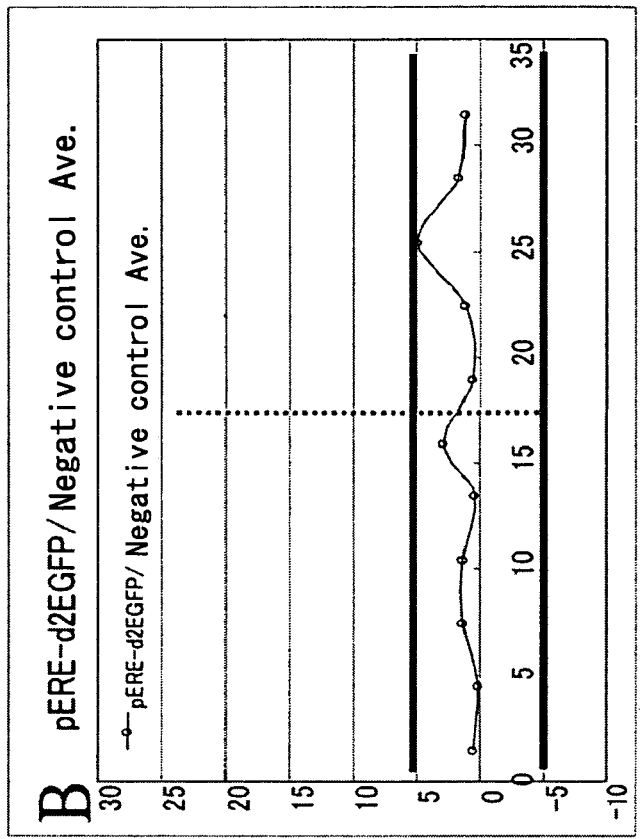
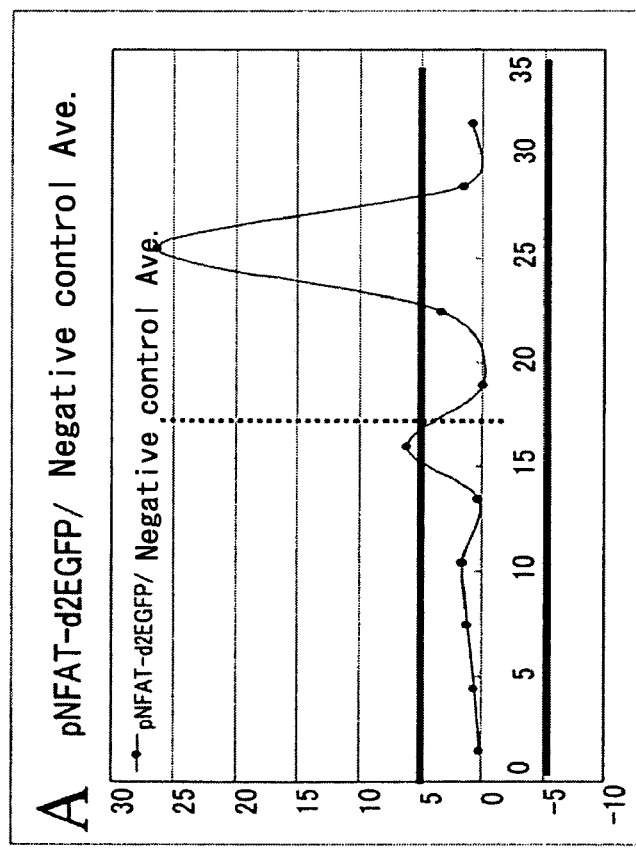

| No induction of differentiation | 0-31.5 | 0-17.5 | 17.5-31.5 |
|---|---|---|---|
| Extraction number=1 | 5.882353 | 5.882353 | 0 |
| Extraction number=2 | 0 | 0 | 0 |
| Extraction number=3 | 0 | 0 | 0 |
| Extraction number=5 | 0 | 0 | 0 |
| Extraction number=8 | 0 | 0 | 0 |
| Extraction number=16 | 0 | 0 | 0 |
| Extraction number=17 | 0 | 0 | 0 |

FIG.24 Construction of transcription factor reporter

| Vector | Pathway | Transcription factor | Cis-acting enhancer element |
|---|---|---|---|
| pNFkB-d2FGFP | IKK/NFkB | NFkB | kB |
| pAP1-d2FGFP | SAPK/JNK | c-Jun, c-Fos | AP1 |
| pSRF-d2FGFP | MAPK/JNK, MAPK/FRK | Flk-1,STAT, TCF,SRF | SRF |
| pGRF-d2FGFP | Glicocorticoide (HXP90 mediation) | GR | GRF |
| pCRF-d2FGFP | PKA/CRFB,JNK/p38 PKA | ATF2/CRFB | CRF |
| pMpc-TA-d2FGFP, pMYC-d2FGFP | Cell cycle | c-myc | F-box |
| pHSF-d2FGFP | HSF | HSF | HSF |
| pNFAT-d2FGFP | NFAT/Calcineurin/PKC | NFAT | NFAT |
| pAP1(PMA)-TA-d2FGFP | PKC | | AP1(PMA) |
| pRb-TA-d2FGFP | Cell cycle | | Rb |
| pF2F-TA-d2FGFP | Cell cycle | | F2F |
| pp53-TA-d2FGFP | Cell cycle apoptosis | | P53 |
| pGAN-TA-d2FGFP | JAK/STAT | STAT1/STAT1 | GAS |
| pISRF-TA-d2FGFP | JAK/STAT | STAT2/STAT1 | ISRF |
| pSTAT3-TA-d2FGFP | JAK/STAT | STAT3/STAT3 | STAT3 |
| pFRF-TA-d2FGFP | Estrogen receptor | | FRF |
| pRARF-TA-d2FGFP | Retinoic acid | | RARF |
| pTRF-TA-d2FGFP | Thyroid receptor | | TRF |

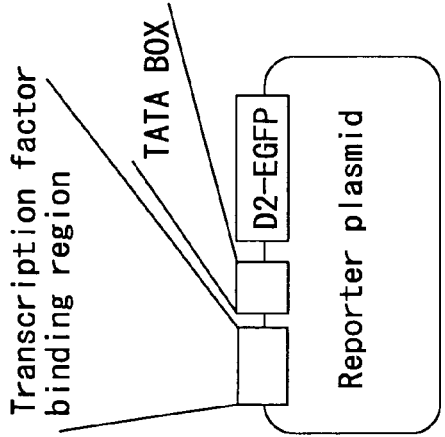

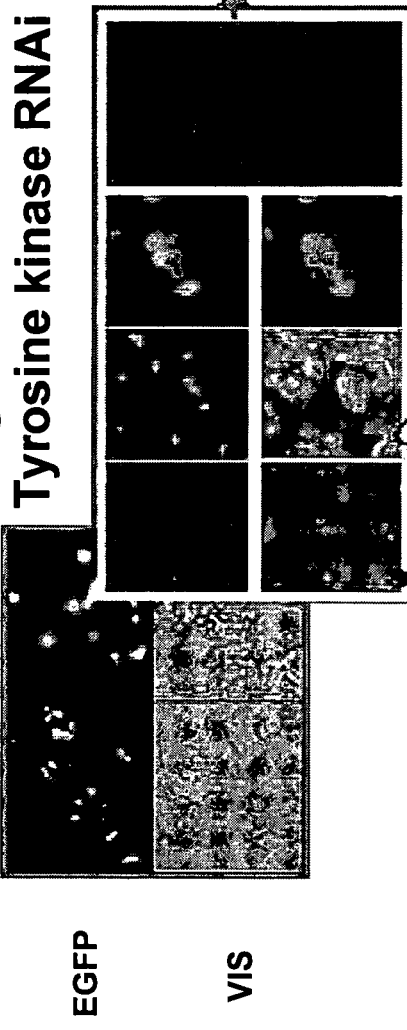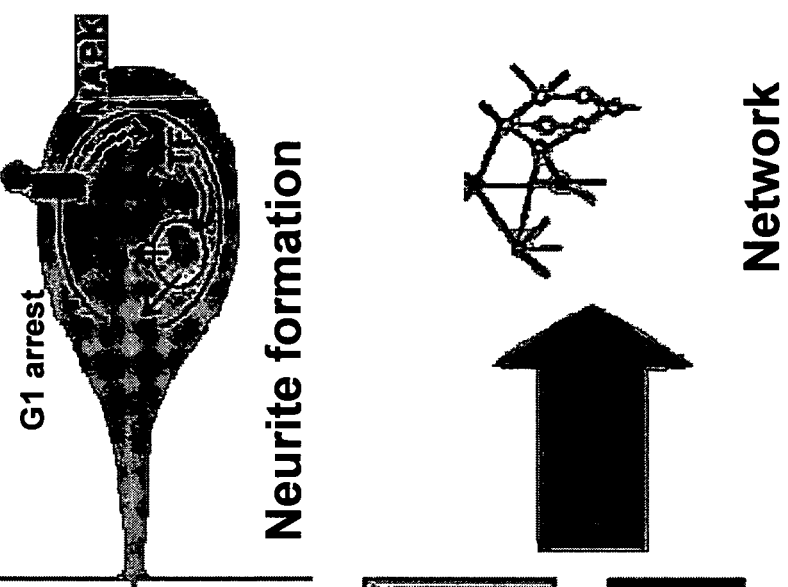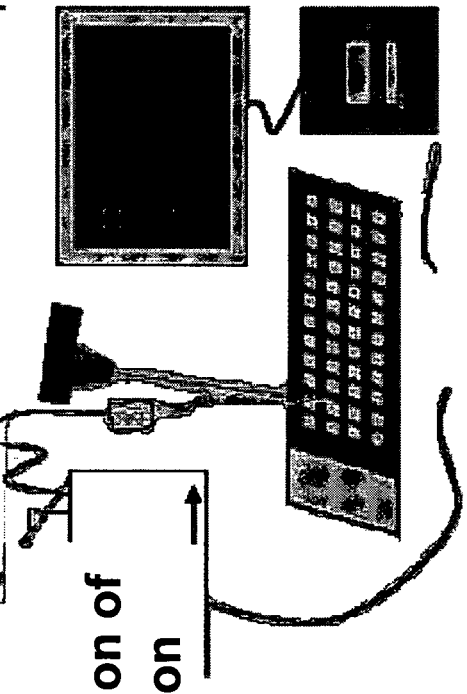
Fig. 31B (*B-bridge siRNAs against Tyrosine kinases)

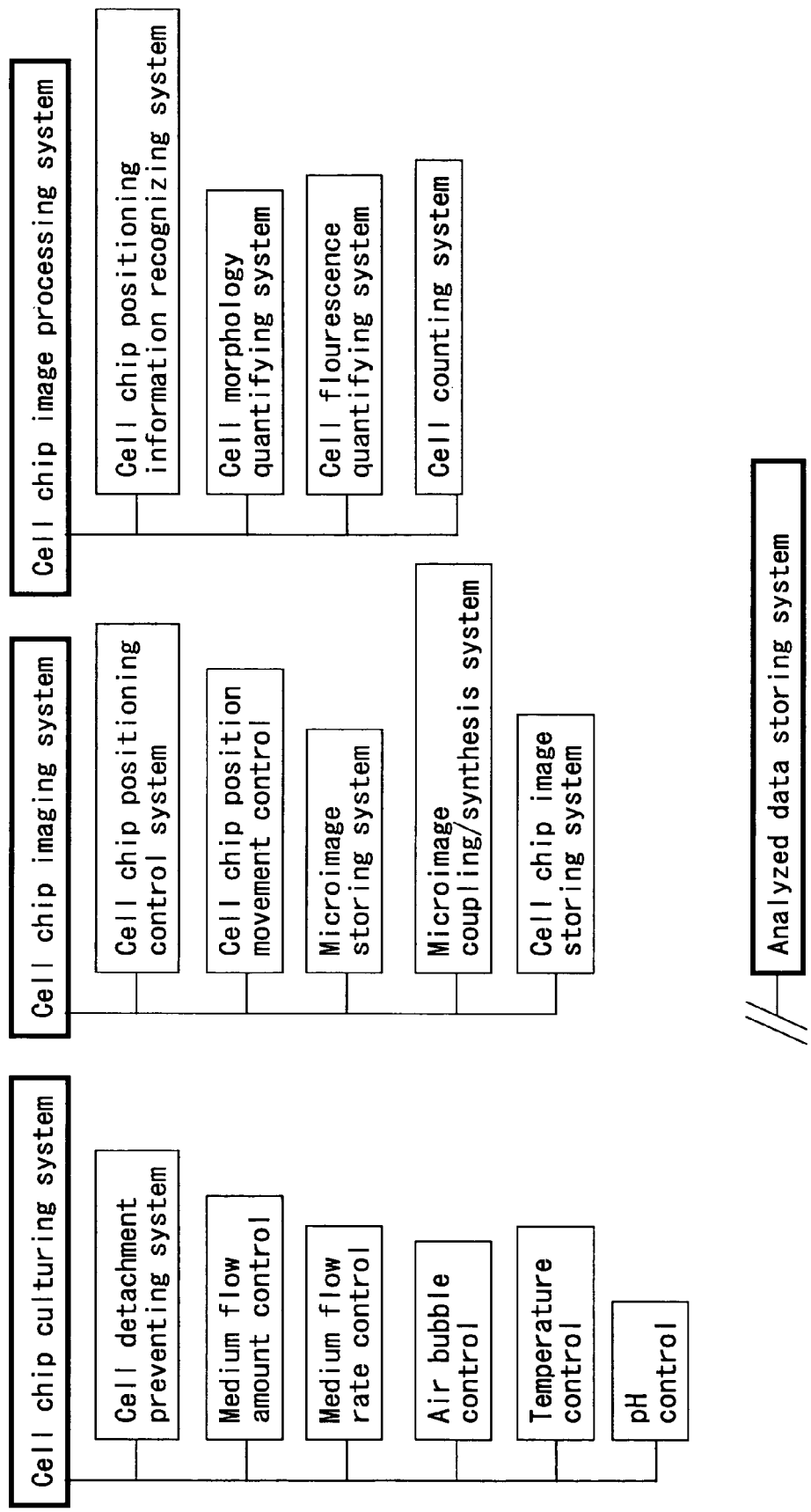
Fig. 32  System configuration for producing data of cell profile data

SEQUENCE LISTING

```
<160> NUMBER OF SEQ ID NOS: 50

<210> SEQ ID NO 1
<211> LENGTH: 1929
<212> TYPE: DNA
<213> ORGANISM: Homo sapiens
<220> FEATURE:
<221> NAME/KEY: CDS
<222> LOCATION: (1)..(1929)
<223> OTHER INFORMATION: fibronectin 1
```

<400> SEQUENCE: 1

| | | | | | | | | | | | | | | | | |
|---|---|---|---|---|---|---|---|---|---|---|---|---|---|---|---|---|
| atg | ctt | agg | ggt | ccg | ggg | ccc | ggg | ctg | ctg | ctg | ctg | gcc | gtc | cag | tgc | 48 |
| Met | Leu | Arg | Gly | Pro | Gly | Pro | Gly | Leu | Leu | Leu | Leu | Ala | Val | Gln | Cys | |
| 1 | | | | 5 | | | | | 10 | | | | | 15 | | |

| ctg | ggg | aca | gcg | gtg | ccc | tcc | acg | gga | gcc | tcg | aag | agc | aag | agg | cag | 96 |
|---|---|---|---|---|---|---|---|---|---|---|---|---|---|---|---|---|
| Leu | Gly | Thr | Ala | Val | Pro | Ser | Thr | Gly | Ala | Ser | Lys | Ser | Lys | Arg | Gln | |
| | | | 20 | | | | | 25 | | | | | 30 | | | |

| gct | cag | caa | atg | gtt | cag | ccc | cag | tcc | ccg | gtg | gct | gtc | agt | caa | agc | 144 |
|---|---|---|---|---|---|---|---|---|---|---|---|---|---|---|---|---|
| Ala | Gln | Gln | Met | Val | Gln | Pro | Gln | Ser | Pro | Val | Ala | Val | Ser | Gln | Ser | |
| | | 35 | | | | | 40 | | | | | 45 | | | | |

| aag | ccc | ggt | tgt | tat | gac | aat | gga | aaa | cac | tat | cag | ata | aat | caa | cag | 192 |
|---|---|---|---|---|---|---|---|---|---|---|---|---|---|---|---|---|
| Lys | Pro | Gly | Cys | Tyr | Asp | Asn | Gly | Lys | His | Tyr | Gln | Ile | Asn | Gln | Gln | |
| 50 | | | | | 55 | | | | | 60 | | | | | | |

| tgg | gag | cgg | acc | tac | cta | ggc | aat | gcg | ttg | gtt | tgt | act | tgt | tat | gga | 240 |
|---|---|---|---|---|---|---|---|---|---|---|---|---|---|---|---|---|
| Trp | Glu | Arg | Thr | Tyr | Leu | Gly | Asn | Ala | Leu | Val | Cys | Thr | Cys | Tyr | Gly | |
| 65 | | | | 70 | | | | | 75 | | | | | 80 | | |

| gga | agc | cga | ggt | ttt | aac | tgc | gag | agt | aaa | cct | gaa | gct | gaa | gag | act | 288 |
|---|---|---|---|---|---|---|---|---|---|---|---|---|---|---|---|---|
| Gly | Ser | Arg | Gly | Phe | Asn | Cys | Glu | Ser | Lys | Pro | Glu | Ala | Glu | Glu | Thr | |
| | | | | 85 | | | | | 90 | | | | | 95 | | |

| tgc | ttt | gac | aag | tac | act | ggg | aac | act | tac | cga | gtg | ggt | gac | act | tat | 336 |
|---|---|---|---|---|---|---|---|---|---|---|---|---|---|---|---|---|
| Cys | Phe | Asp | Lys | Tyr | Thr | Gly | Asn | Thr | Tyr | Arg | Val | Gly | Asp | Thr | Tyr | |
| | | | 100 | | | | | 105 | | | | | 110 | | | |

| gag | cgt | cct | aaa | gac | tcc | atg | atc | tgg | gac | tgt | acc | tgc | atc | ggg | gct | 384 |
|---|---|---|---|---|---|---|---|---|---|---|---|---|---|---|---|---|
| Glu | Arg | Pro | Lys | Asp | Ser | Met | Ile | Trp | Asp | Cys | Thr | Cys | Ile | Gly | Ala | |
| | | 115 | | | | | 120 | | | | | 125 | | | | |

| ggg | cga | ggg | aga | ata | agc | tgt | acc | atc | gca | aac | cgc | tgc | cat | gaa | ggg | 432 |
|---|---|---|---|---|---|---|---|---|---|---|---|---|---|---|---|---|
| Gly | Arg | Gly | Arg | Ile | Ser | Cys | Thr | Ile | Ala | Asn | Arg | Cys | His | Glu | Gly | |
| | 130 | | | | | 135 | | | | | 140 | | | | | |

| ggt | cag | tcc | tac | aag | att | ggt | gac | acc | tgg | agg | aga | cca | cat | gag | act | 480 |
|---|---|---|---|---|---|---|---|---|---|---|---|---|---|---|---|---|
| Gly | Gln | Ser | Tyr | Lys | Ile | Gly | Asp | Thr | Trp | Arg | Arg | Pro | His | Glu | Thr | |
| 145 | | | | | 150 | | | | | 155 | | | | | 160 | |

| ggt | ggt | tac | atg | tta | gag | tgt | gtg | tgt | ctt | ggt | aat | gga | aaa | gga | gaa | 528 |
|---|---|---|---|---|---|---|---|---|---|---|---|---|---|---|---|---|
| Gly | Gly | Tyr | Met | Leu | Glu | Cys | Val | Cys | Leu | Gly | Asn | Gly | Lys | Gly | Glu | |
| | | | | 165 | | | | | 170 | | | | | 175 | | |

| tgg | acc | tgc | aag | ccc | ata | gct | gag | aag | tgt | ttt | gat | cat | gct | gct | ggg | 576 |
|---|---|---|---|---|---|---|---|---|---|---|---|---|---|---|---|---|
| Trp | Thr | Cys | Lys | Pro | Ile | Ala | Glu | Lys | Cys | Phe | Asp | His | Ala | Ala | Gly | |
| | | | 180 | | | | | 185 | | | | | 190 | | | |

| act | tcc | tat | gtg | gtc | gga | gaa | acg | tgg | gag | aag | ccc | tac | caa | ggc | tgg | 624 |
|---|---|---|---|---|---|---|---|---|---|---|---|---|---|---|---|---|
| Thr | Ser | Tyr | Val | Val | Gly | Glu | Thr | Trp | Glu | Lys | Pro | Tyr | Gln | Gly | Trp | |
| | | 195 | | | | | 200 | | | | | 205 | | | | |

| atg | atg | gta | gat | tgt | act | tgc | ctg | gga | gaa | ggc | agc | gga | cgc | atc | act | 672 |
|---|---|---|---|---|---|---|---|---|---|---|---|---|---|---|---|---|
| Met | Met | Val | Asp | Cys | Thr | Cys | Leu | Gly | Glu | Gly | Ser | Gly | Arg | Ile | Thr | |
| | 210 | | | | | 215 | | | | | 220 | | | | | |

| tgc | act | tct | aga | aat | aga | tgc | aac | gat | cag | gac | aca | agg | aca | tcc | tat | 720 |
|---|---|---|---|---|---|---|---|---|---|---|---|---|---|---|---|---|
| Cys | Thr | Ser | Arg | Asn | Arg | Cys | Asn | Asp | Gln | Asp | Thr | Arg | Thr | Ser | Tyr | |
| 225 | | | | | 230 | | | | | 235 | | | | | 240 | |

| aga | att | gga | gac | acc | tgg | agc | aag | aag | gat | aat | cga | gga | aac | ctg | ctc | 768 |
|---|---|---|---|---|---|---|---|---|---|---|---|---|---|---|---|---|
| Arg | Ile | Gly | Asp | Thr | Trp | Ser | Lys | Lys | Asp | Asn | Arg | Gly | Asn | Leu | Leu | |
| | | | | 245 | | | | | 250 | | | | | 255 | | |

| cag | tgc | atc | tgc | aca | ggc | aac | ggc | cga | gga | gag | tgg | aag | tgt | gag | agg | 816 |
|---|---|---|---|---|---|---|---|---|---|---|---|---|---|---|---|---|
| Gln | Cys | Ile | Cys | Thr | Gly | Asn | Gly | Arg | Gly | Glu | Trp | Lys | Cys | Glu | Arg | |
| | | | 260 | | | | | 265 | | | | | 270 | | | |

| cac | acc | tct | gtg | cag | acc | aca | tcg | agc | gga | tct | ggc | ccc | ttc | acc | gat | 864 |
|---|---|---|---|---|---|---|---|---|---|---|---|---|---|---|---|---|
| His | Thr | Ser | Val | Gln | Thr | Thr | Ser | Ser | Gly | Ser | Gly | Pro | Phe | Thr | Asp | |
| | | 275 | | | | | 280 | | | | | 285 | | | | |

| gtt | cgt | gca | gct | gtt | tac | caa | ccg | cag | cct | cac | ccc | cag | cct | cct | ccc | 912 |
|---|---|---|---|---|---|---|---|---|---|---|---|---|---|---|---|---|
| Val | Arg | Ala | Ala | Val | Tyr | Gln | Pro | Gln | Pro | His | Pro | Gln | Pro | Pro | Pro | |
| | 290 | | | | | 295 | | | | | 300 | | | | | |

```
tat ggc cac tgt gtc aca gac agt ggt gtg gtc tac tct gtg ggg atg        960
Tyr Gly His Cys Val Thr Asp Ser Gly Val Val Tyr Ser Val Gly Met
305                 310                 315                 320 cag tgg ctg aag aca caa gga aat aag caa atg ctt tgc acg tgc ctg       1008
Gln Trp Leu Lys Thr Gln Gly Asn Lys Gln Met Leu Cys Thr Cys Leu
                325                 330                 335 ggc aac gga gtc agc tgc caa gag aca gct gta acc cag act tac ggt       1056
Gly Asn Gly Val Ser Cys Gln Glu Thr Ala Val Thr Gln Thr Tyr Gly
340                 345                 350 ggc aac tca aat gga gag cca tgt gtc tta cca ttc acc tac aat ggc       1104
Gly Asn Ser Asn Gly Glu Pro Cys Val Leu Pro Phe Thr Tyr Asn Gly
    355                 360                 365 agg acg gac agc aca act tcg aat tat gag cag gac cag aaa tac tct       1152
Arg Thr Asp Ser Thr Thr Ser Asn Tyr Glu Gln Asp Gln Lys Tyr Ser
370                 375                 380 ttc tgc aca gac cac act gtt ttg gtt cag act cga gga gga aat tcc       1200
Phe Cys Thr Asp His Thr Val Leu Val Gln Thr Arg Gly Gly Asn Ser
385                 390                 395                 400 aat ggt gcc ttg tgc cac ttc ccc ttc cta tac aac aac cac aat tac       1248
Asn Gly Ala Leu Cys His Phe Pro Phe Leu Tyr Asn Asn His Asn Tyr
                405                 410                 415 act gat tgc act tct gag ggc aga aga gac aac atg aag tgg tgt ggg       1296
Thr Asp Cys Thr Ser Glu Gly Arg Arg Asp Asn Met Lys Trp Cys Gly
            420                 425                 430 acc aca cag aac tat gat gcc gac cag aag ttt ggg ttc tgc ccc atg       1344
Thr Thr Gln Asn Tyr Asp Ala Asp Gln Lys Phe Gly Phe Cys Pro Met
        435                 440                 445 gct gcc cac gag gaa atc tgc aca acc aat gaa ggg gtc atg tac cgc       1392
Ala Ala His Glu Glu Ile Cys Thr Thr Asn Glu Gly Val Met Tyr Arg
450                 455                 460 att gga gat cag tgg gat aag cag cat gac atg ggt cac atg atg agg       1440
Ile Gly Asp Gln Trp Asp Lys Gln His Asp Met Gly His Met Met Arg
465                 470                 475                 480 tgc acg tgt gtt ggg aat ggt cgt ggg gaa tgg aca tgc att gcc tac       1488
Cys Thr Cys Val Gly Asn Gly Arg Gly Glu Trp Thr Cys Ile Ala Tyr
                485                 490                 495 tcg cag ctt cga gat cag tgc att gtt gat gac atc act tac aat gtg       1536
Ser Gln Leu Arg Asp Gln Cys Ile Val Asp Asp Ile Thr Tyr Asn Val
            500                 505                 510 aac gac aca ttc cac aag cgt cat gaa gag ggg cac atg ctg aac tgt       1584
Asn Asp Thr Phe His Lys Arg His Glu Glu Gly His Met Leu Asn Cys
        515                 520                 525 aca tgc ttc ggt cag ggt cgg ggc agg tgg aag tgt gat ccc gtc gac       1632
Thr Cys Phe Gly Gln Gly Arg Gly Arg Trp Lys Cys Asp Pro Val Asp
530                 535                 540 caa tgc cag gat tca gag act ggg acg ttt tat caa att gga gat tca       1680
Gln Cys Gln Asp Ser Glu Thr Gly Thr Phe Tyr Gln Ile Gly Asp Ser
545                 550                 555                 560 tgg gag aag tat gtg cat ggt gtc aga tac cag tgc tac tgc tat ggc       1728
Trp Glu Lys Tyr Val His Gly Val Arg Tyr Gln Cys Tyr Cys Tyr Gly
                565                 570                 575 cgt ggc att ggg gag tgg cat tgc caa cct tta cag acc tat cca agc       1776
Arg Gly Ile Gly Glu Trp His Cys Gln Pro Leu Gln Thr Tyr Pro Ser
            580                 585                 590 tca agt ggt cct gtc gaa gta ttt atc act gag act ccg agt cag ccc       1824
Ser Ser Gly Pro Val Glu Val Phe Ile Thr Glu Thr Pro Ser Gln Pro
        595                 600                 605 aac tcc cac ccc atc cag tgg aat gca cca cag cca tct cac att tcc       1872
Asn Ser His Pro Ile Gln Trp Asn Ala Pro Gln Pro Ser His Ile Ser
610                 615                 620
```

```
aag tac att ctc agg tgg aga cct gtg agt atc cca ccc aga aac ctt    1920
Lys Tyr Ile Leu Arg Trp Arg Pro Val Ser Ile Pro Pro Arg Asn Leu
625                 630                 635                 640 gga tac tga                                                         1929
Gly Tyr <210> SEQ ID NO 2
<211> LENGTH: 642
<212> TYPE: PRT
<213> ORGANISM: Homo sapiens

<400> SEQUENCE: 2

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335
```

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
            355                 360                 365

Arg Thr Asp Ser Thr Thr Ser Asn Tyr Glu Gln Asp Gln Lys Tyr Ser
    370                 375                 380

Phe Cys Thr Asp His Thr Val Leu Val Gln Thr Arg Gly Gly Asn Ser
385                 390                 395                 400

Asn Gly Ala Leu Cys His Phe Pro Phe Leu Tyr Asn Asn His Asn Tyr
                405                 410                 415

Thr Asp Cys Thr Ser Glu Gly Arg Arg Asp Asn Met Lys Trp Cys Gly
            420                 425                 430

Thr Thr Gln Asn Tyr Asp Ala Asp Gln Lys Phe Gly Phe Cys Pro Met
            435                 440                 445

Ala Ala His Glu Glu Ile Cys Thr Thr Asn Glu Gly Val Met Tyr Arg
450                 455                 460

Ile Gly Asp Gln Trp Asp Lys Gln His Asp Met Gly His Met Met Arg
465                 470                 475                 480

Cys Thr Cys Val Gly Asn Gly Arg Gly Glu Trp Thr Cys Ile Ala Tyr
                485                 490                 495

Ser Gln Leu Arg Asp Gln Cys Ile Val Asp Asp Ile Thr Tyr Asn Val
            500                 505                 510

Asn Asp Thr Phe His Lys Arg His Glu Glu Gly His Met Leu Asn Cys
            515                 520                 525

Thr Cys Phe Gly Gln Gly Arg Gly Arg Trp Lys Cys Asp Pro Val Asp
    530                 535                 540

Gln Cys Gln Asp Ser Glu Thr Gly Thr Phe Tyr Gln Ile Gly Asp Ser
545                 550                 555                 560

Trp Glu Lys Tyr Val His Gly Val Arg Tyr Gln Cys Tyr Cys Tyr Gly
                565                 570                 575

Arg Gly Ile Gly Glu Trp His Cys Gln Pro Leu Gln Thr Tyr Pro Ser
            580                 585                 590

Ser Ser Gly Pro Val Glu Val Phe Ile Thr Glu Thr Pro Ser Gln Pro
            595                 600                 605

Asn Ser His Pro Ile Gln Trp Asn Ala Pro Gln Pro Ser His Ile Ser
    610                 615                 620

Lys Tyr Ile Leu Arg Trp Arg Pro Val Ser Ile Pro Pro Arg Asn Leu
625                 630                 635                 640

Gly Tyr

<210> SEQ ID NO 3
<211> LENGTH: 1437
<212> TYPE: DNA
<213> ORGANISM: Mus musculus
<220> FEATURE:
<221> NAME/KEY: CDS
<222> LOCATION: (1)..(1437)
<223> OTHER INFORMATION: vitronectin

<400> SEQUENCE: 3

```
atg gca ccc ctg agg ccc ttt ttc ata cta gcc ctg gtg gca tgg gtt      48
Met Ala Pro Leu Arg Pro Phe Phe Ile Leu Ala Leu Val Ala Trp Val
1               5                   10                  15 tct ctg gct gac caa gag tca tgc aag ggc cgc tgc act cag ggt ttc      96
Ser Leu Ala Asp Gln Glu Ser Cys Lys Gly Arg Cys Thr Gln Gly Phe
                20                  25                  30
```

| | |
|---|---|
| atg gcc agc aag aag tgt cag tgt gac gag ctt tgc act tac tat cag<br>Met Ala Ser Lys Lys Cys Gln Cys Asp Glu Leu Cys Thr Tyr Tyr Gln<br>35　　　　　　　　40　　　　　　　　45 | 144 |
| agc tgc tgt gcc gac tac atg gag cag tgc aag ccc caa gta acg cgg<br>Ser Cys Cys Ala Asp Tyr Met Glu Gln Cys Lys Pro Gln Val Thr Arg<br>　50　　　　　　　　55　　　　　　　　60 | 192 |
| ggg gac gtg ttc act atg cca gag gat gat tat tgg agc tat gac tac<br>Gly Asp Val Phe Thr Met Pro Glu Asp Asp Tyr Trp Ser Tyr Asp Tyr<br>65　　　　　　　　70　　　　　　　　75　　　　　　　　80 | 240 |
| gtg gag gag ccc aag aac aat acc aac acc ggt gtg caa ccc gag aac<br>Val Glu Glu Pro Lys Asn Asn Thr Asn Thr Gly Val Gln Pro Glu Asn<br>　　　　　　　85　　　　　　　　90　　　　　　　　95 | 288 |
| acc tct cca ccc ggt gac cta aat cct cgg acg gac ggc act cta aag<br>Thr Ser Pro Pro Gly Asp Leu Asn Pro Arg Thr Asp Gly Thr Leu Lys<br>　　　　100　　　　　　　　105　　　　　　　　110 | 336 |
| ccg aca gcc ttc cta gat cct gag gaa cag cca agc acc cca gcg cct<br>Pro Thr Ala Phe Leu Asp Pro Glu Glu Gln Pro Ser Thr Pro Ala Pro<br>　　　115　　　　　　　　120　　　　　　　　125 | 384 |
| aaa gtg gag caa cag gag gag atc cta agg ccc gac act act gat caa<br>Lys Val Glu Gln Gln Glu Glu Ile Leu Arg Pro Asp Thr Thr Asp Gln<br>130　　　　　　　　135　　　　　　　　140 | 432 |
| ggg acc cct gag ttt cca gag gaa gaa ctg tgc agt gga aag ccc ttt<br>Gly Thr Pro Glu Phe Pro Glu Glu Glu Leu Cys Ser Gly Lys Pro Phe<br>145　　　　　　　　150　　　　　　　　155　　　　　　　　160 | 480 |
| gac gcc ttc acg gat ctc aag aat ggg tcc ctc ttt gcc ttc cga ggg<br>Asp Ala Phe Thr Asp Leu Lys Asn Gly Ser Leu Phe Ala Phe Arg Gly<br>　　　　　　　165　　　　　　　　170　　　　　　　　175 | 528 |
| cag tac cgc tgt gag cta gat gag acg gca gtg agg cct ggg tac ccc<br>Gln Tyr Arg Cys Glu Leu Asp Glu Thr Ala Val Arg Pro Gly Tyr Pro<br>　　　　180　　　　　　　　185　　　　　　　　190 | 576 |
| aaa ctt atc caa gat gtc tgg ggc att gag ggc ccc atc gat gct gcc<br>Lys Leu Ile Gln Asp Val Trp Gly Ile Glu Gly Pro Ile Asp Ala Ala<br>　　　195　　　　　　　　200　　　　　　　　205 | 624 |
| ttc act cgc atc aac tgt cag ggg aag acc tac ttg ttc aag ggt agt<br>Phe Thr Arg Ile Asn Cys Gln Gly Lys Thr Tyr Leu Phe Lys Gly Ser<br>210　　　　　　　　215　　　　　　　　220 | 672 |
| cag tac tgg cgc ttt gag gat ggg gtc ctg gac cct ggt tat ccc cga<br>Gln Tyr Trp Arg Phe Glu Asp Gly Val Leu Asp Pro Gly Tyr Pro Arg<br>225　　　　　　　　230　　　　　　　　235　　　　　　　　240 | 720 |
| aac atc tcc gaa ggc ttc agt ggc ata cca gac aat gtt gat gca gcg<br>Asn Ile Ser Glu Gly Phe Ser Gly Ile Pro Asp Asn Val Asp Ala Ala<br>　　　　　　　245　　　　　　　　250　　　　　　　　255 | 768 |
| ttc gcc ctt cct gcc cac cgt tac agt ggc cgg gaa agg gtc tac ttc<br>Phe Ala Leu Pro Ala His Arg Tyr Ser Gly Arg Glu Arg Val Tyr Phe<br>　　　　260　　　　　　　　265　　　　　　　　270 | 816 |
| ttc aag ggg aag cag tac tgg gag cac gaa ttt cag cag caa ccc agc<br>Phe Lys Gly Lys Gln Tyr Trp Glu His Glu Phe Gln Gln Gln Pro Ser<br>　　　275　　　　　　　　280　　　　　　　　285 | 864 |
| cag gag gag tgc gaa ggc agc tct ctg tca gcc gtg ttt gag cac ttt<br>Gln Glu Glu Cys Glu Gly Ser Ser Leu Ser Ala Val Phe Glu His Phe<br>290　　　　　　　　295　　　　　　　　300 | 912 |
| gcc ttg ctt cag cgg gac agc tgg gag aac att ttc gaa ctc ctc ttc<br>Ala Leu Leu Gln Arg Asp Ser Trp Glu Asn Ile Phe Glu Leu Leu Phe<br>305　　　　　　　　310　　　　　　　　315　　　　　　　　320 | 960 |
| tgg ggc aga tcc tct gat gga gcc aga gaa ccc caa ttc atc agc cgg<br>Trp Gly Arg Ser Ser Asp Gly Ala Arg Glu Pro Gln Phe Ile Ser Arg<br>　　　　　　　325　　　　　　　　330　　　　　　　　335 | 1008 |
| aac tgg cat ggt gtg cca ggg aaa gtg gac gct gct atg gcc ggc cgc<br>Asn Trp His Gly Val Pro Gly Lys Val Asp Ala Ala Met Ala Gly Arg<br>　　　　340　　　　　　　　345　　　　　　　　350 | 1056 |

| | | | | | | | | | | | | | | | | |
|---|---|---|---|---|---|---|---|---|---|---|---|---|---|---|---|---|
| atc | tac | gtc | act | ggc | tcc | tta | tcc | cac | tct | gcc | caa | gcc | aaa | aaa | cag | 1104 |
| Ile | Tyr | Val | Thr | Gly | Ser | Leu | Ser | His | Ser | Ala | Gln | Ala | Lys | Lys | Gln | |
| | | | 355 | | | | | 360 | | | | | 365 | | | |
| ccg | tct | aag | cgt | aga | agc | cga | aag | cgc | tat | cgt | tca | cgc | cga | ggg | cgt | 1152 |
| Pro | Ser | Lys | Arg | Arg | Ser | Arg | Lys | Arg | Tyr | Arg | Ser | Arg | Arg | Gly | Arg | |
| | 370 | | | | | 375 | | | | | 380 | | | | | |
| ggc | cac | aga | cgc | agc | cag | agc | tcg | aac | tcc | cgt | cgt | tca | tca | cgt | tca | 1200 |
| Gly | His | Arg | Arg | Ser | Gln | Ser | Ser | Asn | Ser | Arg | Arg | Ser | Ser | Arg | Ser | |
| 385 | | | | | 390 | | | | | 395 | | | | | 400 | |
| atc | tgg | ttc | tct | ttg | ttc | tcc | agc | gag | gag | agt | ggg | cta | gga | acc | tac | 1248 |
| Ile | Trp | Phe | Ser | Leu | Phe | Ser | Ser | Glu | Glu | Ser | Gly | Leu | Gly | Thr | Tyr | |
| | | | | 405 | | | | | 410 | | | | | 415 | | |
| aac | aac | tat | gat | tat | gat | atg | gac | tgg | ctt | gta | cct | gcc | acc | tgc | gag | 1296 |
| Asn | Asn | Tyr | Asp | Tyr | Asp | Met | Asp | Trp | Leu | Val | Pro | Ala | Thr | Cys | Glu | |
| | | | 420 | | | | | 425 | | | | | 430 | | | |
| ccc | att | cag | agc | gtc | tat | ttc | ttc | tct | gga | gac | aaa | tac | tac | cga | gtc | 1344 |
| Pro | Ile | Gln | Ser | Val | Tyr | Phe | Phe | Ser | Gly | Asp | Lys | Tyr | Tyr | Arg | Val | |
| | 435 | | | | | 440 | | | | | 445 | | | | | |
| aac | ctt | aga | acc | cgg | cga | gtg | gac | tct | gtg | aat | cct | ccc | tac | cca | cgc | 1392 |
| Asn | Leu | Arg | Thr | Arg | Arg | Val | Asp | Ser | Val | Asn | Pro | Pro | Tyr | Pro | Arg | |
| 450 | | | | | 455 | | | | | 460 | | | | | | |
| tcc | att | gct | cag | tat | tgg | ctg | ggc | tgc | ccg | acc | tct | gag | aag | tag | | 1437 |
| Ser | Ile | Ala | Gln | Tyr | Trp | Leu | Gly | Cys | Pro | Thr | Ser | Glu | Lys | | | |
| 465 | | | | 470 | | | | | 475 | | | | | | | |

<210> SEQ ID NO 4
<211> LENGTH: 478
<212> TYPE: PRT
<213> ORGANISM: Mus musculus

<400> SEQUENCE: 4

Met Ala Pro Leu Arg Pro Phe Phe Ile Leu Ala Leu Val Ala Trp Val
1               5                   10                  15

Ser Leu Ala Asp Gln Glu Ser Cys Lys Gly Arg Cys Thr Gln Gly Phe
            20                  25                  30

Met Ala Ser Lys Lys Cys Gln Cys Asp Glu Leu Cys Thr Tyr Tyr Gln
        35                  40                  45

Ser Cys Cys Ala Asp Tyr Met Glu Gln Cys Lys Pro Gln Val Thr Arg
    50                  55                  60

Gly Asp Val Phe Thr Met Pro Glu Asp Tyr Trp Ser Tyr Asp Tyr
65                  70                  75                  80

Val Glu Glu Pro Lys Asn Asn Thr Asn Thr Gly Val Gln Pro Glu Asn
                85                  90                  95

Thr Ser Pro Pro Gly Asp Leu Asn Pro Arg Thr Asp Gly Thr Leu Lys
            100                 105                 110

Pro Thr Ala Phe Leu Asp Pro Glu Glu Gln Pro Ser Thr Pro Ala Pro
        115                 120                 125

Lys Val Glu Gln Gln Glu Glu Ile Leu Arg Pro Asp Thr Thr Asp Gln
    130                 135                 140

Gly Thr Pro Glu Phe Pro Glu Glu Leu Cys Ser Gly Lys Pro Phe
145                 150                 155                 160

Asp Ala Phe Thr Asp Leu Lys Asn Gly Ser Leu Phe Ala Phe Arg Gly
                165                 170                 175

Gln Tyr Arg Cys Glu Leu Asp Glu Thr Ala Val Arg Pro Gly Tyr Pro
            180                 185                 190

Lys Leu Ile Gln Asp Val Trp Gly Ile Glu Gly Pro Ile Asp Ala Ala
        195                 200                 205

```
Phe Thr Arg Ile Asn Cys Gln Gly Lys Thr Tyr Leu Phe Lys Gly Ser
    210                 215                 220

Gln Tyr Trp Arg Phe Glu Asp Gly Val Leu Asp Pro Gly Tyr Pro Arg
225                 230                 235                 240

Asn Ile Ser Glu Gly Phe Ser Gly Ile Pro Asp Asn Val Asp Ala Ala
                245                 250                 255

Phe Ala Leu Pro Ala His Arg Tyr Ser Gly Arg Glu Arg Val Tyr Phe
            260                 265                 270

Phe Lys Gly Lys Gln Tyr Trp Glu His Glu Phe Gln Gln Gln Pro Ser
        275                 280                 285

Gln Glu Glu Cys Glu Gly Ser Ser Leu Ser Ala Val Phe Glu His Phe
290                 295                 300

Ala Leu Leu Gln Arg Asp Ser Trp Glu Asn Ile Phe Glu Leu Leu Phe
305                 310                 315                 320

Trp Gly Arg Ser Ser Asp Gly Ala Arg Glu Pro Gln Phe Ile Ser Arg
                325                 330                 335

Asn Trp His Gly Val Pro Gly Lys Val Asp Ala Ala Met Ala Gly Arg
            340                 345                 350

Ile Tyr Val Thr Gly Ser Leu Ser His Ser Ala Gln Ala Lys Lys Gln
        355                 360                 365

Pro Ser Lys Arg Arg Ser Arg Lys Arg Tyr Arg Ser Arg Arg Gly Arg
    370                 375                 380

Gly His Arg Arg Ser Gln Ser Ser Asn Ser Arg Arg Ser Ser Arg Ser
385                 390                 395                 400

Ile Trp Phe Ser Leu Phe Ser Ser Glu Glu Ser Gly Leu Gly Thr Tyr
                405                 410                 415

Asn Asn Tyr Asp Tyr Asp Met Asp Trp Leu Val Pro Ala Thr Cys Glu
            420                 425                 430

Pro Ile Gln Ser Val Tyr Phe Phe Ser Gly Asp Lys Tyr Tyr Arg Val
        435                 440                 445

Asn Leu Arg Thr Arg Arg Val Asp Ser Val Asn Pro Pro Tyr Pro Arg
    450                 455                 460

Ser Ile Ala Gln Tyr Trp Leu Gly Cys Pro Thr Ser Glu Lys
465                 470                 475

<210> SEQ ID NO 5
<211> LENGTH: 9511
<212> TYPE: DNA
<213> ORGANISM: Mus musculus
<220> FEATURE:
<221> NAME/KEY: CDS
<222> LOCATION: (121)..(9372)
<223> OTHER INFORMATION: laminin-2 alpha chain

<400> SEQUENCE: 5
ggcacgagct gcaactccgt gggctccggg aggagtggat ctgctccggc caggatgcct      60
gcggccaccg ccgggatcct cttgctcctg ctcttgggga cgctcgaagg ctcccagact     120 cag cgg cga cag tcc caa gcg cat caa cag aga ggt tta ttt cct gct      168
Gln Arg Arg Gln Ser Gln Ala His Gln Gln Arg Gly Leu Phe Pro Ala
1               5                   10                  15 gtc ctg aat ctt gct tcg aat gca ctc atc aca acc aat gct aca tgt      216
Val Leu Asn Leu Ala Ser Asn Ala Leu Ile Thr Thr Asn Ala Thr Cys
            20                  25                  30 ggg gaa aaa gga ccc gag atg tac tgc aag ttg gtg gaa cat gtc ccc      264
Gly Glu Lys Gly Pro Glu Met Tyr Cys Lys Leu Val Glu His Val Pro
        35                  40                  45
```

-continued

| | |
|---|---|
| ggg cag cct gtg agg aac cct cag tgc cga atc tgc aat cag aac agc<br>Gly Gln Pro Val Arg Asn Pro Gln Cys Arg Ile Cys Asn Gln Asn Ser<br>50                          55                     60 | 312 |
| agc aat cca tac cag agg cac ccg att acg aat gct att gat ggc aag<br>Ser Asn Pro Tyr Gln Arg His Pro Ile Thr Asn Ala Ile Asp Gly Lys<br>65                    70                   75                  80 | 360 |
| aac aca tgg tgg cag agt ccc agt atc aag aat gga gtg gaa tac cat<br>Asn Thr Trp Trp Gln Ser Pro Ser Ile Lys Asn Gly Val Glu Tyr His<br>                    85                   90                  95 | 408 |
| tat gtg aca att act ctg gat tta cag cag gtg ttc cag att gcc tac<br>Tyr Val Thr Ile Thr Leu Asp Leu Gln Gln Val Phe Gln Ile Ala Tyr<br>                100                105               110 | 456 |
| gta att gtg aag gca gcc aat tcc cct cgg cct gga aac tgg att ttg<br>Val Ile Val Lys Ala Ala Asn Ser Pro Arg Pro Gly Asn Trp Ile Leu<br>                115                120               125 | 504 |
| gaa cgt tcc ctg gat gac gtg gag tac aaa ccc tgg cag tat cat gcg<br>Glu Arg Ser Leu Asp Asp Val Glu Tyr Lys Pro Trp Gln Tyr His Ala<br>130                   135               140 | 552 |
| gtg aca gac acg gag tgc ctg acc ctc tac aat atc tat ccc cgc act<br>Val Thr Asp Thr Glu Cys Leu Thr Leu Tyr Asn Ile Tyr Pro Arg Thr<br>145                  150               155               160 | 600 |
| gga cca cca tcc tac gcc aaa gat gat gag gtc atc tgc act tca ttt<br>Gly Pro Pro Ser Tyr Ala Lys Asp Asp Glu Val Ile Cys Thr Ser Phe<br>                165                170               175 | 648 |
| tat tcg aag atc cac cct tta gaa aat gga gag att cac att tct ttg<br>Tyr Ser Lys Ile His Pro Leu Glu Asn Gly Glu Ile His Ile Ser Leu<br>                180                185               190 | 696 |
| atc aat ggg aga cca agt gct gat gac ccc tcc cct gaa ctc ctg gaa<br>Ile Asn Gly Arg Pro Ser Ala Asp Asp Pro Ser Pro Glu Leu Leu Glu<br>                195                200               205 | 744 |
| ttc acc tct gct cgc tac att cgc ctg aga ttt cag agg atc cgc acc<br>Phe Thr Ser Ala Arg Tyr Ile Arg Leu Arg Phe Gln Arg Ile Arg Thr<br>210                   215                220 | 792 |
| ttg aat gca gac ttg atg atg ttt gct cac aaa gac ccc aga gaa atc<br>Leu Asn Ala Asp Leu Met Met Phe Ala His Lys Asp Pro Arg Glu Ile<br>225                  230               235               240 | 840 |
| gat ccc att gtc aca cga aga tat tac tat tct gtc aag gat att tca<br>Asp Pro Ile Val Thr Arg Arg Tyr Tyr Tyr Ser Val Lys Asp Ile Ser<br>                          245                250               255 | 888 |
| gtt ggc ggg atg tgc atc tgt tat ggt cat gcc cgg gct tgt cca ctt<br>Val Gly Gly Met Cys Ile Cys Tyr Gly His Ala Arg Ala Cys Pro Leu<br>                260                265               270 | 936 |
| gac cct gca aca aat aaa tca cgc tgt gag tgt gaa cat aac acc tgt<br>Asp Pro Ala Thr Asn Lys Ser Arg Cys Glu Cys Glu His Asn Thr Cys<br>275                   280               285 | 984 |
| ggg gaa agc tgt gac agg tgc tgt cca gga ttc cat cag aag cct tgg<br>Gly Glu Ser Cys Asp Arg Cys Cys Pro Gly Phe His Gln Lys Pro Trp<br>290                   295               300 | 1032 |
| aga gct gga acc ttc ctc acc aag tct gag tgt gaa gca tgc aat tgt<br>Arg Ala Gly Thr Phe Leu Thr Lys Ser Glu Cys Glu Ala Cys Asn Cys<br>305                   310               315               320 | 1080 |
| cac gga aaa gct gag gaa tgc tat tat gat gaa act gtt gct agc aga<br>His Gly Lys Ala Glu Glu Cys Tyr Tyr Asp Glu Thr Val Ala Ser Arg<br>                          325                330               335 | 1128 |
| aat cta agt tta aat ata cat ggg aag tac atc gga ggg ggt gtg tgc<br>Asn Leu Ser Leu Asn Ile His Gly Lys Tyr Ile Gly Gly Gly Val Cys<br>                340                345               350 | 1176 |
| atc aac tgc aca cat aac acg gct ggg ata aat tgt gag aca tgt gtt<br>Ile Asn Cys Thr His Asn Thr Ala Gly Ile Asn Cys Glu Thr Cys Val | 1224 |

-continued

```
                355                 360                 365
gat gga ttc ttc aga ccc aaa ggg gtg tca cca aat tat cca aga cca    1272
Asp Gly Phe Phe Arg Pro Lys Gly Val Ser Pro Asn Tyr Pro Arg Pro
370                 375                 380 tgc cag cca tgt cac tgt gat cca act ggc tcc ctt agt gaa gtc tgt    1320
Cys Gln Pro Cys His Cys Asp Pro Thr Gly Ser Leu Ser Glu Val Cys
385                 390                 395                 400 gtc aaa gat gag aaa tac gcc cag cga ggg ttg aaa cct gga tcc tgt    1368
Val Lys Asp Glu Lys Tyr Ala Gln Arg Gly Leu Lys Pro Gly Ser Cys
            405                 410                 415 cac tgc aaa act ggc ttt gga ggc gtg aac tgt gat cgc tgt gtc agg    1416
His Cys Lys Thr Gly Phe Gly Gly Val Asn Cys Asp Arg Cys Val Arg
            420                 425                 430 ggt tac cat ggt tac cca gac tgc caa ccc tgt aac tgt agt ggc ttg    1464
Gly Tyr His Gly Tyr Pro Asp Cys Gln Pro Cys Asn Cys Ser Gly Leu
            435                 440                 445 ggc agc aca aat gag gac cct tgc gtt ggg ccc tgt agc tgt aag gag    1512
Gly Ser Thr Asn Glu Asp Pro Cys Val Gly Pro Cys Ser Cys Lys Glu
450                 455                 460 aat gtt gaa ggt gaa gac tgt agt cgt tgc aaa tct ggt ttc ttc aac    1560
Asn Val Glu Gly Glu Asp Cys Ser Arg Cys Lys Ser Gly Phe Phe Asn
465                 470                 475                 480 ttg caa gaa gat aat cag aaa ggc tgt gag gag tgt ttc tgt tca gga    1608
Leu Gln Glu Asp Asn Gln Lys Gly Cys Glu Glu Cys Phe Cys Ser Gly
            485                 490                 495 gta tca aac aga tgt cag agt tcc tac tgg acc tat ggg aat att caa    1656
Val Ser Asn Arg Cys Gln Ser Ser Tyr Trp Thr Tyr Gly Asn Ile Gln
            500                 505                 510 gac atg cgt ggt tgg tat ctc aca gac ctc tct ggc cgc att cgg atg    1704
Asp Met Arg Gly Trp Tyr Leu Thr Asp Leu Ser Gly Arg Ile Arg Met
            515                 520                 525 gct ccc cag ctt gat aac cct gac tca cct cag cag atc agc atc agt    1752
Ala Pro Gln Leu Asp Asn Pro Asp Ser Pro Gln Gln Ile Ser Ile Ser
530                 535                 540 aac tct gag gcc cgg aaa tcc ctg ctt gat ggt tac tac tgg agt gca    1800
Asn Ser Glu Ala Arg Lys Ser Leu Leu Asp Gly Tyr Tyr Trp Ser Ala
545                 550                 555                 560 ccg cct cca tat ctg gga aac aga ctt cca gct gtt ggg gga cag ttg    1848
Pro Pro Pro Tyr Leu Gly Asn Arg Leu Pro Ala Val Gly Gly Gln Leu
            565                 570                 575 tca ttt acc atc tca tat gac ctc gaa gaa gag gaa gac gat aca gaa    1896
Ser Phe Thr Ile Ser Tyr Asp Leu Glu Glu Glu Glu Asp Asp Thr Glu
            580                 585                 590 aaa ctc ctt cag ctg atg att atc ttt gag gga aat gac tta aga atc    1944
Lys Leu Leu Gln Leu Met Ile Ile Phe Glu Gly Asn Asp Leu Arg Ile
            595                 600                 605 agc aca gcg tat aag gag gtg tac tta gag cca tct gaa gaa cac gtt    1992
Ser Thr Ala Tyr Lys Glu Val Tyr Leu Glu Pro Ser Glu Glu His Val
610                 615                 620 gag gag gtg tca ctc aaa gaa gag gcc ttt act ata cat gga aca aat    2040
Glu Glu Val Ser Leu Lys Glu Glu Ala Phe Thr Ile His Gly Thr Asn
625                 630                 635                 640 ttg cca gtc act aga aaa gat ttc atg att gtt ctc aca aat ttg gga    2088
Leu Pro Val Thr Arg Lys Asp Phe Met Ile Val Leu Thr Asn Leu Gly
            645                 650                 655 gag atc ctt atc caa atc aca tac aac tta ggg atg gac gcc atc ttc    2136
Glu Ile Leu Ile Gln Ile Thr Tyr Asn Leu Gly Met Asp Ala Ile Phe
            660                 665                 670 agg ctg agt tct gtc aat ctt gaa tct cct gtc cct tat cct act gat    2184
```

-continued

```
                Arg Leu Ser Ser Val Asn Leu Glu Ser Pro Val Pro Tyr Pro Thr Asp
                            675                 680                 685 aga cgt att gca act gat gtg gaa gtt tgc cag tgt cca cct ggg tac          2232
Arg Arg Ile Ala Thr Asp Val Glu Val Cys Gln Cys Pro Pro Gly Tyr
            690                 695                 700 agt ggc agc tct tgt gaa aca tgt tgg cct agg cac cga aga gtt aac          2280
Ser Gly Ser Ser Cys Glu Thr Cys Trp Pro Arg His Arg Arg Val Asn
705                 710                 715                 720 ggc acc att ttt ggt ggc att tgt gaa cca tgt cag tgc ttt gct cat          2328
Gly Thr Ile Phe Gly Gly Ile Cys Glu Pro Cys Gln Cys Phe Ala His
                725                 730                 735 gca gaa gcc tgt gat gac atc aca gga gaa tgt ctg aac tgt aag gat          2376
Ala Glu Ala Cys Asp Asp Ile Thr Gly Glu Cys Leu Asn Cys Lys Asp
            740                 745                 750 cac aca ggt ggg ccg tac tgc aat gaa tgt ctc cct gga ttc tat ggt          2424
His Thr Gly Gly Pro Tyr Cys Asn Glu Cys Leu Pro Gly Phe Tyr Gly
        755                 760                 765 gat cct act cga gga agc cct gaa gac tgt cag ccc tgt gcc tgt cca          2472
Asp Pro Thr Arg Gly Ser Pro Glu Asp Cys Gln Pro Cys Ala Cys Pro
    770                 775                 780 ctc aat atc cca tca aat aac ttt agt cca aca tgc cat tta gac cgg          2520
Leu Asn Ile Pro Ser Asn Asn Phe Ser Pro Thr Cys His Leu Asp Arg
785                 790                 795                 800 agt ctg gga ttg atc tgt gac gag tgt cct att ggg tac aca gga ccg          2568
Ser Leu Gly Leu Ile Cys Asp Glu Cys Pro Ile Gly Tyr Thr Gly Pro
                805                 810                 815 cgc tgt gag agg tgt gca gaa ggc tat ttt gga caa cct tcc gta cct          2616
Arg Cys Glu Arg Cys Ala Glu Gly Tyr Phe Gly Gln Pro Ser Val Pro
            820                 825                 830 gga gga tca tgt cag cca tgc caa tgc aat gac aac ctt gac tac tcc          2664
Gly Gly Ser Cys Gln Pro Cys Gln Cys Asn Asp Asn Leu Asp Tyr Ser
        835                 840                 845 atc cct ggc agc tgt gac agc ctg tct ggc tcc tgt ctg att tgt aag          2712
Ile Pro Gly Ser Cys Asp Ser Leu Ser Gly Ser Cys Leu Ile Cys Lys
    850                 855                 860 cca ggt aca aca ggc cgg tac tgt gag ctc tgt gct gat ggg tat ttt          2760
Pro Gly Thr Thr Gly Arg Tyr Cys Glu Leu Cys Ala Asp Gly Tyr Phe
865                 870                 875                 880 gga gac gcg gtt aat aca aag aac tgt caa cca tgc cgt tgt gat atc          2808
Gly Asp Ala Val Asn Thr Lys Asn Cys Gln Pro Cys Arg Cys Asp Ile
                885                 890                 895 aat ggc tcc ttc tca gag gat tgt cac aca aga act ggg caa tgt gag          2856
Asn Gly Ser Phe Ser Glu Asp Cys His Thr Arg Thr Gly Gln Cys Glu
            900                 905                 910 tgc aga ccc aat gtt cag ggg cgg cac tgt gac gag tgt aag cct gaa          2904
Cys Arg Pro Asn Val Gln Gly Arg His Cys Asp Glu Cys Lys Pro Glu
        915                 920                 925 acc ttt ggc ctg caa ctg gga agg ggt tgt ctg ccc tgc aac tgc aat          2952
Thr Phe Gly Leu Gln Leu Gly Arg Gly Cys Leu Pro Cys Asn Cys Asn
    930                 935                 940 tct ttt ggg tct aag tcc ttt gac tgt gaa gca agt ggg cag tgc tgg          3000
Ser Phe Gly Ser Lys Ser Phe Asp Cys Glu Ala Ser Gly Gln Cys Trp
945                 950                 955                 960 tgc cag cct gga gta gca ggg aag aaa tgt gac cgt tgt gcc cat ggc          3048
Cys Gln Pro Gly Val Ala Gly Lys Lys Cys Asp Arg Cys Ala His Gly
                965                 970                 975 tac ttc aac ttc caa gaa gga ggc tgc ata gct tgt gac tgt tct cat          3096
Tyr Phe Asn Phe Gln Glu Gly Gly Cys Ile Ala Cys Asp Cys Ser His
            980                 985                 990
```

```
ctg ggc aac aac tgt gac cca aaa act ggc caa tgc att tgc cca ccc      3144
Leu Gly Asn Asn Cys Asp Pro Lys Thr Gly Gln Cys Ile Cys Pro Pro
        995                1000                1005 aat acc act gga gaa aag tgt tct gag tgt ctt ccc aac acc tgg          3189
Asn Thr Thr Gly Glu Lys Cys Ser Glu Cys Leu Pro Asn Thr Trp
    1010                1015                1020 ggt cac agc att gtc acc ggc tgt aag gtt tgt aac tgc agc act          3234
Gly His Ser Ile Val Thr Gly Cys Lys Val Cys Asn Cys Ser Thr
1025                1030                1035 gtg ggg tcc ttg gct tct cag tgc aat gta aac acg ggc cag tgc          3279
Val Gly Ser Leu Ala Ser Gln Cys Asn Val Asn Thr Gly Gln Cys
    1040                1045                1050 agc tgt cat cca aaa ttc tct ggt atg aaa tgc tca gag tgc agc          3324
Ser Cys His Pro Lys Phe Ser Gly Met Lys Cys Ser Glu Cys Ser
1055                1060                1065 cga ggt cac tgg aac tat cct ctc tgc act cta tgt gac tgc ttc          3369
Arg Gly His Trp Asn Tyr Pro Leu Cys Thr Leu Cys Asp Cys Phe
    1070                1075                1080 ctt cca ggc aca gat gcc acg act tgt gat ctg gag act agg aaa          3414
Leu Pro Gly Thr Asp Ala Thr Thr Cys Asp Leu Glu Thr Arg Lys
1085                1090                1095 tgc tcc tgt agt gat caa act gga cag tgc agc tgt aag gtg aat          3459
Cys Ser Cys Ser Asp Gln Thr Gly Gln Cys Ser Cys Lys Val Asn
    1100                1105                1110 gtg gaa ggc gtc cac tgt gac agg tgc cgg cct ggc aaa ttt gga          3504
Val Glu Gly Val His Cys Asp Arg Cys Arg Pro Gly Lys Phe Gly
1115                1120                1125 cta gat gcc aag aac cca ctt ggc tgc agc agc tgc tac tgc ttt          3549
Leu Asp Ala Lys Asn Pro Leu Gly Cys Ser Ser Cys Tyr Cys Phe
    1130                1135                1140 gga gtt act agt caa tgc tct gaa gca aag ggg ctg atc cgt acg          3594
Gly Val Thr Ser Gln Cys Ser Glu Ala Lys Gly Leu Ile Arg Thr
1145                1150                1155 tgg gtg act ttg agt gat gaa cag acc att cta cct ctg gtg gat          3639
Trp Val Thr Leu Ser Asp Glu Gln Thr Ile Leu Pro Leu Val Asp
    1160                1165                1170 gag gcc ctg cag cac acg act acc aaa ggc att gct ttc cag aaa          3684
Glu Ala Leu Gln His Thr Thr Thr Lys Gly Ile Ala Phe Gln Lys
1175                1180                1185 cca gag att gtt gca aag atg gat gaa gtc agg caa gag ctc cat          3729
Pro Glu Ile Val Ala Lys Met Asp Glu Val Arg Gln Glu Leu His
    1190                1195                1200 ttg gaa cct ttt tac tgg aaa ctc cca caa caa ttt gaa ggg aaa          3774
Leu Glu Pro Phe Tyr Trp Lys Leu Pro Gln Gln Phe Glu Gly Lys
1205                1210                1215 aag ttg atg gct tat ggt ggc aaa ctc aag tat gcc atc tat ttt          3819
Lys Leu Met Ala Tyr Gly Gly Lys Leu Lys Tyr Ala Ile Tyr Phe
    1220                1225                1230 gag gct cgg gat gag aca ggc ttt gcc aca tat aaa cct caa gtt          3864
Glu Ala Arg Asp Glu Thr Gly Phe Ala Thr Tyr Lys Pro Gln Val
1235                1240                1245 atc att cga ggt gga act cct act cat gct aga att att acc aga          3909
Ile Ile Arg Gly Gly Thr Pro Thr His Ala Arg Ile Ile Thr Arg
    1250                1255                1260 cac atg gct gcc cct ctc att ggc cag ttg aca cgg cat gaa ata          3954
His Met Ala Ala Pro Leu Ile Gly Gln Leu Thr Arg His Glu Ile
1265                1270                1275 gaa atg aca gag aaa gaa tgg aaa tat tat ggt gat gat cct cga          3999
Glu Met Thr Glu Lys Glu Trp Lys Tyr Tyr Gly Asp Asp Pro Arg
    1280                1285                1290
```

-continued

| | | |
|---|---|---|
| atc agt aga act gtg acc cgt gaa gac ttc ttg gat ata cta tat<br>Ile Ser Arg Thr Val Thr Arg Glu Asp Phe Leu Asp Ile Leu Tyr<br>1295                         1300                     1305 | 4044 |
| gat att cac tat atc ctt atc aag gct act tat gga aac gtt gtg<br>Asp Ile His Tyr Ile Leu Ile Lys Ala Thr Tyr Gly Asn Val Val<br>1310                         1315                     1320 | 4089 |
| aga caa agc cgc att tct gaa atc tcc atg gaa gta gct gaa cca<br>Arg Gln Ser Arg Ile Ser Glu Ile Ser Met Glu Val Ala Glu Pro<br>1325                         1330                     1335 | 4134 |
| gga cat gta tta gca ggg agc cca cca gca cac ttg ata gaa aga<br>Gly His Val Leu Ala Gly Ser Pro Pro Ala His Leu Ile Glu Arg<br>1340                         1345                     1350 | 4179 |
| tgc gat tgc cct cct ggc tat tct ggc ttg tct tgt gag acg tgt<br>Cys Asp Cys Pro Pro Gly Tyr Ser Gly Leu Ser Cys Glu Thr Cys<br>1355                         1360                     1365 | 4224 |
| gca cca gga ttt tac cga ctt cgt tct gaa cca ggt ggg cgg act<br>Ala Pro Gly Phe Tyr Arg Leu Arg Ser Glu Pro Gly Gly Arg Thr<br>1370                         1375                     1380 | 4269 |
| cct gga cca acc tta ggg acc tgt gtt ccc tgc caa tgt aat gga<br>Pro Gly Pro Thr Leu Gly Thr Cys Val Pro Cys Gln Cys Asn Gly<br>1385                         1390                     1395 | 4314 |
| cac agc agt cag tgt gat cct gag acc tca gta tgc cag aat tgt<br>His Ser Ser Gln Cys Asp Pro Glu Thr Ser Val Cys Gln Asn Cys<br>1400                         1405                     1410 | 4359 |
| cag cat cac act gct ggt gac ttc tgt gag cgc tgt gcc ctt ggc<br>Gln His His Thr Ala Gly Asp Phe Cys Glu Arg Cys Ala Leu Gly<br>1415                         1420                     1425 | 4404 |
| tac tat gga atc gtc agg gga ttg cca aat gac tgc caa cca tgt<br>Tyr Tyr Gly Ile Val Arg Gly Leu Pro Asn Asp Cys Gln Pro Cys<br>1430                         1435                     1440 | 4449 |
| gct tgt cct ctg att tcg ccc agc aac aat ttc agc ccc tct tgt<br>Ala Cys Pro Leu Ile Ser Pro Ser Asn Asn Phe Ser Pro Ser Cys<br>1445                         1450                     1455 | 4494 |
| gta ttg gaa ggt ctg gaa gat tac cgt tgc acc gcc tgc cca agg<br>Val Leu Glu Gly Leu Glu Asp Tyr Arg Cys Thr Ala Cys Pro Arg<br>1460                         1465                     1470 | 4539 |
| ggc tat gaa gga cag tac tgt gaa agg tgt gcc cca ggc tat act<br>Gly Tyr Glu Gly Gln Tyr Cys Glu Arg Cys Ala Pro Gly Tyr Thr<br>1475                         1480                     1485 | 4584 |
| ggc agc cca agc agc ccc gga ggc tcc tgc caa gaa tgt gag tgt<br>Gly Ser Pro Ser Ser Pro Gly Gly Ser Cys Gln Glu Cys Glu Cys<br>1490                         1495                     1500 | 4629 |
| gac cct tat ggc tcc cta ccg gtt ccc tgt gac cgg gtc aca gga<br>Asp Pro Tyr Gly Ser Leu Pro Val Pro Cys Asp Arg Val Thr Gly<br>1505                         1510                     1515 | 4674 |
| ctc tgc acg tgc cgc cct gga gcc aca gga agg aag tgt gat ggc<br>Leu Cys Thr Cys Arg Pro Gly Ala Thr Gly Arg Lys Cys Asp Gly<br>1520                         1525                     1530 | 4719 |
| tgc gag cac tgg cat gca cgc gag ggt gca gag tgt gtc ttt tgt<br>Cys Glu His Trp His Ala Arg Glu Gly Ala Glu Cys Val Phe Cys<br>1535                         1540                     1545 | 4764 |
| gga gac gag tgt aca ggc ctt ctt ctt ggt gac ctg gct cgt cta<br>Gly Asp Glu Cys Thr Gly Leu Leu Leu Gly Asp Leu Ala Arg Leu<br>1550                         1555                     1560 | 4809 |
| gag cag atg acc atg aac atc aac ctc acg ggc cca ctg cct gct<br>Glu Gln Met Thr Met Asn Ile Asn Leu Thr Gly Pro Leu Pro Ala<br>1565                         1570                     1575 | 4854 |
| cca tat aaa att ctg tat ggt ctt gaa aat aca act cag gaa ctc<br>Pro Tyr Lys Ile Leu Tyr Gly Leu Glu Asn Thr Thr Gln Glu Leu | 4899 |

-continued

```
     1580               1585               1590
aag cac ctg cta tca ccg caa cgg gca cca gag agg ctc att cag    4944
Lys His Leu Leu Ser Pro Gln Arg Ala Pro Glu Arg Leu Ile Gln
    1595               1600               1605 ttg gca gag ggc aac gtg aac aca ctt gtg atg gaa aca aat gag    4989
Leu Ala Glu Gly Asn Val Asn Thr Leu Val Met Glu Thr Asn Glu
    1610               1615               1620 ctg cta acc aga gca acc aaa gtg aca gca gat ggt gag caa aca    5034
Leu Leu Thr Arg Ala Thr Lys Val Thr Ala Asp Gly Glu Gln Thr
    1625               1630               1635 gga caa gat gct gag agg acc aac tcc aga gca gaa tcc ttg gaa    5079
Gly Gln Asp Ala Glu Arg Thr Asn Ser Arg Ala Glu Ser Leu Glu
    1640               1645               1650 gaa ttc att aaa ggg ctt gtc cag gat gct gaa gcc ata aat gaa    5124
Glu Phe Ile Lys Gly Leu Val Gln Asp Ala Glu Ala Ile Asn Glu
    1655               1660               1665 aaa gct gta aaa cta aat gaa acc tta gga aat caa gat aag aca    5169
Lys Ala Val Lys Leu Asn Glu Thr Leu Gly Asn Gln Asp Lys Thr
    1670               1675               1680 gca gag aga aac ttg gag gag ctt caa aag gaa atc gac cgg atg    5214
Ala Glu Arg Asn Leu Glu Glu Leu Gln Lys Glu Ile Asp Arg Met
    1685               1690               1695 ctg aag gaa ctg aga agt aaa gat ctt caa aca cag aag gaa gtt    5259
Leu Lys Glu Leu Arg Ser Lys Asp Leu Gln Thr Gln Lys Glu Val
    1700               1705               1710 gct gag gat gag ctc gtg gca gca gaa ggc ctt ctg aag aga gta    5304
Ala Glu Asp Glu Leu Val Ala Ala Glu Gly Leu Leu Lys Arg Val
    1715               1720               1725 aac aag ctg ttt gga gag ccc aga gcc cag aat gaa gat atg gaa    5349
Asn Lys Leu Phe Gly Glu Pro Arg Ala Gln Asn Glu Asp Met Glu
    1730               1735               1740 aag gat ctc cag cag aaa ctg gca gag tac aag aac aaa ctt gat    5394
Lys Asp Leu Gln Gln Lys Leu Ala Glu Tyr Lys Asn Lys Leu Asp
    1745               1750               1755 gat gct tgg gat cta ttg aga gaa gcc act gat aaa acc cga gat    5439
Asp Ala Trp Asp Leu Leu Arg Glu Ala Thr Asp Lys Thr Arg Asp
    1760               1765               1770 gct aat cgt ttg tct gct gcc aat caa aaa aac atg acc ata ctg    5484
Ala Asn Arg Leu Ser Ala Ala Asn Gln Lys Asn Met Thr Ile Leu
    1775               1780               1785 gag aca aag aag gag gct att gaa ggt agc aaa cga caa ata gag    5529
Glu Thr Lys Lys Glu Ala Ile Glu Gly Ser Lys Arg Gln Ile Glu
    1790               1795               1800 aac act tta aag gaa ggc aat gac atc ctt gat gaa gcc aat caa    5574
Asn Thr Leu Lys Glu Gly Asn Asp Ile Leu Asp Glu Ala Asn Gln
    1805               1810               1815 ctc tta ggt gaa atc aac tca gtc ata gat tat gtc gac gac att    5619
Leu Leu Gly Glu Ile Asn Ser Val Ile Asp Tyr Val Asp Asp Ile
    1820               1825               1830 aaa act aag ttg cca cca atg tcc gag gag ctg agt gac aaa ata    5664
Lys Thr Lys Leu Pro Pro Met Ser Glu Glu Leu Ser Asp Lys Ile
    1835               1840               1845 gat gac ctc gcc cag gaa ata aag gac aga agg ctt gct gag aag    5709
Asp Asp Leu Ala Gln Glu Ile Lys Asp Arg Arg Leu Ala Glu Lys
    1850               1855               1860 gtg ttc cag gct gag agc cat gct gct cag ctg aac gac tcg tct    5754
Val Phe Gln Ala Glu Ser His Ala Ala Gln Leu Asn Asp Ser Ser
    1865               1870               1875 gct gta ctt gat gga atc ctg gat gag gct aag aac atc tct ttc    5799
```

```
                Ala Val Leu Asp Gly Ile Leu Asp Glu Ala Lys Asn Ile Ser Phe
                1880                1885                1890 aat gcc acg gca gcc ttc aga gct tac agt aat att aaa gac tac             5844
Asn Ala Thr Ala Ala Phe Arg Ala Tyr Ser Asn Ile Lys Asp Tyr
    1895                1900                1905 att gat gaa gct gag aaa gtg gcc aga gaa gcc aaa gag ctt gcc             5889
Ile Asp Glu Ala Glu Lys Val Ala Arg Glu Ala Lys Glu Leu Ala
1910            1915                1920 caa ggg gct aca aaa ctg gca aca agt cct cag ggc tta tta aaa             5934
Gln Gly Ala Thr Lys Leu Ala Thr Ser Pro Gln Gly Leu Leu Lys
    1925                1930                1935 gaa gat gcc aaa ggc tcc ctt cag aaa agc ttc agg atc ctc aat             5979
Glu Asp Ala Lys Gly Ser Leu Gln Lys Ser Phe Arg Ile Leu Asn
1940            1945                1950 gaa gcc aag aag cta gca aac gat gtg aaa gga aat cac aat gat             6024
Glu Ala Lys Lys Leu Ala Asn Asp Val Lys Gly Asn His Asn Asp
    1955                1960                1965 cta aat gac ctg aaa acc agg tta gaa act gct gac ctt aga aac             6069
Leu Asn Asp Leu Lys Thr Arg Leu Glu Thr Ala Asp Leu Arg Asn
1970            1975                1980 agt gga ctt cta gga gct cta aat gac acc atg gac aag tta tca             6114
Ser Gly Leu Leu Gly Ala Leu Asn Asp Thr Met Asp Lys Leu Ser
    1985                1990                1995 gcc att aca aat gac acg gct gct aaa ctg cag gct gtc aaa gag             6159
Ala Ile Thr Asn Asp Thr Ala Ala Lys Leu Gln Ala Val Lys Glu
2000            2005                2010 aaa gcc aga gaa gcc aat gac aca gca aaa gct gtc ctg gcc cag             6204
Lys Ala Arg Glu Ala Asn Asp Thr Ala Lys Ala Val Leu Ala Gln
    2015                2020                2025 gtt aag gac ctg cat cag aac cta gat ggc ctg aag caa aac tac             6249
Val Lys Asp Leu His Gln Asn Leu Asp Gly Leu Lys Gln Asn Tyr
2030            2035                2040 aat aaa ctg gca gac agc gtg gcc aaa acg aac gct gtg gtg aaa             6294
Asn Lys Leu Ala Asp Ser Val Ala Lys Thr Asn Ala Val Val Lys
    2045                2050                2055 gat cct tcc aaa aac aaa atc att gca gat gca ggc act tcc gtg             6339
Asp Pro Ser Lys Asn Lys Ile Ile Ala Asp Ala Gly Thr Ser Val
2060            2065                2070 aga aat cta gaa cag gaa gct gac cgg cta atc gac aaa ctc aag             6384
Arg Asn Leu Glu Gln Glu Ala Asp Arg Leu Ile Asp Lys Leu Lys
    2075                2080                2085 ccc atc aag gag ctt gag gac aac cta aag aaa aac att tct gaa             6429
Pro Ile Lys Glu Leu Glu Asp Asn Leu Lys Lys Asn Ile Ser Glu
2090            2095                2100 ata aag gaa ctg atc aac caa gct cgg aaa caa gct aac tct atc             6474
Ile Lys Glu Leu Ile Asn Gln Ala Arg Lys Gln Ala Asn Ser Ile
    2105                2110                2115 aaa gta tct gtt tct tcg gga ggt gac tgt gtt cgg aca tac agg             6519
Lys Val Ser Val Ser Ser Gly Gly Asp Cys Val Arg Thr Tyr Arg
2120            2125                2130 cca gaa atc aag aaa gga agc tac aat aac atc gtt gtc cat gtc             6564
Pro Glu Ile Lys Lys Gly Ser Tyr Asn Asn Ile Val Val His Val
    2135                2140                2145 aag acc gct gtt gcc gac aac ctc ctt ttt tat ctt gga agt gcc             6609
Lys Thr Ala Val Ala Asp Asn Leu Leu Phe Tyr Leu Gly Ser Ala
2150            2155                2160 aaa ttt att gac ttt ctt gct ata gaa atg cgc aaa ggc aaa gtc             6654
Lys Phe Ile Asp Phe Leu Ala Ile Glu Met Arg Lys Gly Lys Val
    2165                2170                2175
```

|  |  |
|---|---|
| agc ttc ctc tgg att gtt ggc tct gga gtt ggc cga gta ggg ttt<br>Ser Phe Leu Trp Ile Val Gly Ser Gly Val Gly Arg Val Gly Phe<br>2180                         2185                    2190 | 6699 |
| cca gac ttg acc atc gac gac tcc tat tgg tac cgt att gaa gca<br>Pro Asp Leu Thr Ile Asp Asp Ser Tyr Trp Tyr Arg Ile Glu Ala<br>2195                         2200                    2205 | 6744 |
| tca aga acg gga aga aat gga tct att tct gtg aga gct tta gat<br>Ser Arg Thr Gly Arg Asn Gly Ser Ile Ser Val Arg Ala Leu Asp<br>2210                         2215                    2220 | 6789 |
| gga ccc aaa gcc agt atg gta ccc agc acc tac cat tca gtg tct<br>Gly Pro Lys Ala Ser Met Val Pro Ser Thr Tyr His Ser Val Ser<br>2225                         2230                    2235 | 6834 |
| cct ccc ggg tat act atc cta gat gtg gat gca aat gca atg ctg<br>Pro Pro Gly Tyr Thr Ile Leu Asp Val Asp Ala Asn Ala Met Leu<br>2240                         2245                    2250 | 6879 |
| ttt gtt ggt ggc ctg acc gga aaa ata aag aag gcc gat gct gta<br>Phe Val Gly Gly Leu Thr Gly Lys Ile Lys Lys Ala Asp Ala Val<br>2255                         2260                    2265 | 6924 |
| cgt gtg atc acc ttc acc ggc tgt atg gga gaa aca tac ttt gac<br>Arg Val Ile Thr Phe Thr Gly Cys Met Gly Glu Thr Tyr Phe Asp<br>2270                         2275                    2280 | 6969 |
| aac aaa cct ata ggt tta tgg aac ttc cgg gag aaa gaa ggc gac<br>Asn Lys Pro Ile Gly Leu Trp Asn Phe Arg Glu Lys Glu Gly Asp<br>2285                         2290                    2295 | 7014 |
| tgt aag gga tgt act gtc agc cca caa gtg gaa gat agt gag ggg<br>Cys Lys Gly Cys Thr Val Ser Pro Gln Val Glu Asp Ser Glu Gly<br>2300                         2305                    2310 | 7059 |
| act att cag ttt gat ggt gaa ggc tat gca tta gtg agc cgg ccc<br>Thr Ile Gln Phe Asp Gly Glu Gly Tyr Ala Leu Val Ser Arg Pro<br>2315                         2320                    2325 | 7104 |
| atc cgc tgg tac ccc aac atc tcc aca gtc atg ttc aag ttc cgg<br>Ile Arg Trp Tyr Pro Asn Ile Ser Thr Val Met Phe Lys Phe Arg<br>2330                         2335                    2340 | 7149 |
| aca ttt tca tca agt gct ctc ctg atg tat ctt gcc aca cga gac<br>Thr Phe Ser Ser Ser Ala Leu Leu Met Tyr Leu Ala Thr Arg Asp<br>2345                         2350                    2355 | 7194 |
| ctg aaa gat ttc atg agt gta gag ctc agt gat gga cat gtg aaa<br>Leu Lys Asp Phe Met Ser Val Glu Leu Ser Asp Gly His Val Lys<br>2360                         2365                    2370 | 7239 |
| gtc agc tat gac ctg ggc tca gga atg act tcc gtt gtc agc aat<br>Val Ser Tyr Asp Leu Gly Ser Gly Met Thr Ser Val Val Ser Asn<br>2375                         2380                    2385 | 7284 |
| caa aac cat aat gat ggg aaa tgg aaa gca ttc acg ctg tcg cgg<br>Gln Asn His Asn Asp Gly Lys Trp Lys Ala Phe Thr Leu Ser Arg<br>2390                         2395                    2400 | 7329 |
| att cag aaa caa gcc aac ata tcg att gtc gac atc gat tct aac<br>Ile Gln Lys Gln Ala Asn Ile Ser Ile Val Asp Ile Asp Ser Asn<br>2405                         2410                    2415 | 7374 |
| cag gag gag aat gta gct act tca tct tct gga aac aac ttt ggt<br>Gln Glu Glu Asn Val Ala Thr Ser Ser Ser Gly Asn Asn Phe Gly<br>2420                         2425                    2430 | 7419 |
| ctt gac ttg aaa gca gat gac aaa ata tat ttt ggt ggc ctg cca<br>Leu Asp Leu Lys Ala Asp Asp Lys Ile Tyr Phe Gly Gly Leu Pro<br>2435                         2440                    2445 | 7464 |
| act ctg aga aac ttg agt atg aaa gca agg cca gaa gtc aat gtg<br>Thr Leu Arg Asn Leu Ser Met Lys Ala Arg Pro Glu Val Asn Val<br>2450                         2455                    2460 | 7509 |
| aag aaa tac tcc ggc tgc ctc aaa gat att gaa att tca aga aca<br>Lys Lys Tyr Ser Gly Cys Leu Lys Asp Ile Glu Ile Ser Arg Thr<br>2465                         2470                    2475 | 7554 |

|  |  |
|---|---|
| cct tac aat ata ctc agc agc cct gat tat gtt ggt gtg acc aaa<br>Pro Tyr Asn Ile Leu Ser Ser Pro Asp Tyr Val Gly Val Thr Lys<br>2480 2485 2490 | 7599 |
| ggc tgt tca ctg gag aat gtt aat aca gtt agt ttc ccc aag cct<br>Gly Cys Ser Leu Glu Asn Val Asn Thr Val Ser Phe Pro Lys Pro<br>2495 2500 2505 | 7644 |
| ggt ttt gtg gag ctt gcc gct gtg tct att gat gtt gga aca gaa<br>Gly Phe Val Glu Leu Ala Ala Val Ser Ile Asp Val Gly Thr Glu<br>2510 2515 2520 | 7689 |
| atc aat ctg tcc ttt agt acc agg aac gag tct ggg atc att ctc<br>Ile Asn Leu Ser Phe Ser Thr Arg Asn Glu Ser Gly Ile Ile Leu<br>2525 2530 2535 | 7734 |
| ttg gga agt gga ggg aca ctc aca cca ccc agg aga aaa cgg aga<br>Leu Gly Ser Gly Gly Thr Leu Thr Pro Pro Arg Arg Lys Arg Arg<br>2540 2545 2550 | 7779 |
| caa acc aca cag gct tat tat gcc ata ttc ctc aac aag ggc cgc<br>Gln Thr Thr Gln Ala Tyr Tyr Ala Ile Phe Leu Asn Lys Gly Arg<br>2555 2560 2565 | 7824 |
| ttg gaa gtg cat ctc tcc tcg ggg aca cgg aca atg agg aaa att<br>Leu Glu Val His Leu Ser Ser Gly Thr Arg Thr Met Arg Lys Ile<br>2570 2575 2580 | 7869 |
| gtc atc aaa ccg gag cca aat ttg ttt cat gat ggg aga gaa cat<br>Val Ile Lys Pro Glu Pro Asn Leu Phe His Asp Gly Arg Glu His<br>2585 2590 2595 | 7914 |
| tct gtc cac gta gaa aga acc aga ggc atc ttc act gtt caa att<br>Ser Val His Val Glu Arg Thr Arg Gly Ile Phe Thr Val Gln Ile<br>2600 2605 2610 | 7959 |
| gat gaa gac aga aga cat atc caa aac ctg aca gag gaa cag ccc<br>Asp Glu Asp Arg Arg His Ile Gln Asn Leu Thr Glu Glu Gln Pro<br>2615 2620 2625 | 8004 |
| atc gaa gtg aaa aag ctc ttt gtc ggg ggt gct cct cct gaa ttt<br>Ile Glu Val Lys Lys Leu Phe Val Gly Gly Ala Pro Pro Glu Phe<br>2630 2635 2640 | 8049 |
| cag ccc tcc cca ctc agg aat att ccg gcc ttt caa ggc tgt gtg<br>Gln Pro Ser Pro Leu Arg Asn Ile Pro Ala Phe Gln Gly Cys Val<br>2645 2650 2655 | 8094 |
| tgg aac ctt gtt att aac tcc atc ccc atg gac ttt gcg cag cct<br>Trp Asn Leu Val Ile Asn Ser Ile Pro Met Asp Phe Ala Gln Pro<br>2660 2665 2670 | 8139 |
| ata gcc ttc aaa aat gcc gac att ggt cgc tgt acc tat caa aag<br>Ile Ala Phe Lys Asn Ala Asp Ile Gly Arg Cys Thr Tyr Gln Lys<br>2675 2680 2685 | 8184 |
| ccc cgg gaa gat gag agt gaa gca gtt cca gct gaa gtt att gtc<br>Pro Arg Glu Asp Glu Ser Glu Ala Val Pro Ala Glu Val Ile Val<br>2690 2695 2700 | 8229 |
| cag cct cag tcg gtg ccc acc cct gcc ttc cct ttc cca gtc ccc<br>Gln Pro Gln Ser Val Pro Thr Pro Ala Phe Pro Phe Pro Val Pro<br>2705 2710 2715 | 8274 |
| acc atg gtg cat ggc cct tgt gtt gca gaa tca gaa cca gct ctt<br>Thr Met Val His Gly Pro Cys Val Ala Glu Ser Glu Pro Ala Leu<br>2720 2725 2730 | 8319 |
| ctg aca ggg agc aag cag ttt ggg ctt tcc aga aac agc cac att<br>Leu Thr Gly Ser Lys Gln Phe Gly Leu Ser Arg Asn Ser His Ile<br>2735 2740 2745 | 8364 |
| gca att gtc ttt gat gac acc aaa gtt aaa aac cgc ctc acc att<br>Ala Ile Val Phe Asp Asp Thr Lys Val Lys Asn Arg Leu Thr Ile<br>2750 2755 2760 | 8409 |
| gag ctg gag gta cga act gaa gct gaa tca ggc ttg ctc ttc tac<br>Glu Leu Glu Val Arg Thr Glu Ala Glu Ser Gly Leu Leu Phe Tyr | 8454 |

```
                    2765                2770                2775
atg ggt cgg atc aat cat gct gat ttt ggt act gtt cag ctg agg       8499
Met Gly Arg Ile Asn His Ala Asp Phe Gly Thr Val Gln Leu Arg
    2780                2785                2790 aat ggg ttc ccg ttc ttc agt tat gat ttg ggg agt ggg agc acc       8544
Asn Gly Phe Pro Phe Phe Ser Tyr Asp Leu Gly Ser Gly Ser Thr
    2795                2800                2805 aga acc atg atc ccc aca aaa atc aac gat ggt cag tgg cac aag       8589
Arg Thr Met Ile Pro Thr Lys Ile Asn Asp Gly Gln Trp His Lys
    2810                2815                2820 att aag att gtg aga gtg aag cag gag gga att ctt tat gtg gat       8634
Ile Lys Ile Val Arg Val Lys Gln Glu Gly Ile Leu Tyr Val Asp
    2825                2830                2835 gat gcc tcc agc caa acc atc agt ccc aag aaa gcc gac atc ctg       8679
Asp Ala Ser Ser Gln Thr Ile Ser Pro Lys Lys Ala Asp Ile Leu
    2840                2845                2850 gat gtc ggg ggg att ctg tat gtc ggt gga ttg ccg atc aac tat       8724
Asp Val Gly Gly Ile Leu Tyr Val Gly Gly Leu Pro Ile Asn Tyr
    2855                2860                2865 acc aca cgc aga att ggt cca gtg act tac agc ctg gat ggc tgt       8769
Thr Thr Arg Arg Ile Gly Pro Val Thr Tyr Ser Leu Asp Gly Cys
    2870                2875                2880 gtt agg aat ctt cac atg gaa caa gcc cct gtt gat ctg gac cag       8814
Val Arg Asn Leu His Met Glu Gln Ala Pro Val Asp Leu Asp Gln
    2885                2890                2895 cct acc tcc agc ttt cac gtt ggg aca tgc ttt gcg aat gca gag       8859
Pro Thr Ser Ser Phe His Val Gly Thr Cys Phe Ala Asn Ala Glu
    2900                2905                2910 agt ggg act tac ttt gat gga acc ggt ttt ggt aaa gca gtt ggt       8904
Ser Gly Thr Tyr Phe Asp Gly Thr Gly Phe Gly Lys Ala Val Gly
    2915                2920                2925 ggg ttc atc gtt gga ttg gac ctt ctt gtg gaa ttt gaa ttc cgt       8949
Gly Phe Ile Val Gly Leu Asp Leu Leu Val Glu Phe Glu Phe Arg
    2930                2935                2940 acc aca aga ccc act ggg gtc ctc ctg ggg atc agc agt cag aag       8994
Thr Thr Arg Pro Thr Gly Val Leu Leu Gly Ile Ser Ser Gln Lys
    2945                2950                2955 atg gat gga atg ggt att gaa atg atc gac gag aag ctt atg ttc       9039
Met Asp Gly Met Gly Ile Glu Met Ile Asp Glu Lys Leu Met Phe
    2960                2965                2970 cac gtg gat aat ggc gct ggc cga ttc act gca att tat gat gct       9084
His Val Asp Asn Gly Ala Gly Arg Phe Thr Ala Ile Tyr Asp Ala
    2975                2980                2985 gag atc cca ggc cac atg tgc aat gga cag tgg tat aaa gtc act       9129
Glu Ile Pro Gly His Met Cys Asn Gly Gln Trp Tyr Lys Val Thr
    2990                2995                3000 gcc aag aag atc aaa aac cgt ctt gag ctg gtg gta gat ggg aac       9174
Ala Lys Lys Ile Lys Asn Arg Leu Glu Leu Val Val Asp Gly Asn
    3005                3010                3015 cag gtg gat gcc cag agc cca aac tca gca tcg aca tca gct gat       9219
Gln Val Asp Ala Gln Ser Pro Asn Ser Ala Ser Thr Ser Ala Asp
    3020                3025                3030 aca aac gac cct gtt ttc gtt ggc ggt ttc cca ggt ggc ctc aat       9264
Thr Asn Asp Pro Val Phe Val Gly Gly Phe Pro Gly Gly Leu Asn
    3035                3040                3045 cag ttt ggc ctg acc acc aac att agg ttc cga ggc tgc atc cga       9309
Gln Phe Gly Leu Thr Thr Asn Ile Arg Phe Arg Gly Cys Ile Arg
    3050                3055                3060 tct ctg aag ctc acc aaa ggc act gca aac cgc tgg agg tta att       9354
```

```
Ser Leu Lys Leu Thr Lys Gly Thr Ala Asn Arg Trp Arg Leu Ile
    3065                3070                3075 ttg cca agg ccc tgg aac tgaggggtgt caacctgta tcatgcccga           9402
Leu Pro Arg Pro Trp Asn
    3080 ctacctaata aagatagttc aatcctgagg agaattcatc aaaacaagta tatcaagtta 9462 aacaatatac actcctatca tattaataaa actaatgtgc agcggccgc             9511

<210> SEQ ID NO 6
<211> LENGTH: 3084
<212> TYPE: PRT
<213> ORGANISM: Mus musculus

<400> SEQUENCE: 6

Gln Arg Arg Gln Ser Gln Ala His Gln Gln Arg Gly Leu Phe Pro Ala
1               5                   10                  15

Val Leu Asn Leu Ala Ser Asn Ala Leu Ile Thr Thr Asn Ala Thr Cys
            20                  25                  30

Gly Glu Lys Gly Pro Glu Met Tyr Cys Lys Leu Val Glu His Val Pro
        35                  40                  45

Gly Gln Pro Val Arg Asn Pro Gln Cys Arg Ile Cys Asn Gln Asn Ser
    50                  55                  60

Ser Asn Pro Tyr Gln Arg His Pro Ile Thr Asn Ala Ile Asp Gly Lys
65                  70                  75                  80

Asn Thr Trp Trp Gln Ser Pro Ser Ile Lys Asn Gly Val Glu Tyr His
                85                  90                  95

Tyr Val Thr Ile Thr Leu Asp Leu Gln Gln Val Phe Gln Ile Ala Tyr
            100                 105                 110

Val Ile Val Lys Ala Ala Asn Ser Pro Arg Pro Gly Asn Trp Ile Leu
        115                 120                 125

Glu Arg Ser Leu Asp Asp Val Glu Tyr Lys Pro Trp Gln Tyr His Ala
    130                 135                 140

Val Thr Asp Thr Glu Cys Leu Thr Leu Tyr Asn Ile Tyr Pro Arg Thr
145                 150                 155                 160

Gly Pro Pro Ser Tyr Ala Lys Asp Asp Glu Val Ile Cys Thr Ser Phe
                165                 170                 175

Tyr Ser Lys Ile His Pro Leu Glu Asn Gly Glu Ile His Ile Ser Leu
            180                 185                 190

Ile Asn Gly Arg Pro Ser Ala Asp Asp Pro Ser Pro Glu Leu Leu Glu
        195                 200                 205

Phe Thr Ser Ala Arg Tyr Ile Arg Leu Arg Phe Gln Arg Ile Arg Thr
    210                 215                 220

Leu Asn Ala Asp Leu Met Met Phe Ala His Lys Asp Pro Arg Glu Ile
225                 230                 235                 240

Asp Pro Ile Val Thr Arg Arg Tyr Tyr Tyr Ser Val Lys Asp Ile Ser
                245                 250                 255

Val Gly Gly Met Cys Ile Cys Tyr Gly His Ala Arg Ala Cys Pro Leu
            260                 265                 270

Asp Pro Ala Thr Asn Lys Ser Arg Cys Glu Cys Glu His Asn Thr Cys
        275                 280                 285

Gly Glu Ser Cys Asp Arg Cys Cys Pro Gly Phe His Gln Lys Pro Trp
    290                 295                 300

Arg Ala Gly Thr Phe Leu Thr Lys Ser Glu Cys Glu Ala Cys Asn Cys
305                 310                 315                 320
```

-continued

His Gly Lys Ala Glu Glu Cys Tyr Tyr Asp Glu Thr Val Ala Ser Arg
            325                 330                 335

Asn Leu Ser Leu Asn Ile His Gly Lys Tyr Ile Gly Gly Val Cys
            340                 345                 350

Ile Asn Cys Thr His Asn Thr Ala Gly Ile Asn Cys Glu Thr Cys Val
            355                 360                 365

Asp Gly Phe Phe Arg Pro Lys Gly Val Ser Pro Asn Tyr Pro Arg Pro
        370                 375                 380

Cys Gln Pro Cys His Cys Asp Pro Thr Gly Ser Leu Ser Glu Val Cys
385                 390                 395                 400

Val Lys Asp Glu Lys Tyr Ala Gln Arg Gly Leu Lys Pro Gly Ser Cys
                405                 410                 415

His Cys Lys Thr Gly Phe Gly Gly Val Asn Cys Asp Arg Cys Val Arg
            420                 425                 430

Gly Tyr His Gly Tyr Pro Asp Cys Gln Pro Cys Asn Cys Ser Gly Leu
            435                 440                 445

Gly Ser Thr Asn Glu Asp Pro Cys Val Gly Pro Cys Ser Cys Lys Glu
        450                 455                 460

Asn Val Glu Gly Glu Asp Cys Ser Arg Cys Lys Ser Gly Phe Phe Asn
465                 470                 475                 480

Leu Gln Glu Asp Asn Gln Lys Gly Cys Glu Glu Cys Phe Cys Ser Gly
                485                 490                 495

Val Ser Asn Arg Cys Gln Ser Ser Tyr Trp Thr Tyr Gly Asn Ile Gln
            500                 505                 510

Asp Met Arg Gly Trp Tyr Leu Thr Asp Leu Ser Gly Arg Ile Arg Met
            515                 520                 525

Ala Pro Gln Leu Asp Asn Pro Asp Ser Pro Gln Ile Ser Ile Ser
            530                 535                 540

Asn Ser Glu Ala Arg Lys Ser Leu Leu Asp Gly Tyr Tyr Trp Ser Ala
545                 550                 555                 560

Pro Pro Pro Tyr Leu Gly Asn Arg Leu Pro Ala Val Gly Gly Gln Leu
                565                 570                 575

Ser Phe Thr Ile Ser Tyr Asp Leu Glu Glu Glu Asp Asp Thr Glu
            580                 585                 590

Lys Leu Leu Gln Leu Met Ile Ile Phe Glu Gly Asn Asp Leu Arg Ile
            595                 600                 605

Ser Thr Ala Tyr Lys Glu Val Tyr Leu Glu Pro Ser Glu Glu His Val
        610                 615                 620

Glu Glu Val Ser Leu Lys Glu Ala Phe Thr Ile His Gly Thr Asn
625                 630                 635                 640

Leu Pro Val Thr Arg Lys Asp Phe Met Ile Val Leu Thr Asn Leu Gly
                645                 650                 655

Glu Ile Leu Ile Gln Ile Thr Tyr Asn Leu Gly Met Asp Ala Ile Phe
            660                 665                 670

Arg Leu Ser Ser Val Asn Leu Glu Ser Pro Val Pro Tyr Pro Thr Asp
            675                 680                 685

Arg Arg Ile Ala Thr Asp Val Glu Cys Gln Cys Pro Pro Gly Tyr
        690                 695                 700

Ser Gly Ser Ser Cys Glu Thr Cys Trp Pro Arg His Arg Arg Val Asn
705                 710                 715                 720

Gly Thr Ile Phe Gly Gly Ile Cys Glu Pro Cys Gln Cys Phe Ala His
                725                 730                 735

Ala Glu Ala Cys Asp Asp Ile Thr Gly Glu Cys Leu Asn Cys Lys Asp

-continued

```
            740                 745                 750
His Thr Gly Gly Pro Tyr Cys Asn Glu Cys Leu Pro Gly Phe Tyr Gly
            755                 760                 765

Asp Pro Thr Arg Gly Ser Pro Glu Asp Cys Gln Pro Cys Ala Cys Pro
        770                 775                 780

Leu Asn Ile Pro Ser Asn Asn Phe Ser Pro Thr Cys His Leu Asp Arg
785                 790                 795                 800

Ser Leu Gly Leu Ile Cys Asp Glu Cys Pro Ile Gly Tyr Thr Gly Pro
                805                 810                 815

Arg Cys Glu Arg Cys Ala Glu Gly Tyr Phe Gly Gln Pro Ser Val Pro
            820                 825                 830

Gly Gly Ser Cys Gln Pro Cys Gln Cys Asn Asp Asn Leu Asp Tyr Ser
            835                 840                 845

Ile Pro Gly Ser Cys Asp Ser Leu Ser Gly Ser Cys Leu Ile Cys Lys
        850                 855                 860

Pro Gly Thr Thr Gly Arg Tyr Cys Glu Leu Cys Ala Asp Gly Tyr Phe
865                 870                 875                 880

Gly Asp Ala Val Asn Thr Lys Asn Cys Gln Pro Cys Arg Cys Asp Ile
                885                 890                 895

Asn Gly Ser Phe Ser Glu Asp Cys His Thr Arg Thr Gly Gln Cys Glu
            900                 905                 910

Cys Arg Pro Asn Val Gln Gly Arg His Cys Asp Glu Cys Lys Pro Glu
            915                 920                 925

Thr Phe Gly Leu Gln Leu Gly Arg Gly Cys Leu Pro Cys Asn Cys Asn
        930                 935                 940

Ser Phe Gly Ser Lys Ser Phe Asp Cys Glu Ala Ser Gly Gln Cys Trp
945                 950                 955                 960

Cys Gln Pro Gly Val Ala Gly Lys Lys Cys Asp Arg Cys Ala His Gly
                965                 970                 975

Tyr Phe Asn Phe Gln Glu Gly Gly Cys Ile Ala Cys Asp Cys Ser His
            980                 985                 990

Leu Gly Asn Asn Cys Asp Pro Lys  Thr Gly Gln Cys Ile  Cys Pro Pro
            995                 1000                1005

Asn Thr  Thr Gly Glu Lys Cys  Ser Glu Cys Leu Pro  Asn Thr Trp
    1010                1015                1020

Gly His  Ser Ile Val Thr Gly  Cys Lys Val Cys Asn  Cys Ser Thr
    1025                1030                1035

Val Gly  Ser Leu Ala Ser Gln  Cys Asn Val Asn Thr  Gly Gln Cys
    1040                1045                1050

Ser Cys His Pro Lys Phe Ser  Gly Met Lys Cys Ser  Glu Cys Ser
    1055                1060                1065

Arg Gly  His Trp Asn Tyr Pro  Leu Cys Thr Leu Cys  Asp Cys Phe
    1070                1075                1080

Leu Pro  Gly Thr Asp Ala Thr  Thr Cys Asp Leu Glu  Thr Arg Lys
    1085                1090                1095

Cys Ser  Cys Ser Asp Gln Thr  Gly Gln Cys Ser Cys  Lys Val Asn
    1100                1105                1110

Val Glu  Gly Val His Cys Asp  Arg Cys Arg Pro Gly  Lys Phe Gly
    1115                1120                1125

Leu Asp  Ala Lys Asn Pro Leu  Gly Cys Ser Ser Cys  Tyr Cys Phe
    1130                1135                1140

Gly Val  Thr Ser Gln Cys Ser  Glu Ala Lys Gly Leu  Ile Arg Thr
    1145                1150                1155
```

-continued

```
Trp Val Thr Leu Ser Asp Glu Gln Thr Ile Leu Pro Leu Val Asp
    1160                1165                1170

Glu Ala Leu Gln His Thr Thr Thr Lys Gly Ile Ala Phe Gln Lys
    1175                1180                1185

Pro Glu Ile Val Ala Lys Met Asp Glu Val Arg Gln Glu Leu His
    1190                1195                1200

Leu Glu Pro Phe Tyr Trp Lys Leu Pro Gln Gln Phe Glu Gly Lys
    1205                1210                1215

Lys Leu Met Ala Tyr Gly Gly Lys Leu Lys Tyr Ala Ile Tyr Phe
    1220                1225                1230

Glu Ala Arg Asp Glu Thr Gly Phe Ala Thr Tyr Lys Pro Gln Val
    1235                1240                1245

Ile Ile Arg Gly Gly Thr Pro Thr His Ala Arg Ile Ile Thr Arg
    1250                1255                1260

His Met Ala Ala Pro Leu Ile Gly Gln Leu Thr Arg His Glu Ile
    1265                1270                1275

Glu Met Thr Glu Lys Glu Trp Lys Tyr Tyr Gly Asp Asp Pro Arg
    1280                1285                1290

Ile Ser Arg Thr Val Thr Arg Glu Asp Phe Leu Asp Ile Leu Tyr
    1295                1300                1305

Asp Ile His Tyr Ile Leu Ile Lys Ala Thr Tyr Gly Asn Val Val
    1310                1315                1320

Arg Gln Ser Arg Ile Ser Glu Ile Ser Met Glu Val Ala Glu Pro
    1325                1330                1335

Gly His Val Leu Ala Gly Ser Pro Pro Ala His Leu Ile Glu Arg
    1340                1345                1350

Cys Asp Cys Pro Pro Gly Tyr Ser Gly Leu Ser Cys Glu Thr Cys
    1355                1360                1365

Ala Pro Gly Phe Tyr Arg Leu Arg Ser Glu Pro Gly Gly Arg Thr
    1370                1375                1380

Pro Gly Pro Thr Leu Gly Thr Cys Val Pro Cys Gln Cys Asn Gly
    1385                1390                1395

His Ser Ser Gln Cys Asp Pro Glu Thr Ser Val Cys Gln Asn Cys
    1400                1405                1410

Gln His His Thr Ala Gly Asp Phe Cys Glu Arg Cys Ala Leu Gly
    1415                1420                1425

Tyr Tyr Gly Ile Val Arg Gly Leu Pro Asn Asp Cys Gln Pro Cys
    1430                1435                1440

Ala Cys Pro Leu Ile Ser Pro Ser Asn Asn Phe Ser Pro Ser Cys
    1445                1450                1455

Val Leu Glu Gly Leu Glu Asp Tyr Arg Cys Thr Ala Cys Pro Arg
    1460                1465                1470

Gly Tyr Glu Gly Gln Tyr Cys Glu Arg Cys Ala Pro Gly Tyr Thr
    1475                1480                1485

Gly Ser Pro Ser Ser Pro Gly Gly Ser Cys Gln Glu Cys Glu Cys
    1490                1495                1500

Asp Pro Tyr Gly Ser Leu Pro Val Pro Cys Asp Arg Val Thr Gly
    1505                1510                1515

Leu Cys Thr Cys Arg Pro Gly Ala Thr Gly Arg Lys Cys Asp Gly
    1520                1525                1530

Cys Glu His Trp His Ala Arg Glu Gly Ala Glu Cys Val Phe Cys
    1535                1540                1545
```

-continued

```
Gly Asp Glu Cys Thr Gly Leu Leu Leu Gly Asp Leu Ala Arg Leu
1550                1555                1560

Glu Gln Met Thr Met Asn Ile Asn Leu Thr Gly Pro Leu Pro Ala
1565                1570                1575

Pro Tyr Lys Ile Leu Tyr Gly Leu Glu Asn Thr Thr Gln Glu Leu
1580                1585                1590

Lys His Leu Leu Ser Pro Gln Arg Ala Pro Glu Arg Leu Ile Gln
1595                1600                1605

Leu Ala Glu Gly Asn Val Asn Thr Leu Val Met Glu Thr Asn Glu
1610                1615                1620

Leu Leu Thr Arg Ala Thr Lys Val Thr Ala Asp Gly Glu Gln Thr
1625                1630                1635

Gly Gln Asp Ala Glu Arg Thr Asn Ser Arg Ala Glu Ser Leu Glu
1640                1645                1650

Glu Phe Ile Lys Gly Leu Val Gln Asp Ala Glu Ala Ile Asn Glu
1655                1660                1665

Lys Ala Val Lys Leu Asn Glu Thr Leu Gly Asn Gln Asp Lys Thr
1670                1675                1680

Ala Glu Arg Asn Leu Glu Glu Leu Gln Lys Glu Ile Asp Arg Met
1685                1690                1695

Leu Lys Glu Leu Arg Ser Lys Asp Leu Gln Thr Gln Lys Glu Val
1700                1705                1710

Ala Glu Asp Glu Leu Val Ala Ala Glu Gly Leu Leu Lys Arg Val
1715                1720                1725

Asn Lys Leu Phe Gly Glu Pro Arg Ala Gln Asn Glu Asp Met Glu
1730                1735                1740

Lys Asp Leu Gln Gln Lys Leu Ala Glu Tyr Lys Asn Lys Leu Asp
1745                1750                1755

Asp Ala Trp Asp Leu Leu Arg Glu Ala Thr Asp Lys Thr Arg Asp
1760                1765                1770

Ala Asn Arg Leu Ser Ala Ala Asn Gln Lys Asn Met Thr Ile Leu
1775                1780                1785

Glu Thr Lys Lys Glu Ala Ile Glu Gly Ser Lys Arg Gln Ile Glu
1790                1795                1800

Asn Thr Leu Lys Glu Gly Asn Asp Ile Leu Asp Glu Ala Asn Gln
1805                1810                1815

Leu Leu Gly Glu Ile Asn Ser Val Ile Asp Tyr Val Asp Asp Ile
1820                1825                1830

Lys Thr Lys Leu Pro Pro Met Ser Glu Glu Leu Ser Asp Lys Ile
1835                1840                1845

Asp Asp Leu Ala Gln Glu Ile Lys Asp Arg Arg Leu Ala Glu Lys
1850                1855                1860

Val Phe Gln Ala Glu Ser His Ala Ala Gln Leu Asn Asp Ser Ser
1865                1870                1875

Ala Val Leu Asp Gly Ile Leu Asp Glu Ala Lys Asn Ile Ser Phe
1880                1885                1890

Asn Ala Thr Ala Ala Phe Arg Ala Tyr Ser Asn Ile Lys Asp Tyr
1895                1900                1905

Ile Asp Glu Ala Glu Lys Val Ala Arg Glu Ala Lys Glu Leu Ala
1910                1915                1920

Gln Gly Ala Thr Lys Leu Ala Thr Ser Pro Gln Gly Leu Leu Lys
1925                1930                1935

Glu Asp Ala Lys Gly Ser Leu Gln Lys Ser Phe Arg Ile Leu Asn
```

-continued

```
            1940                1945                1950

Glu Ala Lys Lys Leu Ala Asn Asp Val Lys Gly Asn His Asn Asp
    1955                1960                1965

Leu Asn Asp Leu Lys Thr Arg Leu Glu Thr Ala Asp Leu Arg Asn
    1970                1975                1980

Ser Gly Leu Leu Gly Ala Leu Asn Asp Thr Met Asp Lys Leu Ser
    1985                1990                1995

Ala Ile Thr Asn Asp Thr Ala Ala Lys Leu Gln Ala Val Lys Glu
    2000                2005                2010

Lys Ala Arg Glu Ala Asn Asp Thr Ala Lys Ala Val Leu Ala Gln
    2015                2020                2025

Val Lys Asp Leu His Gln Asn Leu Asp Gly Leu Lys Gln Asn Tyr
    2030                2035                2040

Asn Lys Leu Ala Asp Ser Val Ala Lys Thr Asn Ala Val Val Lys
    2045                2050                2055

Asp Pro Ser Lys Asn Lys Ile Ile Ala Asp Ala Gly Thr Ser Val
    2060                2065                2070

Arg Asn Leu Glu Gln Glu Ala Asp Arg Leu Ile Asp Lys Leu Lys
    2075                2080                2085

Pro Ile Lys Glu Leu Glu Asp Asn Leu Lys Lys Asn Ile Ser Glu
    2090                2095                2100

Ile Lys Glu Leu Ile Asn Gln Ala Arg Lys Gln Ala Asn Ser Ile
    2105                2110                2115

Lys Val Ser Val Ser Ser Gly Gly Asp Cys Val Arg Thr Tyr Arg
    2120                2125                2130

Pro Glu Ile Lys Lys Gly Ser Tyr Asn Asn Ile Val Val His Val
    2135                2140                2145

Lys Thr Ala Val Ala Asp Asn Leu Leu Phe Tyr Leu Gly Ser Ala
    2150                2155                2160

Lys Phe Ile Asp Phe Leu Ala Ile Glu Met Arg Lys Gly Lys Val
    2165                2170                2175

Ser Phe Leu Trp Ile Val Gly Ser Gly Val Gly Arg Val Gly Phe
    2180                2185                2190

Pro Asp Leu Thr Ile Asp Asp Ser Tyr Trp Tyr Arg Ile Glu Ala
    2195                2200                2205

Ser Arg Thr Gly Arg Asn Gly Ser Ile Ser Val Arg Ala Leu Asp
    2210                2215                2220

Gly Pro Lys Ala Ser Met Val Pro Ser Thr Tyr His Ser Val Ser
    2225                2230                2235

Pro Pro Gly Tyr Thr Ile Leu Asp Val Asp Ala Asn Ala Met Leu
    2240                2245                2250

Phe Val Gly Gly Leu Thr Gly Lys Ile Lys Lys Ala Asp Ala Val
    2255                2260                2265

Arg Val Ile Thr Phe Thr Gly Cys Met Gly Glu Thr Tyr Phe Asp
    2270                2275                2280

Asn Lys Pro Ile Gly Leu Trp Asn Phe Arg Glu Lys Glu Gly Asp
    2285                2290                2295

Cys Lys Gly Cys Thr Val Ser Pro Gln Val Glu Asp Ser Glu Gly
    2300                2305                2310

Thr Ile Gln Phe Asp Gly Glu Gly Tyr Ala Leu Val Ser Arg Pro
    2315                2320                2325

Ile Arg Trp Tyr Pro Asn Ile Ser Thr Val Met Phe Lys Phe Arg
    2330                2335                2340
```

```
Thr Phe Ser Ser Ser Ala Leu Leu Met Tyr Leu Ala Thr Arg Asp
    2345                2350                2355

Leu Lys Asp Phe Met Ser Val Glu Leu Ser Asp Gly His Val Lys
    2360                2365                2370

Val Ser Tyr Asp Leu Gly Ser Gly Met Thr Ser Val Val Ser Asn
    2375                2380                2385

Gln Asn His Asn Asp Gly Lys Trp Lys Ala Phe Thr Leu Ser Arg
    2390                2395                2400

Ile Gln Lys Gln Ala Asn Ile Ser Ile Val Asp Ile Asp Ser Asn
    2405                2410                2415

Gln Glu Glu Asn Val Ala Thr Ser Ser Ser Gly Asn Asn Phe Gly
    2420                2425                2430

Leu Asp Leu Lys Ala Asp Asp Lys Ile Tyr Phe Gly Gly Leu Pro
    2435                2440                2445

Thr Leu Arg Asn Leu Ser Met Lys Ala Arg Pro Glu Val Asn Val
    2450                2455                2460

Lys Lys Tyr Ser Gly Cys Leu Lys Asp Ile Glu Ile Ser Arg Thr
    2465                2470                2475

Pro Tyr Asn Ile Leu Ser Ser Pro Asp Tyr Val Gly Val Thr Lys
    2480                2485                2490

Gly Cys Ser Leu Glu Asn Val Asn Thr Val Ser Phe Pro Lys Pro
    2495                2500                2505

Gly Phe Val Glu Leu Ala Ala Val Ser Ile Asp Val Gly Thr Glu
    2510                2515                2520

Ile Asn Leu Ser Phe Ser Thr Arg Asn Glu Ser Gly Ile Ile Leu
    2525                2530                2535

Leu Gly Ser Gly Gly Thr Leu Thr Pro Pro Arg Arg Lys Arg Arg
    2540                2545                2550

Gln Thr Thr Gln Ala Tyr Tyr Ala Ile Phe Leu Asn Lys Gly Arg
    2555                2560                2565

Leu Glu Val His Leu Ser Ser Gly Thr Arg Thr Met Arg Lys Ile
    2570                2575                2580

Val Ile Lys Pro Glu Pro Asn Leu Phe His Asp Gly Arg Glu His
    2585                2590                2595

Ser Val His Val Glu Arg Thr Arg Gly Ile Phe Thr Val Gln Ile
    2600                2605                2610

Asp Glu Asp Arg Arg His Ile Gln Asn Leu Thr Glu Glu Gln Pro
    2615                2620                2625

Ile Glu Val Lys Lys Leu Phe Val Gly Gly Ala Pro Pro Glu Phe
    2630                2635                2640

Gln Pro Ser Pro Leu Arg Asn Ile Pro Ala Phe Gln Gly Cys Val
    2645                2650                2655

Trp Asn Leu Val Ile Asn Ser Ile Pro Met Asp Phe Ala Gln Pro
    2660                2665                2670

Ile Ala Phe Lys Asn Ala Asp Ile Gly Arg Cys Thr Tyr Gln Lys
    2675                2680                2685

Pro Arg Glu Asp Glu Ser Glu Ala Val Pro Ala Glu Val Ile Val
    2690                2695                2700

Gln Pro Gln Ser Val Pro Thr Pro Ala Phe Pro Phe Pro Val Pro
    2705                2710                2715

Thr Met Val His Gly Pro Cys Val Ala Glu Ser Glu Pro Ala Leu
    2720                2725                2730
```

```
Leu Thr Gly Ser Lys Gln Phe Gly Leu Ser Arg Asn Ser His Ile
    2735                2740                2745

Ala Ile Val Phe Asp Asp Thr Lys Val Lys Asn Arg Leu Thr Ile
    2750                2755                2760

Glu Leu Glu Val Arg Thr Glu Ala Glu Ser Gly Leu Leu Phe Tyr
    2765                2770                2775

Met Gly Arg Ile Asn His Ala Asp Phe Gly Thr Val Gln Leu Arg
    2780                2785                2790

Asn Gly Phe Pro Phe Phe Ser Tyr Asp Leu Gly Ser Gly Ser Thr
    2795                2800                2805

Arg Thr Met Ile Pro Thr Lys Ile Asn Asp Gly Gln Trp His Lys
    2810                2815                2820

Ile Lys Ile Val Arg Val Lys Gln Glu Gly Ile Leu Tyr Val Asp
    2825                2830                2835

Asp Ala Ser Ser Gln Thr Ile Ser Pro Lys Lys Ala Asp Ile Leu
    2840                2845                2850

Asp Val Gly Gly Ile Leu Tyr Val Gly Gly Leu Pro Ile Asn Tyr
    2855                2860                2865

Thr Thr Arg Arg Ile Gly Pro Val Thr Tyr Ser Leu Asp Gly Cys
    2870                2875                2880

Val Arg Asn Leu His Met Glu Gln Ala Pro Val Asp Leu Asp Gln
    2885                2890                2895

Pro Thr Ser Ser Phe His Val Gly Thr Cys Phe Ala Asn Ala Glu
    2900                2905                2910

Ser Gly Thr Tyr Phe Asp Gly Thr Gly Phe Gly Lys Ala Val Gly
    2915                2920                2925

Gly Phe Ile Val Gly Leu Asp Leu Leu Val Glu Phe Glu Phe Arg
    2930                2935                2940

Thr Thr Arg Pro Thr Gly Val Leu Leu Gly Ile Ser Ser Gln Lys
    2945                2950                2955

Met Asp Gly Met Gly Ile Glu Met Ile Asp Glu Lys Leu Met Phe
    2960                2965                2970

His Val Asp Asn Gly Ala Gly Arg Phe Thr Ala Ile Tyr Asp Ala
    2975                2980                2985

Glu Ile Pro Gly His Met Cys Asn Gly Gln Trp Tyr Lys Val Thr
    2990                2995                3000

Ala Lys Lys Ile Lys Asn Arg Leu Glu Leu Val Val Asp Gly Asn
    3005                3010                3015

Gln Val Asp Ala Gln Ser Pro Asn Ser Ala Ser Thr Ser Ala Asp
    3020                3025                3030

Thr Asn Asp Pro Val Phe Val Gly Gly Phe Pro Gly Gly Leu Asn
    3035                3040                3045

Gln Phe Gly Leu Thr Thr Asn Ile Arg Phe Arg Gly Cys Ile Arg
    3050                3055                3060

Ser Leu Lys Leu Thr Lys Gly Thr Ala Asn Arg Trp Arg Leu Ile
    3065                3070                3075

Leu Pro Arg Pro Trp Asn
    3080

<210> SEQ ID NO 7
<211> LENGTH: 5583
<212> TYPE: DNA
<213> ORGANISM: Mus musculus
<220> FEATURE:
<221> NAME/KEY: CDS
```

-continued

```
<222> LOCATION: (42)..(5441)
<223> OTHER INFORMATION: laminin, beta 2

<400> SEQUENCE: 7
ccacgcgtcc gggacaccag cccagtaccc acacggtcgg g atg gag tgg gcc tca    56
                                              Met Glu Trp Ala Ser
                                               1               5 gga gaa cca ggg agg ggc agg cag gga cag cct ttg cca tgg gaa ctt    104
Gly Glu Pro Gly Arg Gly Arg Gln Gly Gln Pro Leu Pro Trp Glu Leu
            10                  15                  20 cgc ttg ggc cta ctt cta agt gtg ctg gct gcc aca ttg gcc cag gcc    152
Arg Leu Gly Leu Leu Leu Ser Val Leu Ala Ala Thr Leu Ala Gln Ala
         25                  30                  35 ccg tcc ttg gat gta cct ggc tgt tct cga gga agc tgc tat cca gcc    200
Pro Ser Leu Asp Val Pro Gly Cys Ser Arg Gly Ser Cys Tyr Pro Ala
     40                  45                  50 acc ggt gac ctg ttg gtg ggc cgt gcg gac aga ctg acg gcc tca tcc    248
Thr Gly Asp Leu Leu Val Gly Arg Ala Asp Arg Leu Thr Ala Ser Ser
 55                  60                  65 acg tgt ggc ttg cat agc cct caa ccc tac tgt att gtc agt cac ctg    296
Thr Cys Gly Leu His Ser Pro Gln Pro Tyr Cys Ile Val Ser His Leu
 70                  75                  80                  85 cag gac gaa aag aag tgt ttc ctg tgt gac tcc cga cgt ccc ttc tct    344
Gln Asp Glu Lys Lys Cys Phe Leu Cys Asp Ser Arg Arg Pro Phe Ser
                 90                  95                 100 gct cga gac aac cca aat agt cat cgg atc cag aat gta gtc acc agc    392
Ala Arg Asp Asn Pro Asn Ser His Arg Ile Gln Asn Val Val Thr Ser
            105                 110                 115 ttt gcg cca caa cgc cgg acg gcc tgg tgg caa tcg gag aac ggg gtt    440
Phe Ala Pro Gln Arg Arg Thr Ala Trp Trp Gln Ser Glu Asn Gly Val
        120                 125                 130 cca atg gtc acc atc caa ctg gac ctg gaa gct gag ttt cat ttc acc    488
Pro Met Val Thr Ile Gln Leu Asp Leu Glu Ala Glu Phe His Phe Thr
    135                 140                 145 cac ctc att atg acg ttc aag acg ttc cgg cct gct gct atg ctg gtg    536
His Leu Ile Met Thr Phe Lys Thr Phe Arg Pro Ala Ala Met Leu Val
150                 155                 160                 165 gag cgt tct gca gac ttt ggc cgc acc tgg cac gtg tac cga tat ttt    584
Glu Arg Ser Ala Asp Phe Gly Arg Thr Trp His Val Tyr Arg Tyr Phe
                170                 175                 180 tcc tat gac tgc ggg gct gac ttc ccg gga atc cca ctg gcc ccg cca    632
Ser Tyr Asp Cys Gly Ala Asp Phe Pro Gly Ile Pro Leu Ala Pro Pro
            185                 190                 195 cgt cgc tgg gat gat gta gtg tgt gag tcc cgc tac tca gaa atc gag    680
Arg Arg Trp Asp Asp Val Val Cys Glu Ser Arg Tyr Ser Glu Ile Glu
        200                 205                 210 ccg tct acg gaa ggc gag gtc atc tat cgt gtg ctg gac cct gct att    728
Pro Ser Thr Glu Gly Glu Val Ile Tyr Arg Val Leu Asp Pro Ala Ile
    215                 220                 225 cct atc cca gac ccc tac agc tca cgg att cag aac ctg ttg aag atc    776
Pro Ile Pro Asp Pro Tyr Ser Ser Arg Ile Gln Asn Leu Leu Lys Ile
230                 235                 240                 245 acc aac cta cga gtg aac tta acc cgg ctt cac aca ctg gga gac aac    824
Thr Asn Leu Arg Val Asn Leu Thr Arg Leu His Thr Leu Gly Asp Asn
                250                 255                 260 ttg ctt gac cca cgg agg gag atc cgg gaa aaa tac tat tat gct ctc    872
Leu Leu Asp Pro Arg Arg Glu Ile Arg Glu Lys Tyr Tyr Tyr Ala Leu
            265                 270                 275 tat gaa ctt gtc atc cgt ggc aac tgc ttc tgc tat ggc cac gcc tca    920
Tyr Glu Leu Val Ile Arg Gly Asn Cys Phe Cys Tyr Gly His Ala Ser
```

-continued

```
            280                 285                 290
cag tgt gcg cct gca cca ggg gcg ccg gcc cat gct gag ggc atg gta     968
Gln Cys Ala Pro Ala Pro Gly Ala Pro Ala His Ala Glu Gly Met Val
    295                 300                 305 cac gga gcc tgt atc tgc aag cac aat act cgt gga ctc aac tgt gag    1016
His Gly Ala Cys Ile Cys Lys His Asn Thr Arg Gly Leu Asn Cys Glu
310                 315                 320                 325 cag tgt cag gat ttc tat cag gac ctt ccc tgg cac cct gca gag gac    1064
Gln Cys Gln Asp Phe Tyr Gln Asp Leu Pro Trp His Pro Ala Glu Asp
                330                 335                 340 ggc cat act cac gcc tgt cgg aag tgt gag tgc aac ggg cat act cat    1112
Gly His Thr His Ala Cys Arg Lys Cys Glu Cys Asn Gly His Thr His
            345                 350                 355 agc tgc cac ttt gac atg gct gtc tac ctg gca tct gga aat gta agt    1160
Ser Cys His Phe Asp Met Ala Val Tyr Leu Ala Ser Gly Asn Val Ser
        360                 365                 370 gga ggc gta tgc gat ggg tgt cag cac aac aca gct ggg cgc cat tgt    1208
Gly Gly Val Cys Asp Gly Cys Gln His Asn Thr Ala Gly Arg His Cys
    375                 380                 385 gag ttc tgc cgg ccc ttc ttc tac cgt gac ccc acc aag gac atg cgg    1256
Glu Phe Cys Arg Pro Phe Phe Tyr Arg Asp Pro Thr Lys Asp Met Arg
390                 395                 400                 405 gac cca gct gtg tgc cgt cct tgt gac tgt gac cct atg ggt tct caa    1304
Asp Pro Ala Val Cys Arg Pro Cys Asp Cys Asp Pro Met Gly Ser Gln
                410                 415                 420 gat ggt ggt cgc tgt gat tct cat gat gac cct gtg cta gga ctg gtc    1352
Asp Gly Gly Arg Cys Asp Ser His Asp Asp Pro Val Leu Gly Leu Val
            425                 430                 435 tca ggc cag tgt cgc tgc aaa gaa cac gtg gtt ggc act cgc tgc cag    1400
Ser Gly Gln Cys Arg Cys Lys Glu His Val Val Gly Thr Arg Cys Gln
        440                 445                 450 caa tgc cgt gat ggc ttc ttt gga ctt agt gcc agt gac cct cga ggg    1448
Gln Cys Arg Asp Gly Phe Phe Gly Leu Ser Ala Ser Asp Pro Arg Gly
    455                 460                 465 tgc cag cgt tgc cag tgt aat tca cgg ggc aca gtg cct ggg agc tcc    1496
Cys Gln Arg Cys Gln Cys Asn Ser Arg Gly Thr Val Pro Gly Ser Ser
470                 475                 480                 485 cct tgt gac tcc agt agt gga acc tgt ttc tgc aag cgt ctg gtg acc    1544
Pro Cys Asp Ser Ser Ser Gly Thr Cys Phe Cys Lys Arg Leu Val Thr
                490                 495                 500 gga cat ggc tgt gac cgc tgt ctg cct ggc cac tgg ggc ctg agc cat    1592
Gly His Gly Cys Asp Arg Cys Leu Pro Gly His Trp Gly Leu Ser His
            505                 510                 515 gac ctg ctg ggc tgc cgt ccc tgt gac tgt gat gtg ggc ggt gcc ttg    1640
Asp Leu Leu Gly Cys Arg Pro Cys Asp Cys Asp Val Gly Gly Ala Leu
        520                 525                 530 gat cct cag tgt gat gag gcc acc ggt cag tgc cgc tgc cgc caa cac    1688
Asp Pro Gln Cys Asp Glu Ala Thr Gly Gln Cys Arg Cys Arg Gln His
    535                 540                 545 atg att ggg cgg cgc tgc gaa caa gtg cag cct ggc tac ttc cgg cct    1736
Met Ile Gly Arg Arg Cys Glu Gln Val Gln Pro Gly Tyr Phe Arg Pro
550                 555                 560                 565 ttt ctg gac cat tta acc tgg gag gct gag gct gcc caa ggg cag ggg    1784
Phe Leu Asp His Leu Thr Trp Glu Ala Glu Ala Ala Gln Gly Gln Gly
                570                 575                 580 ctt gag gtg gta gag cgg ctg gtg acc aac cga gag act ccg tcc tgg    1832
Leu Glu Val Val Glu Arg Leu Val Thr Asn Arg Glu Thr Pro Ser Trp
            585                 590                 595 act ggc cca ggc ttt gtg cgg ctg cga gaa ggt cag gaa gtg gag ttc    1880
```

```
                                        -continued

Thr Gly Pro Gly Phe Val Arg Leu Arg Glu Gly Gln Glu Val Glu Phe
        600                 605                 610 ctg gtg acc tct ttg cct agg gcc atg gac tat gac ctg cta ctg cgc    1928
Leu Val Thr Ser Leu Pro Arg Ala Met Asp Tyr Asp Leu Leu Leu Arg
        615                 620                 625 tgg gag ccc cag gtc cct gag caa tgg gca gag ctg gaa ctg atg gtg    1976
Trp Glu Pro Gln Val Pro Glu Gln Trp Ala Glu Leu Glu Leu Met Val
630                 635                 640                 645 cag cgt ccg ggg cct gtg tct gct cac agt ccg tgc ggg cat gtg ctg    2024
Gln Arg Pro Gly Pro Val Ser Ala His Ser Pro Cys Gly His Val Leu
                650                 655                 660 cct aag gat gac cgc att cag ggg atg ctt cac cca aac acc agg ttt    2072
Pro Lys Asp Asp Arg Ile Gln Gly Met Leu His Pro Asn Thr Arg Phe
            665                 670                 675 ttg gtg ttt ccc aga cct gtc tgc ctt gag cct ggc atc tcc tac aag    2120
Leu Val Phe Pro Arg Pro Val Cys Leu Glu Pro Gly Ile Ser Tyr Lys
        680                 685                 690 ctg aag ctg aaa ctg atc gga aca ggg gga cga gcc cag cct gaa acc    2168
Leu Lys Leu Lys Leu Ile Gly Thr Gly Gly Arg Ala Gln Pro Glu Thr
    695                 700                 705 tcc tac tct gga tta ctc att gac tcg ctg gtc ctg cag ccc cac gtc    2216
Ser Tyr Ser Gly Leu Leu Ile Asp Ser Leu Val Leu Gln Pro His Val
710                 715                 720                 725 ttg gtg cta gag atg ttt agt ggg ggc gat gct gct gct ctg gag cgc    2264
Leu Val Leu Glu Met Phe Ser Gly Gly Asp Ala Ala Ala Leu Glu Arg
                730                 735                 740 cgt acc acc ttt gaa cgc tac cgc tgc cat gag gaa ggt ctg atg ccc    2312
Arg Thr Thr Phe Glu Arg Tyr Arg Cys His Glu Glu Gly Leu Met Pro
            745                 750                 755 agc aag gcc cct cta tct gag acc tgt gcc ccc ctc ctc atc agc gtg    2360
Ser Lys Ala Pro Leu Ser Glu Thr Cys Ala Pro Leu Leu Ile Ser Val
        760                 765                 770 tcc gcc ttg atc tac aat ggc gcc ttg cca tgt cag tgt gac cct caa    2408
Ser Ala Leu Ile Tyr Asn Gly Ala Leu Pro Cys Gln Cys Asp Pro Gln
    775                 780                 785 ggc tca ctg agt tct gaa tgc agt cct cac ggt ggc cag tgc cgg tgc    2456
Gly Ser Leu Ser Ser Glu Cys Ser Pro His Gly Gly Gln Cys Arg Cys
790                 795                 800                 805 aaa cct gga gtg gtt gga cgc cgt tgt gat gtc tgt gct act ggc tac    2504
Lys Pro Gly Val Val Gly Arg Arg Cys Asp Val Cys Ala Thr Gly Tyr
                810                 815                 820 tat ggc ttt ggc cct gca ggc tgt caa gcc tgc cag tgt agt cct gat    2552
Tyr Gly Phe Gly Pro Ala Gly Cys Gln Ala Cys Gln Cys Ser Pro Asp
            825                 830                 835 gga gca ctc agt gcc ctc tgt gaa ggg act agt gga cag tgc ccc tgc    2600
Gly Ala Leu Ser Ala Leu Cys Glu Gly Thr Ser Gly Gln Cys Pro Cys
        840                 845                 850 cga cct ggt gcc ttt ggt ctt cgc tgt gac cac tgt caa cgt ggc cag    2648
Arg Pro Gly Ala Phe Gly Leu Arg Cys Asp His Cys Gln Arg Gly Gln
    855                 860                 865 tgg gga ttc cct aat tgc cgg ccg tgt gtc tgc aat ggg cgt gcg gat    2696
Trp Gly Phe Pro Asn Cys Arg Pro Cys Val Cys Asn Gly Arg Ala Asp
870                 875                 880                 885 gag tgt gat acc cac aca ggc gct tgc ctg ggc tgc cgt gat tac acg    2744
Glu Cys Asp Thr His Thr Gly Ala Cys Leu Gly Cys Arg Asp Tyr Thr
                890                 895                 900 ggg ggc gag cac tgt gaa agg tgc att gct ggt ttt cat ggg gac cca    2792
Gly Gly Glu His Cys Glu Arg Cys Ile Ala Gly Phe His Gly Asp Pro
            905                 910                 915
```

```
cgg ctg cca tat ggg ggc cag tgc cgg cct tgt ccc tgc cct gaa ggc    2840
Arg Leu Pro Tyr Gly Gly Gln Cys Arg Pro Cys Pro Cys Pro Glu Gly
            920                 925                 930 cct ggg agc cag cga cac ttt gct act tct tgc cac cgg gat gga tat    2888
Pro Gly Ser Gln Arg His Phe Ala Thr Ser Cys His Arg Asp Gly Tyr
    935                 940                 945 tcc cag caa att gtg tgc cag tgt cga gaa ggc tac aca ggg ctt cgg    2936
Ser Gln Gln Ile Val Cys Gln Cys Arg Glu Gly Tyr Thr Gly Leu Arg
950                 955                 960                 965 tgt gaa gct tgt gcc ccc ggg cac ttt ggg gac cca tca aag cca ggt    2984
Cys Glu Ala Cys Ala Pro Gly His Phe Gly Asp Pro Ser Lys Pro Gly
                970                 975                 980 ggc agg tgc caa ctg tgt gag tgc agt gga aac att gat ccc atg gac    3032
Gly Arg Cys Gln Leu Cys Glu Cys Ser Gly Asn Ile Asp Pro Met Asp
            985                 990                 995 cct gat gcc tgt gat ccc cac acg ggg caa tgc ttg cgt tgt tta        3077
Pro Asp Ala Cys Asp Pro His Thr Gly Gln Cys Leu Arg Cys Leu
        1000                1005                1010 cac aac aca gag ggg ccc cac tgt ggc tat tgc aag cct ggc ttc        3122
His Asn Thr Glu Gly Pro His Cys Gly Tyr Cys Lys Pro Gly Phe
        1015                1020                1025 cat ggg caa gct gcc cga cag agc tgt cac cgc tgt acc tgc aac        3167
His Gly Gln Ala Ala Arg Gln Ser Cys His Arg Cys Thr Cys Asn
        1030                1035                1040 ctt ctg ggc aca gat ccc agg cgg tgc cca tct acc gac ctg tgc        3212
Leu Leu Gly Thr Asp Pro Arg Arg Cys Pro Ser Thr Asp Leu Cys
        1045                1050                1055 cat tgt gac cca agc act ggg cag tgc cca tgc ctt ccc cat gtc        3257
His Cys Asp Pro Ser Thr Gly Gln Cys Pro Cys Leu Pro His Val
        1060                1065                1070 caa ggc ctc aac tgt gac cat tgt gcc ccc aac ttt tgg aac ttc        3302
Gln Gly Leu Asn Cys Asp His Cys Ala Pro Asn Phe Trp Asn Phe
        1075                1080                1085 acc agt ggc cgt ggc tgc cag cct tgt gct tgt cac cca agc cgg        3347
Thr Ser Gly Arg Gly Cys Gln Pro Cys Ala Cys His Pro Ser Arg
        1090                1095                1100 gcc aga ggc cct acc tgc aat gag ttc aca ggg cag tgt cac tgt        3392
Ala Arg Gly Pro Thr Cys Asn Glu Phe Thr Gly Gln Cys His Cys
        1105                1110                1115 cat gct ggc ttt ggt ggg agg act tgt tct gag tgc caa gag ctc        3437
His Ala Gly Phe Gly Gly Arg Thr Cys Ser Glu Cys Gln Glu Leu
        1120                1125                1130 tac tgg gga gac cct ggt ctg cag tgc cgt gcc tgt gac tgt gat        3482
Tyr Trp Gly Asp Pro Gly Leu Gln Cys Arg Ala Cys Asp Cys Asp
        1135                1140                1145 cct aga gga ata gac aaa cct cag tgt cat cgt tcc aca ggc cac        3527
Pro Arg Gly Ile Asp Lys Pro Gln Cys His Arg Ser Thr Gly His
        1150                1155                1160 tgt agc tgc cgc cca ggc gtg tct ggt gtg cgc tgt gac cag tgt        3572
Cys Ser Cys Arg Pro Gly Val Ser Gly Val Arg Cys Asp Gln Cys
        1165                1170                1175 gct cgt ggc ttc tca ggg gtt ttt cct gct tgt cac ccc tgc cac        3617
Ala Arg Gly Phe Ser Gly Val Phe Pro Ala Cys His Pro Cys His
        1180                1185                1190 gct tgc ttt gga gac tgg gat cgt gtg gta cag gac ctg gct gct        3662
Ala Cys Phe Gly Asp Trp Asp Arg Val Val Gln Asp Leu Ala Ala
        1195                1200                1205 cgg acg cgg cgc ctg gag cag tgg gct cag gag ttg cag caa aca        3707
Arg Thr Arg Arg Leu Glu Gln Trp Ala Gln Glu Leu Gln Gln Thr
        1210                1215                1220
```

```
gga gtg ctg ggt gcc ttt gag agc agc ttt ttg aac atg cag ggg        3752
Gly Val Leu Gly Ala Phe Glu Ser Ser Phe Leu Asn Met Gln Gly
        1225                1230                1235 aag cta ggc atg gtg cag gcc att atg agt gcc cgc aat gcc tca        3797
Lys Leu Gly Met Val Gln Ala Ile Met Ser Ala Arg Asn Ala Ser
    1240                1245                1250 gcc gcc tct acg gcg aag ctt gta gag gcc aca gag gga cta cgt        3842
Ala Ala Ser Thr Ala Lys Leu Val Glu Ala Thr Glu Gly Leu Arg
        1255                1260                1265 cat gaa atc ggg aag acc acc gag cgc ctg act cag tta gaa gca        3887
His Glu Ile Gly Lys Thr Thr Glu Arg Leu Thr Gln Leu Glu Ala
        1270                1275                1280 gag cta aca gct gtg cag gat gag aac ttc aat gcc aac cat gca        3932
Glu Leu Thr Ala Val Gln Asp Glu Asn Phe Asn Ala Asn His Ala
        1285                1290                1295 ctc agt ggt ctg gag aga gac ggg ctt gcg ctt aat ctc acc ctg        3977
Leu Ser Gly Leu Glu Arg Asp Gly Leu Ala Leu Asn Leu Thr Leu
        1300                1305                1310 agg cag ctg gat cag cat ctg gag atc ctc aaa cat tca aat ttc        4022
Arg Gln Leu Asp Gln His Leu Glu Ile Leu Lys His Ser Asn Phe
        1315                1320                1325 tta ggt gcc tat gac agc atc cga cat gcc cac agc cag tcc aca        4067
Leu Gly Ala Tyr Asp Ser Ile Arg His Ala His Ser Gln Ser Thr
        1330                1335                1340 gag gca gag cgc cgt gcc aac gcc tcc acc ttt gca gta ccc agc        4112
Glu Ala Glu Arg Arg Ala Asn Ala Ser Thr Phe Ala Val Pro Ser
        1345                1350                1355 cct gtg agc aac tca gca gat acc cgg cgt cgg acg gaa gtg cta        4157
Pro Val Ser Asn Ser Ala Asp Thr Arg Arg Arg Thr Glu Val Leu
        1360                1365                1370 atg ggt gcc caa aaa gaa aac ttc aac cgc caa cat ttg gcc aac        4202
Met Gly Ala Gln Lys Glu Asn Phe Asn Arg Gln His Leu Ala Asn
        1375                1380                1385 cag cag gca ctg gga cgg ctc tct gca cat gcc cac acc ctg agc        4247
Gln Gln Ala Leu Gly Arg Leu Ser Ala His Ala His Thr Leu Ser
        1390                1395                1400 ctg acg ggc ata aat gag ttg gtg tgt ggg gca cca ggg gac gca        4292
Leu Thr Gly Ile Asn Glu Leu Val Cys Gly Ala Pro Gly Asp Ala
        1405                1410                1415 ccc tgt gcc acc agc cct tgt ggg ggt gcc gga tgt cgg gat gaa        4337
Pro Cys Ala Thr Ser Pro Cys Gly Gly Ala Gly Cys Arg Asp Glu
        1420                1425                1430 gat ggg cag ccc cgt tgt ggt ggc ctc ggt tgc agt ggg gca gca        4382
Asp Gly Gln Pro Arg Cys Gly Gly Leu Gly Cys Ser Gly Ala Ala
        1435                1440                1445 gcc acg gca gat cta gcg ctg ggc cgg gct cgg cac acg cag gca        4427
Ala Thr Ala Asp Leu Ala Leu Gly Arg Ala Arg His Thr Gln Ala
        1450                1455                1460 gag ctg cag cgg gca ctg gta gaa ggt ggc ggc atc ctc agc cgg        4472
Glu Leu Gln Arg Ala Leu Val Glu Gly Gly Gly Ile Leu Ser Arg
        1465                1470                1475 gtg tct gag act cgt cgg cag gca gaa gag gca cag cag cga gca        4517
Val Ser Glu Thr Arg Arg Gln Ala Glu Glu Ala Gln Gln Arg Ala
        1480                1485                1490 cag gca gcc ctg gac aag gct aat gct tcc agg ggc cag gtg gaa        4562
Gln Ala Ala Leu Asp Lys Ala Asn Ala Ser Arg Gly Gln Val Glu
        1495                1500                1505 cag gcc aat cag gag ctt cga gaa ctt atc cag aat gtg aaa gac        4607
Gln Ala Asn Gln Glu Leu Arg Glu Leu Ile Gln Asn Val Lys Asp
```

```
                1510                1515                1520
ttc ctc agc cag gag gga gcc gat cct gac agt att gaa atg gta        4652
Phe Leu Ser Gln Glu Gly Ala Asp Pro Asp Ser Ile Glu Met Val
        1525                1530                1535 gcg act cgg gtg cta gac atc tcc atc ccg gcc tca ccc gag cag        4697
Ala Thr Arg Val Leu Asp Ile Ser Ile Pro Ala Ser Pro Glu Gln
        1540                1545                1550 atc cag cgc cta gcc agt gag att gca gaa cgc gtc cga agc ctg        4742
Ile Gln Arg Leu Ala Ser Glu Ile Ala Glu Arg Val Arg Ser Leu
        1555                1560                1565 gcc gac gtg gac aca atc ctg gcc cat acc atg ggc gac gtg cgt        4787
Ala Asp Val Asp Thr Ile Leu Ala His Thr Met Gly Asp Val Arg
        1570                1575                1580 cgg gct gaa cag cta ctg caa gat gcg cac cgg gca cgg agc cgg        4832
Arg Ala Glu Gln Leu Leu Gln Asp Ala His Arg Ala Arg Ser Arg
        1585                1590                1595 gcc gag ggt gag aga cag aag gca gag aca gtc caa gcg gca ctg        4877
Ala Glu Gly Glu Arg Gln Lys Ala Glu Thr Val Gln Ala Ala Leu
        1600                1605                1610 gag gag gct cag agg gca caa gga gct gct cag ggt gcc atc tgg        4922
Glu Glu Ala Gln Arg Ala Gln Gly Ala Ala Gln Gly Ala Ile Trp
        1615                1620                1625 gga gca gtg gtt gac aca caa aac aca gag cag acc ctg cag cgg        4967
Gly Ala Val Val Asp Thr Gln Asn Thr Glu Gln Thr Leu Gln Arg
        1630                1635                1640 gtc cag gag agg atg gca ggt gca gag aag tct ctg aac tct gcc        5012
Val Gln Glu Arg Met Ala Gly Ala Glu Lys Ser Leu Asn Ser Ala
        1645                1650                1655 ggt gag cgg gct cgg caa tta gac gcc ctc ctg gag gcc ctg aaa        5057
Gly Glu Arg Ala Arg Gln Leu Asp Ala Leu Leu Glu Ala Leu Lys
        1660                1665                1670 ctg aaa cgg gca gga aat agc ctg gca gca tct aca gcg gaa gaa        5102
Leu Lys Arg Ala Gly Asn Ser Leu Ala Ala Ser Thr Ala Glu Glu
        1675                1680                1685 aca gca ggc agt gcc cag agc cgt gcc agg gag gct gag aaa caa        5147
Thr Ala Gly Ser Ala Gln Ser Arg Ala Arg Glu Ala Glu Lys Gln
        1690                1695                1700 cta cgg gaa caa gta ggt gac caa tac caa aca gtg agg gcg ttg        5192
Leu Arg Glu Gln Val Gly Asp Gln Tyr Gln Thr Val Arg Ala Leu
        1705                1710                1715 gca gag cgg aag gct gaa ggt gtt ctg gct gca caa gcc agg gca        5237
Ala Glu Arg Lys Ala Glu Gly Val Leu Ala Ala Gln Ala Arg Ala
        1720                1725                1730 gaa caa ctg cgg gat gag gct cgg gac ctg ttg cag gcc gct cag        5282
Glu Gln Leu Arg Asp Glu Ala Arg Asp Leu Leu Gln Ala Ala Gln
        1735                1740                1745 gat aag ctg cag cgg cta cag gag ctg gag ggc aca tat gag gag        5327
Asp Lys Leu Gln Arg Leu Gln Glu Leu Glu Gly Thr Tyr Glu Glu
        1750                1755                1760 aac gag cgt gca ctg gag ggc aaa gcg gcc cag ctg gat ggg ctg        5372
Asn Glu Arg Ala Leu Glu Gly Lys Ala Ala Gln Leu Asp Gly Leu
        1765                1770                1775 gaa gcc agg atg cgc agt gtg ctc cag gcc atc aac ttg cag gtc        5417
Glu Ala Arg Met Arg Ser Val Leu Gln Ala Ile Asn Leu Gln Val
        1780                1785                1790 cag atc tac aac acc tgc cag tga ccactccta gggcctagcc ttgtcgccaa    5471
Gln Ile Tyr Asn Thr Cys Gln
        1795 gcactgttct gcacacgatc gtccgcacat taaagagctc ctggctagca agagctttca  5531
```
ataaacctgt gtgaacctca aaaaaaaaaa aaaaaaaaaa aaaaaaaaaa aa        5583

<210> SEQ ID NO 8
<211> LENGTH: 1799
<212> TYPE: PRT
<213> ORGANISM: Mus musculus

<400> SEQUENCE: 8

```
Met Glu Trp Ala Ser Gly Glu Pro Gly Arg Gly Gln Gly Gln Pro
 1               5                  10                  15

Leu Pro Trp Glu Leu Arg Leu Gly Leu Leu Ser Val Leu Ala Ala
                20                  25                  30

Thr Leu Ala Gln Ala Pro Ser Leu Asp Val Pro Gly Cys Ser Arg Gly
            35                  40                  45

Ser Cys Tyr Pro Ala Thr Gly Asp Leu Leu Val Gly Arg Ala Asp Arg
        50                  55                  60

Leu Thr Ala Ser Ser Thr Cys Gly Leu His Ser Pro Gln Pro Tyr Cys
65                  70                  75                  80

Ile Val Ser His Leu Gln Asp Glu Lys Lys Cys Phe Leu Cys Asp Ser
                85                  90                  95

Arg Arg Pro Phe Ser Ala Arg Asp Asn Pro Asn Ser His Arg Ile Gln
                100                 105                 110

Asn Val Val Thr Ser Phe Ala Pro Gln Arg Arg Thr Ala Trp Trp Gln
            115                 120                 125

Ser Glu Asn Gly Val Pro Met Val Thr Ile Gln Leu Asp Leu Glu Ala
        130                 135                 140

Glu Phe His Phe Thr His Leu Ile Met Thr Phe Lys Thr Phe Arg Pro
145                 150                 155                 160

Ala Ala Met Leu Val Glu Arg Ser Ala Asp Phe Gly Arg Thr Trp His
                165                 170                 175

Val Tyr Arg Tyr Phe Ser Tyr Asp Cys Gly Ala Asp Phe Pro Gly Ile
                180                 185                 190

Pro Leu Ala Pro Pro Arg Arg Trp Asp Asp Val Val Cys Glu Ser Arg
            195                 200                 205

Tyr Ser Glu Ile Glu Pro Ser Thr Glu Gly Glu Val Ile Tyr Arg Val
        210                 215                 220

Leu Asp Pro Ala Ile Pro Ile Pro Asp Pro Tyr Ser Ser Arg Ile Gln
225                 230                 235                 240

Asn Leu Leu Lys Ile Thr Asn Leu Arg Val Asn Leu Thr Arg Leu His
                245                 250                 255

Thr Leu Gly Asp Asn Leu Leu Asp Pro Arg Arg Glu Ile Arg Glu Lys
            260                 265                 270

Tyr Tyr Tyr Ala Leu Tyr Glu Leu Val Ile Arg Gly Asn Cys Phe Cys
        275                 280                 285

Tyr Gly His Ala Ser Gln Cys Ala Pro Ala Pro Gly Ala Pro Ala His
    290                 295                 300

Ala Glu Gly Met Val His Gly Ala Cys Ile Cys Lys His Asn Thr Arg
305                 310                 315                 320

Gly Leu Asn Cys Glu Gln Cys Gln Asp Phe Tyr Gln Asp Leu Pro Trp
                325                 330                 335

His Pro Ala Glu Asp Gly His Thr His Ala Cys Arg Lys Cys Glu Cys
            340                 345                 350

Asn Gly His Thr His Ser Cys His Phe Asp Met Ala Val Tyr Leu Ala
        355                 360                 365
```

-continued

```
Ser Gly Asn Val Ser Gly Val Cys Asp Gly Cys Gln His Asn Thr
    370                 375                 380
Ala Gly Arg His Cys Glu Phe Cys Arg Pro Phe Phe Tyr Arg Asp Pro
385                 390                 395                 400
Thr Lys Asp Met Arg Asp Pro Ala Val Cys Arg Pro Cys Asp Cys Asp
                405                 410                 415
Pro Met Gly Ser Gln Asp Gly Gly Arg Cys Asp Ser His Asp Asp Pro
                420                 425                 430
Val Leu Gly Leu Val Ser Gly Gln Cys Arg Cys Lys Glu His Val Val
            435                 440                 445
Gly Thr Arg Cys Gln Gln Cys Arg Asp Gly Phe Phe Gly Leu Ser Ala
        450                 455                 460
Ser Asp Pro Arg Gly Cys Gln Arg Cys Gln Cys Asn Ser Arg Gly Thr
465                 470                 475                 480
Val Pro Gly Ser Ser Pro Cys Asp Ser Ser Gly Thr Cys Phe Cys
                485                 490                 495
Lys Arg Leu Val Thr Gly His Gly Cys Asp Arg Cys Leu Pro Gly His
            500                 505                 510
Trp Gly Leu Ser His Asp Leu Leu Gly Cys Arg Pro Cys Asp Cys Asp
        515                 520                 525
Val Gly Gly Ala Leu Asp Pro Gln Cys Asp Glu Ala Thr Gly Gln Cys
    530                 535                 540
Arg Cys Arg Gln His Met Ile Gly Arg Arg Cys Glu Gln Val Gln Pro
545                 550                 555                 560
Gly Tyr Phe Arg Pro Phe Leu Asp His Leu Thr Trp Glu Ala Glu Ala
                565                 570                 575
Ala Gln Gly Gln Gly Leu Glu Val Val Glu Arg Leu Val Thr Asn Arg
                580                 585                 590
Glu Thr Pro Ser Trp Thr Gly Pro Gly Phe Val Arg Leu Arg Glu Gly
            595                 600                 605
Gln Glu Val Glu Phe Leu Val Thr Ser Leu Pro Arg Ala Met Asp Tyr
        610                 615                 620
Asp Leu Leu Leu Arg Trp Glu Pro Gln Val Pro Glu Gln Trp Ala Glu
625                 630                 635                 640
Leu Glu Leu Met Val Gln Arg Pro Gly Pro Val Ser Ala His Ser Pro
                645                 650                 655
Cys Gly His Val Leu Pro Lys Asp Asp Arg Ile Gln Gly Met Leu His
                660                 665                 670
Pro Asn Thr Arg Phe Leu Val Phe Pro Arg Pro Val Cys Leu Glu Pro
            675                 680                 685
Gly Ile Ser Tyr Lys Leu Lys Leu Lys Leu Ile Gly Thr Gly Gly Arg
        690                 695                 700
Ala Gln Pro Glu Thr Ser Tyr Ser Gly Leu Leu Ile Asp Ser Leu Val
705                 710                 715                 720
Leu Gln Pro His Val Leu Val Leu Glu Met Phe Ser Gly Gly Asp Ala
                725                 730                 735
Ala Ala Leu Glu Arg Arg Thr Thr Phe Glu Arg Tyr Arg Cys His Glu
                740                 745                 750
Glu Gly Leu Met Pro Ser Lys Ala Pro Leu Ser Glu Thr Cys Ala Pro
            755                 760                 765
Leu Leu Ile Ser Val Ser Ala Leu Ile Tyr Asn Gly Ala Leu Pro Cys
        770                 775                 780
```

-continued

```
Gln Cys Asp Pro Gln Gly Ser Leu Ser Ser Glu Cys Ser Pro His Gly
785                 790                 795                 800
Gly Gln Cys Arg Cys Lys Pro Gly Val Val Gly Arg Arg Cys Asp Val
            805                 810                 815
Cys Ala Thr Gly Tyr Tyr Gly Phe Gly Pro Ala Gly Cys Gln Ala Cys
        820                 825                 830
Gln Cys Ser Pro Asp Gly Ala Leu Ser Ala Leu Cys Glu Gly Thr Ser
    835                 840                 845
Gly Gln Cys Pro Cys Arg Pro Gly Ala Phe Gly Leu Arg Cys Asp His
850                 855                 860
Cys Gln Arg Gly Gln Trp Gly Phe Pro Asn Cys Arg Pro Cys Val Cys
865                 870                 875                 880
Asn Gly Arg Ala Asp Glu Cys Asp Thr His Thr Gly Ala Cys Leu Gly
            885                 890                 895
Cys Arg Asp Tyr Thr Gly Gly Glu His Cys Glu Arg Cys Ile Ala Gly
        900                 905                 910
Phe His Gly Asp Pro Arg Leu Pro Tyr Gly Gly Gln Cys Arg Pro Cys
    915                 920                 925
Pro Cys Pro Glu Gly Pro Gly Ser Gln Arg His Phe Ala Thr Ser Cys
930                 935                 940
His Arg Asp Gly Tyr Ser Gln Gln Ile Val Cys Gln Cys Arg Glu Gly
945                 950                 955                 960
Tyr Thr Gly Leu Arg Cys Glu Ala Cys Ala Pro Gly His Phe Gly Asp
            965                 970                 975
Pro Ser Lys Pro Gly Gly Arg Cys Gln Leu Cys Glu Cys Ser Gly Asn
        980                 985                 990
Ile Asp Pro Met Asp Pro Asp Ala  Cys Asp Pro His Thr Gly Gln Cys
    995                 1000                1005
Leu Arg Cys Leu His Asn Thr  Glu Gly Pro His Cys  Gly Tyr Cys
    1010                1015                1020
Lys Pro Gly Phe His Gly Gln  Ala Ala Arg Gln Ser  Cys His Arg
    1025                1030                1035
Cys Thr Cys Asn Leu Leu Gly  Thr Asp Pro Arg Arg  Cys Pro Ser
    1040                1045                1050
Thr Asp Leu Cys His Cys Asp  Pro Ser Thr Gly Gln  Cys Pro Cys
    1055                1060                1065
Leu Pro His Val Gln Gly Leu  Asn Cys Asp His Cys  Ala Pro Asn
    1070                1075                1080
Phe Trp Asn Phe Thr Ser Gly  Arg Gly Cys Gln Pro  Cys Ala Cys
    1085                1090                1095
His Pro Ser Arg Ala Arg Gly  Pro Thr Cys Asn Glu  Phe Thr Gly
    1100                1105                1110
Gln Cys His Cys His Ala Gly  Phe Gly Gly Arg Thr  Cys Ser Glu
    1115                1120                1125
Cys Gln Glu Leu Tyr Trp Gly  Asp Pro Gly Leu Gln  Cys Arg Ala
    1130                1135                1140
Cys Asp Cys Asp Pro Arg Gly  Ile Asp Lys Pro Gln  Cys His Arg
    1145                1150                1155
Ser Thr Gly His Cys Ser Cys  Arg Pro Gly Val Ser  Gly Val Arg
    1160                1165                1170
Cys Asp Gln Cys Ala Arg Gly  Phe Ser Gly Val Phe  Pro Ala Cys
    1175                1180                1185
His Pro Cys His Ala Cys Phe  Gly Asp Trp Asp Arg  Val Val Gln
```

```
            1190                1195                1200

Asp Leu Ala Ala Arg Thr Arg  Arg Leu Glu Gln Trp  Ala Gln Glu
        1205                 1210                 1215

Leu Gln Gln Thr Gly Val Leu  Gly Ala Phe Glu Ser  Ser Phe Leu
        1220                 1225                 1230

Asn Met Gln Gly Lys Leu Gly  Met Val Gln Ala Ile  Met Ser Ala
        1235                 1240                 1245

Arg Asn Ala Ser Ala Ala Ser  Thr Ala Lys Leu Val  Glu Ala Thr
        1250                 1255                 1260

Glu Gly Leu Arg His Glu Ile  Gly Lys Thr Thr Glu  Arg Leu Thr
        1265                 1270                 1275

Gln Leu Glu Ala Glu Leu Thr  Ala Val Gln Asp Glu  Asn Phe Asn
        1280                 1285                 1290

Ala Asn His Ala Leu Ser Gly  Leu Glu Arg Asp Gly  Leu Ala Leu
        1295                 1300                 1305

Asn Leu Thr Leu Arg Gln Leu  Asp Gln His Leu Glu  Ile Leu Lys
        1310                 1315                 1320

His Ser Asn Phe Leu Gly Ala  Tyr Asp Ser Ile Arg  His Ala His
        1325                 1330                 1335

Ser Gln Ser Thr Glu Ala Glu  Arg Arg Ala Asn Ala  Ser Thr Phe
        1340                 1345                 1350

Ala Val Pro Ser Pro Val Ser  Asn Ser Ala Asp Thr  Arg Arg Arg
        1355                 1360                 1365

Thr Glu Val Leu Met Gly Ala  Gln Lys Glu Asn Phe  Asn Arg Gln
        1370                 1375                 1380

His Leu Ala Asn Gln Gln Ala  Leu Gly Arg Leu Ser  Ala His Ala
        1385                 1390                 1395

His Thr Leu Ser Leu Thr Gly  Ile Asn Glu Leu Val  Cys Gly Ala
        1400                 1405                 1410

Pro Gly Asp Ala Pro Cys Ala  Thr Ser Pro Cys Gly  Gly Ala Gly
        1415                 1420                 1425

Cys Arg Asp Glu Asp Gly Gln  Pro Arg Cys Gly Gly  Leu Gly Cys
        1430                 1435                 1440

Ser Gly Ala Ala Ala Thr Ala  Asp Leu Ala Leu Gly  Arg Ala Arg
        1445                 1450                 1455

His Thr Gln Ala Glu Leu Gln  Arg Ala Leu Val Glu  Gly Gly Gly
        1460                 1465                 1470

Ile Leu Ser Arg Val Ser Glu  Thr Arg Gln Ala Glu  Glu Ala
        1475                 1480                 1485

Gln Gln Arg Ala Gln Ala Ala  Leu Asp Lys Ala Asn  Ala Ser Arg
        1490                 1495                 1500

Gly Gln Val Glu Gln Ala Asn  Gln Glu Leu Arg Glu  Leu Ile Gln
        1505                 1510                 1515

Asn Val Lys Asp Phe Leu Ser  Gln Glu Gly Ala Asp  Pro Asp Ser
        1520                 1525                 1530

Ile Glu Met Val Ala Thr Arg  Val Leu Asp Ile Ser  Ile Pro Ala
        1535                 1540                 1545

Ser Pro Glu Gln Ile Gln Arg  Leu Ala Ser Glu Ile  Ala Glu Arg
        1550                 1555                 1560

Val Arg Ser Leu Ala Asp Val  Asp Thr Ile Leu Ala  His Thr Met
        1565                 1570                 1575

Gly Asp Val Arg Ala Glu Gln  Leu Leu Gln Asp Ala  His Arg
        1580                 1585                 1590
```

```
Ala Arg  Ser Arg Ala Glu  Gly Glu Arg Gln Lys  Ala Glu Thr Val
    1595             1600              1605

Gln Ala  Ala Leu Glu Glu  Ala Gln Arg Ala Gln  Gly Ala Ala Gln
    1610             1615              1620

Gly Ala  Ile Trp Gly Ala  Val Val Asp Thr Gln  Asn Thr Glu Gln
    1625             1630              1635

Thr Leu  Gln Arg Val Gln  Glu Arg Met Ala Gly  Ala Glu Lys Ser
    1640             1645              1650

Leu Asn  Ser Ala Gly Glu  Arg Ala Arg Gln Leu  Asp Ala Leu Leu
    1655             1660              1665

Glu Ala  Leu Lys Leu Lys  Arg Ala Gly Asn Ser  Leu Ala Ala Ser
    1670             1675              1680

Thr Ala  Glu Glu Thr Ala  Gly Ser Ala Gln Ser  Arg Ala Arg Glu
    1685             1690              1695

Ala Glu  Lys Gln Leu Arg  Glu Gln Val Gly Asp  Gln Tyr Gln Thr
    1700             1705              1710

Val Arg  Ala Leu Ala Glu  Arg Lys Ala Glu Gly  Val Leu Ala Ala
    1715             1720              1725

Gln Ala  Arg Ala Glu Gln  Leu Arg Asp Glu Ala  Arg Asp Leu Leu
    1730             1735              1740

Gln Ala  Ala Gln Asp Lys  Leu Gln Arg Leu Gln  Glu Leu Glu Gly
    1745             1750              1755

Thr Tyr  Glu Glu Asn Glu  Arg Ala Leu Glu Gly  Lys Ala Ala Gln
    1760             1765              1770

Leu Asp  Gly Leu Glu Ala  Arg Met Arg Ser Val  Leu Gln Ala Ile
    1775             1780              1785

Asn Leu  Gln Val Gln Ile  Tyr Asn Thr Cys Gln
    1790             1795

<210> SEQ ID NO 9
<211> LENGTH: 5153
<212> TYPE: DNA
<213> ORGANISM: Mus musculus
<220> FEATURE:
<221> NAME/KEY: CDS
<222> LOCATION: (1)..(1476)
<223> OTHER INFORMATION: laminin 12 gamma 3 chain

<400> SEQUENCE: 9 atg gct gta tcc agg gtc ctg tcc ctc ctg gca acg gtg gca tcg atg        48
Met Ala Val Ser Arg Val Leu Ser Leu Leu Ala Thr Val Ala Ser Met
1               5                   10                  15 gcg ctg gtg att cag gag aca cac ttc gcg gca ggc gcg gac atg ggc        96
Ala Leu Val Ile Gln Glu Thr His Phe Ala Ala Gly Ala Asp Met Gly
            20                  25                  30 tct tgc tac gac ggt gtg gga cgc gca cag cgc tgt ctg cct gag ttc       144
Ser Cys Tyr Asp Gly Val Gly Arg Ala Gln Arg Cys Leu Pro Glu Phe
        35                  40                  45 gag aac gcg gcg ttc ggc cga cgc gcc gag gcc tcc cac acg tgc gga       192
Glu Asn Ala Ala Phe Gly Arg Arg Ala Glu Ala Ser His Thr Cys Gly
    50                  55                  60 cgg ccc ccg gag gac ttc tgt cca cac gtg ggg gca cca ggg gct ggg       240
Arg Pro Pro Glu Asp Phe Cys Pro His Val Gly Ala Pro Gly Ala Gly
65                  70                  75                  80 cta cag tgc cag cgc tgc gac gat gct gac ccc gga cga cgc cac gac       288
Leu Gln Cys Gln Arg Cys Asp Asp Ala Asp Pro Gly Arg Arg His Asp
                85                  90                  95
```

-continued

| | | |
|---|---|---|
| gcc tcc tac ctc aca gac ttc cac agc ccc gat gac agc acc tgg tgg<br>Ala Ser Tyr Leu Thr Asp Phe His Ser Pro Asp Asp Ser Thr Trp Trp<br>100 105 110 | | 336 |
| cag agc cca tcc atg gcc ttc ggg gtg cag tac ccc acc tcg gtt aac<br>Gln Ser Pro Ser Met Ala Phe Gly Val Gln Tyr Pro Thr Ser Val Asn<br>115 120 125 | | 384 |
| ctg acc ttg agc tta ggg aag gcc tat gag att acc tat gtg agg ctg<br>Leu Thr Leu Ser Leu Gly Lys Ala Tyr Glu Ile Thr Tyr Val Arg Leu<br>130 135 140 | | 432 |
| aag ttc cac acc agt cgc cct gag agt ttt gcc atc tac aag cgc acg<br>Lys Phe His Thr Ser Arg Pro Glu Ser Phe Ala Ile Tyr Lys Arg Thr<br>145 150 155 160 | | 480 |
| tac gcc agt ggc ccc tgg gag ccc tac caa tac tac agt gcc tcc tgc<br>Tyr Ala Ser Gly Pro Trp Glu Pro Tyr Gln Tyr Tyr Ser Ala Ser Cys<br>165 170 175 | | 528 |
| cag aaa acc tat ggc cgt cct gag ggc cac tac ctg cga ccg ggc gag<br>Gln Lys Thr Tyr Gly Arg Pro Glu Gly His Tyr Leu Arg Pro Gly Glu<br>180 185 190 | | 576 |
| gat gag agg gtg gcc ttc tgc acc tct gag ttc agt gac atc tcc ccc<br>Asp Glu Arg Val Ala Phe Cys Thr Ser Glu Phe Ser Asp Ile Ser Pro<br>195 200 205 | | 624 |
| ttg aac ggg ggc aac gtg gcc ttc tcc acc ctg gaa ggc cgt ccc agt<br>Leu Asn Gly Gly Asn Val Ala Phe Ser Thr Leu Glu Gly Arg Pro Ser<br>210 215 220 | | 672 |
| gcc tac aac ttt gag gag agc cct gtg ctg cag gag tgg gtc acc agc<br>Ala Tyr Asn Phe Glu Glu Ser Pro Val Leu Gln Glu Trp Val Thr Ser<br>225 230 235 240 | | 720 |
| act gac atc ctg atc tct cta gat cgg ctc aac acg ttt ggg gat gac<br>Thr Asp Ile Leu Ile Ser Leu Asp Arg Leu Asn Thr Phe Gly Asp Asp<br>245 250 255 | | 768 |
| atc ttc aag gac ccc aga gtg ctc cag tct tac tac tac gct gtg tct<br>Ile Phe Lys Asp Pro Arg Val Leu Gln Ser Tyr Tyr Tyr Ala Val Ser<br>260 265 270 | | 816 |
| gac ttc tct gtg ggt ggc agg tgc aaa tgc aat ggt cac gcc agt gaa<br>Asp Phe Ser Val Gly Gly Arg Cys Lys Cys Asn Gly His Ala Ser Glu<br>275 280 285 | | 864 |
| tgc gaa ccc aat gcg gct ggt cag ctg gct tgc cgc tgt cag cac aac<br>Cys Glu Pro Asn Ala Ala Gly Gln Leu Ala Cys Arg Cys Gln His Asn<br>290 295 300 | | 912 |
| acc aca gga gtg gac tgc gag cgt tgt ctg ccc ttc ttc cag gac cgt<br>Thr Thr Gly Val Asp Cys Glu Arg Cys Leu Pro Phe Phe Gln Asp Arg<br>305 310 315 320 | | 960 |
| ccg tgg gcc cga ggc acc gcc gag gat gcc aac gag tgt ctg ccc tgc<br>Pro Trp Ala Arg Gly Thr Ala Glu Asp Ala Asn Glu Cys Leu Pro Cys<br>325 330 335 | | 1008 |
| aac tgc agt ggg cac tct gag gag tgc acg ttt gac agg gag ctc tat<br>Asn Cys Ser Gly His Ser Glu Glu Cys Thr Phe Asp Arg Glu Leu Tyr<br>340 345 350 | | 1056 |
| cgg agc aca ggc cat ggt ggg cac tgt cag cgg tgc cgt gac cac aca<br>Arg Ser Thr Gly His Gly Gly His Cys Gln Arg Cys Arg Asp His Thr<br>355 360 365 | | 1104 |
| act ggg cca cac tgt gag cgc tgt gag aag aac tac tac aga tgg tcc<br>Thr Gly Pro His Cys Glu Arg Cys Glu Lys Asn Tyr Tyr Arg Trp Ser<br>370 375 380 | | 1152 |
| ccg aag aca cca tgc caa ccc tgt gac tgc cac cca gca ggc tct ctg<br>Pro Lys Thr Pro Cys Gln Pro Cys Asp Cys His Pro Ala Gly Ser Leu<br>385 390 395 400 | | 1200 |
| agt ctc cag tgt gac aac tca ggc gtc tgt ccc tgc aag ccc aca gtg<br>Ser Leu Gln Cys Asp Asn Ser Gly Val Cys Pro Cys Lys Pro Thr Val<br>405 410 415 | | 1248 |

```
act ggc tgg aag tgt gac cgc tgc ctg cct gga ttc cac tca ctc agt      1296
Thr Gly Trp Lys Cys Asp Arg Cys Leu Pro Gly Phe His Ser Leu Ser
            420                 425                 430 gag ggc ggc tgc aga ccc tgt gcc tgc aat gtc gcc ggc agc ttg ggc      1344
Glu Gly Gly Cys Arg Pro Cys Ala Cys Asn Val Ala Gly Ser Leu Gly
            435                 440                 445 acc tgt gac ccc cgc agt ggg aac tgt ccc tgc aaa gag aat gta gaa      1392
Thr Cys Asp Pro Arg Ser Gly Asn Cys Pro Cys Lys Glu Asn Val Glu
        450                 455                 460 ggc agc ctg tgt gac aga tgc cgc cct ggg aca ttt aac ctg cag ccc      1440
Gly Ser Leu Cys Asp Arg Cys Arg Pro Gly Thr Phe Asn Leu Gln Pro
465                 470                 475                 480 cac aat cca gtg ggc tgc agc agc tgc ttc tgt tat ggccactcca           1486
His Asn Pro Val Gly Cys Ser Ser Cys Phe Cys Tyr
                485                 490 aggtgtgttc tcctgctgcc gggttccagg aacaccacat ccgctcagac ttccgccatg    1546
gagctggtgg ctggcagatc agaagcatgg gagtgtccaa gcgtcctctg caatggagcc    1606
agagtgggct cctcctgggc ctgcgaggag gggaggaact ctcagcccca agaagttcc     1666 tgggagacca gagactcagc tatggacagc cagtcatact gaccctccaa gtacccctg     1726 gaggctcccc acctcctatt cagctgagac tggaggagc aggcttggct ctgtctctga     1786
ggccctccag tctacccagc cctcaggaca ccaggcagcc aagacgagtt cagctccagt    1846
tcctcttgca ggagacttct gaggaggcag agtccccact gcccaccttc cacttccagc    1906
gcctgctttc aatctgact gctctgagca tctggaccag tggccaagga ccgggccatt     1966
ctggccaagt gctcttgtgt gaagttcagc tcacatcggc ctggcccag cgtgagcttg     2026 cccctccagc ctcttgggtg gagacctgct tatgtcccca gggatacaca ggccagttct    2086
gtgaattctg tgctctggga tacaagagag aaatacctca tggggtccc tatgccaact     2146 gcattccctg cacctgcaac cagcatggca cctgtgaccc caacacaggg atctgcctgt    2206
gtggccacca caccgagggt ccatcctgtg agcggtgcat gccaggtttc tacggtaacg    2266
ccttctcagg ccgtgctgat gattgccagc cctgtccgtg ccctggccaa tcagcctgtg    2326
caaccatccc agagagtgga gatgtggtgt gcacacactg ccctcctggt cagagaggac    2386
gacgatgcga gagctgcgaa gatggctttt tggggatcc tctagggctc tctggagctc     2446
cccagccctg ccgccgatgc cagtgcagcg ggaacgtgga tctcaatgct gtgggcaact    2506
gtgatcctca ttctgccac tgcttgcgct gtctgtacaa cacgacaggg cccactgcg      2566 agcactgtcg ggagggttc tacgggagtg ccgtggccac aaggcccgtg acaaatgtg      2626 ctccctgcag ctgtgacctg aggggctcag tcagtgagaa gacctgcaac cctgtgactg    2686
gccagtgtgt ctgcctgcct tatgtctccg ggagggactg cagccgctgc agccctggct    2746
tctatgacct ccagtctggg aggggctgcc agagctgcaa atgtcaccca cttgatcct     2806 tggagaataa gtgccacccc aagactggcc agtgtccctg ccgacctggt gtcactggcc    2866
aagcctgtga cagatgccag ctaggttttct ttggcttctc catcaagggc tgccgagact   2926
gtaggtgctc cccattgggt gctgcctcat ctcagtgcca tgagaacagc acctgtgtgt    2986 gccgcccgg ctttgtgggc tataaatgcg accgctgcca ggacaatttc ttcctcgcgg     3046
atggcgacac aggctgccaa gagtgtccca cttgctatgc cctagtgaag gaagaggcag    3106
ccaagctgaa ggccaggttg atgctgatgg aggggtggct tcaaaggtct gactgtggta    3166
gcccctgggg accactagac attctgcagg gagaagcccc tctgggggat gtctaccaag    3226
```

| | | |
|---|---|---|
| gtcaccacct acttcaagag acccggggga ccttcctgca gcagatggtg ggcctggagg | 3286 |
| attctgtgaa ggccacttgg gagcagttgc aggtgctgag agggcatgta cactgtgccc | 3346 |
| aggctggagc tcagaagacc tgcatccagc tggcagagct ggaggagaca ttgcagtcct | 3406 |
| cagaggagga ggtccttcgt gcagcctcag ctctctcatt tctggcaagt cttcagaaag | 3466 |
| gatccagcac acccaccaat tggagtcacc tggcatcaga ggcccagatc cttgccagaa | 3526 |
| gccacaggga cacggccacc aagatcgaag ctacctcgga aagggccctg ctcgcctcca | 3586 |
| acgccagcta tgagctcctg aagctgatgg aaggcagagt ggcctcggaa gcccagcagg | 3646 |
| aactggagga caggtaccag gaggtgcagg cagctcagac tgccctgggc atagctgtgg | 3706 |
| cagaggcgct gcccaaagct gaaaaggcac tggccacggt gaagcaagtc attggtgacg | 3766 |
| cagccccaca tctaggcttg ctggtcaccc tgaagcaat gaacttccaa gccaggggcc | 3826 |
| tgagctggaa agtgaaggcc ctggagcaga agctggagca aaggagccc gaggtgggcc | 3886 |
| agtctgtggg agccctgcag gtggaggctg aagagcctt ggagaagatg gagccctta | 3946 |
| tgcagctacg caataagacc acagctgcct tcacacgggc ttcctcagct gtgcaagctg | 4006 |
| ccaaggtgac cgtcatagga gcagagaccc tgctagctga cctagaggga atgaagctga | 4066 |
| ggtctcctct acccaaggag caggcagcgc tgaagaagaa agcaggcagc atcaggacca | 4126 |
| ggctcctgga ggacacaaag aggaagacca agcatgcaga gaggatgctg ggaaatgctg | 4186 |
| cctctctctc ctccagcacc aagaagaaaa gcaaagaagc agaactgatg tctaaggaca | 4246 |
| atgccaagct ctccagagct ttgctgaggg aaggcaagca gggctaccgt catgccagcc | 4306 |
| gactcgccag ccagacccag gccacactcc gtcgggcctc tcgcctgctg ctgacctcag | 4366 |
| aagcacacaa gcaggagctg gaggaagcta acaggtgac ctctgggctg agcactgtgg | 4426 |
| agcgccaggt ccgagagtct cggatctcct tggagaagga caccaaggtc ctgtcagagc | 4486 |
| tgcttgtgaa gctgggtcc ctgggtgtcc accaagcccc tgctcagacc ctgaacgaga | 4546 |
| cccagcgggc actagaaagc ttgaggctgc agctggattc ccacggagcc ctgcatcaca | 4606 |
| aactgaggca gctggaggaa gagtctgctc gacaggagct gcagattcag agctttgagg | 4666 |
| acgaccttgc tgagatccgc gctgacaagc acaacttgga gaccattctg agcagtctgc | 4726 |
| cagagaactg tgccagctag accctggtac accctcccca ccctgccgtt tcctgtccac | 4786 |
| tccctgtagg tgtcccaggt ctgcctgtcg tatgttcacg tgaatgcttg tttgctggtg | 4846 |
| catcttcggt ctgagcagga gtgaatacat gctcacacct ccacagatga ccctgtatgt | 4906 |
| agtcctcagt gtgtactctc taaacgtgca tcagcataca caccccagta tttgcacata | 4966 |
| tgtgtatgtg atgcactgat gtgttaagac cacctgtgtg catgcacaca tatgagagtc | 5026 |
| tagagctgtg gagagcagtc ctgagcttgg cacatccaca ttctggtggg ttcctgctat | 5086 |
| gaatatcctg caggatgaca catctacacc tcctcagaat cagggccaac aggtgtactc | 5146 |
| gagctga | 5153 |

```
<210> SEQ ID NO 10
<211> LENGTH: 492
<212> TYPE: PRT
<213> ORGANISM: Mus musculus

<400> SEQUENCE: 10

Met Ala Val Ser Arg Val Leu Ser Leu Leu Ala Thr Val Ala Ser Met
1               5                   10                  15

Ala Leu Val Ile Gln Glu Thr His Phe Ala Ala Gly Ala Asp Met Gly
            20                  25                  30
```

```
Ser Cys Tyr Asp Gly Val Gly Arg Ala Gln Arg Cys Leu Pro Glu Phe
         35                  40                  45

Glu Asn Ala Ala Phe Gly Arg Arg Ala Glu Ala Ser His Thr Cys Gly
 50                  55                  60

Arg Pro Pro Glu Asp Phe Cys Pro His Val Gly Ala Pro Gly Ala Gly
 65                  70                  75                  80

Leu Gln Cys Gln Arg Cys Asp Asp Ala Asp Pro Gly Arg Arg His Asp
                 85                  90                  95

Ala Ser Tyr Leu Thr Asp Phe His Ser Pro Asp Ser Thr Trp Trp
                100                 105                 110

Gln Ser Pro Ser Met Ala Phe Gly Val Gln Tyr Pro Thr Ser Val Asn
            115                 120                 125

Leu Thr Leu Ser Leu Gly Lys Ala Tyr Glu Ile Thr Tyr Val Arg Leu
        130                 135                 140

Lys Phe His Thr Ser Arg Pro Glu Ser Phe Ala Ile Tyr Lys Arg Thr
145                 150                 155                 160

Tyr Ala Ser Gly Pro Trp Glu Pro Tyr Gln Tyr Tyr Ser Ala Ser Cys
                165                 170                 175

Gln Lys Thr Tyr Gly Arg Pro Glu Gly His Tyr Leu Arg Pro Gly Glu
            180                 185                 190

Asp Glu Arg Val Ala Phe Cys Thr Ser Glu Phe Ser Asp Ile Ser Pro
        195                 200                 205

Leu Asn Gly Gly Asn Val Ala Phe Ser Thr Leu Glu Gly Arg Pro Ser
210                 215                 220

Ala Tyr Asn Phe Glu Glu Ser Pro Val Leu Gln Glu Trp Val Thr Ser
225                 230                 235                 240

Thr Asp Ile Leu Ile Ser Leu Asp Arg Leu Asn Thr Phe Gly Asp Asp
                245                 250                 255

Ile Phe Lys Asp Pro Arg Val Leu Gln Ser Tyr Tyr Tyr Ala Val Ser
            260                 265                 270

Asp Phe Ser Val Gly Gly Arg Cys Lys Cys Asn Gly His Ala Ser Glu
        275                 280                 285

Cys Glu Pro Asn Ala Ala Gly Gln Leu Ala Cys Arg Cys Gln His Asn
290                 295                 300

Thr Thr Gly Val Asp Cys Glu Arg Cys Leu Pro Phe Phe Gln Asp Arg
305                 310                 315                 320

Pro Trp Ala Arg Gly Thr Ala Glu Asp Ala Asn Glu Cys Leu Pro Cys
                325                 330                 335

Asn Cys Ser Gly His Ser Glu Glu Cys Thr Phe Asp Arg Glu Leu Tyr
            340                 345                 350

Arg Ser Thr Gly His Gly Gly His Cys Gln Arg Cys Arg Asp His Thr
        355                 360                 365

Thr Gly Pro His Cys Glu Arg Cys Glu Lys Asn Tyr Tyr Arg Trp Ser
        370                 375                 380

Pro Lys Thr Pro Cys Gln Pro Cys Asp Cys His Pro Ala Gly Ser Leu
385                 390                 395                 400

Ser Leu Gln Cys Asp Asn Ser Gly Val Cys Pro Cys Lys Pro Thr Val
            405                 410                 415

Thr Gly Trp Lys Cys Asp Arg Cys Leu Pro Gly Phe His Ser Leu Ser
        420                 425                 430

Glu Gly Gly Cys Arg Pro Cys Ala Cys Asn Val Ala Gly Ser Leu Gly
        435                 440                 445
```

```
Thr Cys Asp Pro Arg Ser Gly Asn Cys Pro Cys Lys Glu Asn Val Glu
    450                 455                 460

Gly Ser Leu Cys Asp Arg Cys Arg Pro Gly Thr Phe Asn Leu Gln Pro
465                 470                 475                 480

His Asn Pro Val Gly Cys Ser Ser Cys Phe Cys Tyr
            485                 490

<210> SEQ ID NO 11
<211> LENGTH: 2265
<212> TYPE: PRT
<213> ORGANISM: Bos taurus

<400> SEQUENCE: 11

Gln Ala Gln Gln Ile Val Gln Pro Gln Ser Pro Leu Thr Val Ser Gln
1               5                   10                  15

Ser Lys Pro Gly Cys Tyr Asp Asn Gly Lys His Tyr Gln Ile Asn Gln
            20                  25                  30

Gln Trp Glu Arg Thr Tyr Leu Gly Ser Ala Leu Val Cys Thr Cys Tyr
        35                  40                  45

Gly Gly Ser Arg Gly Phe Asn Cys Glu Ser Lys Pro Glu Pro Glu Glu
50                  55                  60

Thr Cys Phe Asp Lys Tyr Thr Gly Asn Thr Tyr Arg Val Gly Asp Thr
65                  70                  75                  80

Tyr Glu Arg Pro Lys Asp Ser Met Ile Trp Asp Cys Thr Cys Ile Gly
                85                  90                  95

Ala Gly Arg Gly Arg Ile Ser Cys Thr Ile Ala Asn Arg Cys His Glu
            100                 105                 110

Gly Gly Gln Ser Tyr Lys Ile Gly Asp Thr Trp Arg Arg Pro His Glu
        115                 120                 125

Thr Gly Gly Tyr Met Leu Glu Cys Val Cys Leu Gly Asn Gly Lys Gly
130                 135                 140

Glu Trp Thr Cys Lys Pro Ile Ala Glu Lys Cys Phe Asp Gln Ala Ala
145                 150                 155                 160

Gly Thr Ser Tyr Val Val Gly Glu Thr Trp Glu Lys Pro Tyr Gln Gly
                165                 170                 175

Trp Met Met Val Asp Cys Thr Cys Leu Gly Glu Gly Ser Gly Arg Ile
            180                 185                 190

Thr Cys Thr Ser Arg Asn Arg Cys Asn Asp Gln Asp Thr Arg Thr Ser
        195                 200                 205

Tyr Arg Ile Gly Asp Thr Trp Ser Lys Lys Asp Asn Arg Gly Asn Leu
210                 215                 220

Leu Gln Cys Ile Cys Thr Gly Asn Gly Arg Gly Glu Trp Lys Cys Glu
225                 230                 235                 240

Arg His Thr Ser Leu Gln Thr Thr Ser Ala Gly Ser Gly Ser Phe Thr
                245                 250                 255

Asp Val Arg Thr Ala Ile Tyr Gln Pro Gln Pro His Pro Gln Pro Pro
            260                 265                 270

Pro Tyr Gly His Cys Val Thr Asp Ser Gly Val Val Tyr Ser Val Gly
        275                 280                 285

Met Gln Trp Leu Lys Thr Gln Gly Asn Lys Gln Met Leu Cys Thr Cys
290                 295                 300

Leu Gly Asn Gly Val Ser Cys Gln Glu Thr Ala Val Thr Gln Thr Tyr
305                 310                 315                 320

Gly Gly Asn Ser Asn Gly Glu Pro Cys Val Leu Pro Phe Thr Tyr Asn
                325                 330                 335
```

```
Gly Lys Thr Phe Tyr Ser Cys Thr Thr Glu Gly Arg Gln Asp Gly His
            340                 345                 350

Leu Trp Cys Ser Thr Thr Ser Asn Tyr Glu Gln Asp Gln Lys Tyr Ser
            355                 360                 365

Phe Cys Thr Asp His Thr Val Leu Val Gln Thr Arg Gly Gly Asn Ser
370                 375                 380

Asn Gly Ala Leu Cys His Phe Pro Phe Leu Tyr Asn Asn His Asn Tyr
385                 390                 395                 400

Thr Asp Cys Thr Ser Glu Gly Arg Arg Asp Asn Met Lys Trp Cys Gly
                405                 410                 415

Thr Thr Gln Asn Tyr Asp Ala Asp Gln Lys Phe Gly Phe Cys Pro Met
                420                 425                 430

Ala Ala His Glu Glu Ile Cys Thr Thr Asn Glu Gly Val Met Tyr Arg
                435                 440                 445

Ile Gly Asp Gln Trp Asp Lys Gln His Asp Met Gly His Met Met Arg
450                 455                 460

Cys Thr Cys Val Gly Asn Gly Arg Gly Glu Trp Thr Cys Val Ala Tyr
465                 470                 475                 480

Ser Gln Leu Arg Asp Gln Cys Ile Val Asp Gly Ile Thr Tyr Asn Val
                485                 490                 495

Asn Asp Thr Phe His Lys Arg His Glu Glu Gly His Met Leu Asn Cys
                500                 505                 510

Thr Cys Phe Gly Gln Gly Arg Gly Arg Trp Lys Cys Asp Pro Val Asp
            515                 520                 525

Gln Cys Gln Asp Ser Glu Thr Arg Thr Phe Tyr Gln Ile Gly Asp Ser
530                 535                 540

Trp Glu Lys Tyr Leu Gln Gly Val Arg Tyr Gln Cys Tyr Cys Tyr Gly
545                 550                 555                 560

Arg Gly Ile Gly Glu Trp Ala Cys Gln Pro Leu Gln Thr Tyr Pro Asp
                565                 570                 575

Thr Ser Gly Pro Val Gln Val Ile Ile Thr Glu Thr Pro Ser Gln Pro
            580                 585                 590

Asn Ser His Pro Ile Gln Trp Ser Ala Pro Glu Ser Ser His Ile Ser
            595                 600                 605

Lys Tyr Ile Leu Arg Trp Lys Pro Lys Asn Ser Pro Asp Arg Trp Lys
            610                 615                 620

Glu Ala Thr Ile Pro Gly His Leu Asn Ser Tyr Thr Ile Lys Gly Leu
625                 630                 635                 640

Arg Pro Gly Val Val Tyr Glu Gly Gln Leu Ile Ser Val Gln His Tyr
                645                 650                 655

Gly Gln Arg Glu Val Thr Arg Phe Asp Phe Thr Thr Thr Ser Thr Ser
                660                 665                 670

Pro Ala Val Thr Ser Asn Thr Val Thr Gly Glu Thr Thr Pro Leu Ser
                675                 680                 685

Pro Val Val Ala Thr Ser Glu Ser Val Thr Glu Ile Thr Ala Ser Ser
            690                 695                 700

Phe Val Val Ser Trp Val Ser Ala Ser Asp Thr Val Ser Gly Phe Arg
705                 710                 715                 720

Val Glu Tyr Glu Leu Ser Glu Glu Gly Asp Glu Pro Gln Tyr Leu Asp
                725                 730                 735

Leu Pro Ser Thr Ala Thr Ser Val Asn Ile Pro Asp Leu Leu Pro Gly
            740                 745                 750
```

-continued

```
Arg Lys Tyr Thr Val Asn Val Tyr Glu Ile Ser Glu Glu Gly Glu Gln
    755                 760                 765

Asn Leu Ile Leu Ser Thr Ser Gln Thr Thr Ala Pro Asp Ala Pro Pro
    770                 775                 780

Asp Pro Thr Val Asp Gln Val Asp Thr Ser Ile Val Val Arg Trp
785                 790                 795                 800

Ser Arg Pro Arg Ala Pro Ile Thr Gly Tyr Arg Ile Val Tyr Ser Pro
                805                 810                 815

Ser Val Glu Gly Ser Ser Thr Glu Leu Asn Leu Pro Glu Thr Ala Asn
                820                 825                 830

Ser Val Thr Leu Ser Asp Leu Gln Pro Gly Val Gln Tyr Asn Ile Thr
            835                 840                 845

Ile Tyr Ala Val Glu Glu Asn Gln Glu Ser Thr Pro Val Phe Ile Gln
    850                 855                 860

Gln Glu Thr Thr Gly Val Pro Arg Ser Asp Lys Val Pro Pro Arg
865                 870                 875                 880

Asp Leu Gln Phe Val Glu Val Thr Asp Val Lys Ile Thr Ile Met Trp
                885                 890                 895

Thr Pro Pro Glu Ser Pro Val Thr Gly Tyr Arg Val Asp Val Ile Pro
            900                 905                 910

Val Asn Leu Pro Gly Glu His Gly Gln Arg Leu Pro Val Ser Arg Asn
            915                 920                 925

Thr Phe Ala Glu Val Thr Gly Leu Ser Pro Gly Val Thr Tyr His Phe
    930                 935                 940

Lys Val Phe Ala Val Asn Gln Gly Arg Glu Ser Lys Pro Leu Thr Ala
945                 950                 955                 960

Gln Gln Ala Thr Lys Leu Asp Ala Pro Thr Asn Leu Gln Phe Ile Asn
                965                 970                 975

Glu Thr Asp Thr Thr Val Ile Val Thr Trp Thr Pro Pro Arg Ala Arg
            980                 985                 990

Ile Val Gly Tyr Arg Leu Thr Val Gly Leu Thr Arg Gly Gly Gln Pro
    995                 1000                1005

Lys Gln Tyr Asn Val Gly Pro Ala Ala Ser Gln Tyr Pro Leu Arg
    1010                1015                1020

Asn Leu Gln Pro Gly Ser Glu Tyr Ala Val Ser Leu Val Ala Val
    1025                1030                1035

Lys Gly Asn Gln Gln Ser Pro Arg Val Thr Gly Val Phe Thr Thr
    1040                1045                1050

Leu Gln Pro Leu Gly Ser Ile Pro His Tyr Asn Thr Glu Val Thr
    1055                1060                1065

Glu Thr Thr Ile Val Ile Thr Trp Thr Pro Ala Pro Arg Ile Gly
    1070                1075                1080

Phe Lys Leu Gly Val Arg Pro Ser Gln Gly Gly Glu Ala Pro Arg
    1085                1090                1095

Glu Val Thr Ser Glu Ser Gly Ser Ile Val Val Ser Gly Leu Thr
    1100                1105                1110

Pro Gly Val Glu Tyr Val Tyr Thr Ile Ser Val Leu Arg Asp Gly
    1115                1120                1125

Gln Glu Arg Asp Ala Pro Ile Val Lys Lys Val Val Thr Pro Leu
    1130                1135                1140

Ser Pro Pro Thr Asn Leu His Leu Glu Ala Asn Pro Asp Thr Gly
    1145                1150                1155

Val Leu Thr Val Ser Trp Glu Arg Ser Thr Thr Pro Asp Ile Thr
```

-continued

```
            1160                1165                1170
Gly Tyr Arg Ile Thr Thr Thr Pro Thr Asn Gly Gln Gln Gly Tyr
    1175                1180                1185
Ser Leu Glu Glu Val Val His Ala Asp Gln Ser Ser Cys Thr Phe
    1190                1195                1200
Glu Asn Leu Ser Pro Gly Leu Glu Tyr Asn Val Ser Val Tyr Thr
    1205                1210                1215
Val Lys Asp Asp Lys Glu Ser Val Pro Ile Ser Asp Thr Ile Ile
    1220                1225                1230
Pro Ala Val Pro Pro Thr Asp Leu Arg Phe Thr Asn Val Gly
    1235                1240                1245
Pro Asp Thr Met Arg Val Thr Trp Ala Pro Pro Ser Ser Ile Glu
    1250                1255                1260
Leu Thr Asn Leu Leu Val Arg Tyr Ser Pro Val Lys Asn Glu Glu
    1265                1270                1275
Asp Val Ala Glu Leu Ser Ile Ser Pro Ser Asp Asn Ala Val Val
    1280                1285                1290
Leu Thr Asn Leu Leu Pro Gly Thr Glu Tyr Leu Val Ser Val Ser
    1295                1300                1305
Ser Val Tyr Glu Gln His Glu Ser Ile Pro Leu Arg Gly Arg Gln
    1310                1315                1320
Lys Thr Ala Leu Asp Ser Pro Ser Gly Ile Asp Phe Ser Asp Ile
    1325                1330                1335
Thr Ala Asn Ser Phe Thr Val His Trp Ile Ala Pro Arg Ala Thr
    1340                1345                1350
Ile Thr Gly Tyr Arg Ile Arg His His Pro Glu Asn Met Gly Gly
    1355                1360                1365
Arg Pro Arg Glu Asp Arg Val Pro Pro Ser Arg Asn Ser Ile Thr
    1370                1375                1380
Leu Thr Asn Leu Asn Pro Gly Thr Glu Tyr Val Val Ser Ile Val
    1385                1390                1395
Ala Leu Asn Ser Lys Glu Glu Ser Leu Pro Leu Val Gly Gln Gln
    1400                1405                1410
Ser Thr Val Ser Asp Val Pro Arg Asp Leu Glu Val Ile Ala Ala
    1415                1420                1425
Thr Pro Thr Ser Leu Leu Ile Ser Trp Asp Ala Pro Ala Val Thr
    1430                1435                1440
Val Arg Tyr Tyr Arg Ile Thr Tyr Gly Glu Thr Gly Gly Ser Ser
    1445                1450                1455
Pro Val Gln Glu Phe Thr Val Pro Gly Ser Lys Ser Thr Ala Thr
    1460                1465                1470
Ile Ser Gly Leu Lys Pro Gly Val Asp Tyr Thr Ile Thr Val Tyr
    1475                1480                1485
Ala Val Thr Gly Arg Gly Asp Ser Pro Ala Ser Ser Lys Pro Val
    1490                1495                1500
Ser Ile Asn Tyr Arg Thr Glu Ile Asp Lys Pro Ser Gln Met Gln
    1505                1510                1515
Val Thr Asp Val Gln Asp Asn Ser Ile Ser Val Arg Trp Leu Pro
    1520                1525                1530
Ser Ser Ser Pro Val Thr Gly Tyr Arg Val Thr Thr Ala Pro Lys
    1535                1540                1545
Asn Gly Pro Gly Pro Ser Lys Thr Lys Thr Val Gly Pro Asp Gln
    1550                1555                1560
```

```
Thr Glu Met Thr Ile Glu Gly Leu Gln Pro Thr Val Glu Tyr Val
    1565             1570                1575

Val Ser Val Tyr Ala Gln Asn Gln Asn Gly Glu Ser Gln Pro Leu
    1580             1585                1590

Val Gln Thr Ala Val Thr Thr Ile Pro Ala Pro Thr Asn Leu Lys
    1595             1600                1605

Phe Thr Gln Val Thr Pro Ser Leu Thr Ala Gln Trp Thr Ala
    1610             1615                1620

Pro Asn Val Gln Leu Thr Gly Tyr Arg Val Arg Val Thr Pro Lys
    1625             1630                1635

Glu Lys Thr Gly Pro Met Lys Glu Ile Asn Leu Ala Pro Asp Ser
    1640             1645                1650

Ser Ser Val Val Val Ser Gly Leu Met Val Ala Thr Lys Tyr Glu
    1655             1660                1665

Val Ser Val Tyr Ala Leu Lys Asp Thr Leu Thr Ser Arg Pro Ala
    1670             1675                1680

Gln Gly Val Val Thr Thr Leu Glu Asn Val Ser Pro Pro Arg Arg
    1685             1690                1695

Ala Arg Val Thr Asp Ala Thr Glu Thr Thr Ile Thr Ile Ser Trp
    1700             1705                1710

Arg Thr Lys Thr Glu Thr Ile Thr Gly Phe Gln Val Asp Ala Ile
    1715             1720                1725

Pro Ala Asn Gly Gln Thr Pro Ile Gln Arg Thr Ile Arg Pro Asp
    1730             1735                1740

Val Arg Ser Tyr Thr Ile Thr Gly Leu Gln Pro Gly Thr Asp Tyr
    1745             1750                1755

Lys Ile His Leu Tyr Thr Leu Asn Asp Asn Ala Arg Ser Ser Pro
    1760             1765                1770

Val Val Ile Asp Ala Ser Thr Ala Ile Asp Ala Pro Ser Asn Leu
    1775             1780                1785

Arg Phe Leu Ala Thr Thr Pro Asn Ser Leu Leu Val Ser Trp Gln
    1790             1795                1800

Pro Pro Arg Ala Arg Ile Thr Gly Tyr Ile Ile Lys Tyr Glu Lys
    1805             1810                1815

Pro Gly Ser Pro Pro Arg Glu Val Val Pro Arg Pro Arg Pro Gly
    1820             1825                1830

Val Thr Glu Ala Thr Ile Thr Gly Leu Glu Pro Gly Thr Glu Tyr
    1835             1840                1845

Thr Ile Gln Val Ile Ala Leu Lys Asn Asn Gln Lys Ser Glu Pro
    1850             1855                1860

Leu Ile Gly Arg Lys Lys Thr Asp Glu Leu Pro Gln Leu Val Thr
    1865             1870                1875

Leu Pro His Pro Asn Leu His Gly Pro Glu Ile Leu Asp Val Pro
    1880             1885                1890

Ser Thr Val Gln Lys Thr Pro Phe Ile Thr Asn Pro Gly Tyr Asp
    1895             1900                1905

Thr Gly Asn Gly Ile Gln Leu Pro Gly Thr Ser Gly Gln Gln Pro
    1910             1915                1920

Ser Leu Gly Gln Gln Met Ile Phe Glu Glu His Gly Phe Arg Arg
    1925             1930                1935

Thr Thr Pro Pro Thr Thr Ala Thr Pro Val Arg His Arg Pro Arg
    1940             1945                1950
```

-continued

```
Pro Tyr Pro Pro Asn Val Asn Glu Glu Ile Gln Ile Gly His Val
    1955            1960                1965

Pro Arg Gly Asp Val Asp His His Leu Tyr Pro His Val Val Gly
    1970            1975                1980

Leu Asn Pro Asn Ala Ser Thr Gly Gln Glu Ala Leu Ser Gln Thr
    1985            1990                1995

Thr Ile Ser Trp Thr Pro Phe Gln Glu Ser Ser Glu Tyr Ile Ile
    2000            2005                2010

Ser Cys His Pro Val Gly Ile Asp Glu Glu Pro Leu Gln Phe Arg
    2015            2020                2025

Val Pro Gly Thr Ser Ala Ser Ala Thr Leu Thr Gly Leu Thr Arg
    2030            2035                2040

Gly Ala Thr Tyr Asn Ile Ile Val Glu Ala Val Lys Asp Gln Gln
    2045            2050                2055

Arg Gln Lys Val Arg Glu Glu Val Val Thr Val Gly Asn Ser Val
    2060            2065                2070

Asp Gln Gly Leu Ser Gln Pro Thr Asp Asp Ser Cys Phe Asp Pro
    2075            2080                2085

Tyr Thr Val Ser His Tyr Ala Ile Gly Glu Glu Trp Glu Arg Leu
    2090            2095                2100

Ser Asp Ser Gly Phe Lys Leu Ser Cys Gln Cys Leu Gly Phe Gly
    2105            2110                2115

Ser Gly His Phe Arg Cys Asp Ser Ser Lys Trp Cys His Asp Asn
    2120            2125                2130

Gly Val Asn Tyr Lys Ile Gly Glu Lys Trp Asp Arg Gln Gly Glu
    2135            2140                2145

Asn Gly Gln Met Met Ser Cys Thr Cys Leu Gly Asn Gly Lys Gly
    2150            2155                2160

Glu Phe Lys Cys Asp Pro His Glu Ala Thr Cys Tyr Asp Asp Gly
    2165            2170                2175

Lys Thr Tyr His Val Gly Glu Gln Trp Gln Lys Glu Tyr Leu Gly
    2180            2185                2190

Ala Ile Cys Ser Cys Thr Cys Phe Gly Gly Gln Arg Gly Trp Arg
    2195            2200                2205

Cys Asp Asn Cys Arg Arg Pro Gly Ala Glu Pro Gly Asn Glu Gly
    2210            2215                2220

Ser Thr Ala His Ser Tyr Asn Gln Tyr Ser Gln Arg Tyr His Gln
    2225            2230                2235

Arg Thr Asn Thr Asn Val Asn Cys Pro Ile Glu Cys Phe Met Pro
    2240            2245                2250

Leu Asp Val Gln Ala Asp Arg Glu Asp Ser Arg Glu
    2255            2260                2265
```

<210> SEQ ID NO 12
<211> LENGTH: 21
<212> TYPE: RNA
<213> ORGANISM: Artificial
<220> FEATURE:
<223> OTHER INFORMATION: short interfering RNA and refers to short
      double-stranded RNA of 10 or more base pairs which are
      artificially chemically synthesized or biochemically synthesized

<400> SEQUENCE: 12
aagcagcagg acuucuucaa g                                              21

<210> SEQ ID NO 13

-continued

```
<211> LENGTH: 984
<212> TYPE: DNA
<213> ORGANISM: Mus musculus
<220> FEATURE:
<221> NAME/KEY: CDS
<222> LOCATION: (1)..(984)
<300> PUBLICATION INFORMATION:
<308> DATABASE ACCESSION NUMBER: AF106007
<309> DATABASE ENTRY DATE: 1999-02-08
<313> RELEVANT RESIDUES: (1)..(984)

<400> SEQUENCE: 13 atg gag cga agg aac cac act ggg aga gtg agt gaa ttt gtg ttg ctg      48
Met Glu Arg Arg Asn His Thr Gly Arg Val Ser Glu Phe Val Leu Leu
1               5                  10                  15 ggt ttc cca gct cct gcc cca ctg cgg gca cta cta ttt ttc ctt tct      96
Gly Phe Pro Ala Pro Ala Pro Leu Arg Ala Leu Leu Phe Phe Leu Ser
                20                  25                  30 ctg ttg gcc tac gtg ttg gtg ctg act gaa aac ata ctc atc att aca     144
Leu Leu Ala Tyr Val Leu Val Leu Thr Glu Asn Ile Leu Ile Ile Thr
            35                  40                  45 gca att agg aac cac ccc acc ctc cac aaa ccc atg tat ttt ttc ttg     192
Ala Ile Arg Asn His Pro Thr Leu His Lys Pro Met Tyr Phe Phe Leu
        50                  55                  60 gct aat atg tca ttc ctg gag att tgg tat gtc act gtt acg att cct     240
Ala Asn Met Ser Phe Leu Glu Ile Trp Tyr Val Thr Val Thr Ile Pro
65                  70                  75                  80 aag atg ctt gct ggc ttc att ggt tcc gag gag aat cat gga cag ctg     288
Lys Met Leu Ala Gly Phe Ile Gly Ser Glu Glu Asn His Gly Gln Leu
                85                  90                  95 atc tcc ttt gag gca tgc atg aca cag ctc tac ttt ttc cta ggc ttg     336
Ile Ser Phe Glu Ala Cys Met Thr Gln Leu Tyr Phe Phe Leu Gly Leu
            100                 105                 110 ggt tgc aca gag tgt gtc ctt ctt gct gtc atg gcc tat gac cgc tat     384
Gly Cys Thr Glu Cys Val Leu Leu Ala Val Met Ala Tyr Asp Arg Tyr
        115                 120                 125 gtg gcc atc tgt cac cca ctc cac tat cct gtc att gtc agt agc cgg     432
Val Ala Ile Cys His Pro Leu His Tyr Pro Val Ile Val Ser Ser Arg
    130                 135                 140 cta tgt gtg cag atg gca gct gga tcc tgg gct gga ggt ttt ggt atc     480
Leu Cys Val Gln Met Ala Ala Gly Ser Trp Ala Gly Gly Phe Gly Ile
145                 150                 155                 160 tcc atg gtt aaa gtt ttc ctc att tct cgc ctg tct tac tgt ggc ccc     528
Ser Met Val Lys Val Phe Leu Ile Ser Arg Leu Ser Tyr Cys Gly Pro
                165                 170                 175 aac acc atc aac cac ttt ttc tgt gat gtt tct cca ttg ctc aac ttg     576
Asn Thr Ile Asn His Phe Phe Cys Asp Val Ser Pro Leu Leu Asn Leu
            180                 185                 190 tca tgc act gac atg tcc aca gca gag ctt aca gac ttt atc ctg gcc     624
Ser Cys Thr Asp Met Ser Thr Ala Glu Leu Thr Asp Phe Ile Leu Ala
        195                 200                 205 att ttt att ctg ctg ggg cca ctc tct gtc act ggg gct tcc tat atg     672
Ile Phe Ile Leu Leu Gly Pro Leu Ser Val Thr Gly Ala Ser Tyr Met
    210                 215                 220 gcc atc aca ggt gca gtg atg cgc atc ccc tca gct gct ggc cgc cat     720
Ala Ile Thr Gly Ala Val Met Arg Ile Pro Ser Ala Ala Gly Arg His
225                 230                 235                 240 aag gcc ttt tca acc tgt gcc tcc cac ctc act gtt gtg att atc ttc     768
Lys Ala Phe Ser Thr Cys Ala Ser His Leu Thr Val Val Ile Ile Phe
                245                 250                 255 tat gca gcc agt att ttc atc tat gcc agg cct aag gca ctc tca gct     816
Tyr Ala Ala Ser Ile Phe Ile Tyr Ala Arg Pro Lys Ala Leu Ser Ala
```

```
                  260                 265                 270
ttt gac acc aac aag ctg gtc tct gta ctc tac gct gtc att gta cca    864
Phe Asp Thr Asn Lys Leu Val Ser Val Leu Tyr Ala Val Ile Val Pro
        275                 280                 285 ttg ctc aat ccc atc atc tac tgc ttg cgc aat caa gaa gtc aaa aaa    912
Leu Leu Asn Pro Ile Ile Tyr Cys Leu Arg Asn Gln Glu Val Lys Lys
    290                 295                 300 gcc cta cgt cgc act ctg cac ctg gcc caa ggc cag gac gcc aat acc    960
Ala Leu Arg Arg Thr Leu His Leu Ala Gln Gly Gln Asp Ala Asn Thr
305                 310                 315                 320 aag aaa tcc agc aga gat ggt tag                                    984
Lys Lys Ser Ser Arg Asp Gly
                325

<210> SEQ ID NO 14
<211> LENGTH: 327
<212> TYPE: PRT
<213> ORGANISM: Mus musculus

<400> SEQUENCE: 14

Met Glu Arg Arg Asn His Thr Gly Arg Val Ser Glu Phe Val Leu Leu
1               5                   10                  15

Gly Phe Pro Ala Pro Ala Pro Leu Arg Ala Leu Leu Phe Phe Leu Ser
            20                  25                  30

Leu Leu Ala Tyr Val Leu Val Leu Thr Glu Asn Ile Leu Ile Ile Thr
        35                  40                  45

Ala Ile Arg Asn His Pro Thr Leu His Lys Pro Met Tyr Phe Phe Leu
    50                  55                  60

Ala Asn Met Ser Phe Leu Glu Ile Trp Tyr Val Thr Val Thr Ile Pro
65                  70                  75                  80

Lys Met Leu Ala Gly Phe Ile Gly Ser Glu Glu Asn His Gly Gln Leu
                85                  90                  95

Ile Ser Phe Glu Ala Cys Met Thr Gln Leu Tyr Phe Phe Leu Gly Leu
            100                 105                 110

Gly Cys Thr Glu Cys Val Leu Leu Ala Val Met Ala Tyr Asp Arg Tyr
        115                 120                 125

Val Ala Ile Cys His Pro Leu His Tyr Pro Val Ile Val Ser Ser Arg
    130                 135                 140

Leu Cys Val Gln Met Ala Ala Gly Ser Trp Ala Gly Gly Phe Gly Ile
145                 150                 155                 160

Ser Met Val Lys Val Phe Leu Ile Ser Arg Leu Ser Tyr Cys Gly Pro
                165                 170                 175

Asn Thr Ile Asn His Phe Phe Cys Asp Val Ser Pro Leu Leu Asn Leu
            180                 185                 190

Ser Cys Thr Asp Met Ser Thr Ala Glu Leu Thr Asp Phe Ile Leu Ala
        195                 200                 205

Ile Phe Ile Leu Leu Gly Pro Leu Ser Val Thr Gly Ala Ser Tyr Met
    210                 215                 220

Ala Ile Thr Gly Ala Val Met Arg Ile Pro Ser Ala Ala Gly Arg His
225                 230                 235                 240

Lys Ala Phe Ser Thr Cys Ala Ser His Leu Thr Val Val Ile Ile Phe
                245                 250                 255

Tyr Ala Ala Ser Ile Phe Ile Tyr Ala Arg Pro Lys Ala Leu Ser Ala
            260                 265                 270

Phe Asp Thr Asn Lys Leu Val Ser Val Leu Tyr Ala Val Ile Val Pro
        275                 280                 285
```

```
Leu Leu Asn Pro Ile Ile Tyr Cys Leu Arg Asn Gln Glu Val Lys Lys
    290                 295                 300

Ala Leu Arg Arg Thr Leu His Leu Ala Gln Gly Gln Asp Ala Asn Thr
305                 310                 315                 320

Lys Lys Ser Ser Arg Asp Gly
                325

<210> SEQ ID NO 15
<211> LENGTH: 1325
<212> TYPE: DNA
<213> ORGANISM: Mus musculus
<220> FEATURE:
<221> NAME/KEY: CDS
<222> LOCATION: (138)..(1112)
<300> PUBLICATION INFORMATION:
<308> DATABASE ACCESSION NUMBER: AF121972
<309> DATABASE ENTRY DATE: 1999-04-25
<313> RELEVANT RESIDUES: (1)..(1325)

<400> SEQUENCE: 15
aacacactca aatcaaaata atattggatt ggttccatct ggtttcagaa tactcttgtg      60
tttccttgta gaacttaagt ttgacactca taaaaacctt cagacatatt gaaagtaagg     120
gaattgggat taaactc atg tct ctt ttt ccc caa aga aat tta gat gcc       170
                   Met Ser Leu Phe Pro Gln Arg Asn Leu Asp Ala
                    1               5                  10 atg aac aga tca gca gca cat gta acc gaa ttt gtt ctc ttg gga ttt      218
Met Asn Arg Ser Ala Ala His Val Thr Glu Phe Val Leu Leu Gly Phe
            15                  20                  25 cct ggt tcc tgg aag ata cag att ttc ctc ttc gtg ttg ttt ttg gtg      266
Pro Gly Ser Trp Lys Ile Gln Ile Phe Leu Phe Val Leu Phe Leu Val
        30                  35                  40 ttt tat gtc ttg aca ttg ttg gga aat gga gcc atc atc tgt gca gta      314
Phe Tyr Val Leu Thr Leu Leu Gly Asn Gly Ala Ile Ile Cys Ala Val
    45                  50                  55 aga tgt gac tca cgt cta cat acc ccc atg tac ttc ctc ctg gga aat      362
Arg Cys Asp Ser Arg Leu His Thr Pro Met Tyr Phe Leu Leu Gly Asn
60                  65                  70                  75 ttt tcc ttc ctt gaa atc tgg tat gtt tcc tcc act att cct aac ata      410
Phe Ser Phe Leu Glu Ile Trp Tyr Val Ser Ser Thr Ile Pro Asn Ile
                80                  85                  90 cta gcc aac att ctg tct aag acc aag gcc atc tca ttt tca ggg tgc      458
Leu Ala Asn Ile Leu Ser Lys Thr Lys Ala Ile Ser Phe Ser Gly Cys
            95                 100                 105 ttc ctg cag ttc tat ttc ttc ttt tca ctg ggt aca act gaa tgt ctc      506
Phe Leu Gln Phe Tyr Phe Phe Phe Ser Leu Gly Thr Thr Glu Cys Leu
        110                 115                 120 ttc ctg gca gta atg gct tat gat agg tac ctg gcc att tgc cgc cca      554
Phe Leu Ala Val Met Ala Tyr Asp Arg Tyr Leu Ala Ile Cys Arg Pro
    125                 130                 135 tta cat tac cct act atc atg act agg agg ctg tgt tgc att ctg gta      602
Leu His Tyr Pro Thr Ile Met Thr Arg Arg Leu Cys Cys Ile Leu Val
140                 145                 150                 155 tcc tca tgc tgg ctc att gga ttt ctt ggg tac cca atc cct atc ttc      650
Ser Ser Cys Trp Leu Ile Gly Phe Leu Gly Tyr Pro Ile Pro Ile Phe
                160                 165                 170 tcc att tcc cag ctt ccc ttc tgt ggt tct aat atc att gat cac ttc      698
Ser Ile Ser Gln Leu Pro Phe Cys Gly Ser Asn Ile Ile Asp His Phe
            175                 180                 185 ctc tgt gac atg gac cca ttg atg gct ttg tcc tgt gcc cca gct cct      746
Leu Cys Asp Met Asp Pro Leu Met Ala Leu Ser Cys Ala Pro Ala Pro
```

-continued

```
                190                 195                 200
att act gaa ttt att ttt tat gcc caa agt tcc ttt gtc ctc ttt ttc    794
Ile Thr Glu Phe Ile Phe Tyr Ala Gln Ser Ser Phe Val Leu Phe Phe
    205                 210                 215 act att gca tac att ctt cgg tcc tat att ttg ttg ctc agg gct gtt    842
Thr Ile Ala Tyr Ile Leu Arg Ser Tyr Ile Leu Leu Leu Arg Ala Val
220                 225                 230                 235 ttt cag gtt cct tct gca gct ggc cga cga aaa gcc ttc tct acc tgt    890
Phe Gln Val Pro Ser Ala Ala Gly Arg Arg Lys Ala Phe Ser Thr Cys
                240                 245                 250 ggt tcc cat tta gtt gtg gtg tca ctc ttc tat ggt aca gta atg gta    938
Gly Ser His Leu Val Val Val Ser Leu Phe Tyr Gly Thr Val Met Val
            255                 260                 265 atg tat gtg agt cct aca tat ggc att cca att ttg atg cag aag atc    986
Met Tyr Val Ser Pro Thr Tyr Gly Ile Pro Ile Leu Met Gln Lys Ile
        270                 275                 280 ctt aca ctt gta tac tct gta atg act cct ctc ttt aat cct ctg att   1034
Leu Thr Leu Val Tyr Ser Val Met Thr Pro Leu Phe Asn Pro Leu Ile
    285                 290                 295 tat agc ctt cgt aac aag gac atg aaa ctt gct ctg aga aat gtt ttg   1082
Tyr Ser Leu Arg Asn Lys Asp Met Lys Leu Ala Leu Arg Asn Val Leu
300                 305                 310                 315 tta gga atg aga att gtc aaa aat atg taa ttcaaagctg tttcatactc     1132
Leu Gly Met Arg Ile Val Lys Asn Met
                320 acatgttcta ataaagaaaa aactggagat gaatcaattc attcagttgt ctttacccett  1192 tgttctatgt ttttgagaca ctgtctcatg tggccctggc tagcctcaaa ctcattctct   1252 agccaaggat gaccttgcaa agatcactta tgtatactct catatcatct gccaatagtg   1312 ataccttgac ctc                                                     1325

<210> SEQ ID NO 16
<211> LENGTH: 324
<212> TYPE: PRT
<213> ORGANISM: Mus musculus

<400> SEQUENCE: 16

Met Ser Leu Phe Pro Gln Arg Asn Leu Asp Ala Met Asn Arg Ser Ala
1               5                   10                  15

Ala His Val Thr Glu Phe Val Leu Leu Gly Phe Pro Gly Ser Trp Lys
            20                  25                  30

Ile Gln Ile Phe Leu Phe Val Leu Phe Leu Val Phe Tyr Val Leu Thr
        35                  40                  45

Leu Leu Gly Asn Gly Ala Ile Ile Cys Ala Val Arg Cys Asp Ser Arg
    50                  55                  60

Leu His Thr Pro Met Tyr Phe Leu Leu Gly Asn Phe Ser Phe Leu Glu
65                  70                  75                  80

Ile Trp Tyr Val Ser Ser Thr Ile Pro Asn Ile Leu Ala Asn Ile Leu
                85                  90                  95

Ser Lys Thr Lys Ala Ile Ser Phe Ser Gly Cys Phe Leu Gln Phe Tyr
            100                 105                 110

Phe Phe Phe Ser Leu Gly Thr Thr Glu Cys Leu Phe Leu Ala Val Met
        115                 120                 125

Ala Tyr Asp Arg Tyr Leu Ala Ile Cys Arg Pro Leu His Tyr Pro Thr
    130                 135                 140

Ile Met Thr Arg Arg Leu Cys Cys Ile Leu Val Ser Ser Cys Trp Leu
145                 150                 155                 160
```

```
Ile Gly Phe Leu Gly Tyr Pro Ile Pro Ile Phe Ser Ile Ser Gln Leu
            165                 170                 175
Pro Phe Cys Gly Ser Asn Ile Ile Asp His Phe Leu Cys Asp Met Asp
        180                 185                 190
Pro Leu Met Ala Leu Ser Cys Ala Pro Ala Pro Ile Thr Glu Phe Ile
    195                 200                 205
Phe Tyr Ala Gln Ser Ser Phe Val Leu Phe Phe Thr Ile Ala Tyr Ile
210                 215                 220
Leu Arg Ser Tyr Ile Leu Leu Arg Ala Val Phe Gln Val Pro Ser
225                 230                 235                 240
Ala Ala Gly Arg Arg Lys Ala Phe Ser Thr Cys Gly Ser His Leu Val
                245                 250                 255
Val Val Ser Leu Phe Tyr Gly Thr Val Met Val Met Tyr Val Ser Pro
            260                 265                 270
Thr Tyr Gly Ile Pro Ile Leu Met Gln Lys Ile Leu Thr Leu Val Tyr
        275                 280                 285
Ser Val Met Thr Pro Leu Phe Asn Pro Leu Ile Tyr Ser Leu Arg Asn
    290                 295                 300
Lys Asp Met Lys Leu Ala Leu Arg Asn Val Leu Leu Gly Met Arg Ile
305                 310                 315                 320
Val Lys Asn Met

<210> SEQ ID NO 17
<211> LENGTH: 1134
<212> TYPE: DNA
<213> ORGANISM: Mus musculus
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: CDS
<222> LOCATION: (106)..(1056)
<300> PUBLICATION INFORMATION:
<308> DATABASE ACCESSION NUMBER: AF121980
<309> DATABASE ENTRY DATE: 1999-04-25
<313> RELEVANT RESIDUES: (1)..(1134)

<400> SEQUENCE: 17
ccagtccagc ctggtaggct gggcaggtcc tacaggtctt tcagggactg aacccggcat      60
cctgcccctc ccctctccct ggagcctccc tagccctcng gcgtc atg ttg ggt tgg    117
                                                 Met Leu Gly Trp
                                                   1 agc aat ggc acc tac aat gag tcc tac acc agc ttc ctc ctc atg ggc     165
Ser Asn Gly Thr Tyr Asn Glu Ser Tyr Thr Ser Phe Leu Leu Met Gly
  5              10                  15                  20 ttc cca ggg atg cag gaa gcc aga gcc ctc ctg gtg ctg ccc ttc ctc    213
Phe Pro Gly Met Gln Glu Ala Arg Ala Leu Leu Val Leu Pro Phe Leu
                25                  30                  35 agc ctc tac ctg gtg atc ctc ttc acc aat gcc ctg gtc atc cac acg    261
Ser Leu Tyr Leu Val Ile Leu Phe Thr Asn Ala Leu Val Ile His Thr
            40                  45                  50 gtg gca tcc cag cgc agc ctg cac cag ccc atg tac ctg ctc att gcc    309
Val Ala Ser Gln Arg Ser Leu His Gln Pro Met Tyr Leu Leu Ile Ala
        55                  60                  65 ctg ctc ctg gct gtc aat atc tgt gct gcc acc acg gtg ctg ccc ccc    357
Leu Leu Leu Ala Val Asn Ile Cys Ala Ala Thr Thr Val Leu Pro Pro
    70                  75                  80 atg ctc ttc agc ttc tcc aca cgc ttc aac cgc atc tcc ctc cct cga    405
```

```
Met Leu Phe Ser Phe Ser Thr Arg Phe Asn Arg Ile Ser Leu Pro Arg
 85                  90                  95                 100 tgc ttg gga cag atg ttc tgc atc tac ttt ctg gtt tct atg gac tgc     453
Cys Leu Gly Gln Met Phe Cys Ile Tyr Phe Leu Val Ser Met Asp Cys
                    105                 110                 115 aac atc ctc ctg gtc atg gct cta gat cgc tat gtg gct atc tgc tac     501
Asn Ile Leu Leu Val Met Ala Leu Asp Arg Tyr Val Ala Ile Cys Tyr
                120                 125                 130 cct ctc cgc tac cca gaa ata gtg aca gga cag tta ctg gct ggt ctg     549
Pro Leu Arg Tyr Pro Glu Ile Val Thr Gly Gln Leu Leu Ala Gly Leu
            135                 140                 145 gtg gtg ttg gca gtc acc agg agc aca agc att gtt gct cca gtg gtg     597
Val Val Leu Ala Val Thr Arg Ser Thr Ser Ile Val Ala Pro Val Val
        150                 155                 160 gtg ctg gcc tcg cgg gtt cgc ttc tgc cgc tca gat gtg atc cgc cac     645
Val Leu Ala Ser Arg Val Arg Phe Cys Arg Ser Asp Val Ile Arg His
165                 170                 175                 180 ttt gcc tgt gag cac atg gcc ctg atg aag ctc tcc tgt gga gac atc     693
Phe Ala Cys Glu His Met Ala Leu Met Lys Leu Ser Cys Gly Asp Ile
                    185                 190                 195 tcg ctg aat aaa acg gcg gga ctc att att cga acc ttt aat aga gtc     741
Ser Leu Asn Lys Thr Ala Gly Leu Ile Ile Arg Thr Phe Asn Arg Val
                200                 205                 210 ctg gat atg ctc ctt cta ggc acc tcc tac tcc cgc atc atc cat gct     789
Leu Asp Met Leu Leu Leu Gly Thr Ser Tyr Ser Arg Ile Ile His Ala
            215                 220                 225 gcc ttc agg atc tca tca ggt gga gca cgg tcc aaa gcc ctg aac acc     837
Ala Phe Arg Ile Ser Ser Gly Gly Ala Arg Ser Lys Ala Leu Asn Thr
        230                 235                 240 tgt ggt tcc cac ctg ctg gtc atc ttc acc gtc tac tcc tcc acc atg     885
Cys Gly Ser His Leu Leu Val Ile Phe Thr Val Tyr Ser Ser Thr Met
245                 250                 255                 260 tcc tca tcc att gtc tac cgt gtg gct cgc act gcc tcc caa gat gtg     933
Ser Ser Ser Ile Val Tyr Arg Val Ala Arg Thr Ala Ser Gln Asp Val
                    265                 270                 275 cac aac ctg ctc agt gct ttc tat ctg ttg ctc ccg tgt ctg gtc aac     981
His Asn Leu Leu Ser Ala Phe Tyr Leu Leu Leu Pro Cys Leu Val Asn
                280                 285                 290 ccc atc atc tac ggg gcc aga acc aag gaa atc agg cag cac ctg gta    1029
Pro Ile Ile Tyr Gly Ala Arg Thr Lys Glu Ile Arg Gln His Leu Val
            295                 300                 305 agg tca ttc ctg agt gca ggc ccc tga ctctcctatg atcagtccgt          1076
Arg Ser Phe Leu Ser Ala Gly Pro
        310                 315 gttggcccct cagtattcct ggtgaaactg aggaaggaag aaatggagtc agagggac    1134

<210> SEQ ID NO 18
<211> LENGTH: 316
<212> TYPE: PRT
<213> ORGANISM: Mus musculus

<400> SEQUENCE: 18

Met Leu Gly Trp Ser Asn Gly Thr Tyr Asn Glu Ser Tyr Thr Ser Phe
1               5                   10                  15

Leu Leu Met Gly Phe Pro Gly Met Gln Glu Ala Arg Ala Leu Leu Val
                20                  25                  30

Leu Pro Phe Leu Ser Leu Tyr Leu Val Ile Leu Phe Thr Asn Ala Leu
            35                  40                  45

Val Ile His Thr Val Ala Ser Gln Arg Ser Leu His Gln Pro Met Tyr
```

```
                50                  55                  60
Leu Leu Ile Ala Leu Leu Leu Ala Val Asn Ile Cys Ala Ala Thr Thr
 65                  70                  75                  80

Val Leu Pro Pro Met Leu Phe Ser Phe Ser Thr Arg Phe Asn Arg Ile
                 85                  90                  95

Ser Leu Pro Arg Cys Leu Gly Gln Met Phe Cys Ile Tyr Phe Leu Val
                100                 105                 110

Ser Met Asp Cys Asn Ile Leu Leu Val Met Ala Leu Asp Arg Tyr Val
                115                 120                 125

Ala Ile Cys Tyr Pro Leu Arg Tyr Pro Glu Ile Val Thr Gly Gln Leu
        130                 135                 140

Leu Ala Gly Leu Val Val Leu Ala Val Thr Arg Ser Thr Ser Ile Val
145                 150                 155                 160

Ala Pro Val Val Val Leu Ala Ser Arg Val Arg Phe Cys Arg Ser Asp
                165                 170                 175

Val Ile Arg His Phe Ala Cys Glu His Met Ala Leu Met Lys Leu Ser
                180                 185                 190

Cys Gly Asp Ile Ser Leu Asn Lys Thr Ala Gly Leu Ile Ile Arg Thr
        195                 200                 205

Phe Asn Arg Val Leu Asp Met Leu Leu Leu Gly Thr Ser Tyr Ser Arg
210                 215                 220

Ile Ile His Ala Ala Phe Arg Ile Ser Ser Gly Gly Ala Arg Ser Lys
225                 230                 235                 240

Ala Leu Asn Thr Cys Gly Ser His Leu Leu Val Ile Phe Thr Val Tyr
                245                 250                 255

Ser Ser Thr Met Ser Ser Ser Ile Val Tyr Arg Val Ala Arg Thr Ala
                260                 265                 270

Ser Gln Asp Val His Asn Leu Leu Ser Ala Phe Tyr Leu Leu Leu Pro
        275                 280                 285

Cys Leu Val Asn Pro Ile Ile Tyr Gly Ala Arg Thr Lys Glu Ile Arg
        290                 295                 300

Gln His Leu Val Arg Ser Phe Leu Ser Ala Gly Pro
305                 310                 315

<210> SEQ ID NO 19
<211> LENGTH: 1421
<212> TYPE: DNA
<213> ORGANISM: Mus musculus
<220> FEATURE:
<221> NAME/KEY: CDS
<222> LOCATION: (291)..(1310)
<300> PUBLICATION INFORMATION:
<308> DATABASE ACCESSION NUMBER: AF121976
<309> DATABASE ENTRY DATE: 1999-12-25
<313> RELEVANT RESIDUES: (1)..(1421)

<400> SEQUENCE: 19
agaaagattt caggagtcct taaagacggc acagaaaacc ggtacagact gcaccattca      60
gctgaaagcc agacgtaaca gcaccacggt ggtggtgaac acgtgggct cagagaatcc     120 ggataagcct gcttttttat actaagttgg cattataaaa aagcattgct tatcaatttg    180
ttgcaacgaa caggtcacta tcagtcaaaa taaaatcatt atttgatttc aattttgtcc    240
cactccctgc ctctgtcatc acgatactgt gatgccatgg tgtccgactt atg ccc       296
                                                      Met Pro
                                                        1 gag aag atg ttg agc aaa ctt atc gct tat ctg ctt ctc ata gag tct      344
Glu Lys Met Leu Ser Lys Leu Ile Ala Tyr Leu Leu Leu Ile Glu Ser
```

-continued

```
            5                   10                  15
tgc aga caa act gcg caa ctc gtg aaa ggt agg cgg atc tgg gtc gac      392
Cys Arg Gln Thr Ala Gln Leu Val Lys Gly Arg Arg Ile Trp Val Asp
     20                  25                  30 tct agg cct cac tgg cct aat acg act cac tat agg gag ctc gag gat      440
Ser Arg Pro His Trp Pro Asn Thr Thr His Tyr Arg Glu Leu Glu Asp
 35                  40                  45                  50 cag cat gtt tgg att gct att ccc ttc tgc tcc atg tac atc ctt gct      488
Gln His Val Trp Ile Ala Ile Pro Phe Cys Ser Met Tyr Ile Leu Ala
                 55                  60                  65 ctg gtt gga aat ggt acc atc ctc tat atc att ata aca gac agg gct      536
Leu Val Gly Asn Gly Thr Ile Leu Tyr Ile Ile Ile Thr Asp Arg Ala
                     70                  75                  80 ctc cat gag cca atg tac ctc ttc ttg tgt ctg ctt tct atc act gat      584
Leu His Glu Pro Met Tyr Leu Phe Leu Cys Leu Leu Ser Ile Thr Asp
                 85                  90                  95 ctg gtt ctc tgt tca aca aca ttg cct aaa atg ctg gca ata ttc tgg      632
Leu Val Leu Cys Ser Thr Thr Leu Pro Lys Met Leu Ala Ile Phe Trp
            100                 105                 110 ctc aga tcc cat gtc att tcc tac cat ggc tgc ctc act cag atg ttt      680
Leu Arg Ser His Val Ile Ser Tyr His Gly Cys Leu Thr Gln Met Phe
115                 120                 125                 130 ttt gta cat gca gtc ttt gcc aca gag tca gct gtt ctg ctg gcc atg      728
Phe Val His Ala Val Phe Ala Thr Glu Ser Ala Val Leu Leu Ala Met
                135                 140                 145 gct ttt gat cga tat gtt gct atc tgc aga cca ctc cac tat aca tcc      776
Ala Phe Asp Arg Tyr Val Ala Ile Cys Arg Pro Leu His Tyr Thr Ser
                150                 155                 160 atc ctc aat gct gtt gta att ggg aag att ggc ctg gca tgc gtg act      824
Ile Leu Asn Ala Val Val Ile Gly Lys Ile Gly Leu Ala Cys Val Thr
            165                 170                 175 cgt ggc ctt ctc ttt gtc ttc ccc ttt gtc att ctc att gaa cgt tta      872
Arg Gly Leu Leu Phe Val Phe Pro Phe Val Ile Leu Ile Glu Arg Leu
        180                 185                 190 ccc ttc tgt gga cat cat ata atc cct cac act tac tgt gag cac atg      920
Pro Phe Cys Gly His His Ile Ile Pro His Thr Tyr Cys Glu His Met
195                 200                 205                 210 ggc ata gcc aag ctc gcc tgt gcc agc atc aag cct aac acc atc tat      968
Gly Ile Ala Lys Leu Ala Cys Ala Ser Ile Lys Pro Asn Thr Ile Tyr
                215                 220                 225 ggt ctt act gta gca ctt tca gtc act ggc atg gat gtg gtc ctc att     1016
Gly Leu Thr Val Ala Leu Ser Val Thr Gly Met Asp Val Val Leu Ile
            230                 235                 240 gca acc tcc tac atc ctg att ctg cag gcc gtg ctg cga ctg ccc tca     1064
Ala Thr Ser Tyr Ile Leu Ile Leu Gln Ala Val Leu Arg Leu Pro Ser
        245                 250                 255 aag gat gcc cag ttc cga gca ttc agc aca tgt gga gcc cac att tgt     1112
Lys Asp Ala Gln Phe Arg Ala Phe Ser Thr Cys Gly Ala His Ile Cys
260                 265                 270 gta att ctt gtc ttc tat atc ccc gca ttc ttt tca ttt ttc act cac     1160
Val Ile Leu Val Phe Tyr Ile Pro Ala Phe Phe Ser Phe Phe Thr His
275                 280                 285                 290 cgc ttt ggt cac cac gtg cct cct cag gta cac atc ata ctt gca aat     1208
Arg Phe Gly His His Val Pro Pro Gln Val His Ile Ile Leu Ala Asn
                295                 300                 305 ctt tat ctc ctt gtg cct cct gtt ctc aac ccc cta gtc tat ggc atc     1256
Leu Tyr Leu Leu Val Pro Pro Val Leu Asn Pro Leu Val Tyr Gly Ile
        310                 315                 320 aat acc aaa caa atc cgc ctg aga ata ctt gac ttt ttt gta aag aga     1304
```

```
Asn Thr Lys Gln Ile Arg Leu Arg Ile Leu Asp Phe Phe Val Lys Arg
        325                 330                 335 agg tga caataatctc cacatatacc aaaggctaat gagttcctgg ctttagtttg      1360
Arg ctgcttctgc tgatctcagt aagtcagtgt atgtacattt aagattttga gatctagagc   1420
a                                                                   1421

<210> SEQ ID NO 20
<211> LENGTH: 339
<212> TYPE: PRT
<213> ORGANISM: Mus musculus

<400> SEQUENCE: 20

Met Pro Glu Lys Met Leu Ser Lys Leu Ile Ala Tyr Leu Leu Leu Ile
1               5                   10                  15

Glu Ser Cys Arg Gln Thr Ala Gln Leu Val Lys Gly Arg Arg Ile Trp
            20                  25                  30

Val Asp Ser Arg Pro His Trp Pro Asn Thr Thr His Tyr Arg Glu Leu
        35                  40                  45

Glu Asp Gln His Val Trp Ile Ala Ile Pro Phe Cys Ser Met Tyr Ile
    50                  55                  60

Leu Ala Leu Val Gly Asn Gly Thr Ile Leu Tyr Ile Ile Ile Thr Asp
65                  70                  75                  80

Arg Ala Leu His Glu Pro Met Tyr Leu Phe Leu Cys Leu Leu Ser Ile
                85                  90                  95

Thr Asp Leu Val Leu Cys Ser Thr Thr Leu Pro Lys Met Leu Ala Ile
            100                 105                 110

Phe Trp Leu Arg Ser His Val Ile Ser Tyr His Gly Cys Leu Thr Gln
        115                 120                 125

Met Phe Phe Val His Ala Val Phe Ala Thr Glu Ser Ala Val Leu Leu
    130                 135                 140

Ala Met Ala Phe Asp Arg Tyr Val Ala Ile Cys Arg Pro Leu His Tyr
145                 150                 155                 160

Thr Ser Ile Leu Asn Ala Val Val Ile Gly Lys Ile Gly Leu Ala Cys
                165                 170                 175

Val Thr Arg Gly Leu Leu Phe Val Phe Pro Phe Val Ile Leu Ile Glu
            180                 185                 190

Arg Leu Pro Phe Cys Gly His His Ile Ile Pro His Thr Tyr Cys Glu
        195                 200                 205

His Met Gly Ile Ala Lys Leu Ala Cys Ala Ser Ile Lys Pro Asn Thr
    210                 215                 220

Ile Tyr Gly Leu Thr Val Ala Leu Ser Val Thr Gly Met Asp Val Val
225                 230                 235                 240

Leu Ile Ala Thr Ser Tyr Ile Leu Ile Leu Gln Ala Val Leu Arg Leu
                245                 250                 255

Pro Ser Lys Asp Ala Gln Phe Arg Ala Phe Ser Thr Cys Gly Ala His
            260                 265                 270

Ile Cys Val Ile Leu Val Phe Tyr Ile Pro Ala Phe Phe Ser Phe Phe
        275                 280                 285

Thr His Arg Phe Gly His His Val Pro Pro Gln Val His Ile Ile Leu
    290                 295                 300

Ala Asn Leu Tyr Leu Leu Val Pro Pro Val Leu Asn Pro Leu Val Tyr
305                 310                 315                 320

Gly Ile Asn Thr Lys Gln Ile Arg Leu Arg Ile Leu Asp Phe Phe Val
```

Lys Arg Arg

<210> SEQ ID NO 21
<211> LENGTH: 930
<212> TYPE: DNA
<213> ORGANISM: M.musculus
<220> FEATURE:
<221> NAME/KEY: CDS
<222> LOCATION: (1)..(930)
<300> PUBLICATION INFORMATION:
<308> DATABASE ACCESSION NUMBER: X92969
<309> DATABASE ENTRY DATE: 1996-07-01
<313> RELEVANT RESIDUES: (1)..(930)

<400> SEQUENCE: 21

```
atg cag aga aat aac ttc act gaa gtg ata gag ttc gtc ttc ctg gga      48
Met Gln Arg Asn Asn Phe Thr Glu Val Ile Glu Phe Val Phe Leu Gly
1               5                   10                  15 ttc tcc agc ttt gga aag cat cag ata acc ctc ttt gtg gtt ttc cta      96
Phe Ser Ser Phe Gly Lys His Gln Ile Thr Leu Phe Val Val Phe Leu
                20                  25                  30 acc atc tac att tta act ctg gct ggc aac atc att ata gtg aca atc     144
Thr Ile Tyr Ile Leu Thr Leu Ala Gly Asn Ile Ile Ile Val Thr Ile
            35                  40                  45 aca cac ata gac cac cac ctt cac act ccc atg tac ttc ttt ctg agc     192
Thr His Ile Asp His His Leu His Thr Pro Met Tyr Phe Phe Leu Ser
        50                  55                  60 atg ttg gca agc tca gag act gtg tac aca ctg gtc att gtc cca cga     240
Met Leu Ala Ser Ser Glu Thr Val Tyr Thr Leu Val Ile Val Pro Arg
65                  70                  75                  80 atg ctt tcc agc ctg att ttt tac aac ctt ccc ata tcc ttg gca ggc     288
Met Leu Ser Ser Leu Ile Phe Tyr Asn Leu Pro Ile Ser Leu Ala Gly
                85                  90                  95 tgc gca acc caa atg ttc ttt ttt gtc act ttg gcc acc aac aac tgc     336
Cys Ala Thr Gln Met Phe Phe Phe Val Thr Leu Ala Thr Asn Asn Cys
                100                 105                 110 ttt ctg ctc aca gca atg ggt tat gat cgt tat gtg gct att tgt aat     384
Phe Leu Leu Thr Ala Met Gly Tyr Asp Arg Tyr Val Ala Ile Cys Asn
            115                 120                 125 cct ctg aga tat aca atc atc atg agc aag gga atg tgt gcc ttg ttg     432
Pro Leu Arg Tyr Thr Ile Ile Met Ser Lys Gly Met Cys Ala Leu Leu
        130                 135                 140 gtc tgt ggg tct tta ggc act ggc ctg gtt atg gca gtt ctt cat gtg     480
Val Cys Gly Ser Leu Gly Thr Gly Leu Val Met Ala Val Leu His Val
145                 150                 155                 160 cca gcc atg ttc cat ttg ccc ttt tgt ggc acg gtg gtg gag cac ttt     528
Pro Ala Met Phe His Leu Pro Phe Cys Gly Thr Val Val Glu His Phe
                165                 170                 175 ttc tgt gac ata tac cca gta atg aag ctt tct tgt gtt gat acc act     576
Phe Cys Asp Ile Tyr Pro Val Met Lys Leu Ser Cys Val Asp Thr Thr
                180                 185                 190 gtc aat gag ata atc aat tat ggt gta agt tca ttt gta att ctt gtg     624
Val Asn Glu Ile Ile Asn Tyr Gly Val Ser Ser Phe Val Ile Leu Val
            195                 200                 205 ccc ata ggg ctg ata ttt atc tcc tat gtg ctc att gtc tct tcc atc     672
Pro Ile Gly Leu Ile Phe Ile Ser Tyr Val Leu Ile Val Ser Ser Ile
        210                 215                 220 ctt aaa att gtg tcc act gaa ggc cag aag aaa gcc ttt gcc acc tgt     720
Leu Lys Ile Val Ser Thr Glu Gly Gln Lys Lys Ala Phe Ala Thr Cys
225                 230                 235                 240
```

```
gcc tct cat ctc act gtg gtc att gtc cac tat ggc tgt gcc tcc att       768
Ala Ser His Leu Thr Val Val Ile Val His Tyr Gly Cys Ala Ser Ile
            245                 250                 255 gcc tac ctc aaa ccc aaa tca gaa agt tca gta gaa aaa gac ctt ctt       816
Ala Tyr Leu Lys Pro Lys Ser Glu Ser Ser Val Glu Lys Asp Leu Leu
            260                 265                 270 ctc tct gtg acc tac act atc atc act ccc ttg ctg aac cct gtt gtc       864
Leu Ser Val Thr Tyr Thr Ile Ile Thr Pro Leu Leu Asn Pro Val Val
            275                 280                 285 tac agc ctc agg aac aaa gaa gtc aaa gat gct cta tgc aga gct gtg       912
Tyr Ser Leu Arg Asn Lys Glu Val Lys Asp Ala Leu Cys Arg Ala Val
            290                 295                 300 ggc aga aac act tct taa                                                930
Gly Arg Asn Thr Ser
305
```

<210> SEQ ID NO 22
<211> LENGTH: 309
<212> TYPE: PRT
<213> ORGANISM: M.musculus

<400> SEQUENCE: 22

```
Met Gln Arg Asn Asn Phe Thr Glu Val Ile Glu Phe Val Phe Leu Gly
1               5                   10                  15

Phe Ser Ser Phe Gly Lys His Gln Ile Thr Leu Phe Val Val Phe Leu
                20                  25                  30

Thr Ile Tyr Ile Leu Thr Leu Ala Gly Asn Ile Ile Ile Val Thr Ile
            35                  40                  45

Thr His Ile Asp His His Leu His Thr Pro Met Tyr Phe Phe Leu Ser
        50                  55                  60

Met Leu Ala Ser Ser Glu Thr Val Tyr Thr Leu Val Ile Val Pro Arg
65                  70                  75                  80

Met Leu Ser Ser Leu Ile Phe Tyr Asn Leu Pro Ile Ser Leu Ala Gly
                85                  90                  95

Cys Ala Thr Gln Met Phe Phe Val Thr Leu Ala Thr Asn Asn Cys
            100                 105                 110

Phe Leu Leu Thr Ala Met Gly Tyr Asp Arg Tyr Val Ala Ile Cys Asn
        115                 120                 125

Pro Leu Arg Tyr Thr Ile Ile Met Ser Lys Gly Met Cys Ala Leu Leu
    130                 135                 140

Val Cys Gly Ser Leu Gly Thr Gly Leu Val Met Ala Val Leu His Val
145                 150                 155                 160

Pro Ala Met Phe His Leu Pro Phe Cys Gly Thr Val Val Glu His Phe
                165                 170                 175

Phe Cys Asp Ile Tyr Pro Val Met Lys Leu Ser Cys Val Asp Thr Thr
            180                 185                 190

Val Asn Glu Ile Ile Asn Tyr Gly Val Ser Ser Phe Val Ile Leu Val
        195                 200                 205

Pro Ile Gly Leu Ile Phe Ile Ser Tyr Val Leu Ile Val Ser Ser Ile
    210                 215                 220

Leu Lys Ile Val Ser Thr Glu Gly Gln Lys Lys Ala Phe Ala Thr Cys
225                 230                 235                 240

Ala Ser His Leu Thr Val Val Ile Val His Tyr Gly Cys Ala Ser Ile
                245                 250                 255

Ala Tyr Leu Lys Pro Lys Ser Glu Ser Ser Val Glu Lys Asp Leu Leu
            260                 265                 270
```

```
Leu Ser Val Thr Tyr Thr Ile Ile Thr Pro Leu Leu Asn Pro Val Val
        275                 280                 285

Tyr Ser Leu Arg Asn Lys Glu Val Lys Asp Ala Leu Cys Arg Ala Val
        290                 295                 300

Gly Arg Asn Thr Ser
305

<210> SEQ ID NO 23
<211> LENGTH: 957
<212> TYPE: DNA
<213> ORGANISM: Mus musculus
<220> FEATURE:
<221> NAME/KEY: CDS
<222> LOCATION: (1)..(957)
<300> PUBLICATION INFORMATION:
<308> DATABASE ACCESSION NUMBER: AB061229
<309> DATABASE ENTRY DATE: 2001-09-07
<313> RELEVANT RESIDUES: (1)..(957)

<400> SEQUENCE: 23 atg ata ctg tct gaa aaa aac aat agt ggg att att ttc acc ctc ttg      48
Met Ile Leu Ser Glu Lys Asn Asn Ser Gly Ile Ile Phe Thr Leu Leu
1               5                  10                  15 ggc ttc tca gat tat cct gac ctt aaa gtc cct ctc ttc ttg gtg ttt      96
Gly Phe Ser Asp Tyr Pro Asp Leu Lys Val Pro Leu Phe Leu Val Phe
                20                  25                  30 ctc gtc att tac agc atc act gtg gta gga aat att ggt atg atc ctc     144
Leu Val Ile Tyr Ser Ile Thr Val Val Gly Asn Ile Gly Met Ile Leu
            35                  40                  45 gtg atc aga att aat ccc caa ctg cac tcc cct atg tac ttc ttc ctc     192
Val Ile Arg Ile Asn Pro Gln Leu His Ser Pro Met Tyr Phe Phe Leu
        50                  55                  60 agc cac ctc tcc ttt gtg gat ttc tgc tat tct tcg atc att gct ccc     240
Ser His Leu Ser Phe Val Asp Phe Cys Tyr Ser Ser Ile Ile Ala Pro
65                  70                  75                  80 aag atg ctg gtg aac ctt gtt gca aaa gac ata acc att tca ttt gta     288
Lys Met Leu Val Asn Leu Val Ala Lys Asp Ile Thr Ile Ser Phe Val
                85                  90                  95 gaa tgc ata gta caa tat ttt tta ttt tgt gtc ttt gta gta act gaa     336
Glu Cys Ile Val Gln Tyr Phe Leu Phe Cys Val Phe Val Val Thr Glu
            100                 105                 110 gcc ttt tta tta gtg gtt atg gca tat gac cga ttt gtg gct atc tgt     384
Ala Phe Leu Leu Val Val Met Ala Tyr Asp Arg Phe Val Ala Ile Cys
        115                 120                 125 aac cct ctg ctc tac aca gta gcc atg tcc cag aaa ctc tgt atc aca     432
Asn Pro Leu Leu Tyr Thr Val Ala Met Ser Gln Lys Leu Cys Ile Thr
130                 135                 140 ctg gtg gtg gga tcc tac gca tgg ggg ttc aca tgt tcc ttg aca ctg     480
Leu Val Val Gly Ser Tyr Ala Trp Gly Phe Thr Cys Ser Leu Thr Leu
145                 150                 155                 160 acg tgt tct act gtg caa tta tct ttt cat ggt gtc aat agg atc gat     528
Thr Cys Ser Thr Val Gln Leu Ser Phe His Gly Val Asn Arg Ile Asp
                165                 170                 175 cac ttc ttc tgt gaa ctc tct tca ctg cta gcc ctt tct tcc tct gat     576
His Phe Phe Cys Glu Leu Ser Ser Leu Leu Ala Leu Ser Ser Ser Asp
            180                 185                 190 act ctc atc agt caa tta ctg ctg ttt gtc ttt gcc aca ttt aat gct     624
Thr Leu Ile Ser Gln Leu Leu Leu Phe Val Phe Ala Thr Phe Asn Ala
        195                 200                 205 gtc agc aca tta ctc ctt att ctg ttg tct tac ctg ttc att gtt gtc     672
Val Ser Thr Leu Leu Leu Ile Leu Leu Ser Tyr Leu Phe Ile Val Val
210                 215                 220
```

```
act gtt ctt aag atg cgt tca gcc agt ggg cgt cgt aag gct ttc tcc      720
Thr Val Leu Lys Met Arg Ser Ala Ser Gly Arg Arg Lys Ala Phe Ser
225                 230                 235                 240 acc tgt gca tcc cat ctg gca gcc atc act atc ttc cat ggt acc att      768
Thr Cys Ala Ser His Leu Ala Ala Ile Thr Ile Phe His Gly Thr Ile
            245                 250                 255 tta ttc ctt ttt tgt gtt ccc aac tct aag aat tcc agg ctc aca gtc      816
Leu Phe Leu Phe Cys Val Pro Asn Ser Lys Asn Ser Arg Leu Thr Val
        260                 265                 270 aaa gtg ggc tct gtg ttt tac aca gtg gtg atc ccc atg ctt aac ccc      864
Lys Val Gly Ser Val Phe Tyr Thr Val Val Ile Pro Met Leu Asn Pro
    275                 280                 285 ata atc tat agt ctg aga aat aag gat gtc caa gat act att aga aaa      912
Ile Ile Tyr Ser Leu Arg Asn Lys Asp Val Gln Asp Thr Ile Arg Lys
290                 295                 300 ata atg acc ctt atc tca tgt gtt aag aat gat aga cac aat taa          957
Ile Met Thr Leu Ile Ser Cys Val Lys Asn Asp Arg His Asn
305                 310                 315
```

<210> SEQ ID NO 24
<211> LENGTH: 318
<212> TYPE: PRT
<213> ORGANISM: Mus musculus

<400> SEQUENCE: 24

```
Met Ile Leu Ser Glu Lys Asn Asn Ser Gly Ile Ile Phe Thr Leu Leu
1               5                   10                  15

Gly Phe Ser Asp Tyr Pro Asp Leu Lys Val Pro Leu Phe Leu Val Phe
            20                  25                  30

Leu Val Ile Tyr Ser Ile Thr Val Val Gly Asn Ile Gly Met Ile Leu
        35                  40                  45

Val Ile Arg Ile Asn Pro Gln Leu His Ser Pro Met Tyr Phe Phe Leu
    50                  55                  60

Ser His Leu Ser Phe Val Asp Phe Cys Tyr Ser Ser Ile Ile Ala Pro
65                  70                  75                  80

Lys Met Leu Val Asn Leu Val Ala Lys Asp Ile Thr Ile Ser Phe Val
                85                  90                  95

Glu Cys Ile Val Gln Tyr Phe Leu Phe Cys Val Phe Val Val Thr Glu
            100                 105                 110

Ala Phe Leu Leu Val Val Met Ala Tyr Asp Arg Phe Val Ala Ile Cys
        115                 120                 125

Asn Pro Leu Leu Tyr Thr Val Ala Met Ser Gln Lys Leu Cys Ile Thr
    130                 135                 140

Leu Val Val Gly Ser Tyr Ala Trp Gly Phe Thr Cys Ser Leu Thr Leu
145                 150                 155                 160

Thr Cys Ser Thr Val Gln Leu Ser Phe His Gly Val Asn Arg Ile Asp
                165                 170                 175

His Phe Phe Cys Glu Leu Ser Ser Leu Leu Ala Leu Ser Ser Ser Asp
            180                 185                 190

Thr Leu Ile Ser Gln Leu Leu Leu Phe Val Phe Ala Thr Phe Asn Ala
        195                 200                 205

Val Ser Thr Leu Leu Leu Ile Leu Leu Ser Tyr Leu Phe Ile Val Val
    210                 215                 220

Thr Val Leu Lys Met Arg Ser Ala Ser Gly Arg Arg Lys Ala Phe Ser
225                 230                 235                 240

Thr Cys Ala Ser His Leu Ala Ala Ile Thr Ile Phe His Gly Thr Ile
```

```
                   245                 250                 255
Leu Phe Leu Phe Cys Val Pro Asn Ser Lys Asn Ser Arg Leu Thr Val
            260                 265                 270

Lys Val Gly Ser Val Phe Tyr Thr Val Val Ile Pro Met Leu Asn Pro
            275                 280                 285

Ile Ile Tyr Ser Leu Arg Asn Lys Asp Val Gln Asp Thr Ile Arg Lys
            290                 295                 300

Ile Met Thr Leu Ile Ser Cys Val Lys Asn Asp Arg His Asn
305                 310                 315

<210> SEQ ID NO 25
<211> LENGTH: 1344
<212> TYPE: DNA
<213> ORGANISM: Mus musculus
<220> FEATURE:
<221> NAME/KEY: CDS
<222> LOCATION: (61)..(1020)
<300> PUBLICATION INFORMATION:
<308> DATABASE ACCESSION NUMBER: AJ133424
<309> DATABASE ENTRY DATE: 2003-02-01
<313> RELEVANT RESIDUES: (1)..(1344)

<400> SEQUENCE: 25
ggaggaagac aatgttgatg ctgattgctg agttcctgca ggtttcaaac cgaatgtacc      60 atg gac aga tcc aat gag acc gcc ccc ctg tcc ggc ttc att ctc ctg      108
Met Asp Arg Ser Asn Glu Thr Ala Pro Leu Ser Gly Phe Ile Leu Leu
1               5                   10                  15 ggc ctc tct gcc cac cca aag ctg gag aaa acc ttc ttc gtg ctc atc      156
Gly Leu Ser Ala His Pro Lys Leu Glu Lys Thr Phe Phe Val Leu Ile
            20                  25                  30 ctg atg atg tac ctg gtg atc ctg ctg ggc aac ggc gtc ctc atc ctg      204
Leu Met Met Tyr Leu Val Ile Leu Leu Gly Asn Gly Val Leu Ile Leu
        35                  40                  45 gtg agc atc ctc gac tcc cac ctg cac acg ccc atg tac ttc ttc ctg      252
Val Ser Ile Leu Asp Ser His Leu His Thr Pro Met Tyr Phe Phe Leu
50                  55                  60 ggg aac ctc tcc ttc ctg gac atc tgc tac act acc tcc tct gtc ccc      300
Gly Asn Leu Ser Phe Leu Asp Ile Cys Tyr Thr Thr Ser Ser Val Pro
65                  70                  75                  80 ctc att ctg gac agc ttt ctg act ccc agg aag acc atc tcc ttc tcg      348
Leu Ile Leu Asp Ser Phe Leu Thr Pro Arg Lys Thr Ile Ser Phe Ser
                85                  90                  95 ggc tgt gcc gtg cag atg ttt ctc tcc ttc gcc atg gga gcc acg gag      396
Gly Cys Ala Val Gln Met Phe Leu Ser Phe Ala Met Gly Ala Thr Glu
            100                 105                 110 tgt gtg ctc ctg agt atg atg gcg ttt gat cgt tat gtg gcc atc tgc      444
Cys Val Leu Leu Ser Met Met Ala Phe Asp Arg Tyr Val Ala Ile Cys
        115                 120                 125 aac ccc ctt aga tat cct gtg gtc atg aac aag gct gcc tat gtg ccc      492
Asn Pro Leu Arg Tyr Pro Val Val Met Asn Lys Ala Ala Tyr Val Pro
130                 135                 140 atg gct gcc agt tcc tgg gca ggt ggt atc act aat tct gta gtg cag      540
Met Ala Ala Ser Ser Trp Ala Gly Gly Ile Thr Asn Ser Val Val Gln
145                 150                 155                 160 aca tct ttg gca atg cgg ctg ccc ttc tgt ggg gac aat gtc atc aat      588
Thr Ser Leu Ala Met Arg Leu Pro Phe Cys Gly Asp Asn Val Ile Asn
                165                 170                 175 cac ttc acc tgt gag atc ctg gca gtc ctg aaa ctg gcc tgt gct gac      636
His Phe Thr Cys Glu Ile Leu Ala Val Leu Lys Leu Ala Cys Ala Asp
            180                 185                 190
```

```
atc tcc atc aat gtc atc agc atg gtt gtg gcc aac atg atc ttc ttg      684
Ile Ser Ile Asn Val Ile Ser Met Val Val Ala Asn Met Ile Phe Leu
        195                 200                 205 gca gtc cca gtc ctc ttc atc ttt gtc tcc tat gtc ttc atc ctt gtg      732
Ala Val Pro Val Leu Phe Ile Phe Val Ser Tyr Val Phe Ile Leu Val
    210                 215                 220 aca atc ctg agg atc ccc tct gct gag ggg agg aag aag gcc ttc tcc      780
Thr Ile Leu Arg Ile Pro Ser Ala Glu Gly Arg Lys Lys Ala Phe Ser
225                 230                 235                 240 acc tgc tct gcc cac ctc acc gtg gta ctt gtc ttc tat gga acc atc      828
Thr Cys Ser Ala His Leu Thr Val Val Leu Val Phe Tyr Gly Thr Ile
                245                 250                 255 ctc ttc atg tac ggg aag ccc aag tcc aag gac cca ctg ggg gca gac      876
Leu Phe Met Tyr Gly Lys Pro Lys Ser Lys Asp Pro Leu Gly Ala Asp
            260                 265                 270 aag cag gac ctt gca gac aag ctc atc tcc ctc ttc tat gga gtg gtg      924
Lys Gln Asp Leu Ala Asp Lys Leu Ile Ser Leu Phe Tyr Gly Val Val
        275                 280                 285 acc ccc atg cta aac ccc atc atc tac agc ttg aga aac aag gac gtg      972
Thr Pro Met Leu Asn Pro Ile Ile Tyr Ser Leu Arg Asn Lys Asp Val
    290                 295                 300 agg gct gct gtg agg aac ctg gtg ggc cag aaa cac cta act gag tga     1020
Arg Ala Ala Val Arg Asn Leu Val Gly Gln Lys His Leu Thr Glu
305                 310                 315 ctgtcacagt gcagaacttc caacctcttc attgtgtttg tgagggaaga gtggtgcaat   1080
gaagaggagc cacttcccca aggtccaagt aatgaactca gaactaagac tataaacaaa   1140
ctatcaacgt tccttaagca ccaatgcttc tagttaacag gctggaagga caagccttta   1200
cacctttgga gagaatggct ggttgtcagc tttgtgttca accttagtgg cgtcgtagaa   1260
ctactctttc atgaccagag gctggcacag atctctggaa agatgctgac atgcataact   1320
aggagacaga tgcaaagcct ggtt                                          1344
```

<210> SEQ ID NO 26
<211> LENGTH: 319
<212> TYPE: PRT
<213> ORGANISM: Mus musculus

<400> SEQUENCE: 26

```
Met Asp Arg Ser Asn Glu Thr Ala Pro Leu Ser Gly Phe Ile Leu Leu
1               5                   10                  15

Gly Leu Ser Ala His Pro Lys Leu Glu Lys Thr Phe Phe Val Leu Ile
            20                  25                  30

Leu Met Met Tyr Leu Val Ile Leu Leu Gly Asn Gly Val Leu Ile Leu
        35                  40                  45

Val Ser Ile Leu Asp Ser His Leu His Thr Pro Met Tyr Phe Phe Leu
    50                  55                  60

Gly Asn Leu Ser Phe Leu Asp Ile Cys Tyr Thr Thr Ser Ser Val Pro
65              70                  75                  80

Leu Ile Leu Asp Ser Phe Leu Thr Pro Arg Lys Thr Ile Ser Phe Ser
            85                  90                  95

Gly Cys Ala Val Gln Met Phe Leu Ser Phe Ala Met Gly Ala Thr Glu
        100                 105                 110

Cys Val Leu Leu Ser Met Met Ala Phe Asp Arg Tyr Val Ala Ile Cys
    115                 120                 125

Asn Pro Leu Arg Tyr Pro Val Val Met Asn Lys Ala Ala Tyr Val Pro
130                 135                 140
```

-continued

```
Met Ala Ala Ser Ser Trp Ala Gly Gly Ile Thr Asn Ser Val Val Gln
145                 150                 155                 160

Thr Ser Leu Ala Met Arg Leu Pro Phe Cys Gly Asp Asn Val Ile Asn
                165                 170                 175

His Phe Thr Cys Glu Ile Leu Ala Val Leu Lys Leu Ala Cys Ala Asp
            180                 185                 190

Ile Ser Ile Asn Val Ile Ser Met Val Val Ala Asn Met Ile Phe Leu
        195                 200                 205

Ala Val Pro Val Leu Phe Ile Phe Val Ser Tyr Val Phe Ile Leu Val
    210                 215                 220

Thr Ile Leu Arg Ile Pro Ser Ala Glu Gly Arg Lys Lys Ala Phe Ser
225                 230                 235                 240

Thr Cys Ser Ala His Leu Thr Val Val Leu Val Phe Tyr Gly Thr Ile
                245                 250                 255

Leu Phe Met Tyr Gly Lys Pro Lys Ser Lys Asp Pro Leu Gly Ala Asp
                260                 265                 270

Lys Gln Asp Leu Ala Asp Lys Leu Ile Ser Leu Phe Tyr Gly Val Val
            275                 280                 285

Thr Pro Met Leu Asn Pro Ile Ile Tyr Ser Leu Arg Asn Lys Asp Val
        290                 295                 300

Arg Ala Ala Val Arg Asn Leu Val Gly Gln Lys His Leu Thr Glu
305                 310                 315
```

<210> SEQ ID NO 27
<211> LENGTH: 942
<212> TYPE: DNA
<213> ORGANISM: Mus musculus
<220> FEATURE:
<221> NAME/KEY: CDS
<222> LOCATION: (1)..(942)
<300> PUBLICATION INFORMATION:
<308> DATABASE ACCESSION NUMBER: AF102523
<309> DATABASE ENTRY DATE: 1999-02-08
<313> RELEVANT RESIDUES: (1)..(942)

<400> SEQUENCE: 27

```
atg gcg aac agc act act gtt act gag ttt att ttg ctg ggg ctg tca       48
Met Ala Asn Ser Thr Thr Val Thr Glu Phe Ile Leu Leu Gly Leu Ser
1               5                   10                  15 gat gcc tgt gag ctg cag gtg ctc ata ttc ctg ggc ttt ctc ctg acc       96
Asp Ala Cys Glu Leu Gln Val Leu Ile Phe Leu Gly Phe Leu Leu Thr
                20                  25                  30 tac ttc ctc att ctg ctg gga aac ttc ctc atc atc ttc atc acc ctt      144
Tyr Phe Leu Ile Leu Leu Gly Asn Phe Leu Ile Ile Phe Ile Thr Leu
            35                  40                  45 gtg gac agg cgc ctt tac acc ccc atg tat tac ttc ctc cgc aac ttt      192
Val Asp Arg Arg Leu Tyr Thr Pro Met Tyr Tyr Phe Leu Arg Asn Phe
        50                  55                  60 gcc atg ctg gag atc tgg ttc acc tct gtc atc ttc ccc aag atg cta      240
Ala Met Leu Glu Ile Trp Phe Thr Ser Val Ile Phe Pro Lys Met Leu
65                  70                  75                  80 acc aac atc atc aca gga cat aag acc atc tcc cta cta ggt tgt ttc      288
Thr Asn Ile Ile Thr Gly His Lys Thr Ile Ser Leu Leu Gly Cys Phe
                85                  90                  95 ctc caa gca ttc ctc tat ttc ttc ctt ggc acc act gag ttc ttt cta      336
Leu Gln Ala Phe Leu Tyr Phe Phe Leu Gly Thr Thr Glu Phe Phe Leu
                100                 105                 110 ctg gca gtg atg tcc ttt gac agg tat gtg gcc att tgt aac cct ttg      384
Leu Ala Val Met Ser Phe Asp Arg Tyr Val Ala Ile Cys Asn Pro Leu
            115                 120                 125
```

```
cgt tat gcc acc att atg agc aaa aga gtc tgt gtc cag ctt gtg ttt      432
Arg Tyr Ala Thr Ile Met Ser Lys Arg Val Cys Val Gln Leu Val Phe
    130                 135                 140 tgc tca tgg atg tct gga ttg ctt ctc atc ata gtt cct agt tca att      480
Cys Ser Trp Met Ser Gly Leu Leu Leu Ile Ile Val Pro Ser Ser Ile
145                 150                 155                 160 gta ttt cag cag cca ttc tgt ggc cca aac atc att aat cat ttc ttc      528
Val Phe Gln Gln Pro Phe Cys Gly Pro Asn Ile Ile Asn His Phe Phe
                165                 170                 175 tgt gac aac ttt cca ctt atg gaa ctc ata tgt gca gat act agc ctg      576
Cys Asp Asn Phe Pro Leu Met Glu Leu Ile Cys Ala Asp Thr Ser Leu
                180                 185                 190 gta gag ttc ctg ggt ttt gtt att gcc aat ttc agc ctc ctg ggc act      624
Val Glu Phe Leu Gly Phe Val Ile Ala Asn Phe Ser Leu Leu Gly Thr
            195                 200                 205 ctg gct gtg act gcc acc tgc tat ggc cac att ctc tat acc att cta      672
Leu Ala Val Thr Ala Thr Cys Tyr Gly His Ile Leu Tyr Thr Ile Leu
210                 215                 220 cac att cct tca gcc aag gag agg aag aaa gcc ttc tca act tgc tcc      720
His Ile Pro Ser Ala Lys Glu Arg Lys Lys Ala Phe Ser Thr Cys Ser
225                 230                 235                 240 tct cat att att gtg gtg tct ctc ttc tac ggc agc tgt atc ttc atg      768
Ser His Ile Ile Val Val Ser Leu Phe Tyr Gly Ser Cys Ile Phe Met
                245                 250                 255 tat gtc cgg tct ggc aag aat gga cag ggg gag gat cat aac aag gtg      816
Tyr Val Arg Ser Gly Lys Asn Gly Gln Gly Glu Asp His Asn Lys Val
                260                 265                 270 gtg gca ttg ctc aac act gta gtg aca ccc aca ctc aac ccc ttc atc      864
Val Ala Leu Leu Asn Thr Val Val Thr Pro Thr Leu Asn Pro Phe Ile
            275                 280                 285 tac act ctg agg aac aag cag gtg aag cag gta ttt agg gaa cac gta      912
Tyr Thr Leu Arg Asn Lys Gln Val Lys Gln Val Phe Arg Glu His Val
290                 295                 300 agc aag ttc caa aag ttc agc cag acg tga                              942
Ser Lys Phe Gln Lys Phe Ser Gln Thr
305                 310

<210> SEQ ID NO 28
<211> LENGTH: 313
<212> TYPE: PRT
<213> ORGANISM: Mus musculus

<400> SEQUENCE: 28

Met Ala Asn Ser Thr Thr Val Thr Glu Phe Ile Leu Leu Gly Leu Ser
1               5                   10                  15

Asp Ala Cys Glu Leu Gln Val Leu Ile Phe Leu Gly Phe Leu Leu Thr
                20                  25                  30

Tyr Phe Leu Ile Leu Leu Gly Asn Phe Leu Ile Phe Ile Thr Leu
            35                  40                  45

Val Asp Arg Arg Leu Tyr Thr Pro Met Tyr Tyr Phe Leu Arg Asn Phe
        50                  55                  60

Ala Met Leu Glu Ile Trp Phe Thr Ser Val Ile Phe Pro Lys Met Leu
65                  70                  75                  80

Thr Asn Ile Ile Thr Gly His Lys Thr Ile Ser Leu Leu Gly Cys Phe
                85                  90                  95

Leu Gln Ala Phe Leu Tyr Phe Leu Gly Thr Thr Glu Phe Phe Leu
            100                 105                 110

Leu Ala Val Met Ser Phe Asp Arg Tyr Val Ala Ile Cys Asn Pro Leu
```

-continued

```
             115                 120                 125
Arg Tyr Ala Thr Ile Met Ser Lys Arg Val Cys Val Gln Leu Val Phe
    130                 135                 140
Cys Ser Trp Met Ser Gly Leu Leu Ile Ile Val Pro Ser Ile
145                 150                 155                 160
Val Phe Gln Gln Pro Phe Cys Gly Pro Asn Ile Ile Asn His Phe
                165                 170                 175
Cys Asp Asn Phe Pro Leu Met Glu Leu Ile Cys Ala Asp Thr Ser Leu
                180                 185                 190
Val Glu Phe Leu Gly Phe Val Ile Ala Asn Phe Ser Leu Leu Gly Thr
            195                 200                 205
Leu Ala Val Thr Ala Thr Cys Tyr Gly His Ile Leu Tyr Thr Ile Leu
    210                 215                 220
His Ile Pro Ser Ala Lys Glu Arg Lys Lys Ala Phe Ser Thr Cys Ser
225                 230                 235                 240
Ser His Ile Ile Val Val Ser Leu Phe Tyr Gly Ser Cys Ile Phe Met
                245                 250                 255
Tyr Val Arg Ser Gly Lys Asn Gly Gln Gly Glu Asp His Asn Lys Val
                260                 265                 270
Val Ala Leu Leu Asn Thr Val Val Thr Pro Thr Leu Asn Pro Phe Ile
            275                 280                 285
Tyr Thr Leu Arg Asn Lys Gln Val Lys Gln Val Phe Arg Glu His Val
    290                 295                 300
Ser Lys Phe Gln Lys Phe Ser Gln Thr
305                 310
```

<210> SEQ ID NO 29
<211> LENGTH: 669
<212> TYPE: DNA
<213> ORGANISM: Mus musculus
<220> FEATURE:
<221> NAME/KEY: CDS
<222> LOCATION: (1)..(669)
<300> PUBLICATION INFORMATION:
<308> DATABASE ACCESSION NUMBER: AF102531
<309> DATABASE ENTRY DATE: 1999-02-08
<313> RELEVANT RESIDUES: (1)..(669)

<400> SEQUENCE: 29

```
tgc aac tta gcg acc atg gat att atc tgc acc tcc tct gta ctg ccc      48
Cys Asn Leu Ala Thr Met Asp Ile Ile Cys Thr Ser Ser Val Leu Pro
1               5                   10                  15 aag gcg ctg gtt ggt cta ctg tct gag gaa aac acc acc tcc ttc aaa      96
Lys Ala Leu Val Gly Leu Leu Ser Glu Glu Asn Thr Thr Ser Phe Lys
            20                  25                  30 ggg tgc atg act cag ctc ttc ttt ctt gtg tgg tct gga tcc tct gag     144
Gly Cys Met Thr Gln Leu Phe Phe Leu Val Trp Ser Gly Ser Ser Glu
        35                  40                  45 ctg ctg ctg ctc aca gtc atg gcc tat gac cgc tat gtg gcc atc tgt     192
Leu Leu Leu Leu Thr Val Met Ala Tyr Asp Arg Tyr Val Ala Ile Cys
    50                  55                  60 ttg ccc ctg cat tac agc tct agg atg agt cca cag ctc tgt ggg acc     240
Leu Pro Leu His Tyr Ser Ser Arg Met Ser Pro Gln Leu Cys Gly Thr
65                  70                  75                  80 ttt gcc gtg ggt gta tgg tcc atc tgc gca cta aat gca tct atc aac     288
Phe Ala Val Gly Val Trp Ser Ile Cys Ala Leu Asn Ala Ser Ile Asn
                85                  90                  95 act ggt ctg atg aca cgg ctg tca ttc tgt ggc ccc aag gtc atc acc     336
Thr Gly Leu Met Thr Arg Leu Ser Phe Cys Gly Pro Lys Val Ile Thr
```

-continued

```
                100                 105                 110
cac ttc ttc tgt gag att ccc cca ctc ctc ctg ctc tcc tgt agt cct      384
His Phe Phe Cys Glu Ile Pro Pro Leu Leu Leu Leu Ser Cys Ser Pro
        115                 120                 125 aca tat ata aat agc gtt atg act ctt gtg gca gat gcc ttt tat gga      432
Thr Tyr Ile Asn Ser Val Met Thr Leu Val Ala Asp Ala Phe Tyr Gly
    130                 135                 140 ggc atc aat ttt tta ctt acc ttg cta tcc tat ggc tgc atc att gcc      480
Gly Ile Asn Phe Leu Leu Thr Leu Leu Ser Tyr Gly Cys Ile Ile Ala
145                 150                 155                 160 agc atc ctg cgc atg cgt tct gct gag ggc aag agg aag gcc ttt tct      528
Ser Ile Leu Arg Met Arg Ser Ala Glu Gly Lys Arg Lys Ala Phe Ser
                165                 170                 175 acc tgc tca tcc cac ctc att gtg gtc tct gtg tac tac tca tct gtg      576
Thr Cys Ser Ser His Leu Ile Val Val Ser Val Tyr Tyr Ser Ser Val
            180                 185                 190 ttc tgt gcc tat gtc agc cct gct tct agc tac agc cca gaa aga agc      624
Phe Cys Ala Tyr Val Ser Pro Ala Ser Ser Tyr Ser Pro Glu Arg Ser
        195                 200                 205 aaa gtt tcc tca gtg ctg tac tca gtc ctc agc cca acc ctc aac          669
Lys Val Ser Ser Val Leu Tyr Ser Val Leu Ser Pro Thr Leu Asn
    210                 215                 220

<210> SEQ ID NO 30
<211> LENGTH: 223
<212> TYPE: PRT
<213> ORGANISM: Mus musculus

<400> SEQUENCE: 30

Cys Asn Leu Ala Thr Met Asp Ile Ile Cys Thr Ser Ser Val Leu Pro
1               5                   10                  15

Lys Ala Leu Val Gly Leu Leu Ser Glu Glu Asn Thr Thr Ser Phe Lys
            20                  25                  30

Gly Cys Met Thr Gln Leu Phe Phe Leu Val Trp Ser Gly Ser Ser Glu
        35                  40                  45

Leu Leu Leu Leu Thr Val Met Ala Tyr Asp Arg Tyr Val Ala Ile Cys
    50                  55                  60

Leu Pro Leu His Tyr Ser Ser Arg Met Ser Pro Gln Leu Cys Gly Thr
65                  70                  75                  80

Phe Ala Val Gly Val Trp Ser Ile Cys Ala Leu Asn Ala Ser Ile Asn
                85                  90                  95

Thr Gly Leu Met Thr Arg Leu Ser Phe Cys Gly Pro Lys Val Ile Thr
            100                 105                 110

His Phe Phe Cys Glu Ile Pro Pro Leu Leu Leu Leu Ser Cys Ser Pro
        115                 120                 125

Thr Tyr Ile Asn Ser Val Met Thr Leu Val Ala Asp Ala Phe Tyr Gly
    130                 135                 140

Gly Ile Asn Phe Leu Leu Thr Leu Leu Ser Tyr Gly Cys Ile Ile Ala
145                 150                 155                 160

Ser Ile Leu Arg Met Arg Ser Ala Glu Gly Lys Arg Lys Ala Phe Ser
                165                 170                 175

Thr Cys Ser Ser His Leu Ile Val Val Ser Val Tyr Tyr Ser Ser Val
            180                 185                 190

Phe Cys Ala Tyr Val Ser Pro Ala Ser Ser Tyr Ser Pro Glu Arg Ser
        195                 200                 205

Lys Val Ser Ser Val Leu Tyr Ser Val Leu Ser Pro Thr Leu Asn
    210                 215                 220
```

<210> SEQ ID NO 31
<211> LENGTH: 1661
<212> TYPE: DNA
<213> ORGANISM: Mus musculus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: CDS
<222> LOCATION: (303)..(1307)
<300> PUBLICATION INFORMATION:
<308> DATABASE ACCESSION NUMBER: AF121974
<309> DATABASE ENTRY DATE: 1999-04-25
<313> RELEVANT RESIDUES: (1)..(1661)

<400> SEQUENCE: 31

```
gtntacatag tgagttcgag gccagccagg gctacacaga caaaccctgt ctcgaaaaac      60
caaaaaaaaa aaaaaaaaaa agaattcatt aatgaaaaag aagggggaaa atggagggcc     120
atggaaagta gctacttcta acatacaact cttcatttcc tccatagaaa tgctgtagtt     180
aatgtctaca cccagtccag cctggtgagg ctggggcagg tcctagcagg gcctttcagg     240
gactgaaccc cggcatcctg cccctcccct ctccctggag cctccccaag ccctcaggcg     300 tc atg tca ggg tgg agc aat ggc acc tac aat gag tcc tac acc agc       347
   Met Ser Gly Trp Ser Asn Gly Thr Tyr Asn Glu Ser Tyr Thr Ser
   1               5                   10                  15 ttc ctc ctc atg ggc ttc cca ggg atg cag gaa gcc aga gcc ctc ctg     395
Phe Leu Leu Met Gly Phe Pro Gly Met Gln Glu Ala Arg Ala Leu Leu
                20                  25                  30 gtg ctg ccc ttc ctc agc ctc tac ctg gtg atc ctc ttc acc aat gcc     443
Val Leu Pro Phe Leu Ser Leu Tyr Leu Val Ile Leu Phe Thr Asn Ala
        35                  40                  45 ctg gtc atc cac acg gtg gca tcc cag cgc agc ctg cac cag ccc atg     491
Leu Val Ile His Thr Val Ala Ser Gln Arg Ser Leu His Gln Pro Met
    50                  55                  60 tac ctg ctc att gcc ctg ctc ctg gct gtc aat atc tgc gct gcc acc     539
Tyr Leu Leu Ile Ala Leu Leu Leu Ala Val Asn Ile Cys Ala Ala Thr
65                  70                  75 acc gtg gtg ccc ccc atg ctc ttc agc ttc tcc aca cgc ttc aac cgc     587
Thr Val Val Pro Pro Met Leu Phe Ser Phe Ser Thr Arg Phe Asn Arg
80                  85                  90                  95 atc tcc ctc cct cga tgc ttg gga caa atg ttc tgc atc tac ttc ctt     635
Ile Ser Leu Pro Arg Cys Leu Gly Gln Met Phe Cys Ile Tyr Phe Leu
                100                 105                 110 att gtc ttt gac tgc aac atc ctc ctg gtc atg gct cta gat cgc tat     683
Ile Val Phe Asp Cys Asn Ile Leu Leu Val Met Ala Leu Asp Arg Tyr
            115                 120                 125 gtg gct atc tgc tac cct ctc cgc tac cca gaa ata gtg aca gga cag     731
Val Ala Ile Cys Tyr Pro Leu Arg Tyr Pro Glu Ile Val Thr Gly Gln
        130                 135                 140 tta ctg gct ggt ctg gtg gtg ctg gca gtc acc agg agc aca agc att     779
Leu Leu Ala Gly Leu Val Val Leu Ala Val Thr Arg Ser Thr Ser Ile
    145                 150                 155 gtt gct cca gtg gtg gtg ctg gcc tcg cgg gtt cgc ttc tgt cgc tca     827
Val Ala Pro Val Val Val Leu Ala Ser Arg Val Arg Phe Cys Arg Ser
160                 165                 170                 175 gat gtg atc cgc cac ttt gcc tgt gag cac atg gcc ctg atg aag ctt     875
Asp Val Ile Arg His Phe Ala Cys Glu His Met Ala Leu Met Lys Leu
                180                 185                 190 tcc tgt ggg gac atc tcg ctg aat aag acg gtg gga ctc act gtt cgc     923
Ser Cys Gly Asp Ile Ser Leu Asn Lys Thr Val Gly Leu Thr Val Arg
```

```
Ser Cys Gly Asp Ile Ser Leu Asn Lys Thr Val Gly Leu Thr Val Arg
            195                 200                 205 atc ttc aac cga gtc ctg gat atg ctc ctg tta ggt gcc tcc tac tcc      971
Ile Phe Asn Arg Val Leu Asp Met Leu Leu Leu Gly Ala Ser Tyr Ser
            210                 215                 220 cgc atc atc cat gct gcc ttc agg atc tca tca ggt gga gca cgg tcc     1019
Arg Ile Ile His Ala Ala Phe Arg Ile Ser Ser Gly Gly Ala Arg Ser
            225                 230                 235 aaa gcc ctg aac acc tgt ggc tcc cac ctg ctg gtc atc ttc acc gtc     1067
Lys Ala Leu Asn Thr Cys Gly Ser His Leu Leu Val Ile Phe Thr Val
240                 245                 250                 255 tac tcc tcc acc atg tcc tca tcc att gtc tac cgt gtg gca cgc act     1115
Tyr Ser Ser Thr Met Ser Ser Ser Ile Val Tyr Arg Val Ala Arg Thr
                260                 265                 270 gcc tcc caa gat gtg cac aac ttg ctt agt gct ttc tat ctg ttg ctc     1163
Ala Ser Gln Asp Val His Asn Leu Leu Ser Ala Phe Tyr Leu Leu Leu
            275                 280                 285 ccc tgt ctg gtc aac ccc atc atc tac ggg gcc aga acc aag gaa atc     1211
Pro Cys Leu Val Asn Pro Ile Ile Tyr Gly Ala Arg Thr Lys Glu Ile
        290                 295                 300 agg cag cac ctg gta gct ctg ttc caa agg act cag caa cag gtc ttc     1259
Arg Gln His Leu Val Ala Leu Phe Gln Arg Thr Gln Gln Gln Val Phe
305                 310                 315 act gag aag ccc cag tcc ctg ccc tcg aat aga gag ctt cct gga tga     1307
Thr Glu Lys Pro Gln Ser Leu Pro Ser Asn Arg Glu Leu Pro Gly
320                 325                 330 ttgtccagaa tttgtgggtc tcaaaatcac tttcactatt cagtgaagga ggggcattca   1367
agtgggcatt cgtctctggt atattttgtc tcggctattt tagttcagca tcctatttat   1427
gagaagggtc tattctatat ctccagctgt ctagaactcc ttaagtggcc caggatgacc   1487
tggaacccaa acaattctcc tttcttagtt tgccaaatgc tagcattaga ggcatgagtc   1547
acagtgcctg gctatctgc actcatactg gagagcctca tgtctgcttt ccaaaaagca    1607
cctactcact ctgaactagc aactgaaagc aagctctaac cctggcttga agtt         1661

<210> SEQ ID NO 32
<211> LENGTH: 334
<212> TYPE: PRT
<213> ORGANISM: Mus musculus

<400> SEQUENCE: 32

Met Ser Gly Trp Ser Asn Gly Thr Tyr Asn Glu Ser Tyr Thr Ser Phe
1               5                   10                  15

Leu Leu Met Gly Phe Pro Gly Met Gln Glu Ala Arg Ala Leu Leu Val
            20                  25                  30

Leu Pro Phe Leu Ser Leu Tyr Leu Val Ile Leu Phe Thr Asn Ala Leu
        35                  40                  45

Val Ile His Thr Val Ala Ser Gln Arg Ser Leu His Gln Pro Met Tyr
    50                  55                  60

Leu Leu Ile Ala Leu Leu Ala Val Asn Ile Cys Ala Ala Thr Thr
65                  70                  75                  80

Val Val Pro Pro Met Leu Phe Ser Phe Ser Thr Arg Phe Asn Arg Ile
                85                  90                  95

Ser Leu Pro Arg Cys Leu Gly Gln Met Phe Cys Ile Tyr Phe Leu Ile
            100                 105                 110

Val Phe Asp Cys Asn Ile Leu Leu Val Met Ala Leu Asp Arg Tyr Val
        115                 120                 125
```

```
Ala Ile Cys Tyr Pro Leu Arg Tyr Pro Glu Ile Val Thr Gly Gln Leu
    130                 135                 140

Leu Ala Gly Leu Val Val Leu Ala Val Thr Arg Ser Thr Ser Ile Val
145                 150                 155                 160

Ala Pro Val Val Val Leu Ala Ser Arg Val Arg Phe Cys Arg Ser Asp
                165                 170                 175

Val Ile Arg His Phe Ala Cys Glu His Met Ala Leu Met Lys Leu Ser
            180                 185                 190

Cys Gly Asp Ile Ser Leu Asn Lys Thr Val Gly Leu Thr Val Arg Ile
        195                 200                 205

Phe Asn Arg Val Leu Asp Met Leu Leu Leu Gly Ala Ser Tyr Ser Arg
    210                 215                 220

Ile Ile His Ala Ala Phe Arg Ile Ser Ser Gly Gly Ala Arg Ser Lys
225                 230                 235                 240

Ala Leu Asn Thr Cys Gly Ser His Leu Leu Val Ile Phe Thr Val Tyr
                245                 250                 255

Ser Ser Thr Met Ser Ser Ser Ile Val Tyr Arg Val Ala Arg Thr Ala
                260                 265                 270

Ser Gln Asp Val His Asn Leu Ser Ala Phe Tyr Leu Leu Leu Pro
    275                 280                 285

Cys Leu Val Asn Pro Ile Ile Tyr Gly Ala Arg Thr Lys Glu Ile Arg
290                 295                 300

Gln His Leu Val Ala Leu Phe Gln Arg Thr Gln Gln Val Phe Thr
305                 310                 315                 320

Glu Lys Pro Gln Ser Leu Pro Ser Asn Arg Glu Leu Pro Gly
                325                 330

<210> SEQ ID NO 33
<211> LENGTH: 1116
<212> TYPE: DNA
<213> ORGANISM: Mus musculus
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: CDS
<222> LOCATION: (50)..(1015)
<300> PUBLICATION INFORMATION:
<308> DATABASE ACCESSION NUMBER: AF121975
<309> DATABASE ENTRY DATE: 1999-04-25
<313> RELEVANT RESIDUES: (1)..(1116)

<400> SEQUENCE: 33
caagctggct cttcntactg tctctccatt agttttagtc gtcacggga atg aat tca      58
                                                       Met Asn Ser
                                                         1 aaa gca agc atg ctt gga act aac ttc act atc atc cat cca act gtg      106
Lys Ala Ser Met Leu Gly Thr Asn Phe Thr Ile Ile His Pro Thr Val
  5                  10                  15 ttc atc ctg ctt gga atc cca ggg ctg gag cag tac cac acc tgg ctt      154
Phe Ile Leu Leu Gly Ile Pro Gly Leu Glu Gln Tyr His Thr Trp Leu
 20                  25                  30                  35 tct att cct ttt tgt ctt atg tac att gct gca gtt ttg ggg aac gga      202
Ser Ile Pro Phe Cys Leu Met Tyr Ile Ala Ala Val Leu Gly Asn Gly
                 40                  45                  50 gcc ctc atc ctt gtt gtc ctg agt gaa cgc acc ctc cat gag ccc atg      250
Ala Leu Ile Leu Val Val Leu Ser Glu Arg Thr Leu His Glu Pro Met
         55                  60                  65 tat gtc ttt ctg tcc atg ctg gct ggc act gat att ctc ctg tca acc      298
```

```
                    Tyr Val Phe Leu Ser Met Leu Ala Gly Thr Asp Ile Leu Leu Ser Thr
                                 70                  75                  80 acc act gtg cct aag acc ttg gct atc ttt tgg ttc cat gct ggg gag         346
Thr Thr Val Pro Lys Thr Leu Ala Ile Phe Trp Phe His Ala Gly Glu
         85                  90                  95 atc ccc ttt gat gcc tgc att gct cag atg ttt ttc atc cac gtt gct         394
Ile Pro Phe Asp Ala Cys Ile Ala Gln Met Phe Phe Ile His Val Ala
100                 105                 110                 115 ttt gtg gct gag tcg gga atc ctt ctg gcc atg gca ttt gac cga tat         442
Phe Val Ala Glu Ser Gly Ile Leu Leu Ala Met Ala Phe Asp Arg Tyr
                120                 125                 130 gtg gct att tgt act cct ctg aga tac tca gcc gtc tta aca cct atg         490
Val Ala Ile Cys Thr Pro Leu Arg Tyr Ser Ala Val Leu Thr Pro Met
            135                 140                 145 gca att gga aaa atg acc ctg gcc atc tgg gga cgg agc att ggg aca         538
Ala Ile Gly Lys Met Thr Leu Ala Ile Trp Gly Arg Ser Ile Gly Thr
        150                 155                 160 att ttc cct atc ata ttt ctg ctg aag agg ctg tca tac tgc agg acc         586
Ile Phe Pro Ile Ile Phe Leu Leu Lys Arg Leu Ser Tyr Cys Arg Thr
165                 170                 175 aat gtc atc cca cac tca tat tgt gag cat att ggt gta gcc aga ttg         634
Asn Val Ile Pro His Ser Tyr Cys Glu His Ile Gly Val Ala Arg Leu
180                 185                 190                 195 gct tgt gct gac atc act gtc aat atc tgg tat ggc ttc tcg gtg cca         682
Ala Cys Ala Asp Ile Thr Val Asn Ile Trp Tyr Gly Phe Ser Val Pro
                200                 205                 210 atg gct tca gtt ttg gta gat gtt gca ctc att ggt att tct tat acg         730
Met Ala Ser Val Leu Val Asp Val Ala Leu Ile Gly Ile Ser Tyr Thr
            215                 220                 225 ttg atc ctc cag gct gtg ttt aga ctt cct tcc cag gat gct agg cac         778
Leu Ile Leu Gln Ala Val Phe Arg Leu Pro Ser Gln Asp Ala Arg His
        230                 235                 240 aag gcc ctc aat acc tgt ggt tct cac att ggg gtc att ctc ctc ttt         826
Lys Ala Leu Asn Thr Cys Gly Ser His Ile Gly Val Ile Leu Leu Phe
245                 250                 255 ttc ata cca tca ttt ttt act ttc ctt act cat cgc ttt ggc aag aac         874
Phe Ile Pro Ser Phe Phe Thr Phe Leu Thr His Arg Phe Gly Lys Asn
260                 265                 270                 275 atc ccc cac cat gtg cac att ctt ctg gca aat ctc tat gtg ttg gtt         922
Ile Pro His His Val His Ile Leu Leu Ala Asn Leu Tyr Val Leu Val
                280                 285                 290 ccc ccc atg ctt aac cct atc atc tat ggt gct aag acc aag caa att         970
Pro Pro Met Leu Asn Pro Ile Ile Tyr Gly Ala Lys Thr Lys Gln Ile
            295                 300                 305 agg gac agc atg act cgc atg ttg tct gtt gtg tgg aag tct tga            1015
Arg Asp Ser Met Thr Arg Met Leu Ser Val Val Trp Lys Ser
        310                 315                 320 gagcagtcac agttcacaaa gctgtcttag tttctcttac aaacaggaga gagagagaga      1075
gagagagaga gagagagaga gagagagaga gagagagaga g                          1116

<210> SEQ ID NO 34
<211> LENGTH: 321
<212> TYPE: PRT
<213> ORGANISM: Mus musculus

<400> SEQUENCE: 34

Met Asn Ser Lys Ala Ser Met Leu Gly Thr Asn Phe Thr Ile Ile His
1               5                   10                  15

Pro Thr Val Phe Ile Leu Leu Gly Ile Pro Gly Leu Glu Gln Tyr His
```

-continued

```
                    20                  25                  30
Thr Trp Leu Ser Ile Pro Phe Cys Leu Met Tyr Ile Ala Ala Val Leu
             35                  40                  45
Gly Asn Gly Ala Leu Ile Leu Val Val Leu Ser Glu Arg Thr Leu His
 50                  55                  60
Glu Pro Met Tyr Val Phe Leu Ser Met Leu Ala Gly Thr Asp Ile Leu
 65                  70                  75                  80
Leu Ser Thr Thr Thr Val Pro Lys Thr Leu Ala Ile Phe Trp Phe His
                 85                  90                  95
Ala Gly Glu Ile Pro Phe Asp Ala Cys Ile Ala Gln Met Phe Phe Ile
                100                 105                 110
His Val Ala Phe Val Ala Glu Ser Gly Ile Leu Leu Ala Met Ala Phe
            115                 120                 125
Asp Arg Tyr Val Ala Ile Cys Thr Pro Leu Arg Tyr Ser Ala Val Leu
130                 135                 140
Thr Pro Met Ala Ile Gly Lys Met Thr Leu Ala Ile Trp Gly Arg Ser
145                 150                 155                 160
Ile Gly Thr Ile Phe Pro Ile Ile Phe Leu Leu Lys Arg Leu Ser Tyr
                165                 170                 175
Cys Arg Thr Asn Val Ile Pro His Ser Tyr Cys Glu His Ile Gly Val
            180                 185                 190
Ala Arg Leu Ala Cys Ala Asp Ile Thr Val Asn Ile Trp Tyr Gly Phe
        195                 200                 205
Ser Val Pro Met Ala Ser Val Leu Val Asp Val Ala Leu Ile Gly Ile
210                 215                 220
Ser Tyr Thr Leu Ile Leu Gln Ala Val Phe Arg Leu Pro Ser Gln Asp
225                 230                 235                 240
Ala Arg His Lys Ala Leu Asn Thr Cys Gly Ser His Ile Gly Val Ile
                245                 250                 255
Leu Leu Phe Phe Ile Pro Ser Phe Phe Thr Phe Leu Thr His Arg Phe
            260                 265                 270
Gly Lys Asn Ile Pro His His Val His Ile Leu Leu Ala Asn Leu Tyr
        275                 280                 285
Val Leu Val Pro Pro Met Leu Asn Pro Ile Ile Tyr Gly Ala Lys Thr
290                 295                 300
Lys Gln Ile Arg Asp Ser Met Thr Arg Met Leu Ser Val Val Trp Lys
305                 310                 315                 320
Ser
```

<210> SEQ ID NO 35
<211> LENGTH: 1267
<212> TYPE: DNA
<213> ORGANISM: Mus musculus
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: CDS
<222> LOCATION: (172)..(1200)
<300> PUBLICATION INFORMATION:
<308> DATABASE ACCESSION NUMBER: AF121977
<309> DATABASE ENTRY DATE: 1999-04-25
<313> RELEVANT RESIDUES: (1)..(1267)

<400> SEQUENCE: 35
tctattgctc actgaaatat aaactagcaa catgaagaac atatgattga actatatcaa      60

```
                                                   -continued agaaacaaat ttttctaatc ataaatgacc atgaatcatt gaatttcnta agctgaagtt          120
ctttcatgag gtaccacaca acagcatgtt cctgtacaca tgtaactacc t atg ttt          177
                                                         Met Phe
                                                          1 tgt cat tta tat aat gag aac aat atg caa gtg gca atc ctg gat tcc           225
Cys His Leu Tyr Asn Glu Asn Asn Met Gln Val Ala Ile Leu Asp Ser
     5                  10                  15 att cta ata cct tct tat ttt tct ttc ctg aca gag atg gag cct gga           273
Ile Leu Ile Pro Ser Tyr Phe Ser Phe Leu Thr Glu Met Glu Pro Gly
    20                  25                  30 aac tac aca gtt gta aca gaa ttc att ctt tta ggg tta aca gat gat           321
Asn Tyr Thr Val Val Thr Glu Phe Ile Leu Leu Gly Leu Thr Asp Asp
35                  40                  45                  50 att aca gtc agt gtc att tta ttt gtt atg ttt cta atc gtc tat tct           369
Ile Thr Val Ser Val Ile Leu Phe Val Met Phe Leu Ile Val Tyr Ser
                    55                  60                  65 gtt act tta atg ggt aac ttg aac ata att gtg cta atc aga acc agc           417
Val Thr Leu Met Gly Asn Leu Asn Ile Ile Val Leu Ile Arg Thr Ser
         70                  75                  80 cct cag ctt cac acc ccc atg tac ctt ttc ctt agc cat ttg gcc ttt           465
Pro Gln Leu His Thr Pro Met Tyr Leu Phe Leu Ser His Leu Ala Phe
    85                  90                  95 cta gac att ggg tac tcc agc tca gtt aca ccc atc atg ctg agg ggc           513
Leu Asp Ile Gly Tyr Ser Ser Ser Val Thr Pro Ile Met Leu Arg Gly
100                 105                 110 ttt ctc aga aag gga aca ttt atc cct gtg gct ggc tgt gtg gct caa           561
Phe Leu Arg Lys Gly Thr Phe Ile Pro Val Ala Gly Cys Val Ala Gln
115                 120                 125                 130 ctc tgt att gtg gtg gca ttt ggg aca tct gaa tct ttc ttg cta gct           609
Leu Cys Ile Val Val Ala Phe Gly Thr Ser Glu Ser Phe Leu Leu Ala
                    135                 140                 145 tcc atg gcc tat gac cgc tat gtg gcc atc tgc tca cct ttg ctc tac           657
Ser Met Ala Tyr Asp Arg Tyr Val Ala Ile Cys Ser Pro Leu Leu Tyr
         150                 155                 160 tca aca cag atg tcc tcc aca gtc tgc atc ctc cta gtt gga act tcc           705
Ser Thr Gln Met Ser Ser Thr Val Cys Ile Leu Leu Val Gly Thr Ser
    165                 170                 175 tac cta ggt gga tgg gtg aat gct tgg ata ttt act ggt tgc tcc tta           753
Tyr Leu Gly Gly Trp Val Asn Ala Trp Ile Phe Thr Gly Cys Ser Leu
180                 185                 190 aat ctg tca ttt tgt ggg cca aat aaa att aat cac ttt ttc tgt gac           801
Asn Leu Ser Phe Cys Gly Pro Asn Lys Ile Asn His Phe Phe Cys Asp
195                 200                 205                 210 tat tca cca cta ttg aag ctt tct tgt tct cat gac ttt tct ttt gaa           849
Tyr Ser Pro Leu Leu Lys Leu Ser Cys Ser His Asp Phe Ser Phe Glu
                    215                 220                 225 gtc att cca gca atc tct tcg gga tcc atc att gtg gtc act gtg ttt           897
Val Ile Pro Ala Ile Ser Ser Gly Ser Ile Ile Val Val Thr Val Phe
         230                 235                 240 atc att gct ctg tct tat gtc tac atc ctt gtc atc ctg aag atg           945
Ile Ile Ala Leu Ser Tyr Val Tyr Ile Leu Val Ser Ile Leu Lys Met
    245                 250                 255 cgc tct act gaa ggt cgc cag aag gcc ttc tcc acc tgc act tcc cac           993
Arg Ser Thr Glu Gly Arg Gln Lys Ala Phe Ser Thr Cys Thr Ser His
260                 265                 270 ctc act gca gtc act ctg ttc ttt ggg acc atc aca ttc att tat gtg          1041
Leu Thr Ala Val Thr Leu Phe Phe Gly Thr Ile Thr Phe Ile Tyr Val
275                 280                 285                 290 atg ccc cag tcc agc tac tcc aca gac cag aac aaa gtg gtg tct gtg          1089
```

```
Met Pro Gln Ser Ser Tyr Ser Thr Asp Gln Asn Lys Val Val Ser Val
                295                 300                 305 ttt tac aca gtg gtg atc ccc atg ttg aat ccc ctc atc tac agt ttc        1137
Phe Tyr Thr Val Val Ile Pro Met Leu Asn Pro Leu Ile Tyr Ser Phe
                310                 315                 320 aga aac aaa gag gtt aaa gaa gcc atg aaa aaa ctg att gct aaa aca        1185
Arg Asn Lys Glu Val Lys Glu Ala Met Lys Lys Leu Ile Ala Lys Thr
                325                 330                 335 cat tgg tgg tcc tga aatatttgaa tttacaaaca gtaaattctg ctcttacagg        1240
His Trp Trp Ser
        340 taaatggcag tatactaagt aaattac                                          1267

<210> SEQ ID NO 36
<211> LENGTH: 342
<212> TYPE: PRT
<213> ORGANISM: Mus musculus

<400> SEQUENCE: 36

Met Phe Cys His Leu Tyr Asn Glu Asn Asn Met Gln Val Ala Ile Leu
1               5                   10                  15

Asp Ser Ile Leu Ile Pro Ser Tyr Phe Ser Phe Leu Thr Glu Met Glu
                20                  25                  30

Pro Gly Asn Tyr Thr Val Val Thr Glu Phe Ile Leu Leu Gly Leu Thr
            35                  40                  45

Asp Asp Ile Thr Val Ser Val Ile Leu Phe Val Met Phe Leu Ile Val
        50                  55                  60

Tyr Ser Val Thr Leu Met Gly Asn Leu Asn Ile Ile Val Leu Ile Arg
65                  70                  75                  80

Thr Ser Pro Gln Leu His Thr Pro Met Tyr Leu Phe Leu Ser His Leu
                85                  90                  95

Ala Phe Leu Asp Ile Gly Tyr Ser Ser Val Thr Pro Ile Met Leu
            100                 105                 110

Arg Gly Phe Leu Arg Lys Gly Thr Phe Ile Pro Val Ala Gly Cys Val
        115                 120                 125

Ala Gln Leu Cys Ile Val Val Ala Phe Gly Thr Ser Glu Ser Phe Leu
    130                 135                 140

Leu Ala Ser Met Ala Tyr Asp Arg Tyr Val Ala Ile Cys Ser Pro Leu
145                 150                 155                 160

Leu Tyr Ser Thr Gln Met Ser Ser Thr Val Cys Ile Leu Leu Val Gly
                165                 170                 175

Thr Ser Tyr Leu Gly Gly Trp Val Asn Ala Trp Ile Phe Thr Gly Cys
            180                 185                 190

Ser Leu Asn Leu Ser Phe Cys Gly Pro Asn Lys Ile Asn His Phe Phe
        195                 200                 205

Cys Asp Tyr Ser Pro Leu Leu Lys Leu Ser Cys Ser His Asp Phe Ser
    210                 215                 220

Phe Glu Val Ile Pro Ala Ile Ser Ser Gly Ser Ile Ile Val Val Thr
225                 230                 235                 240

Val Phe Ile Ile Ala Leu Ser Tyr Val Tyr Ile Leu Val Ser Ile Leu
                245                 250                 255

Lys Met Arg Ser Thr Glu Gly Arg Gln Lys Ala Phe Ser Thr Cys Thr
            260                 265                 270

Ser His Leu Thr Ala Val Thr Leu Phe Phe Gly Thr Ile Thr Phe Ile
        275                 280                 285
```

```
Tyr Val Met Pro Gln Ser Ser Tyr Ser Thr Asp Gln Asn Lys Val Val
    290                 295                 300
Ser Val Phe Tyr Thr Val Val Ile Pro Met Leu Asn Pro Leu Ile Tyr
305                 310                 315                 320
Ser Phe Arg Asn Lys Glu Val Lys Glu Ala Met Lys Lys Leu Ile Ala
                325                 330                 335
Lys Thr His Trp Trp Ser
            340

<210> SEQ ID NO 37
<211> LENGTH: 1120
<212> TYPE: DNA
<213> ORGANISM: Mus musculus
<220> FEATURE:
<221> NAME/KEY: CDS
<222> LOCATION: (84)..(1040)
<220> FEATURE:
<221> NAME/KEY: misc_feature
<222> LOCATION: (940)..(940)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<300> PUBLICATION INFORMATION:
<308> DATABASE ACCESSION NUMBER: AF121979
<309> DATABASE ENTRY DATE: 1999-04-25
<313> RELEVANT RESIDUES: (1)..(1120)

<400> SEQUENCE: 37
tgtcattatt agtgctgata aagtgttgtc aagtcctgtg agattccttc aaatgaatat      60
gtccatcaga ggctcctgac aac atg tca cca ggc aac agc tca tgg att cat     113
                        Met Ser Pro Gly Asn Ser Ser Trp Ile His
                          1               5                  10 cct tct tcc ttc ctg ctc ttg gga atc cca gga ctg gaa gag ttg cag       161
Pro Ser Ser Phe Leu Leu Leu Gly Ile Pro Gly Leu Glu Glu Leu Gln
             15                  20                  25 ttc tgg ctt ggt ttg cca ttt gga aca gtc tat ctt att gct gtc cta       209
Phe Trp Leu Gly Leu Pro Phe Gly Thr Val Tyr Leu Ile Ala Val Leu
         30                  35                  40 ggg aat gtc atc att ctc ttt gta atc tat cta gag cac agc ctt cac       257
Gly Asn Val Ile Ile Leu Phe Val Ile Tyr Leu Glu His Ser Leu His
     45                  50                  55 caa cct atg ttc tac tta ctg gcc ata ctg gct gtt act gac ttg ggt       305
Gln Pro Met Phe Tyr Leu Leu Ala Ile Leu Ala Val Thr Asp Leu Gly
 60                  65                  70 ctg tct aca gca act gtt ccc aga gca ctc ggt ata ttc tgg ttt ggc       353
Leu Ser Thr Ala Thr Val Pro Arg Ala Leu Gly Ile Phe Trp Phe Gly
 75                  80                  85                  90 ttc cat aag att gcc ttt agg gac tgt gta gct caa atg ttt ttc ata       401
Phe His Lys Ile Ala Phe Arg Asp Cys Val Ala Gln Met Phe Phe Ile
                 95                 100                 105 cat ctg ttt aca ggc atc gaa aca ttc atg ctt gta gct atg gcc ttt       449
His Leu Phe Thr Gly Ile Glu Thr Phe Met Leu Val Ala Met Ala Phe
             110                 115                 120 gat cgc tac att gcc atc tgt aac cct ctc cga tat aac act atc ctc       497
Asp Arg Tyr Ile Ala Ile Cys Asn Pro Leu Arg Tyr Asn Thr Ile Leu
         125                 130                 135 acc aac aga aca atc tgc att att gtt gga gtt gga cta ttt aaa aat       545
Thr Asn Arg Thr Ile Cys Ile Ile Val Gly Val Gly Leu Phe Lys Asn
     140                 145                 150 ttc att ttg gtt ttt cca ctt ata ttt ctc att cta agg ctt tca ttc       593
Phe Ile Leu Val Phe Pro Leu Ile Phe Leu Ile Leu Arg Leu Ser Phe
```

-continued

```
                 155                 160                 165                 170
tgt gga cac aat atc ata cca cac aca tac tgt gag cac atg ggc att        641
Cys Gly His Asn Ile Ile Pro His Thr Tyr Cys Glu His Met Gly Ile
                 175                 180                 185 gct cga ctg gca tgc gtc agc atc aag gtt aat gta tta ttt gga tta        689
Ala Arg Leu Ala Cys Val Ser Ile Lys Val Asn Val Leu Phe Gly Leu
                 190                 195                 200 ata ctc ata tct atg ata ctt ctg gat gtt gtt ttg agt gct ctg tcc        737
Ile Leu Ile Ser Met Ile Leu Leu Asp Val Val Leu Ser Ala Leu Ser
                 205                 210                 215 tat gcg aaa att ctt cat gct gta ttt aaa ctc cca tcc tgg gaa gcc        785
Tyr Ala Lys Ile Leu His Ala Val Phe Lys Leu Pro Ser Trp Glu Ala
                 220                 225                 230 aga ctc aaa gct ctt aat acc tgt ggt tcc cat gtg tgt gtg atc ttg        833
Arg Leu Lys Ala Leu Asn Thr Cys Gly Ser His Val Cys Val Ile Leu
235                 240                 245                 250 gct ttc ttc act cca gcc ttt ttc tcc ttc ttg act cat cga ttt gga        881
Ala Phe Phe Thr Pro Ala Phe Phe Ser Phe Leu Thr His Arg Phe Gly
                 255                 260                 265 cac aat att cca cga tat atc cac atc ctc ctt gct aac tta tat gtg        929
His Asn Ile Pro Arg Tyr Ile His Ile Leu Leu Ala Asn Leu Tyr Val
                 270                 275                 280 atc att ccc cng gct ctt aac cct att att tat ggg gtg aga acc aaa        977
Ile Ile Pro Xaa Ala Leu Asn Pro Ile Ile Tyr Gly Val Arg Thr Lys
                 285                 290                 295 cag ata caa gat cgt gcg gtg aca ata ttg tgc aac gag gtt gga cag       1025
Gln Ile Gln Asp Arg Ala Val Thr Ile Leu Cys Asn Glu Val Gly Gln
                 300                 305                 310 ctg gca gac gac tag tatgtcttct aatagtctct ttccttccta agaggactac       1080
Leu Ala Asp Asp
315 tgntttgtaa gcttgcatac gtggaacaca ttacacaatg                           1120
```

<210> SEQ ID NO 38
<211> LENGTH: 318
<212> TYPE: PRT
<213> ORGANISM: Mus musculus
<220> FEATURE:
<221> NAME/KEY: misc_feature
<222> LOCATION: (286)..(286)
<223> OTHER INFORMATION: The 'Xaa' at location 286 stands for Gln, Arg,
      Pro, or Leu.

<400> SEQUENCE: 38

```
Met Ser Pro Gly Asn Ser Ser Trp Ile His Pro Ser Ser Phe Leu Leu
1               5                   10                  15

Leu Gly Ile Pro Gly Leu Glu Glu Leu Gln Phe Trp Leu Gly Leu Pro
                20                  25                  30

Phe Gly Thr Val Tyr Leu Ile Ala Val Leu Gly Asn Val Ile Ile Leu
            35                  40                  45

Phe Val Ile Tyr Leu Glu His Ser Leu His Gln Pro Met Phe Tyr Leu
        50                  55                  60

Leu Ala Ile Leu Ala Val Thr Asp Leu Gly Leu Ser Thr Ala Thr Val
65                  70                  75                  80

Pro Arg Ala Leu Gly Ile Phe Trp Phe Gly Phe His Lys Ile Ala Phe
                85                  90                  95

Arg Asp Cys Val Ala Gln Met Phe Phe Ile His Leu Phe Thr Gly Ile
            100                 105                 110

Glu Thr Phe Met Leu Val Ala Met Ala Phe Asp Arg Tyr Ile Ala Ile
```

-continued

```
                115                 120                 125
Cys Asn Pro Leu Arg Tyr Asn Thr Ile Leu Thr Asn Arg Thr Ile Cys
    130                 135                 140

Ile Ile Val Gly Val Gly Leu Phe Lys Asn Phe Ile Leu Val Phe Pro
145                 150                 155                 160

Leu Ile Phe Leu Ile Leu Arg Leu Ser Phe Cys Gly His Asn Ile Ile
                165                 170                 175

Pro His Thr Tyr Cys Glu His Met Gly Ile Ala Arg Leu Ala Cys Val
            180                 185                 190

Ser Ile Lys Val Asn Val Leu Phe Gly Leu Ile Leu Ile Ser Met Ile
        195                 200                 205

Leu Leu Asp Val Val Leu Ser Ala Leu Ser Tyr Ala Lys Ile Leu His
    210                 215                 220

Ala Val Phe Lys Leu Pro Ser Trp Glu Ala Arg Leu Lys Ala Leu Asn
225                 230                 235                 240

Thr Cys Gly Ser His Val Cys Val Ile Leu Ala Phe Phe Thr Pro Ala
                245                 250                 255

Phe Phe Ser Phe Leu Thr His Arg Phe Gly His Asn Ile Pro Arg Tyr
            260                 265                 270

Ile His Ile Leu Leu Ala Asn Leu Tyr Val Ile Ile Pro Xaa Ala Leu
        275                 280                 285

Asn Pro Ile Ile Tyr Gly Val Arg Thr Lys Gln Ile Gln Asp Arg Ala
    290                 295                 300

Val Thr Ile Leu Cys Asn Glu Val Gly Gln Leu Ala Asp Asp
305                 310                 315

<210> SEQ ID NO 39
<211> LENGTH: 2333
<212> TYPE: DNA
<213> ORGANISM: Mus musculus
<220> FEATURE:
<221> NAME/KEY: CDS
<222> LOCATION: (24)..(1088)
<300> PUBLICATION INFORMATION:
<308> DATABASE ACCESSION NUMBER: M36778
<309> DATABASE ENTRY DATE: 1995-08-22
<313> RELEVANT RESIDUES: (1)..(2333)

<400> SEQUENCE: 39
gctgtggcag ggaaggggcc acc atg gga tgt acg ctg agc gca gag gag aga     53
                        Met Gly Cys Thr Leu Ser Ala Glu Glu Arg
                          1               5                  10 gcc gcc ctc gag cgg agc aag gcg att gag aaa aac ctc aaa gaa gat    101
Ala Ala Leu Glu Arg Ser Lys Ala Ile Glu Lys Asn Leu Lys Glu Asp
                 15                  20                  25 ggc atc agc gcc gcc aaa gac gtg aaa tta ctc ctg ctg ggg gct gga    149
Gly Ile Ser Ala Ala Lys Asp Val Lys Leu Leu Leu Leu Gly Ala Gly
             30                  35                  40 gaa tca gga aaa agc acc att gtg aag cag atg aag atc atc cat gaa    197
Glu Ser Gly Lys Ser Thr Ile Val Lys Gln Met Lys Ile Ile His Glu
         45                  50                  55 gat ggc ttc tct ggg gaa gac gtg aag cag tac aag cct gtg gtc tac    245
Asp Gly Phe Ser Gly Glu Asp Val Lys Gln Tyr Lys Pro Val Val Tyr
     60                  65                  70 agc aac acc atc cag tct ctg gcg gcc att gtc cgg gcc atg gac act    293
Ser Asn Thr Ile Gln Ser Leu Ala Ala Ile Val Arg Ala Met Asp Thr
 75                  80                  85                  90 ttg ggc gtg gag tat ggt gac aag gag agg aag acg gac tcc aag atg    341
Leu Gly Val Glu Tyr Gly Asp Lys Glu Arg Lys Thr Asp Ser Lys Met
```

```
                  95                   100                  105
gtg tgt gac gtg gtg agt cgt atg gaa gac act gaa ccg ttc tct gca    389
Val Cys Asp Val Val Ser Arg Met Glu Asp Thr Glu Pro Phe Ser Ala
            110                 115                 120 gaa ctt ctt tct gcc atg atg cga ctc tgg ggc gac tcg ggg atc cag    437
Glu Leu Leu Ser Ala Met Met Arg Leu Trp Gly Asp Ser Gly Ile Gln
        125                 130                 135 gag tgc ttc aac cga tct cgg gag tat cag ctc aat gac tct gcc aaa    485
Glu Cys Phe Asn Arg Ser Arg Glu Tyr Gln Leu Asn Asp Ser Ala Lys
    140                 145                 150 tac tac ctg gac agc ctg gat cgg att gga gcc ggt gac tac cag ccc    533
Tyr Tyr Leu Asp Ser Leu Asp Arg Ile Gly Ala Gly Asp Tyr Gln Pro
155                 160                 165                 170 act gag cag gac atc ctc cga acc aga gtc aaa aca act ggc atc gta    581
Thr Glu Gln Asp Ile Leu Arg Thr Arg Val Lys Thr Thr Gly Ile Val
                175                 180                 185 gaa acc cac ttc acc ttc aag aac ctc cac ttc agg ctg ttt gac gtc    629
Glu Thr His Phe Thr Phe Lys Asn Leu His Phe Arg Leu Phe Asp Val
            190                 195                 200 ggg ggc cag cga tct gaa cgc aag aag tgg atc cac tgc ttt gag gat    677
Gly Gly Gln Arg Ser Glu Arg Lys Lys Trp Ile His Cys Phe Glu Asp
        205                 210                 215 gtc acg gcc atc atc ttc tgt gtc gca ctc agc ggc tat gac cag gtg    725
Val Thr Ala Ile Ile Phe Cys Val Ala Leu Ser Gly Tyr Asp Gln Val
    220                 225                 230 ctc cac gag gac gaa acc acg aac cgc atg cac gaa tcc ctg aag ctc    773
Leu His Glu Asp Glu Thr Thr Asn Arg Met His Glu Ser Leu Lys Leu
235                 240                 245                 250 ttc gac agc atc tgc aac aac aag tgg ttc aca gac aca tct att atc    821
Phe Asp Ser Ile Cys Asn Asn Lys Trp Phe Thr Asp Thr Ser Ile Ile
                255                 260                 265 ctg ttt ctc aac aag aag gac ata ttt gag gag aag atc aag aag tcc    869
Leu Phe Leu Asn Lys Lys Asp Ile Phe Glu Glu Lys Ile Lys Lys Ser
            270                 275                 280 cca ctc acc atc tgc ttt cct gaa tac aca ggc ccc agt gcc ttc aca    917
Pro Leu Thr Ile Cys Phe Pro Glu Tyr Thr Gly Pro Ser Ala Phe Thr
        285                 290                 295 gaa gct gtg gct cac atc caa ggg cag tat gag agt aag aat aag tca    965
Glu Ala Val Ala His Ile Gln Gly Gln Tyr Glu Ser Lys Asn Lys Ser
    300                 305                 310 gct cac aag gaa gtc tac agc cat gtc acc tgt gcc acg gac acc aac   1013
Ala His Lys Glu Val Tyr Ser His Val Thr Cys Ala Thr Asp Thr Asn
315                 320                 325                 330 aac atc caa ttc gtc ttt gat gcc gtg aca gat gtc atc atc gcc aaa   1061
Asn Ile Gln Phe Val Phe Asp Ala Val Thr Asp Val Ile Ile Ala Lys
                335                 340                 345 aac cta cgg ggc tgt gga ctc tac tga gccctggcct cctacccagc         1108
Asn Leu Arg Gly Cys Gly Leu Tyr
            350 ctgccactca ctcctcccct ggacccagag ctctgtcact gctcagatgc cctgttaact  1168 gaagaaaacc tggaggctag ccttgggggc aggaggaggc atcctttgag catcccacc   1228 ccacccaact tcagcctcgt gacacgtggg aacagggttg gcagaggtg tggaacagca   1288 caaggccaga gaccacggca tgccacttgg gtgctgctca ctggtcagct gtgtgtctta  1348 cacagaggcc gagtgggcaa cactgccatc tgattcagaa tgggcatgcc ctgtcctctg  1408 tacctcttgt tcagtgtcct ggtttctctt ccaccttggt gataggatgg ctggcaggaa  1468 ggccccatgg aaggtgctgc ttgattaggg gatagtcgat ggcatctctc agcagtcctc  1528
```

-continued

```
agggtctgtt tggtagaggg tggtttcgtc gacaaaagcc aacatggaat caggccactt    1588
ttggggcgca aagactcaga ctttggggac gggttccctc ctccttcact ttggatcttg    1648 gccctctct  ggtcatcttc ccttgccctt gggctcccca ggatactcag ccctgactcc    1708
catggggttg ggaatattcc ttaagactgg ctgactgcaa aggtcaccga tggagaaaca    1768
tccctgtgct acagaattgg gggtgggaca gctgagggg  caggcggctc tttcctgata    1828
gttgatgaca agccctgaga atgccatctg ctggctccac tcacacgggc tcaactgtcc    1888
tgggtgatag tgacttgcca ggccacaggc tgcaggtcac agacagagca ggcaagcagc    1948
cttgcaactg cagattactt agggagaagc atcggggcct cgtgagccag ccccgtagc    2008 cagtgccctg ctttactcca gccttggtca ggaagtcgaa agcccttggt gtattcctgg    2068
tctcggagca ataatgagc  cagcaccctg aagggtgggc tccaactcag acatgcagcc    2128
agccccctag gtgggtaaac gccctaggga cctaggagga gcctttgctg cagagattcc    2188
taagcaaaac ggcgtggtgg agctttggca accctagccc cagctaactt tggacagtca    2248
gcatatgtcc ctgccatccc tagacatctc cagtcagctg gtatcacagc cagtggttca    2308
gacaggtttg aatgctcatg tggca                                           2333
```

<210> SEQ ID NO 40
<211> LENGTH: 354
<212> TYPE: PRT
<213> ORGANISM: Mus musculus

<400> SEQUENCE: 40

```
Met Gly Cys Thr Leu Ser Ala Glu Glu Arg Ala Ala Leu Glu Arg Ser
1               5                  10                  15

Lys Ala Ile Glu Lys Asn Leu Lys Glu Asp Gly Ile Ser Ala Ala Lys
            20                  25                  30

Asp Val Lys Leu Leu Leu Leu Gly Ala Gly Glu Ser Gly Lys Ser Thr
        35                  40                  45

Ile Val Lys Gln Met Lys Ile Ile His Glu Asp Gly Phe Ser Gly Glu
    50                  55                  60

Asp Val Lys Gln Tyr Lys Pro Val Val Tyr Ser Asn Thr Ile Gln Ser
65                  70                  75                  80

Leu Ala Ala Ile Val Arg Ala Met Asp Thr Leu Gly Val Glu Tyr Gly
                85                  90                  95

Asp Lys Glu Arg Lys Thr Asp Ser Lys Met Val Cys Asp Val Val Ser
            100                 105                 110

Arg Met Glu Asp Thr Glu Pro Phe Ser Ala Glu Leu Leu Ser Ala Met
        115                 120                 125

Met Arg Leu Trp Gly Asp Ser Gly Ile Gln Glu Cys Phe Asn Arg Ser
    130                 135                 140

Arg Glu Tyr Gln Leu Asn Asp Ser Ala Lys Tyr Tyr Leu Asp Ser Leu
145                 150                 155                 160

Asp Arg Ile Gly Ala Gly Asp Tyr Gln Pro Thr Glu Gln Asp Ile Leu
                165                 170                 175

Arg Thr Arg Val Lys Thr Thr Gly Ile Val Glu Thr His Phe Thr Phe
            180                 185                 190

Lys Asn Leu His Phe Arg Leu Phe Asp Val Gly Gly Gln Arg Ser Glu
        195                 200                 205

Arg Lys Lys Trp Ile His Cys Phe Glu Asp Val Thr Ala Ile Ile Phe
    210                 215                 220
```

-continued

| | | | | | | | | | | | | | | |
|---|---|---|---|---|---|---|---|---|---|---|---|---|---|---|
| Cys | Val | Ala | Leu | Ser | Gly | Tyr | Asp | Gln | Val | Leu | His | Glu | Asp | Glu | Thr |
| 225 | | | | | 230 | | | | | 235 | | | | | 240 |
| Thr | Asn | Arg | Met | His | Glu | Ser | Leu | Lys | Leu | Phe | Asp | Ser | Ile | Cys | Asn |
| | | | | 245 | | | | | 250 | | | | | 255 | |
| Asn | Lys | Trp | Phe | Thr | Asp | Thr | Ser | Ile | Ile | Leu | Phe | Leu | Asn | Lys | Lys |
| | | | 260 | | | | | 265 | | | | | 270 | | |
| Asp | Ile | Phe | Glu | Glu | Lys | Ile | Lys | Lys | Ser | Pro | Leu | Thr | Ile | Cys | Phe |
| | | 275 | | | | | 280 | | | | | 285 | | | |
| Pro | Glu | Tyr | Thr | Gly | Pro | Ser | Ala | Phe | Thr | Glu | Ala | Val | Ala | His | Ile |
| | 290 | | | | | 295 | | | | | 300 | | | | |
| Gln | Gly | Gln | Tyr | Glu | Ser | Lys | Asn | Lys | Ser | Ala | His | Lys | Glu | Val | Tyr |
| 305 | | | | | 310 | | | | | 315 | | | | | 320 |
| Ser | His | Val | Thr | Cys | Ala | Thr | Asp | Thr | Asn | Asn | Ile | Gln | Phe | Val | Phe |
| | | | | 325 | | | | | 330 | | | | | 335 | |
| Asp | Ala | Val | Thr | Asp | Val | Ile | Ile | Ala | Lys | Asn | Leu | Arg | Gly | Cys | Gly |
| | | | 340 | | | | | 345 | | | | | 350 | | |
| Leu | Tyr | | | | | | | | | | | | | | |

<210> SEQ ID NO 41
<211> LENGTH: 1135
<212> TYPE: DNA
<213> ORGANISM: Mus musculus
<220> FEATURE:
<221> NAME/KEY: CDS
<222> LOCATION: (41)..(1063)
<300> PUBLICATION INFORMATION:
<308> DATABASE ACCESSION NUMBER: M87286
<309> DATABASE ENTRY DATE: 1993-04-27
<313> RELEVANT RESIDUES: (1)..(1135)

<400> SEQUENCE: 41

```
gctcttcact tgagacgcct gagggaaacc accaggcagg atg agc gag ctg gag      55
                                             Met Ser Glu Leu Glu
                                              1               5 cag ctg agg cag gag gct gaa cag ctt cgg aat cag atc cag gat gct     103
Gln Leu Arg Gln Glu Ala Glu Gln Leu Arg Asn Gln Ile Gln Asp Ala
             10                  15                  20 cgg aag gcc tgc aac gat gcc acg ctg gtt cag atc acg tct aat atg    151
Arg Lys Ala Cys Asn Asp Ala Thr Leu Val Gln Ile Thr Ser Asn Met
         25                  30                  35 gac tcc gtg ggc cga ata caa atg cga aca agg cgc acg ctg cgt ggc    199
Asp Ser Val Gly Arg Ile Gln Met Arg Thr Arg Arg Thr Leu Arg Gly
     40                  45                  50 cac ctc gct aag atc tac gcc atg cac tgg gga tat gat tcc agg cta    247
His Leu Ala Lys Ile Tyr Ala Met His Trp Gly Tyr Asp Ser Arg Leu
 55                  60                  65 cta gtc agt gct tcg caa gat gga aaa tta att att tgg gat agc tat    295
Leu Val Ser Ala Ser Gln Asp Gly Lys Leu Ile Ile Trp Asp Ser Tyr
 70                  75                  80                  85 acg aca aat aag atg cac gcc atc cct ctg agg tcc tcc tgg gtg atg    343
Thr Thr Asn Lys Met His Ala Ile Pro Leu Arg Ser Ser Trp Val Met
                 90                  95                 100 acc tgt gcc tac gcc ccg tcc ggg aac tac gtt gcc tgt gga ggc ttg    391
Thr Cys Ala Tyr Ala Pro Ser Gly Asn Tyr Val Ala Cys Gly Gly Leu
            105                 110                 115 gat aac atc tgc tcc ata tac aac cta aag acc cga gag gga gat gtg    439
Asp Asn Ile Cys Ser Ile Tyr Asn Leu Lys Thr Arg Glu Gly Asp Val
        120                 125                 130 cgg gtg agc cga gaa ttg gca gga cac acg ggc tac ttg tcc tgc tgc    487
Arg Val Ser Arg Glu Leu Ala Gly His Thr Gly Tyr Leu Ser Cys Cys
```

```
                   135                 140                 145
cga ttc tta gat gat gga caa atc att aca agt tcg gga gac acg act    535
Arg Phe Leu Asp Asp Gly Gln Ile Ile Thr Ser Ser Gly Asp Thr Thr
150                 155                 160                 165 tgt gct ttg tgg gac att gag acc gga cag cag act acg acc ttc aca    583
Cys Ala Leu Trp Asp Ile Glu Thr Gly Gln Gln Thr Thr Thr Phe Thr
                170                 175                 180 gga cac tcg ggt gac gtg atg agc ctc tca ctg agt cct gac ttg aag    631
Gly His Ser Gly Asp Val Met Ser Leu Ser Leu Ser Pro Asp Leu Lys
            185                 190                 195 acg ttt gtg tct ggt gct tgt gat gca tcc tca aag ctg tgg gat atc    679
Thr Phe Val Ser Gly Ala Cys Asp Ala Ser Ser Lys Leu Trp Asp Ile
        200                 205                 210 cga gat ggg atg tgt aga cag tct ttc acc gga cac atc tca gac atc    727
Arg Asp Gly Met Cys Arg Gln Ser Phe Thr Gly His Ile Ser Asp Ile
    215                 220                 225 aac gct gtc agt ttc ttc ccg agt gga tat gcc ttt gcc act ggt tct    775
Asn Ala Val Ser Phe Phe Pro Ser Gly Tyr Ala Phe Ala Thr Gly Ser
230                 235                 240                 245 gat gat gcc aca tgc cga ctc ttt gac ctc cgt gca gac cag gag ctc    823
Asp Asp Ala Thr Cys Arg Leu Phe Asp Leu Arg Ala Asp Gln Glu Leu
                250                 255                 260 ctg cta tac tct cat gac aat atc atc tgt ggc att act tct gtg gcc    871
Leu Leu Tyr Ser His Asp Asn Ile Ile Cys Gly Ile Thr Ser Val Ala
            265                 270                 275 ttc tca aag agt ggg cgc ctc ctg tta gcc ggc tat gac gac ttc aac    919
Phe Ser Lys Ser Gly Arg Leu Leu Leu Ala Gly Tyr Asp Asp Phe Asn
        280                 285                 290 tgc agt gtg tgg gac gct ctg aaa gga ggc cgg tca ggt gtc ctt gct    967
Cys Ser Val Trp Asp Ala Leu Lys Gly Gly Arg Ser Gly Val Leu Ala
    295                 300                 305 ggt cat gac aac cgt gtt agc tgc tta ggt gtg act gat gac ggc atg    1015
Gly His Asp Asn Arg Val Ser Cys Leu Gly Val Thr Asp Asp Gly Met
310                 315                 320                 325 gct gtg gcc act ggc tcc tgg gac agt ttt ctt aga atc tgg aat tga    1063
Ala Val Ala Thr Gly Ser Trp Asp Ser Phe Leu Arg Ile Trp Asn
                330                 335                 340 gtgccatatt ttctgttctc caatgatacc tggagaaatc cgtgttacag cctatagctg    1123
tgaggaaaaa aa                                                        1135

<210> SEQ ID NO 42
<211> LENGTH: 340
<212> TYPE: PRT
<213> ORGANISM: Mus musculus

<400> SEQUENCE: 42

Met Ser Glu Leu Glu Gln Leu Arg Gln Glu Ala Glu Gln Leu Arg Asn
1               5                   10                  15

Gln Ile Gln Asp Ala Arg Lys Ala Cys Asn Asp Ala Thr Leu Val Gln
            20                  25                  30

Ile Thr Ser Asn Met Asp Ser Val Gly Arg Ile Gln Met Arg Thr Arg
        35                  40                  45

Arg Thr Leu Arg Gly His Leu Ala Lys Ile Tyr Ala Met His Trp Gly
    50                  55                  60

Tyr Asp Ser Arg Leu Leu Val Ser Ala Ser Gln Asp Gly Lys Leu Ile
65                  70                  75                  80

Ile Trp Asp Ser Tyr Thr Thr Asn Lys Met His Ala Ile Pro Leu Arg
                85                  90                  95
```

```
Ser Ser Trp Val Met Thr Cys Ala Tyr Ala Pro Ser Gly Asn Tyr Val
            100                 105                 110

Ala Cys Gly Gly Leu Asp Asn Ile Cys Ser Ile Tyr Asn Leu Lys Thr
            115                 120                 125

Arg Glu Gly Asp Val Arg Val Ser Arg Glu Leu Ala Gly His Thr Gly
            130                 135                 140

Tyr Leu Ser Cys Cys Arg Phe Leu Asp Asp Gly Gln Ile Ile Thr Ser
145                 150                 155                 160

Ser Gly Asp Thr Thr Cys Ala Leu Trp Asp Ile Glu Thr Gly Gln Gln
                165                 170                 175

Thr Thr Thr Phe Thr Gly His Ser Gly Asp Val Met Ser Leu Ser Leu
            180                 185                 190

Ser Pro Asp Leu Lys Thr Phe Val Ser Gly Ala Cys Asp Ala Ser Ser
            195                 200                 205

Lys Leu Trp Asp Ile Arg Asp Gly Met Cys Arg Gln Ser Phe Thr Gly
            210                 215                 220

His Ile Ser Asp Ile Asn Ala Val Ser Phe Phe Pro Ser Gly Tyr Ala
225                 230                 235                 240

Phe Ala Thr Gly Ser Asp Asp Ala Thr Cys Arg Leu Phe Asp Leu Arg
                245                 250                 255

Ala Asp Gln Glu Leu Leu Leu Tyr Ser His Asp Asn Ile Ile Cys Gly
            260                 265                 270

Ile Thr Ser Val Ala Phe Ser Lys Ser Gly Arg Leu Leu Leu Ala Gly
            275                 280                 285

Tyr Asp Asp Phe Asn Cys Ser Val Trp Asp Ala Leu Lys Gly Gly Arg
            290                 295                 300

Ser Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                325                 330                 335

Arg Ile Trp Asn
            340

<210> SEQ ID NO 43
<211> LENGTH: 307
<212> TYPE: DNA
<213> ORGANISM: Mus musculus
<220> FEATURE:
<221> NAME/KEY: CDS
<222> LOCATION: (40)..(267)
<300> PUBLICATION INFORMATION:
<308> DATABASE ACCESSION NUMBER: U37527
<309> DATABASE ENTRY DATE: 1997-12-30
<313> RELEVANT RESIDUES: (1)..(307)

<400> SEQUENCE: 43
tccaagctgc tgtaccacct ctcagcaggg agtgcagga atg aag gaa ggc atg         54
                                             Met Lys Glu Gly Met
                                              1               5 tct aat aac agc acc acc agc atc tcc cag gcc agg aaa gcc gtg gag       102
Ser Asn Asn Ser Thr Thr Ser Ile Ser Gln Ala Arg Lys Ala Val Glu
                 10                  15                  20 cag ctg aag atg gaa gcc tgc atg gac agg gtg aag gtc tcc cag gct       150
Gln Leu Lys Met Glu Ala Cys Met Asp Arg Val Lys Val Ser Gln Ala
             25                  30                  35 gcc tca gac ctc ctg gcc tac tgt gaa gcc cac gtg cgg gag gac ccc       198
Ala Ser Asp Leu Leu Ala Tyr Cys Glu Ala His Val Arg Glu Asp Pro
         40                  45                  50
```

-continued

| | |
|---|---|
| ctc atc atc cca gtg cct gcc tca gaa aac ccc ttc cgg gag aag aag<br>Leu Ile Ile Pro Val Pro Ala Ser Glu Asn Pro Phe Arg Glu Lys Lys<br>55                   60                  65 | 246 |
| ttc ttc tgc acc atc ctc taa cacccatggc gatgaagcgg gccctttcct<br>Phe Phe Cys Thr Ile Leu<br>70                  75 | 297 |
| gctgtaacag | 307 |

<210> SEQ ID NO 44
<211> LENGTH: 75
<212> TYPE: PRT
<213> ORGANISM: Mus musculus

<400> SEQUENCE: 44

Met Lys Glu Gly Met Ser Asn Asn Ser Thr Thr Ser Ile Ser Gln Ala
1               5                   10                  15

Arg Lys Ala Val Glu Gln Leu Lys Met Glu Ala Cys Met Asp Arg Val
            20                  25                  30

Lys Val Ser Gln Ala Ala Ser Asp Leu Leu Ala Tyr Cys Glu Ala His
        35                  40                  45

Val Arg Glu Asp Pro Leu Ile Ile Pro Val Pro Ala Ser Glu Asn Pro
    50                  55                  60

Phe Arg Glu Lys Lys Phe Phe Cys Thr Ile Leu
65                  70                  75

<210> SEQ ID NO 45
<211> LENGTH: 2666
<212> TYPE: DNA
<213> ORGANISM: Mus musculus
<220> FEATURE:
<221> NAME/KEY: CDS
<222> LOCATION: (252)..(2219)
<300> PUBLICATION INFORMATION:
<308> DATABASE ACCESSION NUMBER: BC023729
<309> DATABASE ENTRY DATE: 2003-04-16
<313> RELEVANT RESIDUES: (1)..(2666)

<400> SEQUENCE: 45

| | |
|---|---|
| ccacgcgtcc ggccccagcg caacgcgcag cagcctccct cctcttcttc ccgcactgtg | 60 |
| cgctcctcct gggctagggc gtctggatcg agtcccggag gctaccgcct cccagacaga | 120 |
| cgacaggtca cctggacgcg agcctgtgtc cgggtctcgt cgttgccggc gcagtcactg | 180 |
| ggcacaaccg tgggactccg tctgtctcgg attaatcccg gagagccaga gccaacctct | 240 |
| cccggtcaga g atg cga ccc tca ggg acc gcg aga acc aca ctg ctg gtg<br>               Met Arg Pro Ser Gly Thr Ala Arg Thr Thr Leu Leu Val<br>               1             5                    10 | 290 |
| ttg ctg acc gcg ctc tgc gcc gca ggt ggg gcg ttg gag gaa aag aaa<br>Leu Leu Thr Ala Leu Cys Ala Ala Gly Gly Ala Leu Glu Glu Lys Lys<br>       15                  20                  25 | 338 |
| gtc tgc caa ggc aca agt aac agg ctc acc caa ctg ggc act ttt gaa<br>Val Cys Gln Gly Thr Ser Asn Arg Leu Thr Gln Leu Gly Thr Phe Glu<br>30                   35                  40                  45 | 386 |
| gac cac ttt ctg agc ctg cag agg atg tac aac aac tgt gaa gtg gtc<br>Asp His Phe Leu Ser Leu Gln Arg Met Tyr Asn Asn Cys Glu Val Val<br>              50                  55                  60 | 434 |
| ctt ggg aac ttg gaa att acc tat gtg caa agg aat tac gac ctt tcc<br>Leu Gly Asn Leu Glu Ile Thr Tyr Val Gln Arg Asn Tyr Asp Leu Ser<br>        65                  70                  75 | 482 |
| ttc tta aag acc atc cag gag gtg gcc ggc tat gtc ctc att gcc ctc<br>Phe Leu Lys Thr Ile Gln Glu Val Ala Gly Tyr Val Leu Ile Ala Leu | 530 |

-continued

```
               80                  85                  90
aac acc gtg gag aga atc cct ttg gag aac ctg cag atc atc agg gga    578
Asn Thr Val Glu Arg Ile Pro Leu Glu Asn Leu Gln Ile Ile Arg Gly
     95                 100                 105 aat gct ctt tat gaa aac acc tat gcc tta gcc atc ctg tcc aac tat    626
Asn Ala Leu Tyr Glu Asn Thr Tyr Ala Leu Ala Ile Leu Ser Asn Tyr
110                 115                 120                 125 ggg aca aac aga act ggg ctt agg gaa ctg ccc atg cgg aac tta cag    674
Gly Thr Asn Arg Thr Gly Leu Arg Glu Leu Pro Met Arg Asn Leu Gln
                130                 135                 140 gaa atc ctg att ggt gct gtg cga ttc agc aac aac ccc atc ctc tgc    722
Glu Ile Leu Ile Gly Ala Val Arg Phe Ser Asn Asn Pro Ile Leu Cys
         145                 150                 155 aat atg gat act atc cag tgg agg gac atc gtc caa aac gtc ttt atg    770
Asn Met Asp Thr Ile Gln Trp Arg Asp Ile Val Gln Asn Val Phe Met
     160                 165                 170 agc aac atg tca atg gac tta cag agc cat ccg agc agt tgc ccc aaa    818
Ser Asn Met Ser Met Asp Leu Gln Ser His Pro Ser Ser Cys Pro Lys
175                 180                 185 tgt gat cca agc tgt ccc aat gga agc tgc tgg gga gga gga gag gag    866
Cys Asp Pro Ser Cys Pro Asn Gly Ser Cys Trp Gly Gly Gly Glu Glu
190                 195                 200                 205 aac tgc cag aaa ttg acc aaa atc atc tgt gcc cag caa tgt tcc cat    914
Asn Cys Gln Lys Leu Thr Lys Ile Ile Cys Ala Gln Gln Cys Ser His
                210                 215                 220 cgc tgt cgt ggc agg tcc ccc agt gac tgc tgc cac aac caa tgt gct    962
Arg Cys Arg Gly Arg Ser Pro Ser Asp Cys Cys His Asn Gln Cys Ala
         225                 230                 235 gcg ggg tgt aca ggg ccc cga gag agt gac tgt ctg gtc tgc caa aag   1010
Ala Gly Cys Thr Gly Pro Arg Glu Ser Asp Cys Leu Val Cys Gln Lys
     240                 245                 250 ttc caa gat gag gcc aca tgc aaa gac acc tgc cca cca ctc atg ctg   1058
Phe Gln Asp Glu Ala Thr Cys Lys Asp Thr Cys Pro Pro Leu Met Leu
255                 260                 265 tac aac ccc acc acc tat cag atg gat gtc aac cct gaa ggg aag tac   1106
Tyr Asn Pro Thr Thr Tyr Gln Met Asp Val Asn Pro Glu Gly Lys Tyr
270                 275                 280                 285 agc ttt ggt gcc acc tgt gtg aag aag tgc ccc cga aac tac gtg gtg   1154
Ser Phe Gly Ala Thr Cys Val Lys Lys Cys Pro Arg Asn Tyr Val Val
                290                 295                 300 aca gat cat ggc tca tgt gtc cga gcc tgt ggg cct gac tac tac gaa   1202
Thr Asp His Gly Ser Cys Val Arg Ala Cys Gly Pro Asp Tyr Tyr Glu
         305                 310                 315 gtg gaa gaa gat ggc atc cgc aag tgt aaa aaa tgt gat ggg ccc tgt   1250
Val Glu Glu Asp Gly Ile Arg Lys Cys Lys Lys Cys Asp Gly Pro Cys
     320                 325                 330 cgc aaa gtt tgt aat ggc ata ggc att ggt gaa ttt aaa gac aca ctc   1298
Arg Lys Val Cys Asn Gly Ile Gly Ile Gly Glu Phe Lys Asp Thr Leu
335                 340                 345 tcc ata aat gct aca aac atc aaa cac ttc aaa tac tgc act gcc atc   1346
Ser Ile Asn Ala Thr Asn Ile Lys His Phe Lys Tyr Cys Thr Ala Ile
350                 355                 360                 365 agc ggg gac ctt cac atc ctg cca gtg gcc ttt aag ggg gat tct ttc   1394
Ser Gly Asp Leu His Ile Leu Pro Val Ala Phe Lys Gly Asp Ser Phe
                370                 375                 380 acg cgc act cct cct cta gac cca cga gaa cta gaa att cta aaa acc   1442
Thr Arg Thr Pro Pro Leu Asp Pro Arg Glu Leu Glu Ile Leu Lys Thr
         385                 390                 395 gta aag gaa ata aca ggc ttt ttg ctg att cag gct tgg cct gat aac   1490
Val Lys Glu Ile Thr Gly Phe Leu Leu Ile Gln Ala Trp Pro Asp Asn
```

```
                Val Lys Glu Ile Thr Gly Phe Leu Leu Ile Gln Ala Trp Pro Asp Asn
                        400                 405                 410 tgg act gac ctc cat gct ttc gag aac cta gaa ata ata cgt ggc aga           1538
Trp Thr Asp Leu His Ala Phe Glu Asn Leu Glu Ile Ile Arg Gly Arg
    415                 420                 425 aca aag caa cat ggt cag ttt tct ttg gcg gtc gtt ggc ctg aac atc           1586
Thr Lys Gln His Gly Gln Phe Ser Leu Ala Val Val Gly Leu Asn Ile
430                 435                 440                 445 aca tca ctg ggg ctg cgt tcc ctc aag gag atc agt gat ggg gat gtg           1634
Thr Ser Leu Gly Leu Arg Ser Leu Lys Glu Ile Ser Asp Gly Asp Val
                450                 455                 460 atc att tct gga aac cga aat ttg tgc tac gca aac aca ata aac tgg           1682
Ile Ile Ser Gly Asn Arg Asn Leu Cys Tyr Ala Asn Thr Ile Asn Trp
            465                 470                 475 aaa aaa ctc ttc ggg aca ccc aat cag aaa acc aaa atc atg aac aac           1730
Lys Lys Leu Phe Gly Thr Pro Asn Gln Lys Thr Lys Ile Met Asn Asn
        480                 485                 490 aga gct gag aaa gac tgc aag gcc gtg aac cac gtc tgc aat cct tta           1778
Arg Ala Glu Lys Asp Cys Lys Ala Val Asn His Val Cys Asn Pro Leu
    495                 500                 505 tgc tcc tcg gaa ggc tgc tgg ggc cct gag ccc agg gac tgt gtc tcc           1826
Cys Ser Ser Glu Gly Cys Trp Gly Pro Glu Pro Arg Asp Cys Val Ser
510                 515                 520                 525 tgc cag aat gtg agc aga ggc agg gag tgc gtg gag aaa tgc aac atc           1874
Cys Gln Asn Val Ser Arg Gly Arg Glu Cys Val Glu Lys Cys Asn Ile
                530                 535                 540 ctg gag ggg gaa cca agg gag ttt gtg gaa aat tct gaa tgc atc cag           1922
Leu Glu Gly Glu Pro Arg Glu Phe Val Glu Asn Ser Glu Cys Ile Gln
            545                 550                 555 tgc cat cca gaa tgt ctg ccc cag gcc atg aac atc acc tgt aca ggc           1970
Cys His Pro Glu Cys Leu Pro Gln Ala Met Asn Ile Thr Cys Thr Gly
        560                 565                 570 agg gga cca gac aac tgc atc cag tgt gcc cac tac att gat ggc cca           2018
Arg Gly Pro Asp Asn Cys Ile Gln Cys Ala His Tyr Ile Asp Gly Pro
    575                 580                 585 cac tgt gtc aag acc tgc cca gct ggc atc atg gga gag aac aac act           2066
His Cys Val Lys Thr Cys Pro Ala Gly Ile Met Gly Glu Asn Asn Thr
590                 595                 600                 605 ctg gtc tgg aag tat gca gat gcc aat aat gtc tgc cac cta tgc cac           2114
Leu Val Trp Lys Tyr Ala Asp Ala Asn Asn Val Cys His Leu Cys His
                610                 615                 620 gcc aac tgt acc tat gga tgt gct ggg cca ggt ctt caa gga tgt gaa           2162
Ala Asn Cys Thr Tyr Gly Cys Ala Gly Pro Gly Leu Gln Gly Cys Glu
            625                 630                 635 gtg tgg cca tct ggg tac gtt caa tgg cag tgg atc tta aag acc ttt           2210
Val Trp Pro Ser Gly Tyr Val Gln Trp Gln Trp Ile Leu Lys Thr Phe
        640                 645                 650 tgg atc taa gaccagaagc catctctgac tcccctctca ccttccagtt                   2259
Trp Ile
    655 tcttccaaat cctctgggcc agccagaggt ctcagattct gccctcttgc cctgtgccca         2319 ccttgttgac cactggacag catatgtgat ggctactgct agtgccagct tcacaagagg         2379 ttaacactac ggactagcca ttcttcctat gtatctgttt ctgcaaatac agccgcttta         2439 cttaagtctc agcacttctt agtctcctct tttcctctca gtagcccaag gggtcatgtc         2499 acaaacatgg tgtgaagggc tactttgtca aatgaaaagg tctatcttgg ggggcatttt         2559 tttcttttct tttttcttg aaacacattg cccagcaaag ccaataaatt tctctcatca          2619
```
ttttgtttct gataaattct tactattgat aaaaaaaaaa aaaaaaa 2666

<210> SEQ ID NO 46
<211> LENGTH: 655
<212> TYPE: PRT
<213> ORGANISM: Mus musculus

<400> SEQUENCE: 46

Met Arg Pro Ser Gly Thr Ala Arg Thr Thr Leu Leu Val Leu Leu Thr
1               5                   10                  15

Ala Leu Cys Ala Ala Gly Gly Ala Leu Glu Glu Lys Lys Val Cys Gln
            20                  25                  30

Gly Thr Ser Asn Arg Leu Thr Gln Leu Gly Thr Phe Glu Asp His Phe
        35                  40                  45

Leu Ser Leu Gln Arg Met Tyr Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Ala Leu
            100                 105                 110

Tyr Glu Asn Thr Tyr Ala Leu Ala Ile Leu Ser Asn Tyr Gly Thr Asn
        115                 120                 125

Arg Thr Gly Leu Arg Glu Leu Pro Met Arg Asn Leu Gln Glu Ile Leu
    130                 135                 140

Ile Gly Ala Val Arg Phe Ser Asn Asn Pro Ile Leu Cys Asn Met Asp
145                 150                 155                 160

Thr Ile Gln Trp Arg Asp Ile Val Gln Asn Val Phe Met Ser Asn Met
                165                 170                 175

Ser Met Asp Leu Gln Ser His Pro Ser Ser Cys Pro Lys Cys Asp Pro
            180                 185                 190

Ser Cys Pro Asn Gly Ser Cys Trp Gly Gly Gly Glu Glu Asn Cys Gln
        195                 200                 205

Lys Leu Thr Lys Ile Ile Cys Ala Gln Gln Cys Ser His Arg Cys Arg
    210                 215                 220

Gly Arg Ser Pro Ser Asp Cys Cys His Asn Gln Cys Ala Ala Gly Cys
225                 230                 235                 240

Thr Gly Pro Arg Glu Ser Asp Cys Leu Val Cys Gln Lys Phe Gln Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Pro Asp Tyr Tyr Glu Val Glu Glu
305                 310                 315                 320

Asp Gly Ile Arg Lys Cys Lys Lys Cys Asp Gly Pro Cys Arg Lys Val
                325                 330                 335

Cys Asn Gly Ile Gly Ile Gly Glu Phe Lys Asp Thr Leu Ser Ile Asn
            340                 345                 350

Ala Thr Asn Ile Lys His Phe Lys Tyr Cys Thr Ala Ile Ser Gly Asp
        355                 360                 365

```
Leu His Ile Leu Pro Val Ala Phe Lys Gly Asp Ser Phe Thr Arg Thr
    370                 375                 380

Pro Pro Leu Asp Pro Arg Glu Leu Glu Ile Leu Lys Thr Val Lys Glu
385                 390                 395                 400

Ile Thr Gly Phe Leu Leu Ile Gln Ala Trp Pro Asp Asn Trp Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Gly Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Arg Asn Leu Cys Tyr Ala Asn Thr Ile Asn Trp Lys Lys Leu
465                 470                 475                 480

Phe Gly Thr Pro Asn Gln Lys Thr Lys Ile Met Asn Asn Arg Ala Glu
                485                 490                 495

Lys Asp Cys Lys Ala Val Asn His Val Cys Asn Pro Leu Cys Ser Ser
            500                 505                 510

Glu Gly Cys Trp Gly Pro Glu Pro Arg Asp Cys Val Ser Cys Gln Asn
        515                 520                 525

Val Ser Arg Gly Arg Glu Cys Val Glu Lys Cys Asn Ile Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Ile Met Gly Glu Asn Asn Thr Leu Val Trp
        595                 600                 605

Lys Tyr Ala Asp Ala Asn Asn Val Cys His Leu Cys His Ala Asn Cys
    610                 615                 620

Thr Tyr Gly Cys Ala Gly Pro Gly Leu Gln Gly Cys Glu Val Trp Pro
625                 630                 635                 640

Ser Gly Tyr Val Gln Trp Gln Trp Ile Leu Lys Thr Phe Trp Ile
                645                 650                 655

<210> SEQ ID NO 47
<211> LENGTH: 21
<212> TYPE: DNA
<213> ORGANISM: Artificial
<220> FEATURE:
<223> OTHER INFORMATION: anti-EGFP siRNA

<400> SEQUENCE: 47
aagcagcagg acuucuucaa g                                          21

<210> SEQ ID NO 48
<211> LENGTH: 21
<212> TYPE: DNA
<213> ORGANISM: Artificial
<220> FEATURE:
<223> OTHER INFORMATION: scrabmle II Duplex RNA

<400> SEQUENCE: 48
aagcgcgcuu uguaggauuc g                                          21
```

-continued

```
<210> SEQ ID NO 49
<211> LENGTH: 21
<212> TYPE: DNA
<213> ORGANISM: Mus musculus

<400> SEQUENCE: 49
ggctacgtcc aggagcgcac c                                              21

<210> SEQ ID NO 50
<211> LENGTH: 19
<212> TYPE: DNA
<213> ORGANISM: Mus musculus

<400> SEQUENCE: 50
gcgcgctttg taggattcg                                                 19
```

DIGITAL CELL

TECHNICAL FIELD

The present invention lies in the field of technology of analyzing a cell. More specifically, the present invention is related to a method for providing a profile of a cell in a consistent environment, a system therefor, and data obtained by such technology and data sequence technology related thereto, as well as digital cell technology. The detailed description of the invention is provided as follows.

BACKGROUND ART

The survival of organisms depends on their ability to perceive and respond to extra-cellular signals. At the molecular level, signals are perceived and transmitted through networks of interacting proteins or the like, that act cooperatively to maintain cellular homeostasis and regulate activities like growth, division and differentiation. Information transfer through biological signaling networks is mediated largely by protein-protein interactions that can assemble and disassemble dynamically in response to signals, creating transient circuits that link external events to specific internal outputs, such as changes in gene expression. Numerous strategies have been developed to map the protein-protein interactions that underlie these networks. These studies have collectively provided a wealth of data delineating genome-wide protein-protein interactions for *Saccharomyces cervisiae* and other organisms. While powerful, these approaches have provided only a partial picture and are likely to overlook many interactions that are context dependent, forming only in the presence of their appropriate signals.

The disruption of protein-protein interactions either by mutation or small-molecules can create biological fulcrums that enable small perturbations of a signaling network to elicit large changes in cellular phenotype. However, not all protein-protein interactions in a given signaling pathway are likely to possess this power. As such, complementary strategies that aim to identify regulatory protein-protein interactions by artificially introducing proteins or peptides into cells which compete with and titrate-out the endogenous regulatory interactions, thereby disrupting the normal circuits that connect external signals to cellular responses, are of interest. By combining this strategy with functional assays, such as the activation of a gene in response to a signal, screens for functional interference can be used to identify peptides that perturb regulatory protein-protein interactions. This strategy, often referred to as dominant-interfering or dominant-negative genetics, has been successfully employed in several model organisms where high-throughput screening methods are easily applied, and to a lesser extent in mammals, which have traditionally been less amenable to these types of screens. One advantage of dominant-negative strategies is that such strategies can pinpoint the functionally relevant protein-protein interaction "fulcrum points" and thereby expose the small number of nodes within the larger web of a protein network that are susceptible to functional modulation by external agents. As such, the results of such strategies can provide vital information about the regulatory components that define a particular pathway and can allow the elucidation of key protein-protein interactions suitable for targeting by drug screening programs.

The difficulty in transfecting cells or producing transgenic organisms hinders the progression of development of dominant negative screening in mammals. To overcome this problem, high-efficiency retrovirus transfection has been developed. Although this retrovirus transfection is potent, it is necessary to produce DNA to be packaged into viral intermediates, and therefore, the applicability of this technique is limited. Alternatively, high-density transfection arrays or cell arrays are being developed, and the use thereof is proposed.

Rosetta Inpharmatics has proposed using cellular information as a profile in some patent applications (Japanese PCT National Phase Laid-Open Publication No.: 2003-505038; Japanese PCT National Phase Laid-Open Publication No.: 2003-505022; Japanese PCT National Phase Laid-Open Publication No.: 2002-533701; Japanese PCT National Phase Laid-Open Publication No.: 2002-533700; Japanese PCT National Phase Laid-Open Publication No.: 2002-533699; Japanese PCT National Phase Laid-Open Publication No.: 2002-528095; Japanese PCT National Phase Laid-Open Publication No.: 2002-526757; Japanese PCT National Phase Laid-Open Publication No.: 2002-518021; Japanese PCT National Phase Laid-Open Publication No.: 2002-518003; Japanese PCT National Phase Laid-Open Publication No.: 2002-514804; Japanese PCT National Phase Laid-Open Publication No.: 2002-514773; Japanese PCT National Phase Laid-Open Publication No.: 2002-514437). In such a profile, information from separate cells is processed as a group of separate pieces of information, but not continuous information. Therefore, this technique is limited in that information analysis is not conducted on a single (the same) cell. Particularly, in this technique, analysis is conducted only at one specific time point before and after a certain change, and a series of temporal changes in a point (gene) are not analyzed.

Recent advances in profiling techniques have led to accurate measurement of cellular components, and thus, profiling of cellular information (e.g., Schena et al., 1995, "Quantitative monitoring of gene expression patterns with a complementary DNA microarray", Science 270:467-470; Lockhart et al., 1996, "Expression monitoring by hybridization to high-density oligonucleotide arrays", Nature Biotechnology 14:1675-1680; Blanchard et al., 1996, "Sequence to array: Probing the genome's secrets", Nature Biotechnology 14:1649; and U.S. Pat. No. 5,569,588). For organisms whose genome is entirely known, it is possible to analyze the transcripts of all genes in a cell. In the case of other organisms, for which the amount of known genomic information is increasing, a number of genes in a cell can be simultaneously monitored.

As array technology advances, arrays also have been utilized in the field of drug screening (e.g., Marton et al., "Drug target validation and identification of secondary drug target effects using Microarrays", Nat. Med., 1998 November, 4(11):1293-301; and Gray et al., 1998, "Exploiting chemical libraries, structure, and genomics in the search for kinase inhibitors", Science, 281:533-538). Analysis using profiles (e.g., U.S. Pat. No. 5,777,888) and clustering of profiles provides information about conditions of cells, transplantation, target molecules and drug candidates, and/or the relevant functions, efficacy and toxicity of drugs. These techniques can be used to determine a common profile which represents ideal drug activity and disease conditions. Comparing profiles assists in detecting diseases in patients at an early stage, and provides prediction of improved clinical outcomes for patients who have been diagnosed as having a disease.

However, to date, there has been no technique which can provide information about the same cell in the true sense. In the above-described techniques, data is obtained as average for a group of heterologous cells. Analyses and evaluations based on such data lack accuracy. Therefore, there is an increasing demand for a method of providing information at the cellular level.

An object of the present invention is to provide a method for obtaining information, profiles or data of a cell. Another object of the present invention is to provide a method for obtaining information and data relating to cell status in a consistent environment, and a method and system for accurately presenting such data. In particular, a particular purpose of the present invention is to provide a system and a method for directly or as such information of a cell in a consistent environment in terms of complex system information, and providing such data and data sequencing technology per se. Another object of the present invention is to provide a digital cell and uses thereof.

SUMMARY OF THE INVENTION

The above-mentioned objects have been achieved or solved by immobilizing a cell onto a substrate, monitoring a biological agent, or a collection thereof, on or in a cell over time to produce cell profile data. As such, sequential collection of data from a cell has been enabled, and production of a digital cell has been achieved.

The above-mentioned object has further been achieved or solved by providing a substrate locating a plurality of cells in a consistent environment. Such a substrate has been provided by immobilizing a cell onto a substrate by means of for example, a salt or an actin-like substance, preferably both a salt and an actin-like substance. As such, the present invention allows one to collect cell profile data from cells of the same type, located in a consistent environment, simultaneously under the same conditions.

Accordingly, the present invention provides the following:

1. A method for producing profile data relating to information of a cell in a consistent environment, said method comprising the steps of:
a) locating a plurality of cells to a support which is capable of maintaining the cells in a consistent environment; and b) monitoring a biological agent, or a collection thereof, on or in the cell to produce the profile data for the cell.

2. A method according to Item 1, wherein the biological agent is a nucleic acid molecule or a molecule derived from the nucleic acid molecule.

3. A method according to Item 1, wherein the cell is immobilized to the support by a composition comprising a) a complex with a positively charged substance and a negatively charged substance; and b) a salt.

4. A method according to Item 1 wherein the cell is provided with an actin-like substance.

5. A method according to Item 1, wherein the cell is immobilized to the support by a composition comprising a) a complex with a positively charged substance and a negatively charged substance; and b) a salt, and is provided with an actin-like substance.

6. A method according to Item 1 wherein the biological agent is selected from the group consisting of a nucleic acid molecule, a protein, a saccharide, a lipid, a low molecular weight molecule, and a complex thereof.

7. A method according to Item 1, wherein the cell is cultured at least about three days before the step of monitoring.

8. A method according to Item 1, wherein the biological agent comprises a nucleic acid molecule encoding a gene.

9. A method according to Item 1, wherein the profile comprises a profile for gene expression.

10. A method according to Item 1, wherein the profile comprises a profile of an apoptosis signal.

11. A method according to Item 1 wherein the profile is a profile of a stress signal.

12. A method according to Item 1 wherein the profile is a profile of the localization of a molecule.

13. A method according to Item 12 wherein the molecule is detected by means selected from the group consisting of fluorescence, phosphorescence, radioactivity, and a combination thereof.

14. A method according to Item 1 wherein the profile comprises a variation in cell morphology.

15. A method according to Item 1 wherein the profile comprises a profile of promoter activity.

16. A method according to Item 1, wherein said profile comprises a profile of a promoter dependent on a specific drug.

17. A method according to Item 1 wherein said profile comprises a profile of a promoter dependent on a specific drug, wherein said method further comprises the step of administering the specific drug.

18. A method according to Item 1 further comprising the step of subjecting the cell to a foreign agent.

19. A method according to Item 18, wherein said foreign agent comprises an RNAi.

20. A method according to Item 18, wherein said foreign agent comprises a chemical not present in a biological body.

21. A method according to Item 1, wherein said profile comprises a profile of an intermolecular interaction.

22. A method according to Item 18, wherein said foreign agent comprises a ligand for a receptor of said cell.

23. A method according to Item 1, wherein said profile comprises a profile of an interaction between a receptor and a ligand.

24. A method according to Item 1, wherein said profile is of a cellular form, and said method further comprises the step of giving to said cell a stimulus selected from the group consisting of overexpression, underexpression or knockdown of a gene, addition of a foreign agent and a change in the environment.

25. A method according to Item 1, wherein said profile comprises a profile of interaction between molecules present in said cell.

26. A method according to Item 1, further comprising the step of conducting observation using a technology selected from the group consisting of two-hybrid method, FRET and BRET.

27. A method according to Item 1, wherein said profile comprises a profile of interaction between molecules present in said cell, wherein the method further comprises the step of conducting observation using a technology selected from the group consisting of two-hybrid method, FRET and BRET.

28. A method according to Item 1, wherein said cell is located on said support in an array format.

29. A method according to Item 1, wherein said cell is located on said support in an array format, and each of said plurality of cells are located at a space of 1 mm at maximum.

30. A method according to Item 1, wherein said profile is obtained in real time.

31. A method according to Item 1 further comprising the step of immobilizing said cell to a solid support.

32. A method according to Item 1, wherein said data comprises information relating to said profile.

33. A method according to Item 1 wherein said data comprises information relating to conditions during said monitoring.

34. A method according Item 1 wherein said data comprises information relating to the status of said cell.

35. A method according to Item 1 wherein said biological agent to be monitored comprises at least two types of biological agent.

36. A method according to Item 1 wherein said biological agent to be monitored comprises at least three types of biological agent.

37. A method according to Item 1 wherein said biological agent to be monitored comprises at least eight types of biological agents.

38. A method according to Item 1 further comprising the step of arbitrarily selecting a biological agent.

39. A method according to Item 1 wherein said cell is selected from the group consisting of a stem cell and a somatic cell.

40. A method according to Item 1 wherein said support comprises a solid support.

41. A method according to Item 1 wherein said support comprises a substrate.

42. A method according to Item 1 wherein said biological agent is a nucleic acid molecule, and said cell is transfected with said nucleic acid molecule.

43. A method according to Item 42, wherein said transfection is conducted on a solid phase or in a liquid phase.

44. A method according to Item 42, wherein said transfection is conducted on a solid support.

45. A method according to Item 1, further comprising the step of comparing a phase of said profile.

46. A method according to Item 1, further comprising the step of subtracting a control profile from the profile of said cell.

47. A method according to Item 1 further comprising the step of processing the profile with a mathematical processing method selected from signal processing and multivariant analysis methods.

48. A method for presenting profile data relating to information of a cell in a consistent environment, comprising the steps of:
   a) locating a plurality of cells on a support which is capable of maintaining the cells in a consistent environment;
   b) monitoring a biological agent, or a collection thereof, on or in the cell to produce the profile data for the cell; and
   c) presenting the data.

49. A method according to Item 48, wherein said step of presenting is conducted in real-time.

50. A method according to Item 48, wherein said step of presenting is conducted such that visual detection is enabled.

51. A method according to Item 48, wherein said step of presenting is conducted such that auditory detection is enabled.

52. A method for determining the state of a cell in a consistent environment, comprising the steps of:
   a) locating a plurality of cells on a support which is capable of maintaining the cells in a consistent environment; b) monitoring a biological agent, or a collection thereof, on or in the cell to produce the profile data for the cell; and
   c) determining the state of said cell from said data.

53. A method according to Item 52, further comprising the step of correlating said profile and the state of said cell in advance.

54. A method according to Item 52, wherein said cell comprises a cell for which the state thereof is known.

55. A method according to Item 52, wherein there are at least two types of said biological agent.

56. A method according to Item 52, further comprising the step of arbitrarily selecting said biological agent.

57. A method according to Item 52, wherein said data is produced in real-time.

58. A method according to Item 52, wherein said status is selected from the group consisting of differentiation state, undifferentiation state, cellular response to a foreign agent, cellular cycle and growth state.

59. A method according to Item 52, wherein said cell is selected from the group consisting of a stem cell and a somatic cell.

60. A method according to Item 52, wherein said solid support comprises a substrate.

61. A method according to Item 52, wherein said biological agent is a nucleic acid molecule, and said cell is transfected with said nucleic acid molecule.

62. A method according to Item 61, wherein said transfection is conducted on a solid phase or in a liquid phase.

63. A method according to Item 52, wherein said biological agent has the capability of binding a different biological agent.

64. A method according to Item 52, wherein said step of determination c) comprises comparing the phases of said profile.

65. A method according to Item 52, wherein said step of determination c) comprises obtaining the difference between said profile and a control profile.

66. A method according to Item 52, wherein said step of determination c) comprises a mathematical processing method selected from the group consisting of signal processing and multivariate analysis methods.

67. A method for correlating a foreign agent and a cellular response to the foreign agent, comprising the steps of:
   a) subjecting a cell to a foreign agent on a support capable of maintaining a plurality of cell in a consistent environment;
   b) monitoring a biological agent or a collection thereof on or in the cell to produce the profile data for the cell; and
   c) correlating the foreign agent and the profile.

68. A method according to Item 68, wherein said cell is immobilized on said support.

69. A method according to Item 69, further comprising the step of using at least two of said foreign agents to obtain profiles of each of the foreign agents.

70. A method according to Item 67, further comprising the step of classifying at least two of said profiles to classify foreign agents corresponding to the profiles.

71. A method according to Item 70, wherein said profile is presented in real-time.

72. A method according to Item 67, wherein said cell is cultured on an array.

73. A method according to Item 67, wherein the monitoring of said profile in step (b) comprises obtaining image data from said array.

74. A method according to Item 67, wherein said correlation between said foreign agent and said profile in step (c) is a step of identifying the identity or difference of the phase of said profile.

75. A method according to Item 67, wherein said foreign agent is selected from the group consisting of temperature changes, humidity changes, electromagnetic waves, potential difference, visible light, infrared light, ultraviolet light, X-rays, chemical substances, pressure, gravity changes, gas partial pressure and osmotic pressure.

76. A method according to Item 75, wherein said chemical substance is a biological molecule, a chemically synthesized substance or a culture medium.

77. A method according to Item 76, wherein said biological molecule is selected from the group consisting of a nucleic acid, a protein, a lipid, a sugar, a proteolipid, a lipoprotein, a glycoprotein and a proteoglycan.

78. A method according to Item 76, wherein said biological molecule comprises at least one biological molecule selected from the group consisting of a hormone, a cytokine, a cell adhesion factor and an extracellular matrix protein.

79. A method according to Item 75, wherein said chemical substance is an agonist or antagonist of a receptor.

80. A method for identifying an unidentified foreign agent given to a cell, from the profile of said cell, comprising the steps of:
    a) subjecting a cell on a support capable of maintaining a plurality of cells in a consistent environment, to a plurality of known foreign agents;
    b) monitoring a biological agent, or a collection thereof, on or in the cell over time to produce the profile data for the cell in response to each of the known foreign agents to produce profile data for the cell;
    c) correlating each of the known foreign agents and each of the profiles;
    d) subjecting the cell to an unidentified foreign agent;
    e) monitoring a biological agent, or a collection thereof, on or in the cell subjected to the unknown foreign agent over time to obtain the profile of the cell relating to the unidentified foreign agent;
    f) determining the profile corresponding to the profile obtained in step e) amongst the profiles obtained in step b);
    g) determining that the unidentified foreign agent is the known foreign agent corresponding to the profile which has been determined in step f).

81. A method for identifying an unidentified foreign agent given to a cell, from the profile of the cell, comprising the steps of:
    a) providing data relating to a correlation between a known foreign agent, and a profile of the cell corresponding to the known foreign agent, with respect to a biological agent, or a collection thereof, on or in the cell;
    b) subjecting the cell to an unidentified foreign agent;
    c) monitoring the biological agent, or the collection thereof, on or in the cell over time to produce a profile of the cell;
    d) determining the profile corresponding to the profile obtained in step c) amongst the profiles provided in step a); and
    e) determining that the unidentified foreign agent is the known foreign agent corresponding to the determined profile.

82. A method for obtaining a profile relating to information of a cell in a consistent environment, comprising the steps of:
    a) locating a plurality of cells to a support which is capable of maintaining the cells in a consistent environment; and
    b) monitoring a biological agent, or a collection thereof, on or in the cell over time to produce the profile data for the cell.

83. A storage medium on which data produced by a method according to Item 1, is stored.

84. A storage medium according to Item 83, wherein said storage medium further comprises data of at least one information relating to one selected from the group consisting of information relating to conditions under said monitoring, information relating to said profile, information relating to the state of said cell and information relating to the biological agent.

85. A storage medium according to Item 84, wherein the data is stored in a format which links a plurality of the data to each other.

86. A storage medium according to Item 84, wherein the data is stored in a format which has links per said cell.

87. Data produced by a method according to Item 1.

88. A transmission medium comprising data produced by a method according to Item 1.

89. A system for producing profile data relating to information of a cell in a consistent environment, said method comprising:
    a) a support which is capable of maintaining the cell in a consistent environment;
    b) means for monitoring a biological agent, or a collection thereof, on or in the cell to produce the profile data for the cell; and
    c) means for producing profile data for the cell from a signal obtained from the means for monitoring.

90. A system according to Item 89, further comprising a plurality of cells, and the plurality of cells are immobilized on to the support.

91. A system according to Item 90, wherein said support is attached at least one substance selected from the group consisting of a salt and an actin-like substance.

92. A system according to Item 89, wherein said means for monitoring comprises at least one means selected from the group consisting of optical microscopes, fluorescence microscopes, phase-contrast microscopes, reading devices using a laser source, means using surface plasmon resonance (SPR) imaging, electric signals, chemical or biochemical markers singly or in combination, radiation, confocal microscopes, nonconfocal microscopes, differential interference microscopes, stereoscopic microscopes, video monitors and infrared cameras.

93. A system for presenting profile data relating to information of a cell in a consistent environment, comprising:
   a) a support which is capable of maintaining the cell in a consistent environment;
   b) means for monitoring a biological agent, or a collection thereof, on or in the cell to produce the profile data for the cell;
   c) means for producing profile data for the cell from a signal obtained from the means for monitoring; and
   d) means for presenting the data.

94. A system according to Item 93, further comprising a plurality of cells, wherein the plurality of cells are immobilized on to the support.

95. A system according to Item 93, wherein said support is attached at least one substance selected from the group consisting of a salt and an actin-like substance.

96. A system according to Item 93, wherein said means for monitoring comprises at least one means selected from the group consisting of optical microscopes, fluorescence microscopes, phase-contrast microscopes, reading devices using a laser source, means using surface plasmon resonance (SPR) imaging, electric signals, chemical or biochemical markers singly or in combination, radiation, confocal microscopes, nonconfocal microscopes, differential interference microscopes, stereoscopic microscopes, video monitors and infrared cameras.

97. A system according to Item 93, wherein said means for presenting data is a display.

98. A system according to Item 93, wherein said means for presenting data is a speaker.

99. A system for determining the state of a cell in a consistent environment, comprising
   a) a support which is capable of maintaining the cell in a consistent environment;
   b) means for monitoring a biological agent, or a collection thereof, on or in the cell to produce the profile data for the cell;
   c) means for producing profile data for the cell from a signal obtained from the means for monitoring; and
   d) means for determining the state of said cell from said data.

100. A system for correlating a foreign agent and a cellular response to the foreign agent, comprising:
   a) a support capable of maintaining a plurality of cells in a consistent environment;
   b) means for subjecting the cells to a foreign agent;
   c) monitoring a biological agent, or a collection thereof, on or in the cells to produce the profile data for the cells;
   d) means for producing profile data for the cells from a signal obtained from the means for monitoring; and
   e) means for correlating the foreign agent and the profile.

101. A system for identifying an unidentified foreign agent given to a cell, from the profile of said cell, comprising:
   a) a support capable of maintaining a plurality of cells in a consistent environment;
   b) means for subjecting the cells to a known foreign agent;
   c) means for monitoring a biological agent, or a collection thereof, on or in a cell over time;
   d) means for obtaining the profile data for the cell in response to each of known foreign agents to produce profile data for the cell;
   e) means for correlating each of the known foreign agents and each of the profiles;
   f) means for subjecting the cells to an unknown foreign agent;
   g) means for comparing the profile of the known foreign agent obtained with means d), and the profile of the unknown foreign agent to determine a profile corresponding to the profile of the unknown foreign agent amongst the profiles of the known foreign agents, wherein said determined unidentified foreign agent is the known foreign agent for which the determined profile corresponds to.

102. A system for identifying an unidentified foreign agent given to a cell, from the profile of the cell, comprising:
   a) a storage medium having stored data relating to a correlation between a known foreign agent, and a profile of the cell corresponding to the known foreign agent, with respect to a biological agent, or a collection thereof, on or in the cell;
   b) means for subjecting the cell to an unidentified foreign agent;
   c) a support which is capable of maintaining a plurality of cells in a consistent environment;
   d) means for monitoring the biological agent or the collection thereof on or in the cell over time to produce a profile of the cell;
   e) means for obtaining the profile of the cell from a signal obtained from the means for monitoring; and
   f) means for determining the profile corresponding to the profile obtained relating to the unidentified foreign agent amongst the profiles stored in storage medium a), wherein the unidentified foreign agent is the known foreign agent for which the determined profile corresponds to.

103. A support capable of immobilizing a plurality of cells and maintaining the cells in a consistent environment.

104. A support according to Item 103, wherein the cells on the support are located in an array format.

105. A support according to Item 103 comprising a complex of a positively charged substance and a negatively charged substance; a salt; or an actin-like substance.

106. A support according to Item 103 comprising a complex of a positively charged substance and a negatively charged substance; a salt; and an actin-like substance.

107. A support according to Item 103, wherein said item is capable of being located within a space of 1 mm or less at maximum.

108. A support according to Item 103, further comprising a cell immobilized thereon.

109. A support according to Item 103, further comprising a biological agent immobilized thereon.

110. A support according to item 109, wherein two or more types of said biological agent are immobilized thereon.

111. A support according to Item 103, wherein a cell and a biological agent are immobilized thereon.

112. A support according to Item 103, wherein a salt; a complex between a positively charged substance and a negatively charged substance; and an actin-like substance are immobilized thereon together with a cell and a biological agent.

113. A support according to Item 103, wherein a salt; a complex between a positively charged substance and a negatively charged substance; and an actin-like substance are immobilized thereon together with a cell and a biological agent, in an array format.

114. A support according to Item 104, wherein a salt, a gene introduction reagent, and an actin-like substance, a nucleic acid molecule, and a cell are immobilized thereon in an array format.

115. A support according to Item 114, wherein the salt is selected from the group consisting of calcium chloride, sodium hydrogen phosphate, sodium hydrogen carbonate, sodium pyruvate, HEPES, calcium chloride, sodium chloride, potassium chloride, magnesium sulfide, iron nitrate, amino acids, and vitamins.

116. A support according to Item 114, wherein the gene introduction reagent is selected from the group consisting of cationic polymers, cationic lipids, polyamine-based reagents, polyimine-based reagents, calcium phosphate, oligofectamine and oligofecter.

117. A support according to Item 114, wherein the actin-like substance comprises at least one protein selected from the group consisting of fibronectin, laminin, and vitronectin, or a variant or fragment thereof.

118. A support according to Item 114, wherein the nucleic acid molecule comprises a sequence encoding a protein selected from the group consisting of cytokines, hormones, cell adhesion molecules, cytoskeleton proteins and enzymes.

119. A support according to Item 114, wherein the cell comprises a cell selected from the group consisting of an animal cell, an insect cell, a plant cell, a bacterial cell and a fungal cell.

120. A support according to Item 114 wherein material of said support comprises material selected from the group consisting of glass, silica and plastics.

121. A method for producing a support comprising a plurality of cells immobilized thereon and capable of maintaining the cells in a consistent environment, comprising the steps of:

A) providing a support; and

B) immobilizing a cell to the support using a complex comprising of a salt, a positively-charged substance and a negatively-charged substance.

122. A method according to Item 121, wherein said step of immobilizing comprises immobilizing a mixture of the salt, a gene introduction reagent as the positively-charged substance, an actin-like substance, a nucleic acid molecule as the negatively-charged substance, and the cell in an array format.

123. A method according to Item 121, wherein said step of immobilizing comprises a printing step.

124. A method according to Item 121, wherein the step of providing the support comprises the step of producing the support from a support material.

125. An apparatus for producing a support comprising a plurality of cells immobilized thereon and capable of maintaining the cells in a consistent environment, comprising:

A) means for providing a support; and

B) means for immobilizing a cell to the support using a complex comprising a salt, a positively-charged substance and a negatively-charged substance.

126. An apparatus according to Item 125, wherein said means for immobilizing comprises means for printing.

127. An apparatus according to Item 125, wherein the means for providing the support comprises means for shaping the support from a support material.

128. A method for producing a digital cell, comprising the steps of:

a) obtaining a cell parameter specifying a cell of experimental interest;

b) obtaining an environment parameter specifying an environment under which the cell specified by the cell parameter is cultured;

c) obtaining a stimulus parameter specifying a stimulus to be given to the cell specified by the cell parameter;

d) obtaining a stimulus response result showing a result which the cell specified by the cell parameter responds to the stimulus specified by the stimulus parameter under the environment specified by the environment parameter;

e) producing an experimental data for the cell, by correlating the cell parameter, the environment parameter, the stimulus parameter and the stimulus response result; and f) optionally repeating steps a) through e) to produce at least one collection of experimental data for the cell, and to provide the at least one collection of experimental data as a digital cell.

129. A method according to Item 128, wherein the environment parameter comprises a parameter indicating culture medium in which the cell is cultured, and a parameter showing the conditions of the culture medium.

130. A method according to Item 128, wherein the stimulus parameter comprises a parameter showing a reporter and a parameter showing a chemical stimulus.

131. A method according to Item 128, wherein said stimulus response result comprises profile data for the cell obtained by monitoring a biological agent, or a collection thereof, on or in the cell over time.

132. A method according to Item 128, further comprising the step of storing the digital cell to a database.

133. An apparatus for producing a digital cell, comprising:

a) means for obtaining a cell parameter specifying a cell of experimental interest;

b) means for obtaining an environment parameter specifying an environment under which the cell specified by the cell parameter is cultured;

c) means for obtaining a stimulus parameter specifying a stimulus to be given to the cell specified by the cell parameter;

d) means for obtaining a stimulus response result showing a result which the cell specified by the cell parameter responds to the stimulus specified by the stimulus parameter under the environment specified by the environment parameter;

e) means for producing an experimental data for the cell, by correlating the cell parameter, the environment parameter, the stimulus parameter and the stimulus response result; and f) means for providing at least one collection of experimental data as a digital cell, by optionally repeating steps performed by the means a) through e) to produce at least one collection of experimental data for the cell.

134. A method for providing a service which reproduces an experimental result of an actual cell using a digital cell by means of a computer system comprising a service requester and a service provider, comprising the steps of:

preparing a database having at least one digital cell stored thereon, wherein the at least one digital cell is expressed as a collection of at least one experimental data of a cell of experimental interest, wherein each of the at least one experimental data comprises a cell parameter specifying the cell, an environment parameter specifying an environment under which the cell specified by the cell parameter is cultured, a stimulus parameter specifying a stimulus to be given to the cell specified by the cell parameter, and a stimulus response result showing a result which the cell specified by the cell parameter responds to the stimulus specified by the stimulus parameter under the environment specified by the environment parameter;

receiving the cell parameter, the environment parameter and the stimulus parameter by the service requester to produce a request comprising the cell parameter, the environment parameter and the stimulus parameter;

providing the request to the service provider by the service requester;

searching the database in response to the request by the service provider to determine whether or not there is the stimulus response result relating to the cell parameter, the environment parameter and the stimulus parameter included in the request, in the database;

providing the stimulus response result to the service requester by the service provider, when it is determined that the stimulus response result relating to the cell parameter, the environment parameter and the stimulus parameter included in the request exists in the database; and presenting the stimulus response result by the service requester.

135. A method for providing a service for reproducing an experimental result of an actual cell using a digital cell, by means of a computer system comprising a service requester and a plurality of service providers, comprising the steps of:

preparing a plurality of databases, each having at least one digital cell stored thereon, wherein the at least one digital cell is expressed as a collection of at least one experimental data of a cell of experimental interest, wherein each of the at least one experimental data comprises a cell parameter specifying the cell, an environment parameter specifying an environment under which the cell specified by the cell parameter is cultured, a stimulus parameter specifying a stimulus to be given to the cell specified by the cell parameter, and a stimulus response result showing a result which the cell specified by the cell parameter responds to the stimulus specified by the stimulus parameter under the environment specified by the environment parameter;

preparing a service registry which stores at least one service capable of being provided by the plurality of service providers;

receiving the cell parameter, the environment parameter and the stimulus parameter by the service requester to produce a request comprising the cell parameter, the environment parameter and the stimulus parameter;

searching the service registry in response to the request by the service requester to determine whether or not there exists a service provider capable of providing a service for the request amongst the plurality of service providers;

providing the request to the service provider by the service requester when it is determined that a service provider capable of providing a service of the request amongst the plurality of service providers exists;

searching the database in response to the request by the service provider to determine whether or not there is the stimulus response result relating to the cell parameter, the environment parameter and the stimulus parameter included in the request in the database;

providing the stimulus response result to the service requester by the service provider, when it is determined that the stimulus response result relating to the cell parameter, the environment parameter and the stimulus parameter included in the request exists in the database; and presenting the stimulus response result by the service requester.

136. A computer system for providing a service which reproduces an experimental result of an actual cell using a digital cell, comprising:

a service requester being composed such that it can have access to a database having at least one digital cell stored thereon, each of the at least one digital cell is expressed as a collection of at least one experimental data of a cell of experimental interest, wherein each of the at least one experimental data comprises a cell parameter specifying the cell, an environment parameter specifying an environment under which the cell specified by the cell parameter is cultured, a stimulus parameter specifying a stimulus to be given to the cell specified by the cell parameter, and a stimulus response result showing a result which the cell specified by the cell parameter responds to the stimulus specified by the stimulus parameter under the environment specified by the environment parameter; and a service provider requesting a service desired by a user;

wherein the service requester comprises:

means for receiving the cell parameter, the environment parameter and the stimulus parameter to produce a request comprising the cell parameter, the environment parameter and the stimulus parameter; and means for providing the request to the service provider, and wherein the service provider comprises:

means for searching the database in response to the request by the service provider to determine whether or not there is the stimulus response result relating to the cell parameter, the environment parameter and the stimulus parameter included in the request in the database; and means for providing the stimulus response result to the service requester by the service provider, when it determined that the stimulus response result relating to the cell parameter, the environment parameter and the stimulus parameter included in the request exists in the database;

wherein the service requester further comprises means for presenting the stimulus response result by the service requester.

137. A computer system according to Item 136 wherein the service requester is a Web browser which the user operates, and the service provider is a Web server linked to the service requester via the Internet.

138. A computer system according to Item 136, wherein the service requester provides the request to the service provider in a format described in XML language.

139. A computer system according to Item 136, wherein the service provider provides the stimulus response result to the service requester in a format described in XML language.

140. A computer system for providing a service which reproduces an experimental result of an actual cell using a digital cell, comprising:

a plurality of service providers, each composed such that the plurality of service providers can have access to a database having at least one digital cell stored thereon, each of the at least one digital cell is expressed as a collection of at least one experimental data of a cell of experimental interest, wherein each of the at least one experimental data comprises a cell parameter specifying the cell, an environment parameter specifying an environment under which the cell specified by the cell parameter is cultured, a stimulus parameter specifying a stimulus to be given to the cell specified by the cell parameter, and a stimulus response result showing a result which the cell specified by the cell parameter responds to the stimulus specified by the stimulus parameter under the environment specified by the environment parameter;

a service registry which stores at least one service which the plurality of service providers can provide; and a service provider requesting a service desired by a user; wherein the service requester comprises:

means for receiving the cell parameter, the environment parameter and the stimulus parameter to produce a request comprising the cell parameter, the environment parameter and the stimulus parameter;

means for searching the service registry in response to the request by the service requester to determine whether or not there exists a service provider capable of providing a service of the request amongst the plurality of service providers and means for providing the request to the service provider by the service requester when it is determined that there exists a service provider capable of providing a service of the request amongst the plurality of service providers, wherein each of the plurality of service providers comprises:

means for searching the database in response to the request by the service provider to determine whether or not there is the stimulus response result relating to the cell parameter, the environment parameter and the stimulus parameter included in the request in the database; and means for providing the stimulus response result to the service requester by the service provider, when it is determined that the stimulus response result relating to the cell parameter, the environment parameter and the stimulus parameter included in the request exists in the database;

wherein the service requester further comprises means for presenting the stimulus response result by the service requester.

141. A computer system according to Item 140, wherein the service requester is a Web server connected to a Web browser which the user operates via the Internet, and each of the plurality of service providers is a Web server connected to the service requester via the Internet.

142. A computer system according to Item 140, wherein the service requester provides the request to the service provider in a format described in XML language.

143. A computer system according to Item 140, wherein the service provider provides the stimulus response result to the service requester in a format described in XML language.

144. A method for producing the profile data relating information of a cell, comprising the steps of:

a) immobilizing and locating a cell on a support; and b) monitoring a biological agent, or a collection thereof, on or in the cell to produce the profile data for the cell.

145. A method according to Item 144, wherein the biological agent is a nucleic acid molecule or a molecule derived from the nucleic acid molecule.

146. A method according to Item 144, wherein the cell is immobilized to the support by a composition comprising a) a complex with a positively charged substance and a negatively charged substance; and b) a salt.

147. A method according to Item 144 wherein the cell is provided with an actin-like substance.

148. A method according to Item 144, wherein the cell is immobilized to the support by a composition comprising a) a complex with a positively charged substance and a negatively charged substance; and b) a salt, and is provided with an actin-like substance.

149. A method according to Item 144 wherein the biological agent is selected from the group consisting of a nucleic acid molecule, a protein, a saccharide, a lipid, a low molecule, and a complex thereof.

150. A method according to Item 144, wherein the cell is cultured for at least about three days before the step of monitoring.

151. A method according to Item 144, wherein the biological agent comprises a nucleic acid molecule encoding a gene.

152. A method according to Item 144, wherein the profile comprises a profile of gene expression.

153. A method according to Item 144, wherein the profile comprises a profile of an apoptosis signal.

154. A method according to Item 144 wherein the profile is a profile of a stress signal.

155. A method according to Item 144 wherein the profile is a profile of the localization of a molecule.

156. A method according to Item 155 wherein the molecule is detected by means selected from the group consisting of fluorescence, phosphorescence, radioactivity, and a combination thereof.

157. A method according to Item 144 wherein the profile comprises a variation of cell morphology.

158. A method according to Item 144 wherein the profile comprises a profile of promoters.

159. A method according to Item 144, wherein said profile comprises a profile of a promoter dependent on a specific drug.

160. A method according to Item 144 wherein said profile comprises a profile of a promoter dependent on a specific drug, wherein said method further comprises the step of administering the specific drug.

161. A method according to Item 144 further comprising the step of subjecting the cell to a foreign agent.

162. A method according to Item 161, wherein said foreign agent comprises an RNAi.

163. A method according to Item 161, wherein said foreign agent comprises a chemical not present in a biological body.

164. A method according to Item 144, wherein said profile comprises a profile of intermolecular interaction.

165. A method according to Item 161, wherein said foreign agent comprises a ligand for a receptor of said cell.

166. A method according to Item 144, wherein said profile comprises a profile of an interaction between a receptor and a ligand.

167. A method according to Item 144, wherein said profile is a cellular form, and said method further comprises the step of giving to said cell a stimulus selected from the group consisting of overexpression, underexpression or knockdown of a gene, addition of a foreign agent and a change in the environment.

168. A method according to Item 144, wherein said profile comprises a profile of interaction between molecules present in said cell.

169. A method according to Item 144, further comprising the step of conducting observation using a technology selected from the group consisting of two-hybrid method, FRET and BRET.

170. A method according to Item 144, wherein said profile comprises a profile of interaction between molecules present in said cell, wherein the method further comprises the step of conducting observation using a technology selected from the group consisting of two-hybrid method, FRET and BRET.

171. A method according to Item 144, wherein said cell is located on said support in an array format.

172. A method according to Item 144, wherein said cell is located on said support in an array format, and each of said plurality of cells are located at a space of 1 mm at maximum.

173. A method according to Item 144, wherein said profile is obtained at real time.

174. A method according to Item 144 further comprising the step of immobilizing said cell to a solid support.

175. A method according to Item 144, wherein said data comprises information relating to said profile.

176. A method according to Item 144 wherein said data comprises information relating to conditions during said monitoring.

177. A method according Item 144 wherein said data comprises information relating to the state of said cell.

178. A method according to Item 144 wherein said biological agent to be monitored comprises at least two types of biological agent.

179. A method according to Item 144 wherein said biological agent to be monitored comprises at least three types of biological agent.

180. A method according to Item 144 wherein said biological agent to be monitored comprises at least eight types of biological agent.

181. A method according to Item 144 further comprising the step of arbitrarily selecting a biological agent.

182. A method according to Item 144 wherein said cell is selected from the group consisting of a stem cell and a somatic cell.

183. A method according to Item 144 wherein said support comprises a solid support.

184. A method according to Item 144 wherein said support comprises a substrate.

185. A method according to Item 144 wherein said biological agent is a nucleic acid molecule, and said cell is transfected with said nucleic acid molecule.

186. A method according to Item 185, wherein said transfection is conducted on a solid phase or in a liquid phase.

187. A method according to Item 185, wherein said transfection is conducted on a solid support.

188. A method according to Item 144, further comprising the step of comparing a phase of said profile.

189. A method according to Item 144, further comprising the step of subtracting a control profile from the profile of said cell.

190. A method according to Item 144 further comprising the step of processing the profile with a mathematical processing method selected from signal processing and multivariant analysis methods.

Hereinafter, the present invention will be described by way of preferred embodiments. It will be understood by those skilled in the art that the embodiments of the present invention can be appropriately made or carried out based on the description of the present specification and the accompanying drawings, and commonly used techniques well known in the art. The function and effect of the present invention can be easily recognized by those skilled in the art.

The present invention provides consecutive information (profile) data relating to the state of a cell. The present invention provides information and data (in particular consecutive information and consecutive profile) relating to the state of a cell in a consistent environment, in a reproducible manner. According to the present invention, a method and a system for presenting such data in an accurate manner are provided. Specifically, it should be surprising a effect to be able to provide a system and a method for information at the cellular level in a consistent environment in terms of a complex system as such or in a direct manner, and to be able to provide such data and technology for aligning such data per se. The present invention further attains the effect of providing a digital cell based on actual, live data and the use thereof, which have not been conventionally possible prior to the present invention.

As such, according to the present invention, it is possible to determine the state of cells by observing a surprisingly small number of factors. Therefore, the present invention is applicable to diagnosis, prevention, and treatment. The present invention is also applicable to the fields of food, cosmetics, agriculture, environmental engineering, and the like. Reproduction of a live experiment on a computer system attains the effect of enabling education and research in the field of biotechnology.

BRIEF DESCRIPTION OF THE DRAWINGS

FIG. 1 shows the effect of each adhesion substance (HEK cell) with respect to transfection efficiency. The HEK cells were transfected with pEGFP-N1 using an Effectene reagent.

FIG. 2 shows exemplary transfection efficiencies when fibronectin fragments were used.

FIG. 4 shows a summary of the results presented in FIGS. 2 and 3.

FIG. 8 provides exemplary photographs showing cell adhesion profiles in the presence or absence of fibronectin.

FIG. 13 shows an experiment in which spatially-spaced DNA was taken into cells after the solid phase transfection of the present invention in Example 4.

FIG. 13A schematically shows a method for producing a solid phase transfection array (SPTA). This figure shows the methodology of a solid transfection.

FIG. 13A depicts the outlines of SPTA determination, and FIG. 13B depicts a result of SPTA using HEK293 cell strain. The bar indicates 3 mm.

Figure 14A:
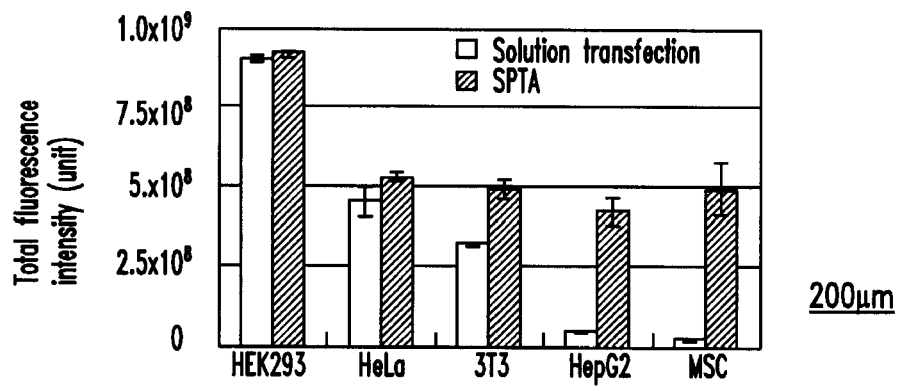
FIG. 14A shows the results of experiments where 5 cell lines were measured with respect to GFP intensity/mm$^2$. Transfection efficiency was determined as fluorescence intensity per unit area.

Fluorescent photographs of EGFP expressing cells corresponding to FIG. 14A are shown with respect to the five types of cells per measured fluorescence/mm$^2$. White circles correspond to plasmid DNA printed regions. Outside these regions, cells express EGFP. Further, regions other than the printed regions are attached cells.

Figure 14B:
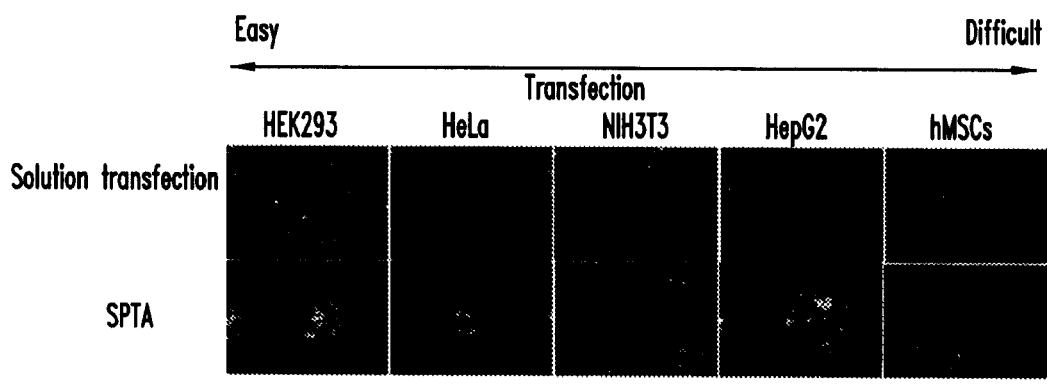
FIG. 14B shows fluorescent images of cells expressing EGFP corresponding to the data presented in FIG. 14A. White circular regions therein were regions in which plasmid DNA was fixed. In other regions, cells were also fixed in solid phase, however, cells expressing EGFP were not observed. The white bar indicates 500 μm.
Figure 14C:
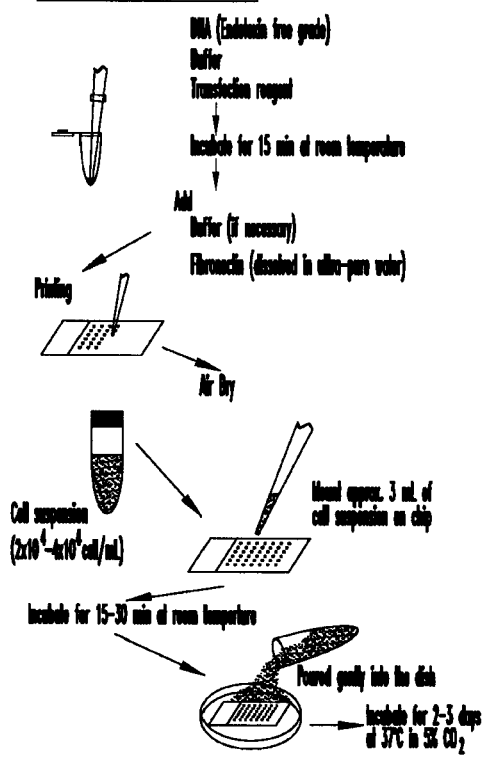
FIG. 14 shows the results of comparison of liquid phase transfection and SPTA.

FIG. 14C shows an exemplary transfection method of the present invention.

FIG. 14D shows an exemplary transfection method of the present invention.

Figure 15B:
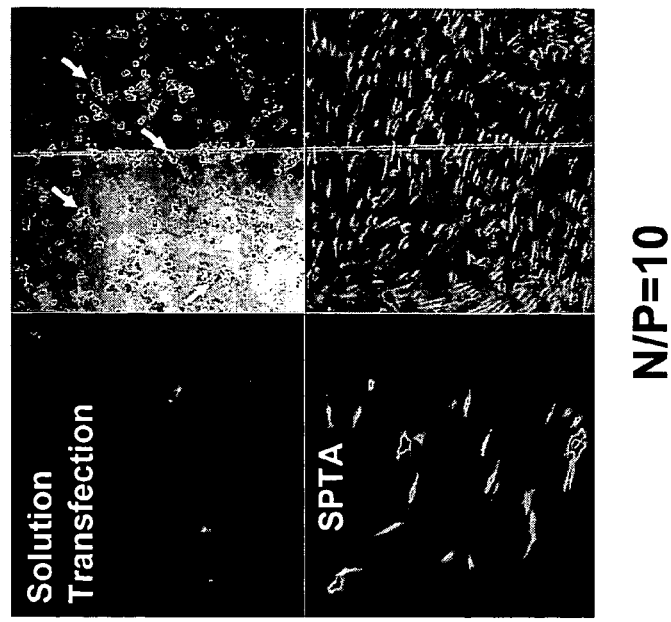
Figure 15A:
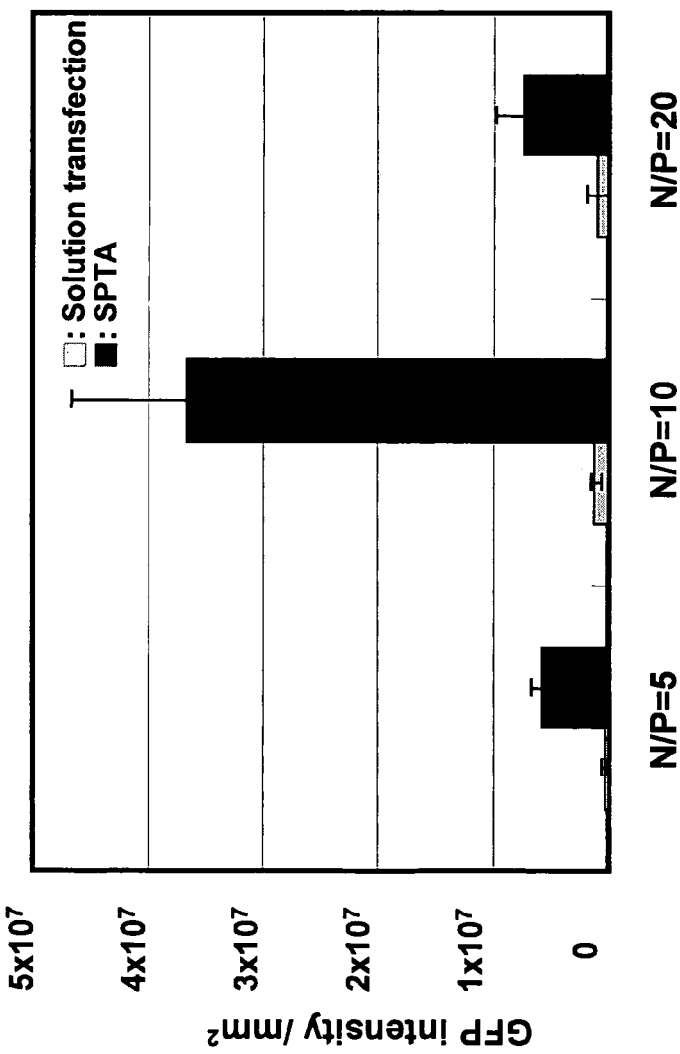

FIG. 15A shows the results of coating a chip, whereby cross contamination was reduced.

FIG. 15B shows the results of liquid phase transfection and SPTA using HEK293 cells, HeLa cells, NIT3T3 cells (also referred to as "3T3"), HepG2 cells, and hMSCs. Transfection efficiency was determined by GFP intensity.

Transfection efficiency of hMSC depending on the N/P ratio used is shown in FIG. 15A. In the phase of prior liquid phase transfection (FIG. 15B, upper panel), hMSC cells were dead and in the case of SPTA, cell morphology was normal (FIG. 15B, lower panel).

Figure 16B:
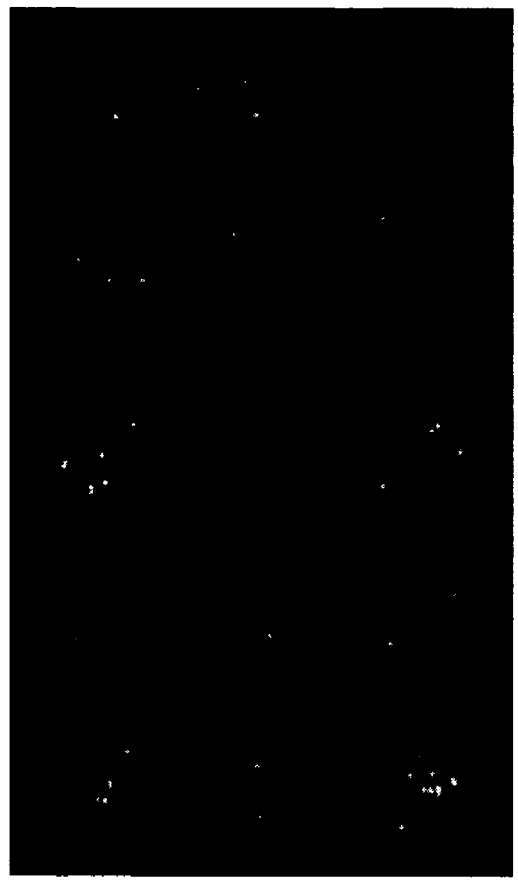
Figure 16A:

FIG. 16 shows cross contamination between each spot. A nucleic acid mixture containing fibronectin having a predetermined concentration was fixed to a chip coated with APS or PLL (poly-L-lysine) FIG. 16A. Cell transfection was performed on the chip. Substantially no cross contamination was observed (upper and middle rows) FIG. 16A. In contrast, significant cross contamination of fixed nucleic acids was observed on an uncoated chip (lower row) FIG. 16B.

FIG. 16C shows a correlation relationship between the types of substances contained in a mixture used for fixation of nucleic acid and the cell adhesion rate. The graph presented in FIG. 16 shows an increase in the proportion of adherent cells over time. A longer time is required for cell adhesion when the slope of the graph is shallow than when the slope of the graph is steep.

Figure 16D:
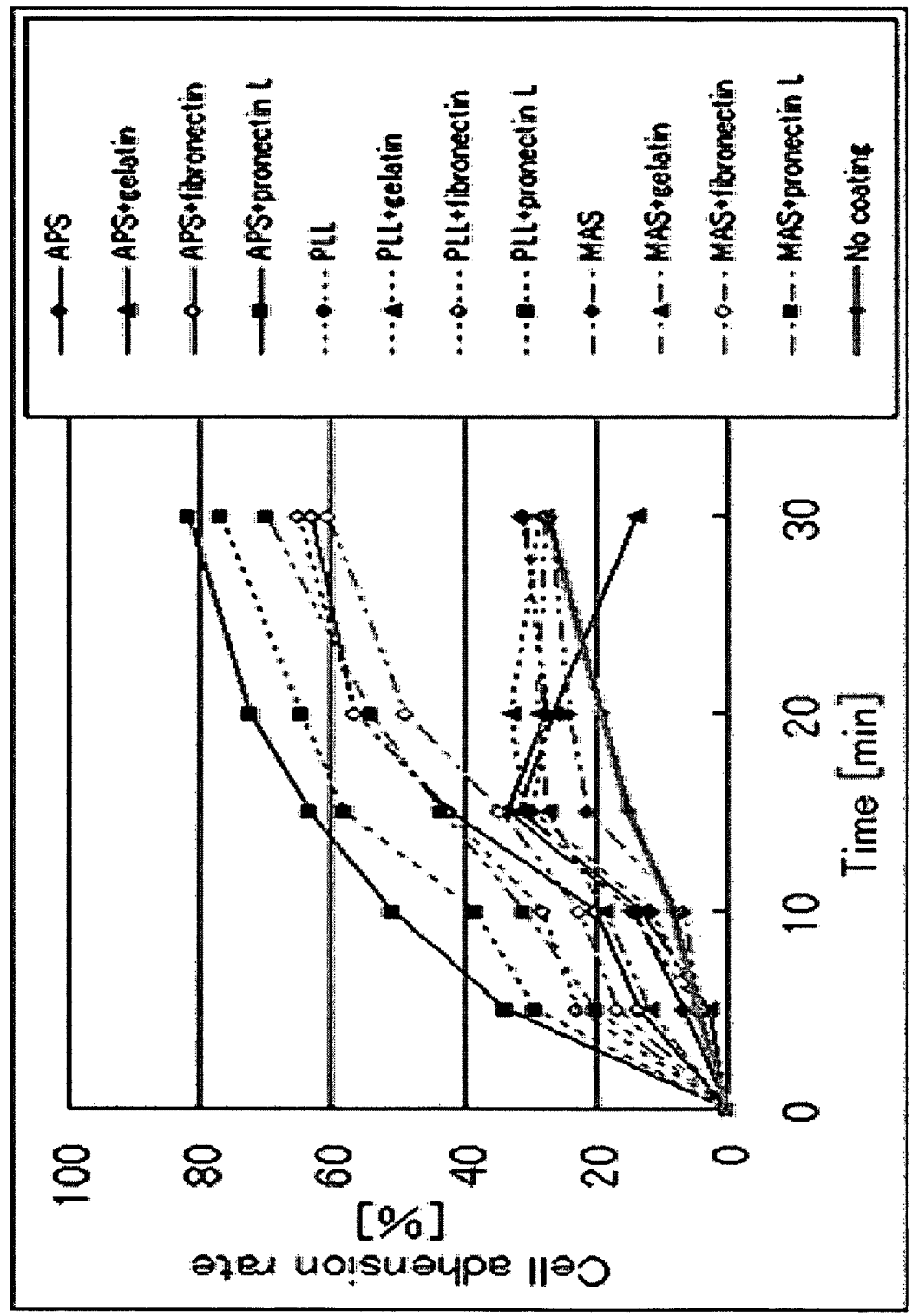

FIG. 16D is an enlarged graph which is presented in FIG. 16C.

Figure 17:
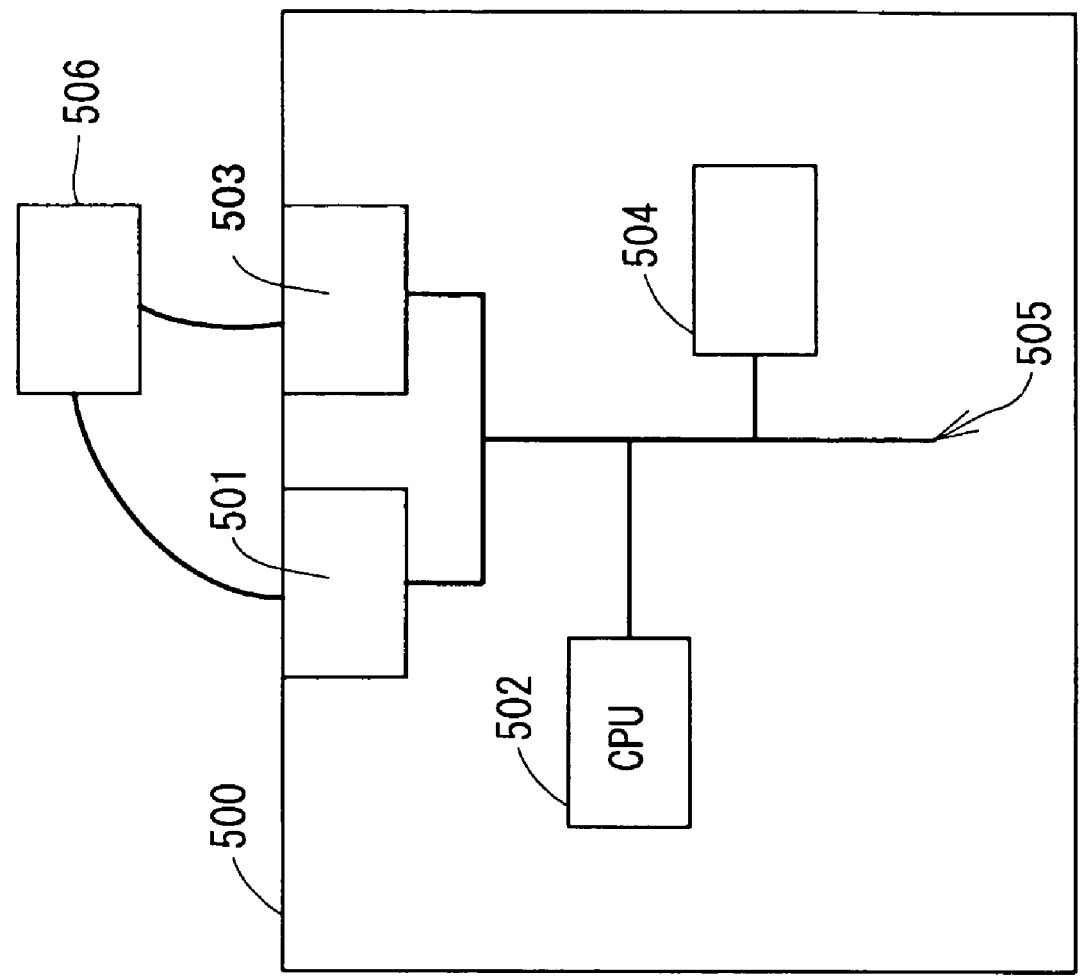

FIG. 17 shows an exemplary configuration of a computer which was used to perform the method of the present invention.

Figure 18B:
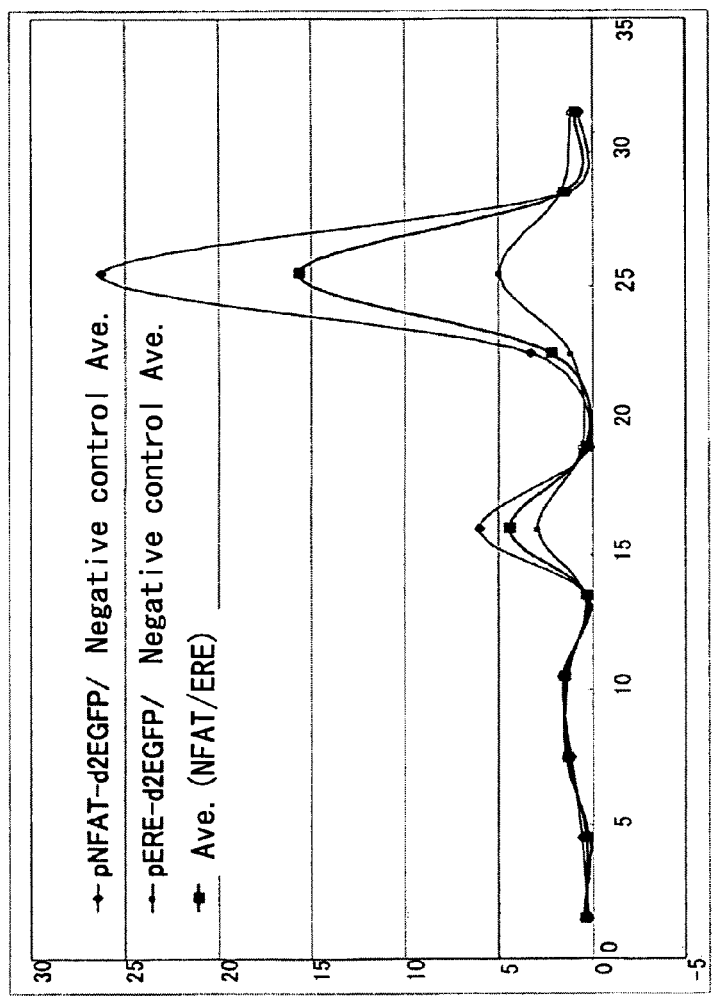

FIG. 18 depicts an example of a mathematical analysis method of the present invention. Profiles of promoters shown in FIG. 18A (average of pNEFAT-d2EGFP/negative control) and FIG. 18B (average of pERE-d2EGFP/negative control) are obtained by measuring the fluorescent intensity thereof over time. These profiles have been normalized using the autologous fluorescence of either the cell or medium used. Thereafter, in order to compare amplitude of the reporter expression fluctuation, an amplitude=5 or more (TH>=5) was determined to have change in expression fluctuation state. Further, differentiation induction was divided into the following sections: start of differentiation induction, early stage (0-17.5 hours), and late stage (17.5-31.5 hours) and total stages (0-31.5 hours); and those observed with a variation in expression of an amplitude of 5 or more (TH>=5) were defined as (+) and those with an amplitude of less than 5 were defined as (−). Based on these definitions, the profiles of A and B were evaluated as shown in the lower tables of FIGS. 18A and 18B. In the table, when extracting any number of reporters, (A+B+ . . . n) have been integrated with respect to n types of wave forms and the sum is divided by n to form the average wave form and if variations beyond the threshold, such variations were deemed as being "changed".

FIG. 18B depicts another example of a mathematical analysis according to the present invention. When a reporter is extracted (A+B+ . . . n), n types of wave types are integrated, and the sum is divided by n to produce an average wave form, which was deemed as being a change of the variation above a threshold. The left hand panel of FIG. 18B depicts the integration of two reporter profiles and draws the average wave form in red or with solid squares. Those with 5 or more variations of the average profile were deemed to be expression variations for evaluation. As a result, evaluation can be conducted for variation of the two extracted reporters, as shown in the table herein.

Figure 19:
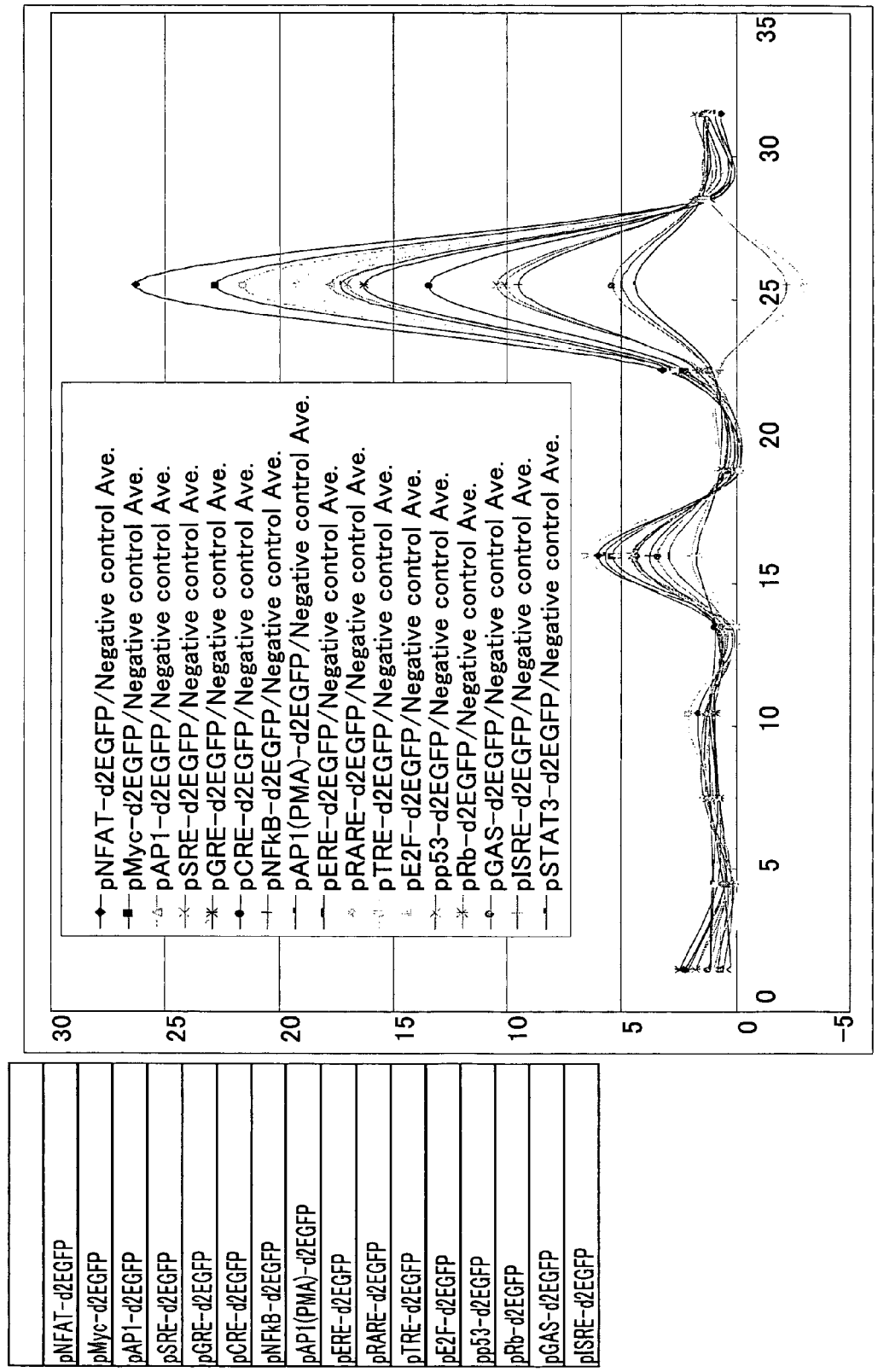

FIG. 19 depicts exemplary plasmids containing promoters used in the present invention and an analysis according to the present invention. Seventeen types of transcriptional factors shown in the left hand panel of FIG. 19 were used as a reporter under the conditions of osteoblast differentiation and maintenance of an undifferentiated mesenchymal stem cell, and the expression profile thereof have been obtained over time (FIG. 19, right handed panel). From these seventeen types of profiles, any number of profiles have been extracted and evaluated by the method as previously described in FIG. 18, taking the change in amplitude of the response profile of each transcriptional factor as a standard.

Figure 20:
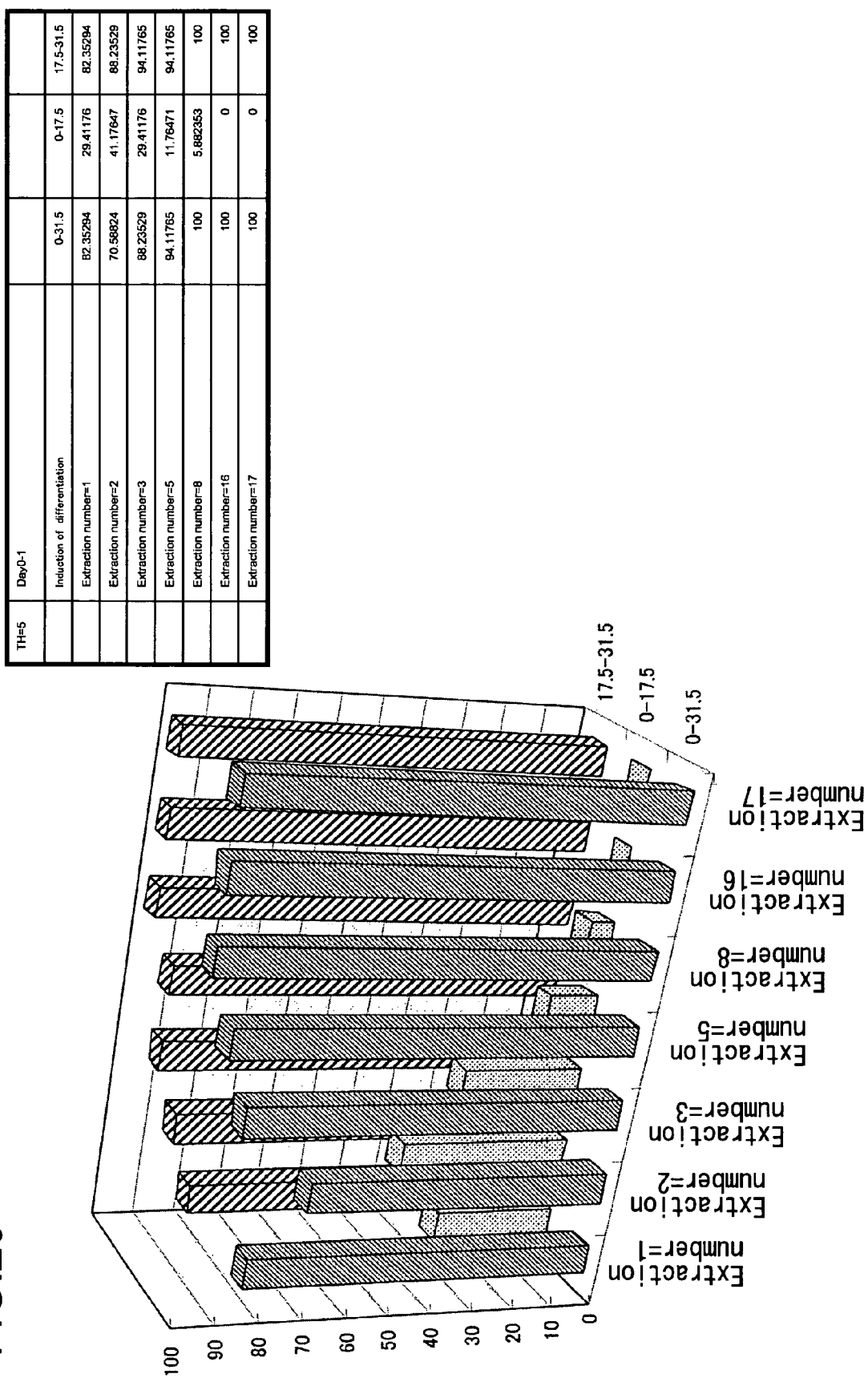

FIG. 20 depicts an example of mathematical analysis at the early stage of induction of differentiation. By changing the combination arbitrarily extracted in the early differentiation induction stage, results as shown in FIG. 20 have been obtained. Any number of reporters were extracted from the reporter group consisting of seventeen species, and calculated for the average profile according to the method shown in FIG. 18. Those having five or more variation widths are the results evaluated with the evaluation windows 0-31.5, 0-17.5 and 17.5-31.5. Each extraction condition has seventeen extraction patterns, except for where the seventeen extraction pattern has only one way of extraction. Amongst these combinations, FIG. 20 shows the ratio in which variation is found therein, including the table and graph included therein. This analysis allows confirmation of differentiation after fifteen hours although it is not possible to understand the very early stages of differentiation. The number of extraction where 100% change is found for variation is eight or more in this instance.

Figure 21:
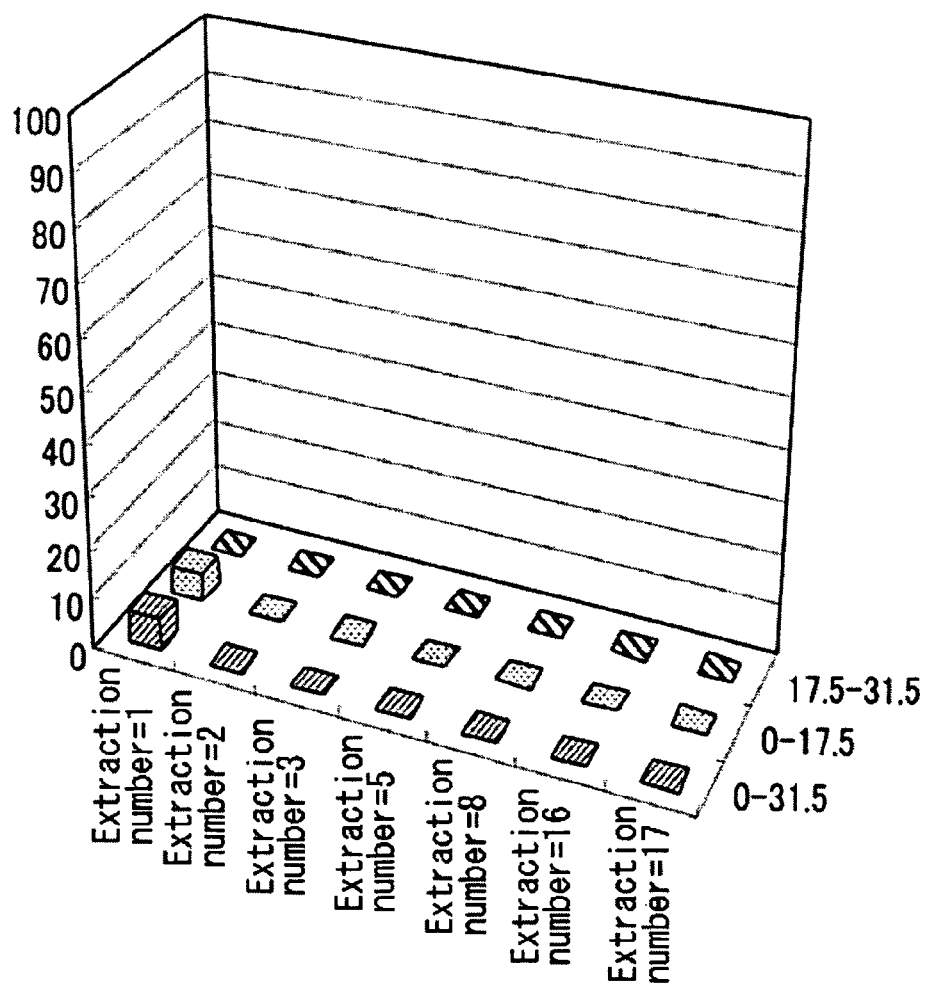

FIG. 21 depicts an example of a mathematical analytical result at the undifferentiation maintenance stage. As in FIG. 20, similar results as shown in the graphs have been obtained when a combination arbitrarily extracted under conditions to maintain undifferentiation. Comparing the results with the stage of differentiation induction, as in FIG. 20, the results are dramatically different. Based on this comparison, it is believed that it is possible to determine whether a cell is moving in the direction of cell differentiation induction, or instead maintaining an undifferentiated state.

Figure 22:
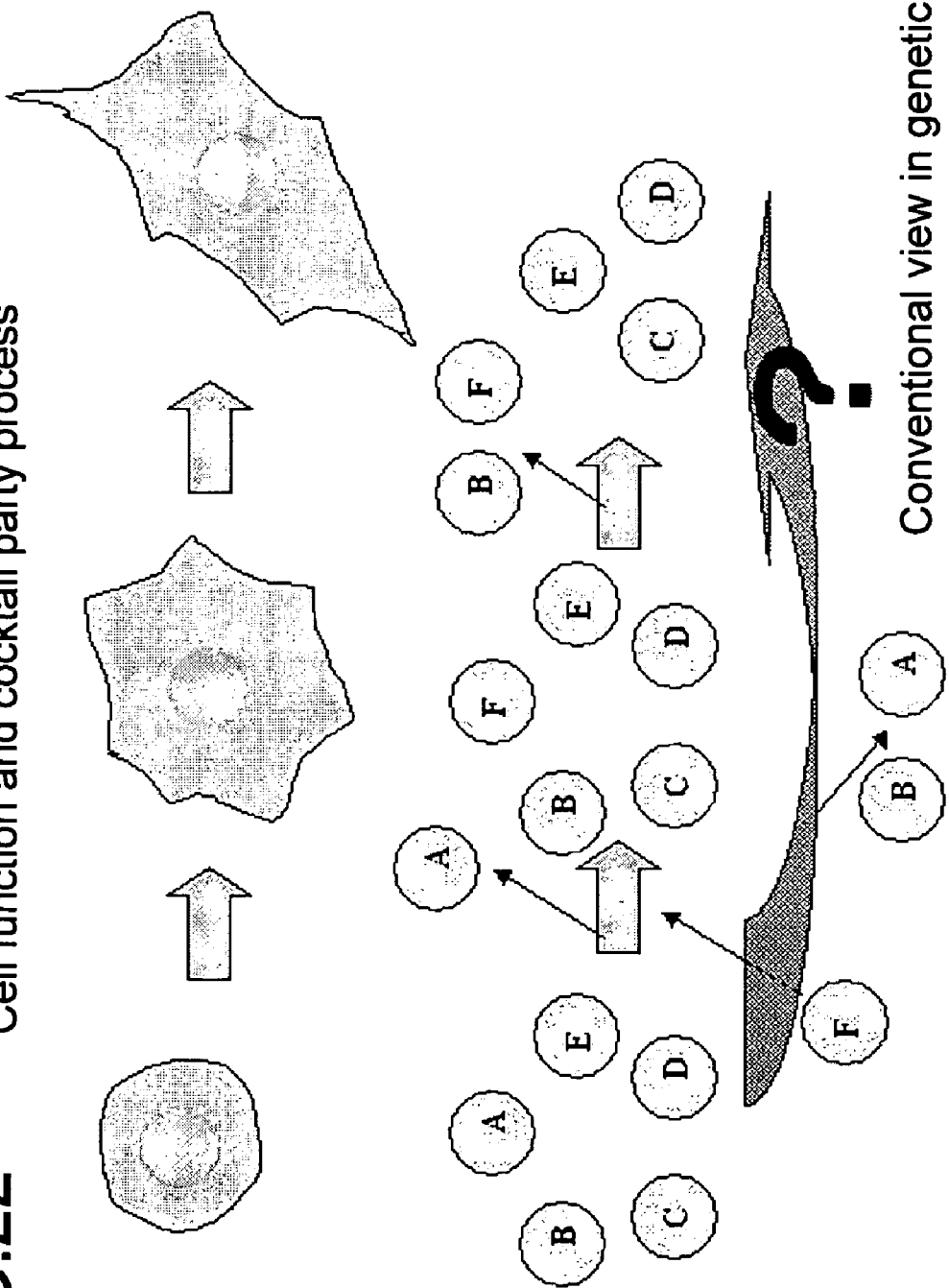

FIG. 22 schematically shows a cocktail party process.

Figure 23:
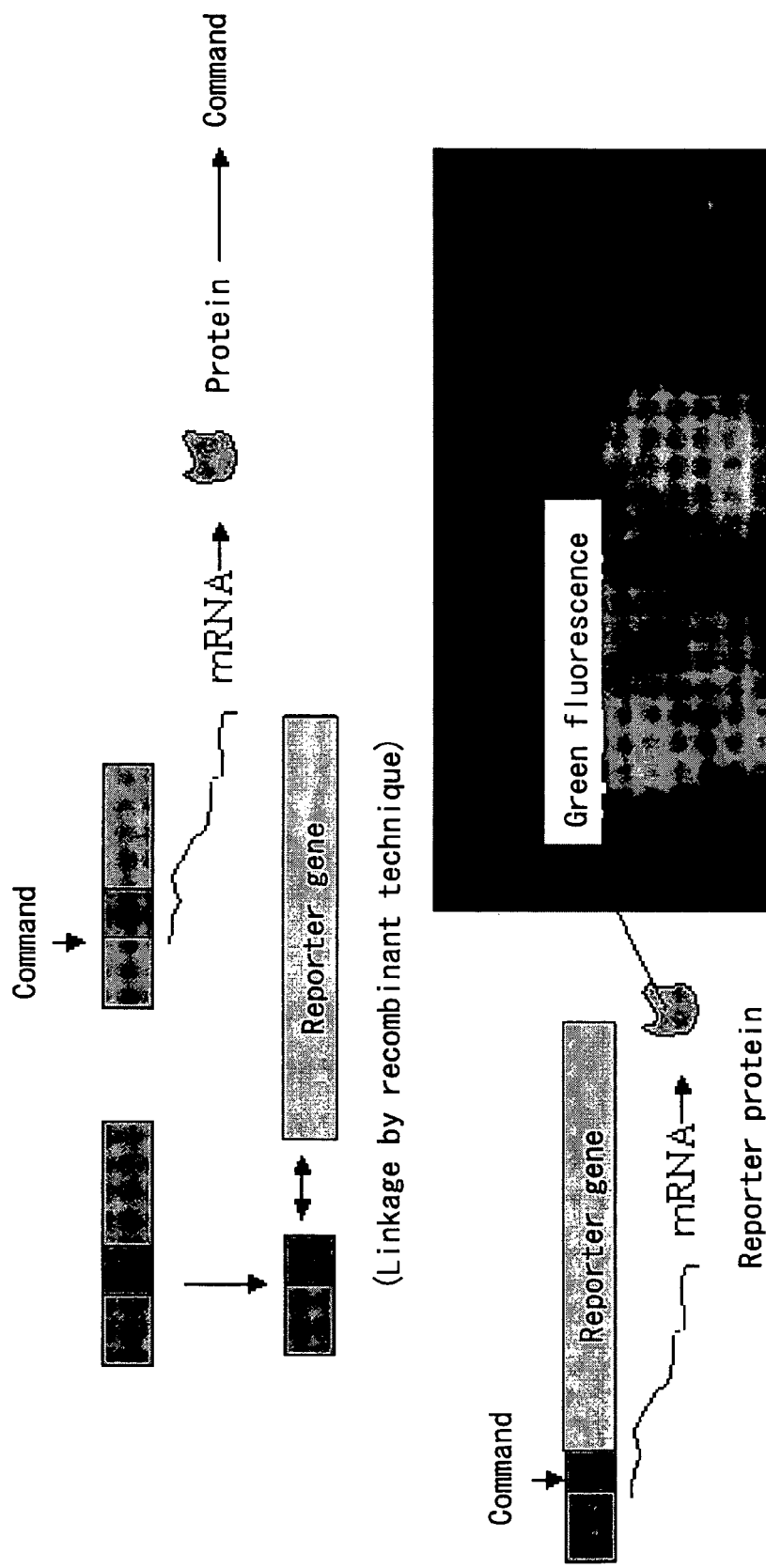

FIG. 23 shows an exemplary construct of a gene transcription switch reporter used in a transfection plasmid of the present invention.

FIG. 24 shows exemplary construction of a set of transcription factor reporters.

Figure 25:
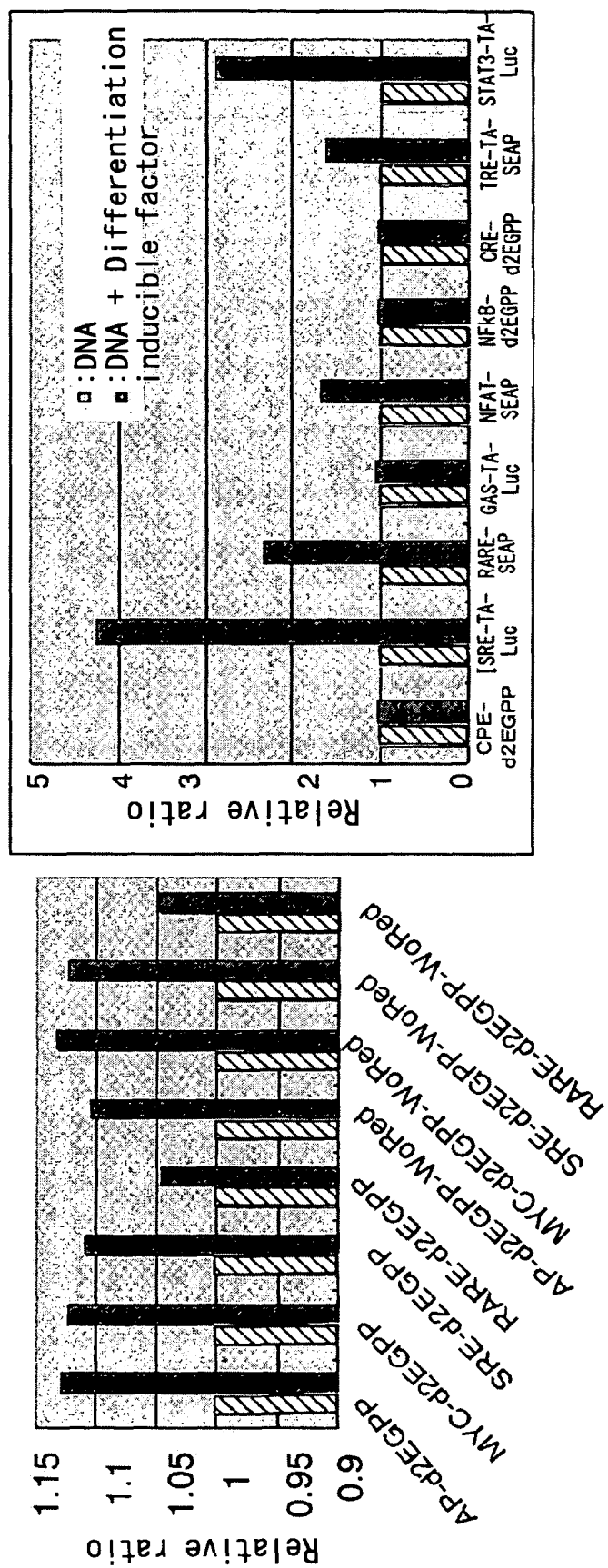

FIG. 25 shows the results of exemplary assays using transcription factor reporters.

Figure 26:
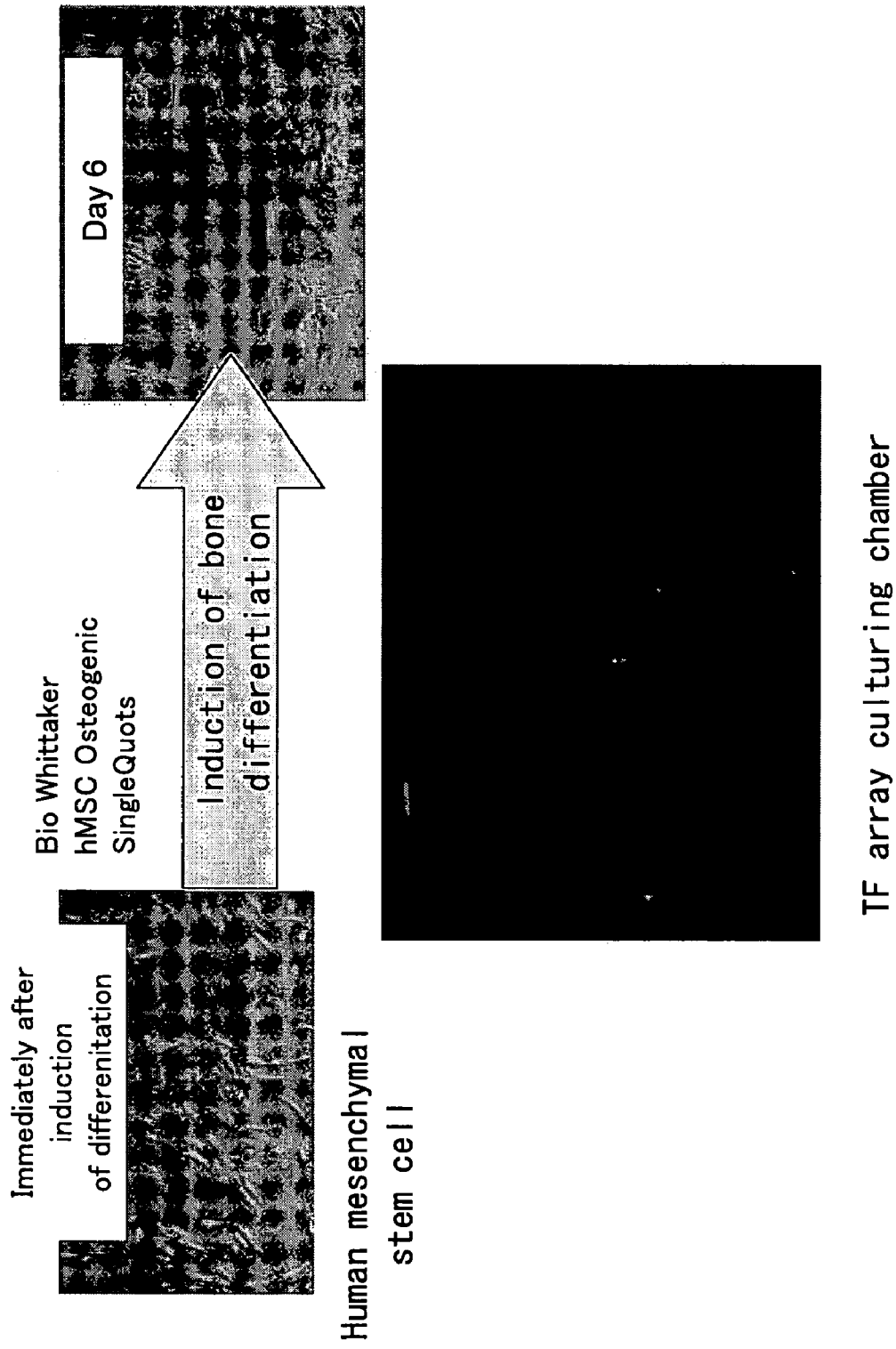

FIG. 26 shows an example of measurements of transcriptional activity in the bone differentiation process, taken in a time-series manner.

Figure 27:
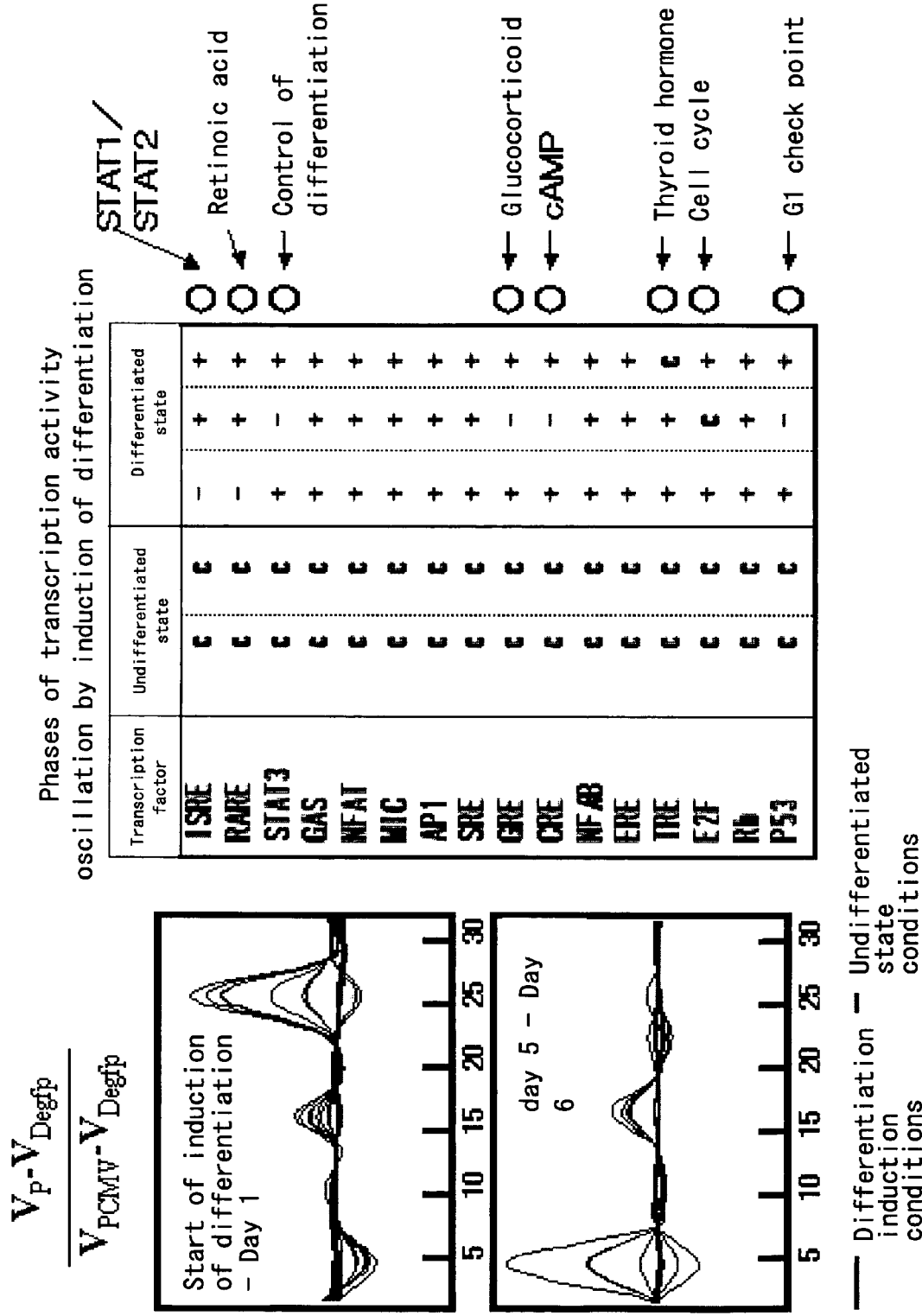

FIG. 27 shows an example of the oscillation phenomenon and phase analyses of transcriptional activity.

Figure 28:
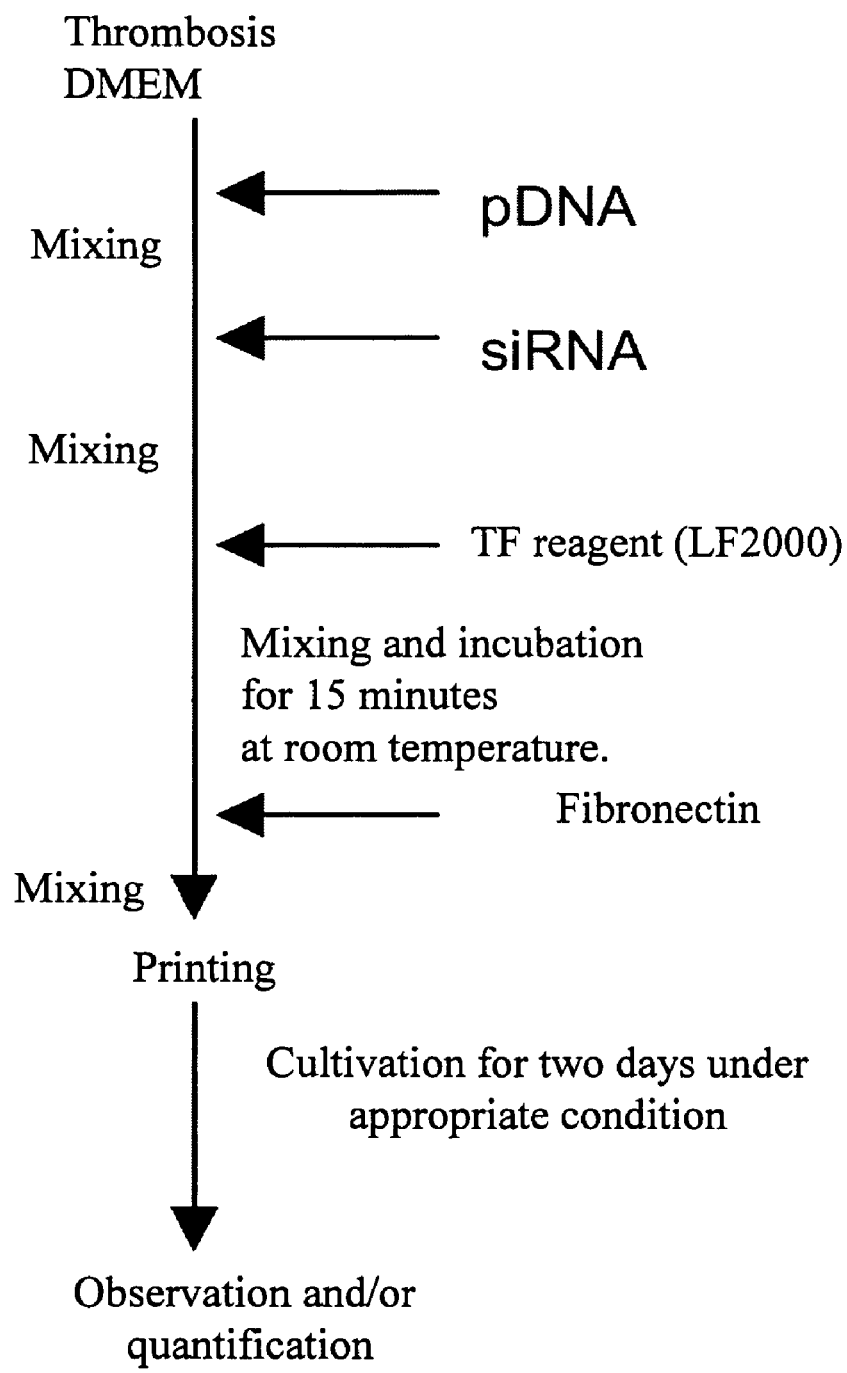

FIG. 28 shows a protocol of siRNA experiment.

Figure 29A:
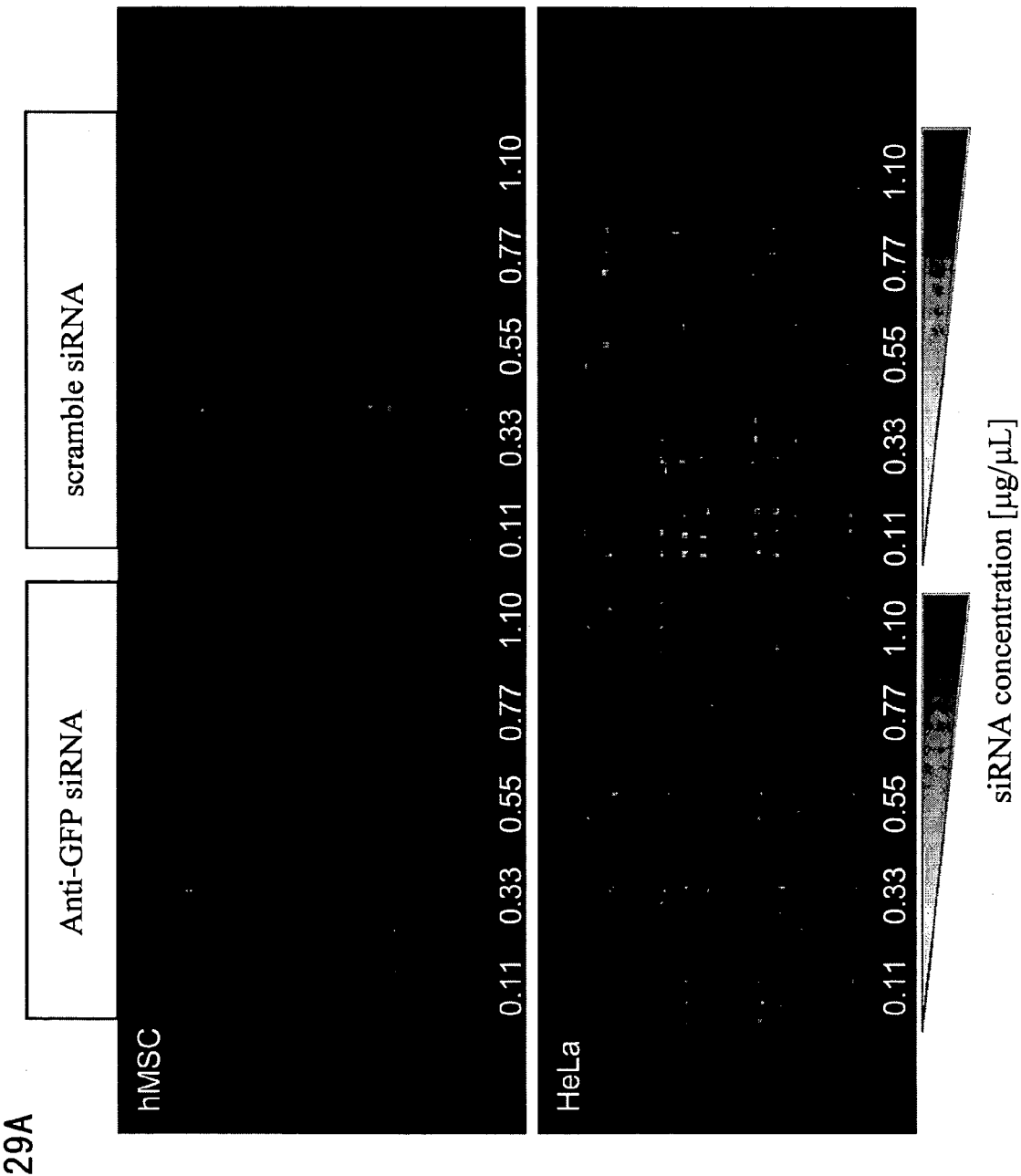

FIG. 29A shows the results of the siRNA experiments. The upper panel shows the results of hMSC, and the lower panel shows the results of HeLa cells. The numerals show the concentrations (μg/μL) of the siRNA used. The results obtained with the anti-GFP siRNA are shown on the left hand side, and the right hand side shows the results with the scramble siRNAs.

Figure 29B:
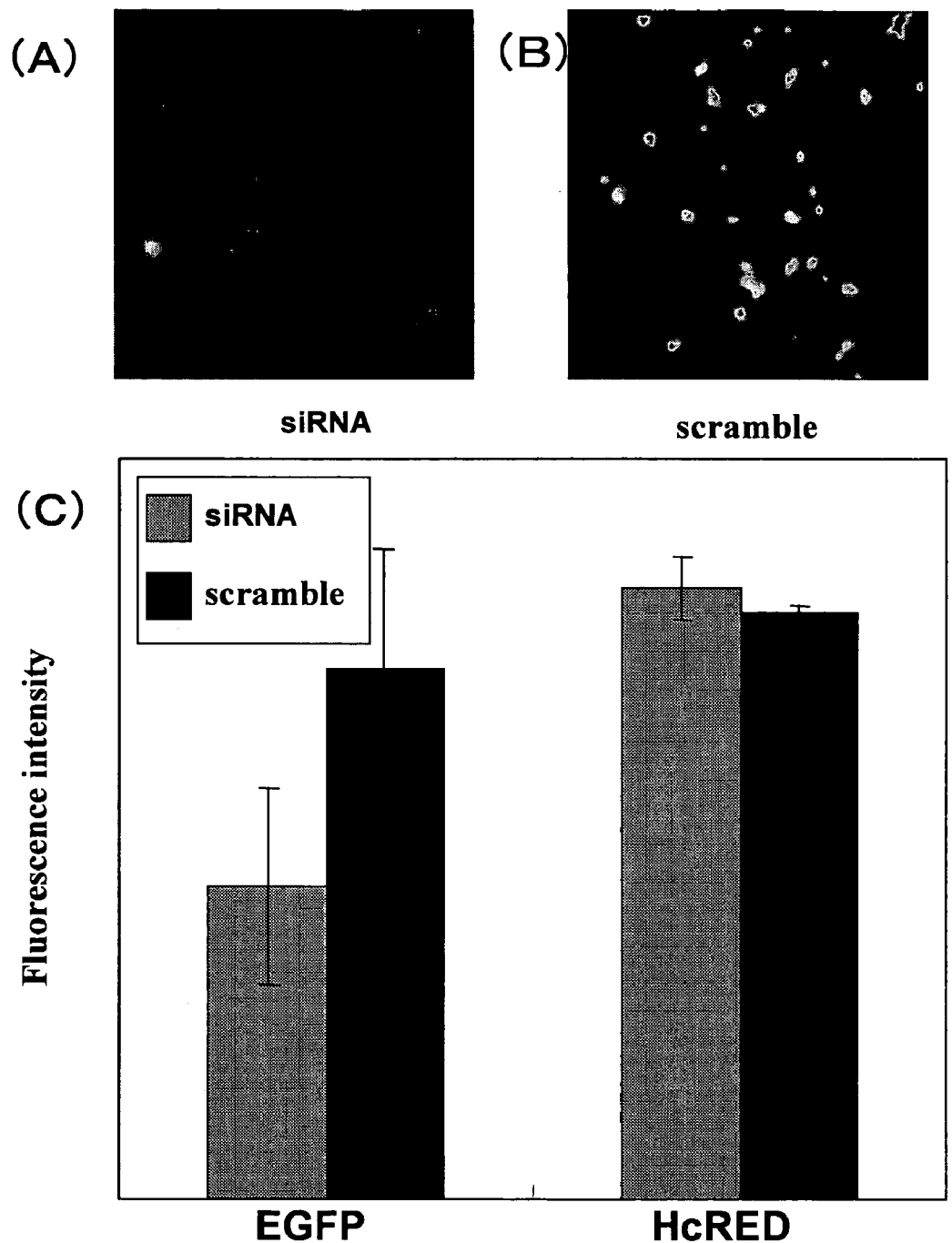

FIG. 29B shows the effects of siRNA when solid transfection (PC12) was conducted on a collagen IV coating. FIG. 29B(A) shows PC12 cells cotransfected with EGFP vector and anti-EGFP siRNA. As shown, it was observed that only HcRed was colored, and green signals derived from pEGFP-N1 were suppressed. On the other hand, FIG. 29B(B) shows an example using scramble siRNA. As shown, green fluorescence was observed and thus the effects observed in FIG. 29B(A) are due to the effects of RNAi. Figures showing the relative fluorescence intensities in FIGS. 29B(A) and 29B(B), are summarized in FIG. 29B(C). The y axis indicates relative intensity. It can be seen that effects induced by EGFP were almost completely suppressed.

Figure 29C:
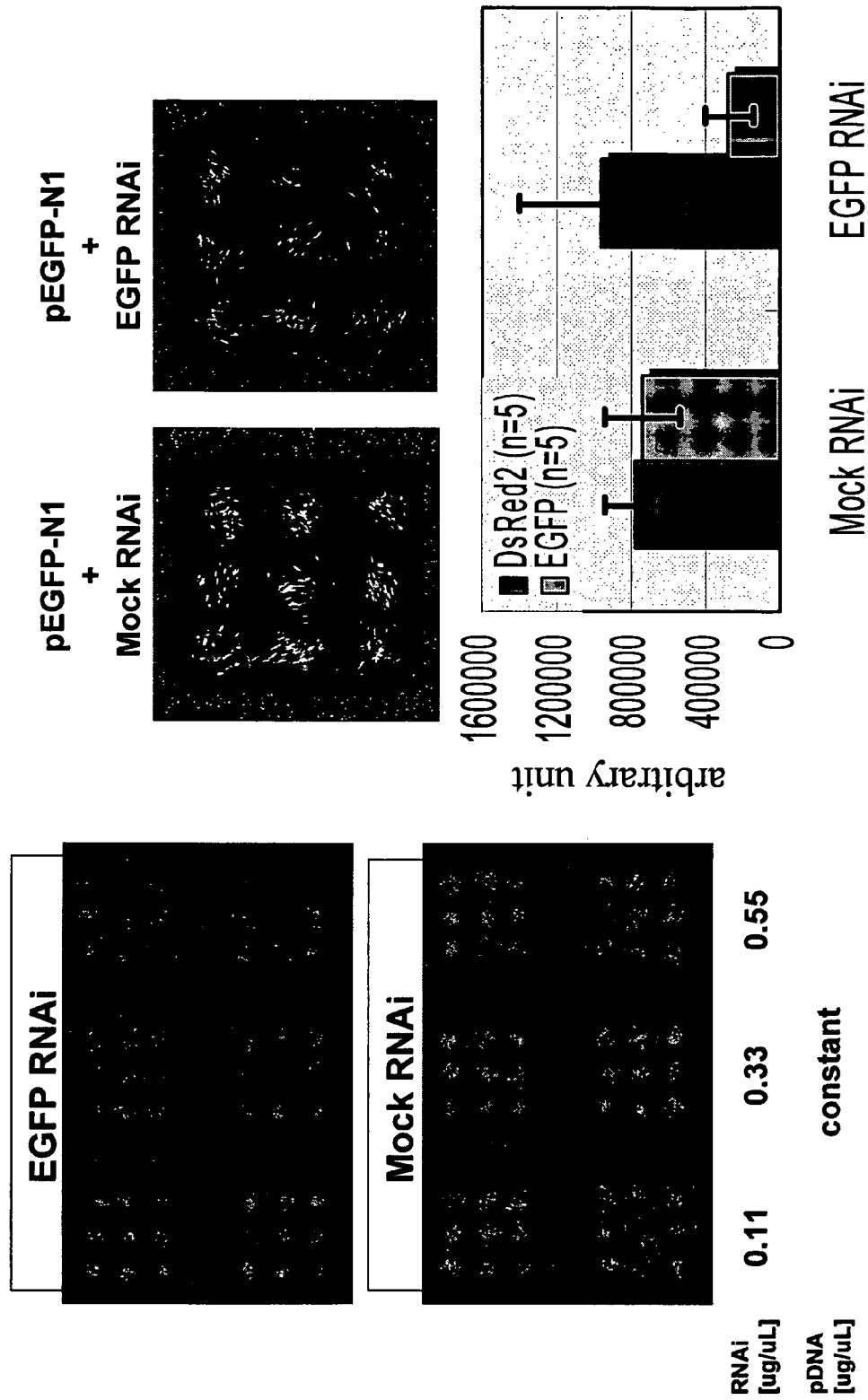

FIG. 29C depicts results and graphs summarizing the above. The left-hand panel is a photograph comparing EGFP RNAi and scramble (mock) RNAi when changing the ratio of RNAi and pRNA. As shown, EGFP RNAi showed inhibitory effects, whereas scramble RNAi did not exert such effects. This is shown in the right-hand panel, together with DsRed2. Experimental conditions were in accordance with those described herein. As a result, red (DsRed derived signal) and green (EGFP derived signal) were found to be in proportion with the effect of RNAi.

Figure 29D:
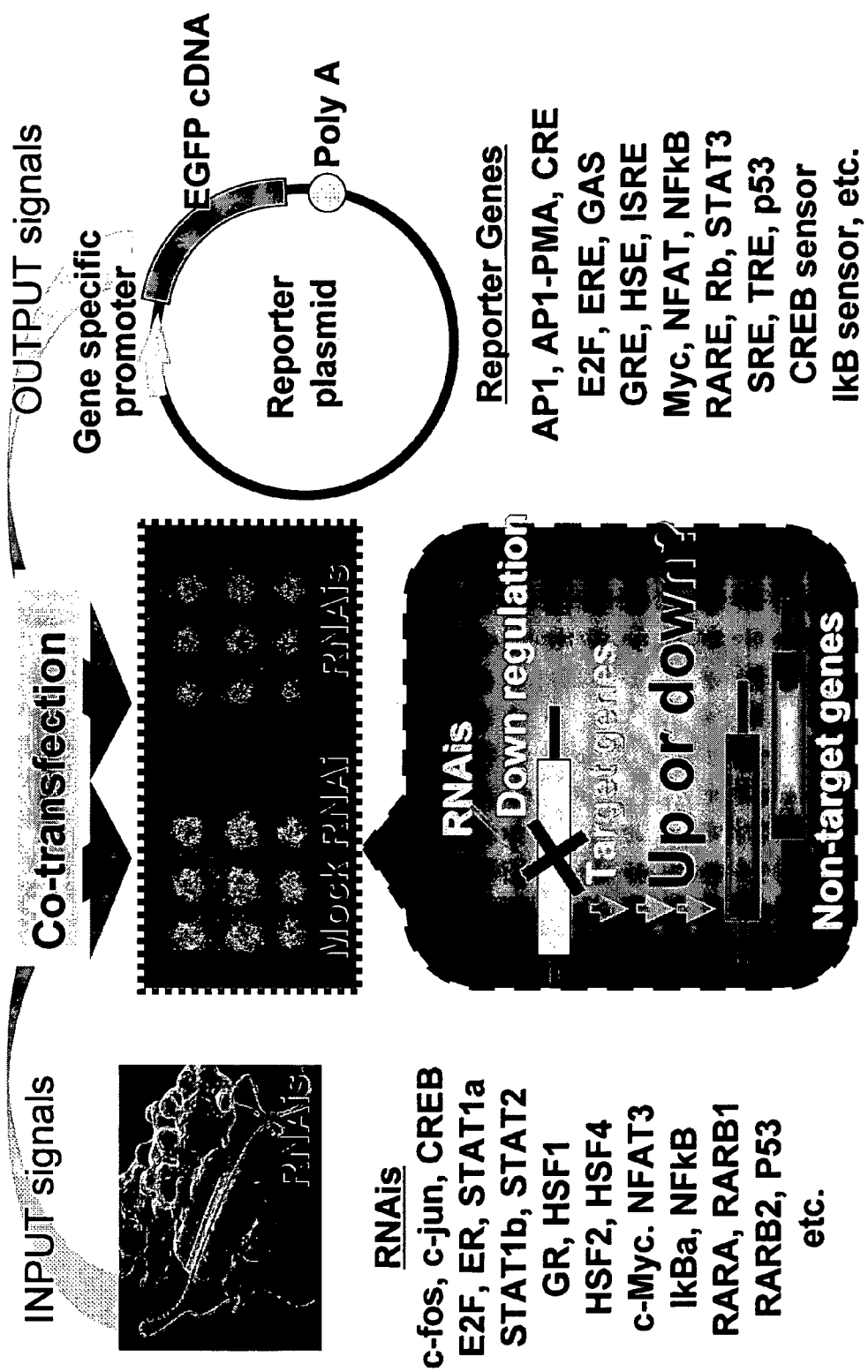

FIG. 29D depicts an exemplary chip used in the RNAi reporter. When using RNAi as input signals and cointroducing a gene product capable of transmitting signals, such as EGF and the like, together with a nucleic acid encoding a gene of interest (including a promoter), observation of such signal transmission as output allows extraction of cell information.

Figure 29E:
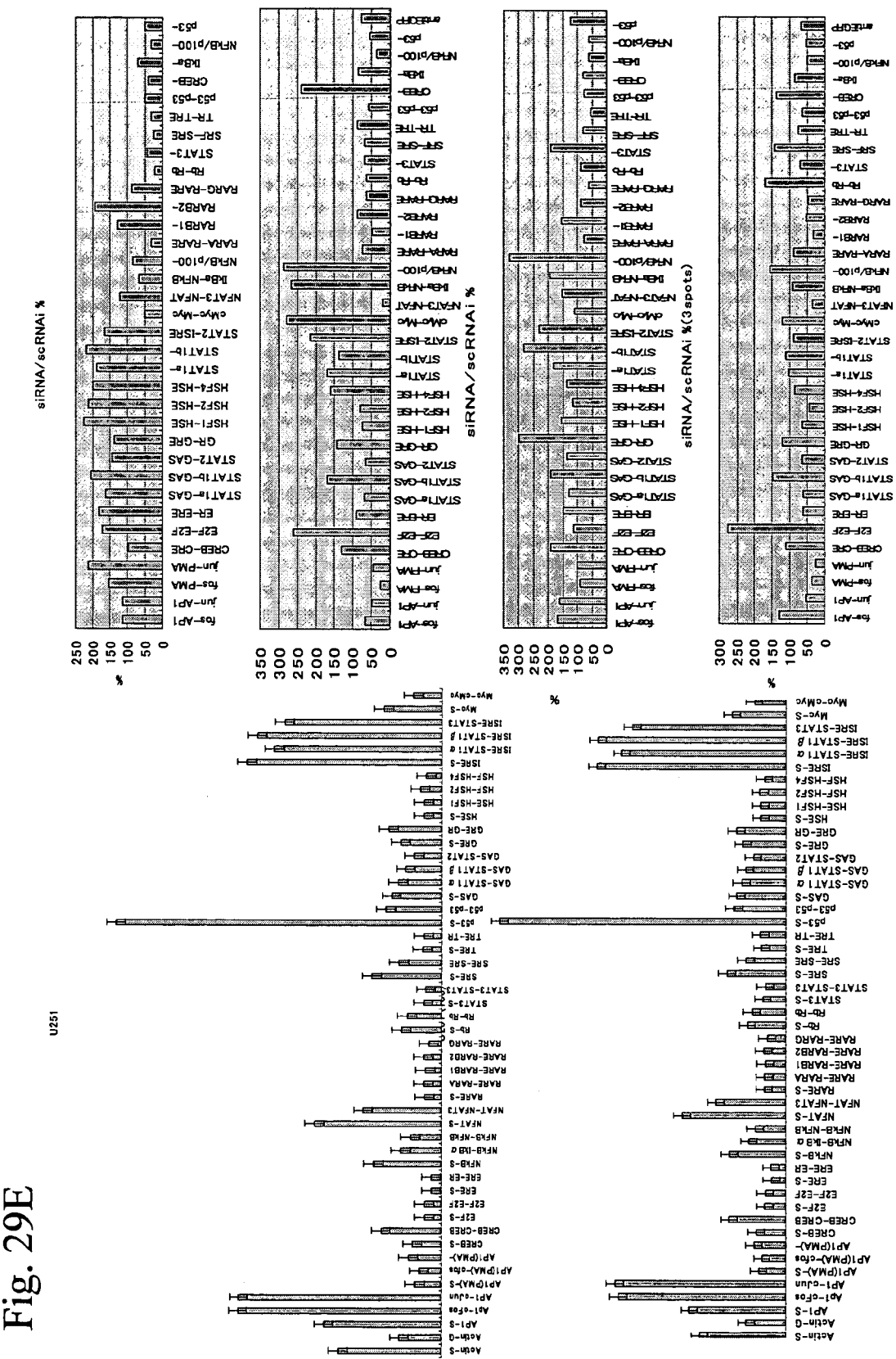

FIG. 29E shows an exemplary experiment using a variety of reporters (pAP1-EGFP, pAP1 (PMA)-EGFP, pCRE-EGFP, pE2F-EGFP, pERE-EGFP, pGAS-EGFP, pGRE-EGFP, pHSE-EGFP, pISRE-EGFP, pMyc-EGFP, pNFAT-EGFP, pNFkB-EGFP, pRARE-EGFP, pRb-EGFP, pSTST3-EGFP, pSRE-EGFP, pTRE-EGFP, pp53-EGFP, pCREB-sensor, pIkB-sensor, pp53-sensor, pCasapase3-sensor); the is-element sequence was purchased from Clontech using a plasmid vector produced by recombining a fluorescence protein gene).

Figure 30:
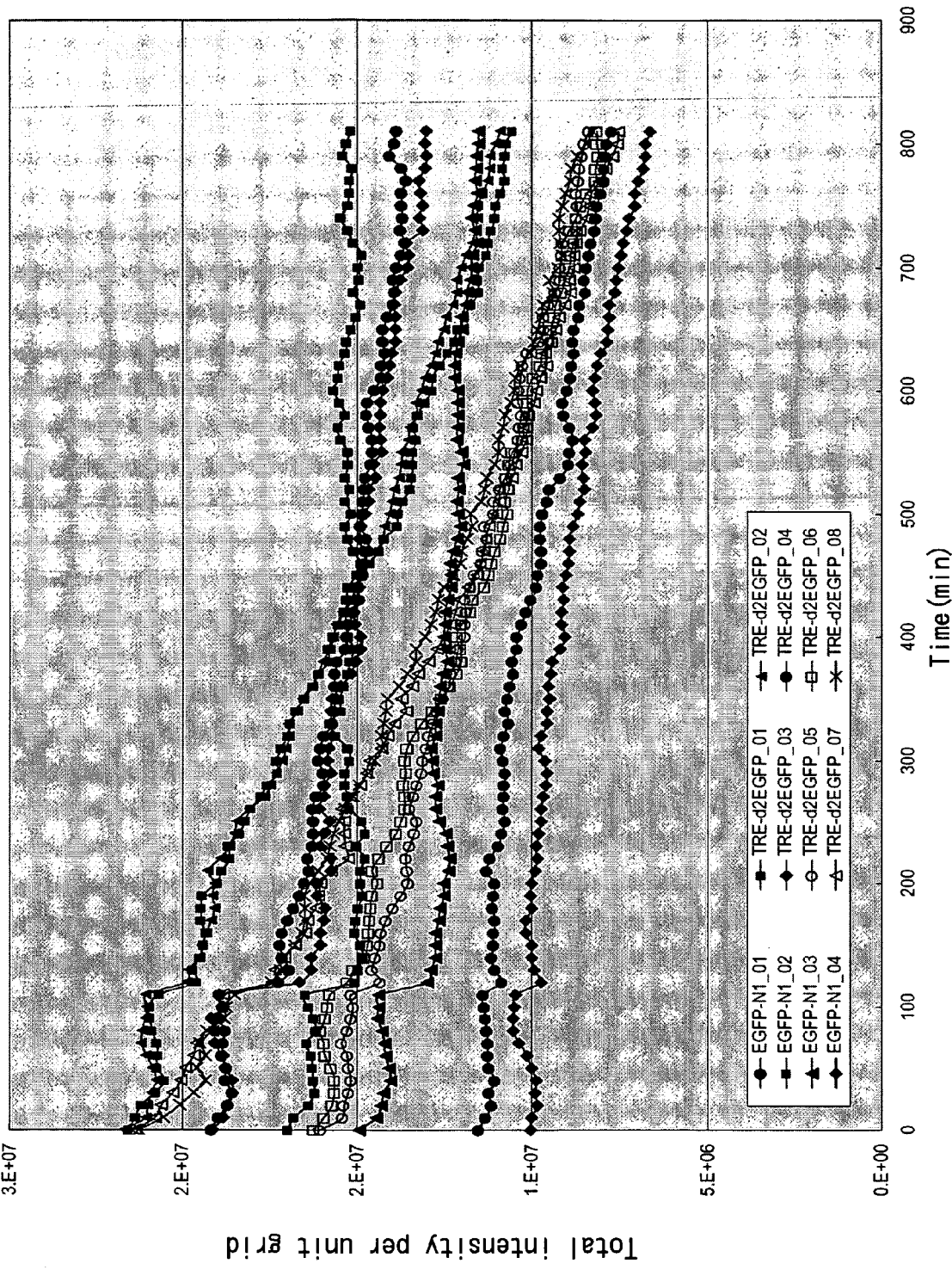

FIG. 30 shows changes in the profile when using tetracycline dependent promoters.

Figure 31:
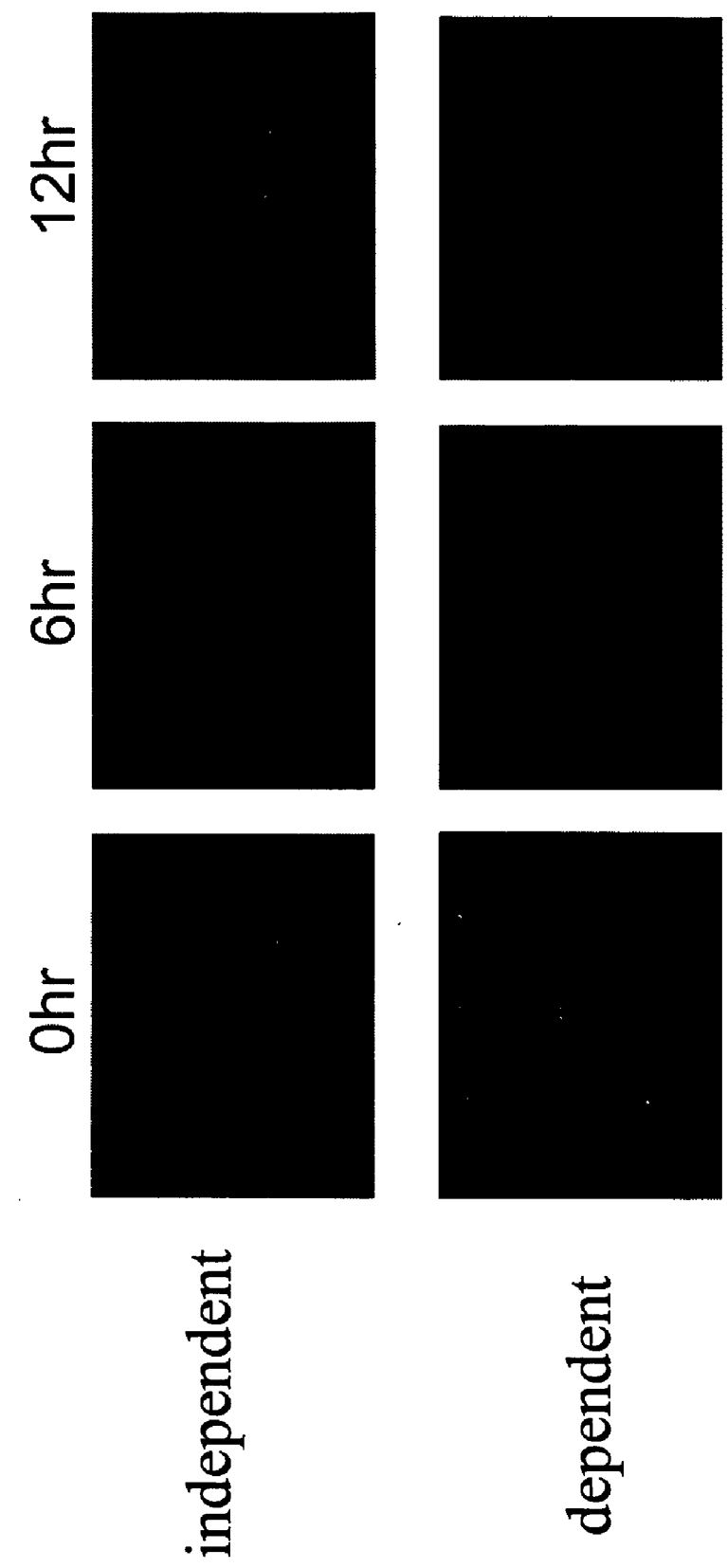

FIG. 31 shows expression when using tetracycline dependent promoters and tetracycline independent promoters.

FIG. 31B shows an exemplary result of analysis using a transfected microarray with respect to the effects of tyrosine kinase RNAi on neurons.

Figure 31C:
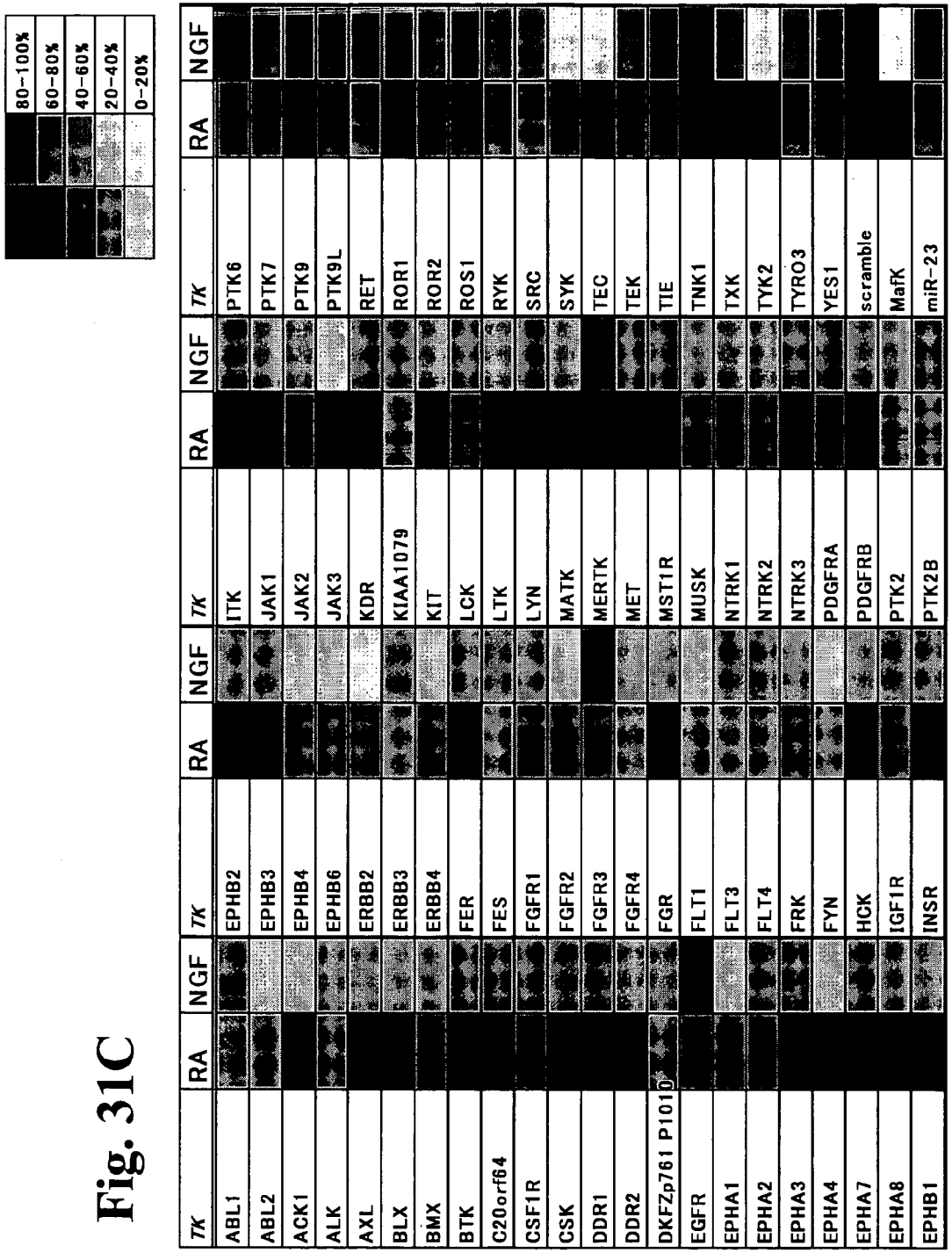

FIG. 31C depicts responses to retinoic acid (RA) and nerve growth factor (NGF) by a variety of tyrosine kinases. Inhibition percent by siRNA is shown.

Figure 31D:
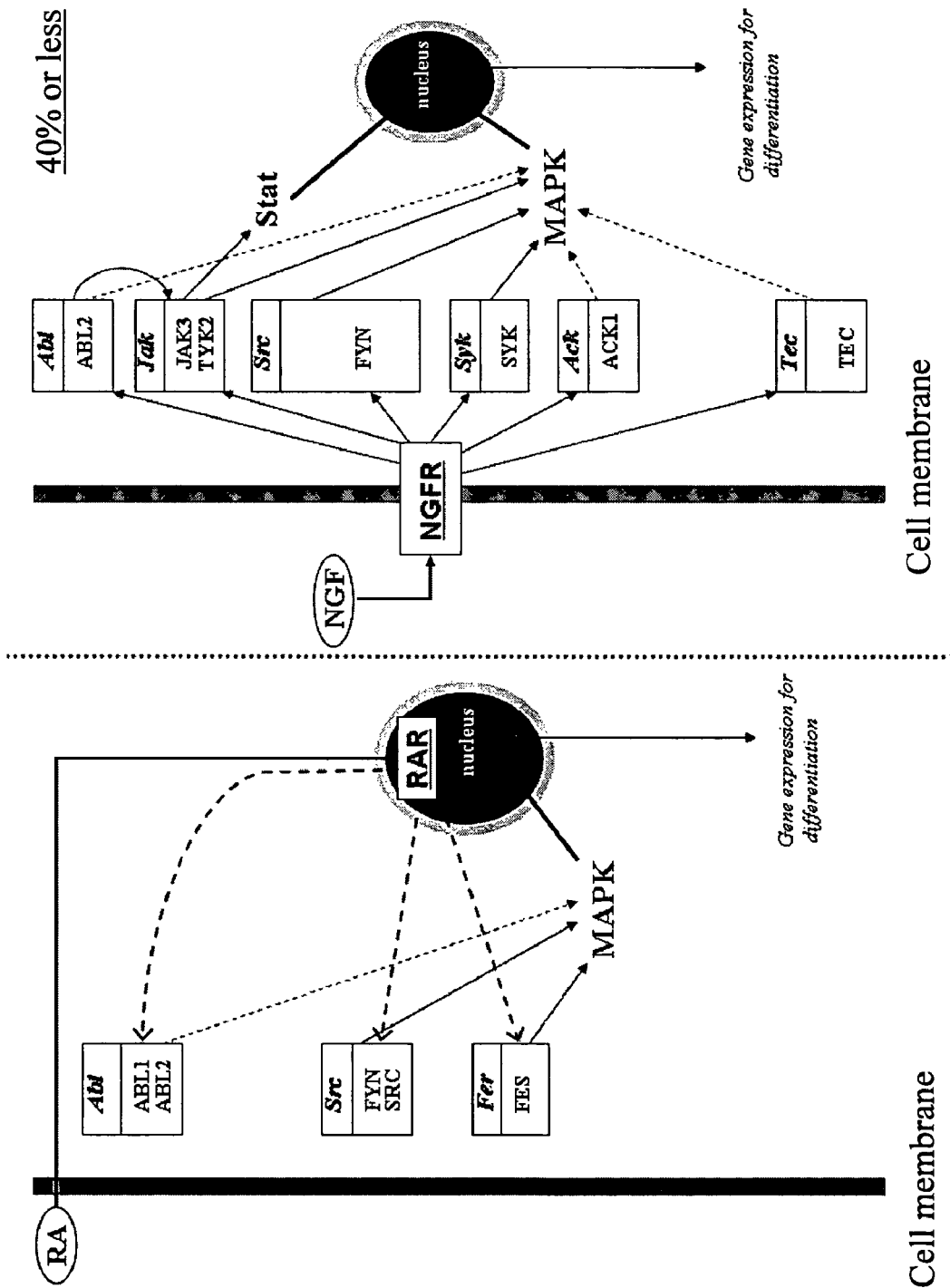

FIG. 31D depicts an example of a signaling pathway obtained as a result of an analysis.

Figure 31E:
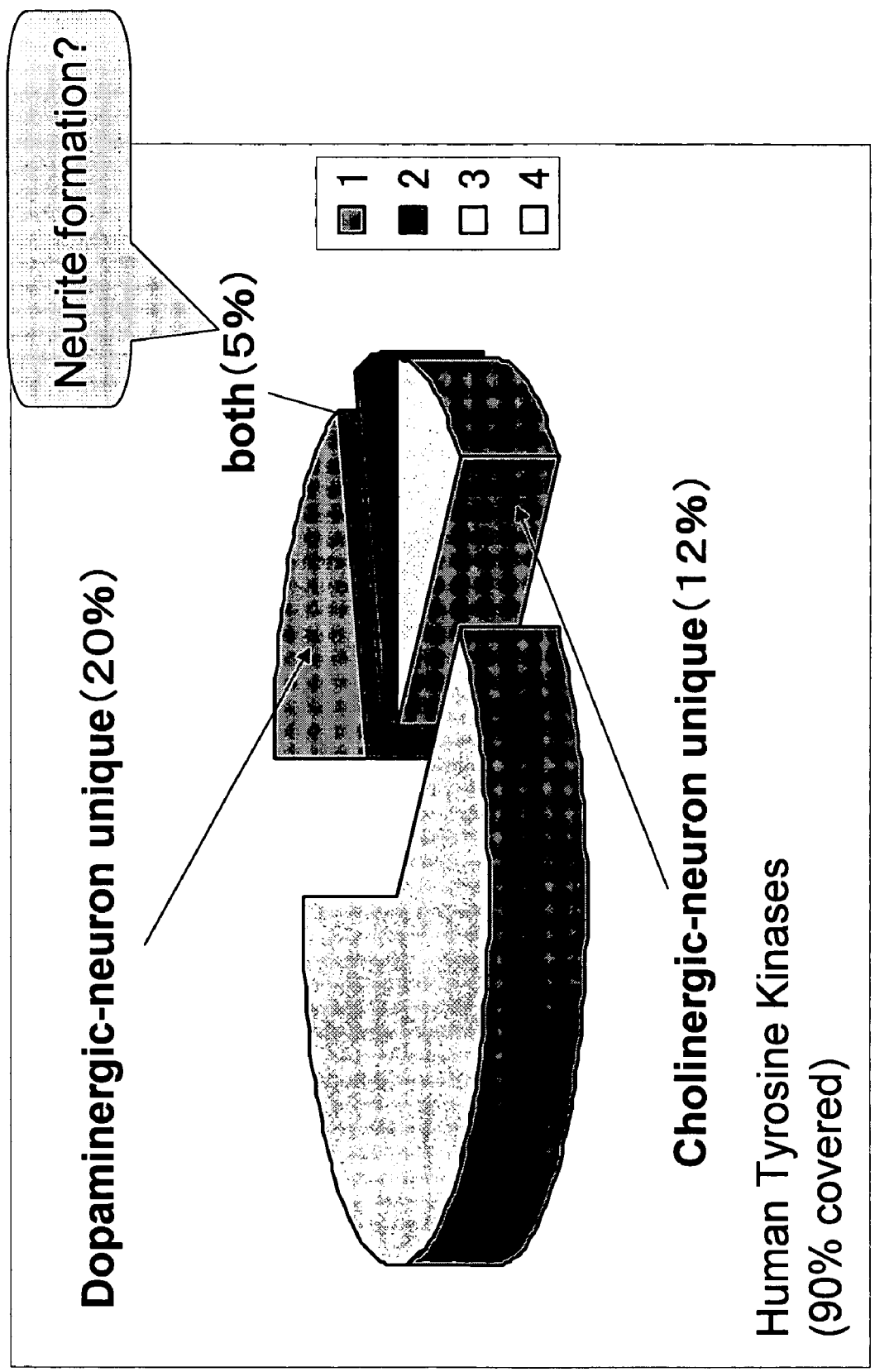

FIG. 31E shows the results obtained by the above-mentioned analysis. It shows a general analysis of the tyrosine kinases responsible for human neuron differentiation. Classification is conducted by determining whether it is dopaminergic neuron, cholinergic neuron, or both, or neither. It can be concluded by the analysis that there is high possibility that those tyrosine kinases relating to both types of neuron are involved in neuron projection formation.

Figure 31F:
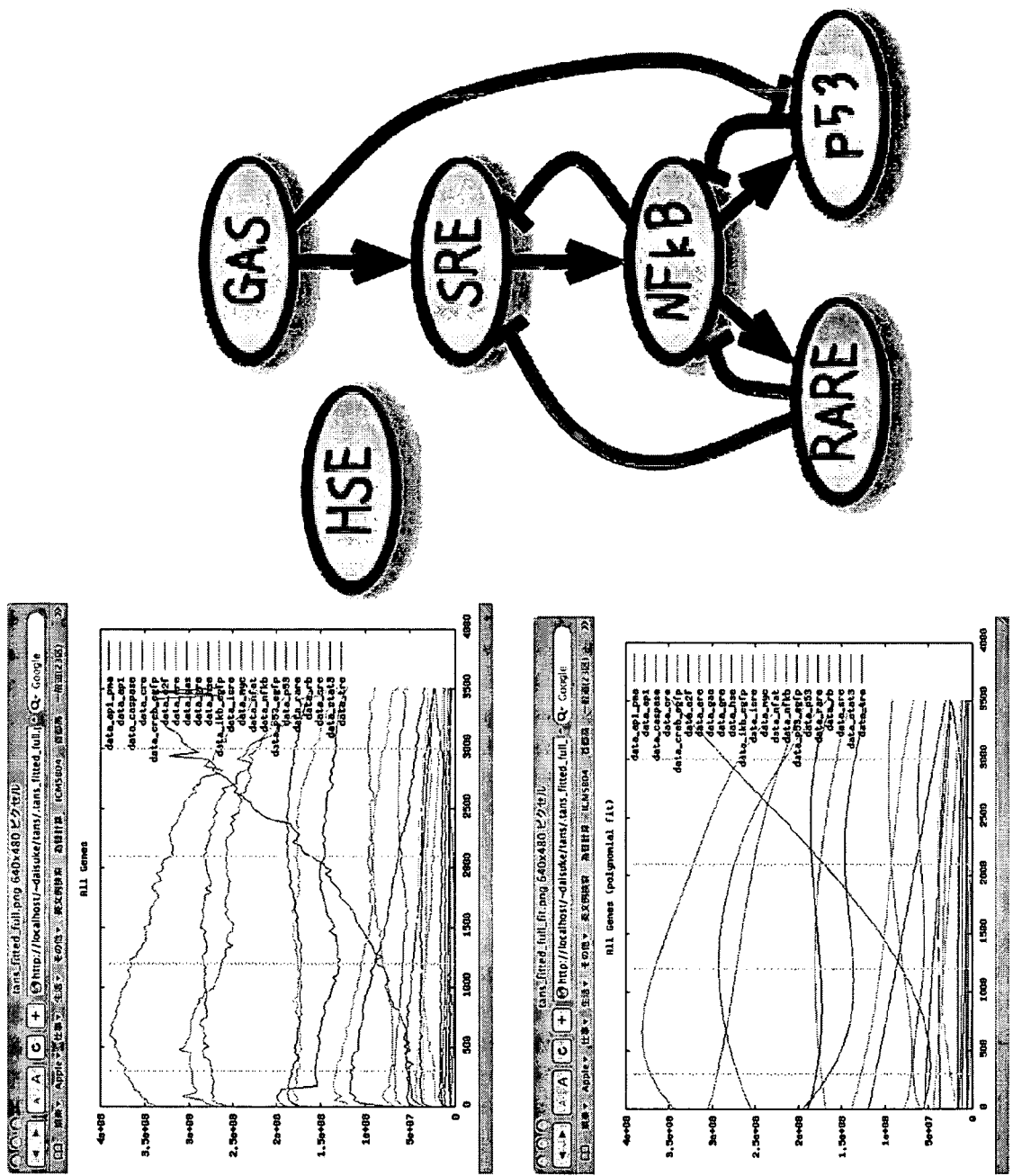

FIG. 31F depicts an example of real-time monitoring of transcription regulation of apoptosis in a HeLa cell. The left handed panel shows the result over time, and the right handed panel shows the result of a signaling pathway based on the analysis thereof.

FIG. 32 depicts an example of a system configuration.

Figure 33A:
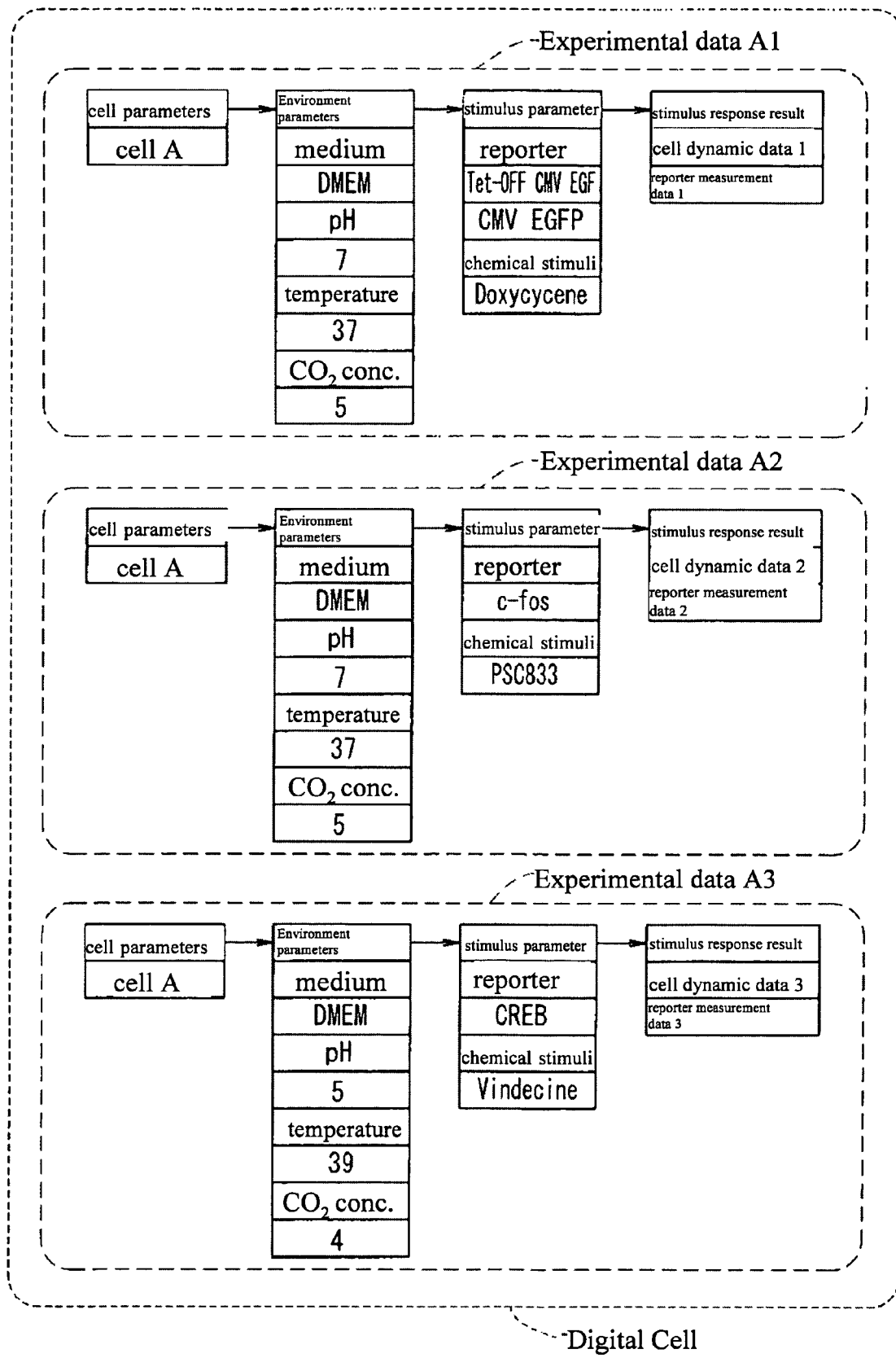

FIG. 33A depicts an example of a digital cell according to the present invention.

Figure 33B:
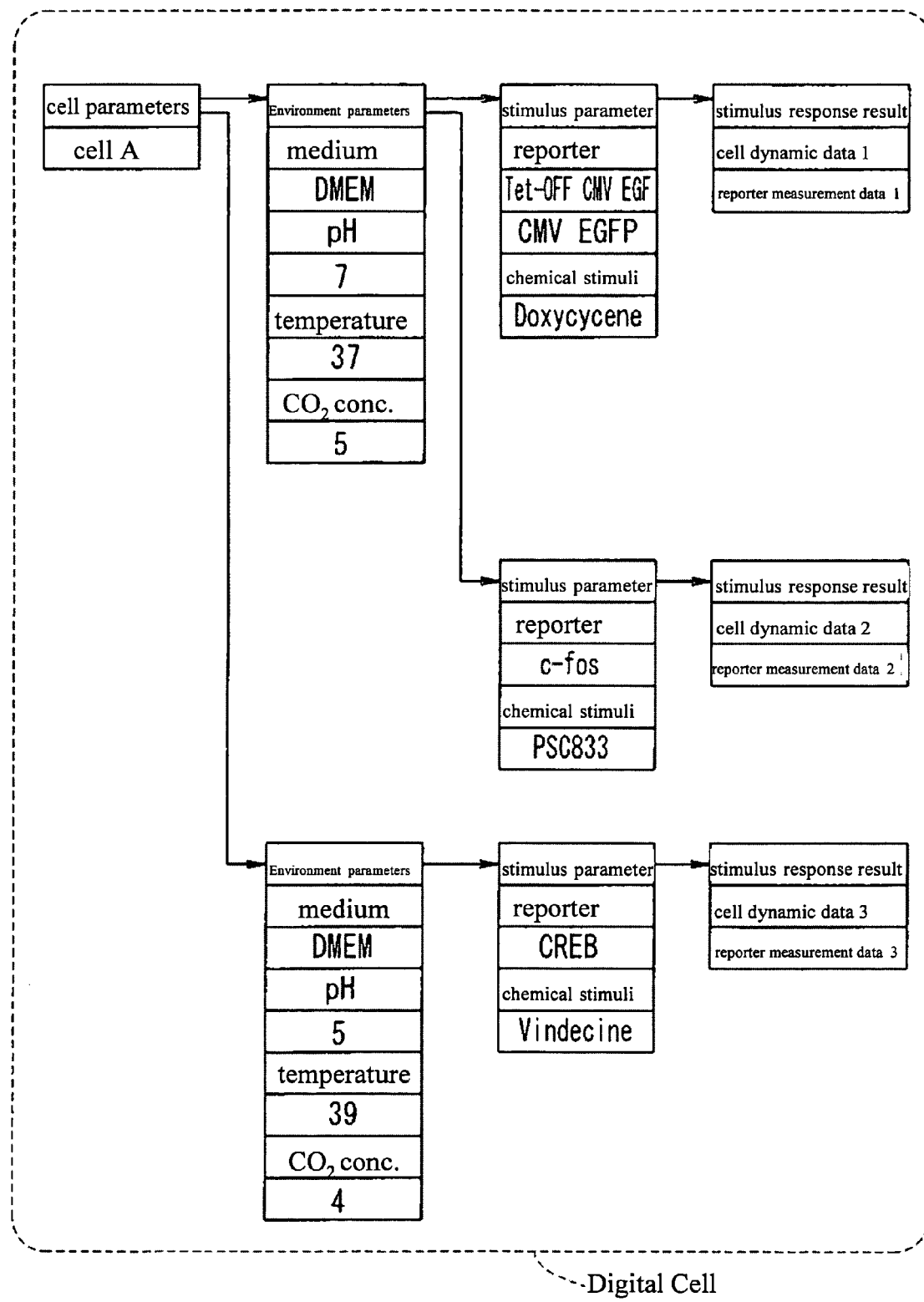

FIG. 33B depicts another example of a digital cell according to the present invention.

Figure 34:
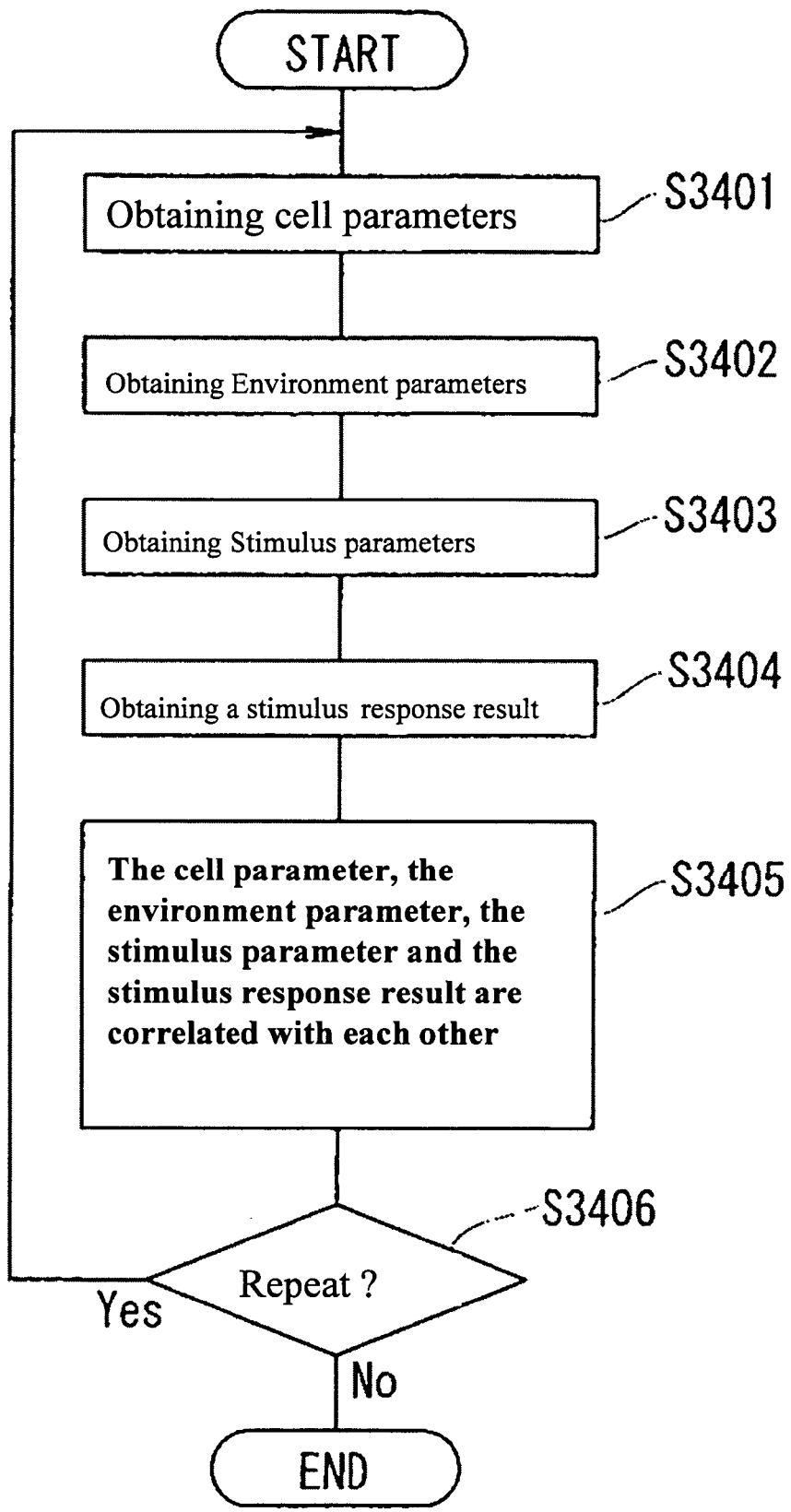

FIG. 34 depicts an example of a method for producing a digital cell according to the present invention.

Figure 35:
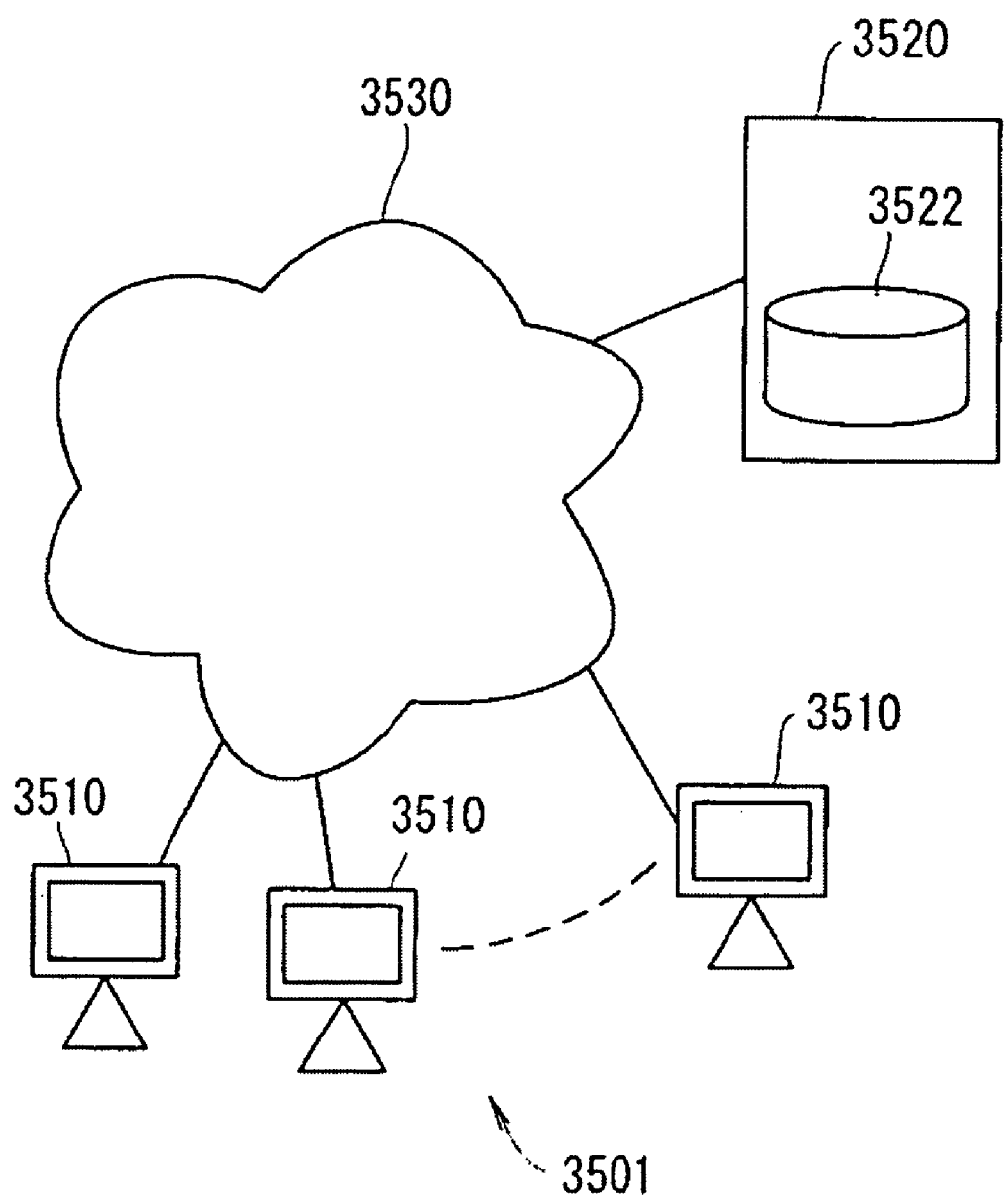

FIG. 35 depicts an example of a configuration of computer system 3501 which provides a service reproducing an experimental result obtained using an actual cell using the digital cell.

Figure 36:
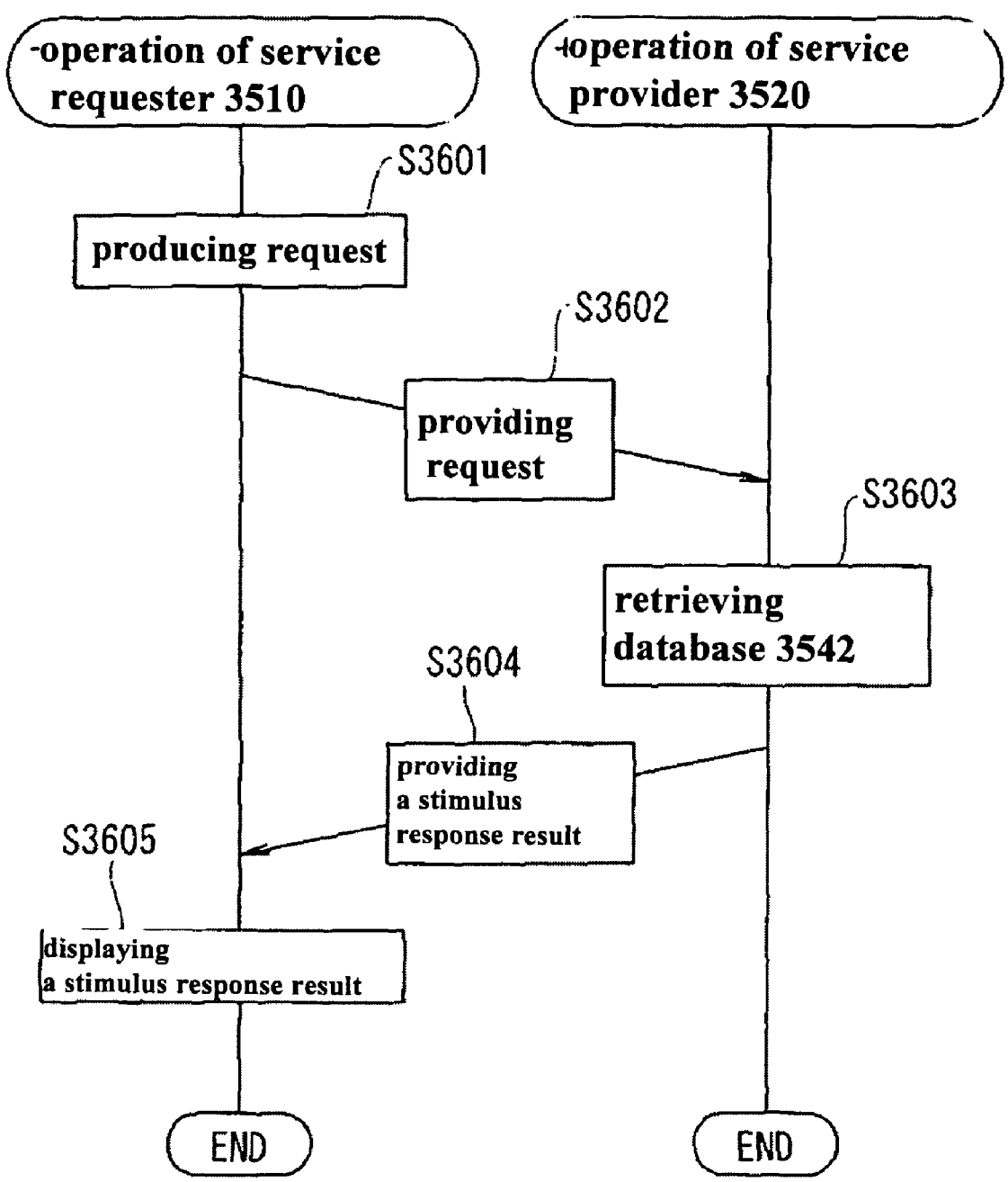

FIG. 36 depicts an example of procedures of a process which provides a service reproducing an experimental result obtained using an actual cell using the digital cell.

Figure 37:
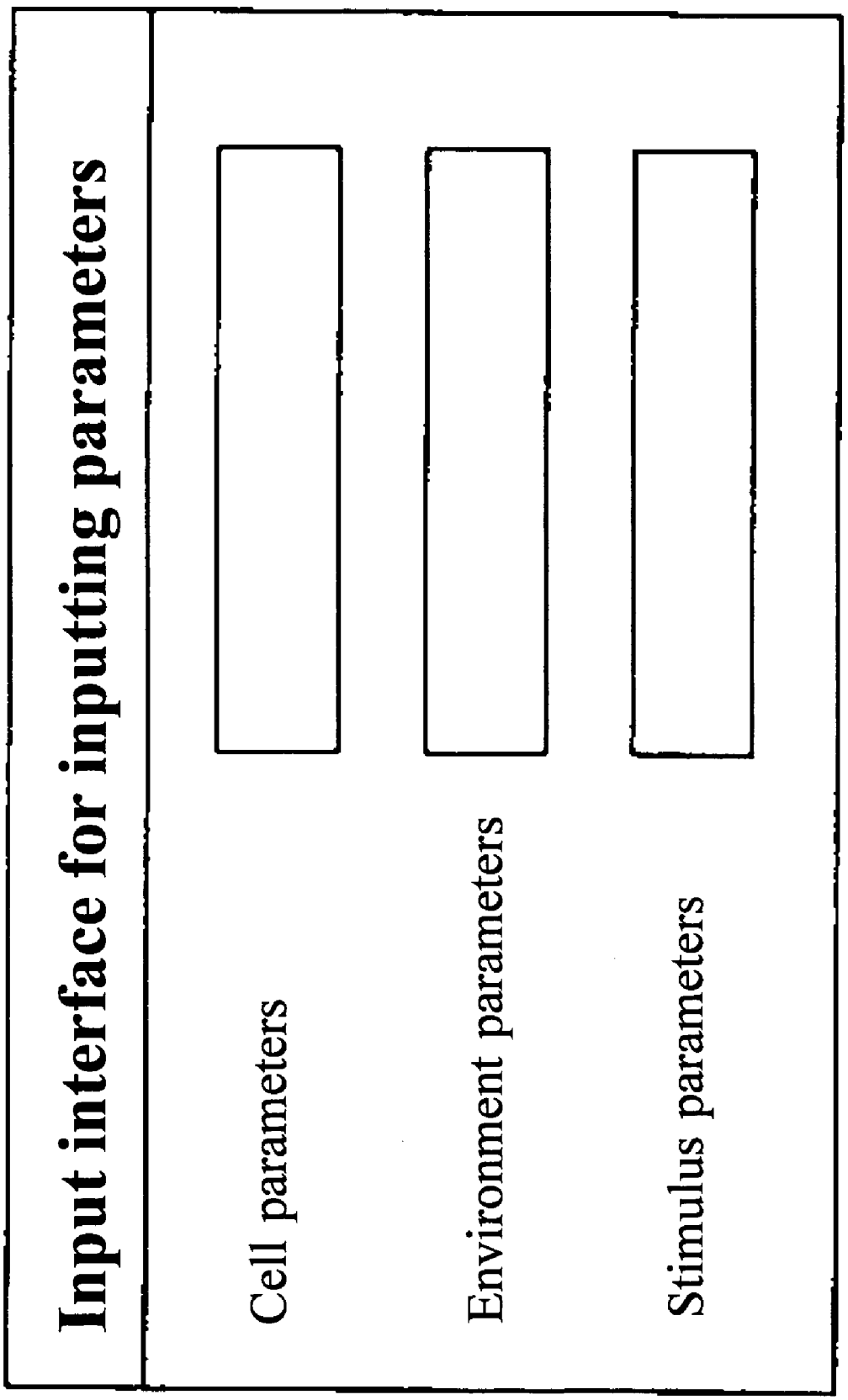

FIG. 37 depicts an example of input interface for inputting cell parameters, environment parameters and stimulus parameters into service requester 3510.

Figure 38:
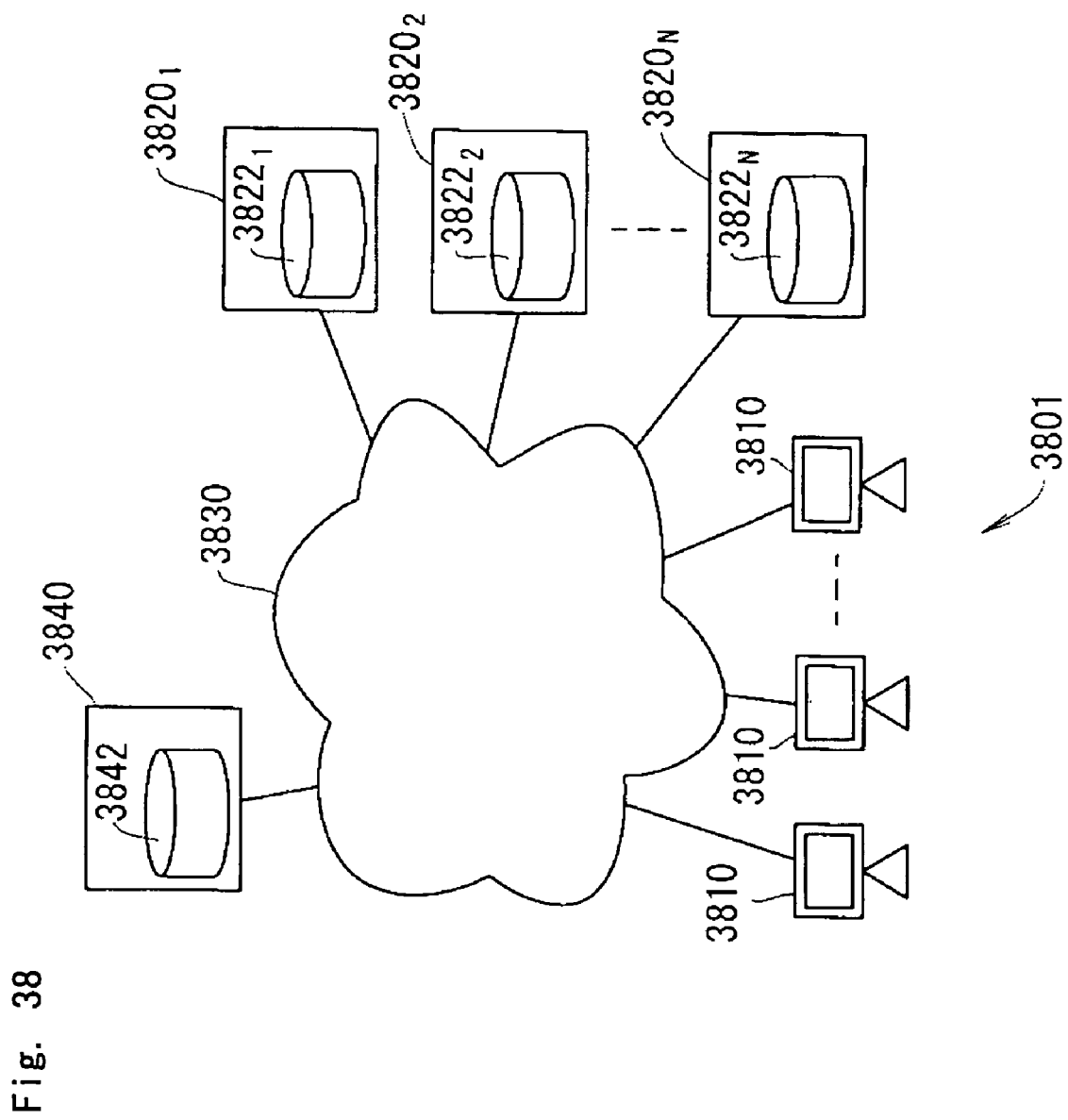

FIG. 38 depicts an example of configurations of computer system 3801 for providing a service of reproducing an experimental result against an actual cell using the digital cell.

Figure 39:
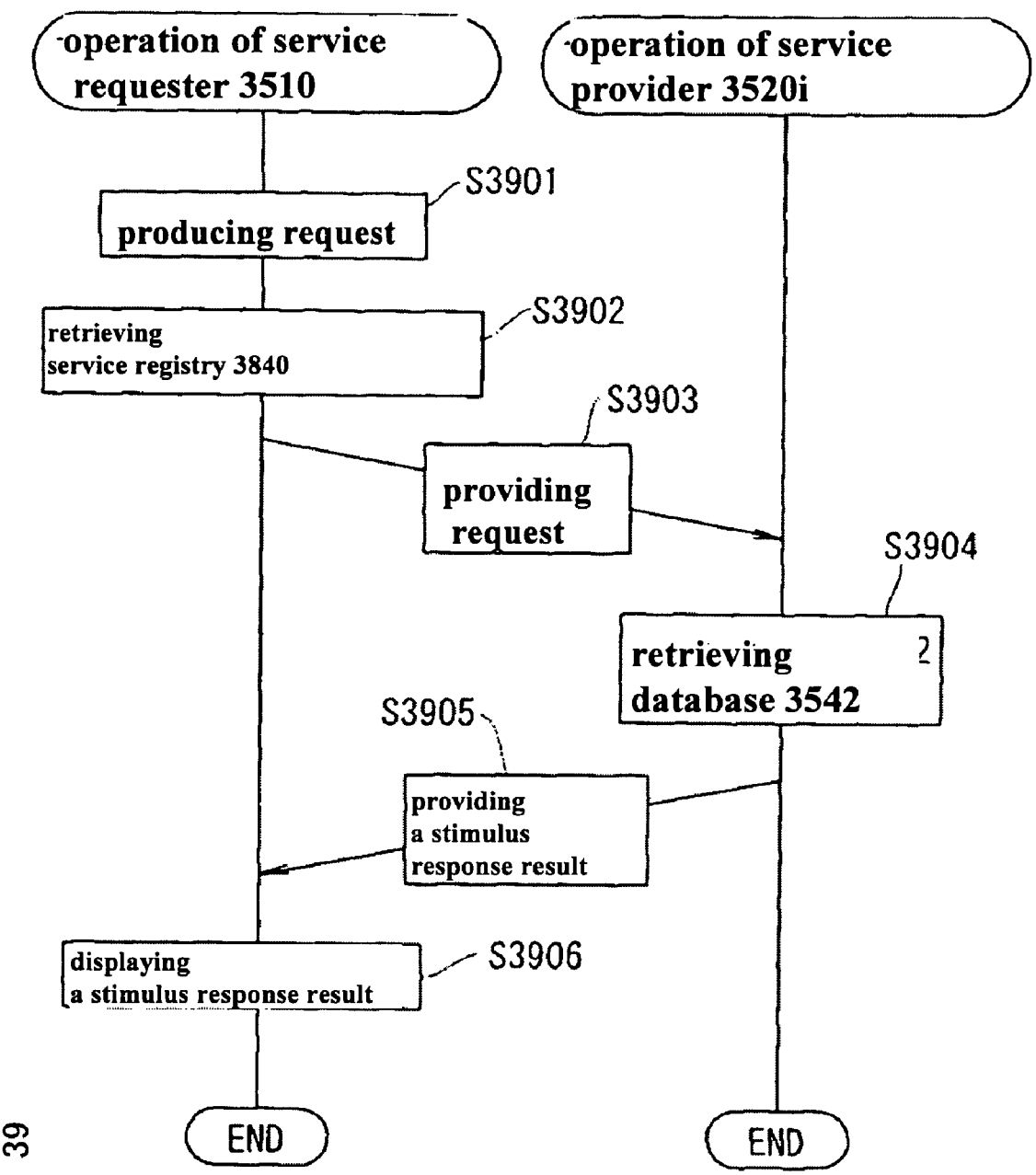

FIG. 39 depicts an example of procedures of a process for providing a service of reproducing an experimental result against an actual cell using the digital cell.

DESCRIPTION OF SEQUENCE LISTING

SEQ ID NO.: 1: a nucleic acid sequence encoding fibronectin (human)

SEQ ID NO.: 2: an amino acid sequence of fibronectin (human)

SEQ ID NO.: 3: a nucleic acid sequence encoding vitronectin (mouse)

SEQ ID NO.: 4: an amino acid sequence of vitronectin (mouse)

SEQ ID NO.: 5: a nucleic acid sequence encoding laminin (mouse α-chain)

SEQ ID NO.: 6: an amino acid sequence of laminin (mouse α-chain)

SEQ ID NO.: 7: a nucleic acid sequence encoding laminin (mouse β-chain)

SEQ ID NO.: 8: an amino acid sequence of laminin (mouse β-chain)

SEQ ID NO.: 9: a nucleic acid sequence encoding laminin (mouse γ-chain)

SEQ ID NO.: 10: an amino acid sequence of laminin (mouse γ-chain)

SEQ ID NO.: 11: an amino acid sequence of fibronectin (bovine)

SEQ ID NO.: 12: siRNA used in the Examples

SEQ ID NO.: 13: mouse olfactory receptor 17 (heptanal-sensitive) nucleic acid (Genbank Accession No. AF106007)

SEQ ID NO.: 14: amino acid sequence of the protein encoded by the nucleic acid set forth in SEQ ID NO.: 13

SEQ ID NO: 15: nucleic acid encoding the murine olfactory receptor S1 (mc9/bc9-equi-sensitive) (Genbank Accession Number AF121972)

SEQ ID NO: 16: amino acid sequence of the protein encoded by the nucleic acid set forth in SEQ ID NO: 15

SEQ ID NO: 17: nucleic acid encoding the murine olfactory receptor S50 (cc9-sensitive) (Genbank Accession Number AF121980)

SEQ ID NO: 18: amino acid sequence of the protein encoded by the nucleic acid set forth in SEQ ID NO: 17

SEQ ID NO: 19: nucleic acid encoding the murine olfactory receptor S19 (mc9/mh9/bc9-equi-sensitive) (Genbank Accession Number AF121976)

SEQ ID NO: 20: amino acid sequence of the protein encoded by the nucleic acid set forth in SEQ ID NO: 19

SEQ ID NO: 21: nucleic acid encoding the murine OR23 (lyral-sensitive) (only coding region of Genbank Accession Number X92969)

SEQ ID NO: 22: amino acid sequence of the protein encoded by the nucleic acid set forth in SEQ ID NO: 21

SEQ ID NO: 23: nucleic acid encoding the murine olfactory receptor mOR-EV (vanillin-sensitive) (Genbank Accession Number AB061229)

SEQ ID NO: 24: amino acid sequence of the protein encoded by the nucleic acid set forth in SEQ ID NO: 23

SEQ ID NO: 25: nucleic acid encoding the murine olfactory receptor or 37a (Genbank Accession Number AJ133424)

SEQ ID NO: 26: amino acid sequence of the protein encoded by the nucleic acid set forth in SEQ ID NO: 25

SEQ ID NO: 27: nucleic acid encoding the murine olfactory receptor C6 (Genbank Accession Number AF102523)

SEQ ID NO: 28: amino acid sequence of the protein encoded by the nucleic acid set forth in SEQ ID NO: 27

SEQ ID NO: 29: nucleic acid encoding the murine olfactory receptor F5 (Genbank Accession Number AF102531)

SEQ ID NO: 30: amino acid sequence of the protein encoded by the nucleic acid set forth in SEQ ID NO: 29

SEQ ID NO: 31: nucleic acid encoding the murine olfactory receptor S6 (Genbank Accession Number AF121974)

SEQ ID NO: 32: amino acid sequence of the protein encoded by the nucleic acid set forth in SEQ ID NO: 31

SEQ ID NO: 33: nucleic acid encoding the murine olfactory receptor S18 (Genbank Accession Number AF121975)

SEQ ID NO: 34: amino acid sequence of the protein encoded by the nucleic acid set forth in SEQ ID NO: 33

SEQ ID NO: 35: nucleic acid encoding the murine olfactory receptor S25 (Genbank Accession Number AF121977)

SEQ ID NO: 36: amino acid sequence of the protein encoded by the nucleic acid set forth in SEQ ID NO: 35

SEQ ID NO: 37: nucleic acid encoding the murine olfactory receptor S46 (Genbank Accession Number AF121979)

SEQ ID NO: 38: amino acid sequence of the protein encoded by the nucleic acid set forth in SEQ ID NO: 37

SEQ ID NO: 39: nucleic acid encoding the α subunit of murine G-coupled protein (Genbank Accession Number M36778)

SEQ ID NO: 40: amino acid sequence of the protein encoded by the nucleic acid set forth in SEQ ID NO: 39

SEQ ID NO: 41: nucleic acid encoding the β subunit of murine G-coupled protein (Genbank Accession Number M87286)

SEQ ID NO: 42: amino acid sequence of the protein encoded by the nucleic acid set forth in SEQ ID NO: 41

SEQ ID NO: 43: nucleic acid encoding the γ subunit of murine G-coupled protein (Genbank Accession Number U37527)

SEQ ID NO: 44: amino acid sequence of the protein encoded by the nucleic acid set forth in SEQ ID NO: 43

SEQ ID NO: 45: nucleic acid encoding the epidermal growth factor receptor (Genbank Accession Number BC023729)

SEQ ID NO: 46: amino acid sequence of the protein encoded by the nucleic acid set forth in SEQ ID NO: 45

SEQ ID NO: 47: the sequence of siRNA used in Example 9

SEQ ID NO: 48: the sequence of scrambled RNA used in Example 9

BEST MODE FOR CARRYING OUT THE INVENTION

Hereinafter, the present invention will be described. It should be understood throughout the present specification that articles for a singular form (e.g., "a", "an", "the", etc. in English) include the concept of their plurality unless otherwise mentioned. It should be also understood that the terms as used herein have definitions typically used in the art unless otherwise mentioned. Accordingly, unless otherwise defined, all technical and scientific terms used herein shall have the same meaning as generally understood by those skilled in the art to which the present invention pertains. If there is any inconsistency, the present specification precedes, including definitions.

DEFINITION OF TERMS

Terms particularly used herein are defined as follows.
(Cellular Biology)

The term "cell" is herein used in its broadest sense in the art, referring to a structural unit of the tissue of a multicellular organism, which is capable of self replicating, has genetic information and a mechanism for expressing it, and is surrounded by a membrane structure which isolates the cell from the outside. Cells used herein may be either naturally-occurring cells or artificially modified cells (e.g., fusion cells, genetically modified cells, etc.), as long as the cell has a chemical receptor or is capable of having such a chemical receptor introduced therein. Examples of cell sources include, but are not limited to, a single-cell culture; the embryo, blood, or body tissue of normally-grown transgenic animals; a mixture of cells derived from normally-grown cell lines; and the like.

As used herein, the term "digital cell" refers to a collection of at least one experimental data on a cell of experimental interest. These experimental data correlate the experimental conditions and the experimental results of an example conducted against an actual cell. The digital cell is constituted such that once an experimental condition is given, the experimental result related to said experimental condition will be reproduced. The digital cell contemplated by the present invention comprises any cell which is amenable to an experiment. It should be understood that the description with respect to all the (living) cells described herein can be applied to a digital cell according to the present invention, as long as such description is applicable to the digital cell.

Using digital cells of the present invention allows reproduction of an experimental result of an experiment conducted using an actual cell, in a computer system. As such, the present invention allow research institutes, educational organizations and individuals having no experimental facilities, to conduct education and advanced research relating to a cell. As a result, business entities in different fields will be able to start business in this field, which has not been possible to date.

Cells used herein may be derived from any organism (e.g., any unicellular organism (e.g., bacteria and yeast) or any multicellular organisms (e.g., animals (e.g., vertebrates and invertebrates), plants (e.g., monocotyledons and dicotyledons, etc.)). For example, cells used herein are derived from a vertebrate (e.g., Myxiniformes, Petronyzoniformes, Chondrichthyes, Osteichthyes, amphibian, reptilian, avian, mammalian, etc.), more preferably mammalian (e.g., monotremata, marsupialia, edentate, dermoptera, chiroptera, carnivore, insectivore, proboscidea, perissodactyla, artiodactyla, tubulidentata, pholidota, sirenia, cetacean, primates, rodentia, lagomorpha, etc.). In one embodiment, cells derived from primates (e.g., chimpanzee, Japanese monkey, human) are used. Particularly, without limitation, cells derived from a human are used. The above-described cells may be either stem cells or somatic cells. Also, the cells may be adherent cells, suspended cells, tissue forming cells, and mixtures thereof. The cells may be used for transplantation.

Any organ may be targeted by the present invention. A tissue or cell targeted by the present invention may be derived from any organ. As used herein, the term "organ" refers to a morphologically independent structure, localized to a particular portion of an individual organism, in which a certain function is performed. In multicellular organisms (e.g., animals, plants), an organ consists of several tissues spatially arranged in a particular manner, each tissue being composed of a number of cells. An example of such an organ includes an organ relating to the vascular system. In one embodiment, organs targeted by the present invention include, but are not limited to, skin, blood vessels, cornea, kidney, heart, liver, umbilical cord, intestine, nerve, lung, placenta, pancreas, brain, peripheral limbs, retina, and the like. As used herein, cells differentiated from a pluripotent cell of the present invention include, but are not limited to: epidermal cells, pancreatic parenchymal cells, pancreatic duct cells, hepatic cells, blood cells, cardiac muscle cells, skeletal muscle cells, osteoblasts, skeletal myoblasts, neurons, vascular endothelial cells, pigment cells, smooth muscle cells, fat cells, bone cells, cartilage cells, and the like.

As used herein, the term "tissue" refers to an aggregate of cells having substantially the same function and/or form in a multicellular organism. "Tissue" is typically an aggregate of cells of the same origin, but may be an aggregate of cells of different origins as long as the cells have the same function and/or form. Therefore, when stem cells of the present invention are used to regenerate tissue, the tissue may be composed of an aggregate of cells of two or more different origins. Typically, a tissue constitutes a part of an organ. Animal tissues are separated into epithelial tissue, connective tissue, muscular tissue, nervous tissue, and the like, on a morphological, functional, or developmental basis. Plant tissues are roughly separated into meristematic tissue and permanent tissue, according to the developmental stage of the cells constituting the tissue. Alternatively, tissues may be separated into single tissues and composite tissues according to the type of cells constituting the tissue. Thus, tissues are separated into various categories.

As used herein, the term "stem cell" refers to a cell capable of self replication and pluripotency. Typically, stem cells can regenerate an injured tissue. Stem cells used herein may be, but are not limited to, embryonic stem (ES) cells or tissue stem cells (also called tissular stem cells, tissue-specific stem cells, or somatic stem cells). A stem cell may be an artificially produced cell (e.g., fusion cells, reprogrammed cells, or the like used herein), as long as it has the above-described abilities. Embryonic stem cells are pluripotent stem cells derived from early embryos. An embryonic stem cell was first established in 1981, and has been applied to the production of knockout mice since 1989. In 1998, a human embryonic stem cell was established, which is currently becoming available for regenerative medicine. Tissue stem cells have a relatively limited level of differentiation, unlike embryonic stem cells. Tissue stem cells are present in tissues and have an undifferentiated intracellular structure. Tissue stem cells have a higher nucleus/cytoplasm ratio and have few intracellular organelles. Most tissue stem cells have pluripotency, a long cell cycle, and proliferative ability beyond the life of the individual. As used herein, stem cells may preferably be embryonic stem cells, though tissue stem cells may also be employed, depending on the circumstance.

Tissue stem cells are separated into categories of sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

As used herein, the term "somatic cell" refers to any cell other than a germ cell, such as an egg, a sperm, or the like, which does not transfer its DNA to the next generation. Typically, somatic cells have limited or no pluripotency. Somatic cells used herein may be naturally-occurring or genetically modified.

The origin of a stem cell is categorized into the ectoderm, endoderm, or mesoderm. Stem cells of ectodermal origin are mostly present in the brain, including neural stem cells. Stem cells of endodermal origin are mostly present in bone marrow, including blood vessel stem cells, hematopoietic stem cells, mesenchymal stem cells, and the like. Stem cells of mesoderm origin are mostly present in organs, including liver stem cells, pancreatic stem cells, and the like. Somatic cells may be herein derived from any germ layer. Preferably, somatic cells, such as lymphocytes, spleen cells or testis-derived cells, may be used.

As used herein, the term "isolated" means that naturally accompanying material is at least reduced, or preferably substantially completely eliminated, in the normal environment. Therefore, the term "isolated cell" refers to a cell substantially free from other accompanying substances (e.g., other cells, proteins, nucleic acids, etc.) in the natural environment. The term "isolated" in relation to nucleic acids or polypeptides means that, for example, the nucleic acids or the polypeptides are substantially free from cellular substances or culture media when they are produced by recombinant DNA techniques; or precursory chemical substances or other chemical substances when they are chemically synthesized. Isolated nucleic acids are preferably free from sequences that naturally flank the nucleic acid within an organism from which the nucleic acid is derived (i.e., sequences positioned at the 5' terminus and the 3' terminus of the nucleic acid).

As used herein, the term "established" in relation to cells refers to a state of a cell in which a particular property (pluripotency) of the cell is maintained and the cell undergoes stable proliferation under culture conditions. Therefore, established stem cells maintain pluripotency.

As used herein, the term "differentiated cell" refers to a cell having a specialized function and form (e.g., muscle cells, neurons, etc.). Unlike stem cells, differentiated cells have no or little pluripotency. Examples of differentiated cells include epidermic cells, pancreatic parenchymal cells, pancreatic duct cells, hepatic cells, blood cells, cardiac muscle cells, skeletal muscle cells, osteoblasts, skeletal myoblasts, neurons, vascular endothelial cells, pigment cells, smooth muscle cells, fat cells, bone cells, cartilage cells, and the like.

As used herein, the term "state" refers to a condition concerning various parameters of a cell (e.g., cell cycle, response to an external factor, signal transduction, gene expression, gene transcription, etc.). Examples of such a state include, but are not limited to, differentiated states, undifferentiated states, responses to external factors, cell cycles, growth states, and the like.

As used herein, the terms "differentiation" or "cell differentiation" refers to a phenomenon where two or more types of cells having qualitative differences in form and/or function occur in a daughter cell population derived from the division of a single cell. Therefore, "differentiation" includes a process during which a population (family tree) of cells, which do not originally have a specific detectable feature, acquire a feature, such as the production of a specific protein, or the like. At present, cell differentiation is generally considered to be a state of a cell in which a specific group of genes in the genome are expressed. Cell differentiation can be identified by searching for intracellular or extracellular agents or conditions which elicit the above-described state of gene expression. Differentiated cells are stable in principle. Particularly, animal cells which have been differentiated once rarely re-differentiate into other types of cells.

As used herein, the term "pluripotency" refers to a nature of a cell, i.e., an ability to differentiate into one or more, preferably two or more, tissues or organs. Therefore, the terms "pluripotent" and "undifferentiated" are herein used interchangeably unless otherwise mentioned. Typically, the pluripotency of a cell is limited during development, and in an adult, cells constituting a tissue or organ rarely differentiate into different cells, that is, the pluripotency is usually lost. Particularly, epithelial cells resist altering into other types of epithelial cells. Such alteration typically occurs in pathological conditions, and is called metaplasia. However, mesenchymal cells tend to easily undergo metaplasia, i.e., alter to other mesenchymal cells, with relatively simple stimuli. Therefore, mesenchymal cells have a high level of pluripotency. Embryonic stem cells have pluripotency. Tissue stem cells have pluripotency. Thus, the term "pluripotency" may include the concept of totipotency. An example of an in vitro assay for determining whether or not a cell has pluripotency, includes, but is not limited to, culturing under conditions for inducing the formation and differentiation of embryoid bodies. Examples of an in vivo assay for determining the presence or absence of pluripotency, include, but are not limited to, implantation of a cell into an immunodeficient mouse so as to form teratoma, injection of a cell into a blastocyst so as to form a chimeric embryo, implantation of a cell into a tissue of an organism (e.g., injection of a cell into ascites) so as to undergo proliferation, and the like. As used herein, one type of pluripotency is "totipotency", which refers to the ability to be differentiated into all kinds of cells which constitute an organism. The idea of pluripotency encompasses totipotency. An example of a totipotent cell is a fertilized ovum. An ability to be differentiated into only one type of cell is called "unipotency".

(Biochemistry and Molecular Biology)

As used herein, the term "agent" may refer to any substance or element as long as an intended object can be achieved (e.g., energy, such as ionizing radiation, radiation, light, acoustic waves, and the like). Examples of such a substance include, but are not limited to, proteins, polypeptides, oligopeptides, peptides, polynucleotides, oligonucleotides, nucleotides, nucleic acids (e.g., DNA such as cDNA, genomic DNA and the like, or RNA such as mRNA, RNAi and the like), polysaccharides, oligosaccharides, lipids, low molecular weight organic molecules (e.g., hormones, ligands, information transduction substances, low molecular weight organic molecules, molecules synthesized by combinatorial chemistry, low molecular weight molecules usable as medicaments (e.g., low molecular weight molecule ligands, etc.), etc.), and composite molecules thereof. External agents may be used singly or in combination. Examples of an agent specific to a polynucleotide include, but are not limited to, representatively, a polynucleotide having complementarity to the sequence of the polynucleotide with a predetermined sequence homology (e.g., 70% or more sequence identity), a polypeptide such as a transcriptional agent binding to a promoter region, and the like. Examples of an agent specific to a polypeptide include, but are not limited to, representatively, an antibody specifically directed to the polypeptide or derivatives or analogs thereof (e.g., single chain antibody), a specific ligand or receptor when the polypeptide is a receptor or ligand, a substrate when the polypeptide is an enzyme, and the like.

As used herein the term "biological agent" refers to an agent relating to a biological organism (for example, a cell). Preferably, an agent present in a cell in a normal state is referred to a biological agent. Such biological agents include, but are not limited to, for example: nucleic acid molecules, proteins, sugars, lipids, metabolites, low molecular weight molecules, and complexes thereof, and agents including time elements and the like. Alternatively, it should be understood that such biological agents include electric current, electric potential (such as membrane potential), pH, osmotic pressure and the like in the present invention. Useful biological agents as used herein include, for example, transcriptional controlling sequence (for example, promoters and the like), structural genes, and nucleic acids encoding the same. As used herein a "collection" of "biological agents" refer to a plurality of biological agents (of the same or different types). Preferably, the collection refers to biological agents which cooperate with each other.

As used herein, the term "gene" refers to an element defining a genetic trait. A gene is typically arranged in a given sequence on a chromosome. A gene which defines the primary structure of a protein is called a structural gene. A gene which regulates the expression of a structural gene is called a regulatory gene (e.g., promoter). Genes herein include structural genes and regulatory genes unless otherwise specified. Therefore, the term "cyclin gene" typically includes the structural gene of cyclin and the promoter of cyclin. As used herein, "gene" may refer to "polynucleotide", "oligonucleotide", "nucleic acid", and "nucleic acid molecule" and/or "protein", "polypeptide", "oligopeptide" and "peptide". As used herein, "gene product" includes "polynucleotide", "oligonucleotide", "nucleic acid" and "nucleic acid molecule" and/or "protein", "polypeptide", "oligopeptide" and "peptide", which are expressed by a gene. Those skilled in the art understand what a gene product is, according to the context.

As used herein, the term "homology" in relation to a sequence (e.g., a nucleic acid sequence, an amino acid sequence, etc.) refers to the level of identity between two or more gene sequences. Therefore, the greater the homology between two given genes, the greater the identity or similarity between their sequences. Whether or not two genes have homology is determined by comparing their sequences directly or by a hybridization method under stringent conditions. When two gene sequences are directly compared with each other, these genes have homology if the DNA sequences of the genes have representatively at least 50% identity, preferably at least 70% identity, more preferably at least 80%, 90%, 95%, 96%, 97%, 98%, or 99% identity with each other. As used herein, the term "similarity" in relation to a sequence (e.g., a nucleic acid sequence, an amino acid sequence, or the like) refers to the level of identity between two or more sequences when conservative substitution is regarded as positive (identical) in the above-described homology. Therefore, homology and similarity differ from each other in the presence of conservative substitutions. If no conservative substitutions are present, homology and similarity have the same value.

As used herein, the comparison of similarity, identity and homology of an amino acid sequence and a nucleotide sequence is calculated with FAST, a tool for sequence analysis using default parameters.

The terms "protein", "polypeptide", "oligopeptide" and "peptide" as used herein have the same meaning and refer to an amino acid polymer having any length. This polymer may be a straight, branched or cyclic chain. An amino acid may be a naturally-occurring or nonnaturally-occurring amino acid, or a variant amino acid. The term may include those assembled into a composite of a plurality of polypeptide chains. The term also includes a naturally-occurring or artificially modified amino acid polymers. Such modification includes, for example, disulfide bond formation, glycosylation, lipidation, acetylation, phosphorylation, or any other manipulation or modification (e.g., conjugation with a labeling moiety). This definition encompasses a polypeptide containing at least one amino acid analog (e.g., nonnaturally-occurring amino acid, etc.), a peptide-like compound (e.g., peptoid), and other variants known in the art, for example. Gene products, such as extracellular matrix proteins (e.g., fibronectin, etc.), are usually in the form of a polypeptide.

The terms "polynucleotide", "oligonucleotide", "nucleic acid molecule" and "nucleic acid" as used herein have the same meaning and refer to a nucleotide polymer having any length. This term also includes an "oligonucleotide derivative" or a "polynucleotide derivative". An "oligonucleotide derivative" or a "polynucleotide derivative" includes a nucleotide derivative, or refers to an oligonucleotide or a polynucleotide having different linkages between nucleotides from typical linkages, which are interchangeably used. Examples of such an oligonucleotide specifically include 2'-O-methyl-ribonucleotide, an oligonucleotide derivative in which a phosphodiester bond in an oligonucleotide is converted to a phosphorothioate bond, an oligonucleotide derivative in which a phosphodiester bond in an oligonucleotide is converted to a N3'-P5' phosphoroamidate bond, an oligonucleotide derivative in which a ribose and a phosphodiester bond in an oligonucleotide are converted to a peptide-nucleic acid bond, an oligonucleotide derivative in which uracil in an oligonucleotide is substituted with C-5 propynyl uracil, an oligonucleotide derivative in which uracil in an oligonucleotide is substituted with C-5 thiazole uracil, an oligonucleotide derivative in which cytosine in an oligonucleotide is substituted with C-5 propynyl cytosine, an oligonucleotide derivative in which cytosine in an oligonucleotide is substituted with phenoxazine-modified cytosine, an oligonucleotide derivative in which ribose in DNA is substituted with 2'-O-propyl ribose, and an oligonucleotide derivative in which ribose in an oligonucleotide is substituted with 2'-methoxyethoxy ribose. Unless otherwise indicated, a particular nucleic acid sequence also implicitly encompasses conservatively-modified variants thereof (e.g. degenerate codon substitutions) and complementary sequences as well as the sequence explicitly indicated. Specifically, degenerate codon substitutions may be produced by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). A gene encoding an extracellular matrix protein (e.g., fibronectin, etc.) or the like is usually in the form of polynucleotide. A molecule to be transfected is in the form of a polynucleotide.

As used herein, the term "corresponding" amino acid or nucleic acid refers to an amino acid or nucleotide in a given polypeptide or polynucleotide molecule, which has, or is anticipated to have, a function similar to that of a predetermined amino acid or nucleotide in a polypeptide or polynucleotide as a reference for comparison. Particularly, in the case of enzyme molecules, the term refers to an amino acid which is present at a similar position in an active site and similarly contributes to catalytic activity. For example, in the case of a transcriptional controlling sequence of a polynucleotide, it may be a portion similar to that of corresponding ortholog in the particular portion of the transcription controlling sequence.

As used herein, the term "corresponding" gene (e.g., a polypeptide or polynucleotide molecule) refers to a gene in a given species, which has, or is anticipated to have, a function similar to that of a predetermined gene in a species as a reference for comparison. When there are a plurality of genes having such a function, the term refers to a gene having the same evolutionary origin. Therefore, a gene corresponding to a given gene may be an ortholog of the given gene. Therefore, genes corresponding to mouse cyclin genes can be found in other animals. Such a corresponding gene can be identified by techniques well known in the art. Therefore, for example, a corresponding gene in a given animal can be found by searching a sequence database of the animal (e.g., human, rat) using the sequence of a reference gene (e.g., mouse cyclin gene, etc.) as a query sequence.

As used herein, the term "fragment" with respect to a polypeptide or polynucleotide refers to a polypeptide or polynucleotide having a sequence length ranging from 1 to n−1 with respect to the full length of the reference polypeptide or polynucleotide (of length n). The length of the fragment can be appropriately changed depending on the purpose. For example, in the case of polypeptides, the lower limit of the length of the fragment includes 3, 4, 5, 6, 7, 8, 9, 10, 15, 20, 25, 30, 40, 50 or more amino acids. Lengths represented by integers which are not herein specified (e.g., 11 and the like) may be appropriate as a lower limit. For example, in the case of polynucleotides, the lower limit of the length of the fragment includes 5, 6, 7, 8, 9, 10, 15, 20, 25, 30, 40, 50, 75, 100 or more nucleotides. Lengths represented by integers which are not herein specified (e.g., 11 and the like) may be appropriate as a lower limit. As used herein, the length of polypeptides or polynucleotides can be represented by the number of amino acids or nucleic acids, respectively. However, the above-described numbers are not absolute. The above-described numbers as the upper or lower limit are intended to include some greater or smaller numbers (e.g., ±10%), as long as the same function is maintained. For this purpose, "about" may be herein put ahead of the numbers. However, it should be understood that the interpretation of numbers is not affected by the presence or absence of "about" in the present specification.

As used herein, the term "biological activity" refers to activity possessed by an agent (e.g., a polynucleotide, a protein, etc.) within an organism, including activities exhibiting various functions (e.g., transcription promoting activity, etc.). For example, when a certain factor is an enzyme, the biological activity thereof includes its enzyme activity. In another example, when a certain factor is a ligand, the biological activity thereof includes the binding of the ligand to a receptor corresponding thereto. The above-described biological activity can be measured by techniques well-known in the art.

As used herein, the term "polynucleotides hybridizing under stringent conditions" refers to conditions commonly used and well known in the art. Such a polynucleotide can be obtained by conducting colony hybridization, plaque hybridization, Southern blot hybridization, or the like, using a polynucleotide selected from the polynucleotides of the present invention. Specifically, a filter on which DNA derived from a colony or plaque is immobilized is used to conduct hybridization at 65° C. in the presence of 0.7 to 1.0 M NaCl. Thereafter, a 0.1 to 2-fold concentration SSC (saline-sodium citrate) solution (1-fold concentration SSC solution is composed of 150 mM sodium chloride and 15 mM sodium citrate) is used to wash the filter at 65° C. Polynucleotides identified by this method are referred to as "polynucleotides hybridizing under stringent conditions". Hybridization can be conducted in accordance with a method described in, for example, Molecular Cloning 2nd ed., Current Protocols in Molecular Biology, Supplement 1-38, DNA Cloning 1: Core Techniques, A Practical Approach, Second Edition, Oxford University Press (1995), and the like. Here, sequences hybridizing under stringent conditions exclude, preferably, sequences containing only A or T. "Hybridizable polynucleotide" refers to a polynucleotide which can hybridize to other polynucleotides under the above-described hybridization conditions. Specifically, the hybridizable polynucleotide includes at least a polynucleotide having a homology of at least 60% to the base sequence of DNA encoding a polypeptide having an amino acid sequence specifically herein disclosed, preferably a polynucleotide having a homology of at least 80%, and more preferably a polynucleotide having a homology of at least 95%.

As used herein, the term "salt" has the same meaning as that commonly understood by those skilled in the art, including both inorganic and organic salts. Salts are typically generated by neutralizing reactions between acids and bases. Salts include NaCl, $K_2SO_4$, and the like, which are generated by neutralization, and in addition, $PbSO_4$, $ZnCl_2$, and the like, which are generated by reactions between metals and acids. The latter salts may not be generated directly by neutralizing reactions, but may be regarded as a product of neutralizing reactions between acids and bases. Salts may be divided into the following categories: normal salts (salts without any H-groups from acids or without any OH-groups from bases, including, for example, NaCl, $NH_4Cl$, $CH_3COONa$, and $Na_2CO_3$), acid salts (salts with remaining H-groups from acids, including, for example, $NaHCO_3$, $KHSO_4$, and $CaHPO_4$), and basic salts (salts with remaining OH-groups from bases, including, for example, MgCl (OH) and CuCl (OH)). This classification is not very important in the present invention. Examples of preferable salts include salts constituting media (e.g., calcium chloride, sodium hydrogen phosphate, sodium hydrogen carbonate, sodium pyruvate, HEPES, sodium chloride, potassium chloride, magnesium sulfide, iron nitrate, amino acids, vitamins, etc.), salts constituting buffer (e.g., calcium chloride, magnesium chloride, sodium hydrogen phosphate, sodium chloride, etc.), and the like. These salts are preferable as they have a high affinity for cells and thus are better able to maintain cells in culture. These salts may be used singly or in combination. Preferably, these salts may be used in combination. This is because a combination of salts tends to have a higher affinity for cells. Therefore, a plurality of salts (e.g., calcium chloride, magnesium chloride, sodium hydrogen phosphate, and sodium chloride) are preferably contained in a medium, rather than only NaCl or the like. More preferably, all salts suitable for cell culture medium may be added to the medium. In another preferred embodiment, glucose may be added to medium.

As used herein the term "material" or "substance" is used in the broadest meaning as used in the art to refer to any thing that is positively or negatively charged.

As used herein, the term "positively charged substance" encompasses all substances having a positive charge. Such substances include cationic substances such as cationic polymers, cationic lipids and the like, but are not limited to these. Advantageously, such positively charged substances can form a complex. Such positively charged substances which can form a complex include, for example, substances having a certain molecular weight (for example, cationic polymers) and substances which can remain insoluble, that is, without being dissolved to a certain extent in a specific solvent such as water, an aqueous solution or the like (for example, cationic lipids), but are not limited to these. Preferable positively charged substances include, for example, polyethylene imine, poly-L-lysine, synthetic polypeptides, or derivatives thereof, but are not limited to these. Positively charged substances include, for example, biological molecules such as histone and synthetic polypeptides, but are not limited to these. The type of preferable positively charged substances changes in accordance with the type of negatively charged substances, which act as a complex partner to form complexes with the positively charged substances. It requires no specific creativity for those skilled in the art to select a preferable complex partner using technology well known in the art. For selecting a preferable complex partner, various parameters are considered including, but not limited to, charge, molecular weight, hydrophobicity, hydrophilicity, properties of substituents, pH, temperature, salt concentration, pressure, and other physical and chemical parameters.

As used herein, the term "cationic polymer" refers to a polymer having a cationic functional group, and encompasses, for example, polyethylene imine, poly-L-lysine, synthetic polypeptides, and derivatives thereof, but is not limited to these.

As used herein, the term "cationic lipid" refers to a lipid having a cationic functional group, and encompasses, for example, phosphatidyl choline, phosphatidyl ethanol amine, phosphatidyl serine, and derivatives thereof, but is not limited to these.

Cationic functional groups include, for example, primary amines, secondary amines, and tertiary amines, but are not limited to these.

As used herein, the term "negatively charged substance" encompasses all substances having a negative charge. Such substances include biological molecular polymers, anionic substances such as anionic lipids, and the like, but are not limited to these. Advantageously, such negatively charged substances can form a complex. Such negatively charged substances which can form a complex include, for example, substances having a certain molecular weight (for example, anionic polymers such as DNA) and substances which can remain insoluble, that is, without being dissolved to a certain extent in a specific solvent such as water, an aqueous solutions or the like (for example, anionic lipids), but are not limited to these. Preferable negatively charged substances include, for example, DNA, RNA, PNA, polypeptides, chemical compounds, and complexes thereof, but are not limited to these. Negatively charged substances include, for example, DNA, RNA, PNA, polypeptides, chemical compounds, and complexes thereof, but are not limited to these. The type of preferable negatively charged substances changes in accordance with the type of positively charged substances, which act as a complex partner to form complexes with the negatively charged substances. It requires no specific creativity for those skilled in the art to select a preferable complex partner using technology well known in the art. For selecting a preferable complex partner, various parameters are considered as described above with regard to negatively charged substances.

As used herein, the term "anionic polymer" encompasses polymers having an anionic functional group, and includes, for example, DNA, RNA, PNA, polypeptides, chemical compounds, and complexes thereof, but is not limited to these.

As used herein, the term "anionic lipid" encompasses lipids having an anionic functional group, and include, for example, phosphatidic acid, phosphatidyl serine, but is not limited to these.

Anionic functional groups include, for example, carboxylic groups and phosphoric acid groups, but are not limited to these.

The type of charge of a target substance can be converted by adding a part of a substituent or the like having a positive charge or a negative charge to the target substance.

In the case where a preferable complex partner has the same type of charge as that of the target substance, formation of a complex can be promoted by converting the type of charge of either the complex partner or the target substance.

As used herein, the term "complex" refers to two or more substances which directly or indirectly interact with each other and as a result, act as if they were one substance as a whole.

As used herein, the term "complex partner" used for a certain member forming a complex refers to another member interacting with the certain member directly or indirectly.

As used herein, the condition for forming a complex changes in accordance with the type of complex partner. Such a condition can be easily understood by those skilled in the art. Those skilled in the art can easily form a complex from any complex partners (for example, a positively charged substance and a negatively charged substance) using a technique well known in the art.

As used herein, when a complex of positively and negatively charged substances is used, either or both thereof may be identical to a biological agent.

As used herein, the term "immobilization" used for a solid-phase support refers to a state in which a substance as a subject of immobilization (e.g., a biological molecule) is held on the support for at least a certain time period, or an act-of placing the substance into such a state. As such, in the case where the condition is changed after the substance is immobilized on the solid-phase support (for example, the substance is immersed in another solvent), the substance may be released from the immobilization state.

As used herein, the term "cell affinity" refers to a property of a substance that when the substance is placed in an interactable state with a cell (e.g. germ cell, animal cell, yeast, plant cell) or an object containing a cell (e.g., tissue, organs, biological organisms), the substance does not have any adverse influence on the cell or the object containing the cell. Preferably, substances having cell affinity may be substances with which a cell interacts as a priority, but are not limited to these. According to the present invention, the substance to be immobilized (e.g., positively charged substances and/or negatively charged substances) preferably have cell affinity, but cell affinity is not absolutely necessary. It was unexpectedly found that when the substance to be immobilized has cell affinity, the cell affinity of the substance is maintained or improved when the substance is immobilized according to the present invention. In light of the past situation where a substance having cell affinity does not necessarily maintain its cell affinity when immobilized on a solid-phase support, the effect of the present invention is enormous.

As used herein, the term "probe" refers to a substance for use in searching, which is used in a biological experiment, such as in vitro and/or in vivo screening or the like, including, but not limited to, for example, a nucleic acid molecule having a specific base sequence or a peptide containing a specific amino acid sequence.

Examples of a nucleic acid molecule as a common probe include one having a nucleic acid sequence having a length of at least 8 contiguous nucleotides, which is homologous or complementary to the nucleic acid sequence of a gene of interest. Such a nucleic acid sequence may be preferably a nucleic acid sequence having a length of at least 9 contiguous nucleotides, more preferably a length of at least 10 contiguous nucleotides, and even more preferably a length of at least 11 contiguous nucleotides, a length of at least 12 contiguous nucleotides, a length of at least 13 contiguous nucleotides, a length of at least 14 contiguous nucleotides, a length of at least 15 contiguous nucleotides, a length of at least 20 contiguous nucleotides, a length of at least 25 contiguous nucleotides, a length of at least 30 contiguous nucleotides, a length of at least 40 contiguous nucleotides, or a length of at least 50 contiguous nucleotides. A nucleic acid sequence used as a probe includes a nucleic acid sequence having at least 70% homology to the above-described sequence, more preferably at least 80%, and even more preferably at least 90% or at least 95%.

As used herein, the term "search" indicates that a given nucleic acid sequence is utilized to find other nucleic acid base sequences having a specific function and/or property either electronically or biologically, or using other methods. Examples of an electronic search include, but are not limited to, BLAST (Altschul et al., J. Mol. Biol. 215:403-410 (1990)), FASTA (Pearson & Lipman, Proc. Natl. Acad. Sci., USA 85:2444-2448 (1988)), the Smith and Waterman method (Smith and Waterman, J. Mol. Biol. 147:195-197 (1981)), and the Needleman and Wunsch method (Needleman and Wunsch, J. Mol. Biol. 48:443-453 (1970)), and the like. Examples of a biological search include, but are not limited to, a macroarray in which genomic DNA is attached to a nylon membrane or the like or a microarray (microassay) in which genomic DNA is attached to a glass plate under stringent hybridization conditions, PCR, in situ hybridization, and the like.

As used herein, the term "primer" refers to a substance required for the initiation of a reaction of a macromolecule compound to be synthesized, in a macromolecule synthesis enzymatic reaction. In a reaction for synthesizing a nucleic acid molecule, a nucleic acid molecule (e.g., DNA, RNA, or the like) which is complementary to part of a macromolecule compound to be synthesized may be used.

A nucleic acid molecule which is ordinarily used as a primer includes one that has a nucleic acid sequence having a length of at least 8 contiguous nucleotides, which is complementary to the nucleic acid sequence of a gene of interest. Such a nucleic acid sequence preferably has a length of at least 9 contiguous nucleotides, more preferably a length of at least 10 contiguous nucleotides, even more preferably a length of at least 11 contiguous nucleotides, a length of at least 12 contiguous nucleotides, a length of at least 13 contiguous nucleotides, a length of at least 14 contiguous nucleotides, a length of at least 15 contiguous nucleotides, a length of at least 16 contiguous nucleotides, a length of at least 17 contiguous nucleotides, a length of at least 18 contiguous nucleotides, a length of at least 19 contiguous nucleotides, a length of at least 20 contiguous nucleotides, a length of at least 25 contiguous nucleotides, a length of at least 30 contiguous nucleotides, a length of at least 40 contiguous nucleotides, and a length of at least 50 contiguous nucleotides. A nucleic acid sequence used as a primer includes a nucleic acid sequence having at least 70% homology to the above-described sequence, more preferably at least 80%, even more preferably at least 90%, and most preferably at least 95%. An appropriate sequence as a primer may vary depending on the property of the sequence to be synthesized (amplified). Those skilled in the art can design an appropriate primer depending on the sequence of interest. Such primer design is well known in the art and may be performed manually or using a computer program (e.g., LASERGENE, Primer Select, DNAStar).

As used herein, the term "epitope" refers to an antigenic determinant. Therefore, the term "epitope" includes a set of amino acid residues which are involved in recognition by a particular immunoglobulin, or in the context of T cells, those residues necessary for recognition by the T cell receptor proteins and/or Major Histocompatibility Complex (MHC) receptors. This term is also used interchangeably with "antigenic determinant" or "antigenic determinant site". In the field of immunology, in vivo or in vitro, an epitope is the features of a molecule (e.g., primary, secondary and tertiary peptide structure, and charge) that form a site recognized by an immunoglobulin, T cell receptor or HLA molecule. An epitope including a peptide comprises 3 or more amino acids in a spatial conformation which is unique to the epitope. Generally, an epitope consists of at least 5 such amino acids, and more ordinarily, consists of at least 6, 7, 8, 9 or 10 such amino acids. The greater the length of an epitope, the more the similarity of the epitope to the original peptide, i.e., longer epitopes are generally preferable. This is not necessarily the case when the conformation is taken into account. Methods of determining the spatial conformation of amino acids are known in the art, and include, for example, X-ray crystallography and 2-dimensional nuclear magnetic resonance spectroscopy. Furthermore, the identification of epitopes in a given protein is readily accomplished using techniques well known in the art. See, also, Geysen et al., Proc. Natl. Acad. Sci. USA (1984) 81: 3998 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., Molecular immunology (1986) 23: 709 (technique for identifying peptides with high affinity for a given antibody). Antibodies that recognize the same epitope can be identified in a simple immunoassay. Thus, methods for determining epitopes including a peptide are well known in the art. Such an epitope can be determined using a well-known, common technique by those skilled in the art if the primary nucleic acid or amino acid sequence of the epitope is provided.

Therefore, an epitope including a peptide requires a sequence having a length of at least 3 amino acids, preferably at least 4 amino acids, more preferably at least 5 amino acids, at least 6 amino acids, at least 7 amino acids, at least 8 amino acids, at least 9 amino acids, at least 10 amino acids, at least 15 amino acids, at least 20 amino acids, and 25 amino acids. Epitopes may be linear or conformational.

As used herein, the term "agent binding specifically to" a certain nucleic acid molecule or polypeptide refers to an agent which has a level of binding to the nucleic acid molecule or polypeptide equal to or higher than a level of binding to other nucleic acid molecules or polypeptides. Examples of such an agent include, but are not limited to, when a target is a nucleic acid molecule, a nucleic acid molecule having a complementary sequence of a nucleic acid molecule of interest, a polypeptide capable of binding to a nucleic acid sequence of interest (e.g., a transcription agent, etc.), and the like, and when a target is a polypeptide, an antibody, a single chain antibody, either of a pair of a receptor and a ligand, either of a pair of an enzyme and a substrate, and the like.

As used herein, the term "antibody" encompasses polyclonal antibodies, monoclonal antibodies, human antibodies, humanized antibodies, polyfunctional antibodies, chimeric antibodies, and anti-idiotype antibodies, and fragments thereof (e.g., F(ab')2 and Fab fragments), and other recombinant conjugates. These antibodies may be fused with an enzyme (e.g., alkaline phosphatase, horseradish peroxidase, α-galactosidase, and the like) via a covalent bond or by recombination.

As used herein, the term "monoclonal antibody" refers to an antibody composition having a group of homologous antibodies. This term is not limited by the production manner thereof. This term encompasses all immunoglobulin molecules and Fab molecules, F(ab')2 fragments, Fv fragments, and other molecules having an immunological binding property of the original monoclonal antibody molecule. Methods for producing polyclonal antibodies and monoclonal antibodies are well known in the art, and will be more sufficiently described below.

Monoclonal antibodies are prepared by using the standard technique well known in the art (e.g., Kohler and Milstein, Nature (1975) 256:495) or a modification thereof (e.g., Buck et al. (1982) In Vitro 18:377). Representatively, a mouse or rat is immunized with a protein bound to a protein carrier, and boosted. Subsequently, the spleen (and optionally several large lymph nodes) is removed and dissociated into a single cell suspension. If desired, the spleen cells may be screened (after removal of nonspecifically adherent cells) by applying the cell suspension to a plate or well coated with a protein antigen. B-cells that express membrane-bound immunoglobulin specific for the antigen bind to the plate, and are not rinsed away with the rest of the suspension. Resulting B-cells, or all dissociated spleen cells, are then induced to fuse with myeloma cells to form hybridomas. The hybridomas are used to produce monoclonal antibodies.

As used herein, the term "antigen" refers to any substrate to which an antibody molecule may specifically bind. As used herein, the term "immunogen" refers to an antigen capable of initiating activation of the antigen-specific immune response of a lymphocyte.

In a given protein molecule, a given amino acid may be substituted with another amino acid in a structurally important region, such as a cationic region or a substrate molecule binding site, without a clear reduction or loss of interactive binding ability. A given biological function of a protein is defined by the interactive ability or other property of the protein. Therefore, a particular amino acid substitution may be performed in an amino acid sequence, or at the DNA sequence level, to produce a protein which maintains the original property after the substitution. Therefore, various modifications of peptides as disclosed herein and DNA encoding such peptides may be performed without clear losses of biological activity.

When the above-described modifications are designed, the hydrophobicity indices of amino acids may be taken into consideration. The hydrophobic amino acid indices play an important role in providing a protein with an interactive biological function, which is generally recognized in the art (Kyte, J. and Doolittle, R. F., J. Mol. Biol. 157(1):105-132, 1982). The hydrophobic property of an amino acid contributes to the secondary structure of a protein and then regulates interactions between the protein and other molecules (e.g., enzymes, substrates, receptors, DNA, antibodies, antigens, etc.). Each amino acid is given a hydrophobicity index based on the hydrophobicity and charge properties thereof as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamic acid (−3.5); glutamine (−3.5); aspartic acid (−3.5); asparagine (−3.5); lysine (−3.9); and arginine (−4.5).

It is well known that if a given amino acid is substituted with another amino acid having a similar hydrophobicity index, the resultant protein may still have a biological function similar to that of the original protein (e.g., a protein having an equivalent enzymatic activity). For such an amino acid substitution, the hydrophobicity index is preferably within ±2, more preferably within ±1, and even more preferably within ±0.5. It is understood in the art that such an amino acid substitution based on hydrophobicity is efficient.

Hydrophilicity may also be considered for conservative substitution. As described in U.S. Pat. No. 4,554,101, amino acid residues are given the following hydrophilicity indices: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid may be substituted with another amino acid which has a similar hydrophilicity index and can still provide a biological equivalent. For such an amino acid substitution, the hydrophilicity index is preferably within ±2, more preferably ±1, and even more preferably ±0.5.

(Profile and its Relevant Techniques)

As used herein, the term "profile" in relation to a cell refers to a set of measurements of the biological state of the cell. Particularly, the term "profile of a cell" refers to a set of discrete or continuous values obtained by quantitatively measuring a level of a "cellular component". A level of a cellular component includes the expression level of a gene, the transcription level of a gene (the activity level of a transcription control sequence), the amount of mRNA encoding a specific gene, and the expression level of a protein in biological systems. The level of each cellular component, such as the expression level of mRNA and/or protein, is known to alter in response to treatment with drugs or cellular biological perturbation or vibration. Therefore, the measurement of a plurality of "cellular components" generates a large amount of information about the effects of stimuli on the biological state of a cell. Therefore, the profile is more and more important in the analysis of cells. Mammalian cells contain about 30,000 or more cellular components. Therefore, the profile of an individual cell is usually complicated. A profile in a predetermined state of a biological system may often be measured after stimulating the biological system. Such stimulation is performed under experimental or environmental conditions associated with the biological system. Examples of a stimulus include exposure of a biological system to a drug candidate, introduction of an exogenous gene, passage of time, deletion of a gene from the system, alteration of culture conditions, and the like. The wide range measurement of cellular components (i.e., profiles of gene replication or transcription, protein expression, and response to stimuli) has a high level of utility including comparison and investigation of the effects of drugs, diagnosis of diseases, and optimization of drug administration to patients as well as investigation of cells. Further, profiles are useful for basic life science research. Such profile data may be produced and presented as data in a variety of formats. Such formats include, but are not limited to: a function between a numerical value and a period of time, a graphic format, a image format and the like. Accordingly, data relating to a profile may also be called "profile data" as used herein. Such data production may readily be carried out by using a computer. Coding of an appropriate program may also be carried out by using well known technology in the art.

In the cell analysis of the present application, as regards to information derived from a cell or a substance interacting with the cell, a variety of processes and means for detection may be used. Such process and means for detection include, but are not limited to: those using visual inspection, optical microscopes, fluorescence microscopes, reading apparatus using a laser light source, surface plasmon resonance (SPR) imaging, electric signal, chemical and biochemical markers, or a combination thereof.

As used herein, the term "time-lapse profile" in relation to a certain cell refers to a profile which indicates time-lapse changes in a parameter relating to the cell. Examples of a time-lapse profile include, but are not limited to, a time-lapse profile of transcription levels, a time-lapse profile of expression levels (translation levels), a time-lapse profile of signal transduction, a time-lapse profile of neural potential, and the like. A time-lapse profile may be produced by continuously recording a certain parameter (e.g., a signal caused by a label associated with a transcription level). Time-lapse measurement may mean continuous measurement. Therefore, the term "time-lapse profile" as used herein may also be referred to as "continuous profile".

As used herein the term "information" of a cell refers to those acting to direct an object as a whole by binding a number of elements present in the cell. A collection of information can be said to constitute a digital cell.

As used herein, the term "state" refers to a condition concerning various parameters of a cell (e.g., cell cycle, response to an external factor, signal transduction, gene expression, gene transcription, etc.). Examples of such a state include, but are not limited to, differentiated states, undifferentiated states, responses to external factors, cell cycles, growth states, and the like. The responsiveness or resistance of an organism of interest with respect to the following parameters of the, particularly, environment of the organism may be used herein as a measure of the state of the organism: temperature, humidity (e.g., absolute humidity, relative humidity, etc.), pH, salt concentration (e.g., the concentration of all salts or a particular salt), nutrients (e.g., the amount of carbohydrate, etc.), metals (e.g., the amount or concentration of all metals or a particular metal (e.g., a heavy metal, etc.)), gas (e.g., the amount of all gases or a particular gas), organic solvent (e.g., the amount of all organic solvents or a particular organic solvent (e.g., ethanol, etc.)), pressure (e.g., local or global pressure, etc.), atmospheric pressure, viscosity, flow rate (e.g., the flow rate of a medium in which an organism is present, etc.), light intensity (e.g., the quantity of light having a particular wavelength, etc.), light wavelength (e.g., visible light, ultraviolet light, infrared light, etc.), electromagnetic waves, radiation, gravity, tension, acoustic waves, organisms other than an organism of interest (e.g., parasites, pathogenic bacteria, etc.), chemicals (e.g., pharmaceuticals, etc.), antibiotics, naturally-occurring substances, metal stresses, physical stresses, and the like.

As used herein, the term "environment" (or "Umgebung" in German) in relation to an entity refers to a circumstance which surrounds the entity. In an environment, various components and quantities of state are recognized, which are called environmental factors. Examples of environmental factors include the above-described parameters. Environmental factors are typically roughly divided into non-biological environmental factors and biological environmental factors. Non-biological environmental factors (inorganic environment factors) may be divided into physical factors and chemical factors, or alternatively, climatic factors and soil factors. Various environmental factors do not always act on organisms independently, but may be associated with one another. Therefore, environment factors may be herein observed one by one or as a whole (a whole of various parameters). It has been believed that it was difficult to maintain such an environment in a consistent state. This is particularly the case since it has been difficult to maintain cells and to immobilize cells, and to introduce substances such as nucleic acids into a cell. The present invention has also solved at least one of these problems. As used herein the term "consistent environment" refers to substantially all of the circumstances surrounding a cell of interest. Accordingly, as long as a cell can grow or differentiate in a similar manner, such environments are deemed to be consistent environments. As used herein, a consistent environment refers to an environment where the parameters are the same except for a specific stimulus (for example, an external stimulus).

Examples of such an environment include at least one factor, as a parameter, selected from the group consisting of temperature, humidity, pH, salt concentration, nutrients, metal, gas, organic solvent, pressure, atmospheric pressure, viscosity, flow rate, light intensity, light wavelength, electromagnetic waves, radiation, gravity, tension, acoustic waves, organisms (e.g., parasites, etc.) other than the organism, chemical agents, antibiotics, natural substances, mental stress, and physical stress, and any combination thereof.

Examples of temperature include, but are not limited to, high temperature, low temperature, very high temperature (e.g., 95° C., etc.), very low temperature (e.g., −80° C., etc.), a wide range of temperature (e.g., 150 to −270° C., etc.), and the like.

Examples of humidity include, but are not limited to, a relative humidity of 100%, a relative humidity of 0%, an arbitrary point from 0% to 100%, and the like.

Examples of pH include, but are not limited to, an arbitrary point from 0 to 14, and the like.

Examples of salt concentration include, but are not limited to, a NaCl concentration (e.g., 3%, etc.), an arbitrary point of other salt concentrations from 0 to 100%, and the like.

Examples of nutrients include, but are not limited to, proteins, glucose, lipids, vitamins, inorganic salts, and the like.

Examples of metals include, but are not limited to, heavy metals (e.g., mercury, cadmium, etc.), lead, gold, uranium, silver, and the like.

Examples of gas include, but are not limited to, oxygen, nitrogen, carbon dioxide, carbon monoxide, and a mixture thereof, and the like.

Examples of organic solvents include, but are not limited to, ethanol, methanol, xylene, propanol, and the like.

Examples of pressure include, but are not limited to, an arbitrary point from 0 to 10 ton/cm$^2$, and the like.

Examples of atmospheric pressure include, but are not limited to, an arbitrary point from 0 to 100 atmospheric pressure, and the like.

Examples of viscosity include, but are not limited to the viscosity of any fluid (e.g., water, glycerol, etc.) or a mixture thereof, and the like.

Examples of flow rate include, but are not limited to an arbitrary point from 0 to the velocity of light.

Examples of light intensity include, but are not limited to, a point between darkness and the level of sunlight.

Examples of light wavelength include, but are not limited to visible light, ultraviolet light (UV-A, UV-B, UV-C, etc.), infrared light (far infrared light, near infrared light, etc.), and the like.

Examples of electromagnetic waves include ones having an arbitrary wavelength.

Examples of radiation include ones having an arbitrary intensity.

Examples of gravity include, but are not limited to, an arbitrary gravity on the Earth or an arbitrary point from zero gravity to the gravity on the Earth, or an arbitrary gravity greater than or equal to a gravity on the Earth.

Examples of tension include ones having an arbitrary strength.

Examples of acoustic waves include ones having an arbitrary intensity and wavelength.

Examples of organisms other than an organism of interest include, but are not limited to, parasites, pathogenic bacteria, insects, nematodes, and the like.

Examples of chemicals include, but are not limited to hydrochloric acid, sulfuric acid, sodium hydroxide, and the like.

Examples of antibiotics include, but are not limited to, penicillin, kanamycin, streptomycin, quinoline, and the like.

Examples of naturally-occurring substances include, but are not limited to, puffer toxin, snake venom, alkaloid, and the like.

Examples of mental stress include, but are not limited to starvation, population density, confined spaces, high places, and the like.

Examples of physical stress include, but are not limited to vibration, noise, electricity, impact, and the like.

As used herein when referring to a digital cell of the present invention, the environment is presented as an "environment parameter". Such environment parameters include, but are not limited to, medium (type, composition), pH, temperature, moisture, $CO_2$ concentration, $O_2$ concentration, the presence or absence of an antibiotic, the presence or absence of a particular nutrient and the like.

As used herein the term "stimulant" refers to an acting agent which causes or induces expression or enhancement of a specific living action given to a cell from outside. Stimuli include, but are not limited to: a physical stimulus, a chemical stimulus, a biological stimulus, a biochemical stimulus, and the like. Physical stimuli include, but are not limited to: for example, light, electric waves, electric current, pressure, sound (vibration) and the like. Chemical stimuli include but are not limited to: for example, stimuli from chemicals such as antibiotics, nutrients, vitamins, metals, ions, acids, alkalis, salts, buffers and the like. Biological stimuli include, but are not limited to: for example, the existence of another organism such as the existence of a parasitic organism or the density of a cell population and the like. Biochemical stimuli include, but are not limited to the existence of cell signaling transduction agents, and the like.

As used herein, when the digital cell of the present invention is used, a stimulus is presented as a "stimulus parameter". A stimulus parameter corresponding to those in response to any stimulus as described herein may be used. As used herein, it should be understood that the stimulus parameter includes agents for transducing a stimulus such as a reporter and the like. Such reporters include, but are not limited to: for example, on-off regulation of expression against an antibiotic, a transcription-controlling sequence, radioactivity, fluorophores and the like.

As used herein the term "response" to a stimulus refers to any response of a cell to a stimulus such as a change in cell morphology, change in metabolism, change in other cellular behaviors, change in signal transduction and the like. Therefore, for example, results of experiments using the digital cell of the present invention may be recorded as cell dynamics data. Alternatively, when using the above reporter, the result of such a response to the stimulus may be raw data of the reporter, or data transformed from the data of the reporter.

As used herein, the term "transcription control sequence" refers to a sequence which can regulate the transcription level of a gene. Such a sequence is at least two nucleotides in length. Examples of such a sequence include, but are not limited to, promoters, enhancers, silencers, terminators, sequences flanking other genomic structural genes, genomic sequences other than exons, sequences within exons, and the like. A transcription control sequence used herein is not related to a particular type. Rather, important information about a transcription control sequence is time-lapse fluctuation. Such fluctuation is referred to as a process (changes in a state of a cell). Therefore, such a transcription control sequence may be herein arbitrarily selected. Such a transcription control sequence may include those which are not conventionally used as markers. Preferably, a transcription control sequence has the ability to bind to a transcription factor.

As used herein, the term "transcription factor" refers to a factor which regulates the process of transcription of a gene. The term "transcription factor" mainly indicates a factor which regulates a transcription initiation reaction. Transcription factors are roughly divided into the following groups: basic transcription factors required for placing an RNA polymerase into a promoter region on DNA; and transcription regulatory factors which bind to cis-acting elements present upstream or downstream of a transcription region to regulate the synthesis initiation frequency of RNA.

Basic transcription factors are prepared depending on the type of RNA polymerase. A TATA-binding protein is believed to be common to all transcription systems. Although there are a number of types of transcription factors, a typical transcription factor consists of a portion structurally required for binding to DNA and a portion required for activating or suppressing transcription. Factors which have a DNA-binding portion and can bind to cis-acting elements are collectively referred to as trans-acting factors.

A portion required for activating or suppressing transcription is involved in interaction with other transcription factors or basic transcription factors. Such a portion is believed to play a role in regulating transcription via a structural change in DNA or a transcription initiating complex. Transcription regulatory factors are divided into several groups or families according to the structural properties of these portions, including factors which play an important role in the development or differentiation of a cell.

Examples of such a transcription factor include, but are not limited to, STAT1, STAT2, STAT3, GAS, NFAT, Myc, AP1, CREB, NFκB, E2F, Rb, p53, RUNX1, RUNX2, RUNX3, Nkx-2, CF2-II, Skn-1, SRY, HFH-2, Oct-1, Oct-3, Sox-5, HNF-3b, PPARγ, and the like.

As used herein, the term "terminator" refers to a sequence which is located downstream of a protein-encoding region of a gene and which is involved in the termination of transcription when DNA is transcribed into mRNA, and the addition of a poly-A sequence. It is known that a terminator contributes to the stability of mRNA, and has an influence on the level of gene expression.

As used herein, the term "promoter" refers to a base sequence which determines the initiation site of transcription of a gene and is a DNA region which directly regulates the frequency of transcription. Transcription is started by RNA polymerase binding to a promoter. A promoter region is usually located within about 2 kbp upstream of the first exon of a putative protein coding region. Therefore, it is possible to estimate a promoter region by predicting a protein coding region in a genomic base sequence using DNA analysis software. A putative promoter region is usually located upstream of a structural gene, but is dependent on the structural gene, i.e., a putative promoter region may be located downstream of a structural gene. Preferably, a putative promoter region is located within about 2 kbp upstream of the translation initiation site of the first exon. Such promoters include, but are not limited to constitutive promoters, specific promoters and inductive promoters and the like.

As used herein, the term "enhancer" refers to a sequence which is used so as to enhance the expression efficiency of a gene of interest. One or more enhancers may be used, or no enhancer may be used.

As used herein, the term "silencer" refers to a sequence which has a function of suppressing and arresting the expression of a gene. Any silencer which has such a function may be herein used. No silencer may be used.

As used herein, the term "operably linked" indicates that a desired sequence is located such that expression (operation) thereof is under control of a transcription and translation regulatory sequence (e.g., a promoter, an enhancer, and the like) or a translation regulatory sequence. In order for a promoter to be operably linked to a gene, typically, the promoter is located immediately upstream of the gene. A promoter is not necessarily adjacent to a structural gene.

Sequences flanking other genome structural genes, genomic sequences other than exons, and sequences within exons may also be herein used. For example, in addition to the above-described sequences having specific names, structural gene-flanking sequences are thought to be involved in the control of transcription in terms of "processes". Therefore, such flanking sequences are also included in transcription control sequences. Genomic sequences other than exons and sequences within exons are also expected to be involved in the control of transcription in terms of "processes". Therefore, genomic sequences other than exons and sequences within exons are also included in transcription control sequences.

As used herein, the term "RNAi" is an abbreviation of RNA interference and refers to a phenomenon where an agent for causing RNAi, such as double-stranded RNA (also called dsRNA), is introduced into cells and mRNA homologous thereto is specifically degraded, so that the synthesis of gene products is suppressed, and techniques using the phenomenon. As used herein, RNAi may have the same meaning as that of an agent which causes RNAi.

As used herein, the term "an agent causing RNAi" refers to any agent capable of causing RNAi. As used herein, "an agent causing RNAi of a gene" indicates that the agent causes RNAi relating to the gene and that the effect of RNAi is achieved (e.g., suppression of expression of the gene, and the like). Examples of such an agent causing RNAi include, but are not limited to, a sequence having at least about 70% homology to the nucleic acid sequence of a target gene or a sequence hybridizable thereto under stringent conditions, RNA containing a double-stranded portion having a length of at least 10 nucleotides or variants thereof. Here, this agent may be preferably DNA containing a 3' protruding end, and more preferably the 3' protruding end has a length of 2 or more nucleotides (e.g., 2-4 nucleotides in length).

Though not wishing to be bound by any theory, a mechanism which causes RNAi is considered to be as follows. When a molecule which causes RNAi, such as dsRNA, is introduced into a cell, an RNaseIII-like nuclease having a helicase domain (called dicer) cleaves the molecule at about 20 base pair intervals from the 3' terminus in the presence of ATP in the case where the RNA is relatively long (e.g., 40 or more base pairs). As used herein, the term "siRNA" is an abbreviation of short interfering RNA and refers to short double-stranded RNA of 10 or more base pairs which are artificially chemically synthesized or biochemically synthesized, synthesized by an organism, or produced by double-stranded RNA of about 40 or more base pairs being degraded within the organism. siRNA typically has a structure comprising 5'-phosphate and 3'-OH, where the 3' terminus projects by about 2 bases. A specific protein is bound to siRNA to form RISC (RNA-induced-silencing-complex). This complex recognizes and binds to mRNA having the same sequence as that of siRNA and cleaves mRNA at the middle of siRNA due to RNaseIII-like enzymatic activity. It is preferable that the relationship between the sequence of siRNA and the sequence of mRNA to be cleaved as a target is a 100% match. However, base mutations at a site away from the middle of siRNA do not completely remove the cleavage activity by RNAi, leaving partial activity, while base mutations in the middle of siRNA have a large influence and the mRNA cleavage activity by RNAi is considerably lowered. By utilizing such a nature, only mRNA having a mutation can be specifically degraded. Specifically, siRNA in which the mutation is provided in the middle thereof is synthesized and is introduced into a cell. Therefore, in the present invention, siRNA per se, as well as an agent capable of producing siRNA (e.g., representatively dsRNA of about 40 or more base pairs) can be used as an agent capable of eliciting RNAi.

Also, though not wishing to be bound by any theory, apart from the above-described pathway, the antisense strand of siRNA binds to mRNA and siRNA functions as a primer for RNA-dependent RNA polymerase (RdRP), so that dsRNA is synthesized. This dsRNA is a substrate for a dicer again, leading to production of new siRNA. It is intended that such a reaction is amplified. Therefore, in the present invention, siRNA per se, as well as an agent capable of producing siRNA are useful. In fact, in insects and the like, for example, 35 dsRNA molecules can substantially completely degrade 1,000 or more copies of intracellular mRNA, and therefore, it will be understood that siRNA per se, as well as an agent capable of producing siRNA, is useful.

In the present invention, double-stranded RNA having a length of about 20 bases (e.g., representatively about 21 to 23 bases) or less than about 20 bases, called siRNA, can be used. Expression of siRNA in cells can suppress expression of a pathogenic gene targeted by the siRNA. Therefore, siRNA can be used for the treatment, prophylaxis, prognosis, and the like of diseases.

The siRNA of the present invention may be in any form as long as it can elicit RNAi.

In another embodiment, an agent capable of causing RNAi may have a short hairpin structure having a sticky portion at the 3' terminus (shRNA; short hairpin RNA). As used herein, the term "shRNA" refers to a molecule of about 20 or more base pairs in which a single-stranded RNA partially contains a palindromic base sequence and forms a double-strand structure therein (i.e., a hairpin structure). shRNA can be artificially chemically synthesized. Alternatively, shRNA can be produced by linking sense and antisense strands of a DNA sequence in reverse directions and synthesizing RNA in vitro with T7 RNA polymerase using the DNA as a template. Though not wishing to be bound by any theory, it should be understood that after shRNA is introduced into a cell, the shRNA is degraded in the cell to a length of about 20 bases (e.g., representatively 21, 22, 23 bases), and causes RNAi as with siRNA, leading to the treatment effects of the present invention. It should be understood that such an effect is exhibited in a wide range of organisms, such as insects, plants, animals (including mammals), and the like. Thus, shRNA elicits RNAi as with siRNA and therefore can be used as an effective component of the present invention. shRNA may preferably have a 3' protruding end. The length of the double-stranded portion is not particularly limited, but is preferably about 10 or more nucleotides, and more preferably about 20 or more nucleotides. Here, the 3' protruding end may be preferably DNA, more preferably DNA of at least 2 nucleotides in length, and even more preferably DNA of 2-4 nucleotides in length.

An agent capable of causing RNAi used in the present invention may be artificially synthesized (chemically or biochemically) or naturally occurring. There is substantially no difference there between in terms of the effect of the present invention. A chemically synthesized agent is preferably purified by liquid chromatography or the like.

An agent capable of causing RNAi used in the present invention can be produced in vitro. In this synthesis system, T7 RNA polymerase and T7 promoter are used to synthesize antisense and sense RNAs from template DNA. These RNAs are annealed and thereafter introduced into a cell. In this case, RNAi is caused via the above-described mechanism, thereby achieving the effect of the present invention. Here, for example, the introduction of RNA into cell can be carried out using a calcium phosphate method.

Another example of an agent capable of causing RNAi according to the present invention is a single-stranded nucleic acid hybridizable to mRNA, or all nucleic acid analogs thereof. Such agents are useful for the method and composition of the present invention.

As used herein, the term "time-lapse" means any action or phenomenon that is related to the passage of time.

As used herein, the term "monitor" refers to the measurement of a state of a cell using at least one parameter as a measure (e.g., a labeling signal attributed to transcription, etc.). Preferably, monitoring is performed using a device, such as a detector, a measuring instrument, or the like. More preferably, such a device is connected to a computer for recording and/or processing data. Monitoring may comprise the step of obtaining image data of a solid phase support (e.g., an array, a plate, etc.).

As used herein, the term "real time" means that a certain state is substantially simultaneously displayed in another form (e.g., as an image on a display or a graph with processed data). In such a case, the "real time" lags behind an actual event by the time required for data processing. Such a time lag is included in the scope of "real time" if it is substantially negligible. Such a time lag may be typically within 10 seconds, and preferably within 1 second, without limitation. A time lag exceeding 10 seconds may be included in the scope of "real time".

As used herein, the determination of a state of a cell can be performed using various methods. Examples of such methods include, but are not limited to, mathematical processing (e.g., signal processing, multivariate analysis, etc.), empirical processing, phase changes, and the like.

As used herein, the term "difference" refers to a result of mathematical processing in which a value of a control profile (e.g., without a stimulus) is subtracted from a certain profile.

As used herein, the term "phase" in relation to a time-lapse profile refers to a result of a determination of whether the profile is positive or negative with respect to a reference point (typically 0), which is expressed with + or −, and also refers to analysis based on such a result.

As used herein, the term "correlate" or "correlation" in relation to a profile (e.g., a time-lapse profile, etc.) and a state of a cell refers to an act of associating the profile or particular information about changes, with the state of the cell. A relationship between them is referred to as "correlation" or a "correlation relationship". Conventionally, it was substantially impossible to associate a profile (e.g., a time-lapse profile, etc.) with a state of a cell. No relationship between them was known. The present invention has an advantageous effect of performing such a correlation.

As used herein, correlation can be performed by associating at least one profile (e.g., a time-lapse profile, etc.) or changes therein, with a state of a cell, a tissue, an organ or an organism (e.g., drug resistance, etc.). For example, a profile (e.g., a time-lapse profile, etc.) or changes therein is quantitatively or qualitatively associated with at least one parameter indicating a state of a cell. A small number of profiles (e.g., time-lapse profile, etc.) may be used for correlation as long as correlation can be performed, typically including, without limitation, 1, preferably 2, and more preferably 3. The present invention demonstrated that at least 2, preferably at least 3, profiles (e.g., a time-lapse profile, etc.) are sufficient for specifying substantially all cells. Such an effect could not be expected by conventional profiling or assays which use point observation, and can be said to be realized by the present invention. At least one profile (e.g., a time-lapse profile, etc.) may be subjected to mathematical processing by utilizing a matrix to associate the profile with a state of a cell. In one preferred embodiment, at least 8 profiles (e.g., a time-lapse profile, etc.) may be advantageously used. By observing increases or decreases in 8 profiles, 256 results can be theoretically obtained, based on which about 300 types of cells constituting an organism can be substantially distinguished from one another. In this context, it may be more advantageous to use at least 9 or 10 structures as profiles. On the other hand, by using the technology of the present invention, it is possible to substantially understand the state of a cell, merely by selecting any single biological agent and obtaining the profile data thereof.

Examples of a specific method for correlation include, but are not limited to, signal processing (e.g., wavelet analysis, etc.), multivariate analysis (e.g., cluster analysis, etc.), and the like.

Correlation may be performed in advance or may be performed at the time of determination of cells using a control.

As used herein, the term "external factor" in relation to a cell refers to a factor which is not usually present in the cell (e.g., a substance, energy, etc.). As used herein, the term "factor" may refer to any substance or element as long as an intended object can be achieved (e.g., energy, such as ionizing radiation, radiation, light, acoustic waves, and the like). Examples of such a substance include, but are not limited to, proteins, polypeptides, oligopeptides, peptides, polynucleotides, oligonucleotides, nucleotides, nucleic acids (e.g., DNA such as cDNA, genomic DNA and the like, or RNA such as mRNA, RNAi and the like), polysaccharides, oligosaccharides, lipids, low molecular weight organic molecules (e.g., hormones, ligands, information transduction substances, low molecular weight organic molecules, molecules synthesized by combinatorial chemistry, low molecular weight molecules usable as medicaments (e.g., low molecular weight molecule ligands, etc.), etc.), and composite molecules thereof. External factors may be used singly or in combination. Examples of an external factor as used herein include, but are not limited to, temperature changes, humidity changes, electromagnetic wave, potential difference, visible light, infrared light, ultraviolet light, X-rays, chemical substances, pressure, gravity changes, gas partial pressure, osmotic pressure, and the like. In one embodiment, an external factor may be a biological molecule or a chemically synthesized substance.

As used herein, the term "biological molecule" refers to molecules relating to an organism and aggregations thereof. As used herein, the term "biological" or "organism" refers to a biological organism, including, but being not limited to, an animal, a plant, a fungus, a virus, and the like. Biological molecules include molecules extracted from an organism and aggregations thereof, though the present invention is not limited to this. Any molecule capable of affecting an organism and aggregations thereof fall within the definition of a biological molecule. Therefore, low molecular weight molecules (e.g., low molecular weight molecule ligands, etc.), capable of being used as medicaments fall within the definition of a biological molecule as long as an effect on an organism is intended. Examples of such a biological molecule include, but are not limited to, proteins, polypeptides, oligopeptides, peptides, polynucleotides, oligonucleotides, nucleotides, nucleic acids (e.g., DNA such as cDNA and genomic DNA; RNA such as mRNA), polysaccharides, oligosaccharides, lipids, low molecular weight molecules (e.g., hormones, ligands, information transmitting substances, low molecular weight organic molecules, etc.), and composite molecules thereof and aggregations thereof (e.g., glycolipids, glycoproteins, lipoproteins, etc.), and the like. A biological molecule may include a cell itself or a portion of tissue as long as it is intended to be introduced into a cell. Typically, a biological molecule may be a nucleic acid, a protein, a lipid, a sugar, a proteolipid, a lipoprotein, a glycoprotein, a proteoglycan, or the like. Preferably, a biological molecule may include a nucleic acid (DNA or RNA) or a protein. In another preferred embodiment, a biological molecule is a nucleic acid (e.g., genomic DNA or cDNA, or DNA synthesized by PCR or the like). In another preferred embodiment, a biological molecule may be a protein. Preferably, such a biological molecule may be a hormone or a cytokine.

As used herein, the term "chemically synthesized substance" or "chemical" refers to any substance which may be synthesized by using typical chemical techniques. Such synthesis techniques are well known in the art. Those skilled in the art can produce chemically synthesized substances by combining such techniques as appropriate.

The term "cytokine" is used herein in the broadest sense in the art and refers to a physiologically active substance which is produced by a cell and acts on the same or a different cell. Cytokines are generally proteins or polypeptides having a function of controlling an immune response, regulating the endocrine system, regulating the nervous system, acting against a tumor, acting against a virus, regulating cell growth, regulating cell differentiation, or the like. Cytokines are used herein in the form of a protein or a nucleic acid or in other forms. In actual practice, cytokines are typically proteins. The terms "growth factor" refers to a substance which promotes or controls cell growth. Growth factors are also called "proliferation factors" or "development factors". Growth factors may be added to cell or tissue culture medium, substituting for serum macromolecules. It has been revealed that a number of growth factors have a function of controlling differentiation in addition to a function of promoting cell growth. Examples of cytokines representatively include, but are not limited to, interleukins, chemokines, hematopoietic factors (e.g., colony stimulating factors), tumor necrosis factor, and interferons. Representative examples of growth factors include, but are not limited to, platelet-derived growth factor (PDGF), epidermal growth factor (EGF), fibroblast growth factor (FGF), hepatocyte growth factor (HGF), endothelial cell growth factor (VEGF), cardiotrophin, and the like, which have proliferative activity.

The term "hormone" is herein used in its broadest sense in the art, referring to a physiological organic compound which is produced in a particular organ or cell of an animal or plant, and has a physiological effect on an organ apart from the site producing the compound. Examples of such a hormone include, but are not limited to, growth hormones, sex hormones, thyroid hormones, and the like. The scope of hormones may overlap partially with that of cytokines.

As used herein, the term "actin-like substance" refers to a substance which interacts directly or indirectly with actin within cells to alter the form or state of actin. Examples of such a substance include, but are not limited to, extracellular matrix proteins (e.g., fibronectin, vitronectin, laminin, etc.), and the like. Such actin-like substances include substances identified by the following assays. As used herein, interaction with actin is evaluated by visualizing actin with an actin staining reagent (Molecular Probes, Texas Red-X phalloidin) or the like, followed by microscopic inspection to observe and determine actin aggregation, actin reconstruction or an improvement in cellular outgrowth rate. Such evaluation may be performed quantitatively or qualitatively. Actin-like substances are herein utilized so as to increase transfection efficiency. An actin-like substance used herein is derived from any organism, including, for example, mammals, such as human, mouse, bovine, and the like.

As used herein, the terms "cell adhesion agent", "cell adhesion molecule", "adhesion agent" and "adhesion molecule" are used interchangeably to refer to a molecule capable of mediating the joining of two or more cells (cell adhesion) or adhesion between a substrate and a cell. In general, cell adhesion molecules are divided into two groups: molecules involved in cell-cell adhesion (intercellular adhesion) (cell-cell adhesion molecules) and molecules involved in cell-extracellular matrix adhesion (cell-substrate adhesion) (cell-substrate adhesion molecules). For a method of the present invention, either type of molecule is useful and can be effectively used. Therefore, cell adhesion molecules herein include a substrate protein and a cellular protein (e.g., integrin, etc.) involved in cell-substrate adhesion. A molecule other than a protein can fall within the concept of a cell adhesion molecule as long as it can mediate cell adhesion.

For cell-cell adhesion, cadherin, a number of molecules belonging in an immunoglobulin superfamily (NCAM, L1, ICAM, fasciclin II, III, etc.), selectin, and the like are known, each of which is known to connect cell membranes via a specific molecular reaction.

On the other hand, a major cell adhesion molecule functioning for cell-substrate adhesion is integrin, which recognizes and binds to various proteins contained in extracellular matrices. These cell adhesion molecules are all located on cell membranes and can be regarded as a type of receptor (cell adhesion receptor). Therefore, receptors present on cell membranes can also be used in a method of the present invention. Examples of such a receptor include, but are not limited to, α-integrin, β-integrin, CD44, syndecan, aggrecan, and the like. Techniques for cell adhesion are well known as described above and as described in, for example, "Saibogaimatorikkusu-Rinsho heno Oyo-[Extracellular matrix— Clinical Applications—], Medical Review.

It can be determined whether or not a certain molecule is a cell adhesion molecule, by an assay, such as biochemical quantification (an SDS-PAGE method, a labeled-collagen method, etc.), immunological quantification (an enzyme antibody method, a fluorescent antibody method, an immunohistological study, etc.), a PDR method, a hybridization method, or the like, in which a positive reaction is detected. Examples of such a cell adhesion molecule include, but are not limited to, collagen, integrin, fibronectin, laminin, vitronectin, fibrinogen, immunoglobulin superfamily members (e.g., CD2, CD4, CD8, ICM1, ICAM2, VCAM1), selectin, cadherin, and the like. Most of these cell adhesion molecules transmit an auxiliary signal for cell activation into a cell due to intercellular interaction as well as cell adhesion. It can be determined whether or not such an auxiliary signal can be transmitted into a cell, by an assay, such as biochemical quantification (an SDS-PAGE method, a labeled-collagen method, etc.), immunological quantification (an enzyme antibody method, a fluorescent antibody method, an immunohistological study, etc.), a PDR method, a hybridization method, or the like, in which a positive reaction is detected.

Examples of cell adhesion molecules include, but are not limited to, immunoglobulin superfamily molecules (LFA-3, ICAM-1, CD2, CD4, CD8, ICM1, ICAM2, VCAM1, etc.); integrin family molecules (LFA-1, Mac-1, gpIIbIIIa, p150, p95, VLA1, VLA2, VLA3, VLA4, VLA5, VLA6, etc.); selectin family molecules (L-selectin, E-selectin, P-selectin, etc.), and the like.

As used herein, the term "extracellular matrix protein" refers to a protein constituting an "extracellular matrix". As used herein, the term "extracellular matrix" (ECM) is also called "extracellular substrate" and has the same meaning as commonly used in the art, and refers to a substance existing between somatic cells no matter whether the cells are epithelial cells or non-epithelial cells. Extracellular matrices are involved in supporting tissue as well as in internal environmental structures essential for survival of all somatic cells. Extracellular matrices are generally produced from connective tissue cells. Some extracellular matrices are secreted from cells possessing basal membrane, such as epithelial cells or endothelial cells. Extracellular matrices are roughly divided into fibrous components and matrices filling there between. Fibrous components include collagen fibers and elastin fibers. A basic component of matrices is glycosaminoglycan (acidic mucopolysaccharide), most of which is bound to non-collagenous protein to form a polymer of a proteoglycan (acidic mucopolysaccharide-protein complex). In addition, matrices include glycoproteins, such as laminin of basal membrane, microfibrils around elastin fibers, fibers, fibronectins on cell surfaces, and the like. Specifically differentiated tissue has the same basic structure. For example, in hyaline cartilage, chondroblasts characteristically produce a large amount of cartilage matrices including proteoglycans. In bones, osteoblasts produce bone matrices which cause calcification. Examples of extracellular matrices for use in the present invention include, but are not limited to, collagen, elastin, proteoglycan, glycosaminoglycan, fibronectin, laminin, elastic fiber, collagen fiber, and the like.

As used herein, the term "receptor" refers to a molecule which is present on cells, within nuclei, or the like, and is capable of binding to an extracellular or intracellular agent where the binding mediates signal transduction. Receptors are typically in the form of proteins. The binding partner of a receptor is usually referred to as a ligand.

As used herein, the term "agonist" refers to an agent which binds to the receptor of a certain biologically acting substance (e.g., ligand, etc.), and has the same or similar function as the function of the substance.

As used herein, the term "antagonist" refers to a factor which competitively binds to the receptor of a certain biologically acting substance (ligand), and does not produce a physiological action via the receptor. Antagonists include antagonist drugs, blockers, inhibitors, and the like.

(Devices and Solid Phase Supports)

As used herein, the term "device" refers to a part which can constitute the whole or a portion of an apparatus, and comprises a support (preferably, a solid phase support) and a target substance carried thereon. Examples of such a device include, but are not limited to, chips, arrays, microtiter plates, cell culture plates, Petri dishes, films, beads, and the like.

As used herein, the term "support" refers to a material which can fix a substance, such as a biological molecule. Such a support may be made from any fixing material which has a capability of binding to a biological molecule as used herein via covalent or noncovalent bonds, or which may be induced to have such a capability.

Examples of materials used for supports include any material capable of forming a solid surface, such as, without limitation, glass, silica, silicon, ceramics, silicon dioxide, plastics, metals (including alloys), naturally-occurring and synthetic polymers (e.g., polystyrene, cellulose, chitosan, dextran, and nylon), and the like. A support may be formed of layers made of a plurality of materials. For example, a support may be made of an inorganic insulating material, such as glass, quartz glass, alumina, sapphire, forsterite, silicon oxide, silicon carbide, silicon nitride, or the like. A support may be made of an organic material, such as polyethylene, ethylene, polypropylene, polyisobutylene, polyethylene terephthalate, unsaturated polyester, fluorine-containing resin, polyvinyl chloride, polyvinylidene chloride, polyvinyl acetate, polyvinyl alcohol, polyvinyl acetal, acrylic resin, polyacrylonitrile, polystyrene, acetal resin, polycarbonate, polyamide, phenol resin, urea resin, epoxy resin, melamine resin, styrene-acrylonitrile copolymer, acrylonitrile-butadiene-styrene copolymer, silicone resin, polyphenylene oxide, polysulfone, and the like. Also in the present invention, nitrocellulose film, nylon film, PVDF film, or the like, which are used in blotting, may be used as a material for a support. When a material constituting a support is in the solid phase, such a support is herein particularly referred to as a "solid phase support". A solid phase support may be herein in the form of a plate, a microwell plate, a chip, a glass slide, a film, beads, a metal (surface), or the like. A support may be uncoated or may be coated.

As used herein, the term "liquid phase" has the same meanings as are commonly understood by those skilled in the art, typically referring to a state in solution.

As used herein, the term "solid phase" has the same meanings as are commonly understood by those skilled in the art, typically referring to a solid state. As used herein, liquid and solid may be collectively referred to as a "fluid".

As used herein, the term "substrate" refers to a material (preferably, solid) which is used to construct a chip or array according to the present invention. Therefore, substrates are included in the concept of plates. Such a substrate may be made from any solid material which has a capability of binding to a biological molecule as used herein via covalent or noncovalent bonds, or which may be induced to have such a capability.

Examples of materials used for plates and substrates include any material capable of forming a solid surface, such as, without limitation, glass, silica, silicon, ceramics, silicon dioxide, plastics, metals (including alloys), naturally-occurring and synthetic polymers (e.g., polystyrene, cellulose, chitosan, dextran, and nylon), and the like. A support may be formed of layers made of a plurality of materials. For example, a support may be made of an inorganic insulating material, such as glass, quartz glass, alumina, sapphire, forsterite, silicon oxide, silicon carbide, silicon nitride, or the like. A support may be made of an organic material, such as polyethylene, ethylene, polypropylene, polyisobutylene, polyethylene terephthalate, unsaturated polyester, fluorine-containing resin, polyvinyl chloride, polyvinylidene chloride, polyvinyl acetate, polyvinyl alcohol, polyvinyl acetal, acrylic resin, polyacrylonitrile, polystyrene, acetal resin, polycarbonate, polyamide, phenol resin, urea resin, epoxy resin, melamine resin, styrene-acrylonitrile copolymer, acrylonitrile-butadiene-styrene copolymer, silicone resin, polyphenylene oxide, polysulfone, and the like. A material preferable as a substrate varies depending on various parameters such as a measuring device, and can be selected from the above-described various materials as appropriate by those skilled in the art. For transfection arrays, glass slides are preferable. Preferably, such a substrate may be coated with a substance or have a coating.

As used herein, the term "coating" in relation to a solid phase support or substrate refers to an act of forming a film of a material on a surface of the solid phase support or substrate, and also refers to a film itself. Coating is performed for various purposes, such as, for example, improvement in the quality of a solid phase support and substrate (e.g., elongation of life span, improvement in resistance to hostile environment, such as resistance to acids, etc.), an improvement in affinity to a substance integrated with a solid phase support or substrate, and the like. Various materials may be used for such coating, including, without limitation, biological substances (e.g., DNA, RNA, protein, lipid, etc.), polymers (e.g., poly-L-lysine, MAS (available from Matsunami Glass, Kishiwada, Japan), and hydrophobic fluorine resin), silane (APS (e.g., γ-aminopropylsilane, etc.)), metals (e.g., gold, etc.), in addition to the above-described solid phase support and substrate. The selection of such materials is within the technical scope of those skilled in the art and thus can be performed using techniques well known in the art. In one preferred embodiment, such a coating may be advantageously made of poly-L-lysine, silane (e.g., epoxy silane or mercaptosilane, APS (γ-aminopropyl silane), etc.), MAS, hydrophobic fluorine resin, a metal (e.g., gold, etc.). Such a material may be preferably a substance suitable for cells or objects containing cells (e.g., organisms, organs, etc.).

As used herein, the terms "chip" or "microchip" are used interchangeably to refer to a micro-integrated circuit which has versatile functions and constitutes a portion of a system. Examples of a chip include, but are not limited to, DNA chips, protein chips, and the like.

As used herein, the term "array" refers to a substrate (e.g., a chip, etc.) which has a pattern of a composition containing at least one (e.g., 1000 or more, etc.) target substance (e.g., DNA, proteins, transfection mixtures, etc.), which are arrayed. Among arrays, patterned substrates having a small size (e.g., 10×10 mm, etc.) are particularly referred to as microarrays. The terms "microarray" and "array" are used interchangeably. Therefore, a patterned substrate having a larger size than that which is described above may be referred to as a microarray. For example, an array comprises a set of desired transfection mixtures fixed to a solid phase surface or a film thereof. An array preferably comprises at least $10^2$ antibodies of the same or different types, more preferably at least $10^3$, even more preferably at least $10^4$, and still even more preferably at least $10^5$. These antibodies are placed on a surface of up to 125×80 mm, more preferably 10×10 mm. An array includes, but is not limited to, a 96-well microtiter plate, a 384-well microtiter plate, a microtiter plate the size of a glass slide, and the like. A composition to be fixed may contain one or a plurality of types of target substances. Such a number of target substance types may be in the range of from one to the number of spots, including, without limitation, about 10, about 100, about 500, and about 1,000.

As described above, any number of target substances (e.g., proteins, such as antibodies) may be provided on a solid phase surface or film, typically including no more than $10^8$ biological molecules per substrate, in another embodiment no more than $10^7$ biological molecules, no more than $10^6$ biological molecules, no more than $10^5$ biological molecules, no more than $10^4$ biological molecules, no more than $10^3$ biological molecules, or no more than $10^2$ biological molecules. A composition containing more than $10^8$ biological molecule target substances may be provided on a substrate. In these cases, the size of a substrate is preferably small. Particularly, the size of a spot of a composition containing target substances (e.g., proteins such as antibodies) may be as small as the size of a single biological molecule (e.g., 1 to 2 nm order). In some cases, the minimum area of a substrate may be determined based on the number of biological molecules on a substrate. A composition containing target substances, which are intended to be introduced into cells, are herein typically arrayed on and fixed via covalent bonds or physical interaction to a substrate in the form of spots having a size of 0.01 mm to 10 mm.

"Spots" of biological molecules may be provided on an array. As used herein, the term "spot" refers to a certain set of compositions containing target substances. As used herein, the term "spotting" refers to an act of preparing a spot of a composition containing a certain target substance on a substrate or plate. Spotting may be performed by any method, for example, pipetting or the like, or alternatively, by using an automatic device. These methods are well known in the art.

As used herein, the term "address" refers to a unique position on a substrate, which may be distinguished from other unique positions. Addresses are appropriately associated with spots. Addresses can have any distinguishable shape such that substances at each address may be distinguished from substances at other addresses (e.g., optically). A shape defining an address may be, for example, without limitation, a circle, an ellipse, a square, a rectangle, or an irregular shape. Therefore, the term "address" is used to indicate an abstract concept, while the term "spot" is used to indicate a specific concept. Unless it is necessary to distinguish them from each other, the terms "address" and "spot" may be herein used interchangeably.

The size of each address particularly depends on the size of the substrate, the number of addresses on the substrate, the amount of a composition containing target substances and/or available reagents, the size of microparticles, and the level of resolution required for any method used for the array. The size of each address may be, for example, in the range of from 1-2 nm to several centimeters, though the address may have any size suited to an array.

The spatial arrangement and shape which define an address are designed so that the microarray is suited to a particular application. Addresses may be densely arranged or sparsely distributed, or subgrouped into a desired pattern appropriate for a particular type of material to be analyzed.

Microarrays are widely reviewed in, for example, "Genomu Kino Kenkyu Purotokoru [Genomic Function Research Protocol] (Jikken Igaku Bessatsu [Special Issue of Experimental Medicine], Posuto Genomu Jidai no Jikken Koza 1 [Lecture 1 on Experimentation in Post-genome Era), "Genomu Ikagaku to korekarano Genomu Iryo [Genome Medical Science and Futuristic Genome Therapy (Jikken Igaku Zokan [Special Issue of Experimental Medicine]), and the like.

A vast amount of data can be obtained from a microarray. Therefore, data analysis software is important for facilitating correspondence between clones and spots, data analysis, and the like. Such software may be attached to various detection systems (e.g., Ermolaeva O. et al., (1998) Nat. Genet., 20: 19-23). The format of such a database includes, for example, GATC (genetic analysis technology consortium) proposed by Affymetrix.

Micromachining for arrays is described in, for example, Campbell, S. A. (1996), "The Science and Engineering of Microelectronic Fabrication", Oxford University Press; Zaut, P. V. (1996), "Micromicroarray Fabrication: a Practical Guide to Semiconductor Processing", Semiconductor Services; Madou, M. J. (1997), "Fundamentals of Microfabrication", CRC1 5 Press; Rai-Choudhury, P. (1997), "Handbook of Microlithography, Micromachining, & Microfabrication: Microlithography"; and the like, portions related thereto of which are herein incorporated by reference.

(Detection)

In cell analysis or determination in the present invention, various detection methods and means can be used as long as they can be used to detect information attributed to a cell or a substance interacting therewith. Examples of such detection methods and means include, but are not limited to, visual inspection, optical microscopes, confocal microscopes, reading devices using a laser light source, surface plasmon resonance (SPR) imaging, electric signals, chemical or biochemical markers, which may be used singly or in combination.

Examples of such a detecting device include, but are not limited to, fluorescence analyzing devices, spectrophotometers, scintillation counters, CCD, luminometers, and the like. Any means capable of detecting a biological molecule may be used.

As used herein, the term "marker" refers to a biological agent for indicating a level or frequency of a substance or state of interest. Examples of such a marker include, but are not limited to, nucleic acids encoding a gene, gene products, metabolic products, receptors, ligands, antibodies, and the like.

Therefore, as used herein, the term "marker" in relation to a state of a cell refers to an agent (e.g., ligands, antibodies, complementary nucleic acids, etc.) interacting with intracellular factors indicating the state of the cell (e.g., nucleic acids encoding a gene, gene products (e.g., mRNA, proteins, post-transcriptionally modified proteins, etc.), metabolic products, receptors, etc.) in addition to transcription control factors. In the present invention, such a marker may be used to produce a time-lapse profile which is in turn analyzed. Such a marker may preferably interact with a factor of interest. As used herein, the term "specificity" in relation to a marker refers to a property of the marker which interacts with a molecule of interest to a significantly higher extent than with similar molecules. Such a marker is herein preferably present within cells or may be present outside cells.

As used herein, the term "label" refers to a factor which distinguishes a molecule or substance of interest from others (e.g., substances, energy, electromagnetic waves, etc.). Examples of labeling methods include, but are not limited to, RI (radioisotope) methods, fluorescence methods, biotinylation methods, chemoluminance methods, and the like. When the above-described nucleic acid fragments and complementary oligonucleotides are labeled by fluorescence methods, fluorescent substances having different fluorescence emission maximum wavelengths are used for labeling. The difference between each fluorescence emission maximum wavelength may be preferably 10 nm or more. Any fluorescent substance which can bind to a base portion of a nucleic acid may be used, preferably including a cyanine dye (e.g., Cy3 and Cy5 in the Cy Dye™ series, etc.), a rhodamine 6G reagent, N-acetoxy-N-2-acetyl amino fluorine (AAF), AAIF (iodine derivative of AAF), and the like. Examples of fluorescent substances having a difference in fluorescence emission maximum wavelength of 10 nm or more include a combination of Cy5 and a rhodamine 6G reagent, a combination of Cy3 and fluorescein, a combination of a rhodamine 6G reagent and fluorescein, and the like. In the present invention, such a label can be used to alter a sample of interest so that the sample can be detected by detecting means. Such alteration is known in the art. Those skilled in the art can perform such alteration using a method appropriate for a label and a sample of interest.

As used herein, the term "interaction" refers to, without limitation, hydrophobic interactions, hydrophilic interactions, hydrogen bonds, Van der Waals forces, ionic interactions, nonionic interactions, electrostatic interactions, and the like.

As used herein, the term "interaction level" in relation to interaction between two substances (e.g., cells, etc.) refers to the extent or frequency of interaction between the two substances. Such an interaction level can be measured by methods well known in the art. For example, the number of cells which are fixed and actually perform an interaction is counted directly or indirectly (e.g., the intensity of reflected light), for example, without limitation, by using an optical microscope, a fluorescence microscope, a phase-contrast microscope, or the like, or alternatively by staining cells with a marker, an antibody, a fluorescent label or the like specific thereto and measuring the intensity thereof. Such a level can be displayed directly from a marker or indirectly via a label. Based on the measured value of such a level, the number or frequency of genes, which are actually transcribed or expressed in a certain spot, can be calculated.

(Presentation and Display)

As used herein, the terms "display" and "presentation" are used interchangeably to refer to an act of providing a profile obtained by a method of the present invention, or information derived therefrom, directly or indirectly, or in an information-processed form. Examples of such displayed forms include, but are not limited to, various methods, such as graphs, photographs, tables, animations, and the like. Such techniques are described in, for example, METHODS IN CELL BIOLOGY, VOL. 56, ed. 1998, pp: 185-215, A High-Resolution Multimode Digital Microscope System (Sluder & Wolf, Salmon), which discusses application software for automating a microscope and controlling a camera and the design of a hardware device comprising an automated optical microscope, a camera, and a Z-axis focusing device, which can be used herein. Image acquisition by a camera is described in detail in, for example, Inoue and Spring, Video Microscopy, 2d. Edition, 1997, which is herein incorporated by reference.

Real time display can also be performed using techniques well known in the art. For example, after all images are obtained and stored in a semi-permanent memory, or substantially at the same time as when an image is obtained, the image can be processed with appropriate application software to obtain processed data. For example, data may be processed by a method for playing back a sequence of images without interruption, a method for displaying images in real time, or a method for displaying images as a "movie" showing irradiating light as changes or continuation on a focal plane.

In another embodiment, application software for measurement and presentation typically includes software for setting conditions for applying stimuli or conditions for recording detected signals. With such a measurement and presentation application, a computer can have a means for applying a stimulus to cells and a means for processing signals detected from cells, and in addition, can control an optically observing means (a SIT camera and an image filing device) and/or a cell culturing means.

By inputting conditions for stimulation on a parameter setting screen using a keyboard, a touch panel, a mouse, or the like, it is possible to set the desired complex conditions for stimulation. In addition, various conditions, such as a temperature for cell culture, pH, and the like, can be set using a keyboard, a mouse, or the like.

A display screen displays a time-lapse profile detected from a cell or information derived therefrom in real time or after recording. In addition, another recorded profile or information derived therefrom of a cell can be displayed while being superimposed with a microscopic image of the cell. In addition to recorded information, measurement parameters in recording (stimulation conditions, recording conditions, display conditions, process conditions, various conditions for cells, temperature, pH, etc.) can be displayed in real time. The present invention may be equipped with a function of issuing an alarm when a temperature or pH departs from the tolerable range.

On a data analysis screen, it is possible to set conditions for various mathematical analyses, such as Fourier transformation, cluster analysis, FFT analysis, coherence analysis, correlation analysis, and the like. The present invention may be equipped with a function of temporarily displaying a profile, a function of displaying topography, or the like. The results of these analyses can be displayed while being superimposed with microscopic images stored in a recording medium.

(Gene Introduction)

Any technique may be used herein for introduction of a nucleic acid molecule into cells, including, for example, transformation, transduction, transfection, and the like. In the present invention, transfection is preferable.

As used herein, the term "transfection" refers to an act of performing gene introduction or transfection by culturing cells with genomic DNA, plasmid DNA, viral DNA, viral RNA or the like in a substantially naked form (excluding viral particles), or adding such a genetic material into cell suspension to allow the cells to take in the genetic material. A gene introduced by transfection is typically expressed within cells in a temporary manner or may be incorporated into cells in a permanent manner.

Such a nucleic acid molecule introduction technique is well known in the art and commonly used, and is described in, for example, Ausubel F. A. et al., editors, (1988), Current Protocols in Molecular Biology, Wiley, New York, N.Y.; Sambrook J. et al. (1987) Molecular Cloning: A Laboratory Manual, 2nd Ed. and its 3rd Ed., Cold Spring Harbor Laboratory Press, Cold Spring Harbor, N.Y.; Special issue, Jikken Igaku [Experimental Medicine] "Experimental Methods for Gene introduction & Expression Analysis", Yodo-sha, 1997; and the like. Gene introduction can be confirmed by method as described herein, such as Northern blotting analysis and Western blotting analysis, or other well-known, common or routine techniques.

When a gene is mentioned herein, the term "vector" or "recombinant vector" refers to a vector transferring a polynucleotide sequence of interest to a target cell. Such a vector is capable of self-replication or incorporation into a chromosome in a host cell (e.g., a prokaryotic cell, yeast, an animal cell, a plant cell, an insect cell, an individual animal, and an individual plant, etc.), and contains a promoter at a site suitable for transcription of a polynucleotide of the present invention. A vector suitable for performing cloning is referred to as a "cloning vector". Such a cloning vector ordinarily contains a multiple cloning site containing a plurality of restriction sites. Restriction enzyme sites and multiple cloning sites as described above are well known in the art and can be used as appropriate by those skilled in the art depending on the purpose in accordance with publications described herein (e.g., Sambrook et al., supra).

As used herein, the term "expression vector" refers to a nucleic acid sequence comprising a structural gene and a promoter for regulating expression thereof, and in addition, various regulatory elements in a state that allows them to operate within host cells. The regulatory element may include, preferably, terminators, selectable markers such as drug-resistance genes, and enhancers.

Examples of "recombinant vectors" for prokaryotic cells include, but are not limited to, pcDNA3(+), pBluescript-SK (+/−), pGEM-T, pEF-BOS, pEGFP, pHAT, pUC18, pFT-DEST™42GATEWAY (Invitrogen), and the like.

Examples of "recombinant vectors" for animal cells include, but are not limited to, pcDNAI/Amp, pcDNAI, pCDM8 (all commercially available from Funakoshi), pAGE107 [Japanese Laid-Open Publication No. 3-229 (Invitrogen), pAGE103 [J. Biochem., 101, 1307(1987)], pAMo, pAMoA [J. Biol. Chem., 268, 22782-22787(1993)], a retrovirus expression vector based on a murine stem cell virus (MSCV), pEF-BOS, pEGFP, and the like.

Examples of recombinant vectors for plant cells include, but are not limited to, pPCVICEn4HPT, pCGN1548, pCGN1549, pBI221, pBI121, and the like.

Any of the above-described methods for introducing DNA into cells can be used as a vector introduction method, including, for example, transfection, transduction, transformation, and the like (e.g., a calcium phosphate method, a liposome method, a DEAE dextran method, an electroporation method, a particle gun (gene gun) method, and the like), a lipofection method, a spheroplast method (Proc. Natl. Acad. Sci. USA, 84, 1929(1978)), a lithium acetate method (J. Bacteriol., 153, 163(1983); and Proc. Natl. Acad. Sci. USA, 75, 1929(1978)), and the like.

As used herein, the term "operably linked" indicates that a desired sequence is located such that expression (operation) thereof is under control of a transcription and translation regulatory sequence (e.g., a promoter, an enhancer, and the like) or a translation regulatory sequence. In order for a promoter to be operably linked to a gene, typically, the promoter is located immediately upstream of the gene. A promoter is not necessarily adjacent to a structural gene.

As used herein, the term "gene introduction reagent" refers to a reagent which is used in a gene introduction method so as to enhance introduction efficiency. Examples of such a gene introduction reagent include, but are not limited to, cationic polymers, cationic lipids, polyamine-based reagents, polyimine-based reagents, calcium phosphate, and the like. Specific examples of a reagent used in transfection include reagents available from various sources, such as, without limitation, Effectene Transfection Reagent (cat. no. 301425, Qiagen, Calif.), TransFast™ Transfection Reagent (E2431, Promega, Wis.), Tfx™-20 Reagent (E2391, Promega, Wis.), SuperFect Transfection Reagent (301305, Qiagen, Calif.), PolyFect Transfection Reagent (301105, Qiagen, Calif.), LipofectAMINE 2000 Reagent (11668-019, Invitrogen corporation, CA), JetPEI (×4) conc. (101-30, Polyplus-transfection, France) and ExGen 500 (R0511, Fermentas Inc., MD), and the like.

Gene expression (e.g., mRNA expression, polypeptide expression) may be "detected" or "quantified" by an appropriate method, including mRNA measurement and immunological measurement methods. Examples of molecular biological measurement methods include Northern blotting methods, dot blotting methods, PCR methods, and the like. Examples of immunological measurement methods include ELISA methods, RIA methods, fluorescent antibody methods, Western blotting methods, immunohistological staining methods, and the like, where a microtiter plate may be used. Examples of quantification methods include ELISA methods, RIA methods, and the like. A gene analysis method using an array (e.g., a DNA array, a protein array, etc.) may be used. The DNA array is widely reviewed in Saibo-Kogaku [Cell Engineering], special issue, "DNA Microarray and Up-to-date PCR Method", edited by Shujun-sha. The protein array is described in detail in Nat Genet. 2002 December; 32 Suppl: 526-32. Examples of methods for analyzing gene expression include, but are not limited to, RT-PCR methods, RACE methods, SSCP methods, immunoprecipitation methods, two-hybrid systems, in vitro translation methods, and the like, in addition to the above-described techniques. Other analysis methods are described in, for example, "Genome Analysis Experimental Method, Yusuke Nakamura's Lab-Manual, edited by Yusuke Nakamura, Yodosha (2002), and the like. All of the above-described publications are herein incorporated by reference.

As used herein, the term "expression level" refers to the amount of a polypeptide or mRNA expressed in a subject cell.

The term "expression level" includes the level of protein expression of a polypeptide evaluated by any appropriate method using an antibody, including immunological measurement methods (e.g., an ELISA method, an RIA method, a fluorescent antibody method, a Western blotting method, an immunohistological staining method, and the like, or the mRNA level of expression of a polypeptide evaluated by any appropriate method, including molecular biological measurement methods (e.g., a Northern blotting method, a dot blotting method, a PCR method, and the like). The term "change in expression level" indicates that an increase or decrease in the protein or mRNA level of expression of a polypeptide evaluated by an appropriate method including the above-described immunological measurement methods or molecular biological measurement methods.

(Screening)

As used herein, the term "screening" refers to selection of a target, such as an organism, a substance, or the like, a given specific property of interest from a population containing a number of elements using a specific operation/evaluation method. For screening, an agent (e.g., an antibody), a polypeptide or a nucleic acid molecule of the present invention can be used.

As used herein, screening by utilizing an immunological reaction is also referred to as "immunophenotyping". In this case, an antibody or a single chain antibody may be used for immunophenotyping a cell line and a biological sample. A transcription or translation product of a gene may be useful as a cell specific marker, or more particularly, a cell marker which is distinctively expressed in various stages in differentiation and/or maturation of a specific cell type. A monoclonal antibody directed to a specific epitope, or a combination of epitopes allows for screening of a cell population expressing a marker. Various techniques employ monoclonal antibodies to screen for a cell population expressing a marker. Examples of such techniques include, but are not limited to, magnetic separation using magnetic beads coated with antibodies, "panning" using antibodies attached to a solid matrix (i.e., a plate), flow cytometry, and the like (e.g., U.S. Pat. No. 5,985, 660; and Morrison et al., Cell, 96:737-49(1999)).

These techniques may be used to screen cell populations containing undifferentiated cells, which can grow and/or differentiate as seen in human umbilical cord blood or which are treated and modified into an undifferentiated state (e.g., embryonic stem cells, tissue stem cells, etc.).

(Diagnosis)

As used herein, the term "diagnosis" refers to an act of identifying various parameters associated with a disease, a disorder, a condition, or the like of a subject and determining a current state of the disease, the disorder, the condition, or the like. A method, device, or system of the present invention can be used to analyze a sugar chain structure, a drug resistance level, or the like. Such information can be used to select parameters, such as a disease, a disorder, a condition, and a prescription or method for treatment or preventative method for a subject.

A diagnosis method of the present invention can use, in principle, a sample which is derived from the body of a subject. Therefore, it is possible for some one which is not a medical practitioner, such as a medical doctor, to deal with such a sample. The present invention is industrially useful.

(Therapy)

As used herein, the term "therapy" refers to an act of preventing progression of a disease or a disorder, preferably maintaining the current state of a disease or a disorder, more preferably alleviating a disease or a disorder, and more preferably extinguishing a disease or a disorder.

As used herein, the term "subject" refers to an organism which is subjected to the treatment of the present invention. A subject is also referred to as a "patient". A patient or subject may preferably be a human.

As used herein, the term "cause" or "pathogen" in relation to a disease, a disorder or a condition of a subject refers to an agent associated with the disease, the disorder or the condition (also collectively referred to as a "lesion", or "disease damage" in plants), including, without limitation, a causative or pathogenic substance (pathogenic agent), a disease agent, a disease cell, a pathogenic virus, and the like.

A disease targeted by the present invention may be any disease associated with a pathogenic gene. Examples of such a disease include, but are not limited to, cancer, infectious diseases due to viruses or bacteria, allergy, hypertension, hyperlipemia, diabetes, cardiac diseases, cerebral infarction, dementia, obesity, arteriosclerosis, infertility, mental and nervous diseases, cataract, progeria, hypersensitivity to ultraviolet radiation, and the like.

A disorder targeted by the present invention may be any disorder associated with a pathogenic gene.

Examples of such a disease, disorder or condition include, but are not limited to, circulatory diseases (anemia (e.g., aplastic anemia (particularly, severe aplastic anemia), renal anemia, cancerous anemia, secondary anemia, refractory anemia, etc.), cancer or tumors (e.g., leukemia, multiple myeloma), etc.); neurological diseases (dementia, cerebral stroke and sequela thereof, cerebral tumor, spinal injury, etc.); immunological diseases (T-cell deficiency syndrome, leukemia, etc.); motor organ and the skeletal system diseases (fracture, osteoporosis, luxation of joints, subluxation, sprain, ligament injury, osteoarthritis, osteosarcoma, Ewing's sarcoma, osteogenesis imperfecta, osteochondrodysplasia, etc.); dermatologic diseases (atrichia, melanoma, cutis malignant lymphoma, hemangiosarcoma, histiocytosis, hydroa, pustulosis, dermatitis, eczema, etc.); endocrinologic diseases (hypothalamus/hypophysis diseases, thyroid gland diseases, accessory thyroid gland (parathyroid) diseases, adrenal cortex/medulla diseases, saccharometabolism abnormality, lipid metabolism abnormality, protein metabolism abnormality, nucleic acid metabolism abnormality, inherent metabolic disorders (phenylketonuria, galactosemia, homocystinuria, maple syrup urine disease), analbuminemia, lack of ascorbic acid synthetic ability, hyperbilirubinemia, hyperbilirubinuria, kallikrein deficiency, mast cell deficiency, diabetes insipidus, vasopressin secretion abnormality, dwarfism, Wolman's disease (acid lipase deficiency, mucopolysaccharidosis VI, etc.); respiratory diseases (pulmonary diseases (e.g., pneumonia, lung cancer, etc.), bronchial diseases, lung cancer, bronchial cancer, etc.); alimentary diseases (esophageal diseases (e.g., esophagial cancer, etc.), stomach/duodenum diseases (e.g., stomach cancer, duodenum cancer, etc.), small intestine diseases/large intestine diseases (e.g., polyps of the colon, colon cancer, rectal cancer, etc.), bile duct diseases, liver diseases (e.g., liver cirrhosis, hepatitis (A, B, C, D, E, etc.), fulminant hepatitis, chronic hepatitis, primary liver cancer, alcoholic liver disorders, drug induced liver disorders, etc.), pancreatic diseases (acute pancreatitis, chronic pancreatitis, pancreas cancer, cystic pancreas diseases, etc.), peritoneum/abdominal wall/diaphragm diseases (hernia, etc.), Hirschsprung's disease, etc.); urinary diseases (kidney diseases (e.g., renal failure, primary glomerulus diseases, renovascular disorders, tubular function abnormality, interstitial kidney diseases, kidney disorders due to systemic diseases, kidney cancer, etc.), bladder diseases (e.g., cystitis, bladder cancer, etc.); genital diseases (male genital organ diseases (e.g., male sterility, prostatomegaly, prostate cancer, testicular cancer, etc.), female genital organ diseases (e.g., female sterility, ovary function disorders, hysteromyoma, adenomyosis uteri, uterine cancer, endometriosis, ovarian cancer, villosity diseases, etc.), etc); circulatory diseases (heart failure, angina pectoris, myocardial infarct, arrhythmia, valvulitis, cardiac muscle/pericardium diseases, congenital heart diseases (e.g., atrial septal defect, arterial canal patency, tetralogy of Fallot, etc.), artery diseases (e.g., arteriosclerosis, aneurysm), vein diseases (e.g., phlebeurysm, etc.), lymphoduct diseases (e.g., lymphedema, etc.), etc.); and the like.

As used herein, the term "cancer" refers to a malignant tumor which has a high level of atypism, grows faster than normal cells, tends to disruptively invade surrounding tissue or metastasize to new body sites or a condition characterized by the presence of such a malignant tumor. In the present invention, cancer includes, without limitation, solid cancer and hematological cancer.

As used herein, the term "solid cancer" refers to a cancer having a solid shape in contrast to hematological cancer, such as leukemia and the like. Examples of such a solid cancer include, but are not limited to, breast cancer, liver cancer, stomach cancer, lung cancer, head and neck cancer, uterocervical cancer, prostate cancer, retinoblastoma, malignant lymphoma, esophagus cancer, brain tumor, osteoncus, and the like.

As used herein, the term "cancer therapy" encompasses administration of an anticancer agent (e.g., a chemotherapeutic agent, radiation therapy, etc.) or surgical therapy, such as surgical excision and the like.

Chemotherapeutic agents used herein are well known in the art and are described in, for example, Shigeru Tsukagoshi et al. editors, "Kogan zai Manuaru [Manual of Anticancer agents]", 2nd ed., ChugaiIgaku sha; Pharmacology; and Lippincott Williams & Wilkins, Inc. Examples of such chemotherapeutic agents are described below: 1) alkylating agents which alkylate cell components, such as DNA, protein, and the like, to produce cytotoxicity (e.g., cyclophosphamide, busulfan, thiotepa, dacarbazine, etc.); 2) antimetabolites which mainly inhibit synthesis of nucleic acids (e.g., antifolics (methotrexate, etc.), antipurines (6-mercaptopurine, etc.), antipyrimidines (fluorourasil (5-FU), etc.); 3) DNA topoisomerase inhibitors (e.g., camptothecin and etoposide, each of which inhibits topoisomerases I and II)); 4) tubulin agents which inhibit formation of microtubules and suppress cell division (vinblastine, vincristine, etc.); 5) platinum compounds which bind to DNA and proteins to exhibit cytotoxicity (cisplatin, carboplatin, etc.); 6) anticancer antibiotics which bind to DNA to inhibit synthesis of DNA and RNA (adriamycin, dactinomycin, mitomycin C, bleomycin, etc.); 7) hormone agents which are applicable to hormone-dependent cancer, such as breast cancer, uterus cancer, prostate cancer, and the like (e.g., tamoxifen, leuprorelin (LH-RH), etc.); 8) biological formulations (asparaginase effective for asparagine requiring blood malignant tumor, interferon exhibiting direct antitumor action and indirect action by immunopotentiation, etc.); 9) immunostimulants which exhibit capability of immune response, indirectly leading to antitumor activity (e.g., rentinan which is a polysaccharide derived from shiitake mushroom, bestatin which is a peptide derived from a microorganism, etc.).

An "anticancer agent" used herein selectively suppresses the growth of cancerous (tumor) cells, and includes both pharmaceutical agents and radiation therapy. Such an anticancer agent is well known in the art and described in, for example, Shigeru Tsukagoshi et al. editors, "Kogan zai Manuaru [Manual of Anticancer agents]", 2nd ed., ChugaiIgaku sha; Pharmacology; and Lippincott Williams & Wilkins, Inc.

As used herein, the term "radiation therapy" refers to a therapy for diseases using ionizing radiation or radioactive substances. Representative examples of radiation therapy include, but are not limited to, X-ray therapy, γ-ray therapy, electron beam therapy, proton beam therapy, heavy particle beam therapy, neutron capture therapy, and the like. For example, heavy particle beam therapy is preferable. However, heavy particle beam therapy requires a large-size device and is not generally used. The above-described radiation therapies are well known in the art and are described in, for example, Sho Kei Zen, "Hoshasenkensa to Chiryo no Kiso: Hoshasen Chiryo to Shugakuteki Chiryo [Basics of Radiation Examination and Therapies: Radiation Therapy and Incentive Therapy]", (Shiga Medical School, Radiation): Total digestive system care, Vol. 6, No. 6, Pages 79-89, 6-7 (2002.02). For drug resistance to be identified in the present invention, chemotherapies are typically considered. However, resistance to radiation therapy is also associated with time-lapse profiles. Therefore, radiation therapy is herein encompassed by the concept of pharmaceutical agents.

As used herein, the term "pharmaceutically acceptable carrier" refers to a material for use in production of a medicament, an animal drug or an agricultural chemical, which does not have an adverse effect on an effective component. Examples of such a pharmaceutically acceptable carrier include, but are not limited to, antioxidants, preservatives, colorants, flavoring agents, diluents, emulsifiers, suspending agents, solvents, fillers, bulking agents, buffers, delivery vehicles, excipients, agricultural or pharmaceutical adjuvants, and the like.

The type and amount of a pharmaceutical agent used in a treatment method of the present invention can be easily determined by those skilled in the art based on information obtained by a method of the present invention (e.g., information about the level of drug resistance, etc.) and with reference to the purpose of use, a target disease (type, severity, and the like), the patient's age, weight, sex, and case history, the form or type of the cell, and the like. The frequency of the treatment method of the present invention applied to a subject (or patient) is also determined by those skilled in the art with respect to the purpose of use, target disease (type, severity, and the like), the patient's age, weight, sex, and case history, the progression of the therapy, and the like. Examples of the frequency include once per day to several months (e.g., once per week to once per month). Preferably, administration is performed once per week to once per month with reference to the progression of the therapy.

As used herein, the term "instructions" refers to a description of a tailor made therapy of the present invention for a person who performs administration, such as a medical doctor, a patient, or the like. Instructions state when to administer a medicament of the present invention, such as immediately after or before radiation therapy (e.g., within 24 hours, etc.). The instructions are prepared in accordance with a format defined by an authority of a country in which the present invention is practiced (e.g., Health, Labor and Welfare Ministry in Japan, Food and Drug Administration (FDA) in the U.S., and the like), explicitly describing that the instructions are approved by the authority. The instructions are so-called package insert and are typically provided in paper media. The instructions are not so limited and may be provided in the form of electronic media (e.g., web sites, electronic mails, and the like provided on the internet).

In a therapy of the present invention, two or more pharmaceutical agents may be used as required. When two or more pharmaceutical agents are used, these agents may have similar properties or may be derived from similar origins, or alternatively, may have different properties or may be derived from different origins. A method of the present invention can be used to obtain information about the drug resistance level of a method of administering two or more pharmaceutical agents.

Also, in the present invention, gene therapy can be performed based on the resultant information about drug resistance. As used herein, the term "gene therapy" refers to a therapy in which a nucleic acid, which has been expressed or can be expressed, is administered into a subject. In such an embodiment of the present invention, a protein encoded by a nucleic acid is produced to mediate a therapeutic effect.

In the present invention, it will be understood by those skilled in the art that if the result of analysis of a certain specific time-lapse profile is correlated with a state of a cell in a similar organism (e.g., mouse with respect to human, etc.), the result of an analysis of a corresponding time-lapse profile can be correlated with a state of a cell. This feature is supported by, for example, Dobutsu Baiyo Saibo Manuaru [Animal Culture Cell Manual], Seno, ed., Kyoritsu Shuppan, 1993, which is herein incorporated by reference.

The present invention may be applied to gene therapies. As used herein, the term "gene therapy" refers to a therapy in which a nucleic acid, which has been expressed or can be expressed, is administered into a subject. In such an embodiment of the present invention, a protein encoded by a nucleic acid is produced to mediate a therapeutic effect.

Any methods for gene therapy available in the art may be used in accordance with the present invention. Illustrative methods will be described below.

Methods for gene therapy are generally reviewed in, for example, Goldspiel et al., Clinical Pharmacy 12: 488-505 (1993); Wu and Wu, Biotherapy 3: 87-95(1991); Tolstoshev, Ann. Rev. Pharmacol. Toxicol., 32: 573-596(1993); Mulligan, Science 260: 926-932(1993); Morgan and Anderson, Ann. Rev. Biochem., 62: 191-217(1993); and May, TIBTECH 11(5): 155-215(1993). Commonly known recombinant DNA techniques used in gene therapy are described in, for example, Ausubel et al. (ed.), Current Protocols in Molecular Biology, John Wiley & Sons, NY (1993); and Kriegler, Gene Transfer and Expression, A Laboratory Manual, Stockton Press, NY (1990).

(Basic Techniques)

Techniques used herein are within the technical scope of the present invention unless otherwise specified. These techniques are commonly used in the fields of fluidics, micromachining, organic chemistry, biochemistry, genetic engineering, molecular biology, microbiology, genetics, and their relevant fields. The techniques are well described in documents described below and the documents mentioned herein elsewhere.

Microfabrication is described in, for example, Campbell, S. A. (1996), "The Science and Engineering of Microelectronic Fabrication", Oxford University Press; Zaut, P. V. (1996), "Micromicroarray Fabrication: a Practical Guide to Semiconductor Processing", Semiconductor Services; Madou, M. J. (1997), "Fundamentals of Microfabrication", CRC1 5 Press; Rai-Choudhury, P. (1997), "Handbook of Microlithography, Micromachining, & Microfabrication: Microlithography". Relevant portions (or possibly the entirety) of each of these publications are herein incorporated by reference.

Molecular biology techniques, biochemistry techniques, and microbiology techniques used herein are well known and commonly used in the art, and are described in, for example, Sambrook J. et al. (1989), "Molecular Cloning: A Laboratory Manual", Cold Spring Harbor and its 3rd Ed. (2001); Ausubel, F. M. (1987), "Current Protocols in Molecular Biology", Greene Pub. Associates and Wiley-Interscience; Ausubel, F. M. (1989), "Short Protocols in Molecular Biology: A Compendium of Methods from Current Protocols in Molecular Biology", Greene Pub. Associates and Wiley-Interscience; Innis, M. A. (1990), "PCR Protocols: A Guide to Methods and Applications", Academic Press; Ausubel, F. M. (1992), "Short Protocols in Molecular Biology: A Compendium of Methods from Current Protocols in Molecular Biology", Greene Pub. Associates; Ausubel, F. M. (1995), "Short Protocols in Molecular Biology: A Compendium of Methods from Current Protocols in Molecular Biology", Greene Pub. Associates; Innis, M. A. et al. (1995), "PCR Strategies", Academic Press; Ausubel, F. M. (1999), "Short Protocols in Molecular Biology: A Compendium of Methods from Current Protocols in Molecular Biology", Wiley, and annual updates; Sninsky, J. J. et al. (1999), "PCR Applications: Protocols for Functional Genomics", Academic Press; Special issue, Jikken Igaku [Experimental Medicine] "Idenshi Donyu & Hatsugenkaiseki Jikkenho [Experimental Method for Gene introduction & Expression Analysis]", Yodo-sha, 1997; and the like. Relevant portions (or possibly the entirety) of each of these publications are herein incorporated by reference.

DNA synthesis techniques and nucleic acid chemistry for producing artificially synthesized genes are described in, for example, Gait, M. J. (1985), "Oligonucleotide Synthesis: A Practical Approach", IRL Press; Gait, M. J. (1990), "Oligonucleotide Synthesis: A Practical Approach", IRL Press; Eckstein, F. (1991), "Oligonucleotides and Analogues: A Practical Approach", IRL Press; Adams, R. L. et al. (1992), "The Biochemistry of the Nucleic Acids", Chapman & Hall; Shabarova, Z. et al. (1994), "Advanced Organic Chemistry of Nucleic Acids", Weinheim; Blackburn, G. M. et al. (1996), "Nucleic Acids in Chemistry and Biology", Oxford University Press; Hermanson, G. T. (1996), "Bioconjugate Techniques", Academic Press; and the like. Relevant portions (or possibly the entirety) of each of these publications are herein incorporated by reference.

(Analysis of Co-Regulation of Genes)

Mathematical processes used herein can be performed by using well-known techniques described in, for example, Kazuyuki Shimizu, "Seimei Sisutemu Kaiseki notameno Sugaku [Mathematics for Analyzing Biological Systems]", Corona sha, 1999; and the like. Among these techniques, representative analysis techniques will be described below.

In one embodiment, such a mathematical process may be regression analysis. Examples of regression analysis include, but are not limited to, linear regression (e.g., simple regression analysis, multiple regression analysis, robust estimation, etc.), nonlinear estimation, and the like.

In simple regression analysis, n sets of data $(x_1, y_1)$ to $(x_n, y_n)$ are fitted to $y_i=ax_i+b+e_i$ ($i=1, 2, \ldots, n$) where a and b are model parameters, and $e_i$ represents a deviation or an error from the straight line. The parameters a and b are typically determined so that the mean of a sum of squares of the distance between a data point and the straight line is minimal. In this case, the rms of the distance is partially differentiated to produce simultaneous linear equations. These equations are solved for a and b which minimize the square errors. Such values are called least square estimates.

Next, a regression line is calculated based on the value obtained by subtracting the mean of all data values from each data value. A regression line represented by:

$$A\Sigma_i X_i + B = \Sigma Y_i$$

is assumed. Further, it is assumed that B=0. The mean ($x_{ave}$, $y_{ave}$) of ($x_i$, $y_i$) (i=1, 2, . . . , n) is calculated, and the variance of x ($s_{xx}$) and the covariance of x and y ($s_{xy}$) are calculated. The above-described regression line can be represented by:

$$y - y_{ave} = (s_{xy}/s_{xx})(x - x_{ave})$$

The correlation coefficient $r_{xy}$ is represented by:

$$r_{xy} = s_{xy}/\sqrt{(s_{xx} s_{yy})}.$$

In this case, the relationship $\Sigma e_i^2/n = s_{yy}(1 - r_{xy}^2)$ is satisfied. Therefore, as $|r_{xy}|$ approaches 1, the error is decreased, which means that data can be satisfactorily represented by the regression line.

In another embodiment, multiple regression analysis is used. In this technique, y is not a single independent variable, and is considered to be a function of two or more variables, e.g., is represented by:

$$y = a_0 + a_1 x_1 + a_2 x_2 + \ldots + a_n x_n.$$

This equation is called a multiple regression equation. $a_0$ and the like are called (partial) regression coefficients. In multiple regression analysis, a least square method is used and normal equations are solved to obtain least square estimates. Evaluation can be performed as with single regression analysis.

In another embodiment, robust estimation is used. The least square method is based on the premise that measurement values are not biased and measurement errors have a normal distribution, and models have no approximation error. In actual situations, however, there may be errors in measurement. In robust estimation, unreliable data is detected and separated as outliers from the great majority of data which are reliable, or is subjected to a statistical process. Such a robust estimation may be utilized herein.

Nonlinear estimation may also be used herein. With nonlinear estimation, it is possible to represent a nonlinear model as vector equations which are in turn solved.

Other mathematical processes used herein include principal component analysis, which utilizes two-dimensional data principal component analysis, multi-dimensional data principal component analysis, singular value decomposition, and generalized inverse matrix. Alternatively, canonical correlation analysis, factor analysis, discrimination analysis, cluster analysis, and the like may be used herein.

(Gene Set Classification by Cluster Analysis)

For a number of applications, it may be desirable to obtain a set of reference transcription control sequences which are cooperatively controlled under a wide range of conditions. An embodiment of identifying such a set of reference transcription control sequences is, for example, a clustering algorithm, which is reviewed in, for example, Fukunaga, 1990, "Statistical Pattern Recognition", 2nd ed., Academic Press, San Diego; Anderberg, 1973, "Cluster Analysis for Applications", Academic Press: New York; Everitt, 1974, "Cluster Analysis", London: Heinemann Educ. Books; Hartigan, 1975, "Clustering Algorithms", New York: Wiley; and Sneath and Sokal, 1973, "Numerical Taxonomy", Freeman.

A set of transcription control sequences can also be defined based on a transcription control mechanism. Transcription control sequences having a transcription factor binding site for the same or similar sequences in a regulatory region are likely to be cooperatively regulated. In a certain embodiment, the regulatory regions of transcription control sequences of interest are compared with one another using multiple alignment analysis, so that a possible common transcription factor binding site can be determined (Stormo and Hartzell, 1989, "Identifying protein binding sites from unaligned DNA fragments", Proc. Natl. Acad. Sci., 86: 1183-1187; Hertz and Stormo, 1995, "Identification of consensus patterns in unaligned DNA and protein sequences: a large-deviation statistical basis for penalizing gaps", Proc. of 3rd Intl. Conf. on Bioinformatics and Genome Research, Lim and Cantor, ed., World Scientific Publishing Co., Ltd. Singapore, pp. 201-216).

It may be desirable to obtain a set of basic transcription control sequences which are cooperatively regulated under various conditions. With such a set, a method of the present invention can satisfactorily and efficiently carry out determination based on profiles. A preferable embodiment for identifying such a set of basic transcription control sequences includes a clustering algorithm.

In an embodiment using cluster analysis, the transcription levels of a number of transcription control sequences can be monitored while applying various stimuli to biological samples. A table of data containing measurements of the transcription levels of transcription control sequences is used in cluster analysis. In order to obtain a set of basic transcription control sequences containing transcription control sequences which simultaneously vary under various conditions, typically at least two, preferably at least 3, more preferably at least 10, even more preferably more than 50, and most preferably more than 100 stimuli or conditions are used. Cluster analysis is performed for a table of data having m×k dimensions where m is the total number of conditions or stimuli and k is the number of transcription control sequences to be measured.

A number of clustering algorithms are useful for clustering analysis. In clustering algorithms, differences or distances between samples are used to form clusters. In a certain embodiment, a distance used is a Euclidean distance in multi-dimensional space:

$$I(x, y) = \left\{ \sum_i (X_i - Y_i)^2 \right\}^{1/2} \quad (1)$$

where (x, y) represents a distance between gene X and gene Y (or any other cellular components X and Y (e.g., transcription control sequences)); $X_i$ and $Y_i$ represent gene expression in response to i stimuli. Euclidean distances may be squared and then multiplied with weighting which are increased with an increase in the distance. Alternatively, a distance reference may be, for example, a distance between transcription control sequences X and Y, or a Manhattan distance represented by:

$$I(x, y) = \sum_i |X_i - Y_i| \quad (2)$$

where $X_i$ and $Y_i$ represent responses of transcription control sequences or gene expression when i stimuli are applied. Several other definitions of distance include Chebyshev distance, power distance, and mismatch rate. When dimensional data can be categorized without modification, a mismatch rate defined as I(x, y)=(the number of $X_i \neq Y_i$)/i may be used in a method of the present invention. Such a method is particularly useful in terms of cellular responses. Another useful definition of distance is I=1−r where r is a correlation coefficient of response vectors X and Y, e.g., a normalized inner product X·Y/|X||Y|. Specifically, an inner product X·Y is defined by:

$$X \cdot Y = \sum_i X_i \times Y_i. \quad (3)$$

Also, $$|X| = (X \cdot X)^{1/2} \text{ and } |Y| = (Y \cdot Y)^{1/2}.$$

Most preferably, a distance reference is suited to a biological problem in order to identify cellular components (e.g., transcription control sequences, etc.) which are simultaneously changed and/or simultaneously regulated. For example, in a particularly preferred embodiment, a distance reference is I=1−r having a correlation coefficient containing a weighted inner product of genes X and Y. Specifically, in such a preferred embodiment, $r_n$ is defined by:

$$r = \frac{\sum_i \frac{X_i Y_i}{\sigma_i^{(X)} \sigma_i^{(Y)}}}{\left[\sum_i \left(\frac{X_i}{\sigma_i^{(X)}}\right)^2 \left(\frac{Y_i}{\sigma_i^{(Y)}}\right)^2\right]^{1/2}} \quad (4)$$

where $\sigma_i^{(X)}$ and $\sigma_i^{(Y)}$ represent standard errors in measurement of genes X and Y in experiment i.

The above-described normalized and weighted inner products (correlation coefficients) are constrained between values +1 (two response vectors are completely correlated, i.e., the two vectors are essentially the same) and −1 (two response vectors are not correlated or do not have the same orientation (i.e., opposing orientations)). These correlation coefficients are particularly preferable in an embodiment of the present invention which tries to detect a set or cluster of cellular components (e.g., transcription control sequences, etc.) having the same sign or response.

In another embodiment, it is preferable to identify a set or cluster of cellular components (e.g., transcription control sequences, etc.) which simultaneously regulate the same biological response or pathway or are involved in such regulation, or have similar or non-correlated responses. In such a embodiment, it is preferable to use the absolute value of either the above-described normalized or weighted inner product, i.e., |r| as a correlation coefficient.

In still another embodiment, the relationship between cellular components (e.g., transcription control sequences, etc.), which are simultaneously regulated and/or simultaneously changed, are more complicated, e.g., a number of biological pathways (e.g., signal transduction pathways, etc.) are involved with the same cellular component (e.g., a transcription control sequence, etc.) so that different results may be obtained. In such an embodiment, it is preferable to use a correlation coefficient $f=r^{(change)}$ which can identify cellular components (other transcription control sequences as controls which are not involved in change) which are simultaneously changed and/or simultaneously regulated. A correlation coefficient represented by expression (5) is particularly useful for the above-described embodiment:

$$r = \frac{\sum_i \left|\frac{X_i}{\sigma_i^{(X)}}\right| \left|\frac{Y_i}{\sigma_i^{(Y)}}\right|}{\left[\sum_i \left(\frac{X_i}{\sigma_i^{(X)}}\right)^2 \left(\frac{Y_i}{\sigma_i^{(Y)}}\right)^2\right]^{1/2}}. \quad (5)$$

Various cluster linkage methods are useful in a method of the present invention.

Examples of such a technique include a simple linkage method, a nearest neighbor method, and the like. In these techniques, a distance between the two closest samples is measured. Alternatively, in a complete linkage method, which may be herein used, a maximum distance between two samples in different clusters is measured. This technique is particularly useful when genes or other cellular components naturally form separate "clumps".

Alternatively, the mean of non-weighted pairs is used to define the mean distance of all sample pairs in two different clusters. This technique is also useful in clustering genes or other cellular components which naturally form separate "clumps". Finally, a weighted pair mean technique is also available. This technique is the same as a non-weighted pair mean technique, except that in the former, the size of each cluster is used as a weight. This technique is particularly useful in an embodiment in which it is suspected that the size of a cluster of transcription control sequences or the like varies considerably (Sneath and Sokal, 1973, "Numerical taxonomy", San Francisco: W.H. Freeman & Co.). Other cluster linkage methods, such as, for example, non-weighted and weighted pair group centroid and Ward's method, are also useful in several embodiments of the present invention. See, for example, Ward, 1963, J. Am. Stat. Assn., 58: 236; and Hartigan, 1975, "Clustering algorithms", New York: Wiley.

In a certain preferred embodiment, cluster analysis can be performed using a well-known hclust technique (e.g., see a well-known procedure in "hclust" available from Program S-Plus, MathSoft, Inc., Cambridge, Mass.).

According to the present invention, it was found that even if the versatility of stimuli to a clustering set is increased, a state of a cell can be substantially elucidated by analyzing typically at least two, preferably at least 3, profiles using a method of the present invention. Stimulation conditions include treatment with a pharmaceutical agent in different concentrations, different measurement times after treatment, response to genetic mutations in various genes, a combination of treatment of a pharmaceutical agent and mutation, and changes in growth conditions (temperature, density, calcium concentration, etc.).

As used herein, the term "significantly different" in relation to two statistics means that the two statistics are different from each other with a statistical significance. In an embodiment of the present invention, data of a set of experiments assessing the responses of cellular components can be randomized by a Monte Carlo method to define an objective test.

In a certain embodiment, an objective test can be defined by the following technique. $p_{ki}$ represents a response of a component k in experiment i. $\Pi_{(i)}$ represents a random permutation of the indices of experiments. Next, $p_{k\Pi(i)}$ is calculated for a number of different random permutations (about 100 to 1,000). For each branch of the original tree and each permutation:

(1) hierarchical clustering is performed using the same algorithm as that which has been used for the original data which is not permutated (in this case, "hclust"); and (2) an improvement fin classification in total variance about the center of clusters when transition is made from one cluster to two clusters:

$$f=1-\Sigma D_k^{(1)}/\Sigma D_k^{(2)} \quad (6).$$

where $D_k$ is the square of the distance reference (mean) of component k with respect to the center of a cluster to which component k belongs. Superscript 1 or 2 indicates the center of all branches or the center of the more preferable cluster of the two subclusters. The distance function D used in this clustering technique has a considerable degree of freedom. In these examples, D=1−r, where r is a correlation coefficient of one response with respect to another response of a component appearing in a set of experiments (or of the mean cluster response).

Specifically, an objective statistical test can be preferably used to determine the statistical reliability of grouping any clustering methods or algorithms. Preferably, similar tests can be applied to both hierarchical and nonhierarchical clustering methods. The compactness of a cluster is quantitatively defined as, for example, the mean of squares of the distances of elements in the cluster from the "mean of the cluster", or more preferably, the inverse of the mean of squares of the distances of elements from the mean of the cluster. The mean of a specific cluster is generally defined as the mean of response vectors of all elements in the cluster. However, in a specific embodiment (e.g., the definition of the mean of the cluster is doubtful), for example, the absolute values of normalized or weighted inner products are used to evaluate the distance function of a clustering algorithm (i.e., I=1−|r|). Typically, the above-described definition of the mean may raise a problem in an embodiment in which response vectors have opposing directions so that the mean of the cluster as defined above is zero. Therefore, in such an embodiment, a different definition is preferably selected for the compactness of a cluster, for example, without limitation, the mean of squares of the distances of all pairs of elements in a cluster. Alternatively, the compactness of a cluster may be defined as the mean of distances between each element (e.g., a cellular component) of a cluster and another element of the cluster (or more preferably the inverse of the mean distance).

Other definitions, which may be used in statistical techniques used in the present invention, are obvious to those skilled in the art.

In another embodiment, a profile of the present invention can be analyzed using signal processing techniques. In these signal processing techniques, a correlation function is defined, a correlation coefficient is calculated, an autocorrelation function and a cross-correlation function are defined, and these functions are weighted where the sum of the weights is equal to 1. Thereby, moving averages can be obtained.

In signal processing, it is important to consider a time domain and a frequency domain. Rhythm often plays an important role in dynamic characteristic analysis for natural phenomena, particularly life and organisms. If a certain time function f(t) satisfies the following condition, the function is called a periodic function:

$$f(t)=f(t+T).$$

At time 0, the function takes a value of f(0). The function takes a value of f(0) at time T again after taking various values after time 0. Such a function is called aperiodic function. Such a function includes a sine wave. T is called a period. The function has one cycle per time T. Alternatively, this feature may be represented by 1/T which means the number of cycles per unit time (cycles/time) without loss of the information. The concept represented by the number of cycles per unit time is called frequency. If the frequency is represented by f, f is represented by:

$$f=1/T.$$

Thus, the frequency is an inverse of the time. The time is dealt in a time domain, while the frequency is dealt in a frequency domain. The frequency may be represented in an electrical engineering manner. For example, the frequency is represented by angular measure where one period corresponds to 360° or $2\pi$ radians. In this case, f (cycles/sec) is converted to $2\pi f$ (radians/sec), which is generally represented by $\omega(=2\pi f)$ and is called angular frequency.

Now, a sine wave is compared with a cosine wave. The cosine wave is obtained by translating the sine wave by 90° or $\pi/2$ radians. The sine wave may be represented by the delayed cosine wave. This time delay is called phase. For example, when a pure cosine wave has a phase of 0, a sine wave has a phase of 90°. When a sine wave is added to a cosine wave, the amplitude of the resultant wave is increased by a factor of $\sqrt{2}$ and the phase is $\pi/4$.

In such analysis, Fourier series and frequency analysis may be available. In addition, Fourier transformation, discrete Fourier transformation, and power spectrum may be available. In Fourier expansion, techniques, such as wavelet transformation and the like, may be available. These techniques are well known in the art and are described in, for example, Yukio Shimizu, "Seimei Sisutemu Kaiseki notameno Sugaku [Mathematics for analyzing life systems]", Corona sha, (1999); and Yasuhiro Ishikawa, "Rinsho Igaku notameno Ueburetto Kaiseki [Wavelet analysis for clinical medicine]", Igaku Shuppan.

DESCRIPTION OF PREFERRED EMBODIMENTS

Hereinafter, the present invention will be described by way of embodiments. The embodiments described below are provided only for illustrative purposes. Accordingly, the scope of the present invention is not limited by the embodiments except as by the appended claims.

In one aspect, the present invention provides a method for representing a state of a cell. The method comprises the steps of: a) obtaining a time-lapse profile of the cell by time-lapse monitoring of a gene state (e.g., the expression of a gene (transcription, translation, etc.), etc.) associated with at least one gene selected from genes derived from the cell; and b) presenting the time-lapse profile. For example, the profile of the intensity of a signal obtained by monitoring is subjected to interval differentiation, thereby obtaining a function of changes which can be in turn displayed. In this case, preferably, for example a constitutive promoter or the like, which is assumed to be changed, can be used as a reference to obtain a difference, thereby obtaining a time-lapse profile. The present invention is not limited to this.

Time-lapse profiles may be displayed using any method, for example, they may be visually displayed using a display device (e.g., an x axis showing time while the y axis shows signal intensity), or alternatively, may be displayed as a table of numerical values. Alternatively, signal intensity may be displayed as optical intensity. Furthermore, profiles may be presented by means of sound.

Preferably, cells are fixed to a solid phase support (e.g., an array, a plate, a microtiter plate, etc.) when they are monitored. Such fixation can be carried out using techniques known in the art or techniques as described herein. Fixation or immobilization of a cell allows systematic investigation thereof.

In a preferred embodiment, such a time-lapse profile may be presented in real time. The real time presentation may contain a time lag to some extent if it is performed substantially in real time. A tolerable time lag is, for example, 10 seconds at maximum, and more preferably 1 second at maximum, though the tolerable time lag depends on the required level of real time (simultaneity).

In another aspect, the present invention provides a method for determining a state of a cell. Such determination of the cellular state is achieved by monitoring changes in a transcriptional state of a transcription control factor, which are not conventionally observed. Therefore, the method of the present invention for determining the cellular state allows determination of various states which cannot be conventionally observed. Such a method comprises the steps of: a) obtaining a time-lapse profile of the cell by time-lapse monitoring of a transcriptional state associated with at least one biological agent selected from a biological agent group derived from the cell; and b) determining the state of the cell based on the time-lapse profile of the transcription level.

Preferably, cells are fixed to a solid phase support (e.g., an array, a plate, a microtiter plate, etc.) when they are monitored. Such fixation can be carried out using techniques known in the art or techniques as described herein.

In a preferred embodiment, advantageously, the cellular state determination method of the present invention may further comprise correlating the time-lapse profile with the state of the cell before obtaining the time-lapse profile. Alternatively, such correlation information may be provided from known information. Such a correlating step may be performed at every determining step or correlation information may be stored in a database and used as required.

In a preferred embodiment, the transcription control sequence may be, without limitation, a promoter, an enhancer, a silencer, another flanking sequence of a structural gene in a genome, and a genomic sequence other than exons. A promoter is preferable. This is because a transcription level can be directly measured, and the state of transcription directly reflects the state of a cell. In a particular embodiment, the transcription control sequences may include constitutive promoters, specific promoters, inducible promoters, and the like.

In certain embodiments, any promoter may be used. The present invention is characterized in that any type of promoter can be used. According to the method of the present invention, profiles can be analyzed from a viewpoint of "procession". Therefore, it is possible to determine a state of a cell using any promoter or any set of promoters. Such determination cannot be achieved by conventional techniques. The present invention is highly useful since the present invention achieves what cannot be achieved by conventional techniques.

In a preferred embodiment, at least two biological agents (for example, transcriptional control sequence) are monitored. By observing at least two biological agents, 80% of the states of a cell can be typically identified. More preferably, at least 3 biological agents are monitored. By observing at least three biological agents, at least 90% of the states of a cell can be typically identified. In a most preferred embodiment, at least 8 biological agents are monitored. By observing at least 8 biological agents, substantially all of the states of a cell can be typically identified. Thus, although any biological agents are selected, substantially all of the states of a cell can be determined by selecting and monitoring a small number of biological agents, as described above. This feature has not been conventionally expected. The method of the present invention is simpler, more precise and more accurate than conventional determination methods in which observation is made at time points and resultant data is statistically processed as heterologous groups.

Therefore, the determination method of the present invention preferably further comprises arbitrarily selecting at least one biological agent from a biological agent group before monitoring. An important feature of the present invention is such that a biological agent, which does not exhibit specificity when investigated from point to point, can be used. Further, the present invention allows accurate reflection of the resultant data to the state of a cell of interest, since data linearly measured data under a consistent environment can be used. Such accurate data cannot be obtained conventionally.

In a preferred embodiment, such a time-lapse profile obtained in the present invention may be presented in real time. Alternatively, in the present invention, data may be obtained in a real time manner. The real time presentation may contain a time lag to some extent if it is performed substantially in real time. A tolerable time lag is, for example, 10 seconds at maximum, and more preferably 1 second at maximum, though the tolerable time lag depends on the required level of real time (simultaneity) As used herein, the term "real time" means that the real time presentation may contain a time lag to some extent if it is performed substantially in real time. A tolerable time lag is, for example, 10 seconds at maximum, and more preferably 1 second at maximum, though the tolerable time lag depends on the required level of real time (simultaneity) For example, the level of real time may be preferably 30 seconds at maximum, or even longer in the case of, for example, therapies required for real time diagnosis.

In a particular preferable embodiment, states determined by the cellular state determination method of the present invention includes, for example, differentiated states, undifferentiated states, cellular responses to external factors, cell cycles, growth states, and the like. More specifically, such a state includes, for example, without limitation, a response of a cancer cell to an anticancer agent, drug resistance, a response to a biological clock, a differentiated state of a stem cell (e.g., a mesenchymal stem cell, a neural stem cell, etc.), an undifferentiated state of a purified stem cell (e.g., an embryonic stem cell, etc.), a change in cellular morphology, a state of cellular migration, intracellular localization of a molecule, production of a secreted substance, and the like.

Therefore, in a preferred embodiment, a cell assessed by the cellular state determination method of the present invention includes, for example, without limitation, a stem cell or a somatic cell, or a mixture thereof. Alternatively, such a cell includes an adherent cell, a suspended cell, a tissue forming cell, and a mixture thereof.

In a preferred embodiment, the cellular state determination method of the present invention may be performed upon a cell fixed on a substrate which is a solid phase support. In such a case, the solid phase support is called a chip. When cells are arrayed on the substrate, the substrate is also called an array.

In a particularly preferred embodiment of the cellular state determination method of the present invention, advantageously, when a biological agent (for example, a transcription control sequence) used for determination is a nucleic acid molecule, such a nucleic acid molecule may be operably linked to a reporter gene sequence and may be transfected into a cell. In this case, the transcription level of the transcription control sequence can be measured as a signal from the reporter gene.

Such transfection may be performed in the solid phase or in the liquid phase. For transfection, a technique for increasing the efficiency of introduction of a target substance into a cell may be used. In the present invention, a target substance (e.g., DNA, RNA, a polypeptide, a sugar chain, or a composite substance thereof, etc.), which cannot be substantially introduced into cells under typical conditions, is presented (preferably, contacted) along with an actin-like substance, such as fibronectin, to a cell, thereby making it possible to efficiency introduce the target substance into cells. Therefore, the transfection method comprises the steps of: A) providing a target substance (i.e., DNA comprising a transcription control sequence) and B) providing an actin-like substance (e.g., fibronectin), wherein the order of steps of A) and B) is not particularly limited, and C) contacting the target substance and the actin-like substance with the cell. The target substance and the actin-like substance may be provided together or separately. The actin-like acting substance may be used as described in detail above for the composition of the present invention for increasing the efficiency of introduction of a target substance into a cell. Such a technique can be carried out as appropriate based on the present specification by those skilled in the art. Therefore, the actin-like substance may be used in a manner which is described in detail above for the composition of the present invention for increasing the efficiency of introduction of a target substance into a cell. Preferably, the actin-like acting substance may be an extracellular matrix protein (e.g., fibronectin, vitronectin, laminin, etc.) or a variant thereof. More preferably, fibronectin or a variant or fragment thereof may be used.

In one embodiment, a transcription control sequence used in the present invention may be capable of binding to a transcription factor. Examples of such a transcription factor include, but are not limited to, ISRE, RARE, STAT3, GAS, NFAT, MIC, AP1, SRE, GRE, CRE, NFκB, ERE, TRE, E2F, Rb, p53, and the like. These transcription factors are commercially available from BD Biosciences Clonetech, Calif., USA. ISRE is related to STAT1/2. RARE is related to retinoic acid. STAT3 is related to the control of differentiation. GRE is related to the metabolism of sugar. CRE is related to cAMP. TRE is related to thyroid hormone. E2F is related to cell cycle. p53 is related to G1 check point. Therefore, such information can be used to determine a state of a cell.

In a preferred embodiment, the determination step of b) of the present invention comprises comparing the phases of the time-lapse profiles. Phases can be calculated by those skilled in the art using general techniques as described herein above and techniques described in the examples below.

In another preferred embodiment, the determination step of b) of the present invention comprises calculating a difference between the time-lapse profile of the cell and a control profile. The difference can be calculated by those skilled in the art using general techniques as described herein above and techniques described in Examples below.

In another preferred embodiment, the determination step of b) of the present invention comprises a mathematical process selected from the group consisting of signal processing and multivariate analysis. Such a mathematical process can be easily carried out by those skilled in the art based on the description of the present specification.

In another aspect, the present invention provides a method for correlating an external factor with a cellular response to the external factor. The method comprises the steps of: a) exposing a plurality of cells to an external factor on a support capable of retaining the cells in a consistent environment; b) monitoring a transcriptional state relating to at least one of a transcriptional factor group present on or within the cells over time to generate profile data for the cells; and c) correlating the external factor with the profile.

Any external factor to be correlated in the present invention may be used. Such an external factor is preferably directly or indirectly applicable to a cell. A method for applying such an external factor is well known in the art, depending on the type of the external factor used. When a substance is used, the substance is dissolved into a solvent, and the resultant solution is added to a medium containing a cell.

The correlation method of the present invention may utilize the production method of profiles as described hereinabove.

A variety of methods can be provided for correlating a foreign agent and a profile in the method of correlation of the present invention. In brief, profiles obtained when a foreign agent is applied to a cell, are patternized, and if there is little difference between the patternized profiles, it can be inferred that the particular foreign agent has been applied to the cells.

Preferably, a cell may be monitored in an immobilized state to a solid support such as an array, a plate, a microtiterplate and the like. Such a method for immobilization can be conducted based on any known methodology in the art or the methods described herein.

In a preferred embodiment, a correlation method of the present invention may further comprise using at least two external factors to obtain a profile for each external factor. In certain embodiments, at least three, or at least four, more preferably at least ten such foreign agents may be used but the present invention is not limited thereto.

More preferably, the correlation step may further comprise dividing at least two profiles into categories and classifying the external factors corresponding to the respective profiles into the categories. Such categorization may be readily conducted by those skilled in the art based on the description of the present specification. Such categorization or classification allows correlation and identification of an unknown foreign agent by means of the method of the present invention.

In a preferred embodiment, a transcription control sequence used in the present invention may be, without limitation, a promoter, an enhancer, a silencer, other flanking sequences of structural genes in genomes, and genomic sequences other than exons. A promoter is preferable, since the transcription level can be directly measured.

In a particular embodiment, transcription control sequences used in the present invention may be constitutive promoters, specific promoters, inducible promoters, and the like. The present invention is characterized in that any type of promoter can be used. According to the method of the present invention, profiles can be analyzed from a viewpoint of "process" or "procession" Therefore, it is possible to determine a state of a cell using any promoter or any set of promoters. Such determination cannot be achieved by conventional techniques. The present invention is highly useful since the present invention achieves what cannot be achieved by conventional techniques.

In a preferred embodiment, at least two transcription control sequences are monitored. By observing at least two transcription control sequences, at least 80% of the states of a cell can be typically identified. More preferably, at least 3 transcription control sequences are monitored. By observing at least three transcription control sequences, at least 90% of the states of a cell can be typically identified. In a most preferred embodiment, at least 8 transcription control sequences are monitored. By observing at least 8 transcription control sequences, substantially all of the states of a cell can be typically identified. Thus, although any transcription control sequences are selected, substantially all of the states of a cell can be determined by selecting and monitoring a small number of transcription control sequences as described above. This feature has not been conventionally expected. The method of the present invention is simpler, more precise and more accurate than conventional determination methods in which observation is made at time points and resultant data is statistically processed as heterologous groups.

Therefore, the determination method of the present invention preferably further comprises arbitrarily selecting at least one transcription control sequence from a group of transcription control sequences before monitoring. An important feature of the present invention is such that a transcription control sequence, which does not exhibit specificity when investigated from point to point, can be used.

In a preferred embodiment, such a time-lapse profile may be presented in real time. The real time presentation may contain a time lag to some extent if it is performed substantially in real time. A tolerable time lag is, for example, 10 seconds at maximum, and more preferably 1 second at maximum, though the tolerable time lag depends on the required level of real time (simultaneity). For example, in the case of environment measurement requiring real time identification of external factors, the tolerable time lag may be, for example, 1 sec at maximum, 0.1 sec at maximum, or the like. Alternatively, after data is stored on a storage medium at real time, profiles may be presented corresponding to the data based on the stored data, with some time lag.

In a preferred embodiment, in the correlation step of c) of the present invention, the phase of the time-lapse profile may be used as information about the time-lapse profile in order to correlate the external factor with the time-lapse profile. The phase is represented by plus or minus depending on the signal intensity at a certain time. Even using such a simplified method, a cell or an external factor can be identified, thus demonstrating the precision of the method of the present invention.

Preferably, in the method of the present invention, cells are advantageously cultured on an array. This is because a number of cells can be simultaneously observed. Preferably, when a cell is immobilized on a solid support such as an array, a salt may be used.

In a preferred embodiment, the step of monitoring the transcription level over time may comprise obtaining image data from the array. This is because image data can be subjected to visual inspection and a human (particularly, a person skilled in the art, such as a medical practitioner or the like) can easily examine image data with his/her eyes.

In a preferred embodiment of the present invention, the step of correlating the external factor with the time-lapse profile may comprise distinguishing the phases of the time-lapse profiles. As described above, phase is a simple parameter, and its information processing is simple. Thus, cells can be well identified by such simple information processing.

In a preferred embodiment, examples of an external factor to be identified by the method of the present invention include, but are not limited to, a temperature change, a humidity change, an electromagnetic wave, a potential difference, visible light, infrared light, ultraviolet light, X-ray, a chemical substance, a pressure, a gravity change, a gas partial pressure, an osmotic pressure, and the like. These factors cannot be satisfactorily identified by conventional methods. By using the cell determination method of the present invention which places an importance on "procession", an influence of a factor on a cell can be well examined.

In a particularly preferred embodiment, an external factor to be identified by the method of the present invention may be a chemical substance. Examples of such a chemical substance include, but are not limited to, biological molecules, chemical compound, media, and the like.

Examples of biological molecules include, but are not limited to, nucleic acids, proteins, lipids, sugars, proteolipids, lipoproteins, glycoproteins, proteoglycans, and the like. These biological molecules are known to have an influence on organisms. Unknown biological molecules are also highly likely to have an influence on organisms and are considered to be important targets for study.

Particularly preferably, hormones, cytokine, cell adhesion factors, extracellular matrices, receptor agonists, receptor antagonists, and the like, which are expected to have an influence on cells, are used as biological molecules to be investigated.

In another aspect, the present invention provides a method for inferring an unidentified external factor given to a cell based on a time-lapse profile of the cell. The method comprises the steps of: a) exposing the cell to a plurality of known external factors; b) obtaining a time-lapse profile of the cell for each known external factor by time-lapse monitoring of a transcription level associated with at least one biological agent selected from the group consisting of biological agents derived from the cell; c) correlating the known external factors with the respective time-lapse profiles; d) exposing the cell to the unidentified external factor; e) obtaining a time-lapse profile of the unidentified external factor by time-lapse monitoring of the transcription level of the selected biological agent; f) determining a profile corresponding to the time-lapse profile obtained in the step of e) from the time-lapse profiles obtained in the step of b); and g) determining that the unidentified external factor is the known external factor corresponding to the profile determined in the step of f).

In the method of the present invention, the step of exposing a cell to external factors can be performed as described above herein or as illustrated in the examples described below. The step of obtaining a time-lapse profile can be performed as described above herein or as illustrated in the examples described below. The correlation step can be performed as described above herein or as illustrated in the examples described below. After information about all known external factors has been obtained, an unidentified external factor is similarly monitored. These pieces of information are compared to determine whether or not the unidentified external factor is a known one. If the profile of an unidentified factor fully matches the profile of a known factor, these two factors can be determined as being identical. Also, if the profile of an unidentified factor substantially matches the profile of a known factor, these two factors can be determined to be identical. Such determination depends on the information quantity and quality of the known external factor. Such determination can be easily carried out by those skilled in the art considering various elements.

In another aspect, the present invention provides a method for inferring an unidentified external factor given to a cell based on a time-lapse profile of the cell. The method comprises: a) providing data relating to a correlation relationship between known external factors and time-lapse profiles of the cell in response to the known external factors, in relation to at least one promoter selected from promoters present in the cell; b) exposing the cell to the unidentified external factor; c) obtaining a time-lapse profile of the cell by time-lapse monitoring of a transcription level associated with the selected promoter; d) determining a profile corresponding to the time-lapse profile obtained in the step of c) from the time-lapse profiles obtained in the step of a); and e) determining that the unidentified external factor is the known external factor corresponding to the profile determined in the step of d).

Exposure to external factors, profile generation, correlation, and the like can be carried out using techniques as described herein above or as illustrated in the examples below.

In another aspect, the present invention provides a system for presenting a state of a cell. The system comprises: a) means for obtaining a time-lapse profile of the cell by time-lapse monitoring of a transcription level associated with at least one transcription control sequence selected from the group consisting of transcription control sequences derived from the cell; and b) means for presenting the time-lapse profile. An exemplary system configuration is presented in FIG. 32.

A configuration of a computer or system for implementing the cellular state presenting method of the present invention is shown in FIG. 17. FIG. 17 shows an exemplary configuration of a computer 500 for executing the cellular state presenting method of the present invention. An exemplary system configuration is presented in FIG. 32.

The computer 500 comprises an input section 501, a CPU 502, an output section 503, a memory 504, and a bus 505. The input section 501, the CPU 502, the output section 503, and the memory 504 are connected via a bus 505. The input section 501 and the output section 503 are connected to an I/O device 506.

An outline of a process for presenting a state of a cell, which is executed by the computer 500, will be described below.

A program for executing the cellular state presenting method (hereinafter referred to as a "cellular state presenting program") is stored in, for example, the memory 502. Alternatively, each component of the cellular state presenting program may be stored in any type of recording medium, such as a floppy disk, MO, CD-ROM, CD-R, DVD-ROM, or the like, separately or together. Alternatively, the program may be stored in an application server. The cellular state presenting program stored in such a recording medium is loaded via the I/O device 506 (e.g., a disk drive, a network (e.g., the Internet)) to the memory 504 of the computer 500. The CPU 502 executes the cellular state presenting program, so that the computer 500 functions as a device for performing the cellular state presenting method of the present invention.

Information about a cell or the like is input via the input section 501 as well as profile data obtained. Known information may be input as appropriate.

The CPU 502 generates display data based on the information about profile data and cells through the input section 501, and stored the display data into the memory 504. Thereafter, the CPU 502 may store the information in the memory 504. Thereafter, the output section 503 outputs a cellular state selected by the CPU 502 as display data. The output data is output through the I/O device 506.

In another aspect, the present invention provides a system for determining a state of a cell. The system comprises: a) means for obtaining a time-lapse profile of the cell by time-lapse monitoring of a transcription level associated with at least one biological agent selected from the group consisting of biological agents derived from the cell; and b) means for determining the state of the cell based on the time-lapse profile. An exemplary system configuration is presented in FIG. 32.

A configuration of a computer or system for implementing the cellular state determining method of the present invention is shown in FIG. 17. FIG. 17 shows an exemplary configuration of a computer 500 for executing the cellular state determining method of the present invention. An exemplary system configuration is presented in FIG. 32.

The computer 500 comprises an input section 501, a CPU 502, an output section 503, a memory 504, and a bus 505. The input section 501, the CPU 502, the output section 503, and the memory 504 are connected via a bus 505. The input section 501 and the output section 503 are connected to an I/O device 506.

An outline of a process for determining a state of a cell, which is executed by the computer 500, will be described below.

A program for executing the cellular state determining method (hereinafter referred to as a "cellular state determining program") is stored in, for example, the memory 502. Alternatively, each component of the cellular state determining program may be stored in any type of recording medium, such as a floppy disk, MO, CD-ROM, CD-R, DVD-ROM, or the like, separately or together. Alternatively, the program may be stored in an application server. The cellular state determining program stored in such a recording medium is loaded via the I/O device 506 (e.g., a disk drive, a network (e.g., the Internet)) to the memory 504 of the computer 500. The CPU 502 executes the cellular state presenting program, so that the computer 500 functions as a device for performing the cellular state determining method of the present invention.

Information about a cell or the like is input via the input section 501, as well as profile data obtained. Known information may be input as appropriate.

The CPU 502 determines a state of a cell based on the information about profile data and cells input through the input section 501, generates the results as determination result data, and stores the determination result data in the memory 504. Thereafter, the CPU 502 may store the information in the memory 504. Thereafter, the output section 503 outputs a cellular state selected by the CPU 502 as determination result data. The output data is output through the I/O device 506.

In another aspect, the present invention provides a system for correlating an external factor with a response of a cell to the external factor. The system comprises: a) means for exposing the cell to the external factor; b) means for obtaining a time-lapse profile of the cell by time-lapse monitoring of a transcription level associated with at least one promoter selected from the group consisting of promoters derived from the cell; and c) means for correlating the external factor with the time-lapse profile. Such a system can be implemented using a computer as with the above-described systems. An exemplary system configuration is presented in FIG. 32.

In another aspect, the present invention provides a system for inferring an unidentified external factor given to a cell based on a time-lapse profile. The system comprising: a) means for exposing the cell to a plurality of known external factors; b) means for obtaining a time-lapse profile of the cell for each known external factor by time-lapse monitoring of a transcription level associated with at least one biological agent selected from the group consisting of biological agents derived from the cell; c) means for correlating the known external factors with the respective time-lapse profiles; d) means for exposing the cell to the unidentified external factor; e) means for obtaining a time-lapse profile of the unidentified external factor by time-lapse monitoring of the transcription level of the selected transcription control sequence; f) means for determining a profile corresponding to the time-lapse profile obtained in the means of e) from the time-lapse profiles obtained in the means of b); and g) means for determining that the unidentified external factor is the known external factor corresponding to the profile determined in the means of f). Such a system can be implemented using a computer as with the above-described systems. An exemplary system configuration is presented in FIG. 32.

In another aspect, the present invention provides a system for inferring an unidentified external factor given to a cell based on a time-lapse profile, comprising: a) means for providing data relating to a correlation relationship between known external factors and time-lapse profiles of the cell in response to the known external factors, in relation to at least one biological agent selected from biological agents present in the cell; b) means for exposing the cell to the unidentified external factor; c) means for obtaining a time-lapse profile of the cell by time-lapse monitoring of a transcription level associated with the selected transcription control sequence; d) means for determining a profile corresponding to the time-lapse profile obtained in the means of c) from the time-lapse profiles obtained in the means of a); and e) determining that the unidentified external factor is the known external factor corresponding to the profile determined in the means of d). Such a system can be implemented using a computer as with the above-described systems. An exemplary system configuration is presented in FIG. 32.

When the present invention is provided in the form of a system as described above, each constituent element thereof can be implemented as with the detailed or preferred embodiments of the method of the present invention. Preferred embodiments of such a system can be easily selected by those skilled in the art and can be made or carried out by those skilled in the art based on the present specification. An exemplary system configuration is presented in FIG. 32.

In another aspect, the present invention provides a computer recordable recording medium recording a program for executing a process for presenting a state of a cell to a computer. The recording medium records at least a program for executing the procedures of: a) obtaining a time-lapse profile of the cell by time-lapse monitoring of a transcription level associated with at least one biological agent selected from the group consisting of biological agents derived from the cell; and b) presenting the time-lapse profile.

In another aspect, the present invention provides a computer recordable recording medium recording a program for executing a process for determining a state of a cell to a computer. The recording medium records at least a program for executing the procedures of: a) obtaining a time-lapse profile of the cell by time-lapse monitoring of a transcription level associated with at least one biological agent selected from the group consisting of biological agents derived from the cell; and b) determining the state of the cell based on the time-lapse profile of the transcription level.

In another aspect, the present invention provides a computer recordable recording medium recording a program for executing a process for correlating an external factor with a response of a cell to the external factor. The recording medium records at least a program for executing the procedures of: a) exposing the cell to the external factor; b) obtaining a time-lapse profile of the cell by time-lapse monitoring of a transcription level associated with at least one transcription control factor selected from the group consisting of transcription control factors derived from the cell; and c) correlating the external factor with the time-lapse profile.

In another aspect, the present invention provides a computer recordable recording medium recording a program for executing a process for inferring an unidentified external factor given to a cell based on a time-lapse profile. The recording medium records at least a program for executing the procedures of: a) exposing the cell to a plurality of known external factors; b) obtaining a time-lapse profile of the cell for each known external factor by time-lapse monitoring of a transcription level associated with at least one transcription control factor selected from the group consisting of transcription control factors derived from the cell; c) correlating the known external factors with the respective time-lapse profiles; d) exposing the cell to the unidentified external factor; e) obtaining a time-lapse profile of the unidentified external factor by time-lapse monitoring of the transcription level of the selected transcription control sequence; f) determining a profile corresponding to the time-lapse profile obtained in the procedure of e) from the time-lapse profiles obtained in the procedure of b); and g) determining that the unidentified external factor is the known external factor corresponding to the profile determined in the procedure of f).

In another aspect, the present invention provides a computer recordable recording medium recording a program for executing a process for inferring an unidentified external factor given to a cell based on a time-lapse profile. The recording medium records at least a program for executing the procedures of: a) providing data relating to a correlation relationship between known external factors and time-lapse profiles of the cell in response to the known external factors, in relation to at least one transcription control sequence selected from transcription control sequences present in the cell; b) exposing the cell to the unidentified external factor; c) obtaining a time-lapse profile of the cell by time-lapse monitoring of a transcription level associated with the selected transcription control sequence; d) determining a profile corresponding to the time-lapse profile obtained in the procedure of c) from the time-lapse profiles obtained in the procedure of a); and e) determining that the unidentified external factor is the known external factor corresponding to the profile determined in the procedure of d).

When the present invention is provided in the form of a recording medium as described above, each constituent element thereof can be implemented as with the detailed or preferred embodiments of the method of the present invention. Preferred embodiments of such a recording medium can be easily selected by those skilled in the art and can be made or carried out by those skilled in the art based on the present specification.

In another aspect, the present invention provides a program for executing a process for presenting a state of a cell to a computer. The program executes the procedures of: a) obtaining a time-lapse profile of the cell by time-lapse monitoring of a transcription level associated with at least one biological agent selected from the group consisting of biological agents derived from the cell; and b) presenting the time-lapse profile.

In another aspect, the present invention provides a program for executing a process for determining a state of a cell to a computer. The program executes the procedures of: a) obtaining a time-lapse profile of the cell by time-lapse monitoring of a transcription level associated with at least one biological agent selected from the group consisting of biological agents derived from the cell; and b) determining the state of the cell based on the time-lapse profile of the transcription level.

In another aspect, the present invention provides a program for executing a process for correlating an external factor with a response of a cell to the external factor. The program executes the procedures of: a) exposing the cell to the external factor; b) obtaining a time-lapse profile of the cell by time-lapse monitoring of a transcription level associated with at least one transcription control factor selected from the group consisting of transcription control factors derived from the cell; and c) correlating the external factor with the time-lapse profile.

In another aspect, the present invention provides a program for executing a process for inferring an unidentified external factor given to a cell based on a time-lapse profile. The program executes the procedures of: a) exposing the cell to a plurality of known external factors; b) obtaining a time-lapse profile of the cell for each known external factor by time-lapse monitoring of a transcription level associated with at least one transcription control factor selected from the group consisting of transcription control factors derived from the cell; c) correlating the known external factors with the respective time-lapse profiles; d) exposing the cell to the unidentified external factor; e) obtaining a time-lapse profile of the unidentified external factor by time-lapse monitoring of the transcription level of the selected transcription control sequence; f) determining a profile corresponding to the time-lapse profile obtained in the procedure of e) from the time-lapse profiles obtained in the procedure of b); and g) determining that the unidentified external factor is the known external factor corresponding to the profile determined in the procedure of f).

In another aspect, the present invention provides a program for executing a process for inferring an unidentified external factor given to a cell based on a time-lapse profile. The program executes the procedures of: a) providing data relating to a correlation relationship between known external factors and time-lapse profiles of the cell in response to the known external factors, in relation to at least one transcription control sequence selected from transcription control sequences present in the cell; b) exposing the cell to the unidentified external factor; c) obtaining a time-lapse profile of the cell by time-lapse monitoring of a transcription level associated with the selected transcription control sequence; d) determining a profile corresponding to the time-lapse profile obtained in the procedure of c) from the time-lapse profiles obtained in the procedure of a); and e) determining that the unidentified external factor is the known external factor corresponding to the profile determined in the procedure of d).

When the present invention is provided in the form of a program as described above, each constituent element thereof can be implemented as with the detailed or preferred embodiments of the method of the present invention. Preferred embodiments of such a program can be easily selected by those skilled in the art and can be made or carried out by those skilled in the art based on the present specification. Description formats of such a program are well known to those skilled in the art and include, for example, the C+ language, and the like.

In another aspect, the present invention provides a method and system for diagnosing a subject. The diagnosis method comprises the steps of: a) obtaining a time-lapse profile of the cell by time-lapse monitoring of a transcription level associated with at least one transcription control sequence selected from the group consisting of transcription control sequences derived from the cell; b) determining the state of the cell based on the time-lapse profile of the transcription level; and c) determining a condition, disorder or disease of a subject based on the state of the cell. The diagnosis method is provided in the form of a system, the system of the present invention comprises: a) means for obtaining a time-lapse profile of the cell by time-lapse monitoring of a transcription level associated with at least one transcription control sequence selected from the group consisting of transcription control sequences derived from the cell; b) means for determining the state of the cell based on the time-lapse profile of the transcription level; and c) means for determining a condition, disorder or disease of a subject based on the state of the cell. The present invention is applicable to tailor-made diagnoses and therapies, such as drug resistance, selection of appropriate anticancer agents, selection of appropriate transplant cells, and the like. Preferably, the diagnosis method of the present invention may be provided as a therapeutic or preventative method comprising the step of treating a subject with a therapy or preventative method selected based on the result of diagnosis. In another preferred embodiment, the diagnosis system of the present invention may be provided as a therapeutic or preventative system comprising means for treating a subject with a therapy or preventative method, selected based on the result of diagnosis. An exemplary system configuration is shown in FIG. 32.

A configuration of a computer or system for implementing the diagnosis method and system of the present invention is shown in FIG. 17. FIG. 17 shows an exemplary configuration of a computer 500 for executing the cellular state determining method of the present invention. An exemplary system configuration is shown in FIG. 32.

The computer 500 comprises an input section 501, a CPU 502, an output section 503, a memory 504, and a bus 505. The input section 501, the CPU 502, the output section 503, and the memory 504 are connected via a bus 505. The input section 501 and the output section 503 are connected to an I/O device 506.

An outline of a correlation process, which is executed by the computer 500, will be described below.

A program for executing the correlation method and/or selection of treatment or preventative method (hereinafter referred to as a "correlation program" and a "selection program", respectively) is stored in, for example, the memory 502. Alternatively, the correlation program and the selection program may be stored in any type of recording medium, such as a floppy disk, MO, CD-ROM, CD-R, DVD-ROM, or the like, separately or together. Alternatively, the programs may be stored in an application server. The correlation program and the selection program stored in such a recording medium are loaded via the I/O device 506 (e.g., a disk drive, a network (e.g., the Internet)) to the memory 504 of the computer 500. The CPU 502 executes the correlation program and the selection program, so that the computer 500 functions as a device for performing the correlation method and the selection method of the present invention.

The result of analysis of a time-lapse profile (e.g., phase, etc.) and information about a cell or the like are input via the input section 501. Secondary information about a condition, disorder or disease to be correlated with a time-lapse profile and information about treatment and/or preventative methods may be input as required.

The CPU 502 correlates information about a time-lapse profile with a state of a cell or a condition, disorder or disease of a subject and a preventative or therapeutic method as required, based on the information input through the input section 501, and stores correlation data into the memory 504. Thereafter, the CPU 502 may store the information in the memory 504. Thereafter, the output section 503 outputs information about a state of a cell or a condition, disorder or disease of a subject and a preventative or therapeutic method as required, which has been selected by the CPU 502 as diagnostic information. The output data is output through the I/O device 506.

(Generation of Data)

In one aspect, the present invention provides a method for generating profile data of information of a cell. The method comprises the steps of: a) providing and fixing the cell to a support; and b) monitoring a biological agent or an aggregation of biological agents on or within the cell over time to generate data on the profile of the cell. In this aspect, the present invention is characterized in that the cell is fixed to substantially the same site of the support so that information can be continuously (e.g., in a time-lapse manner, etc.)

obtained from the same cell. Thereby, it is possible to monitor a biological agent and an aggregation of biological agents over time. The time-lapse monitoring makes it possible to obtain a profile of a cell and construct a digital cell. To fix a cell to a support, a fixing agent, such as a salt or the like, may be used for the support in the present invention. A combination of a salt, a complex of a positively charged substance and a negatively charged substance, and a cell may fix the cell to the support. Any salt may be used in the present invention. Examples of such a salt include, but are not limited to, calcium chloride, sodium hydrogen phosphate, sodium hydrogen carbonate, sodium pyruvate, HEPES, sodium chloride, potassium chloride, magnesium sulfide, iron nitrate, amino acids, vitamins, and the like. Examples of the above-described combination of a positively charged substance and a negatively charged substance include, but are not limited to, complexes of a negatively charged substance selected from the group consisting of DNA, RNA, PNA, a polypeptide, a chemical compound, and a complex thereof and a positively charged substance selected from the group consisting of a cationic polymer, a cationic lipid, a cationic polyamino acid, and a complex thereof. In a preferred embodiment of the present invention, a biological agent of interest may be a nucleic acid molecule or a molecule derived from such a nucleic acid molecule. This is because most nucleic acid molecules carry genetic information, from which cellular information can be obtained.

In another aspect, the present invention relates to data obtained by a method comprising the steps of: a) providing and fixing the cell to a support; and b) monitoring a biological agent or an aggregation of biological agents on or within the cell over time to generate data of the profile of the cell. Such data is obtained by the method which is not conventionally available, and is thus novel. Therefore, the present invention provides a recording medium storing such data.

In another aspect, the present invention relates to a method for generating profile data of information of a plurality of cells in a consistent environment. The method comprises the steps of: a) providing a plurality of cells on a support which can maintain a consistent environment; and b) monitoring a biological agent or an aggregation of biological agents on or within the cells over time to generate profile data for the cells. In this aspect, the present invention is characterized in that profile data or information for a plurality of cells in a consistent environment can be obtained. Techniques for providing such an environment is also within the scope of the present invention. To provide a consistent environment for a plurality of cells, a fixing agent, such as a salt or the like, may be used for the support in the present invention. A combination of a salt, a complex of a positively charged substance and a negatively charged substance, and cells may fix the cells to the support. Any salt may be used in the present invention. Examples of such a salt include, but are not limited to, calcium chloride, sodium hydrogen phosphate, sodium hydrogen carbonate, sodium pyruvate, HEPES, sodium chloride, potassium chloride, magnesium sulfide, iron nitrate, amino acids, vitamins, and the like. Examples of the above-described combination of a positively charged substance and a negatively charged substance include, but are not limited to, complexes of a negatively charged substance selected from the group consisting of DNA, RNA, PNA, a polypeptide, a chemical compound, and a complex thereof and a positively charged substance selected from the group consisting of a cationic polymer, a cationic lipid, a cationic polyamino acid and a complex thereof. In a preferred embodiment of the present invention, a biological agent of interest may be a nucleic acid molecule or a molecule derived from such a nucleic acid molecule. This is because most nucleic acid molecules carry genetic information, from which cellular information can be obtained.

In a preferred embodiment, an actin-like acting substance is preferably provided to the cells in the method of the present invention. The actin-like acting substance acts on actin within the cells to deform the internal cytoskeleton to facilitate introduction of an external factor into the cells. The presence of such an actin-like acting substance makes it possible to investigate an influence of an external factor of interest on the cells.

In one embodiment, a biological agent targeted by the present invention is at least one factor selected from the group consisting of nucleic acids, proteins, sugar chains, lipids, low molecular weight molecules, and composite molecules thereof.

In a preferred embodiment, cells targeted by the present invention are preferably cultured for a certain period of time without stimulation before monitoring. This procedure is performed for the purpose of synchronizing the target cells. The period of time required for synchronization is, for example, advantageously at least one day, more preferably at least two days, even more preferably at least 3 days, and still even more preferably at least 5 days. It should be noted that as the period of time for culture is increased, the necessity of maintaining the culture conditions increases. In the synchronization procedure, the same medium is preferably supplied to cells. Therefore, the culture medium is preferably consistent or at least changed in a consistent manner. To achieve this, a means for causing convection in the medium may be preferably provided and used.

In a more preferred embodiment, a biological agent provided to a cell in the present invention may comprise a nucleic acid molecule encoding a gene. The nucleic acid molecule encoding a gene is preferably transfected into a cell. Preferably, such a biological agent may be provided along with a transfection reagent (gene introduction reagent). More preferably, the nucleic acid molecule encoding a gene may be provided to a cell along with a gene introduction reagent and an actin-like acting substance. In this case, the cell is preferably provided with a complex of a salt, a positively charged substance, and a negatively charged substance (in this case, a nucleic acid molecule and a gene introduction reagent). Thus, the cell and the target molecule are fixed on a support. In addition, this technique makes it possible to allow separate biological agents (e.g., nucleic acid molecules) to be separately introduced into cells without a partition. As substantially no partition is used, a plurality of cells can be monitored in substantially a consistent environment. Further, different biological agents can be introduced into a cell, thereby making it possible to obtain a profile of a state of the cell affected by the biological agents. Such a profile can be stored as data. Such data may be stored in a certain standard format, and therefore, can be reproduced and compared. Thus, the present invention has an effect which is not achieved by conventional biological assays. Such data, once obtained and stored in such a standard format, can be extracted and used for various purposes and a number of times. For example, researchers can perform "virtual experiments" to conduct various analyses under the same conditions while taking into consideration differences in a substantially infinite number of parameters. In addition, since virtual experiments and the results thereof are stored in a raw data format, undergraduate and graduate students, who otherwise spend most of their school life doing laboratory work, can receive education in data analysis in the true sense. The above-described cellular profile data can be easily standardized, thereby making it possible to do research based on data which may have been obtained by experiments under the same conditions over the world. Such data may be distributed in a standardized form. Such a standardized form may be readable to typical computers (e.g., computers having a commonly available OS, such as Windows, Mac, UNIX, LINUX, or the like). Data produced in the present invention may include generated cellular profile data, information about experimental conditions used in data generation, information about cells, information about environments, and the like.

In a preferred embodiment, a profile targeted by the present invention may include a profile of gene expression, a profile of an apoptotic signal, a profile of a stress signal, a profile of the localization of a molecule (preferably, the molecule is labeled with a fluorescent, phosphorescent, or radioactive substance, or a combination thereof), a profile of changes in cellular morphology, a profile of a promoter, a profile of a promoter dependent on a specific pharmaceutical agent (e.g., antibiotics, ligands, toxins, nutrients, vitamins, hormones, cytokines, etc.), a profile of an intermolecular interaction, and the like. In an embodiment in which the present invention targets a profile of a promoter dependent on a specific pharmaceutical agent, it is preferable that the present invention may further comprise administering the specific pharmaceutical agent.

In a preferred embodiment, the present invention may further comprise providing an external stimulus to the cell. Such an external stimulus may or may not be a biological agent. The external factor may be any factor and includes, without limitation, substances or other elements (e.g., energy, such as ionizing radiation, radiation, light, acoustic waves, and the like).

In one embodiment, an external factor used in the present invention may be RNAi. RNAi can be used to substantially suppress an arbitrary gene. It is possible to produce RNAi for all existing genes and investigate the effect of RNAi on the genes. RNAi can be created by techniques well known in the art.

In another embodiment, an external factor of the present invention may comprise a chemical substance which does not exist in organisms. By providing such a chemical substance which does not exist in organisms, it is possible to collect a variety of information. Once collected, such data can be reused. Therefore, assuming that a chemical substance which does not exist in organisms is not substantially available, if data can be obtained once for such a chemical substance in accordance with the present invention, research can continue without worrying about the availability of such a chemical substance.

In one embodiment, an external factor targeted by the present invention may comprise a ligand to a cellular receptor. By analyzing a ligand, it is possible to study various signal transduction pathways. Therefore, in such a case, a profile obtained according to the present invention may be a profile of receptor-ligand interactions.

In a preferred embodiment of the present invention, a profile of cellular morphology may be obtained. In this case, a method of the present invention may further comprise applying a stimulus to a cell which may be selected from the group consisting of overexpression of a gene, underexpression of a gene, knock down of a gene, addition of an external factor, and a change in an environment.

In a preferred embodiment, a profile obtained according to the present invention may be a profile of interactions between molecules present within a cell. Such an intermolecular interaction includes, but is not limited to, interaction between molecules present in a signal transduction pathway, interaction between a receptor and a ligand, interaction between a transcription factor and a transcription factor sequence, and the like.

In another preferred embodiment, a profile obtained according to the present invention may be a profile of interaction between molecules present in a cell. In this case, a method of the present invention may further comprise observing a cell using a technique selected from the group consisting of a two-hybrid method, FRET, and BRET. The two-hybrid method detects intermolecular interaction within a cell. Specifically, this technique is described in, for example, Protein-Protein Interactions, A MOLECULAR CLONING MANUAL, Edited by Erica Golemis, Cold Spring Habor Laboratory Press, Cold Spring Harbor, N.Y. (this document also describes FRET). FRET is a technique for detecting inter- or intra-molecular resonance energy shift as a fluorescent wavelength, and is described in, for example, Protein-Protein Interactions (supra); and Miyawaki A., Visualization of the spatial and temporal dynamics of intracellular signaling, Dev. Cell, 2003 March; 4(3):295-305. BRET is an intermolecular interaction assay system and is described, for example, Boute N., The use of resonance energy transfer in high-throughput screening: BRET versus FRET, Trends Pharmacol Sci., 2002 August; 23(8):351-4.

In a preferred embodiment, cells targeted by the present invention are preferably arranged on a support in a pattern of an array. In this case, preferably, a plurality of cells targeted by the present invention may be spaced at intervals of 10 cm at maximum, more preferably 1 cm at maximum, even more preferably 1 mm at maximum, and most preferably 0.1 mm at maximum. The cells need to be spaced at minimum intervals. Such intervals may be preferably set so that substantially no interaction occurs.

In one embodiment, a profile obtained according to the present invention may or may not be obtained in real time. A real time profile may be advantageous. When simultaneity is important, it is important to obtain a profile in real time. Alternatively, when a profile is intended to be stored, the profile is not necessarily obtained in real time.

In an additional embodiment, the present invention further comprises fixing a cell to a solid phase support. In this case, the cell is fixed to the solid phase support along with a salt, a complex, an actin-like acting substance, or the like.

In one embodiment, data generated according to the present invention may contain information about a profile. In a preferred embodiment, data generated according to the present invention may contain information about conditions for monitoring, information about a cellular state, information about an external factor, information about an environment, and the like.

In a preferred embodiment, at least two biological agents may be preferably monitored in the present invention, more preferably at least 3 biological agents, and even more preferably at least 8 biological agents. Alternatively, all biological agents in a certain specific category (e.g., all olfactory receptors, all gustatory receptors, etc.) may be preferably monitored.

Alternatively, in another preferred embodiment, the present invention may further comprise arbitrarily selecting the above-described biological agents.

In a preferred embodiment, a cell targeted by the present invention may be selected from the group consisting of stem cells and somatic cells.

In one embodiment, a support used in the present invention is preferably a solid phase support. This is because cells are easily fixed to such a support. Such a solid phase support may be made of any material known in the art. The support may be in the form of a substrate.

In one embodiment of the present invention, the above-described biological agent may be a nucleic acid and the above-described cell may be transfected with the nucleic acid. By transfecting the cell with the nucleic acid, an influence of the nucleic acid on the cell can be collected in real time or in a standardized storable format into data or a profile. This cannot be achieved by conventional techniques. In a preferred embodiment, transfection may be performed in solid a phase or in a liquid phase. More preferably, transfection may be advantageously performed in a solid phase. This is because data collection and standardization or normalization can be more easily carried out.

In a preferred embodiment of the present invention, a profile may be subjected to a process selected from the group consisting of phase comparison, calculation of a difference from a control profile, signal processing, and multivariate analysis. Data processed in such a manner may fall within the scope of the present invention.

In another aspect, the present invention provides a method for presenting profile data of information about a plurality of cells in a consistent environment. The method comprises the steps of: a) providing a plurality of cells on a support capable of retaining the cells in a consistent environment; b) monitoring a biological agent or an aggregation of biological agents on or within the cells over time to generate profile data for the cells; and c) presenting the data.

The above-described support capable of retaining a plurality of cells in a consistent environment can be achieved as described elsewhere herein. The step of generating data can be performed as described elsewhere herein. The step of presenting data can be performed as described elsewhere herein. Examples of a method of performing such presentation include, but are not limited to, techniques of using various sensory means, such as visual means, auditory means, olfactory means, tactile means, gustatory means, and the like. Preferably, a visually presentation means may be used. Such visual means include, without limitation, a computer display and the like.

Preferably, in the presentation method of the present invention, presentation may be performed in real time. Alternatively, stored data may be stored and presentation may be delayed. When presentation should be performed in real time, data signals may be transferred directly to, for example, a display.

In another aspect, the present invention provides a method for determining states of cells in a consistent environment. The method comprises the steps of: a) providing a plurality of cells on a support capable of retaining the cells in a consistent environment; b) monitoring a biological agent or an aggregation of biological agents on or within the cells over time to generate profile data for the cells; and c) determining the states of the cells based on the data.

The above-described support capable of retaining a plurality of cells in a consistent environment can be achieved as described elsewhere herein. The step of generating data can be performed as described elsewhere herein. The step of determining the states of the cells may be performed by correlating the generated data with information about the cells, or comparing the generated data with standard data. In this case, the data may be statistically processed.

Therefore, in a certain embodiment, the present invention may further comprise correlating a profile obtained according to the present invention with a state of a cell before obtaining the time-lapse profile. To perform determination smoothly, the cells targeted by the present invention may advantageously include cells whose states are known. It is possible to store data of cells whose states are known, determination can thus be quickly performed by comparing data between the known cell and unknown cells.

During determination, at least two biological agents are preferably present. In this case, the plurality of biological agents may belong to heterologous categories (e.g., proteins and nucleic acids, etc.) or homologous categories.

Preferably, the present invention may further comprise arbitrarily selecting a biological agent. Any biological agent can be selected and used to characterize a state of a cell to some extent, and in some cases, identification is possible. Thus, the present invention has an effect which cannot be expected from conventional techniques.

In the determination method of the present invention, data may be preferably generated in real time. When data is generated in real time, an unknown substance or state of an unknown cell may be determined in real time.

In the determination method of the present invention, examples of a state of a target cell include, but are not limited to, differentiated states, undifferentiated states, cellular responses to external factors, cell cycles, growth states, and the like.

A cell targeted by the present invention may be either a stem cell or a somatic cell. Any somatic cell may be used. A cell may be selected by those skilled in the art, depending on the purpose of use of the cell.

A solid phase support used in the determination method of the present invention may comprise a substrate. In the present invention, such a substrate can be used as a part of a computer system, so that determination can be automated. An exemplary configuration of such a system is shown in FIG. 32.

In a preferred embodiment, in the determination method of the present invention, the biological agent may be a nucleic acid molecule, and the cell is transfected with the nucleic acid molecule. Transfection may be performed on a solid phase support using any material, but preferably a gene introduction agent, more preferably a salt, an actin-like acting substance, or the like. Transfection may be performed in solid phase or in liquid phase, and preferably in solid phase.

In a determination method of the present invention, a target biological agent may be capable of binding to another biological agent. By investigating a biological agent having such a property, a network mechanism in a cell may be elucidated.

In a determination method of the present invention, the determination step may comprise a mathematical process selected from the group consisting of comparison of phases of profiles, collection of differences from a control profile, signal processing, and multivariate analysis. Such processing techniques are well known in the art and described in detail herein.

In another aspect, the present invention provides a method for correlating an external factor with a cellular response to the external factor. The method comprises the steps of: a) exposing a plurality of cells to an external factor on a support capable of retaining the cells in a consistent environment; b) monitoring a biological agent or an aggregation of biological agents on or within the cells over time to generate profile data for the cells; and c) correlating the external factor with the profile. Exposure of the cells to the external factor may be achieved by placing the cells and the external factor into an environment in which the cells are contacted with the external factor. For example, when the cells are fixed on the support, the external factor is added to the support to achieve exposure. Techniques for generating and correlating data are also well known in the art, and may be used singly or in combination.

Preferably, statistical processes are performed to generate statistically significant data and information.

In a preferred embodiment, in the correlation method of the present invention, the cells may be fixed on the support. Since the cells are fixed, data can be easily standardized, so that data can be significantly efficiently processed.

In a preferred embodiment, a correlation method of the present invention may further comprise using at least two external factors to obtain a profile for each external factor. Techniques for obtaining such a profile are well described herein.

More preferably, the correlation step may further comprise dividing at least two profiles into categories and classifying the external factors corresponding to the respective profiles into the categories. By categorization, data can be processed in a more standardized manner.

In a preferred embodiment, a profile obtained by the present invention may be presented in real time. When data is intended to be stored, data may not be particularly presented in real time.

In a preferred embodiment, a cell used in the present invention may be cultured on an array. In such a case, therefore, the cell is preferably covered with medium. Any medium which is commonly used for cells may be used.

In a preferred embodiment of the present invention, the step of monitoring a profile may comprise obtaining image data from the array. Particularly, when a profile contains visual information (e.g., emission of fluorescence due to gene expression), the profile can be obtained by capturing image data.

In a correlation method of the present invention, the step of correlating an external factor with a profile may comprise distinguishing between phases of the profile. Distinguishing phases of the profile can be achieved only after the present invention provides time-lapse profiles obtained in a consistent environment.

An external factor targeted by the present invention may be selected from the group consisting of a temperature change, a humidity change, an electromagnetic wave, a potential difference, visible light, infrared light, ultraviolet light, X-rays, a chemical substance, a pressure, a gravity change, a gas partial pressure, and an osmotic pressure. Preferably, the chemical substance may be a biological molecule, a chemical compound, or a medium. Examples of such a biological molecule include, but are not limited to, nucleic acid molecules, proteins, lipids, sugars, proteolipids, lipoproteins, glycoproteins, proteoglycans, and the like. Such a biological molecule may also be, for example, a hormone, a cytokine, a cell adhesion factor, an extracellular matrix, or the like. Alternatively, the chemical substance may be either a receptor agonist or antagonist.

In another aspect, the present invention relates to a method for identifying an unidentified external factor given to a cell from a profile of the cell. The method comprises the steps of: a) exposing a cell to a plurality of known external factors on a support capable of retaining the cell in a consistent environment; b) monitoring a biological agent or an aggregation of biological agents on or within the cell over time to generate a profile of the cell to each of the known external factors and to generate profile data for the cell; c) correlating each of the known external factors with each of the profiles; d) exposing the cell to an unidentified external factor; e) monitoring a biological agent or an aggregation of biological agents on or within the cell exposed to the external factors over time to obtain a profile of the cell with respect to the unidentified external factor; f) determining, from the profiles obtained in the step of b), a profile corresponding to the profile obtained the step of e); and g) determining that the unidentified external factor is the known external factor corresponding to the profile determined in the step of f). Techniques for exposure to external factors, data generation, correlation, exposure to unidentified external factors, and the like are described elsewhere herein and can be selected as appropriate depending on the purpose by those skilled in the art taking such descriptions into consideration.

In another aspect, the present invention provides a method for identifying an unidentified external factor given to a cell from a profile of the cell. The method comprises the steps of: a) providing data relating to a correlation relationship between known external factors and profiles of the cell in response to the known external factors, in relation to a biological agent or an aggregation of biological agents on or within the cell; b) exposing the cell to the unidentified external factor; c) monitoring the biological agent or the aggregation of the biological agents on or within the cell to obtain a profile of the cell; d) determining, from the profiles provided in the step of a), a profile corresponding to the profile obtained in the step of c); and e) determining that the unidentified external factor is the known external factor corresponding to the profile determined in the step of d). Techniques for exposure to external factors, data generation, correlation, exposure to unidentified external factors, and the like are described elsewhere herein and can be selected as appropriate depending on the purpose by those skilled in the art taking such descriptions into consideration.

In another aspect, the present invention provides a method for obtaining a profile relating to information for a plurality of cells in a consistent environment. The method comprises the steps of: a) providing a plurality of cells on a support capable of retaining the cells in a consistent environment; and b) monitoring a biological agent or an aggregation of biological agents on or within the cell over time to generate a profile of the cells. Techniques for exposure to external factors, data generation, correlation, exposure to unidentified external factors, and the like are described elsewhere herein and can be selected as appropriate, depending on the purpose by those skilled in the art taking such descriptions into consideration.

In another aspect, the present invention relates to a recording medium in which data generated by a method for generating cellular profile data of the present invention is stored. Data may be stored in any format. Any recording medium may be used. Examples of such a recording medium include, but are not limited to, CD-ROMs, flexible disks, CD-Rs, CD-RWs, MOs, mini disks, DVD-ROMs, DVD-Rs, memory sticks, hard disks, and the like. The present invention also relates to a transmission medium in which data generated by a method for generating cellular profile data of the present invention is stored. Examples of such a transmission medium include, but are not limited to, networks, such as intranets, the Internet, and the like.

A recording medium or transmission medium of the present invention may further contain data relating to at least one piece of information selected from the group consisting of information about conditions for the monitoring step, information about the profile, information about the cellular state, and information about the biological agent. Data relating to such information may be stored while being linked to one another. Preferably, the data may be advantageously standardized. Standardized data can be distributed on general distribution pathways. The above-described linkage may be constructed for each cell or for each biological agent, or for both.

In another aspect, the present invention relates to data generated by a method for generating cellular profile data of the present invention. Such data cannot be generated by conventional techniques and is thus novel.

In another aspect, the present invention provides a system for generating profile data of information for a plurality of cells in a consistent environment. The system comprises: a) a support capable of retaining a plurality of cells in a consistent environment; b) means for monitoring a biological factor or an aggregation of biological factors on or within the cells over time; and c) means for generating profile data for the cells from a signal obtained from the monitoring means. The support capable of retaining cells in a consistent environment can be made by those skilled in the art using a technique first provided by the present invention. Such a technique is attributed to the finding that cells are fixed and arrayed without a partition. Examples of the monitoring means include, but are not limited to, microscopes (e.g., optical microscopes, fluorescence microscopes, phase-contrast microscopes, etc.), electron microscopes, scanners, naked eyes, infrared cameras, confocal/nonconfocal microscopes, CCD cameras, and the like. An exemplary configuration of such a system is shown in FIG. 32.

In a system of the present invention, the system may not necessarily contain cells from the start, but preferably may contain cells which are advantageously fixed on a support. In such a case, fixation is preferably standardized. In addition, the cells are fixed and spaced, for example, without limitation, at intervals of 1 mm or the like.

In a preferred embodiment, at least one substance selected from the group consisting of salts and actin-like acting substances may be preferably adhered to the support. By adhering cells to the support with a salt or an actin-like acting substance, or preferably with both, fixation of the cells and/or introduction of a substance into the cells can be enhanced.

Examples of the monitoring means used in the system of the present invention include, but are not limited to, optical microscopes, fluorescence microscopes, phase-contrast microscopes, reading devices using a laser source, means using surface plasmon resonance (SPR) imaging, electric signals, chemical or biochemical markers singly or in combination, radiation, confocal microscopes, nonconfocal microscopes, differential interference microscopes, stereoscopic microscopes, video monitors, infrared cameras, and the like. Preferably, a scanner (e.g., a scanner for scanning a surface of a substrate using a white light source or laser) may be used. The reason a scanner is preferable is that fluorescence can efficiently transmit excited energy and microscopic technology can be easily applied. Further, measurement can be advantageously performed without significant damage to cells. An exemplary configuration of such a system is shown in FIG. 32.

In another aspect, the present invention provides a system for presenting a profile of information for a plurality of cells in a consistent environment. The system comprises: a) a support capable of retaining a plurality of cells in a consistent environment; b) means for monitoring a biological factor or an aggregation of biological factors on or within the cells over time; c) means for generating profile data for the cells from a signal obtained from the monitoring means; and d) means for presenting the data. The support, the monitoring means, and the data generating means can be made as described elsewhere herein. The means for presenting data can be achieved by techniques well known in the art. Examples of such a data presenting means include, but are not limited to, computer displays, loudspeakers, and the like. An exemplary configuration of such a system is shown in FIG. 32.

A presentation system of the present invention may further comprise a plurality of cells, in which the cells are preferably fixed to the support. In such a case, at least one substance selected from the group consisting of salts and actin-like acting substances may be preferably adhered to the support. By adhering cells to the support with a salt or an actin-like acting substance, or preferably with both, fixation of the cells and/or introduction of a substance into the cells can be enhanced.

Any monitoring means may be used. Examples of the monitoring means include, but are not limited to, optical microscopes; fluorescence microscopes; phase microscopes; reading devices using a laser source; means using surface plasmon resonance (SPR) imaging, electric signals, chemical or biochemical markers singly or in combination; and the like.

Any data presenting means may be used, including, without limitation, displays, loudspeakers, and the like.

In another aspect, the present invention provides a system for determining a state of a cell. The system comprises: a) a support capable of retaining a plurality of cells in a consistent environment; b) means for monitoring a biological factor or an aggregation of biological factors on or within the cells over time; c) means for generating data from a signal obtained by the monitoring means; and d) means for extrapolating the state of the cell from the data. The support, the monitoring means, and the data generating means can be made by those skilled in the art as described elsewhere herein. The means for extrapolating a state of a cell from data may be produced and used by techniques well known in the art. For example, measured data can be compared with standard data for known cells to achieve extrapolation. A device storing a program for such extrapolation or a computer capable of executing such a program may be used as the extrapolation means. An exemplary configuration of such a system is shown in FIG. 32.

In another aspect, the present invention provides a system for correlating an external factor with responses of cells to the external factor. The system comprises: a) a support capable of retaining a plurality of cells in a consistent environment; b) means for exposing the cell to the external factor; c) means for monitoring a biological factor or an aggregation of biological factors on or within the cells over time; d) generating profile data for the cells from a signal from the monitoring means; and e) means for correlating the external factor with the profile. The support, the monitoring means, and the data generating means can be made by those skilled in the art as described elsewhere herein. The means for exposing the cells to the external factor can be designed and carried out as appropriate by those skilled in the art depending on the properties of the external factor. The correlation means can employ a recording medium storing a program for correlation or a computer capable of executing such a program. Preferably, a system of the present invention comprises a plurality of cells. An exemplary configuration of such a system is shown in FIG. 32.

In another aspect, the present invention provides a system for identifying an unidentified external factor given to a cell based on a profile of the cell. The system comprises: a) a support capable of retaining a plurality of cells in a consistent environment; b) means for exposing the cell to one or more known external factors; c) means for monitoring a biological factor or an aggregation of biological factors on or within the cells over time; d) means for obtaining a profile of the cell with respect to each of the known external factors to generate profile data for the cell; e) means for correlating each of the known external factors with each profile; f) means for exposing the cell to the unidentified external factor; g) means for comparing the profiles of the known external factors obtained by the means of d) with the profile of the unidentified external factor to determine a profile of the unidentified external factor from the profiles of the known external factors, wherein the determined unidentified external factor is the known external factor corresponding to the determined profile. The support, the exposure means, the monitoring means, the data generating means, and the correlation means, and the other exposure means can be made and carried out as appropriate by those skilled in the art as described elsewhere herein. The means for determining a corresponding profile can also be made and carried out by utilizing a recording medium storing a program capable of executing such a determination process and a computer capable of executing such a program. Preferably, a system of the present invention comprises a plurality of cells. An exemplary configuration of such a system is shown in FIG. 32.

In another aspect, the present invention provides a system for identifying an unidentified external factor given to a cell based on a profile of the cell. The system comprises: a) a recording medium storing providing data relating to a correlation relationship between known external factors and profiles of the cell in response to the known external factors, in relation to a biological factor or an aggregation of biological factors on or within the cell; b) means for exposing the cell to the unidentified external factor; c) a support capable of retaining a plurality of cells in a consistent environment; d) means for monitoring a biological factor or an aggregation of biological factors on or within the cells over time; e) means for obtaining a profile of the cell from a signal obtained by the monitoring means; f) means for determining, from the profiles stored in the recording medium of a), a profile corresponding to the profile obtained with respect to the unidentified external factor, wherein the determined unidentified external factor is the known external factor corresponding to the determined profile. The support, the exposure means, the monitoring means, the data generating means, and the correlation means, and the other exposure means can be made and carried out as appropriate by those skilled in the art as described elsewhere herein. The means for determining a corresponding profile can also be made and carried out by utilizing a recording medium storing a program capable of executing such a determination process and a computer capable of executing such a program. Preferably, a system of the present invention comprises a plurality of cells. An exemplary configuration of such a system is shown in FIG. 32.

In another aspect, the present invention relates to a support capable of maintaining a consistent environment for a plurality of cells. Such a support was first provided by the present invention. By utilizing such a support, a plurality of cells can be analyzed in a consistent environment.

Preferably, cells are arranged on a support in the form of an array. This is because standardized analysis can be achieved. In this case, the support may preferably comprise a salt or an actin-like acting substance. More preferably, the support may advantageously comprise a complex of a positively charged substance and a negatively charged substance. This is because cells can be easily fixed to the support using such a complex. Actin-like acting substances are preferable when the interior of cells is analyzed, since the actin-like acting substances increase the efficiency of introduction of external factors into cells. Therefore, in a preferred embodiment of the present invention, the support may comprise a salt and an actin-like acting substance, and more preferably may comprise a complex of a positively charged substance and a negatively charged substance.

A support of the present invention is characterized in that cells may be provided and spaced at intervals of 1 mm. In the case of such intervals, it is not conventionally possible to provide an environment without a partition. Therefore, the present invention has a remarkable effect, as well as practicability, applicability and utility.

In a preferred embodiment, a support of the present invention may comprise a cell fixed thereto. In a more preferred embodiment, a support of the present invention may comprise a biological factor fixed thereto.

In a preferred embodiment, at least two biological factors may be fixed to the support. Such biological factors may be factors selected from the group consisting of nucleic acid molecules, proteins, sugars, lipids, metabolites, low molecular weight molecules, and complexes thereof, and factors containing physical elements and/or temporal elements.

In a more preferred embodiment, a cell and a biological factor may be fixed to a support of the present invention in a mixed manner. The biological factor and the cell may be provided so that they can interact with each other. Such interaction may vary depending on the biological factor. According to the properties of the biological factor, those skilled in the art can understand how the biological factor interacts with the cell and where the biological factor is positioned so as to interact with the cell.

In a preferred embodiment, a salt, a complex of a positively charged substance and a negatively charged substance, and an actin-like acting substance are fixed along with a cell and a biological factor to a support of the present invention.

In a more preferred embodiment, a salt, a complex of a positively charged substance and a negatively charged substance, and an actin-like acting substance are fixed along with a cell and a biological factor to a support of the present invention in the form of an array. With such a structure, a cell chip capable of generating the profile data of a cell can be provided. The support has a structure in which a salt, a complex of a positively charged substance and a negatively charged substance, and an actin-like acting substance are fixed along with a cell and a biological factor in the form of an array. Such a support is also called a "transfection array".

Examples of a salt used in the support of the present invention include, but are not limited to, calcium chloride, sodium hydrogen phosphate, sodium hydrogen carbonate, sodium pyruvate, HEPES, sodium chloride, potassium chloride, magnesium sulfide, iron nitrate, amino acids, vitamins, and the like. A preferable salt is, for example, without limitation, sodium chloride or the like.

Examples of a gene introduction agent used in the support of the present invention include, but are not limited to, cationic polymers, cationic lipids, polyamine-based reagents, polyimine-based reagents, calcium phosphate, oligofectamin, and oligofectors and the like. Preferably the gene introduction reagents used may be preferably, but are not limited to lipofectamines, oligofectamines and oligofectors.

Examples of an actin-like acting substance used in the support of the present invention include, but are not limited to, fibronectin, laminin, vitronectin, and the like. A preferable actin-like acting substance is, for example, without limitation, fibronectin.

Examples of a nucleic acid molecule used in the support of the present invention include, but are not limited to, nucleic acid molecules comprising transcription control sequences (e.g., promoters, enhancers, etc.), gene coding sequences, genomic sequences containing nontranslation regions, nucleic acid sequences encoded by the genome of a host (a fluorescent protein gene, *E. coli*/yeast self-replication origins, a GAL4 domain, etc.), and the like. Preferable nucleic acid molecules include, but are not limited to, transcription control sequences (e.g., promoters, enhancers, etc.), gene coding sequences, genomic sequences containing nontranslation regions, and the like.

Examples of a cell used in the support of the present invention include, but are not limited to, stem cells, established cell lines, primary culture cells, insect cells, bacterial cells, and the like. Preferable cells include, but are not limited to, stem cells, established cell lines, primary culture cells, and the like.

Examples of a material for a support of the present invention include, but are not limited to, glass, silica, plastics, and the like. Preferable materials include, but are not limited to, the above-described materials with coating.

In another aspect, the present invention provides a method for producing a support comprising a plurality of cells fixed thereto and capable of maintaining a consistent environment for the cells. The method comprises the steps of: A) providing the support; and B) fixing the cells via a salt and a complex of a positively charged substance and a negatively charged substance onto the support. The step of providing a support may be achieved by obtaining a commercially available support or molding a support material. A support material may be prepared by mixing starting materials for the material as required. The fixing step can be carried out by using techniques known in the art. Examples of such fixing techniques include, but are not limited to, an ink jet printing technique, a pin array technique, a stamping technique, and the like. These techniques are well known and can be performed as appropriate by those skilled in the art.

In a preferred embodiment, the fixing step in the present invention may comprise fixing a mixture of the salt, the complex of a gene introduction agent and an actin-like acting substance (positively charged substances) and a nucleic acid molecule (a negatively charged substance), and the cell in the form of an array. Such a fixing step may be achieved by printing techniques.

In another aspect, the present invention provides a device for producing a support comprising a plurality of cells fixed thereto and capable of maintaining a consistent environment for the cells. The device comprises: A) means for providing the support; and B) means for fixing the cells via a salt and a complex of a positively charged substance and a negatively charged substance onto the support. The support may be obtained using means which can perform the above-described methods. Examples of such means include, but are not limited to, a support molding means, a material formulating means (e.g., a mixing means), and the like. The molding means can employ techniques well known in the art. The fixing means may comprise a printing means. As such a printing means, commercially available ink jet printers can be used.

(Digital Cell)

As used herein the term "digital cell" refers to a collection of at least one experimental data corresponding to a cell of experimental interest. Such experimental data is a correlation between the conditions used for the experiments conducted on an actual cell in the real world, and the experimental results thereof. The digital cell is composed such that when an experimental condition is given, an experimental result relating to the experimental condition will be reproduced.

By using the digital cell, experimental results conducted on an actual cell can be reproduced on a computer system. This allows institutions or individuals having no experimental facilities to conduct cutting-edge studies relating to a cell. As a result, it allows the introduction of business entities having a primary interest in disciplines other than that of the present technical art, which could not been achieved to date, prior to the disclosure of the present invention.

FIG. 33A depicts an example of data structure of a digital cell. This example represents a digital cell by a collection of three experimental data A1, A2 and A3 relating to cell A.

Each of experimental data A1, A2 and A3, comprises cell parameter, environment parameter and stimulus parameter as parameters indicating experimental conditions, and stimulus response result as an experimental result.

As used herein, the cell parameter specifies a cell of experimental interest. The environment parameter specifies an environment under which the cell specified by the cell parameter is cultured. The stimulus parameter specifies a stimulus given to the cell specified by the cell parameter. The stimulus response result shows a result which the cell specified by the cell parameter responded to the stimulus specified by the stimulus parameter under the environment specified by the environment parameter.

Experimental data A1 shows that cell A was cultured in a medium called "DMEM", under the culture condition of pH "7", temperature "37" degree Celsius, $CO_2$ concentration "5"%, and a stimulus consisting of a reporter called "Tet-OFF CMV EGF" or "MCV EGFP" and a chemical stimulus (agent) "Doxycycene" is given thereto to obtain a stimulus response result. The stimulus response result is represented by "cell dynamic data 1" and "reporter measurement data 1".

Experimental data A2 shows that cell A was cultured in a medium called "DMEM", under the culture condition of pH "7", temperature "37" degree Celsius, $CO_2$ concentration "5" %, and a stimulus consisting of a reporter called "c-fos" and a chemical stimulus (agent) "PSC833" is given thereto to obtain a stimulus response result. The stimulus response result is represented by "cell dynamic data 2" and "reporter measurement data 2".

Experimental data A3 shows that cell A was cultured in a medium called "DMEM", under the culture condition of pH "5", temperature "39" degree Celcius, $CO_2$ concentration "4" %, and a stimulus consisting of a reporter called "CREB" and a chemical stimulus (agent) "Vindecine" is given thereto to obtain a stimulus response result. The stimulus response result is represented by "cell dynamic data 3" and "reporter measurement data 3".

As such, parameters indicating experimental conditions (a cell parameter, an environment parameter and a stimulus parameter) and a stimulus response result showing an experimental result are correlated. Such correlation and data correlated thereby are called experimental data. The digital cell is provided as a collection of at least one experimental data on a cell of experimental interest.

FIG. 33B shows another example of data structure of the digital cell. This example shows the layered structure of the data structure shown in FIG. 33A. As such, layering the structure of the data structure of the digital cell allows expression of the same content with less data than the data structure shown in FIG. 33A.

In the examples of FIGS. 33A and 33B, correlation has been presented by a unidirectional link (arrows in the Figures) between the parameter showing the experimental conditions and experimental results. However, methods of correlation are not limited thereto. Any methods of correlation may be used herein.

(Production of a Digital Cell)

FIG. 34 shows an example of the procedure of a process of producing a digital cell. This procedure may be implemented by any type of computer.

Step S3401: Cell parameters specifying a cell of experimental interest are obtained. Cell parameters can be obtained by, for example, receiving cell parameters inputted by a user into a computer. Alternatively, data outputted from an experimental apparatus may be obtained by collection or analysis of the same in an automatic manner by a computer to obtain cell parameters.

Step S3402: Environment parameters specifying an environment under which the cell specified by the cell parameters is cultured, are obtained. The environment parameters are obtained by receiving, by a computer, environment parameters inputted by a user, for example. Alternatively, environment parameters may be obtained by automatically collecting or analyzing data outputted from an experimental apparatus (for example, sensors measuring experimental environment and the like) and the like, by a computer. The environment parameters include, for example, parameters representing a medium for culturing a cell and a parameter representing conditions for such culture. Parameters of such culture conditions include for example, pH, temperature, $CO_2$ concentration of the medium, and the like.

Step S3403: Stimulus parameter specifying a stimulus to be given to a cell specified by the cell parameter. A stimulus parameter is obtained by, for example, receiving, by a computer, a stimulus parameter inputted by a user. Alternatively, a stimulus parameter may be obtained by automatically collecting or analyzing, by a computer, data outputted by an experimental apparatus. Such a stimulus parameter may comprise, for example, a parameter representing a reporter and a parameter representing a chemical stimulus.

Step S3404: A stimulus response result showing the result in response to a stimulus by the stimulus parameter, by a cell specified by the cell parameter under the environment specified by the environment parameter, is obtained. The stimulus response result is obtained by automatically collecting or analyzing data outputted from an experimental apparatus such as monitoring apparatus for monitoring the course of experiments.

Step S3405: The cell parameter, the environment parameter, the stimulus parameter and the stimulus response result are correlated with each other. This correlation allows production of an experimental data against a cell of experimental interest. Such a correlation is conducted by linking in a single direction shown in FIG. 33A. However, methods correlation is not limited to such.

Step S3406: Steps S3401 through S3405 are repeated as necessary. This allows production of at least one experimental data against a cell of experimental interest. The collection of at least one experimental data is provided as a digital cell.

The computer implementing the process for producing a digital cell, functions as an apparatus or device for producing a digital cell. The digital cell produced is stored on, for example, a database which can be accessed by the computer.

As such, provision of a digital cell of a collection of at least one experimental data, is only possible by the present inventors by providing and developing technologies for locating a plurality of cells on a substrate under a consistent environment. Conventionally, in the prior art, it was not possible to maintain a plurality of cells under a consistent environment, and thus the experimental conditions have not been reliable, and thus no significance is found when accumulating experimental data between experiments. As such, the "production of a digital cell" is a real advance in technology which is feasible for the first time through the technological innovation of the present inventors.

(Provision of a Method of Reproducing Experimental Results Against an Actual Cell)

FIG. 35 depicts an example of a configuration of computer system 3501 which provides a service reproducing an experimental result obtained using an actual cell using the digital cell.

Computer system 3501 comprises service requester 3510 requesting a service desired by a user, and service provider 3520 providing the desired service in response to the request.

Computer system 3501 may comprise a plurality of service requesters 3510.

Service provider 3520 is configured so as to be capable of accessing database 3522 with at least one digital cell stored thereon. A database structure of the digital cell stored on database 3522 is shown in, for example, FIGS. 33A and 33B. Database 3522 may be provided inside service provider 3520, or may be located outside service provider 3520.

Service provider 3520 may be configured so as to be capable of accessing a plurality of databases stored thereon with respect to at least one digital cell.

Service requester 3510 and service provider 3520 may independently be any type of computer.

Service requester 3510 and service provider 3520 are connected to each other via network 3530. Network 3530 may be any type of network, but in view of feasibility of connection or cost, most preferably, the network is the Internet.

When network 3530 is the Internet, service requester 3510 may be a Web browser operated by a user, and service provider 3520 may be a Web server connected to service requester via the Internet. Such a configuration allows any user across the entire world easy access to service provider 3520.

FIG. 36 depicts an example of process for providing a service of reproducing an experimental result against an actual cell using a digital cell. This process may be implemented by cooperating service requester 3510 and service provider 3520.

Step S3601: Service requester 3510 receives cell and environment parameters and produces request comprising the cell parameter, the environment parameter and the stimulus parameter. The request is described in, for example, XML.

Step S3602: Service request 3510 provides the request to service provider 3520.

Step S3603: Service provider 3520 searches for database 3522 in response to the request, to determine whether or not there is a stimulus response result relating to the cell parameter, the environment parameter and the stimulus parameter included in the request in database 3522.

Step S3604: when it is determined that there exists a stimulus response result relating to the cell parameter, the environment parameter and the stimulus parameter included in the request in database 3522, service provider 3520 provides service requester 3510 with the stimulus response result. The stimulus response result is described in, for example, XML.

Step S3605: Service requester 3510 displays the stimulus response result provided by service provider 3520.

If it is determined there is no stimulus response result relating to the cell parameter, the environment parameter and the stimulus parameter included in the requested in database 3522, service provider 3520 provides service requester 3510 with a result of "no hit", for example.

Procedures as shown in FIG. 36 may be processed in a single computer. For example, a single computer program in a single computer may be used for implementing the procedures of steps S3601 through S3605 shown in FIG. 36. In this case, such a single computer functions as an apparatus having the combined functions of service requester 3510 and service provider 3520.

FIG. 37 depicts an example of input interface for inputting a cell parameter, an environment parameter and a stimulus parameter to service 3510. In this example, these parameters are inputted by inputting these parameters as texts by a user into a desired region.

Any number of methods may be employed as a method for inputting these parameters into service requester 3510. For example, these parameters may be inputted by choosing these parameters from a menu (such as, pull-down menu, pop-up menu and the like) by a user.

Service requester 3510 may employ any embodiment for displaying the stimulus response result. For example, service requester 3510 may display the stimulus response result on a display screen, or may output the stimulus response result to a printer. Service requester 3510 may display the stimulus response result using a still image or display the stimulus response result using movie display.

The stimulus response result may include profile data of a cell obtained by monitoring a biological agent or a collection thereof on or in a cell over time. In such a case, for example, the profile data of a cell shown in FIG. 19 may be displayed by service requester 3510 as the stimulus response result.

As such, according to computer system 3510, it is now possible to provide a service of reproducing an experimental result for an actual cell using the digital cell. As such, it is possible to conduct an advanced search relating to a cell even by a research organization or an individual without experimental facilities.

FIG. 38 depicts an example of configurations of computer system 3801 for providing a service of reproducing an experimental result against an actual cell using the digital cell.

Computer system 3801 comprises service requester 3810 requesting a service desired by a user; a plurality of service providers $3820_1 3820_N$; and service registry 3840 with registration of at least one service which can be provided by a plurality of service providers $3820_1 3820_N$, wherein N is an any integer of two or more.

Computer system 3801 may include a plurality of service requesters 3810. Service provider $3820_i$ is configured so as to be capable of accessing database $3822_i$ at least one digital cell stored thereon. A data structure of a digital cell stored on database $3822_i$ is as shown in FIGS. 33A and 33B. Database $3822_i$ may be provided in service provider $3820_i$ or outside service provider 3820, wherein i=1, 2, N.

Service provider 3820$i$ may be configured to be capable of accessing a plurality of databases with at least one digital cell each stored thereon.

Service registry 3840 is configured to be capable of accessing database 3842 with data stored thereon representing services being capable of being provided by service providers $3820_i$ to $3820_N$. Database 3842 may be provided in service registry or outside service registry 3840. Storing data representing services on database 3842 allows registration of services to service registry 3840. Formats of data stored on database 3842 are preferably pre-normalized. Storage of data to database 3842 may be performed manually by a firm managing service registry 3840 or by transmitting data from service providers $3820_i$ to $3820_N$ via network 3830 to service registry 3840.

Each service requester 3810, service provider $3820_1$ to $3820_N$ and service registry 3840 may be any type of computer.

Each of service providers $3820_i$ to $3820_N$ is preferably conducted by research carried out by any of organizations, firms or any other corporation possessing experimental facilities which conducts research on an actual cell. Each of service requester 3810 and service registry 3840 is preferably conducted by any of organizations, firms or any other corporation (for example, an association for promoting digital cells) managing provision of services of reproducing experimental results against an actual cell using the digital cell. Further, in order to secure the quality of services registered to service registry 3840, it is preferable to oblige such an organization which manages service providers $3820_i$ to $3820_N$ to satisfy a predetermined standard.

Service requester 3810, service provider $3820_i$ to $3820_N$ and service registry 3840 are connected via network 3830. Network 3830 is of any type but most preferably, in view of ease of connection and cost, is the Internet.

When network 3830 is the Internet, service requester 3810 may be a Web server connected to a Web browser operated by a user via the Internet. Each of $3820_1 3820_N$ may be a Web server connected to service requester 3810 via the Internet. In this case, service requester 3810 functions as portal or Website interrelaying to a Web browser operated by a user and a Web server of service provider $3820_i$. This configuration allows easy access to service providers of $3820_i$ to $3820_N$ by users all over the world, and it is now possible for research institutes and/or firms all over the world to participate in the business of providing the service of reproducing experimental results against an actual cell using a digital cell.

FIG. 39 depicts an example of a process for providing a service of reproducing an experimental result against an actual cell using the digital cell. This procedure is implemented by cooperating service requester 3810 and service providers $3820_i$ with $3820_N$.

Step S3910: Service requester 3810 receives a cell parameter, an environment parameter, and a stimulus parameter, and produces a request comprising such a cell parameter, an environment parameter, and a stimulus parameter. Such a request is described in, for example, XML.

Step S3902: Service requester 3810 searches service registry 3840 responding to the request, and determines whether or not there exists a service provider $3820_i$ which can provide a service of the requester amongst service provides $3820_i$ to $3820_N$, wherein i is any integer of 1 to N.

Service providers $3820_i$ to $3820_N$ may employ any type of method for register services which can be provided by service providers $3820_i$ to $3820_N$ on service registry 3840. For example, when service provider 3820, is capable of providing a service of reproducing an experimental result against cell A, then cell parameters specifying cell A and addresses (for example, URL and the like) specifying the locations of service provider $3820_1$ may be stored on database 3842. For example, if service provider $3820_2$ can provide services of reproducing cells B and C, then cell parameters specifying cell A and addresses (for example, URL and the like) specifying the locations of service provider $3820_2$ may be stored on database 3842. Alternatively, when service provider can provide the service of reproducing experimental results satisfying specific experimental conditions against cell D, then parameters such as environment parameters and stimulus parameters specifying the experimental conditions and addresses (for example, a URL and the like) specifying the locations of service provider $3820_3$ may be stored on database 3842.

Step S3903: If there exists a service provider 3820$i$ which can provide a service of the requester, amongst service providers $3820_i$ to $3820_N$, such service requester 3810 provides service provider $3820_i$ with the request. The location of service provider $3820_i$ may be specified by referring to database 3842 of service registry 3840.

Step S3904: service provider $3820_i$ searches database $3822_i$ in response to the request, and determines whether or not there exists the stimulus response result relating to the cell parameter, the environment parameter and the stimulus parameter included in the request in database 3822$i$.

Step S3905: If determined that there exists a stimulus response result relating to the cell parameter, the environment parameter and the stimulus parameter included in the request in database $3822_i$, service provider $3820_i$ provides service requester 3810 with the stimulus response result. The stimulus response result is described in, for example, XML.

Step S3906: service requester 3810 displays stimulus response result provided by service provider $3820_i$.

If determined that there is no stimulus response result relating to the cell parameter, environment parameter and stimulus parameter contained in the request in database $3822_i$, service provider $3820_i$ will provide service requester 3810 with, for example, the result of "no hit".

As described above, any number of methodologies may be employed as a method for inputting a cell parameter, an environment parameter and a stimulus parameter to service requester 3810, and further any forms may be employed as a form of displaying stimulus response result by service requester 3810.

As such, according to computer system 3810, it is possible to provide a service of reproducing an experimental result against an actual cell using the digital cell. This allows research institutes or individual having no experimental facilities to perform advanced research activities relating to a cell. Further, according to computer system 3801, registration of services capable of being provided by a plurality of service providers $3820_i$ to $3820_N$, provides opportunities to participate in the business of providing the service of reproducing experimental results against an actual cell using the digital cell to research organizations or firms all over the world.

All patents, published patent applications and publications cited herein are incorporated by reference as if set forth fully herein.

The preferred embodiments of the present invention have been heretofore described for a better understanding of the present invention. Hereinafter, the present invention will be described by way of examples. Examples described below are provided only for illustrative purposes. Accordingly, the scope of the present invention is not limited except as by the appended claims. According to the examples below, it will be understood that those skilled in the art can select cells, supports, biological agents, salts, positively charged substances, negatively charged substances, actin-like acting substances, and the like, as appropriate, and can make or carry out the present invention.

EXAMPLES

Hereinafter, the present invention will be described in greater detail by way of examples, though the present invention is not limited to the examples below. Reagents, supports, and the like are commercially available from Sigma (St. Louis, USA), Wako Pure Chemical Industries (Osaka, Japan), Matsunami Glass (Kishiwada, Japan) unless otherwise specified.

Example 1

Reagents

Formulations below were prepared in Example 1.

As candidates for an actin-like acting substance, various extracellular matrix proteins and variants or fragments thereof were prepared in Example 1, as listed below. Fibronectin and the like were commercially available. Fragments and variants were obtained by genetic engineering techniques:

1) fibronectin (SEQ ID NO.: 11);

2) fibronectin 29 kDa fragment;

3) fibronectin 43 kDa fragment;

4) fibronectin 72 kDa fragment;

5) fibronectin variant (SEQ ID NO.: 11, alanine at 152 was substituted with leucine);

6) ProNectin F (Sanyo Chemical Industries, Kyoto, Japan);

7) ProNectin L (Sanyo Chemical Industries);

8) ProNectin Plus (Sanyo Chemical Industries);

9) laminin (SEQ ID NO.: 6);

10) RGD peptide (tripeptide);

11) RGD-containing 30 kDa peptide;

12) 5 amino acids of laminin (IKVAV, SEQ ID NO.: 28); and 13) gelatin.

Plasmids were prepared as DNA for transfection. Plasmids, pEGFP-N1 and pDsRed2-N1 (both from BD Biosciences, Clontech, Calif., USA) were used. In these plasmids, gene expression was under the control of cytomegalovirus (CMV). The plasmid DNA was amplified in *E. coli* (XL1 blue, Stratgene, Tex., USA) and the amplified plasmid DNA was used as a complex partner. The DNA was dissolved in distilled water free from DNase and RNase.

The following transfection reagents were used: Effectene Transfection Reagent (cat. no. 301425, Qiagen, Calif.), TransFast™ Transfection Reagent (E2431, Promega, Wis.), Tfx™-20 Reagent (E2391, Promega, Wis.), SuperFect Transfection Reagent (301305, Qiagen, Calif.), PolyFect Transfection Reagent (301105, Qiagen, Calif.), LipofectAMINE 2000 Reagent (11668-019, Invitrogen corporation, CA), JetPEI (×4) conc. (101-30, Polyplus-transfection, France), and ExGen 500 (R0511, Fermentas Inc., MD). These transfection reagents were added to the above-described DNA and actin-like acting substances in advance, or complexes thereof with the DNA were produced in advance.

The thus-obtained solution was used in assays using transfection arrays described below.

Example 2

Transfection Array—Demonstration Using Mesenchymal Stem Cells

In Example 2, an improvement in the transfection efficiency in solid phase was observed. The protocol used in Example 2 will be described below.

(Protocol)

The final concentration of DNA was adjusted to 1 µg/µL. An actin-like acting substance was preserved as a stock having a concentration of 10 µg/µL in ddH$_2$O. All dilutions were made using PBS, ddH$_2$O, or Dulbecco's MEM. A series of dilutions, for example, 0.2 µg/µL, 0.27 µg/µL, 0.4 µg/µL, 0.53 µg/µL, 0.6 µg/µL, 0.8 µg/µL, 1.0 µg/µL, 1.07 µg/µL, 1.33 µg/µL, and the like, were formulated.

Transfection reagents were used in accordance with instructions provided by each manufacturer.

Plasmid DNA was removed from a glycerol stock and amplified in 100 mL L-amp overnight. Qiaprep Miniprep or Qiagen Plasmid Purification Maxi was used to purify DNA in accordance with a standard protocol provided by the manufacturer.

In Example 2, the following 5 cells were used to confirm an effect: human mesenchymal stem cell (hMSCs, PT-2501, Cambrex BioScience Walkersville, Inc., MD); human embryonic renal cell (HEK293, RCB1637, RIKEN Cell Bank, JPN); NIH3T3-3 cell (RCB0150, RIKEN Cell Bank, JPN); HeLa cell (RCB0007, RIKEN Cell Bank, JPN); and HepG2 (RCB1648, RIKEN Cell Bank, JPN). These cells were cultured in DMEM/10% IFS containing L-glut and pen/strep.

(Dilution and DNA Spots)

Transfection reagents and DNA were mixed to form a DNA-transfection reagent complex. Formation of the complex requires a certain period of time. Therefore, the mixture was spotted onto a solid phase support (e.g., a poly-L-lysine slide) using an arrayer. In Example 2, as a solid phase support, an APS slide, a MAS slide, and an uncoated slide were used as well as a poly-L-lysine slide. These slides are available from Matsunami Glass (Kishiwada, Japan) or the like.

For complex formation and spot fixation, the slides were dried overnight in a vacuum dryer. Drying was performed for a duration in the range of 2 hours to 1 week.

Although the actin-like acting substance might be used during the complex formation, it was also used immediately before spotting in Example 2.

(Formulation of Mixed Solution and Application to Solid Phase Supports)

300 µL of DNA concentrated buffer (EC buffer)+16 µL of an enhancer were mixed in an Eppendorf tube. The mixture was mixed with a Vortex, followed by incubation for 5 minutes. 50 µL of a transfection reagent (Effectene, etc.) was added to the mixture, followed by mixing by pipetting. To apply a transfection reagent, an annular wax barrier was formed around the spots on the slide. 366 µL of the mixture was added to the spot region surrounded by the wax, followed by incubation at room temperature for 10 to 20 minutes. Thereby, the fixation to the support was manually achieved.

(Distribution of Cells)

Next, a protocol for adding cells will be described. Cells were distributed for transfection. The distribution was typically performed by reduced-pressure suction in a hood. A slide was placed on a dish, and a solution containing cells was added to the dish for transfection. The cells were distributed as follows.

The growing cells were distributed to a concentration of $10^7$ cells/25 mL. The cells were plated on the slide in a 100×100×15 mm squared Petri dish or a 100 mm (radius)×15 mm circular dish. Transfection was conducted for about 40 hours. This period of time corresponded to about 2 cell cycles. The slide was treated for immunofluorescence.

(Evaluation of Gene Introduction)

Gene introduction was evaluated by detection using, for example, immunofluorescence, fluorescence microscope examination, laser scanning, radioactive labels, and sensitive films, or emulsion.

When an expressed protein to be visualized is a fluorescent protein, such a protein can be observed with a fluorescence microscope and a photograph thereof can be taken. For large-sized expression arrays, slides may be scanned using a laser scanner for storage of data. If an expressed protein can be detected using fluorescent antibodies, an immunofluorescence protocol can be successively performed. If detection is based on radioactivity, the slide may be adhered as described above, and autoradiography using film or emulsion can be performed to detect radioactivity.

(Laser Scanning and Quantification of Fluorescence Intensity)

To quantify transfection efficiency, the present inventors use a DNA microarray scanner (GeneTAC UC4×4, Genomic Solutions Inc., MI). Total fluorescence intensity (arbitrary unit) was measured, and thereafter, fluorescence intensity per unit surface area was calculated.

(Cross-Sectional Observation by Confocal Scanning Microscope)

Cells were seeded on tissue culture dishes at a final concentration of $1\times10^5$ cells/well and cultured in appropriate medium (Human Mesenchymal Cell Basal Medium (MSCGM BulletKit PT-3001, Cambrex BioScience Walkersville, Inc., MD). After fixation of the cell layer with 4% paraformaldehyde solution, SYTO and Texas Red-X phalloidin (Molecular Probes Inc., OR, USA) was added to the cell layer for observation of nuclei and F-actin. The samples emitting light due to gene products and the stained samples were observed with a confocal laser microscope (LSM510: Carl Zeiss Co., Ltd., pinhole size=Ch1=123 µm, Ch2=108 µm, image interval=0.4) to obtain cross sectional views.

(Results)

Figure 1:
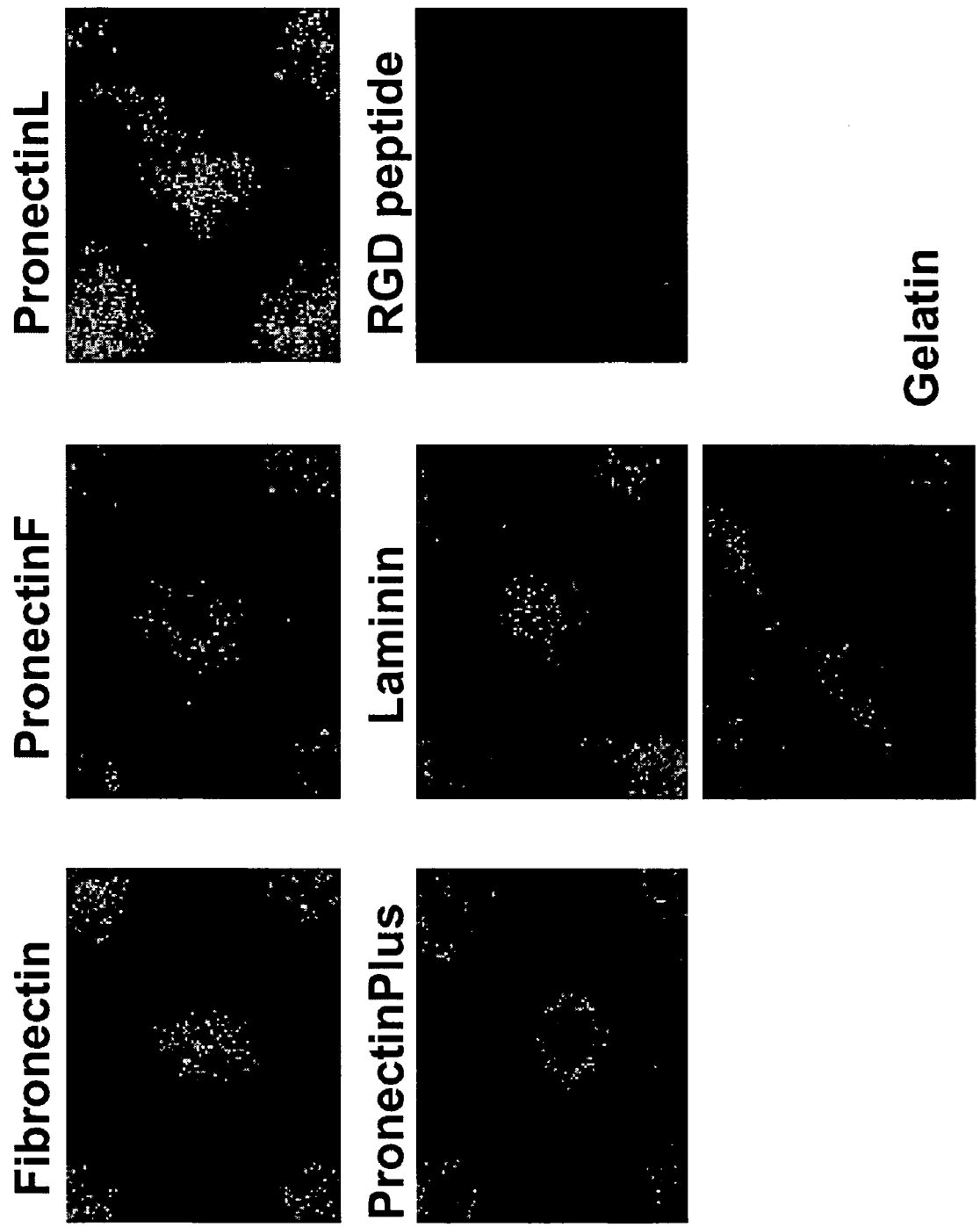
FIG. 1 shows the results of experiments in which various actin-like substances and HEK293 cells were used, where gelatin was used as a control.

FIG. 1 shows the results of experiments in which various actin-like acting substances and HEK293 cells were used where gelatin was used as a control.

As can be seen from the results, whereas transfection was not very successful in a system using gelatin, transfection took place to a significant level in systems using fibronectin, ProNectin (ProNectin F, ProNectin L, ProNectin Plus) which is a variant of fibronectin, and laminin. Therefore, it was demonstrated that these molecules significantly increased transfection efficiency. Use of the RGD peptide alone exhibited substantially no effect.

Figure 3:
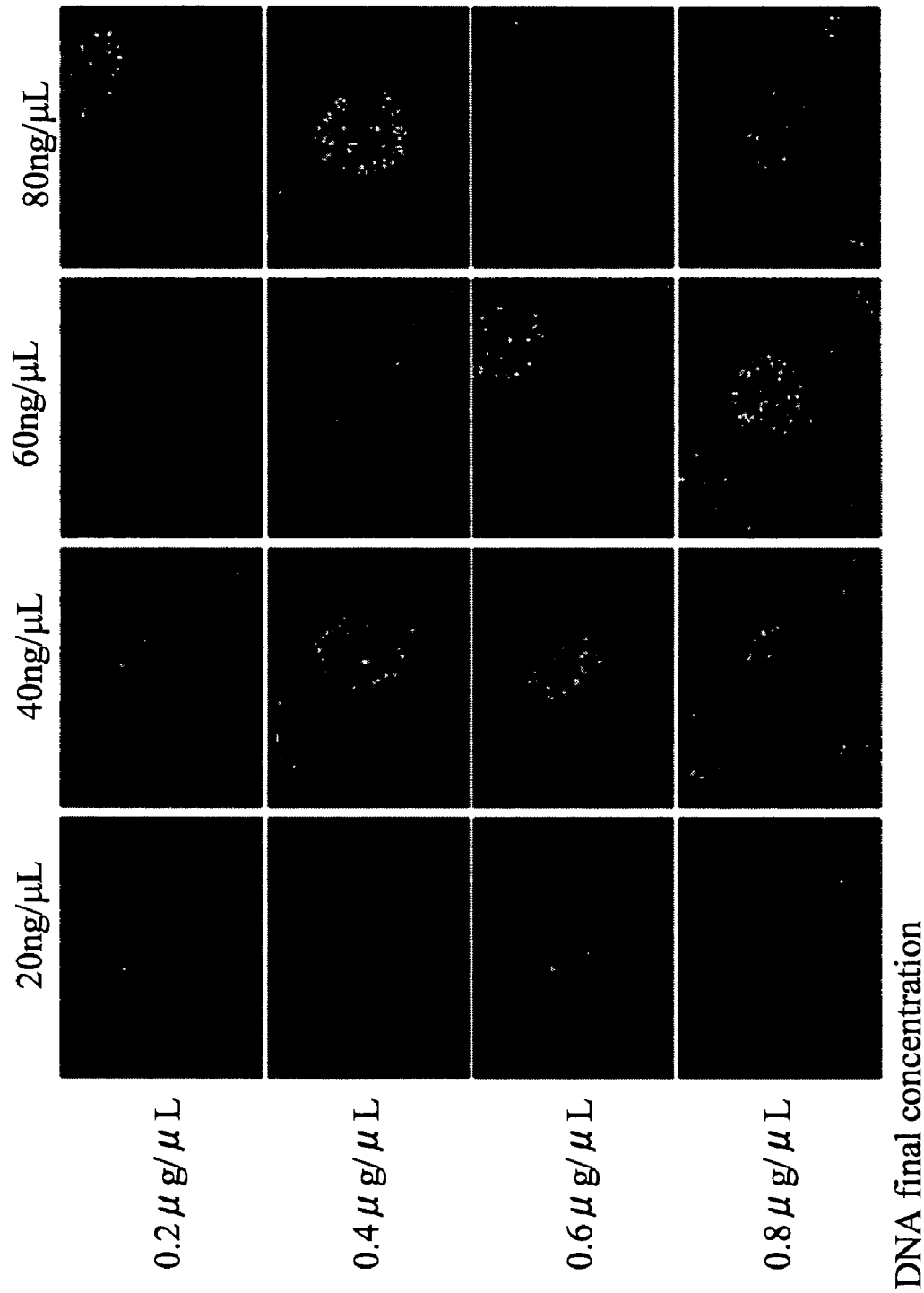
FIG. 3 shows exemplary transfection efficiencies when fibronectin fragments were used.

FIGS. 2 and 3 show transfection efficiency when fibronectin fragments were used. FIG. 4 shows the summary of the results. 29 kDa and 72 kDa fragments exhibited a significant level of transfection activity, while a 43 kDa fragment had activity but its level was low. Therefore, it was suggested that an amino acid sequence contained in the 29 kDa fragment played a role in an increase in transfection efficiency. Substantially no contamination was found in the case of the 29 kDa fragment, while contamination was observed in the case of the other two fragments (43 kDa and 72 kDa). Therefore, only the 29 kDa domain may be preferably used as an actin-like acting substance. When only the RGD peptide was used, increased transfection efficiency was not exhibited. The 29-kDa peptide therefore exhibited activity with respect to enhancing transfection efficiency. Such a system with an additional 6 amino acids of laminin (higher molecular weight) exhibited transfection activity. Therefore, these peptide sequences may also play an important role in increased transfection efficiency, without limitation. In such a case, a molecular weight of at least 5 kDa, preferably at least 10 kDa, and more preferably at least 15 kDa may be required for an increase in transfection efficiency.

Figure 5:
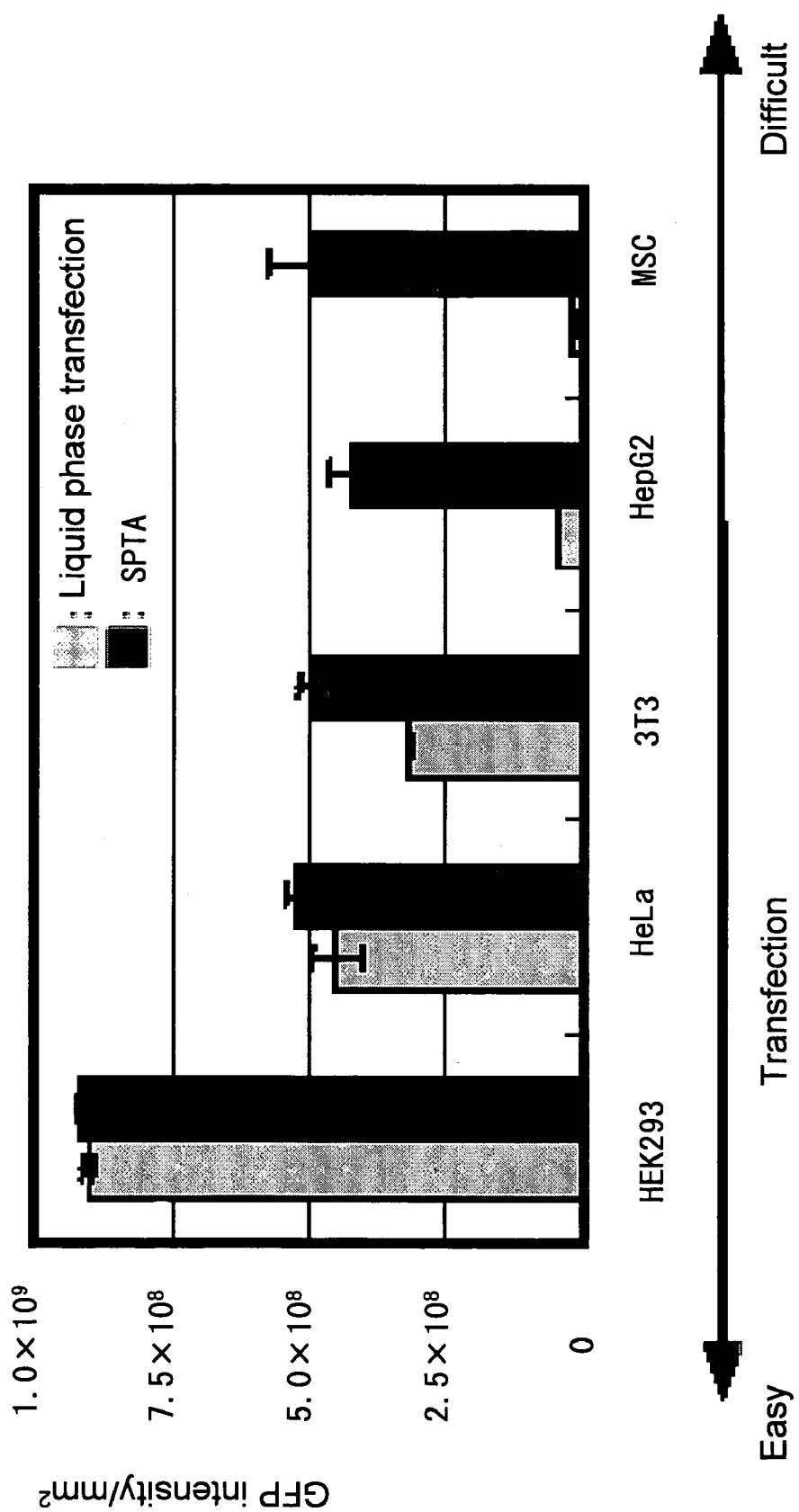
FIG. 5 shows the results of an example in which transfection efficiency was studied for various cells.

Next, FIG. 5 shows the result of studies on the transfection efficiency of cells. In FIG. 5, HEK293 cells, HeLa cells, and 3T3 cells, which were conventionally transfectable, and HepG2 cells and mesenchymal stem cells (MSC) which were conventionally believed to be substantially impossible to transfect, were used to show the effect of the transfection method of the present invention. The vertical axis represents the intensity of GFP.

In FIG. 5, the transfection method of the present invention using a solid phase support was compared with a conventional liquid phase transfection method. The conventional liquid phase transfection method was conducted in accordance with a protocol recommended by the kit manufacturer.

As can be seen from FIG. 5, transfection efficiency comparable to HeLa and 3T3 was achieved in HepG2 cells and mesenchymal stem cells (MSC) which were conventionally believed to be substantially impossible to transfect, as well as HEK293 cells, HeLa cells, and 3T3 cells, which were conventionally transfectable. Such an effect was not achieved by conventional transfection systems. The present invention was the first to provide a system which can increase transfection efficiency for substantially all cells and can provide practicable transfection to all cells. By using solid phase conditions, cross contamination was significantly reduced. Therefore, it was demonstrated that the present invention using a solid phase support is appropriate for production of an integrated bioarray.

Figure 6:
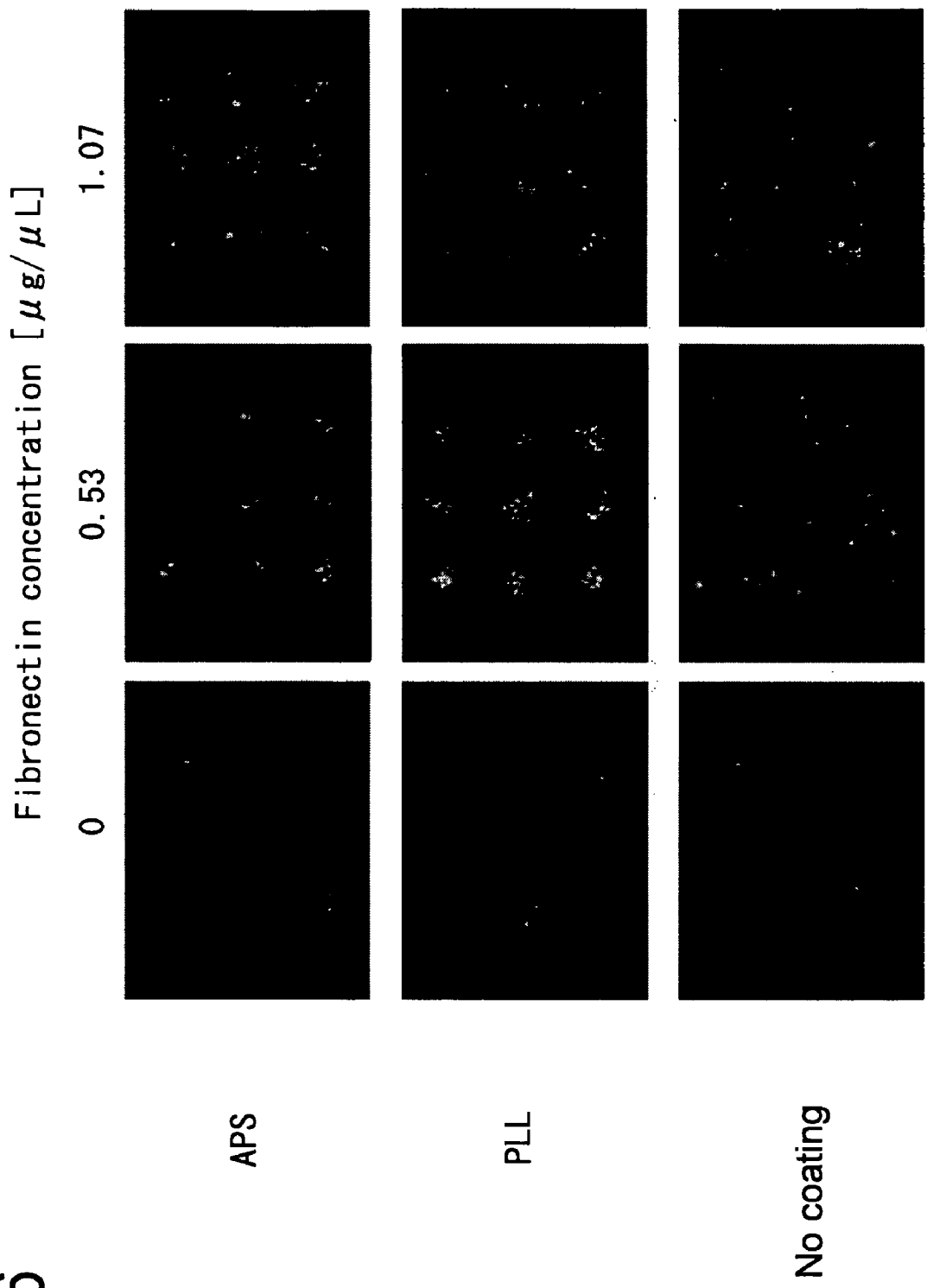
FIG. 6 shows the results of transfection when various plates were used.

Next, FIG. 6 shows the results of transfection when various plates were used. As can be seen from the results of FIG. 6, when coating was provided, contamination was reduced as compared with when coating was not provided and transfection efficiency was increased.

Figure 7:
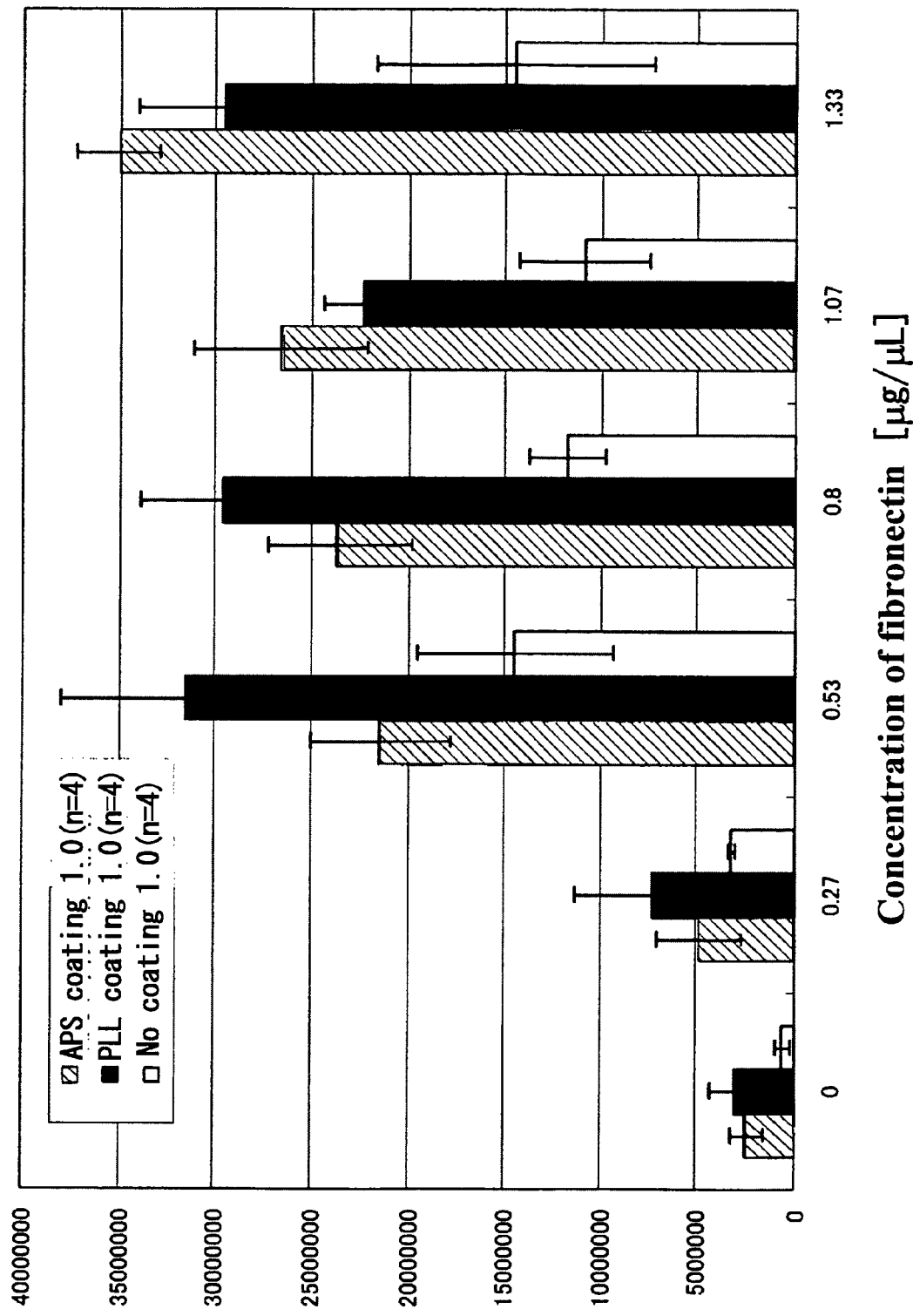
FIG. 7 shows the results of transfection when various plates were used at a fibronectin concentration of 0, 0.27, 0.53, 0.8, 1.07, and 1.33 (μg/μL).

Next, FIG. 7 shows the results of transfection where the concentration of fibronectin was 0, 0.27, 0.53, 0.8, 1.07, and 1.33 (μg/μL for each). In FIG. 7, slides coated with PLL (poly-L-lysine), APS and uncoated slides were shown.

As can be seen from the results of FIG. 7, transfection efficiency was increased with an increase in fibronectin concentration. Note that in the case of PLL coating and the absence of coating, the transfection efficiency reached a plateau at a fibronectin concentration of more than 0.53 μg/μL. In the case of APS, it was found that the effect was further increased at a fibronectin concentration of more than of 1.07 μg/μL.

Figure 9:
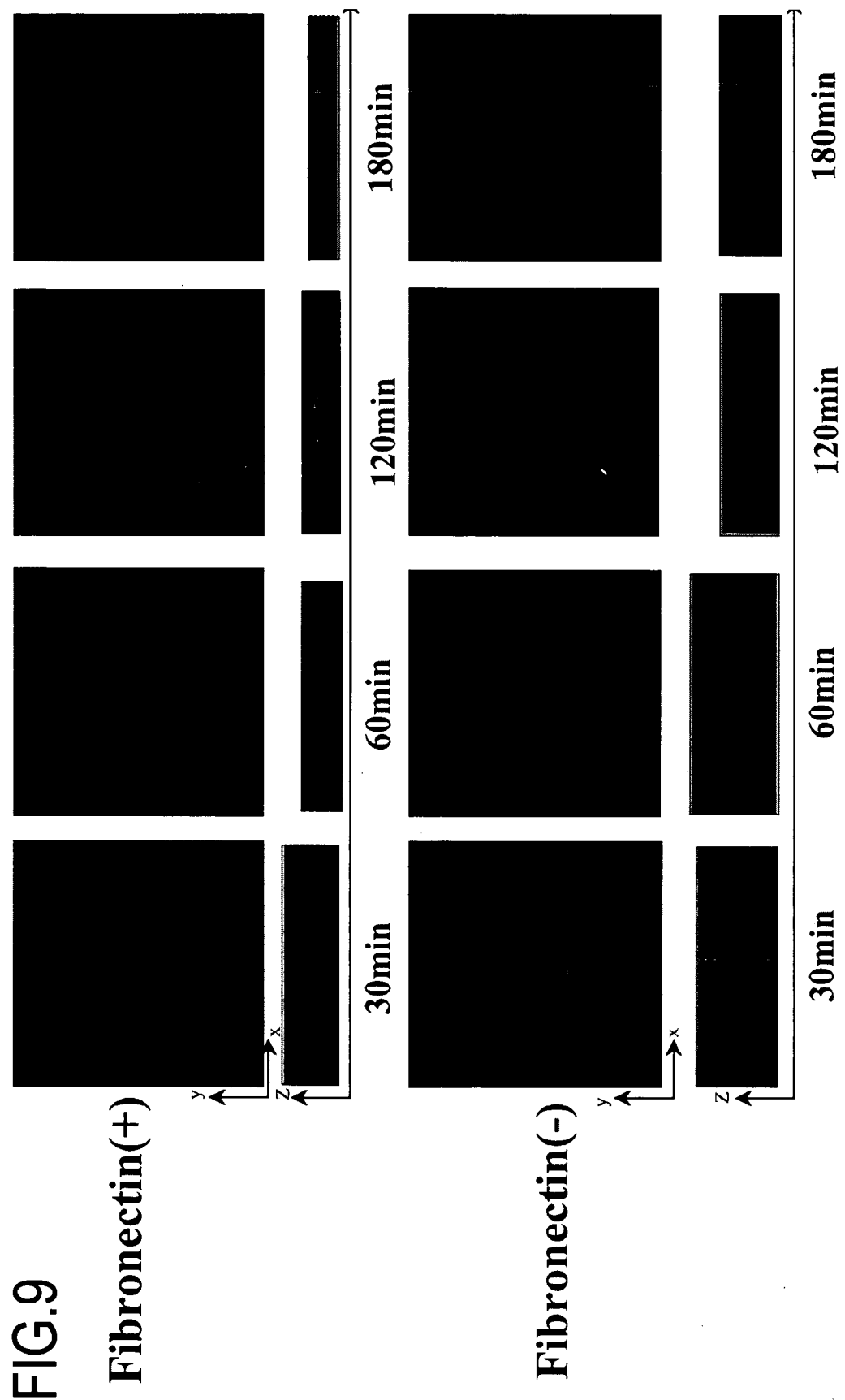
FIG. 9 shows exemplary cross-sectional photographs of cell adhesion profiles in the presence or absence of fibronectin. Cross-sections of human mesenchymal stem cells (hMSC) were observed using a confocal laser scanning microscope. hMSC were stained with SYTO61 (blue fluorescence) and Texas red-X phalloidin (red fluorescence) and fixed with 4% PFA. Blue fluorescence (nuclei: SYTO61) and red fluorescence (nuclei: Texas red-X phalloidin) were obtained using a confocal laser microscope (LSM510, Carl Zeiss Co., Ltd., pin hole size=1.0, image interval=0.4).
Figure 10:
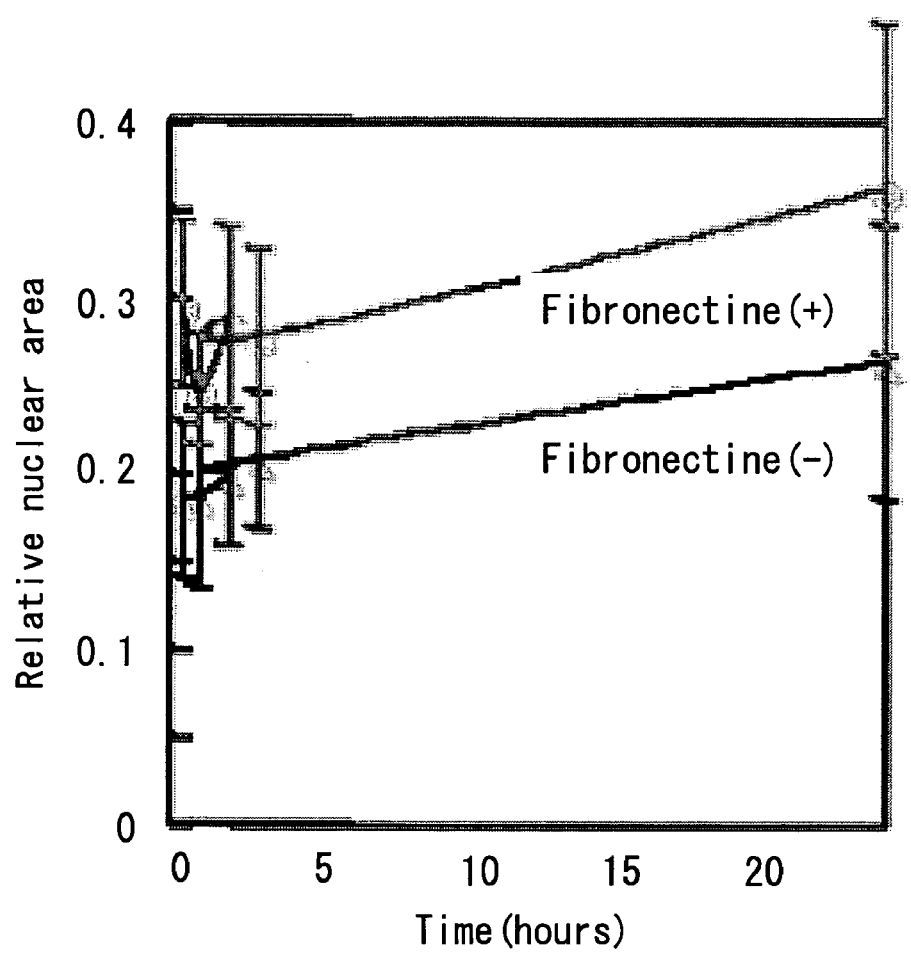
FIG. 10 shows transition of nuclear surface area. Relative nuclear surface area was determined by cross-sections of hMSC observed with confocal laser scanning microscopy. hMSC was fixed with 4% PFA.

Next, FIG. 8 shows photographs indicating cell adhesion profiles in the presence or absence of fibronectin. FIG. 9 shows cross-sectional photographs. It was revealed that the morphology of adherent cells were significantly different (FIG. 8). The full extension of cells was found for the initial 3 hours of culture in the presence of fibronectin, while extension was limited in the absence of fibronectin (FIG. 9). Considering the behavior of filaments (FIG. 9) and the results of the time-lapse observation, it was considered that an actin-like acting substance, such as fibronectin, attached to a solid phase support had an influence on the shape and orientation of actin filaments, and the efficiency of introduction of a substance into a cell, such as transfection efficiency or the like, was thus increased. Specifically, actin filaments quickly change their location in the presence of fibronectin, and disappear from the cytoplasmic space under the nucleus as the cell extends. It is considered that actin depletion in the perinuclear space, which is induced by an actin-like acting substance, such as fibronectin, allows the transport of a target substance, such as DNA or the like, into cells or nuclei. Though not wishing to be bound by any theory, the reason is considered to be that the viscosity of cytoplasm is reduced and positively charged DNA particles are prevented from being trapped by negatively charged actin filaments. Additionally, it is considered that the surface area of the nucleus is significantly increased in the presence of fibronectin (FIG. 10), possibly facilitating the transfer of a target substance, such as DNA or the like, into nuclei.

Example 3

Application to Bioarrays

Next, larger-scale experiments were conducted to determine whether or not the above-described effect was demonstrated when arrays were used.

(Experimental Protocols)
(Cell sources, culture media, and culture conditions)

In this example, five different cell lines were used: human mesenchymal stem cells (hMSCs, PT-2501, Cambrex BioScience Walkersville, Inc., MD), human embryonic kidney cell HEK293 (RCB1637, RIKEN Cell Bank, JPN), NIH3T3-3 (RCB0150, RIKEN Cell Bank, JPN), HeLa (RCB0007, RIKEN Cell Bank, JPN), and HepG2 (RCB1648, RIKEN Cell Bank, JPN). In the case of human MSCs, cells were maintained in commercialized Human Mesenchymal Cell Basal Medium (MSCGM BulletKit PT-3001, Cambrex BioScience Walkersville, Inc., MD). In case of HEK293, NIH3T3-3, HeLa and HepG2, cells were maintained in Dulbecco's Modified Eagle's Medium (DMEM, high glucose 4.5 g/L with L-Glutamine and sodium pyruvate; 14246-25, Nakalai Tesque, JPN) with 10% fetal bovine serum (FBS, 29-167-54, Lot No. 2025F, Dainippon Pharmaceutical CO., LTD., JPN). All cells were cultivated in a controlled incubator at 37° C. in 5% $CO_2$. In experiments involving hMSCs, we used hMSCs of less than five passages, in order to avoid phenotypic changes.

(Plasmids and Transfection Reagents)

To evaluate the efficiency of transfection, the pEGFP-N1 and pDsRed2-N1 vectors (cat. no. 6085-1, 6973-1, BD Biosciences Clontech, Calif.) were used. Both genes' expressions were under the control of cytomegalovirus (CMV) promoter. Transfected cells continuously expressed EGFP or DsRed2, respectively. Plasmid DNAs were amplified using *Escherichia coli*, XL1-blue strain (200249, Stratagene, Tex.), and purified by EndoFree Plasmid Kit (EndoFree Plasmid Maxi Kit 12362, QIAGEN, Calif.). In all cases, plasmid DNA was dissolved in DNase and RNase free water. Transfection reagents were obtained as below: Effectene Transfection Reagent (cat. no. 301425, Qiagen, Calif.), TransFast™ Transfection Reagent (E2431, Promega, Wis.), Tfx™-20 Reagent (E2391, Promega, Wis.), SuperFect Transfection Reagent (301305, Qiagen, Calif.), PolyFect Transfection Reagent (301105, Qiagen, Calif.), LipofectAMINE 2000 Reagent (11668-019, Invitrogen corporation, CA), JetPEI (×4) conc. (101-30, Polyplus-transfection, France), and ExGen 500 (R0511, Fermentas Inc., MD).

(Solid-Phase Transfection Array (SPTA) Production)

The detail of protocols for 'reverse transfection' are described in the web site, 'Reverse Transfection Homepage' (http://staffa.wi.mit.edu/sabatini_public/reverse_transfection.htm) or J. Ziauddin, D. M. Sabatini, Nature, 411, 2001, 107; and R. W. Zu, S. N. Bailey, D. M. Sabatini, Trends in Cell Biology, Vol. 12, No. 10, 485. In our solid phase transfection (SPTA method), three types of glass slides were studied (silanized glass slides; APS slides, and poly-L-lysine coated glass slides; PLL slides, and MAS coated slides; Matsunami Glass, JPN) with a 48 square pattern (3 mm×3 mm) separated by a hydrophobic fluoride resin coating.

(Plasmid DNA Printing Solution Preparation)

Two different ways to produce a SPTA were developed. The main differences reside in the preparation of the plasmid DNA printing solution.

(Method A)

In the case of using Effectene Transfection Reagent, the printing solution contained plasmid DNA and cell adhesion molecules (bovine plasma fibronectin (cat. no. 16042-41, Nakalai Tesque, JPN), dissolved in ultra-pure water at a concentration of 4 mg/mL). The above solution was applied on the surface of the slide using an inkjet printer (synQUAD™, Cartesian Technologies, Inc., CA) or manually, using a 0.5 to 10 μL tip. This printed slide was dried up over 15 minutes at room temperature in a safety-cabinet. Before transfection, total Effectene reagent was gently poured on the DNA-printed glass slide and incubated for 15 minutes at room temperature. The excess Effectene solution was removed from the glass slide using a vacuum aspirator and dried up at room temperature for 15 minutes in a safety-cabinet. The DNA-printed glass slide obtained was set in the bottom of a 100-mm culture dish and approximately 25 mL of cell suspension (2 to $4\times10^4$ cells/mL) was gently poured into the dish. Then, the dish was transferred to the incubator at 37° C. in 5% $CO_2$ and incubated for 2 or 3 days.

(Method B)

In case of other transfection reagents (TransFast™, Tfx™-20, SuperFect, PolyFect, LipofectAMINE 2000, JetPEI (×4) conc., or ExGen), plasmid DNA, fibronectin, and the transfection reagent were mixed homogeneously in a 1.5-mL micro-tube according to the ratios indicated in the manufacturer's instructions and incubated at room temperature for 15 minutes before printing on a chip. The printing solution was applied onto the surface of the glass-slide using an inkjet printer or a 0.5- to 10-μL tip. The printed glass-slide was completely dried up at room temperature over 10 minutes in a safety-cabinet. The printed glass-slide was placed in the bottom of a 100-mm culture dish and approximately 3 mL of cell suspension (2 to $4\times10^4$ cells/mL) was added and incubated at room temperature over 15 minutes in a safety-cabinet. After incubation, fresh medium was poured gently into the dish. Then, the dish was transferred to an incubator at 37° C. in 5% $CO_2$ and incubated for 2 to 3 days. After incubation, using fluorescence microscopy (IX-71, Olympus PROMARKETING, INC., JPN), we observed the transfectants, based on their expression of enhanced fluorescent proteins (EFP, EGFP and DsRed2). Phase contrast images were taken with the same microscope. In both protocols, cells were fixed using a paraformaldehyde (PFA) fixation method (4% PFA in PBS, treatment time was 10 minutes at room temperature).

(Laser Scanning and Fluorescence Intensity Quantification)

In order to quantify the transfection efficiency, we used a DNA micro-array scanner (GeneTAC UC4×4, Genomic Solutions Inc., MI). The total fluorescence intensity (arbitrary units) was measured, and thereafter, the fluorescence intensity per surface area was calculated.

(Results)

(Fibronectin-Supported Localized Transfection)

Figure 11:
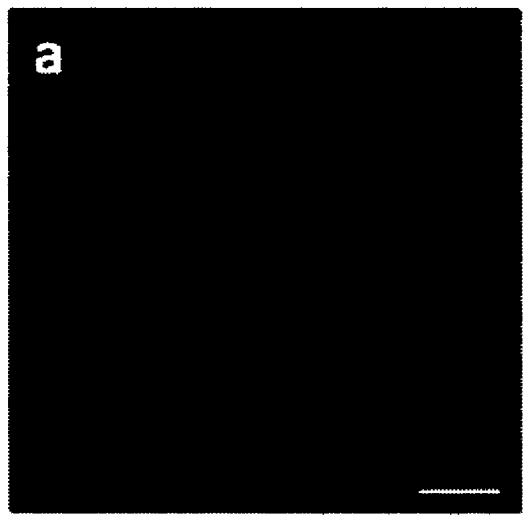
FIG. 11 shows the results of an exemplary transfection experiment when a transfection array chip was constructed and used.

A transfection array chip was constructed as shown in FIG. 11. The transfection array chip was constructed by microprinting a cell cultivation medium solution containing fibronectin and DNA/transfection reagent onto a poly L lysine (PLL) coated glass slide.

Figure 12:
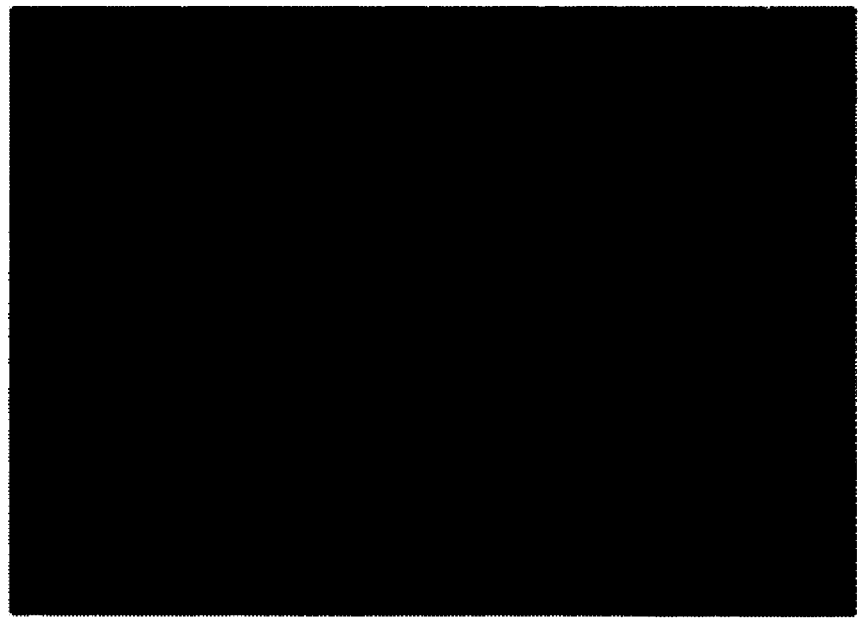
FIG. 12 shows exemplary contamination between each spot on an array.

Various cells were used for this example. The cells were cultivated under typical cell cultivation conditions. As they adhered to the glass slide, the cells efficiently incorporated and expressed the genes corresponding to the DNA printed at a given position on the array. As compared to conventional transfection methods (e.g., cationic lipid or cationic polymer-mediated transfection), the efficiency of transfection using the method of the present invention was high in all the cells tested. Importantly, it was found that tissue stem cells, such as HepG2 and hMSC, which were conventionally believed to resist transfection, were efficiently transfected. hMSC was transfected at an efficiency 40 or more times higher than that of conventional techniques. In addition, high spatial localization, which is required for high-density arrays, was achieved (low cross contamination between adjacent spots on the array). This was confirmed by production of a checkered pattern array of EGFP and Ds-Red. hMSC cultivated on this array expressed the corresponding fluorescent proteins with virtually total space resolution. The result is shown in FIG. 12. As can be seen from FIG. 12, it was found that there was little cross contamination. Based on the study of the role of the individual components of the printed mixture, transfection efficiency can be optimized.

(Solid-Phase Transfection Array of Human Mesenchymal Stem Cells)

The capacity of human Mesenchymal Stem Cells (hMSC) to differentiate into various kinds of cells is particularly intriguing in studies which target tissue regeneration and renewal. In particular, the genetic analysis of transformation of these cells has attracted attention with expectation of understanding of a factor that controls the pluripotency of hMSC. In conventional hMSC studies, it is not possible to perform transfection with desired genetic materials.

(Solid-Phase Transfection Array of Human Mesenchymal Stem Cells)

The capacity of human Mesenchymal Stem Cells (hMSC) to differentiate into various kinds of cells is particularly intriguing in studies which target tissue regeneration and renewal. In particular, the genetic analysis of transformation of these cells has attracted attention with expectation of understanding a factor that controls the pluripotency of hMSC. In conventional hMSC studies, it is not possible to perform transfection with desired genetic materials.

To achieve this, conventional methods include either a viral vector technique or electroporation. The present inventors developed a complex-salt system, which could be used to achieve solid phase transfection which makes it possible to obtain high transfection efficiency to various cell lines (including hMSC) and special localization in high-density arrays. An outline of solid phase transfection is shown in FIG. 13A.

It was demonstrated that solid phase transfection can be used to achieve a "transfection patch" capable of being used for in vivo gene delivery and a solid phase transfection array (SPTA) for high-throughput genetic function research on hMSC.

Although a number of standard techniques are available for transfecting mammalian cells, it is known that it is inconvenient and difficult to introduce genetic material into hMSC as compared with cell lines, such as HEK293, HeLa, and the like. Conventional viral vector delivery and electroporation techniques are both important. However, these techniques have the following inconveniences: potential toxicity (for the virus technique); difficulty in high-throughput analysis at the genomic scale; and limited applications in vivo studies (for electroporation).

The present inventors developed a solid phase support fixed system which can be easily fixed to a solid phase support and has sustained-release capability and cell affinity, whereby most of the above-described drawbacks could be overcome.

Figure 13B:
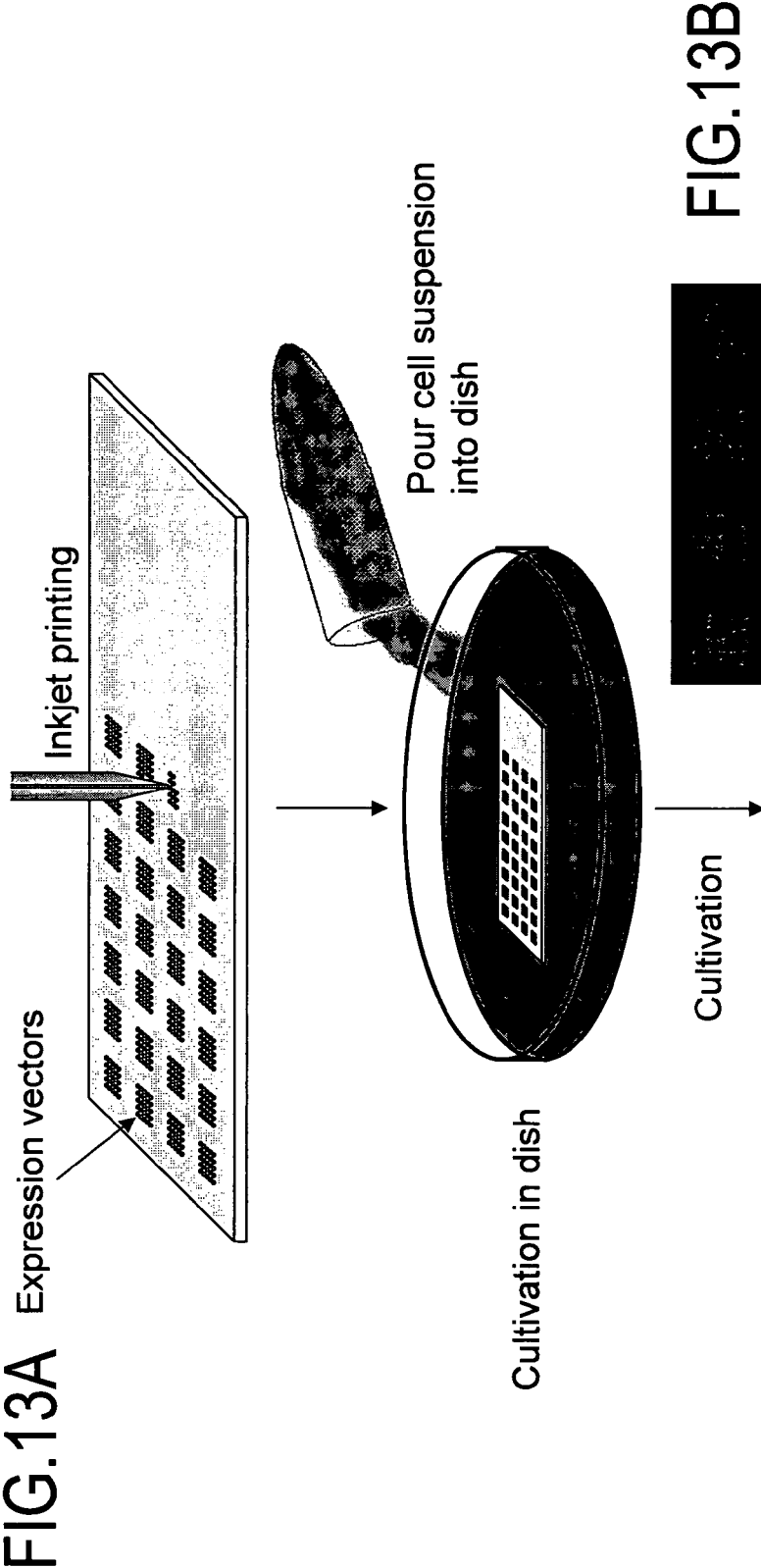
FIG. 13B shows the results of a solid phase transfection. A HEK293 cell line was used to produce a SPTA. Green colored portions indicate transfected adherent cells. According to this result, the method of the present invention can be used to produce a group of cells separated spatially and transfected with different genes. As such, FIG. 13A-B, as a whole, depicts schematically the procedure of transfection (SPTA).

An example of the results of the above-described experiment is shown in FIG. 13B. The present inventors used our microprinting technique to fix a mixture of a selected genetic material, a transfection reagent, an appropriate cell adhesion molecule, and a salt onto a solid support. By culturing cells on a support having such a mixture fixed thereto, the gene contained in the mixture was taken in by the cultured cells. As a result, it became possible to facilitate support-adherent cells to take in DNA spatially separated therefrom (FIG. 13B).

As a result of this example, several important effects were achieved: high transfection efficiency (thereby making it possible to study a group of cells on a statistically significant scale); low cross contamination between regions having different DNA molecules (thereby making it possible to study the effects of different genes separately); the extended survival of transfected cells; high-throughput, compatible and simple detecting procedure. SPTA having these features serves as an appropriate basis for further studies.

Figure 13C:
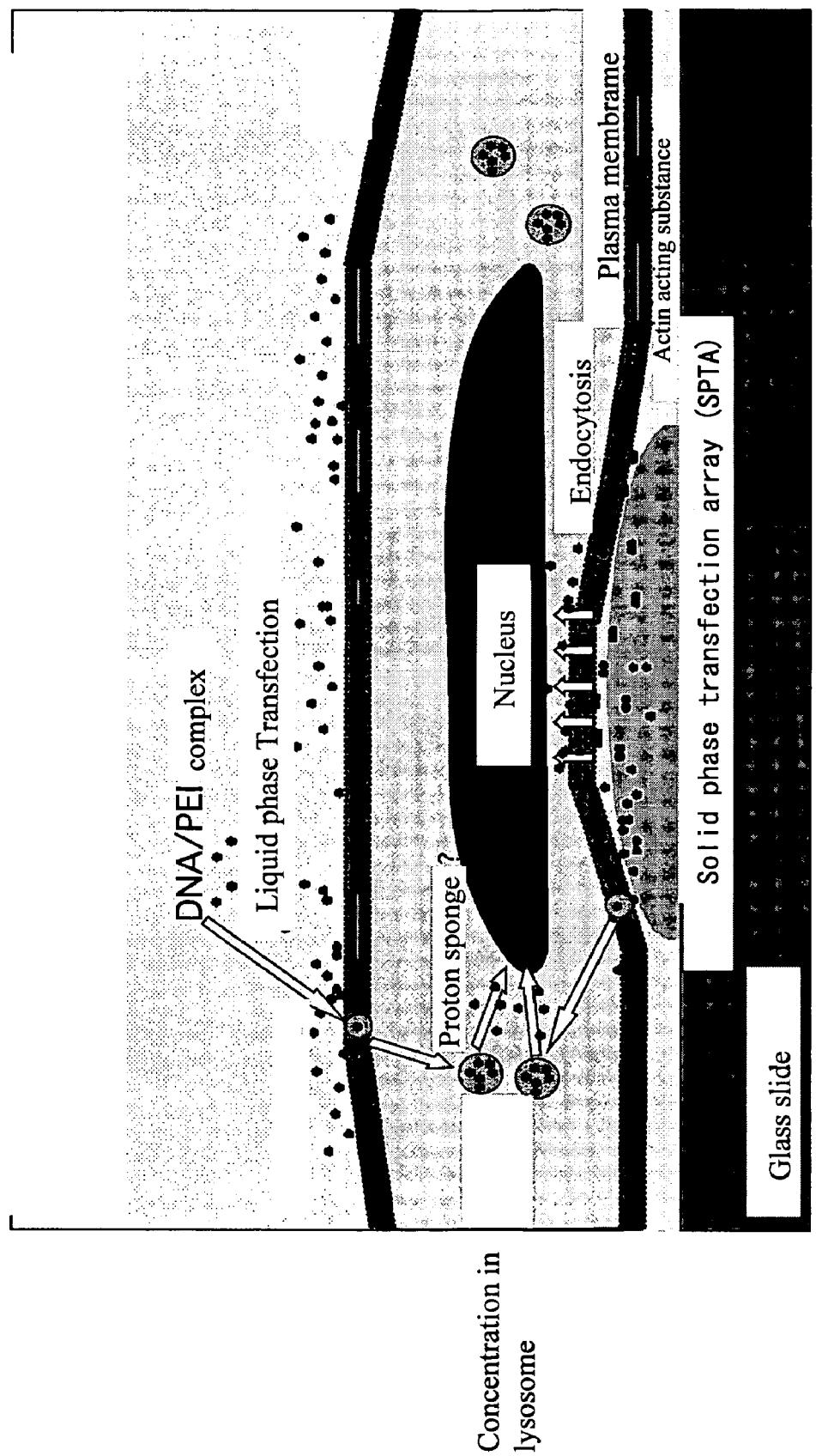
FIG. 13C shows the difference between conventional liquid phase transfection and SPTA.

To achieve the above-described objects, the present inventors studied five different cell lines (HEK293, HeLa, NIH3T3, HepG2 and hMSC) as described above with both our methodology (transfection in a solid phase system) (see FIGS. 13A and 13C) and conventional liquid-phase transfection under a series of transfection conditions. Cross contamination was evaluated for both systems as follows. In the case of SPTA, we printed DNA's encoding a red fluorescent protein (RFP) and a green fluorescent protein (GFP) on glass supports in a checked pattern. In the case of experiments including conventional liquid phase transfection (where cells to be transfected cannot be spatially separated from one another spontaneously), a DNA encoding GFP was used. Several transfection reagents were evaluated: four liquid transfection reagents (Effectene, TransFast™, Tfx™-20, LopofectAMINE 2000), two polyamine (SuperFect, PolyFect), and two polyimine (JetPEI (×4) and ExGen 500).

Transfection efficiency: transfection efficiency was determined as total fluorescence intensity per unit area (FIG. 14A and FIG. 14B (images)). The results of liquid phase optimal for cell lines used were obtained using different transfection reagents (see FIGS. 14C to 14D). Next, these efficient transfection reagents were used to optimize a solid phase protocol. Several tendencies were observed. For cell lines which are readily transfectable (e.g., HEK293, HeLa, NIH3T3, etc.), the transfection efficiency observed in the solid phase protocol was slightly superior to, but essentially similar to, that of the standard liquid phase protocol (FIG. 14A to 14D).

However, for cells which are difficult to transfect (e.g., hMSC, HepG2, etc.), we observed that transfection efficiency was increased up to 40 fold while the features of the cells were retained under conditions optimized to the SPTA methodology (see the above-described protocol and FIGS. 14C and 14D). In the case of hMSC (FIGS. 15A and 15B), the best conditions included use of a polyethylene imine (PEI) transfection reagent. As expected, important factors for achieving high transfection efficiency are the charge balance (N/P ratio) between the number of nitrogen atoms (N) in the polymer and the number of phosphate residues (P) in plasmid DNA, and DNA concentration. Generally, increases in the N/P ratio and the concentration lead to an increase in transfection efficiency. We also observed a significant reduction in the survival rate of hMSC cells in liquid phase transfection experiments where the DNA concentration was high and the N/P ratio was high. Because of these two opposing factors, the liquid phase transfection of hMSC had a relatively low cell survival rate (N/P ratio>10). In the case of the SPTA protocol, however, a considerably high N/P ratio (fixed to the solid support) and DNA concentration were tolerable (probably attributable to the effect of the solid support stabilizing cell membranes) while the cell survival rate and the cellular state were not significantly affected. Therefore, this is probably responsible for the dramatic improvement in transfection efficiency. It was found that the N/P ratio of 10 was optimal for SPTA, and a sufficient transfection level was provided while minimizing cytotoxicity. Another reason for the increase in transfection efficiency observed in the case of the SPTA protocol is that a high local ratio of the DNA concentration to the transfection reagent concentration was achieved (this leads to cell death in liquid phase transfection experiments).

The coating agent used is crucial to achieving of high transfection efficiency on chips. It was found that when a glass chip is used, PLL provided best results both for transfection efficiency and cross contamination (described below). When fibronectin coating was not used, few transfectants were observed (all the other experimental conditions were retained unchanged). Although it's function is not completely established, fibronectin probably plays a role in accelerating the cell adhesion process (data not shown), and thus limits the time which permits the diffusion of DNA released from the surface.

Low cross contamination: apart from the higher transfection efficiency observed in the SPTA protocol, an important advantage of the technique of the present invention is the provision of an array of separated cells, in which selected genes are expressed in the separate positions. The present inventors printed JetPEI (see the "Experimental protocols" section) and two different reporter genes (RFP and GFP) mixed with fibronectin on glass surface coated with fibronectin. The resultant transfection chip was subjected to appropriate cell culture. Expressed GFP and RFP were localized in regions in which corresponding cDNA had been spotted, under experimental conditions which had been found to be best. Substantially no cross contamination was observed (FIGS. 16A to 16D). In the absence of fibronectin or PLL, however, cross contamination which hinders solid phase transfection was observed, and the transfection efficiency was significantly lower (see FIG. 6). This result demonstrated the hypothesis that the relative proportion of plasmid DNA, which was released from the cell adhesion and the support surface, is an important factor in high transfection efficiency and high cross contamination.

Another cause of cross contamination may be the mobility of transfected cells on a solid support. The present inventors measured both the rate of cell adhesion (FIG. 16C) and the diffusion rate of plasmid DNA on several supports. As a result, substantially no DNA diffusion occurred under optimum conditions. However, a considerable amount of plasmid DNA diffused under high cross contamination conditions until cell adhesion was completed, so that plasmid DNA was depleted from the solid phase surface.

This established technique is of particular importance in the context of cost-effective high-throughput gene function screening. Indeed, the small amounts of transfection reagent and DNA required, as well as the possible automatization of the entire process (from plasmid isolation to detection) increase the utility of the above presented method.

In conclusion, the present invention has successfully realized a hMSC transfection array in a system using complex-salt. With this technique, it will be possible to achieve high-throughput studies using solid phase transfection, such as the elucidation of the genetic mechanism underpinning the differentiation of pluripotent stem cells. The detailed mechanism of the solid phase transfection as well as methodologies for the use of this technology for high throughput, real time gene expression monitoring can be applied for various purposes.

Example 4

Mathematical Analysis

Next, time-lapse profiles were produced based on data obtained using the techniques described in Examples 2 and 3.

(Induction of Differentiation)

Each reporter was fixed to a solid phase support and cultured in undifferentiated mesenchymal stem cell maintenance medium (MSCGM, PT-3001, PT-3238, PT-4105, Cambrex, BioWhittaker, USA) for two days. Thereafter, the medium was replaced with differentiation-inducing medium (hMSC Differentiation, PT-3002, PT-4120, Cambrex, BioWhittaker, USA). The response profile of each reporter was measured.

(Mathematical Analysis Technique)

A mathematical analysis technique used herein is shown in FIGS. 18A and 18B (18-1 to 18-2).

(Transcription Factors Used Herein)

As shown in FIGS. 19 and 24, plasmids (commercially available from Clontech), in which 17 transcription factors (ISRE, RARE, STAT3, GAS, NFAT, MIC, AP1, SRE, GRE, CRE, NFκB, ERE, TRE, E2F, Rb, p53) were operably linked to GFP, were used to observe the differentiation of mesenchymal stem cells into osteoblasts. The resultant time-lapse profiles are shown in FIG. 19. Reporters for the transcription factors were constructed as shown in FIG. 23.

An assay was conducted using the reporters for the transcription factors under control conditions (cells, supplemental factors, culture conditions, etc.) published by Clontech.

The results are shown in FIG. 25. It was demonstrated that when compared only to DNA in this manner, most of the transcription factors were induced when inducing agents were added.

Next, the activity of the transcription factors was measured over time in the course of induction of differentiation into bone. In this case, time-lapse profiles, which were obtained during the induction of differentiation under the above-described conditions, were compared with each other. The time-lapse profiles were obtained as follows. Each reporter gene was introduced into mesenchymal stem cells by a solid phase transfection method. The cells were cultured in undifferentiated state maintenance medium for two days. Thereafter, the medium was replaced with osteoblast differentiation medium. This time point was referred to as the osteoblast differentiation start time. Supplement factors were added at concentrations recommended for the osteoblast differentiation medium. The other culture conditions were in accordance with Cambrex's instructions.

The results are shown in FIG. 26. The profile pattern on the left of FIG. 26 was obtained 10 hours to 30 hours after replacement of the medium. The profile pattern on the right of FIG. 26 was obtained 5 to 6 days after replacement of the medium. Thus, it was demonstrated that the pattern significantly changed over time. The phases of the profiles were calculated using a formula shown in FIG. 27 and the results were summarized in a table to the right of FIG. 27. As can be seen, the inversion of the phase of the profile was deeply associated with differentiation for ISRE, RARE, STAT3, GRE, CRE, TRE, E2F, and p53. Therefore, it was demonstrated that by examining the phase, changes in process, i.e., the occurrence of transcription control, could be detected.

(Arbitrary Combination of Reporters)

Next, it was demonstrated that differentiation could be identified using an arbitrary combination of promoters for which data was extracted at the initial stage of induction of differentiation. Briefly, the analysis was conducted as shown in FIG. 20.

The results are shown in FIG. 20. This analysis revealed that although differentiation could not be detected at its very initial stage (potentially due to noise), but could be confirmed about 15 hours after induction of differentiation. In this example, when data was extracted for 8 or more promoters, differentiation could be detected at a detection rate of 100%. When data was extracted for 3 promoters, differentiation could be detected at a detection rate of more than 90%. When data was extracted for two promoters, differentiation could be detected at a detection rate of 88%. When data was extracted for one promoter, differentiation could be detected at a detection rate of 82%. Thus, it was revealed that one, two or at least three promoters are sufficient for determination or identification of the state of cells.

(Maintenance of Undifferentiated State)

Next, the maintenance of undifferentiated state was analyzed using an arbitrary combination of transcription control sequences for which data was extracted. Analysis was conducted as described in FIG. 20.

The results are shown in FIG. 21. As is largely different from the results of induction of differentiation, by comparing the profiles of the transcription control sequences with one another, it could be determined whether or not stem cells were induced into differentiation or remained undifferentiated. Such a determination could be achieved using at least one transcription control sequence. The determination of the state of cells using such a small number of transcription control sequences cannot be achieved by conventional techniques. It can be said that the present invention achieved an excellent effect.

By analyzing a cellular process in such a fashion, the formation of cellular functions can be described as a cocktail party process as shown in FIG. 22. With such a process description, the present invention made it possible to analyze the progression of a cellular response to drugs and the progression of the induction of differentiation.

Example 5

Anticancer Agent

In this example, cisplatin was used as an exemplary anticancer agent and was mixed into the medium of exposed cells. The concentration of the anticancer agent was selected as appropriate, such as 1 μM, 5 μM, 10 μM, and the like, to observe the reaction of the cells. Cisplatin was applied to cells resistant or sensitive to the anticancer agent. Time-lapse observation was conducted to produce profiles as in the above-described examples. As a result, it was revealed that time-lapse profiles varied depending on the difference in cisplatin concentration and resistance/sensitivity.

Example 6

RNAi

The present Example demonstrated that it was possible to obtain a profile relating to gene knockdown effect using a cell was immobilized as described in Example 1, RNAi was used as a biological agent. The following was used as RNAi for experimentation. Gene expression inhibition methods using ribozymes and siRNA and the like allows obtaining profiles of response reactions in a cell for which gene expression inhibition is conducted using the same.

RNAi: those sequences available at the URL: http://www.nippongene.jp/pages/products/sirna/review/ were used (for example, Control siRNA duplex).

(RNAi Transfection)

First, it was confirmed whether the siRNA could achieve knockdown effects. Synthesis of siRNA 5'-AAGCAGCAG-GACUUCUUCAAG-3' (SEQ ID NO:12) corresponding to EGFP was performed to prepare an array substrate as described herein above in the Examples. The preparation of array substrate using siRNA instead of nucleic acid molecules including promoter sequences was performed. Transfection using these array substrates confirmed effective inhibition of expression of a target gene. The protocols thereof are presented in FIG. 28.

(Results)

FIG. 29A shows the effects of target gene inhibition by siRNA. Expression of the target gene has actually been inhibited. The results using this gel may be stored as a profile in any data format.

Next, results of siRNA are stored as a profile data (image data of TIFF format having resolution at the level of 5 μm/pixel or less). As such, the results of siRNA may be stored as a profile data. Such a format is not limited to those specifically presented in this Example, but those skilled in the art may employ any type of formats.

(FIG. 9: Applications using siRNA and a transfection microarray of PC12 cells on a collagen IV coated chip)

Next, the present Example conducted a gene expression inhibition experiment using siRNA. The present Example evaluated whether or not the present invention functions by observing whether or not siRNAs against EGFP can specifically inhibit the expression of the EGFP as an indicator.

Using the conditions described in Example 7, transfection of PC12 was conducted on an array coated with collagen IV. In lieu of the gene used in Example 7, the following conditions were used:

0.75 ng of an expression vector (pEGFP-N1), HcRed (available from BD Clontech) were each spotted on a single, specific spot of the array. Thereafter, 16.5 ng of siRNA (available from Dharmacon, target sequence: 5'-GGC TAC GTC CAG GAG CGC ACC-3' (SEQ ID NO:49)=a) or scrambled siRNA (available from Dharmacon, target sequence: 5'-gCg CgC TTT gTA ggA TTC g-3' (SEQ ID NO:50)=b) were also spotted.

FIG. 29B shows the results. As shown in FIG. 29 B(A), in the case of PC12 cells co-transfected with EGFP vector and anti-EGFP siRNA, it was observed that only signals from HcRed were detected, and the green signal which should be derived from pEGFP-N1 had been inhibited. On the other hand, as shown in FIG. 29 B(B), in the case of scrambled siRNA, green fluorescence was been observed and thus it was confirmed that the effects seen in FIG. 29 B(A) is the result of RNAi. Relative intensities of the fluorescence in FIGS. 29B (A) and 29B(B) are shown in FIG. 29B(C). y-axis is shown with relative luminance. It can be seen that the effect by EGFP is substantially completely inhibited.

FIG. 29C shows a result and graph summarizing the above. The left-hand panel shows a photograph comparing an EGFP RNAi and a scrambled (Mock) RNAi. As shown in the figure, the use of RNAi of EGFP showed and inhibitory effect, whereas the use of scrambled RNAi did not show such an inhibitory effect. The right-hand panel shows the same together with DsRed2. Experimental conditions are similar to the above Examples. As a result, red (signal derived from DsRed) and green (signal derived from EGFP) were presented in the proportion of the effects of RNAi.

FIG. 29D shows an illustrative drawing of a chip using an RNAi reporter. When using RNAi as an input signal, and introducing a nucleic acid encoding both a gene product capable of signaling such as EGF and the like, and a gene of interest (including a promoter) as an output, observation of the signaling as the output allows one to produce cellular information.

FIG. 29E shows an exemplary experiments using a variety of reporters (pAP1-EGFP, pAP1(PMA)-EGFP, pCRE-EGFP, pE2F-EGFP, pERE-EGFP, pGAS-EGFP, pGRE-EGFP, pHSE-EGFP, pISRE-EGFP, pMyc-EGFP, pNFAT-EGFP, pNFkB-EGFP, pRARE-EGFP, pRb-EGFP, pSTST3-EGFP, pSRE-EGFP, pTRE-EGFP, pp53-EGFP, pCREB-sensor, pIkB-sensor, pp53-sensor, pCasapase3-sensor; cis-element sequence was commercially available from Clontech; these are plasmid vectors produced by recombining a fluorescent protein gene). As such, the system of the present invention will function regardless of the types of reporters used.

Example 7

Regulation of Gene Expression Using a Tetracycline-Dependent Promoter

As described in the Examples 1-3, it was demonstrated that a tetracycline-dependent promoter could be used to produce a profile showing how gene expression is regulated. The sequences described below were used.

As the tetracycline-dependent promoter (and its gene vector construct), pTet-Off and pTet-On vectors (BD Biosciences) were used (see http://www.clontech.com/techinfo/vectors/cattet.shtml). As a vector, pTRE-d2EGFP (SEQ ID NO.: 29) was used (see http://www.clontech.com/techinfo/vectors/vectorsT-Z/pTR E-d2EGFP.shtml).

(Protocol)

pTet-Off and pTet-On (SEQ ID NOS.: 26 and 27, respectively) were printed onto array substrates. Real time measurement was performed on the array substrates to determine whether or not tetracycline regulates gene expression. The results are shown in FIG. 30. As shown in FIG. 30, a change in gene expression was detected only for the tetracycline-dependent promoter. FIG. 31 is a photograph showing the actual states of expression for the tetracycline-dependent promoter and the tetracycline-independent promoter. As can be seen, the difference between them is measurable by the naked eye.

(Measurement of Profile Data)

Images are taken in real time. Changes in intensity per cell or area are plotted on a graph. The resultant data may be subjected to linear transformation, such as noise reduction, and then multivariate analysis, signal processing, or the like, to obtain profile data. The resultant data is compared between phenomena or cells, thereby making it possible to determine a specific response or identity for the cells.

Example 8

Gene Expression

Next, nucleic acid molecules encoding structural genes were used to produce cellular profiles. In this example, an olfactory receptor 17 (SEQ ID NOS: 13, 14) was used as a structural gene. The protocol used in Examples 1-3 was used.

As a result, as with promoters, it was demonstrated that cellular profiles could be produced by measuring the amount of gene products or the like.

Example 9

Apoptotic Signals

Next, it was investigated that cellular profiles could be produced by monitoring the activation of caspase 3 present within cells. Transfection and array preparation were performed in the above-described examples.

pCaspase3-Sensor Vector (BD Biosciences Clontech, 1020 East Meadow Circle, Palo Alto, Calif. 94303; cat. No. 8185-1) was used to monitor an apoptotic signal from caspase 3.

As a result, as with promoters, it was demonstrated that cellular profiles could be produced by measuring apoptotic signals or the like.

Example 10

Stress Signal

Next, it was investigated whether cellular profiles characterizing stress signals from JNK, ERK, p38 or the like could be produced using transcription factor reporters. Transfection and array preparation were performed as in the above-described examples.

pAP1-EGFP, pCRE-EGFP, and pSRE-EGFP available from BD Bioscience Clontech were used to monitor stress signals from JNK, ERK, and p38.

As a result, as in the above-described examples, it was demonstrated that cellular profiles could be produced by measuring stress signals.

Example 11

Localization of Molecules

Next, it was demonstrated that a gene of interest could be fused with a fluorescent protein so that the expression profile of the gene product and the cellular localization of the gene product could be visualized.

GFP, RFP, CFP and BFP, were used as fluorescent proteins and cloned KIAA cDNA libraries or the like were used as genes of interest to produce gene constructs. These materials are specifically described below:

cloned KIAA cDNA (KIAA=Kazusa DNA Research Institute, Kazusa, Chiba, Japan); and cDNA libraries commercially available from Invitrogen.

Transfection and array preparation were performed as in the above-described examples.

The expression of cloned KIAA, KIAA1474, was monitored to produce a profile of the expression and investigate the localization of the expression product.

As a result, as in the above-described examples, it was demonstrated that intentionally constructed gene constructs could be used to produce cellular profiles for target characteristics.

Example 12

Changes in Cellular Morphology

Next, it was demonstrated that cellular profiles characterizing cellular morphology could be produced by expressing or knocking out genes or adding substances (glycerophosphate as a chemical substance and dexamethasone as a cytokine). Cellular morphology, such as multinucleated cells, cellular outgrowth, outgrowth projections, and the like, was measured and analyzed as three-dimensional data.

The specific sequences of the introduced nucleic acid molecules are described below:

Cloned KIAA (supra); and

RNAi for transcription factors (CBFA-1, AP1).

Transfection and array preparation were performed as in the above-described examples.

Mesenchymal stem cells as used in the above-described examples were used to monitor the morphology of cells which were induced to be differentiated into osteoblasts.

As a result, as in the above-described examples, it was demonstrated that intentionally constructed gene constructs could be used to produce cellular profiles for target characteristics. Event descriptors can be produced based on the profile data using the process as used in the above-described examples.

Example 13

Intermolecular Interaction

Next, it was demonstrated that cellular profiles could be produced by using a technique such as a two-hybrid system, FRET, BRET, or the like.

The specific sequences of the introduced nucleic acid molecules are described below:

olfactory receptors (SEQ ID NOS: 13 to 38); and

G proteins (SEQ ID NOS: 39 to 44).

Transfection and array preparation were performed as in the above-described examples.

The dissociation of the olfactory receptor and G protein was monitored through induction of a scented substance, which was captured as changes in fluorescent wavelength. In this manner, cells were monitored.

The two-hybrid system, FRET, and BRET were specifically performed as follows.

The two-hybrid system was available from Clontech (http://www.clontech.co.jp/product/catalog/007003006.shtml). FRET and BRET were performed using devices available from Berthold Japan.

As a result, as in the above-described examples, it was demonstrated that intentionally constructed gene constructs could be used in a two-hybrid system, FRET, BRET, or the like, to produce cellular profiles.

Example 14

Receptor-Ligand

Next, it was demonstrated that a cellular profile can be produced by employing the interaction between a receptor and its ligand as an indicator. It is useful for network formation in a cell, to obtain interactive information between a receptor protein present in the cell membrane or nuclear membrane, or the like, and a ligand thereto.

In the present Example, the following was prepared:

(Cell Adhesion Molecules)

A variety of extracellular matrix protein and variants and fragments thereof were prepared as candidates for cell adhesion molecules. What was prepared in the present Example is as follows. Cell adhesion molecules were commercially available.

1) ProNectin F (Sanyo Chemical Industries, Kyoto, Japan);

2) ProNectin L (Sanyo Chemical Industries);

3) ProNectin Plus (Sanyo Chemical Industries);

4) fibronectin (SEQ ID NO.: 2);

5) gelatin.

Plasmids were prepared as DNA for transfection. Plasmids, pEGFP-N1 and pDsRed2-N1 (both from BD Biosciences, Clontech, Calif., USA) were used. In these plasmids, gene expression was under the control of cytomegalovirus (CMV). The plasmid DNA was amplified in *E. coli* (XL1 blue, Stratgene, Tex., USA) and the amplified plasmid DNA was used as a complex partner. The DNA was dissolved in distilled water free from DNase and RNase.

The following transfection reagents were used: Effectene Transfection Reagent (cat. no. 301425, Qiagen, Calif.), TransFast™ Transfection Reagent (E2431, Promega, Wis.), Tfx™-20 Reagent (E2391, Promega, Wis.), SuperFect Transfection Reagent (301305, Qiagen, Calif.), PolyFect Transfection Reagent (301105, Qiagen, Calif.), LipofectAMINE 2000 Reagent (11668-019, Invitrogen corporation, CA), JetPEI (×4) conc. (101-30, Polyplus-transfection, France), and ExGen 500 (R0511, Fermentas Inc., MD). These transfection reagents were added to the above-described DNA and actin-like acting substance in advance or complexes thereof with the DNA were produced in advance.

The thus-obtained solution was used in assays using transfection arrays described below. Next, transfection effects on a solid phage were observed. The protocols therefor are described below:

(Protocol)

The final concentration of DNA was adjusted to 1 μg/μL. A cell adhesion molecule was preserved as a stock having a concentration of 10 μg/μL in ddH$_2$O. All dilutions were made using PBS, ddH$_2$O, or Dulbecco's MEM. A series of dilutions, for example, 0.2 μg/μL, 0.27 μg/μL, 0.4 μg/μL, 0.53 μg/μL, 0.6 μg/μL, 0.8 μg/μL, 1.0 μg/μL, 1.07 μg/μL, 1.33 μg/μL, and the like, were formulated.

Transfection reagents were used in accordance with instructions provided by each manufacturer.

Plasmid DNA was removed from a glycerol stock and amplified in 100 mL L-amp overnight. Qiaprep Miniprep or Qiagen Plasmid Purification Maxi was used to purify DNA in accordance with a standard protocol provided by the manufacturer.

In the present Example, the following five cells were used to confirm an effect: human mesenchymal stem cell (hMSCs, PT-2501, Cambrex BioScience Walkersville, Inc., MD); human embryonic renal cell (HEK293, RCB1637, RIKEN Cell Bank, JPN); NIH3T3-3 cell (RCB0150, RIKEN Cell Bank, JPN); HeLa cell (RCB0007, RIKEN Cell Bank, JPN); and HepG2 (RCB1648, RIKEN Cell Bank, JPN). These cells were cultured in DMEM/10% IFS containing L-glut and pen/strep.

(Dilution and DNA Spots)

Transfection reagents and DNA were mixed to form a DNA-transfection reagent complex. The complex formation requires a certain period of time. Therefore, the mixture was spotted onto a solid phase support (e.g., a poly-L-lysine slide) using an arrayer. In the present Example, as a solid phase support, an APS slide, a MAS slide, and an uncoated slide were used, as well as a poly-L-lysine slide. These slides are available from Matsunami Glass (Kishiwada, Japan) or the like.

For complex formation and spot fixation, the slides were dried overnight in a vacuum dryer. Drying was performed for a duration in the range of 2 hours to 1 week.

Although the cell adhesion molecule might be used during the complex formation, it was also used immediately before spotting in the present Example.

(Formulation of Mixed Solution and Application to Solid Phase Supports)

300 μL of DNA concentrated buffer (EC buffer)+16 μL of an enhancer were mixed in an Eppendorf tube. The mixture was mixed with a Vortex, followed by incubation for 5 minutes. 50 μL of a transfection reagent (Effectene, etc.) was added to the mixture, followed by mixing by pipetting. To apply a transfection reagent, an annular wax barrier was formed around the spots on the slide. 366 μL of the mixture was added to the spot region surrounded by the wax, followed by incubation at room temperature for 10 to 20 minutes. Thereby, the fixation to the support was manually achieved.

(Distribution of Cells)

Next, a protocol for adding cells will be described. Cells were distributed for transfection. The distribution was typically performed by reduced-pressure suction in a hood. A slide was placed on a dish, and a solution containing cells was added to the dish for transfection. The cells were distributed as follows.

The growing cells were seeded at a concentration of $10^7$ cells/25 mL. The cells were plated on the slide in a 100×100×15 mm squared Petri dish or a 100 mm (radius)×15 mm circular dish. Transfection was conducted for about 40 hours. This period of time corresponded to about 2 cell cycles. The slide was treated for immunofluorescence.

(Evaluation of Gene Introduction)

Gene introduction was evaluated by detection using, for example, immunofluorescence, fluorescence microscope examination, laser scanning, radioactive labels, and sensitive films, or emulsion.

When an expressed protein to be visualized is a fluorescent protein, such a protein can be observed with a fluorescence microscope and a photograph thereof can be taken. For large-sized expression arrays, slides may be scanned using a laser scanner for storage of data. If an expressed protein can be detected using specific fluorescence in the case of calcium, a protocol specific for detection of a specific fluorescence can be successively performed to detect signals. If an expressed protein can be detected using fluorescence antibodies, an immunofluorescence protocol can be successively performed.

(Laser Scanning and Quantification of Fluorescence Intensity)

To quantify transfection efficiency, the present inventors used a DNA microarray scanner (GeneTAC UC4×4, Genomic Solutions Inc., MI). Total fluorescence intensity (arbitrary units) was measured, and thereafter, fluorescence intensity per unit surface area was calculated.

(Cross-Sectional observation by Confocal Scanning Microscope)

Cells were seeded on tissue culture dishes at a final concentration of $1\times10^5$ cells/well and cultured in appropriate medium (Human Mesenchymal Cell Basal Medium (MSCGM BulletKit PT-3001, Cambrex BioScience Walkersville, Inc., MD). After fixation of the cell layer with 4% paraformaldehyde solution, SYTO and Texas Red-X phalloidin (Molecular Probes Inc., OR, USA) was added to the cell layer for observation of nuclei and F-actin. The samples emitting light due to gene products and the stained samples were observed with a confocal laser microscope (LSM510: Carl Zeiss Co., Ltd., pin hole size=Ch1=123 μm, Ch2=108 μm, image interval=0.4) to obtain cross sectional views.

Next, an Example, to which the present invention is applied to, is described wherein an olfactory receptor is selected as a typical example of a chemical substance receptor. When a preliminary example was implemented, it was proved that transfection arrays can also be used for an olfactory receptor The olfactory receptor expression vector group was spotted per every kind of receptor, on a cover glass, which was made like an array, was secured with screws and the like in a chamber for signal measurement, and cells having an almost homogeneous nature, were cultured thereon. Regarding a chamber for signal measurement, sample gas was introduced into a known structure (Proc. Natl. Acad. Sci. USA, 96(1999): 4040-4045 and the like). Other devised chambers are also intended. During response measurement, culture medium was passed through the chamber at a constant speed. Culture media was supplied to the chamber for measurement from the opening of a culture medium supply tube, and a sample gas supplying tube was secured at the position preferably near the liquid level, which is the upper portion of an interval whose boundary is defined by reaching a wall which prevents the approach of culture media over a cover-slip that forms the ceiling of the measurement member, so that sample gas can be supplied to culture medium flowing across the interval. This sample gas supplying tube is preferably made of materials to which lipophilic odor substances such as Teflon and peak, and dust are not readily adsorbed. The higher effect was obtained in the situation wherein, at the time other than introducing sample gas, sample gas remaining in a tube was removed, and to preferably keep the interior clean, the tube (preferably with a broad opening) could be purged with odorless air by setting a three-way valve in the mid course, or by setting a check valve at a joint of an odorless air supplying tube. However, it was not necessary. The example could also be implemented in the situation wherein, at a time other than when introducing sample gas from outside for an appropriate time such as 0.5-4 seconds, odorless air was introduced from mid course of a sample gas supplying tube near a opening for collecting gas from outside, the interior of the tube was washed therewith, and at the same time, odorless gas was supplied to the culture medium as sample gas to promote the removal of remaining gas in a measurement chamber. A supporting base for the upper-glass cover slip is made of a water repellent opaque plastic such as Teflon. A width of flow channel, where culture medium flows, is about 2-fold of a width of an array, and the array is disposed in the center of the flow channel. Regarding a culture medium supplying tube and an overflow culture medium sucking tube, a portion several millimeters from the opening at the side of the measurement chamber is made using materials which have high hydrophilicity and are difficult to deform, such as stainless steel. The upper portion of the supporting base of the upper glass cover-slip where culture medium flows, from the openings of both tubes to an array, was coated, or covered with a pieces of lens paper and the like in order to provide sufficient hydrophilicity. Negative pressure for suction was adjusted at the grade such that measurements were not affected by vibration from sound generated by aspiration culture.

Generally, response measurement could be implemented 2 days after the gene introduced by the vector was expressed. Since an upper glass cover-slip was required only at the time of measurement, it was not required to install it during culture until the gene was expressed. Therefore, the Example could be implemented, adding an upper glass cover slip integrated with a wall which prevents leakage of culture medium, and a supporting base for the upper glass cover slip, to a chamber for measurement, when setting a chamber for measurement of a change in fluorescence measured by an apparatus after the gene expressed. The Example could also be implemented in the situation wherein culture medium was exchanged without using a culture medium supply tube and an overflow culture suction line tube during culture until the gene was expressed. An amount of about 10 ml of culture medium was supplied and exchanged at the frequency of about once per several hours to one day, only during the time tissue culture was performed.

The size of odor response could be optically measured using a two-dimensional image sensor such as a sensitive video camera, with a calcium ion sensitive fluorescent dye fura-2 and the like absorbed into the cell. The measurement interval preferably has time resolution which can evaluate time constants of build-up and recovery of response of about $1/3$-1 second. However, if average response time curve or its theoretical formula had been obtained, actual change was estimated from measurement results at 5 points with 5-second-intervals, 5, 10, 15, 20, and 25 seconds after stimulation. The obtained estimates of the time constant of the response starting time, response build-up time, and response recovery time was set as an index, and evaluation could be made as to whether a signal was induced by odor, or generated by spontaneous activity of a cell, or other abnormalities.

In this Example, the response of an expressed olfactory receptor in olfactory receptor neuron was studied by measuring the change in fluorescence intensity of calcium sensitive fluorescent dye. Decrease of fluorescence intensity (downward change) corresponds to the response of an olfactory receptor. Odor molecules were added to the culture at the concentration indicated above them as stimulation source, and administered to a cell during the time indicated by a bar (4 or 2 seconds). As understood from this example, responses measured simultaneously in a simultaneously adjusted cell have high intercommunity in response time characteristics, response threshold concentration corresponding to different stimulation per cell, and relative value of response amplitude. However, cells adjusted at a different times show some differences. These results show that the highest measurement reliability can be obtained by measuring odor response using a sensor arrayed to a size that allows a homogeneous administration of sample gas, providing the same adjustment conditions.

Example 15

Application to Neuron Differentiation

Next, experiments similar to those of Example 14 have been conducted with neurons to analyze the effects of tyrosine kinase RNAi with a transfection microarray. The exemplified drawings are shown in FIG. 31B.

As shown in FIG. 31B, network analysis can be conducted by taking photographs of signal represented by a reporter and collecting information thereon.

FIG. 31C shows the responses of retinoic acid (RA) and nerve growth factor (NGF) to a variety of tyrosine kinases. Inhibition % by siRNA is shown.

FIG. 31D depicts an exemplary drawing of a signal transduction pathway obtained as a result of analysis.

FIG. 31E shows results obtained by the above-mentioned analysis. Classification has been made regardless of whether the subject cells were dopaminergic neurons, cholinergic neuron, both, or neither. It can be concluded that those kinases relating to both cell types have high probability of relating to nerve projection formation.

Example 16

Data Production

Data produced in Examples 5-15 can be analyzed using a mathematical analysis with an appropriate modification as described in Example 4. Such data have been presented in a variety of formats.

Example 17

Production of a Digital Cell

Data produced in Examples 5-15 and additional data produced using the protocols described therein were used to produce a digital cell. In order to produce digital cells, parameters for data produced in these Examples have been extracted, and medium, pH, temperature, $CO_2$ concentration, and the like have been used as environment parameters. Database production may be performed using, for example, a spreadsheet software such as Excel™ available from Microsoft, or a database software such as Access™ also available from Microsoft. Next, as cell parameters, a database including cell species such as those used in Examples 5-15 can be used. A variety of stimulus parameters such as a variety of chemical stimuli (for example, including a variety of growth factors or cytokines such as HGF, FGF, PDGF, VEGF, CSF and the like) can be input to produce cell dynamics data, measurement data of reporters such as fluorescence intensity and the like. As such, a database constituting digital cell can be produced. Such examples are shown in FIGS. 33A and 33B.

Example 18

Use of Digital Cells: In Silico Live Experiments

The digital cells produced in Example 17 have been used to conduct experiments on a computer. In the present Example, a mesenchymal stem cell is used to study which agents are differentiation agents. In the case of FIG. 33A, cell A is selected as cell (for example, mesenchymal stem cell or the like). Further, DMEM is selected as a medium, pH 7.4 is selected as the pH, 37 degree Celcius is selected as the temperature, 5% is selected as the $CO_2$ concentration. Moreover, a variety of chemical stimuli such as growth factors or cytokines such as HGF, FGF, PDGF, VEGF, and CSF are selected. With respect to such a variety of chemical stimuli, concentrations are also appropriately selected, such as 1 nM to 1 mM. Combinations of these two or three thereof are also selected as a variety of chemical stimuli. Depending these combination and concentration, data regarding responses with respect to how a mesenchymal stem cell responds is output. As an output, cell dynamic is included. From such cell dynamic, it is confirmed that the mesenchymal stem cell is differentiated (e.g. to bone marrow or adipocyte or the like) or not. If morphology is not sufficient, combinations between transcriptional factors and EGF as reporters are used to output further measurement data. As such, it can be confirmed whether or not a mesenchymal stem cell is differentiated to which a specific differentiated cell. Using the present method, one can specify a chemical stimulus which induces differentiation to a specific differentiated cell.

Example 19

Use of Digital Cells—Education by In Silico Live experiments

In silico live experiments described in Example 18 are conducted during school education. In this example, the experimental theme as described above is given to a student. The student selects a variety of parameters from a database of a given digital cells. The student composes his/her own research based on the data selected. The student submits the composed research results as assignment/report. As such, education to a student can be conducted without using a live experimental system.

Example 20

Provision of a Digital Service

A database of the digital cell may be provided as an external service. Databases produced in Example 18 may use those embodiment described in FIG. 35. As such, the configuration of computer system 3501 providing a service reproducing experimental results to an actual cell using the digital cells is shown. Computer system 3501 comprises service requester 3510 requesting services desired by a user, and service provider 3520 providing a determined service in response to the request. Users such as research institutes, educational organizations or institutions request desired services. Service provider 3510 providing commercial service provides appropriate data to the research institutes, educational organizations or institutions upon request. For the purpose of school education, for example, a particular data base only directed to a particular cell or parameters or the like may be of service target.

As such, it is demonstrated that the digital cell of the present invention can be used to provide services.

Although certain preferred embodiments have been described herein, it is not intended that such embodiments be construed as limitations on the scope of the invention except as set forth in the appended claims. Various other modifications and equivalents will be apparent to and can be readily made by those skilled in the art, after reading the description herein, without departing from the scope and spirit of this invention. All patents, published patent applications and publications cited herein are incorporated by reference as if set forth fully herein.

INDUSTRIAL APPLICABILITY

According to the present invention, it is possible to determine the state of cells by observing a surprisingly small number of factors. Therefore, the present invention is applicable to diagnosis, prevention, and treatment. The present invention is also applicable to the fields of food, cosmetics, agriculture, environmental engineering, and the like. As live experiments can be reproduced on a computer, education and research in the field of biotechnology can be conducted on such a computer, which is industrially applicable.

What is claimed is:

1. An apparatus for producing a digital cell, comprising:
   a) means for obtaining a cell parameter specifying a cell of experimental interest;
   b) means for obtaining an environment parameter specifying environment under which the cell specified by the cell parameter is cultured;
   c) means for obtaining a stimulus parameter specifying a stimulus to be given to the cell specified by the cell parameter;
   d) means for obtaining a stimulus response result showing a result which the cell specified by the cell parameter responds to the stimulus specified by the stimulus parameter under the environment specified by the environment parameter wherein the stimulus response comprises profile data for the cell obtained by monitoring a biological agent or a collection thereof on or in the cell over time, and wherein during the monitoring, the cell is immobilized to a support by a composition comprising a salt, and a 29 kDa fragment of fibronectin;
   e) means for producing an experimental data against the cell, by correlating the cell parameter, the environment parameter, the stimulus parameter and the stimulus response result; and
   f) means for providing at least one collection of experimental data as a digital cell, by optionally repeating steps performed by the means a) through e) to produce at least one collection of experimental data against the cell, wherein the apparatus further comprises a means for storing the at least one collection of experimental data against the cell.

2. A computer system for providing a service which reproduces an experimental result on an actual cell using a digital cell produced by the apparatus of claim 1, comprising:
   a service requester being composed such that it can have access to a database having at least one digital cell stored thereon, each of the at least one digital cell is expressed as a collection of at least one experimental data on a cell of experimental interest, wherein each of the at least one experimental data comprises a cell parameter specifying the cell, an environment parameter specifying an environment under which the cell specified by the cell parameter is culture, a stimulus parameter specifying a stimulus to be given to the cell specified by the cell parameter, and a stimulus response result showing a result which the cell specified by the cell parameter responds to the stimulus specified by the stimulus parameter under the environment specified by the environment parameter; and
   a service provider requesting a service desired by a user;
   wherein the service requester comprises:
      means for receiving the cell parameter, the environment parameter and the stimulus parameter to produce a request comprising the cell parameter, the environment parameter and the stimulus parameter; and
      means for providing the request to the service provider, and
   wherein the service provider comprises:
      means for searching the database in response to the request by the service provider to determine whether or not there is the stimulus response result relating to the cell parameter, the environment parameter and the stimulus parameter included in the request in the database; and
      means for providing the stimulus response result to the service requester by the service provider, when determined that there exists the stimulus response result relating to the cell parameter, the environment parameter and the stimulus parameter included in the request in the database;
   wherein the service requester further comprises
      means for presenting the stimulus response result by the service requester.

3. A computer system according to claim 2 wherein the service requester is a Web browser which the user operates, the service provider is a Web server linked to the service requester via the Internet.

4. A computer system according to claim 2, wherein the service requester provides the request to the service provider in a format described in the XML language.

5. A computer system according to claim 2, wherein the service provider provides the stimulus response result to the service requester in a format described in the XML language.

6. A computer system for providing a service which reproduces an experimental result on an actual cell using a digital cell produced by the apparatus of claim 1, comprising:
   a plurality of service providers, each composed such that the plurality of service providers can have access to a database having at least one digital cell stored thereon, each of the at least one digital cell is expressed as a collection of at least one experimental data on a cell of experimental interest, wherein each of the at least one experimental data comprises a cell parameter specifying the cell, an environment parameter specifying an environment under which the cell specified by the cell parameter is cultured a stimulus parameter specifying a stimulus to be given to the cell specified by the cell parameter, and a stimulus response result showing a result which the cell specified by the cell parameter responds to the stimulus specified by the stimulus parameter under the environment specified by the environment parameter;

a service registry which stores at least one service which the plurality of service providers can provide; and a service provider requesting a service desired by a user;

wherein the service requester comprises:

means for receiving the cell parameter, the environment parameter and the stimulus parameter to produce a request comprising the cell parameter, the environment parameter and the stimulus parameter;

means for searching the service registry in response to the request by the service requester to determine whether or not there exists a service provider capable of providing a service of the request amongst the plurality of service providers and means for providing the request to the service provider by the service requester when determined that there exists a service provider capable of providing a service of the request amongst the plurality of service providers, wherein each of the plurality of service providers comprises:

means for searching the database in response to the request by the service provider to determine whether or not there is the stimulus response result relating to the cell parameter, the environment parameter and the stimulus parameter included in the request in the database; and means for providing the stimulus response result to the service requester by the service provider, when determined that there exists the stimulus response result relating to the cell parameter, the environment parameter and the stimulus parameter included in the request in the database;

wherein the service requester further comprises means for presenting the stimulus response result by the service requester.

7. A computer system according to claim 6, wherein the service requester is a Web server connected to a Web browser which the user operates via the Internet, each of the plurality of service providers is a Web server connected to the service requester via the Internet.

8. A computer system according to claim 6, wherein the service requester provides the request to the service provider in a format described in the XML language.

9. A computer system according to claim 6, wherein the service provider provides the stimulus response result to the service requester in a format described in the XML language.

* * * * *

UNITED STATES PATENT AND TRADEMARK OFFICE
CERTIFICATE OF CORRECTION

PATENT NO. : 7,747,390 B2  Page 1 of 1
APPLICATION NO. : 10/562469
DATED : June 29, 2010
INVENTOR(S) : Masato Miyake et al.

It is certified that error appears in the above-identified patent and that said Letters Patent is hereby corrected as shown below:

Column 293, Line 3
"parameter is cultured a stimulus parameter specifying a" should read -- parameter is cultured, a stimulus parameter specifying a --.

Signed and Sealed this

Sixteenth Day of November, 2010

David J. Kappos
*Director of the United States Patent and Trademark Office*